(12) United States Patent
Kuntz et al.

(10) Patent No.: US 10,155,002 B2
(45) Date of Patent: *Dec. 18, 2018

(54) ARYL- OR HETEROARYL-SUBSTITUTED BENZENE COMPOUNDS

(71) Applicant: Epizyme, Inc., Cambridge, MA (US)

(72) Inventors: Kevin Wayne Kuntz, Woburn, MA (US); Richard Chesworth, Concord, MA (US); Kenneth William Duncan, Norwood, MA (US); Heike Keilhack, Belmont, MA (US); Natalie Warholic, Brighton, MA (US); Christine Klaus, Waban, MA (US); Sarah Kathleen Knutson, Cambridge, MA (US); Timothy James Nelson Wigle, Waltham, MA (US); Masashi Seki, Tsukuba (JP); Syuji Shirotori, Tsukuba (JP); Satoshi Kawano, Tsukuba (JP)

(73) Assignee: Epizyme, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/346,677

(22) Filed: Nov. 8, 2016

(65) Prior Publication Data

US 2017/0119780 A1    May 4, 2017

Related U.S. Application Data

(63) Continuation of application No. 14/876,658, filed on Oct. 6, 2015, now Pat. No. 9,522,152, which is a continuation of application No. 14/742,481, filed on Jun. 17, 2015, now Pat. No. 9,549,931, which is a continuation of application No. 14/275,667, filed on May 12, 2014, now Pat. No. 9,090,562, which is a continuation of application No. 13/722,807, filed on
(Continued)

(51) Int. Cl.
| | | |
|---|---|---|
| *A61K 31/5377* | (2006.01) |
| *C07D 498/08* | (2006.01) |
| *C07D 213/64* | (2006.01) |
| *C07D 401/12* | (2006.01) |
| *C07D 405/12* | (2006.01) |
| *C07D 409/12* | (2006.01) |
| *C07D 413/12* | (2006.01) |
| *C07D 417/12* | (2006.01) |
| *C07D 491/08* | (2006.01) |
| *C07D 491/107* | (2006.01) |
| *C07D 405/14* | (2006.01) |
| *A61K 31/4412* | (2006.01) |
| *A61K 31/443* | (2006.01) |
| *A61K 31/4433* | (2006.01) |
| *A61K 31/4436* | (2006.01) |
| *A61K 31/4439* | (2006.01) |
| *A61K 31/444* | (2006.01) |
| *A61K 31/4545* | (2006.01) |
| *A61K 31/4709* | (2006.01) |
| *A61K 31/496* | (2006.01) |
| *A61K 31/506* | (2006.01) |
| *A61K 31/551* | (2006.01) |
| *A61K 31/553* | (2006.01) |

(52) U.S. Cl.
CPC ........ *A61K 31/5377* (2013.01); *A61K 31/443* (2013.01); *A61K 31/444* (2013.01); *A61K 31/4412* (2013.01); *A61K 31/4433* (2013.01); *A61K 31/4436* (2013.01); *A61K 31/4439* (2013.01); *A61K 31/4545* (2013.01); *A61K 31/4709* (2013.01); *A61K 31/496* (2013.01); *A61K 31/506* (2013.01); *A61K 31/551* (2013.01); *A61K 31/553* (2013.01); *C07D 213/64* (2013.01); *C07D 401/12* (2013.01); *C07D 405/12* (2013.01); *C07D 405/14* (2013.01); *C07D 409/12* (2013.01); *C07D 413/12* (2013.01); *C07D 417/12* (2013.01); *C07D 491/08* (2013.01); *C07D 491/107* (2013.01); *C07D 498/08* (2013.01)

(58) Field of Classification Search
IPC .................................................. A61K 31/5377
See application file for complete search history.

(56) References Cited

U.S. PATENT DOCUMENTS

| | | |
|---|---|---|
| 5,716,993 A | 2/1998 | Ozaki et al. |
| 5,948,803 A | 9/1999 | Maeda et al. |
(Continued)

FOREIGN PATENT DOCUMENTS

| | | |
|---|---|---|
| CN | 1683526 A | 10/2005 |
| CN | 101365806 A | 2/2009 |
(Continued)

OTHER PUBLICATIONS

Kent et al. Curr Treat Options Oncol. Apr. 2001;2(2):169-76. (abstract only).*
(Continued)

*Primary Examiner* — Shirley V Gembeh
(74) *Attorney, Agent, or Firm* — Cooley LLP; Heidi A. Erlacher; Xixi Sun

(57) ABSTRACT

The present invention relates to aryl- or heteroaryl-substituted benzene compounds. The present invention also relates to pharmaceutical compositions containing these compounds and methods of treating cancer by administering these compounds and pharmaceutical compositions to subjects in need thereof. The present invention also relates to the use of such compounds for research or other non-therapeutic purposes.

29 Claims, 8 Drawing Sheets

Specification includes a Sequence Listing.

Related U.S. Application Data

Dec. 20, 2012, now Pat. No. 8,765,732, which is a continuation of application No. 13/447,007, filed on Apr. 13, 2012, now Pat. No. 8,410,088.

(60) Provisional application No. 61/474,821, filed on Apr. 13, 2011, provisional application No. 61/499,595, filed on Jun. 21, 2011.

(56) References Cited

U.S. PATENT DOCUMENTS

| | | |
|---|---|---|
| 6,689,583 B1 | 2/2004 | Jenuwein et al. |
| 7,122,547 B1 | 10/2006 | Huth et al. |
| 7,252,968 B2 | 8/2007 | Jenuwein et al. |
| 7,442,685 B2 | 10/2008 | Zhang et al. |
| 7,563,589 B2 | 7/2009 | Zhang et al. |
| 7,923,219 B2 | 4/2011 | Wang et al. |
| 8,410,088 B2 | 4/2013 | Kuntz et al. |
| 8,598,167 B1 | 12/2013 | Kuntz et al. |
| 8,691,507 B2 | 4/2014 | Copeland et al. |
| 8,754,230 B2 | 6/2014 | Livingston et al. |
| 8,765,732 B2 | 7/2014 | Kuntz et al. |
| 8,895,245 B2 | 11/2014 | Copeland et al. |
| 8,962,620 B2 | 2/2015 | Kuntz et al. |
| 9,006,242 B2 | 4/2015 | Kuntz et al. |
| 9,090,562 B2 | 7/2015 | Kuntz et al. |
| 9,175,331 B2 | 11/2015 | Kuntz et al. |
| 9,206,157 B2 | 12/2015 | Kuntz et al. |
| 9,333,217 B2 | 5/2016 | Copeland et al. |
| 9,334,527 B2 | 5/2016 | Kuntz et al. |
| 9,376,422 B2 | 6/2016 | Kuntz et al. |
| 9,394,283 B2 | 7/2016 | Kuntz et al. |
| 9,522,152 B2 | 12/2016 | Kuntz et al. |
| 9,549,931 B2 | 1/2017 | Kuntz et al. |
| 9,855,275 B2 | 1/2018 | Kuntz et al. |
| 9,872,862 B2 | 1/2018 | Kuntz et al. |
| 9,949,999 B2 | 4/2018 | Copeland et al. |
| 2002/0183324 A1 | 12/2002 | Jacobson et al. |
| 2004/0082619 A1 | 4/2004 | Tada et al. |
| 2005/0059682 A1 | 3/2005 | Rubinfeld |
| 2005/0266473 A1 | 12/2005 | Zhang et al. |
| 2008/0182844 A1 | 7/2008 | Bjergarde et al. |
| 2008/0222741 A1 | 9/2008 | Chinnaiyan |
| 2008/0269289 A1 | 10/2008 | Frank et al. |
| 2008/0312292 A1 | 12/2008 | Yasui et al. |
| 2009/0012031 A1 | 1/2009 | Chinnaiyan et al. |
| 2009/0012175 A1 | 1/2009 | Bacopoulos et al. |
| 2009/0061443 A1 | 3/2009 | Zhang et al. |
| 2009/0203057 A1 | 8/2009 | Zhang et al. |
| 2010/0035912 A1 | 2/2010 | Debnath et al. |
| 2010/0113415 A1 | 5/2010 | Rajapakse et al. |
| 2011/0021362 A1 | 1/2011 | Trojer et al. |
| 2012/0071418 A1 | 3/2012 | Copeland et al. |
| 2013/0040906 A1 | 2/2013 | Kuntz et al. |
| 2014/0107122 A1 | 4/2014 | Kuntz et al. |
| 2014/0142083 A1 | 5/2014 | Kuntz et al. |
| 2015/0051163 A1 | 2/2015 | Keilhack et al. |
| 2015/0065483 A1 | 3/2015 | Kuntz et al. |
| 2015/0353494 A1 | 12/2015 | Kuntz et al. |
| 2017/0065600 A1 | 3/2017 | Kuntz et al. |

FOREIGN PATENT DOCUMENTS

| | | |
|---|---|---|
| CN | 101977905 A | 2/2011 |
| EP | 1357111 A1 | 10/2003 |
| JP | 7033729 A | 2/1995 |
| KR | 20070029617 A | 3/2007 |
| WO | WO 96/040100 A1 | 12/1996 |
| WO | WO 00/018725 A1 | 4/2000 |
| WO | WO 02/060492 A1 | 8/2002 |
| WO | WO 2003/059884 A1 | 7/2003 |
| WO | WO 03/079788 A2 | 10/2003 |
| WO | WO 2004/060377 A1 | 7/2004 |
| WO | WO 05/014599 A1 | 2/2005 |
| WO | WO 2005/018578 A2 | 3/2005 |
| WO | WO 2005/034845 A2 | 4/2005 |
| WO | WO 2005/094816 A1 | 10/2005 |
| WO | WO 06/116713 A1 | 11/2006 |
| WO | WO 07/045462 A2 | 4/2007 |
| WO | WO 07/050347 A1 | 5/2007 |
| WO | WO 07/070818 A1 | 6/2007 |
| WO | WO 2007/072225 A2 | 6/2007 |
| WO | WO 07/136592 A2 | 11/2007 |
| WO | WO 08/073138 A2 | 6/2008 |
| WO | WO 08/103277 A2 | 8/2008 |
| WO | WO 08/104077 A1 | 9/2008 |
| WO | WO 08/108825 A2 | 9/2008 |
| WO | WO 08/113006 A1 | 9/2008 |
| WO | WO 09/058298 A1 | 5/2009 |
| WO | WO 09/077766 A1 | 6/2009 |
| WO | WO 09/094427 A1 | 7/2009 |
| WO | WO 09/124137 A2 | 10/2009 |
| WO | WO 2010/007116 A2 | 1/2010 |
| WO | WO 10/018328 A1 | 2/2010 |
| WO | WO 10/109084 A1 | 9/2010 |
| WO | WO 10/111653 A2 | 9/2010 |
| WO | WO 11/082044 A1 | 7/2011 |
| WO | WO 11/140324 A1 | 11/2011 |
| WO | WO 11/140325 A1 | 11/2011 |
| WO | WO 2011/160206 A1 | 12/2011 |
| WO | WO 12/005805 A1 | 1/2012 |
| WO | WO 12/034132 A2 | 3/2012 |
| WO | WO 12/068589 A2 | 5/2012 |
| WO | WO 12/075080 A1 | 6/2012 |
| WO | WO 12/075500 A2 | 6/2012 |
| WO | WO 12/118812 A2 | 9/2012 |
| WO | WO 12/142504 A1 | 10/2012 |
| WO | WO 12/142513 A1 | 10/2012 |
| WO | WO 2013/049770 A2 | 4/2013 |
| WO | WO 13/138361 A1 | 9/2013 |
| WO | WO 2013/155317 A1 | 10/2013 |
| WO | WO 2013/155464 A1 | 10/2013 |
| WO | WO 13/173441 A2 | 11/2013 |
| WO | WO 14/062732 | 4/2014 |
| WO | WO 14/062733 | 4/2014 |
| WO | WO 2014/062720 A2 | 4/2014 |

OTHER PUBLICATIONS

Braña et al. "Reaction of N-(2-Pyridylmethyl)-3,5-dimethylbenzamide and N-(3-Pyridylmethyl)-3,5-dimethylbenzamide N-Oxides With Acetic Anhydride." *J. Het. Chem.* 19.6(1982):1297-1300.

Chemical Abstracts Service Registry Nos. 1111568-29-6, 1111508-57-6, and 1111473-93-8 entered Feb. 25, 2009.

Chemical Abstracts Service Registry Nos. 1118856-92-0, 1118847-80-5, 1118847-59-8, 1118826-65-5, 1118826-02-0, 1118825-96-9, 1118825-75-4, 1118825-72-1, and 1118825-69-6 entered Mar. 11, 2009.

Chemical Abstracts Service Registry Nos. 1278089-60-3, 1277914-52-9, and 1277529-83-5, entered Apr. 10, 2011.

Chemical Abstracts Service Registry Nos. 1278854-92-4 and 127885491-3, entered Apr. 12, 2011.

Chemical Abstracts Service Registry Nos. 919939-47-2 and 919873-05-5 entered Feb. 8, 2007.

Chemical Abstracts Service Registry Nos. 923162-97-4, 923152-74-3, and 923111-85-7 entered Feb. 26, 2007.

Chemical Abstracts Service Registry Nos. 923774-47-4, 923730-10-3, and 923690-12-4 entered Feb. 28, 2007.

Chemical Abstracts Service Registry Nos. 941139-86-2 and 941091-93-6 entered Jul. 4, 2007.

Gura et al. "Systems for Identifying New Drugs are Often Faulty." *Science.* 278.5340(1997):1041-1042.

Johnson et al. "Relationships Between Drug Activity in NCI Preclinical in vitro and in vivo Models and Early Clinical Trials." *Brit. J. Cancer.* 84.10(2001):1424-1431.

Knutson et al. "A Selective Inhibitor of EZH2 Blocks H3K27 Methylation and Kills Mutant Lymphoma Cells." *Nat. Chem. Biol.* (2012):1-7. Epub: Sep. 30, 2012.

Lohr et al. "Discovery and Prioritization of Somatic Mutations in Diffuse Large B-Cell Lymphoma (DLBCL) by Whole-Exome Sequencing." *PNAS.* 109.10(2012):3879-3884. Epub Feb. 17, 2012.

(56) References Cited

OTHER PUBLICATIONS

Martinez-Garcia et al. "The MMSET Histone Methyl Transferase Switches Global Histone Methylation and Alters Gene Expression in t(4;14) Multiple Myeloma Cells." *Blood.* 117(2011):211-220.
McCabe et al. "EZH2 Inhibition as a Therapeutic Strategy for Lymphoma With EZH2-Activating Mutations." *Nature.* Epub: Oct. 10, 2012.
McCabe et al. "Mutation of A677 in Histone Methyltransferase EZH2 in Human B-Cell Lymphoma Promotes Hypertrimethylation of Histone H3 on Lysine 27 (H3K27)." *PNAS.* 109.8(2012):2989-2994.
Miranda et al. "DZNep is a Global Histone Methylation Inhibitor That Reactivates Developmental Genes not Silenced by DNA Methylation." *Mol. Cancer Ther.* 8.6(2009):1579-1588.
Morin et al. "Somatic Mutations Altering EZH2 (Tyr641) in Follicular and Diffuse Large B-Cell Lymphomas of Germinal-Center Origin." *Nat. Genet.* 42.2(2010):181-185.
Pearce et al. "Failure Modes in Anticancer Drug Discovery and Development." *Cancer Drug Design and Discovery.* Neidle, ed. Boston: Elsevier. (2008):424-435.
Sculley et al. "Some Amide Derivatives of Certain Aminomethylpyridines." *J. Am. Chem. Soc.* 75.14(1953):3400-3403.
Simone. "Oncology: Introduction." Cecil Textbook of Medicine. Bennett et al., eds. Philadelphia: W. B. Saunders Co. 20th ed. 1(1996):1004-1104.
Sneeringer et al. "Coordinated Activities of Wild-Type Plus Mutant EZH2 Drive Tumor-Associated Hypertrimethylation of Lysine 27 on Histone H3 (H3K27) in Human B-Cell Lymphomas." *PNAS.* 107.49(2010):20980-20985.
Wigle et al. "The Y641C Mutation of EZH2 Alters Substrate Specificity for Histone H3 Lysine 27 Methylation States." *FEBS Lett.* 585.19(2011):3011-3014.
Wilson et al. "Epigenetic Antagonism Between Polycomb and SWI/SNF Complexes During Oncogenic Transformation." *Cancer Cell.* 18(2010):316-328.
Yap et al. "Somatic Mutations at EZH2 Y641 Act Dominantly Through a Mechanism of Selectively Altered PRC2 Catalytic Activity, to Increase H3K27 Trimethylation." *Blood.* 117.8(2010):2451-2459.
U.S. Appl. No. 15/598,078, filed May 17, 2017, Kuntz et al.
Declaration of Mr. Martin Brandt, European Patent No. EP-B-2614369, Application No. 11824247.8, Mar. 15, 2018, 3 pages.
Ernst, T. et al., "Inactivating mutations of the histone Methyltransferase gene EZH2 in myeloid disorders," Nature Genetics, vol. 42, No. 9, pp. 722-726, 2010.
http://cancer.sanger.ac.uk/cosmic/sample/overview?id=1451273, accessed Mar. 15, 2018, 5 pages.
PLoS One Website Screen Shot showing article views of Wu; Mar. 15, 2018, 1 page.
Richon, V. M. et al., "Lymphoma-Associated Mutations of EZH2 Result in a Change-of-Function," Blood 2010, Abstract, 5 pages.
Segalat, L., "Loss-of-function genetic diseases and the concept of pharmaceutical targets," Orphanet Journal of Rare Diseases, 2:30; doi:10.1186/1750-1172-2-30, 2007, 9 pages.
Simon, J. A. et al., "Roles of the EZH2 histone methyltransferase in cancer epigenetics," Mutation Research 647(2008):21-29.
Velichutina, I. et al., "EZH2-mediated epigenetic silencing in germinal center B cells contributes to proliferation and lymphomagenesis," Blood, vol. 116, No. 24, pp. 5247-5255, 2010.
Wu, H. et al., "Structural Biology of Human H3K9 Methyltransferases," PLoS One, vol. 5, Issue 1, https://doi.org/10.1371/journal.pone.0008570, 10 pages, 2010.
Zhang, G. -J. et al., "Cancer Genetics and Drug Target Selection," Chapter 3, Molecular Cancer Therapeutics: Strategies for Drug Discovery and Development, George C. Prendergast, Ed., pp. 42-53, John Wiley & Sons, Inc. 2004.
Barski et al. (2007) "High-Resolution Profiling of Histone Methylations in the Human Genome" *Cell,* 129(4):823-837.
Beisel et al. (2002) "Histone Methylation by the *Drosophila* Epigenetic Transcriptional Regulator Ash1" *Nature.* 419:857-862.
Bernstein et al. (2006) "A Bivalent Chromatin Structure Marks Key Developmental Genes in Embryonic Stem Cells" *Cell.* 125(2):315-326.
Bracken et al. (2003) "EZH2 is Downstream of the pRB-E2F Pathway, Essential for Proliferation and Amplified in Cancer" *EMBO J.* 22(20):5323-5335.
Cao et al. (2002) "Role of Histone H3 Lysine 27 Methylation in Polycomb-Group Silencing" *Science.* 298:1039-1043.
Cao et al. (2004) "SUZ12 is Required for Both the Histone Methyltransferase Activity and the Silencing Function of the EED-EZH2 Complex" *Mol. Cell.* 15(1):57-67.
Cao et al. (2008) "Role of hPHF1 in H3K27 Methylation and Hox Gene Silencing" *Mol. Cell. Biol.* 28(5):1862-1872.
Chen et al. (1996) "Cloning of a Human Homolog of the *Drosophila* Enhancer of zeste Gene (EZH2) That Maps to Chromosome 21q22.2" *Genomics,* 38:30-37.
Copeland et al. (2009) "Protein methyltransferases as a target class for drug discovery" *Nature Reviews Drug Discovery,* 8:724-732.
Copeland et al. (2010) "Targeting Epigenetic Enzymes for Drug Discovery" *Curr. Opin. Chem. Biol.* 14(4):505-510.
Cui et al.(2009) "Chromatin Signatures in Multipotent Human Hematopoietic Stem Cells Indicate the Fate of Bivalent Genes During Differentiation" *Cell Stem Cell,* 4(1):80-93.
Czermin et al. (2002) "*Drosphila* Enhancer of Zeste/ESC Complexes Have a Histone H3 Methyltransferase Activity That Marks Chromosomal Polycomb Sites" *Cell.* 111(2):185-196.
Ernhardt et al. (2003) "Consequence of the Depletion of Zygotic and Embryonic Enhancer of Zeste 2 During Preimplantation Mouse Development" *Development,* 130:4235-4248.
Fiskus et al. (2008) "Combined Epigenetic Therapy with the Novel Histone Methyl Transferase EZH2 Inhibitor 3-Deazaneplanocin and Histone Deacetylase Inhibitor Panobinostat Exerts Synergistic Activity against Human Mantle Cell Lymphoma Cells" Blood (ASH Annual Meeting Abstracts), 112: Abstract 3622.
Fiskus et al. (2009) "Combined epigenetic therapy with the histone methyltransferase EZH2 inhibitor 3-deazaneplanocin A and the histone deacetylase inhibitor panobinostat against human AML cells" *Blood,* 114(13):2733-2743.
Francis et al. (2001) "Mechanisms of Transcriptional Memory" *Nat Rev Mol Cell Biol,* 2:409-421.
Garapaty-Rao et al. (Nov. 21, 2013) "Identification of EZH2 and EZH1 Small Molecule Inhibitors with Selective Impact on Diffuse Large B Cell Lymphoma Cell Growth" *Chemistry & Biology,* 20(11)1329-1339, DOI: 10.1016/j.chembiol.2013.09.013.
GenBank Accession No. CAB02546, Apr. 18, 2005.
GenBank Accession No. NM_001203249.1, Jun. 26, 2012.
GenBank Accession No. NM_003797, Jun. 27, 2012.
GenBank Accession No. NM_004447, Jun. 26, 2012.
GenBank Accession No. NM_004456, Jun. 26, 2012.
GenBank Accession No. NM_005610, Jun. 27, 2012.
GenBank Accession No. NM_015355, Jun. 28, 2012.
GenBank Accession No. NM_152998, Jun. 26, 2012.
GenBank Accession No. NM_153207, Jun. 30, 2012.
GenBank Accession No. NP_001190178.1, Jun. 26, 2012.
GenBank Accession No. NP_694543, Jun. 26, 2012.
Kirmizis et al. (2003) "Identification of the Polycomb Group Protein SU(Z)12 as a Potential Molecular Target for Human Cancer Therapy" *Mol. Cancer Ther.* 2:113-121.
Kirmizis et al. (2004) "Silencing of Human Polycomb Target Genes is Associated With Methylation of Histone H3 Lys 27" *Genes Dev.* 18:1592-1605.
Kleer et al. (2003) "EZH2 is a Marker of Aggressive Breast Cancer and Promotes Neoplastic Transformation of Breast Epithelial Cells" *PNAS.* 100(20):11606-11611.
Kubicek et al. (2007) "Reversal of H3K9me2 by a Small Molecule Inhibitor for the G9a Histone Methytransferase" *Mol. Cell.* 25:473-481.
Kuzmichev et al. (2002) "Histone Methyltransferase Activity Associated With a Human Multiprotein Complex Containing the Enhancer of Zeste Protein" *Genes Dev.* 16:2893-2905.

(56) References Cited

OTHER PUBLICATIONS

Majer, C.R. et al. (Jul. 28, 2012) "A687V EZH2 is a gain-of-function mutation found in lymphoma patients" *FEBS Lett,* 586(19):3448-3451.
Martinez-Garcia et al. (2010) "Deregulation of H3K27 Methylation in Cancer" *Nat. Genet.* 42:100-101.
Milne et al. (2002) "MLL Targets SET Domain Methyltransferase Activity to Hox Gene Promoters" *Mol. Cell.* 10(5):1107-1117.
Müller et al. (2002) "Histone Methyltransferase Activity of a *Drosophila* Polycomb Group Repressor Complex" *Cell.* 111(2):197-208.
Nakamura et al. (2002) "ALL-1 Is a Histone Methyltransferase That Assembles a Supercomplex of Proteins Involved in Transcriptional Regulation" *Mol. Cell.* 10(5):1119-1128.
Otte et al. (2003) "Gene Repression by Polycomb Group Protein Complexes: A Distinct Complex for Every Occasion?" *Curr. Opin. Genet. Dev.* 13(5):448-454.
"Personalised Medicine Briefsheet" Cancer Research UK, Oct. 2010 [online]. Retrieved from www.cancerresearchuk.org, 2 pages.
Plath et al. (2003) "Role of Histone H3 Lysince 27 Methylation in X Inactivation" *Science.* 300:131-135.
Pollock et al. (2009) "Epigenetic approaches to cancer therapy" *Drug Discovery Today: Therapeutic Strategies,* 6(2):71-79.
Ryan, R.J.H. et al. (Dec. 14, 2011) "EZH2 Codon 641 Mutations Are Common in BCL2-Rearranged Germinal Center B Cell Lymphomas" *PLOSone,* 6(12):e28585, doi: 10.1371/journal.pone. 0028585, 7 pages.
Sarma et al. (2008) "EZH2 Requires PHF1 to Efficiently Catalyze H3 Lysine 27 Trimethylation In Vivo" *Mol. Cell. Biol.* 28(8):2718-2731.
Shen et al. (2008) "EZH1 Mediates Methylation on Histone H3 Lysine 27 and Complements EZH2 in Maintaining Stem Cell Identity and Executing Pluripotency" *Mol. Cell.* 32(4):491-502.
Siegel et al. (2013) "Cancer Statistics, 2013" *CA: A Cancer Journal for Clinicians,* 63(1):11-30.
Silva et al. (2003) "Establishment of Histone H3 Methylation on the Inactive X Chromosome Requires Transient Recruitment of Eed-Enx1 Polycomb Group Complexes" *Dev. Cell.* 4(4):481-495.
Swiss-Protein Accession No. Q15910, Mar. 21, 2012, 10 pages.
*The Japanese Pharmacopeia.* 16th Edition, 2011; pp. 64-68, 2070, with translation, 27 pages total.
Townsend et al. (2009) "New S-Adenosyl-L-Methionine Analogues: Synthesis and Reactivity Studies" *Org. Lett.* 11(14):2976-2979.
Van Haaften et al. (2009) "Somatic Mutations of the Histone H3K27 Demethylase Gene UTXin Human Cancer" *Nat. Genet.* 41:521-523.
Varambally et al. (2002) "The Polycomb Group Protein EZH2 is Involved in Progression of Prostate Cancer" *Nature,* 419:624-629.
Wang et al. (2004) "A Novel Human Homologue of *Drosophila* Polycomblike Gene is Up-Regulated in Multiple Cancers" *Gene,* 343(1):69-78.
Qi et al. (Dec. 26, 2012) "Selective inhibition of Ezh2 by a small molecule inhibitor blocks tumor cells proliferation" *PNAS,* 109(52):21360-21365.

\* cited by examiner

SEQUENCE LISTING

```
<160> NUMBER OF SEQ ID NOS: 2

<210> SEQ ID NO 1
<211> LENGTH: 26
<212> TYPE: PRT
<213> ORGANISM: Artificial Sequence
<220> FEATURE:
<223> OTHER INFORMATION: Chemically synthesized polypeptide
<220> FEATURE:
<221> NAME/KEY: MISC_FEATURE
<222> LOCATION: (26)..(26)
<223> OTHER INFORMATION: wherein a biotin and an amide are conjugated

<400> SEQUENCE: 1

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25

<210> SEQ ID NO 2
<211> LENGTH: 26
<212> TYPE: PRT
<213> ORGANISM: Artificial Sequence
<220> FEATURE:
<223> OTHER INFORMATION: Chemically synthesized polypeptide
<220> FEATURE:
<221> NAME/KEY: MISC_FEATURE
<222> LOCATION: (7)..(7)
<223> OTHER INFORMATION: wherein the lysine is dimethylated
<220> FEATURE:
<221> NAME/KEY: MISC_FEATURE
<222> LOCATION: (26)..(26)
<223> OTHER INFORMATION: wherein a biotin and an amide are conjugated

<400> SEQUENCE: 2

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25
```

ARYL- OR HETEROARYL-SUBSTITUTED BENZENE COMPOUNDS

RELATED APPLICATIONS

This application is a continuation application of U.S. application Ser. No. 14/876,658, filed Oct. 6, 2015 (now allowed), which is a continuation application of U.S. application Ser. No. 14/742,481, filed Jun. 17, 2015 (now allowed), which is a continuation application of U.S. application Ser. No. 14/275,667, filed May 12, 2014, now U.S. Pat. No. 9,090,562, which is a continuation application of U.S. application Ser. No. 13/722,807, filed Dec. 20, 2012, now U.S. Pat. No. 8,765,732, which is a continuation application of U.S. application Ser. No. 13/447,007, filed Apr. 13, 2012, now U.S. Pat. No. 8,410,088, which claims priority to, and the benefit of, U.S. provisional application Nos. 61/474,821, filed Apr. 13, 2011, and 61/499,595 filed Jun. 21, 2011. The entire contents of each of these applications are incorporated herein by reference in their entireties.

INCORPORATION-BY-REFERENCE OF SEQUENCE LISTING

The contents of the text file named "41478_507001WOST25.txt," which was created on Mar. 28, 2012 and is 2 KB in size, are hereby incorporated by reference in their entireties.

BACKGROUND OF THE INVENTION

In eukaryotic cells DNA is packaged with histones to form chromatin. Changes in the ordered structure of chromatin can lead to alterations in transcription of associated genes. Control of changes in chromatin structure (and hence of transcription) is mediated by covalent modifications to histones, most notably of their N-terminal tails. These modifications are often referred to as epigenetic because they can lead to heritable changes in gene expression, but do not affect the sequence of the DNA itself. Covalent modifications (for example, methylation, acetylation, phosphorylation, and ubiquitination) of the side chains of amino acids are enzymatically mediated. The selective addition of methyl groups to specific amino acid sites on histones is controlled by the action of a unique family of enzymes known as histone methyltransferases (HMTs).

The orchestrated collection of biochemical systems behind transcriptional regulation must be tightly controlled in order for cell growth and differentiation to proceed optimally. Disease states result when these controls are disrupted by aberrant expression and/or activity of the enzymes responsible for DNA and histone modification. In human cancers, for example, there is a growing body of evidence to suggest that dysregulated epigenetic enzyme activity contributes to the uncontrolled cell proliferation associated with cancer as well as other cancer-relevant phenotypes such as enhanced cell migration and invasion. Beyond cancer, there is growing evidence for a role of epigenetic enzymes in a number of other human diseases, including metabolic diseases (such as diabetes), inflammatory diseases (such as Crohn's disease), neurodegenerative diseases (such as Alzheimer's disease) and cardiovascular diseases. Therefore, selectively modulating the aberrant action of epigenetic enzymes may hold promise for the treatment of a range of diseases.

Polycomb group (PcG) and trithorax group (trxG) proteins are known to be part of the cellular memory system. See, e.g., Francis et al. (2001) *Nat Rev Mol Cell Biol* 2:409-21 and Simon et al. (2002) *Curr Opin Genet Dev* 12:210-8. In general, PcG proteins are transcriptional repressors that maintain the "off state," and trxG proteins are transcriptional activators that maintain the "on state." Because members of PcG and trxG proteins contain intrinsic histone methyltransferase (HMTase) activity, PcG and trxG proteins may participate in cellular memory through methylation of core histones. See, e.g., Beisel et al. (2002) *Nature* 419:857-62; Cao et al. (2002) *Science* 298:1039-43; Czermin et al. (2002) *Cell* 111:185-96; Kuzmichev et al. (2002) *Genes Dev* 16:2893-905; Milne et al. (2002) *Mol Cell* 10:1107-17; Muller et al. (2002) *Cell* 111:197-208; and Nakamura et al. (2002) *Mol Cell* 10:1119-28.

Biochemical and genetic studies have provided evidence that *Drosophila* PcG proteins function in at least two distinct protein complexes, the Polycomb repressive complex 1 (PRC1) and the ESC-E(Z) complex (also known as Polycomb repressive complex 2 (PRC2)). Otte et al. (2003) *Curr Opin Genet Dev* 13:448-54. Studies in *Drosophila* have demonstrated that the ESC-E(Z)/EED-EZH2 (i.e., PRC2) complexes have intrinsic histone methyltransferase activity. Although the compositions of the complexes isolated by different groups are slightly different, they generally contain EED, EZH2, SUZ12, and RbAp48 or *Drosophila* homologs thereof. However, a reconstituted complex comprising only EED, EZH2, and SUZ12 retains histone methyltransferase activity for lysine 27 of histone H3. U.S. Pat. No. 7,563,589.

Of the various proteins making up PRC2 complexes, EZH2 (Enhancer of Zeste Homolog 2) is the catalytic subunit. The catalytic site of EZH2 in turn is present within a SET domain, a highly conserved sequence motif (named after Su(var)3-9, Enhancer of Zeste, Trithorax) that is found in several chromatin-associated proteins, including members of both the Trithorax group and Polycomb group. SET domain is characteristic of all known histone lysine methyltransferases except the H3-K79 methyltransferase DOT1.

In addition to Hox gene silencing, PRC2-mediated histone H3-K27 methylation has been shown to participate in X-inactivation. Plath et al. (2003) *Science* 300:131-5; Silva et al. (2003) *Dev Cell* 4:481-95. Recruitment of the PRC2 complex to Xi and subsequent trimethylation on histone H3-K27 occurs during the initiation stage of X-inactivation and is dependent on Xist RNA. Furthermore, EZH2 and its associated histone H3-K27 methyltransferase activity were found to mark differentially the pluripotent epiblast cells and the differentiated trophectoderm, and consistent with a role of EZH2 in maintaining the epigenetic modification patterns of pluripotent epiblast cells, Cre-mediated deletion of EZH2 results in loss of histone H3-K27 methylation in the cells. Erhardt et al. (2003) *Development* 130:4235-48). Further, studies in prostate and breast cancer cell lines and tissues have revealed a strong correlation between the levels of EZH2 and SUZ12 and the invasiveness of these cancers, indicating that dysfunction of the PRC2 complex may contribute to cancer. Bracken et al. (2003) *EMBO J* 22:5323-35; Kirmizis et al. (2003) *Mol Cancer Ther* 2:113-21; Kleer et al. (2003) *Proc Natl Acad Sci USA* 100:11606-11; Varambally et al. (2002) *Nature* 419:624-9.

Recently, somatic mutations of tyrosine 641 (Y641C, Y641F, Y641N, Y641S and Y641H, sometimes also referred to as Y646C, Y646F, Y646N, Y646S and Y646H, respectively) of EZH2 were reported to be associated with follicular lymphoma (FL) and the germinal center B cell-like (GCB) subtype of diffuse large B-cell lymphoma (DLBCL). Morin et al. (2010) *Nat Genet* 42:181-5. In all cases, occurrence of the mutant EZH2 gene was found to be heterozygous, and expression of both wild-type and mutant alleles was detected in the mutant samples profiled by transcriptome sequencing. It was also demonstrated that all of the mutant forms of EZH2 could be incorporated into the multi-protein PRC2 complex, but that the resulting complexes lacked the ability to catalyze methylation of the H3-K27 equivalent residue of a peptidic substrate. Hence, it was concluded that the disease-associated changes at Tyr641 of EZH2 resulted in loss of function with respect to EZH2-catalyzed H3-K27 methylation.

SUMMARY OF THE INVENTION

In one aspect, the present invention features an aryl- or heteroaryl-substituted benzene compound of Formula (I) below or a pharmaceutically acceptable salt or ester thereof.

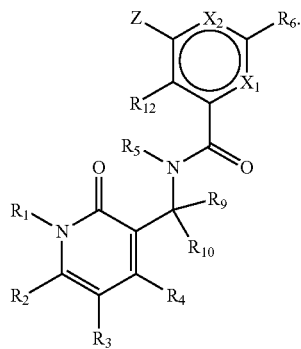

(I)

In this formula, $X_1$ is N or $CR_{11}$;

$X_2$ is N or $CR_{13}$;

Z is $NR_7R_8$, $OR_7$, $S(O)_nR_7$, or $CR_7R_8R_{14}$, in which n is 0, 1, or 2;

each of $R_1$, $R_5$, $R_9$, and $R_{10}$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

each of $R_2$, $R_3$, and $R_4$, independently, is -$Q_1$-$T_1$, in which $Q_1$ is a bond or $C_1$-$C_3$ alkyl linker optionally substituted with halo, cyano, hydroxyl or $C_1$-$C_6$ alkoxy, and $T_1$ is H, halo, hydroxyl, COOH, cyano, or $R_{S1}$, in which $R_{S1}$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, amino, mono-$C_1$-$C_6$ alkylamino, di-$C_1$-$C_6$ alkylamino, 4 to 12-membered heterocycloalkyl, or 5- or 6-membered heteroaryl, and $R_{S1}$ is optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_6$ is $C_6$-$C_{10}$ aryl or 5- or 6-membered heteroaryl, each of which is optionally substituted with one or more -$Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is H, halo, cyano, —$OR_a$, —$NR_aR_b$, —$(NR_aR_bR_c)^+A^-$, —$C(O)R_a$, —$C(O)OR_a$, —$C(O)NR_aR_b$, —$NR_bC(O)R_a$, —$NR_bC(O)OR_a$, —$S(O)_2R_a$, —$S(O)_2NR_aR_b$, or $R_{S2}$, in which each of $R_a$, $R_b$, and $R_c$, independently, is H or $R_{S3}$, $A^-$ is a pharmaceutically acceptable anion, each of $R_{S2}$ and $R_{S3}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_a$ and $R_b$, together with the N atom to which they are attached, form a 4 to 12-membered heterocycloalkyl ring having 0 or 1 additional heteroatom, and each of $R_{S2}$, $R_{S3}$, and the 4 to 12-membered heterocycloalkyl ring formed by $R_a$ and $R_b$, is optionally substituted with one or more one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_d$, $COOR_d$, —$S(O)_2R_d$, —$NR_dR_e$, and —$C(O)NR_dR_e$, each of $R_d$ and $R_e$ independently being H or $C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, —$OR_f$, —$C(O)R_f$, —$C(O)OR_f$, —$C(O)NR_fR_g$, —$C(O)NR_fOR_g$, —$NR_fC(O)R_g$, —$S(O)_2R_f$, or $R_{S4}$, in which each of $R_f$ and $R_g$, independently is H or $R_{S5}$, each of $R_{S4}$ and $R_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and each of $R_{S4}$ and $R_{S5}$ is optionally substituted with one or more -$Q_5$-$T_5$, wherein $Q_5$ is a bond, C(O), C(O)$NR_k$, $NR_kC(O)$, $S(O)_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo;

each of $R_8$, $R_{11}$, $R_{12}$, and $R_{13}$, independently, is H, halo, hydroxyl, COOH, cyano, $R_{S6}$, $OR_{S6}$, or $COOR_{S6}$, in which $R_{S6}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 11-membered heterocycloalkyl ring having 0 to 2 additional heteroatoms, or $R_7$ and $R_8$, together with the C atom to which they are attached, form $C_3$-$C_8$ cycloalkyl or a 4 to 11-membered heterocycloalkyl ring having 1 to 3 heteroatoms, and each of the 4 to 11-membered heterocycloalkyl rings or $C_3$-$C_8$ cycloalkyl formed by $R_7$ and $R_8$ is optionally substituted with one or more -$Q_6$-$T_6$, wherein $Q_6$ is a bond, C(O), C(O)$NR_m$, $NR_m$C(O), S(O)$_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or S(O)$_p$$R_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo; and $R_{14}$ is absent, H, or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

One subset of the compounds of Formula (I) includes those of Formula (Ia):

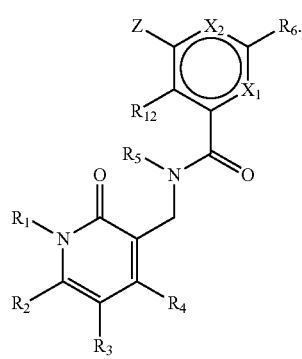

Another subset of the compounds of Formula (I) includes those of Formula (Ib), (Ic), or (Id):

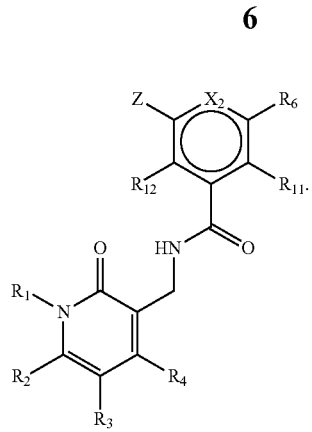

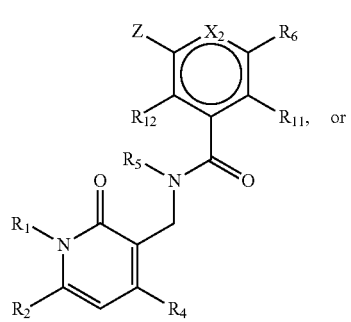

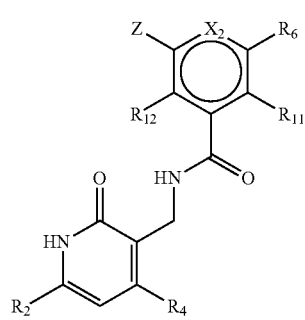

Still another subset of the compounds of formula (I) includes those of Formula (Ie), (Ig), (II), or (IIa):

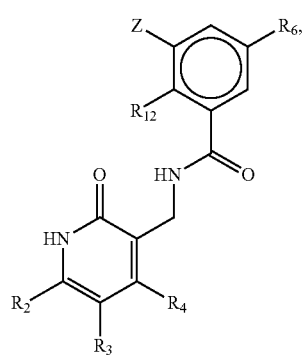

-continued (Ig)

(II)

(IIa)

The compounds of Formula (I), (Ia), (Ib), (Ic), (Id), (Ie), (Ig), (II) or (IIa) can include one or more of the following features:

$X_1$ is $CR_{11}$ and $X_2$ is $CR_{13}$.
$X_1$ is $CR_{11}$ and $X_2$ is N.
$X_1$ is N and $X_2$ is $CR_{13}$.
$X_1$ is N and $X_2$ is N.
Z is $NR_7R_8$.
Z is $CR_7R_8R_{14}$.
Z is $OR_7$.
Z is $S(O)_nR_7$, in which n is 0, 1, or 2.
$R_6$ is unsubstituted $C_6$-$C_{10}$ aryl or unsubstituted 5- or 6-membered heteroaryl.
$R_6$ is $C_6$-$C_{10}$ aryl substituted with one or more -$Q_2$-$T_2$ or 5- or 6-membered heteroaryl substituted with one or more -$Q_2$-$T_2$.
$R_6$ is phenyl substituted with one or more -$Q_2$-$T_2$.
$R_6$ is 5- or 6-membered heteroaryl containing 1-3 additional heteroatoms selected from N, O, and S and optionally substituted with one or more -$Q_2$-$T_2$.
$R_6$ is quinolinyl, tetrazolyl, oxazolyl, isoxazolyl, thiazolyl, isothiazolyl, furyl, or thienyl, each of which is optionally substituted with one or more -$Q_2$-$T_2$.

$T_2$ is $C_1$-$C_6$ alkyl, $C_6$-$C_{10}$ aryl, halo, —$OR_a$, —$NR_aR_b$, —$(NR_aR_bR_c)^+A^-$, —$C(O)R_a$, —$C(O)OR_a$, —$C(O)NR_aR_b$, —$NR_bC(O)R_a$, —$NR_bC(O)OR_a$, —$S(O)_2R_a$, or —$S(O)_2NR_aR_b$.
$T_2$ is —$NR_aR_b$, in which each of $R_a$ and $R_b$, independently is H or $C_1$-$C_6$ alkyl, or $R_a$ and $R_b$, together with the N atom to which they are attached, form a 4 to 7-membered heterocycloalkyl ring having 0 or 1 additional heteroatom, the $C_1$-$C_6$ alkyl and the 4 to 12-membered (e.g., 4 to 7-membered) heterocycloalkyl ring being optionally substituted with one or more -$Q_3$-$T_3$.
$Q_2$ is $C_1$-$C_3$ alkyl linker optionally substituted with halo or hydroxyl.
$Q_2$ is a bond or methyl or ethyl linker and $T_2$ is H, halo, —$OR_a$, —$NR_aR_b$, —$(NR_aR_bR_c)^+A^-$, or —$S(O)_2NR_aR_b$.
$R_7$ is not H.
$R_7$ is $C_1$-$C_6$ alkyl, $C_3$-$C_8$ cycloalkyl or 4 to 12-membered (e.g., 4 to 7-membered) heterocycloalkyl, each optionally substituted with one or more -$Q_5$-$T_5$.
$R_7$ is 4 to 7-membered heterocycloalkyl optionally substituted with one or more -$Q_5$-$T_5$.
$R_7$ is piperidinyl, tetrahydropyran, cyclopentyl, or cyclohexyl, each optionally substituted with one -$Q_5$-$T_5$.
$T_5$ is H, halo, $C_1$-$C_6$ alkyl, $C_1$-$C_6$ alkoxyl, $C_3$-$C_8$ cycloalkyl, $C_6$-$C_{10}$ aryl, or 4 to 12-membered (e.g., 4 to 7-membered) heterocycloalkyl.
$Q_5$ is a bond and $T_5$ is $C_1$-$C_6$ alkyl, $C_3$-$C_8$ cycloalkyl, or 4 to 12-membered (e.g., 4 to 7-membered) heterocycloalkyl.
$Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 12-membered (e.g., 4 to 7-membered) heterocycloalkyl.
$Q_5$ is $C_1$-$C_3$ alkyl linker and $T_5$ is H or $C_6$-$C_{10}$ aryl.
$Q_5$ is $C_1$-$C_3$ alkyl linker and $T_5$ is $C_3$-$C_8$ cycloalkyl, 4 to 7-membered heterocycloalkyl, or $S(O)_qR_q$.
$R_{11}$ is H.
$R_7$ is cyclopentyl or cyclohexyl, each optionally substituted with one -$Q_5$-$T_5$.
$Q_5$ is NHC(O) and $T_5$ is $C_1$-$C_6$ alkyl or $C_1$-$C_6$ alkoxy.
$R_7$ is isopropyl.
Each of $R_2$ and $R_4$, independently is H or $C_1$-$C_6$ alkyl optionally substituted with amino, mono-$C_1$-$C_6$ alkylamino, di-$C_1$-$C_6$ alkylamino, or $C_6$-$C_{10}$ aryl.
Each of $R_2$ and $R_4$ is methyl.
$R_1$ is H.
$R_{12}$ is H, methyl, ethyl, ethenyl, or halo.
$R_{12}$ is methyl.
$R_{12}$ is ethyl.
$R_{12}$ is ethenyl.
$R_8$ is H, methyl, or ethyl.
$R_8$ is methyl.
$R_8$ is ethyl.
$R_8$ is 4 to 7-heterocycloalkyl, e.g., tetrahydropyran.
Z is $NR_7R_8$ or $CR_7R_8R_{14}$ wherein $R_7$ and $R_8$, together with the atom to which they are attached, form a ring selected from the group consisting of piperidinyl, morpholinyl, piperazinyl, and cyclohexenyl, each optionally substituted with one -$Q_6$-$T_6$.
$R_{13}$ is H or methyl.
$R_{13}$ is H.
$R_3$ is H.
$A^-$ is $Br^-$ or $Cl^-$.

The present invention also provides pharmaceutical compositions comprising one or more pharmaceutically acceptable carriers and one or more compounds selected from those of any Formula disclosed herein.

Another aspect of this invention is a method of treating or preventing cancer. The method includes administering to a subject in need thereof a therapeutically effective amount of one or more compounds selected from those of any Formula disclosed herein.

Unless otherwise stated, any description of a method of treatment includes uses of the compounds to provide such treatment or prophylaxis as is described in the specification, as well as uses of the compounds to prepare a medicament to treat or prevent such condition. The treatment includes treatment of human or non-human animals including rodents and other disease models.

For example, the method comprises the step of administering to a subject having a cancer with aberrant H3-K27 methylation an effective amount of one or more compounds of any of the Formulae disclosed herein, wherein the compound(s) inhibits histone methyltransferase activity of EZH2, thereby treating the cancer. Examples of aberrant H3-K27 methylation may include a global increase in and/or altered distribution of H3-K27 di or tri-methylation within the cancer cell chromatin.

For example, the cancer is selected from the group consisting of cancers that overexpress EZH2 or other PRC2 subunits, contain loss-of-function mutations in H3-K27 demethylases such as UTX, or overexpress accessory proteins such as PHF19/PCL3 capable of increasing and or mislocalizing EZH2 activity (see references in Sneeringer et al. *Proc Natl Acad Sci USA* 107(49):20980-5, 2010).

For example, the method comprises the step of administering to a subject having a cancer overexpressing EZH2 a therapeutically effective amount of one or more compounds of any of the Formulae disclosed herein, wherein the compound(s) inhibits histone methyltransferase activity of EZH2, thereby treating the cancer.

For example, the method comprises the step of administering to a subject having a cancer with a loss-of-function mutation in the H3-K27 demethylase UTX a therapeutically effective amount of one or more compounds of any Formula disclosed herein, wherein the compound(s) inhibits histone methyltransferase activity of EZH2, thereby treating the cancer.

For example, the method comprises the step of administering to a subject having a cancer overexpressing an accessory component(s) of the PRC2, such as PHF19/PCL3, a therapeutically effective amount of one or more compounds of any Formula disclosed herein, wherein the compound(s) inhibits histone methyltransferase activity of EZH2, thereby treating the cancer.

In still another aspect, this invention relates to a method of modulating the activity of the wild-type EZH2, the catalytic subunit of the PRC2 complex which catalyzes the mono-through tri-methylation of lysine 27 on histone H3 (H3-K27). For example, the present invention relates to a method of inhibiting the activity of EZH2 in a cell. This method can be conducted either in vitro or in vivo.

In yet another aspect, this invention features to a method of inhibiting in a subject conversion of H3-K27 to trimethylated H3-K27. The method comprises administering to a subject a therapeutically effective amount of one or more of the compound of any of the Formulae disclosed herein to inhibit histone methyltransferase activity of EZH2, thereby inhibiting conversion of H3-K27 to trimethylated H3-K27 in the subject.

For example, the method comprises the step of administering to a subject having a cancer expressing a Y641 mutant of EZH2 a therapeutically effective amount of one or more compounds of any Formula disclosed herein, wherein the compound(s) inhibits histone methyltransferase activity of EZH2, thereby treating the cancer.

For example, the cancer is selected from the group consisting of follicular lymphoma and diffuse large B-cell lymphoma (DLBCL) of germinal center B cell-like (GCB) subtype. For example, the cancer is lymphoma, leukemia or melanoma. Preferably, the lymphoma is non-Hodgkin lymphoma, follicular lymphoma or diffuse large B-cell lymphoma. Alternatively, the leukemia is chronic myelogenous leukemia (CML), acute myeloid leukemia, acute lymphocytic leukemia or mixed lineage leukemia.

The precancerous condition is myelodysplastic syndromes (MDS, formerly known as preleukemia).

For example, the cancer is a hematological cancer.

For example, the method comprises the step of administering to a subject having a cancer expressing a Y641 mutant of EZH2 a therapeutically effective amount of one or more compounds of any Formulae disclosed herein, wherein the compound(s) selectively inhibits histone methyltransferase activity of the Y641 mutant of EZH2, thereby treating the cancer.

For example, the method further comprises the steps of performing an assay to detect a Y641 mutant of EZH2 in a sample comprising cancer cells from a subject having a cancer.

In still another aspect, this invention relates to a method of modulating the activity of the wild-type and mutant histone methyltransferase EZH2, the catalytic subunit of the PRC2 complex which catalyzes the mono- through tri-methylation of lysine 27 on histone H3 (H3-K27). For example, the present invention relates to a method of inhibiting the activity of certain mutant forms of EZH2 in a cell. The mutant forms of EZH2 include a substitution of another amino acid residue for tyrosine 641 (Y641, also Tyr641) of wild-type EZH2. The method includes contacting the cell with an effective amount of one or more of the compound of any of Formulae disclosed herein. This method can be conducted either in vitro or in vivo.

In yet another aspect, this invention features to a method of inhibiting in a subject conversion of H3-K27 to trimethylated H3-K27. The method comprises administering to a subject expressing a Y641 mutant of EZH2 a therapeutically effective amount of one or more of the compound of any of Formulae disclosed herein to inhibit histone methyltransferase activity of EZH2, thereby inhibiting conversion of H3-K27 to trimethylated H3-K27 in the subject. For example, the histone methyltransferase activity inhibited is that of the Y641 mutant of EZH2. For example, the compound of this invention selectively inhibits histone methyltransferase activity of the Y641 mutant of EZH2. For example, the Y641 mutant of EZH2 is selected from the group consisting of Y641C, Y641F, Y641H, Y641N, and Y641S.

The method of inhibiting in a subject conversion of H3-K27 to trimethylated H3-K27 may also comprise performing an assay to detect a Y641 mutant of EZH2 in a sample from a subject before administering to the subject expressing a Y641 mutant of EZH2 a therapeutically effective amount of one or more of the compound of any of Formulae disclosed herein. For example, performing the assay to detect the Y641 mutant of EZH2 includes whole-genome resequencing or target region resequencing that detects a nucleic acid encoding the Y641 mutant of EZH2. For example, performing the assay to detect the Y641 mutant of EZH2 includes contacting the sample with an antibody that binds specifically to a polypeptide or fragment thereof characteristic of the Y641 mutant of EZH2. For example, performing the assay to detect the Y641 mutant of EZH2 includes contacting the sample under highly stringent conditions with a nucleic acid probe that hybridizes to a nucleic acid encoding a polypeptide or fragment thereof characteristic of the Y641 mutant of EZH2.

Further, the invention also relates to a method of identifying an inhibitor of a Y641 mutant of EZH2. The method comprises the steps of combining an isolated Y641 mutant of EZH2 with a histone substrate, a methyl group donor, and a test compound, wherein the histone substrate comprises a form of H3-K27 selected from the group consisting of unmethylated H3-K27, monomethylated H3-K27, dimethylated H3-K27, and any combination thereof; and performing an assay to detect methylation of H3-K27 (e.g., formation of trimethylated H3-K27) in the histone substrate, thereby identifying the test compound as an inhibitor of the Y641 mutant of EZH2 when methylation of H3-K27 (e.g., formation of trimethylated H3-K27) in the presence of the test compound is less than methylation of H3-K27 (e.g., formation of trimethylated H3-K27) in the absence of the test compound.

In one embodiment, performing the assay to detect methylation of H3-K27 in the histone substrate comprises measuring incorporation of labeled methyl groups.

In one embodiment, the labeled methyl groups are isotopically labeled methyl groups.

In one embodiment, performing the assay to detect methylation of H3-K27 in the histone substrate comprises contacting the histone substrate with an antibody that binds specifically to trimethylated H3-K27.

Also within the scope of the invention is a method of identifying a selective inhibitor of a Y641 mutant of EZH2. The method comprises the steps of combining an isolated Y641 mutant of EZH2 with a histone substrate, a methyl group donor, and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a test mixture; combining an isolated wild-type EZH2 with a histone substrate, a methyl group donor, and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a control mixture; performing an assay to detect trimethylation of the histone substrate in each of the test mixture and the control mixture; calculating the ratio of (a) trimethylation with the Y641 mutant of EZH2 and the test compound (M+) to (b) trimethylation with the Y641 mutant of EZH2 without the test compound (M−); calculating the ratio of (c) trimethylation with wild-type EZH2 and the test compound (WT+) to (d) trimethylation with wild-type EZH2 without the test compound (WT−); comparing the ratio (a)/(b) with the ratio (c)/(d); and identifying the test compound as a selective inhibitor of the Y641 mutant of EZH2 when the ratio (a)/(b) is less than the ratio (c)/(d).

The present invention further provides a method of identifying a subject as a candidate for treatment with one or more compounds of the invention. The method comprises the steps of performing an assay to detect a Y641 mutant of EZH2 in a sample from a subject; and identifying a subject expressing a Y641 mutant of EZH2 as a candidate for treatment with one or more compounds of the invention, wherein the compound(s) inhibits histone methyltransferase activity of EZH2.

Still another aspect of the invention is a method of inhibiting conversion of H3-K27 to trimethylated H3-K27. The method comprises the step of contacting a Y641 mutant of EZH2 with a histone substrate comprising H3-K27 and an effective amount of a compound of the present invention, wherein the compound inhibits histone methyltransferase activity of EZH2, thereby inhibiting conversion of H3-K27 to trimethylated H3-K27.

Further, the compounds or methods described herein can be used for research (e.g., studying epigenetic enzymes) and other non-therapeutic purposes.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTIONS OF FIGURES

FIG. 1(B) is an idealized plot of ln(cell count) as a function of time for the data from panel (A).

Figure 2:
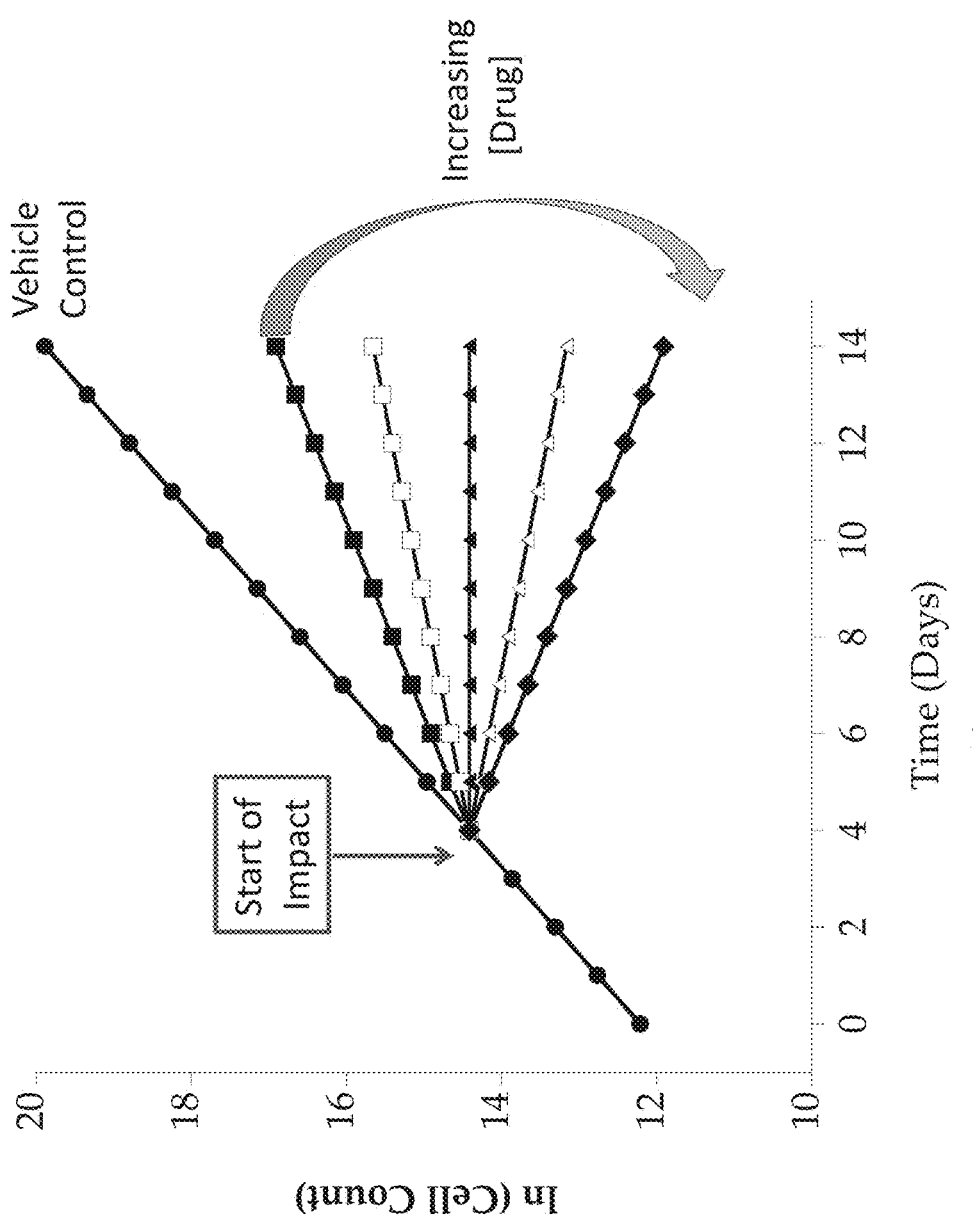

FIG. 2 is a graph showing biphasic cell growth curves in the presence of an antiproliferative compound for which there is a delay before the impact of the compound on cell growth is realized. The compound begins to affect cell growth at the time point labeled "start of impact." The solid circles represent idealized data for the vehicle (or solvent) control sample that is not treated with compound. The other symbols represent biphasic growth curves for cells treated with different concentrations of compound (i.e., drug).

Figure 3:
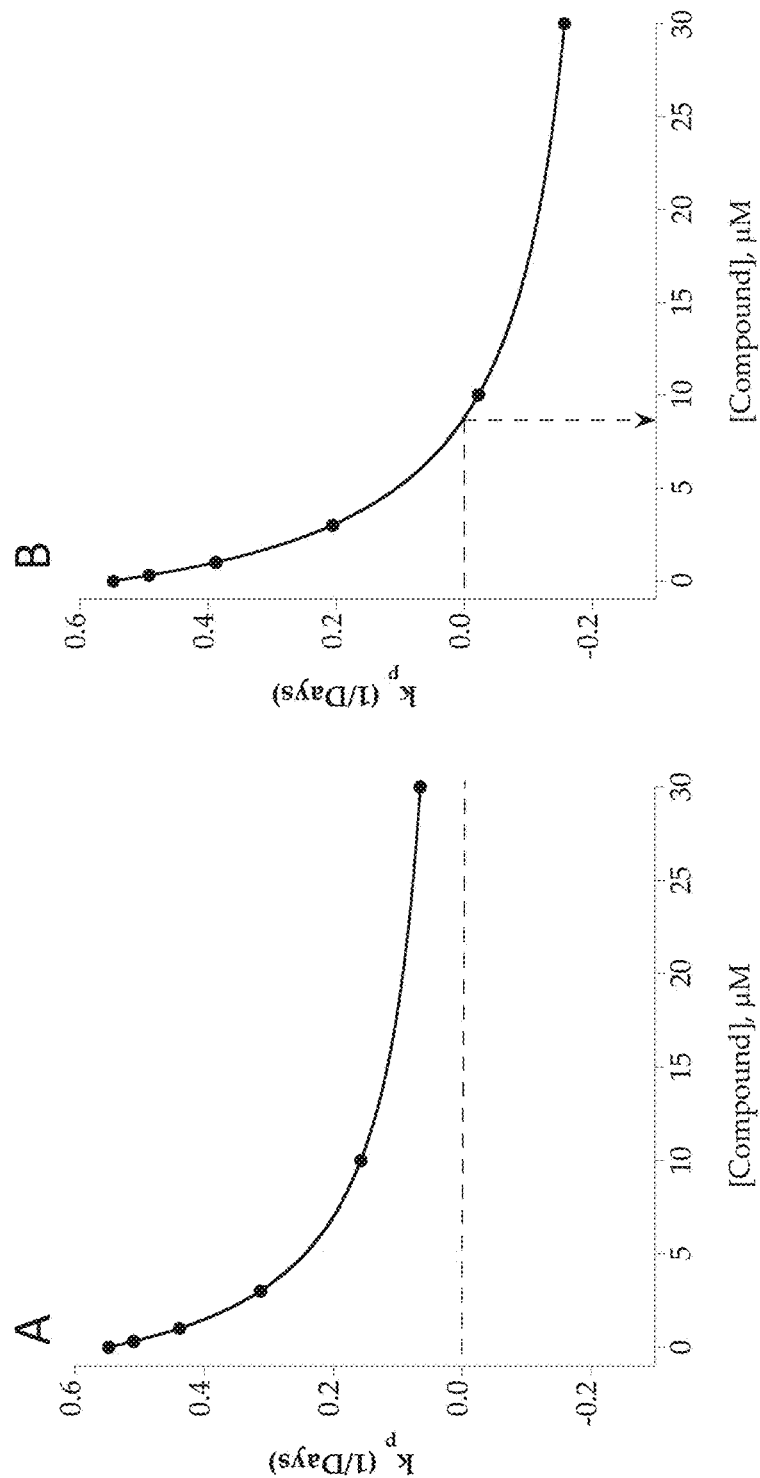

FIG. 3 is a replot of $k_p$ as a function of compound concentration for (A) a cytostatic and (B) a cytotoxic compound, illustrating the graphic determination of the LCC for a cytotoxic agent. Note that for a cytostatic compound (panel A), the value of $k_p$ can never drop below zero.

Figure 4:
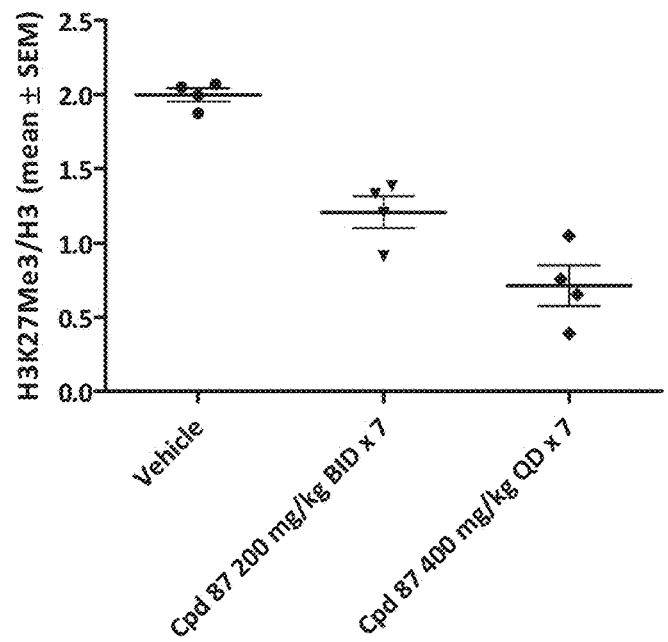

FIG. 4 is a diagram showing global H3K27me3 methylation in WSU-DLCL2 tumors from mice treated with Compound 87 for 7 days.

Figure 5:
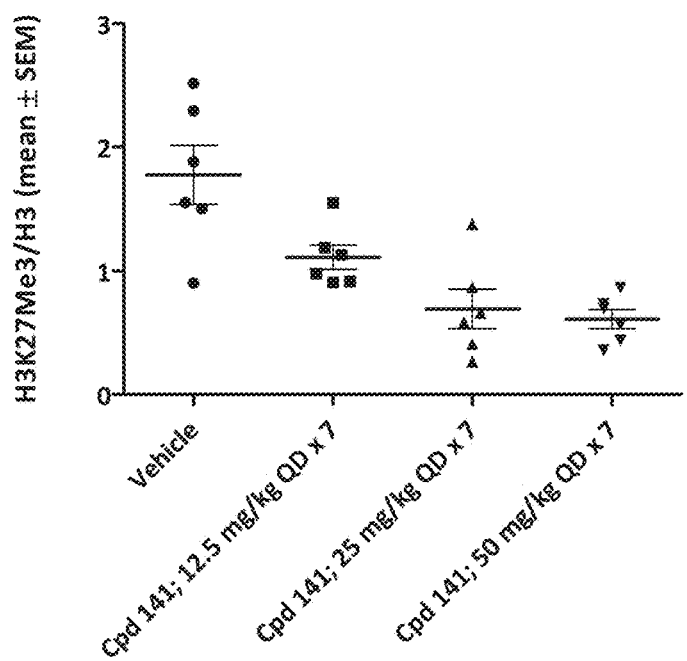

FIG. 5 is a diagram showing global H3K27me3 methylation in WSU-DLCL2 tumors from mice treated with Compound 141 for 7 days.

Figure 6:
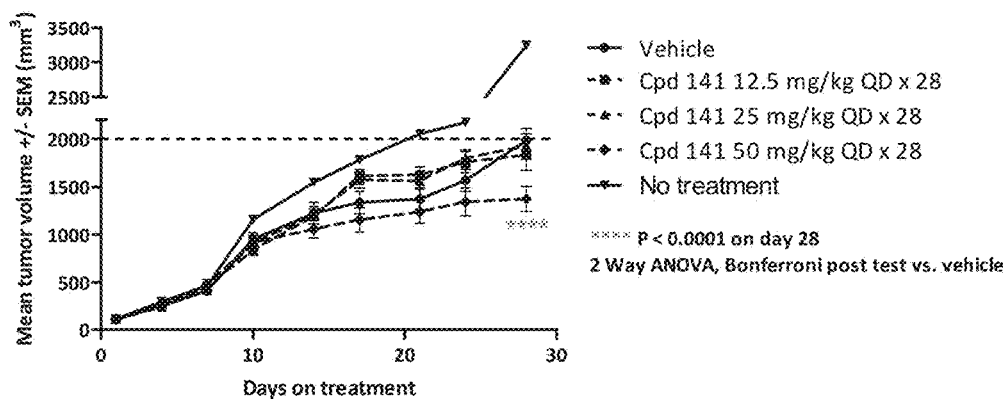

FIG. 6 is a diagram showing tumor growth of WSU-DLCL2 xenograft bearing mice over the treatment course of 28 days treated with vehicle or Compound 141.

Figure 7:
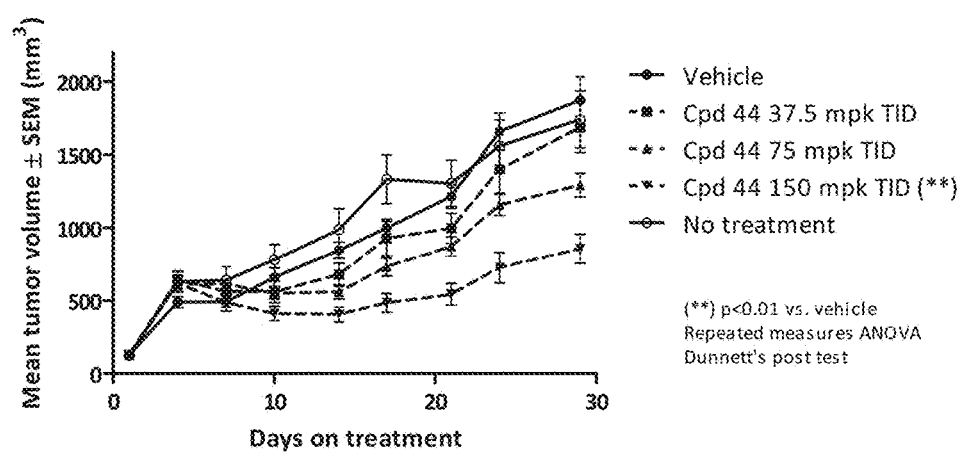

FIG. 7 is a diagram showing tumor growth of WSU-DLCL2 xenograft bearing mice treated with Compound 44.

Figure 8:
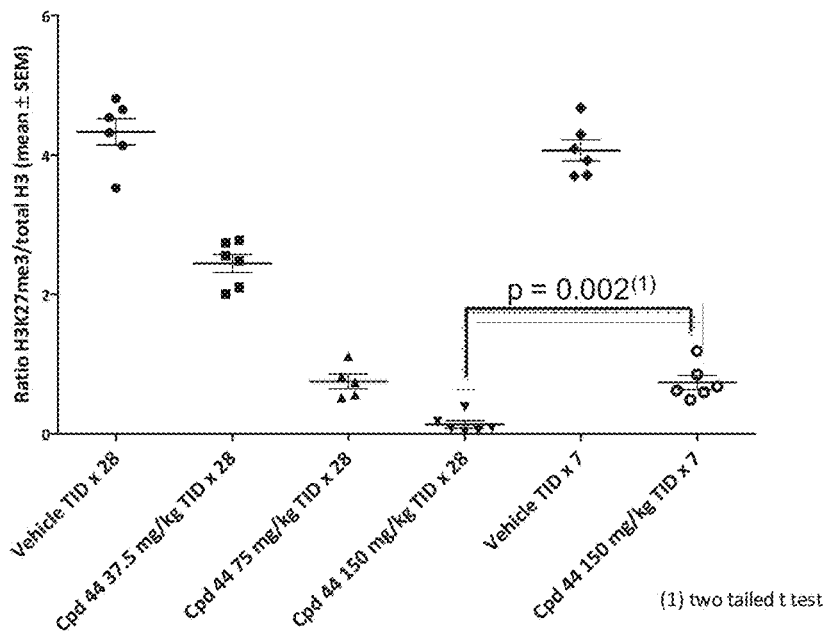

FIG. 8 is a diagram showing global H3K27me3 methylation in WSU-DLCL2 tumors from mice treated with Compound 44 for 28 and 7 days.

Figure 9:
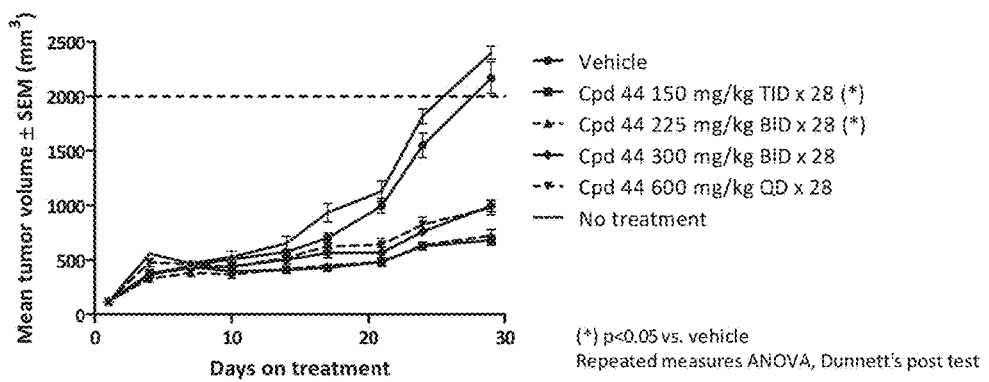

FIG. 9 is a diagram showing tumor growth of WSU-DLCL2 xenograft bearing mice with Compound 44 treatment at different dosing schedules.

Figure 10:
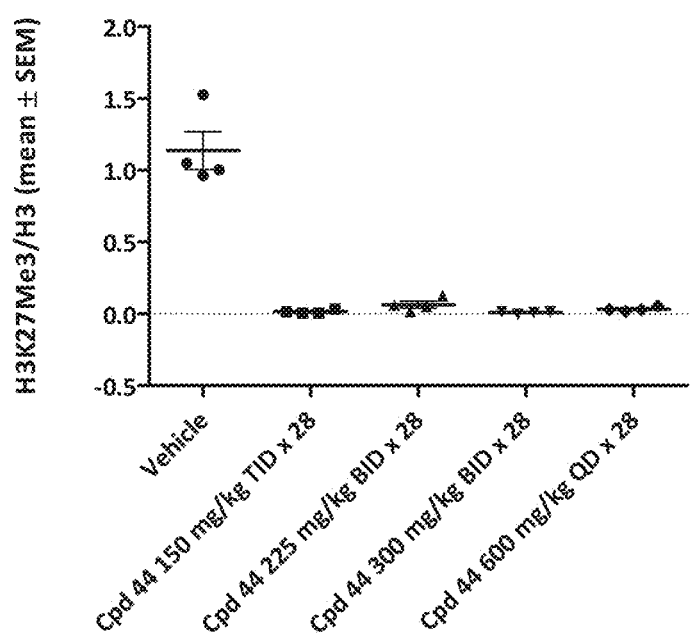

FIG. 10 is a diagram showing global H3K27me3 methylation in WSU-DLCL2 tumors from mice treated with Compound 44 at different dosing schedules for 28 days.

Figure 11:
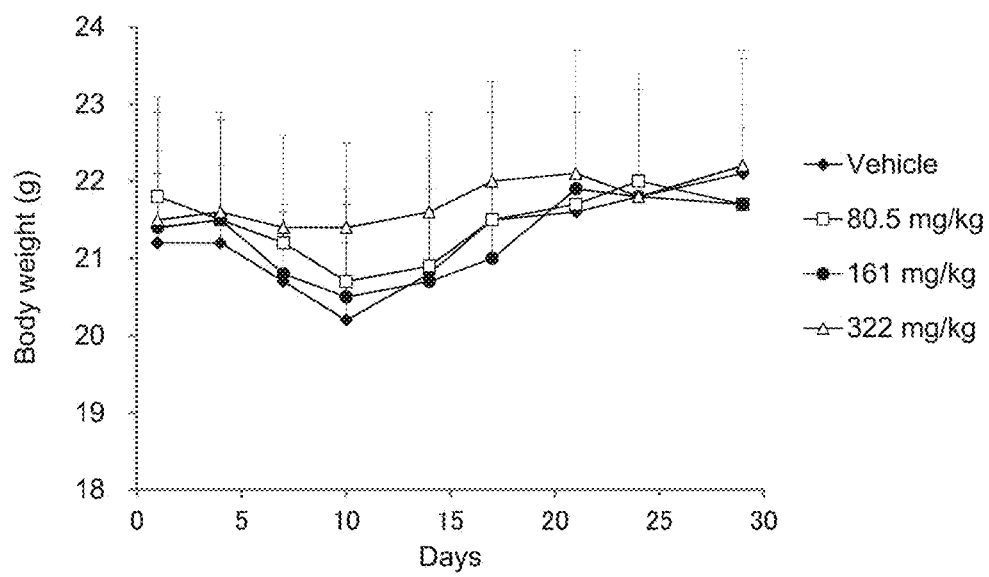

FIG. 11 is a diagram showing effect of Compound 44 on mouse body weight. Data represent the mean+SD (n=9). Dosages which resulted in mortalities are not plotted.

Figure 12:
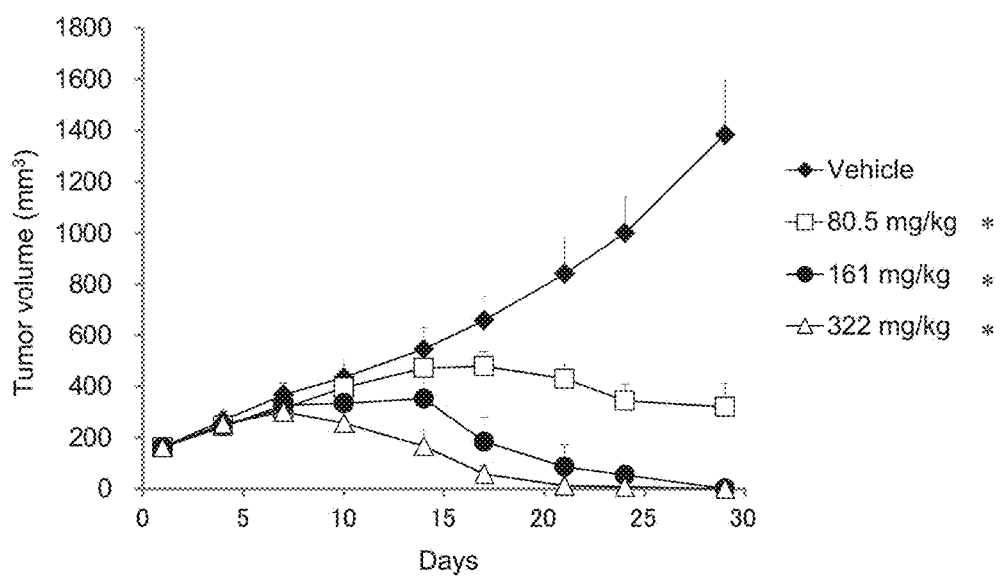

FIG. 12 is a diagram showing antitumor effects of orally administered Compound 44 against a diffuse large B cell lymphoma KARPAS-422 xenograft in mice. Data represent the mean+SD (n=9). * P<0.05 versus vehicle control on day 29 (repeated measures ANOVA followed by Dunnett-type multiple comparison test). Dosages which resulted in mortalities are not plotted.

DETAILED DESCRIPTION OF THE INVENTION

The present invention provides novel aryl- or heteroaryl-substituted benzene compounds, synthetic methods for making the compounds, pharmaceutical compositions containing them and various uses of the compounds.

1. ARYL- OR HETEROARYL-SUBSTITUTED BENZENE COMPOUNDS

The present invention provides the compounds of Formula (I):

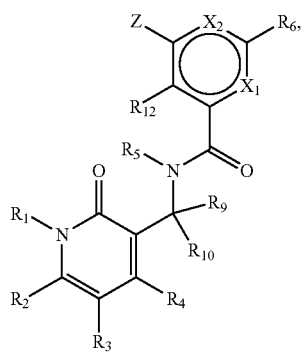

(I)

or a pharmaceutically acceptable salt or ester thereof. In this formula:

$X_1$ is N or $CR_{11}$;

$X_2$ is N or $CR_{13}$;

Z is $NR_7R_8$, $OR_7$, $S(O)_nR_7$, or $CR_7R_8R_{14}$, in which n is 0, 1, or 2;

each of $R_1$, $R_5$, $R_9$, and $R_{10}$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

each of $R_2$, $R_3$, and $R_4$, independently, is -$Q_1$-$T_1$, in which $Q_1$ is a bond or $C_1$-$C_3$ alkyl linker optionally substituted with halo, cyano, hydroxyl or $C_1$-$C_6$ alkoxy, and $T_1$ is H, halo, hydroxyl, COOH, cyano, or $R_{S1}$, in which $R_{S1}$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, amino, mono-$C_1$-$C_6$ alkylamino, di-$C_1$-$C_6$ alkylamino, 4 to 12-membered heterocycloalkyl, or 5- or 6-membered heteroaryl, and $R_{S1}$ is optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_6$ is $C_6$-$C_{10}$ aryl or 5- or 6-membered heteroaryl, each of which is optionally substituted with one or more -$Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is H, halo, cyano, —$OR_a$, —$NR_aR_b$, —$(NR_aR_bR_c)^+A^-$, —$C(O)R_a$, —$C(O)OR_a$, —$C(O)NR_aR_b$, —$NR_bC(O)R_a$, —$NR_bC(O)OR_a$, —$S(O)_2R_a$, —$S(O)_2NR_aR_b$, or $R_{S2}$, in which each of $R_a$, $R_b$, and $R_c$, independently is H or $R_{S3}$, $A^-$ is a pharmaceutically acceptable anion, each of $R_{S2}$ and $R_{S3}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_a$ and $R_b$, together with the N atom to which they are attached, form a 4 to 12-membered heterocycloalkyl ring having 0 or 1 additional heteroatom, and each of $R_{S2}$, $R_{S3}$, and the 4 to 12-membered heterocycloalkyl ring formed by $R_a$ and $R_b$, is optionally substituted with one or more one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_d$, $COOR_d$, —$S(O)_2R_d$, —$NR_dR_e$, and —$C(O)NR_dR_e$, each of $R_d$ and $R_e$ independently being H or $C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, —$OR_f$, —$C(O)R_f$, —$C(O)OR_f$, —$C(O)NR_fR_g$, —$C(O)NR_fOR_g$, —$NR_fC(O)R_g$, —$S(O)_2R_f$, or $R_{S4}$, in which each of $R_f$ and $R_g$, independently is H or $R_{S5}$, each of $R_{S4}$ and $R_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and each of $R_{S4}$ and $R_{S5}$ is optionally substituted with one or more -$Q_5$-$T_5$, wherein $Q_5$ is a bond, C(O), C(O)$NR_k$, $NR_kC(O)$, $S(O)_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo;

each of $R_8$, $R_{11}$, $R_{12}$, and $R_{13}$, independently, is H, halo, hydroxyl, COOH, cyano, $R_{S6}$, $OR_{S6}$, or $COOR_{S6}$, in which $R_{S6}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 11-membered heterocycloalkyl ring having 0 to 2 additional heteroatoms, or $R_7$ and $R_8$, together with the C atom to which they are attached, form $C_3$-$C_8$ cycloalkyl or a 4 to 11-membered heterocycloalkyl ring having 1 to 3 heteroatoms, and each of the 4 to 11-membered heterocycloalkyl rings or $C_3$-$C_8$ cycloalkyl formed by $R_7$ and $R_8$ is optionally substituted with one or more -$Q_6$-$T_6$, wherein $Q_6$ is a bond, C(O), C(O)$NR_m$, $NR_m$C(O), $S(O)_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo; and $R_{14}$ is absent, H, or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, $X_1$ is $CR_{11}$ and $X_2$ is $CR_{13}$.

For example, $X_1$ is $CR_{11}$ and $X_2$ is N.

For example, $X_1$ is N and $X_2$ is $CR_{13}$.

For example, $X_1$ is N and $X_2$ is N.

For example, Z is $NR_7R_8$.

For example, Z is $CR_7R_8R_{14}$.

For example, Z is $OR_7$.

For example, Z is $S(O)_nR_7$, in which n is 0, 1, or 2.

For example, Z is $SR_7$.

For example, $R_6$ is unsubstituted $C_6$-$C_{10}$ aryl or unsubstituted 5- or 6-membered heteroaryl.

For example, $R_6$ is $C_6$-$C_{10}$ aryl substituted with one or more -$Q_2$-$T_2$ or 5- or 6-membered heteroaryl substituted with one or more -$Q_2$-$T_2$.

For example, $R_6$ is unsubstituted phenyl.

For example, $R_6$ is phenyl substituted with one or more -$Q_2$-$T_2$.

For example, $R_6$ is 5 to 6-membered heteroaryl containing 1-3 additional heteroatoms selected from N, O, and S and optionally substituted with one or more -$Q_2$-$T_2$.

For example, $R_6$ is pyridinyl, pyrazolyl, pyrimidinyl, quinolinyl, tetrazolyl, oxazolyl, isoxazolyl, thiazolyl, isothiazolyl, furyl, or thienyl, each of which is optionally substituted with one or more -$Q_2$-$T_2$.

For example, $Q_2$ is a bond.

For example, $Q_2$ is an unsubstituted $C_1$-$C_3$ alkyl linker.

For example, $T_2$ is $C_1$-$C_6$ alkyl or $C_6$-$C_{10}$ aryl, each optionally substituted with one or more -$Q_3$-$T_3$.

For example, $T_2$ is an unsubstituted substituted straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, $T_2$ is phenyl.

For example, $T_2$ is halo (e.g., fluorine, chlorine, bromine, and iodine).

For example, $T_2$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahydrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and the like) optionally substituted with one or more -$Q_3$-$T_3$.

For example, $T_2$ is —$OR_a$, —$NR_aR_b$, —$(NR_aR_bR_c)^+A^-$, —$C(O)R_a$, —$C(O)OR_a$, —$C(O)NR_aR_b$, —$NR_bC(O)R_a$, —$NR_bC(O)OR_a$, —$S(O)_2R_a$, or —$S(O)_2NR_aR_b$.

For example, $T_2$ is —$NR_aR_b$ or —$C(O)NR_aR_b$, in which each of $R_a$ and $R_b$, independently is H or $C_1$-$C_6$ alkyl, or $R_a$ and $R_b$, together with the N atom to which they are attached, form a 4 to 7-membered heterocycloalkyl ring having 0 or 1 additional heteroatom, the $C_1$-$C_6$ alkyl and the 4 to 7-membered heterocycloalkyl ring being optionally substituted with one or more -$Q_3$-$T_3$.

For example, $Q_2$ is $C_1$-$C_3$ alkyl linker optionally substituted with halo or hydroxyl.

For example, $Q_2$ is a bond or methyl linker and $T_2$ is H, halo, —$OR_a$, —$NR_aR_b$, —$(NR_aR_bR_c)^+A^-$, or —$S(O)_2NR_aR_b$.

For example, each of $R_a$, $R_b$, and $R_e$, independently is H or $C_1$-$C_6$ alkyl optionally substituted with one or more -$Q_3$-$T_3$.

For example, one of $R_a$, $R_b$, and $R_c$ is H.

For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and the like) and the ring is optionally substituted with one or more -$Q_3$-$T_3$.

For example, -$Q_3$-$T_3$ is oxo.

For example, $T_2$ is 4 to 7-membered heterocycloalkyl or $C_3$-$C_8$ cycloalkyl and one or more -$Q_3$-$T_3$ are oxo.

For example, $Q_3$ is a bond or unsubstituted or substituted $C_1$-$C_3$ alkyl linker.

For example, $T_3$ is H, halo, 4 to 7-membered heterocycloalkyl, $C_1$-$C_3$ alkyl, $OR_d$, $COOR_d$, —$S(O)_2R_d$, or —$NR_dR_e$.

For example, one of $R_d$ and $R_e$ is H.

For example, $R_7$ is not H.

For example, $R_7$ is —$C(O)R_f$.

For example, $R_7$ is —$C(O)R_f$, in which $R_f$ is $C_3$-$C_8$ cycloalkyl.

For example, $R_7$ is $C_6$-$C_{10}$ aryl substituted with one or more -$Q_5$-$T_5$.

For example, $R_7$ is phenyl optionally substituted with one or more $-Q_5-T_5$.

For example, $R_7$ is $C_1-C_6$ alkyl optionally substituted with one or more $-Q_5-T_5$.

For example, $R_7$ is $C_3-C_8$ cycloalkyl optionally substituted with one or more $-Q_5-T_5$.

For example, $R_7$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, and morpholinyl, and the like) optionally substituted with one or more $-Q_5-T_5$.

For example, $R_7$ is 5 to 6-membered heterocycloalkyl optionally substituted with one or more $-Q_5-T_5$.

For example, $R_7$ is isopropyl.

For example, $R_7$ is pyrrolidinyl, piperidinyl, tetrahydropyran, cyclopentyl, cyclohexyl, or cycloheptyl, each optionally substituted with one $-Q_5-T_5$.

For example, $R_7$ is cyclopentyl or cyclohexyl, each optionally substituted with one $-Q_5-T_5$.

For example, $R_7$ is pyrrolidinyl, piperidinyl, tetrahydropyran, tetrahydro-2H-thiopyranyl, cyclopentyl, cyclohexyl, or cycloheptyl, each optionally substituted with one or more $-Q_5-T_5$.

For example, $R_7$ is cyclopentyl, cyclohexyl or tetrahydro-2H-thiopyranyl, each optionally substituted with one or more $-Q_5-T_5$.

For example, one or more $-Q_5-T_5$ are oxo.

For example, $R_7$ is 1-oxide-tetrahydro-2H-thiopyranyl or 1,1-dioxide-tetrahydro-2H-thiopyranyl.

For example, $Q_5$ is a bond and $T_5$ is amino, mono-$C_1-C_6$ alkylamino, or di-$C_1-C_6$ alkylamino.

For example, $Q_5$ is NHC(O) and $T_5$ is $C_1-C_6$ alkyl or $C_1-C_6$ alkoxy.

For example, $-Q_5-T_5$ is oxo.

For example, $T_4$ is 4 to 7-membered heterocycloalkyl or $C_3-C_8$ cycloalkyl and one or more $-Q_5-T_5$ are oxo.

For example, $T_5$ is H, halo, $C_1-C_6$ alkyl, $C_1-C_6$ alkoxyl, $C_3-C_8$ cycloalkyl, $C_6-C_{10}$ aryl, or 4 to 7-membered heterocycloalkyl.

For example, $Q_5$ is a bond and $T_5$ is $C_1-C_6$ alkyl, $C_3-C_8$ cycloalkyl, or 4 to 7-membered heterocycloalkyl.

For example, $Q_5$ is CO, $S(O)_2$, or NHC(O); and $T_5$ is $C_1-C_6$ alkyl, $C_1-C_6$ alkoxyl, $C_3-C_8$ cycloalkyl, or 4 to 7-membered heterocycloalkyl.

For example, $T_5$ is $C_1-C_6$ alkyl or $C_1-C_6$ alkoxyl, each optionally substituted with halo, hydroxyl, cyano, $C_1-C_6$ alkoxyl, amino, mono-$C_1-C_6$ alkylamino, di-$C_1-C_6$ alkylamino, or $C_3-C_8$ cycloalkyl.

For example, $Q_5$ is $C_1-C_3$ alkyl linker and $T_5$ is H or $C_6-C_{10}$ aryl.

For example, $Q_5$ is $C_1-C_3$ alkyl linker and $T_5$ is $C_3-C_8$ cycloalkyl, 4 to 7-membered heterocycloalkyl, or $S(O)_qR_q$.

For example, $R_{11}$ is H.

For example, each of $R_2$ and $R_4$, independently, is H or $C_1-C_6$ alkyl optionally substituted with amino, mono-$C_1-C_6$ alkylamino, di-$C_1-C_6$ alkylamino, or $C_6-C_{10}$ aryl.

For example, each of $R_2$ and $R_4$, independently is $C_1-C_3$ alkyl optionally substituted with $C_1-C_6$ alkoxyl.

For example, each of $R_2$ and $R_4$ is methyl.

For example, $R_1$ is H.

For example, $R_{12}$ is H, methyl, ethyl, ethenyl, or halo.

For example, $R_{12}$ is methyl.

For example, $R_{12}$ is ethyl.

For example, $R_{12}$ is ethenyl.

For example, $R_8$ is H, methyl, ethyl, or ethenyl.

For example, $R_8$ is methyl.

For example, $R_8$ is ethyl.

For example, $R_8$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and the like).

For example, $R_8$ is tetrahydropyran.

For example, $R_8$ is tetrahydropyran and $R_7$ is $-Q_4-T_4$, in which $Q_4$ is a bond or $C_1-C_4$ alkyl linker and $T_4$ is H, $C_1-C_6$ alkyl, $C_3-C_8$ cycloalkyl or 4 to 7-membered heterocycloalkyl.

For example, Z is $NR_7R_8$ or $CR_7R_8R_{14}$ wherein $R_7$ and $R_8$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, and morpholinyl, 1,4-dioxa-8-azaspiro[4.5]decanyl, and the like) or $C_3-C_8$ cycloalkyl, each optionally substituted with one or more $-Q_6-T_6$.

For example, the ring formed by $R_7$ and $R_8$ is selected from the group consisting of azetidinyl, pyrrolidinyl, piperidinyl, morpholinyl, piperazinyl, 1,4-dioxa-8-azaspiro[4.5]decanyl, and cyclohexenyl, each optionally substituted with one $-Q_6-T_6$.

For example, $-Q_6-T_6$ is oxo.

For example, $T_6$ is H, halo, $C_1-C_6$ alkyl, $C_1-C_6$ alkoxyl, $C_3-C_8$ cycloalkyl, $C_6-C_{10}$ aryl, or 4 to 7-membered heterocycloalkyl.

For example, $Q_6$ is a bond and $T_6$ is $C_1-C_6$ alkyl, $C_3-C_8$ cycloalkyl, or 4 to 7-membered heterocycloalkyl.

For example, $Q_6$ is CO, $S(O)_2$, or NHC(O); and $T_6$ is $C_1-C_6$ alkyl, $C_1-C_6$ alkoxyl, $C_3-C_8$ cycloalkyl, or 4 to 7-membered heterocycloalkyl.

For example, $T_6$ is $C_1-C_6$ alkyl or $C_1-C_6$ alkoxyl, each optionally substituted with halo, hydroxyl, cyano, $C_1-C_6$ alkoxyl, amino, mono-$C_1-C_6$ alkylamino, di-$C_1-C_6$ alkylamino, or $C_3-C_8$ cycloalkyl.

For example, $Q_6$ is $C_1-C_3$ alkyl linker and $T_6$ is H or $C_6-C_{10}$ aryl.

For example, $Q_6$ is $C_1-C_3$ alkyl linker and $T_6$ is $C_3-C_8$ cycloalkyl, 4 to 7-membered heterocycloalkyl, or $S(O)_pR_p$.

For example, each of $R_p$ and $R_q$, independently, is $C_1-C_6$ alkyl.

For example, $R_{13}$ is H or methyl.

For example, $R_{13}$ is H.

For example, $R_3$ is H.

For example, $A^-$ is $Br^-$ or $Cl^-$.

For example, each of $R_5$, $R_9$, and $R_{10}$ is H.

The present invention provides the compounds of Formula (Ia)

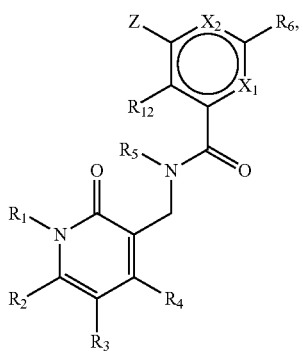

(Ia)

or a pharmaceutically acceptable salt or ester thereof, wherein:

$X_1$ is N or $CR_{11}$;

$X_2$ is N or $CR_{13}$;

Z is $NR_7R_8$, $OR_7$, $S(O)_nR_7$, or $CR_7R_8R_{14}$, in which n is 0, 1, or 2;

each of $R_1$ and $R_5$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

each of $R_2$, $R_3$, and $R_4$, independently, is -$Q_1$-$T_1$, in which $Q_1$ is a bond or $C_1$-$C_3$ alkyl linker optionally substituted with halo, cyano, hydroxyl or $C_1$-$C_6$ alkoxy, and $T_1$ is H, halo, hydroxyl, COOH, cyano, or $R_{S1}$, in which $R_{S1}$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, amino, mono-$C_1$-$C_6$ alkylamino, di-$C_1$-$C_6$ alkylamino, 4 to 12-membered heterocycloalkyl, or 5- or 6-membered heteroaryl, and $R_{S1}$ is optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_6$ is $C_6$-$C_{10}$ aryl or 5- or 6-membered heteroaryl, each of which is optionally substituted with one or more -$Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is H, halo, cyano, —$OR_a$, —$NR_aR_b$, —$(NR_aR_bR_c)^+A^-$, —$C(O)R_a$, —$C(O)OR_a$, —$C(O)NR_aR_b$, —$NR_bC(O)R_a$, —$NR_bC(O)OR_a$, —$S(O)_2R_a$, —$S(O)_2NR_aR_b$, or $R_{S2}$, in which each of $R_a$, $R_b$, and $R_c$, independently is H or $R_{S3}$, $A^-$ is a pharmaceutically acceptable anion, each of $R_{S2}$ and $R_{S3}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_a$ and $R_b$, together with the N atom to which they are attached, form a 4 to 12-membered heterocycloalkyl ring having 0 or 1 additional heteroatom, and each of $R_{S2}$, $R_{S3}$, and the 4 to 12-membered heterocycloalkyl ring formed by $R_a$ and $R_b$, is optionally substituted with one or more one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_d$, $COOR_d$, —$S(O)_2R_d$, —$NR_dR_e$, and —$C(O)NR_dR_e$, each of $R_d$ and $R_e$ independently being H or $C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, —$OR_f$, —$C(O)R_f$, —$C(O)OR_f$, —$C(O)NR_fR_g$, —$C(O)NR_fOR_g$, —$NR_fC(O)R_g$, —$S(O)_2R_f$, or $R_{S4}$, in which each of $R_f$ and $R_g$, independently is H or $R_{S5}$, each of $R_{S4}$ and $R_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and each of $R_{S4}$ and $R_{S5}$ is optionally substituted with one or more -$Q_5$-$T_5$, wherein $Q_5$ is a bond, C(O), C(O)$NR_k$, $NR_kC(O)$, $S(O)_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo;

each of $R_8$, $R_{11}$, $R_{12}$, and $R_{13}$, independently, is H, halo, hydroxyl, COOH, cyano, $R_{S6}$, $OR_{S6}$, or $COOR_{S6}$, in which $R_{S6}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 11-membered heterocycloalkyl ring having 0 to 2 additional heteroatoms, or $R_7$ and $R_8$, together with the C atom to which they are attached, form C3-C8 cycloalkyl or a 4 to 11-membered heterocycloalkyl ring having 1 to 3 heteroatoms, and each of the 4 to 11-membered heterocycloalkyl rings or $C_3$-$C_8$ cycloalkyl formed by $R_7$ and $R_8$ is optionally substituted with one or more -$Q_6$-$T_6$, wherein $Q_6$ is a bond, C(O), C(O)$NR_m$, $NR_mC(O)$, $S(O)_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo; and $R_{14}$ is absent, H, or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl.

For example, $X_2$ is $CR_{13}$.

For example, $X_2$ is N.

For example, Z is $NR_7R_8$.

For example, Z is $CR_7R_8R_{14}$.

For example, Z is $OR_7$.

For example, Z is $S(O)_nR_7$, in which n is 0, 1, or 2.

For example, Z is $SR_7$.

For example, $R_6$ is unsubstituted $C_6$-$C_{10}$ aryl or unsubstituted 5- or 6-membered heteroaryl.

For example, $R_6$ is $C_6$-$C_{10}$ aryl substituted with one or more -$Q_2$-$T_2$ or 5- or 6-membered heteroaryl substituted with one or more -$Q_2$-$T_2$.

For example, $R_6$ is unsubstituted phenyl.

For example, $R_6$ is phenyl substituted with one or more -$Q_2$-$T_2$.

For example, $R_6$ is 5 to 6-membered heteroaryl containing 1-3 additional heteroatoms selected from N, O, and S and optionally substituted with one or more -$Q_2$-$T_2$.

For example, $R_6$ is pyridinyl, pyrazolyl, pyrimidinyl, quinolinyl, tetrazolyl, oxazolyl, isoxazolyl, thiazolyl, isothiazolyl, furyl, or thienyl, each of which is optionally substituted with one or more -$Q_2$-$T_2$.

For example, $Q_2$ is a bond.

For example, $Q_2$ is an unsubstituted $C_1$-$C_3$ alkyl linker.

For example, $T_2$ is $C_1$-$C_6$ alkyl or $C_6$-$C_{10}$ aryl, each optionally substituted with one or more -$Q_3$-$T_3$.

For example, $T_2$ is an unsubstituted substituted straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, $T_2$ is phenyl.

For example, $T_2$ is halo (e.g., fluorine, chlorine, bromine, and iodine).

For example, $T_2$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and the like) optionally substituted with one or more -$Q_3$-$T_3$.

For example, $T_2$ is —$OR_a$, —$NR_aR_b$, —$(NR_aR_bR_c)^+A^-$, —$C(O)R_a$, —$C(O)OR_a$, —$C(O)NR_aR_b$, —$NR_aC(O)R_a$, —$NR_bC(O)OR_a$, —$S(O)_2R_a$, or —$S(O)_2NR_aR_b$.

For example, $T_2$ is —$NR_aR_b$ or —$C(O)NR_aR_b$, in which each of $R_a$ and $R_b$, independently is H or $C_1$-$C_6$ alkyl, or $R_a$ and $R_b$, together with the N atom to which they are attached, form a 4 to 7-membered heterocycloalkyl ring having 0 or 1 additional heteroatom, the $C_1$-$C_6$ alkyl and the 4 to 7-membered heterocycloalkyl ring being optionally substituted with one or more -$Q_3$-$T_3$.

For example, $Q_2$ is $C_1$-$C_3$ alkyl linker optionally substituted with halo or hydroxyl.

For example, $Q_2$ is a bond or methyl linker and $T_2$ is H, halo, —$OR_a$, —$NR_aR_b$, —$(NR_aR_bR_c)^+A^-$, or —$S(O)_2NR_aR_b$.

For example, each of $R_a$, $R_b$, and $R_c$, independently is H or $C_1$-$C_6$ alkyl optionally substituted with one or more -$Q_3$-$T_3$.

For example, one of $R_a$, $R_b$, and $R_c$ is H.

For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and the like) and the ring is optionally substituted with one or more -$Q_3$-$T_3$.

For example, -$Q_3$-$T_3$ is oxo.

For example, $T_2$ is 4 to 7-membered heterocycloalkyl or $C_3$-$C_8$ cycloalkyl and one or more -$Q_3$-$T_3$ are oxo.

For example, $Q_3$ is a bond or unsubstituted or substituted $C_1$-$C_3$ alkyl linker.

For example, $T_3$ is H, halo, 4 to 7-membered heterocycloalkyl, $C_1$-$C_3$ alkyl, $OR_d$, $COOR_d$, —$S(O)_2R_d$, or —$NR_dR_e$.

For example, one of $R_d$ and $R_e$ is H.

For example, $R_7$ is not H.

For example, $R_7$ is —$C(O)R_f$.

For example, $R_7$ is —$C(O)R_f$, in which $R_f$ is $C_3$-$C_8$ cycloalkyl.

For example, $R_7$ is $C_6$-$C_{10}$ aryl substituted with one or more -$Q_5$-$T_5$.

For example, $R_7$ is phenyl optionally substituted with one or more -$Q_5$-$T_5$.

For example, $R_7$ is $C_1$-$C_6$ alkyl optionally substituted with one or more -$Q_5$-$T_5$.

For example, $R_7$ is $C_3$-$C_8$ cycloalkyl optionally substituted with one or more -$Q_5$-$T_5$.

For example, $R_7$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, and morpholinyl, and the like) optionally substituted with one or more -$Q_5$-$T_5$.

For example, $R_7$ is 5 to 6-membered heterocycloalkyl optionally substituted with one or more -$Q_5$-$T_5$.

For example, $R_7$ is isopropyl.

For example, $R_7$ is pyrrolidinyl, piperidinyl, tetrahydropyran, cyclopentyl, cyclohexyl, or cycloheptyl, each optionally substituted with one -$Q_5$-$T_5$.

For example, $R_7$ is cyclopentyl or cyclohexyl, each optionally substituted with one -$Q_5$-$T_5$.

For example, $R_7$ is pyrrolidinyl, piperidinyl, tetrahydropyran, tetrahydro-2H-thiopyranyl, cyclopentyl, cyclohexyl, or cycloheptyl, each optionally substituted with one or more -$Q_5$-$T_5$.

For example, $R_7$ is cyclopentyl, cyclohexyl or tetrahydro-2H-thiopyranyl, each optionally substituted with one or more -$Q_5$-$T_5$.

For example, one or more -$Q_5$-$T_5$ are oxo.

For example, $R_7$ is 1-oxide-tetrahydro-2H-thiopyranyl or 1,1-dioxide-tetrahydro-2H-thiopyranyl.

For example, $Q_5$ is a bond and $T_5$ is amino, mono-$C_1$-$C_6$ alkylamino, or di-$C_1$-$C_6$ alkylamino.

For example, $Q_5$ is NHC(O) and $T_5$ is $C_1$-$C_6$ alkyl or $C_1$-$C_6$ alkoxy.

For example, -$Q_5$-$T_5$ is oxo.

For example, $T_4$ is 4 to 7-membered heterocycloalkyl or $C_3$-$C_8$ cycloalkyl and one or more -$Q_5$-$T_5$ are oxo.

For example, $T_5$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, $Q_5$ is a bond and $T_5$ is $C_1$-$C_6$ alkyl, $C_3$-$C_8$ cycloalkyl, or 4 to 7-membered heterocycloalkyl.

For example, $Q_5$ is CO, $S(O)_2$, or NHC(O); and $T_5$ is $C_1$-$C_6$ alkyl, $C_1$-$C_6$ alkoxyl, $C_3$-$C_8$ cycloalkyl, or 4 to 7-membered heterocycloalkyl.

For example, $T_5$ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, $Q_5$ is $C_1$-$C_3$ alkyl linker and $T_5$ is H or $C_6$-$C_{10}$ aryl.

For example, $Q_5$ is $C_1$-$C_3$ alkyl linker and $T_5$ is $C_3$-$C_8$ cycloalkyl, 4 to 7-membered heterocycloalkyl, or $S(O)_qR_q$.

For example, $R_{11}$ is H.

For example, each of $R_2$ and $R_4$, independently, is H or $C_1$-$C_6$ alkyl optionally substituted with amino, mono-$C_1$-$C_6$ alkylamino, di-$C_1$-$C_6$ alkylamino, or $C_6$-$C_{10}$ aryl.

For example, each of $R_2$ and $R_4$, independently is $C_1$-$C_3$ alkyl optionally substituted with $C_1$-$C_6$ alkoxyl.

For example, each of $R_2$ and $R_4$ is methyl.

For example, $R_1$ is H.

For example, $R_5$ is H.

For example, $R_{12}$ is H, methyl, ethyl, ethenyl, or halo.

For example, $R_{12}$ is methyl.

For example, $R_{12}$ is ethyl.

For example, $R_{12}$ is ethenyl.

For example, $R_8$ is H, methyl, ethyl, or ethenyl.

For example, $R_8$ is methyl.

For example, $R_8$ is ethyl.

For example, $R_8$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, and the like).

For example, $R_8$ is tetrahydropyran.

For example, $R_8$ is tetrahydropyran and $R_7$ is -$Q_4$-$T_4$, in which $Q_4$ is a bond or $C_1$-$C_4$ alkyl linker and $T_4$ is H, $C_1$-$C_6$ alkyl, $C_3$-$C_8$ cycloalkyl or 4 to 7-membered heterocycloalkyl.

For example, Z is $NR_7R_8$ or $CR_7R_8R_{14}$ wherein $R_7$ and $R_8$, together with the atom to which they are attached, form a 4 to 11-membered heterocycloalkyl ring having 1 to 3 heteroatoms (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyranyl, morpholinyl, 1,4-dioxa-8-azaspiro[4.5]decanyl, and the like) or $C_3$-$C_8$ cycloalkyl, each optionally substituted with one or more -$Q_6$-$T_6$.

For example, the ring formed by $R_7$ and $R_8$ is selected from the group consisting of azetidinyl, pyrrolidinyl, piperidinyl, morpholinyl, piperazinyl, 1,4-dioxa-8-azaspiro[4.5]decanyl, and cyclohexenyl, each optionally substituted with one -$Q_6$-$T_6$.

For example, -$Q_6$-$T_6$ is oxo.

For example, $T_6$ is H, halo, $C_1$-$C_6$ alkyl, $C_1$-$C_6$ alkoxyl, $C_3$-$C_8$ cycloalkyl, $C_6$-$C_{10}$ aryl, or 4 to 7-membered heterocycloalkyl.

For example, $Q_6$ is a bond and $T_6$ is $C_1$-$C_6$ alkyl, $C_3$-$C_8$ cycloalkyl, or 4 to 7-membered heterocycloalkyl.

For example, $Q_6$ is CO, $S(O)_2$, or NHC(O); and $T_6$ is $C_1$-$C_6$ alkyl, $C_1$-$C_6$ alkoxyl, $C_3$-$C_8$ cycloalkyl, or 4 to 7-membered heterocycloalkyl.

For example, $T_6$ is $C_1$-$C_6$ alkyl or $C_1$-$C_6$ alkoxyl, each optionally substituted with halo, hydroxyl, cyano, $C_1$-$C_6$ alkoxyl, amino, mono-$C_1$-$C_6$ alkylamino, di-$C_1$-$C_6$ alkylamino, or $C_3$-$C_8$ cycloalkyl.

For example, $Q_6$ is $C_1$-$C_3$ alkyl linker and $T_6$ is H or $C_6$-$C_{10}$ aryl.

For example, $Q_6$ is $C_1$-$C_3$ alkyl linker and $T_6$ is $C_3$-$C_8$ cycloalkyl, 4 to 7-membered heterocycloalkyl, or $S(O)_pR_p$.

For example, each of $R_p$ and $R_q$, independently, is $C_1$-$C_6$ alkyl.

For example, $R_{13}$ is H or methyl.

For example, $R_{13}$ is H.

For example, $R_3$ is H.

For example, $A^-$ is $Br^-$ or $Cl^-$.

The present invention provides the compounds of Formula (Ib), (Ic), or (Id):

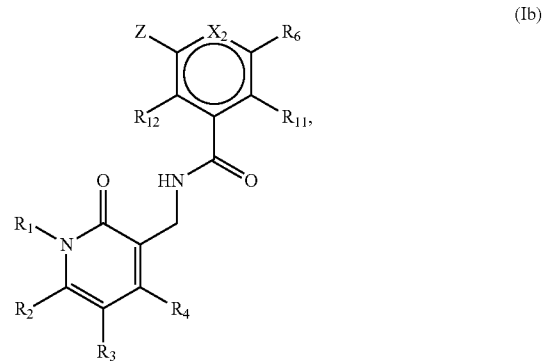

(Ib)

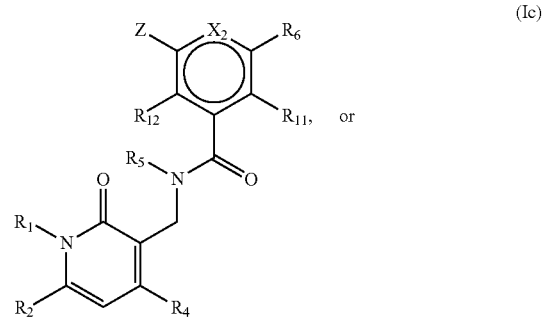

(Ic)
or

25

-continued

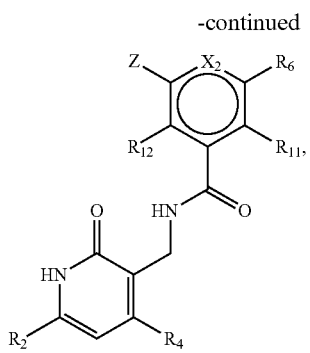

(Id)

or pharmaceutically acceptable salts or esters thereof, wherein Z, $X_2$, $R_1$, $R_2$, $R_3$, $R_4$, $R_5$, $R_6$, $R_{11}$, and $R_{12}$ are defined herein.

Still another subset of the compounds of formula (I) includes those of Formula (Ie), or (Ig):

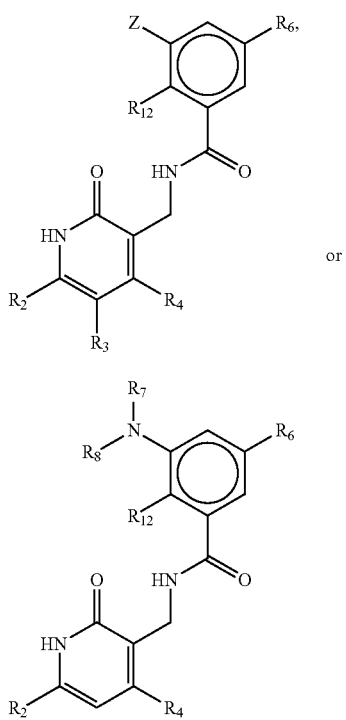

or a pharmaceutically acceptable salts or esters thereof, wherein Z, $X_2$, $R_2$, $R_3$, $R_4$, $R_6$, and $R_{12}$ are defined herein.

For example, $R_2$, $R_4$ and $R_{12}$ are each, independently $C_{1-6}$ alkyl.

For example, $R_6$ is $C_6$-$C_{10}$ aryl or 5- or 6-membered heteroaryl, each of which is optionally, independently substituted with one or more -$Q_2$-$T_2$, wherein $Q_2$ is a bond or $C_1$-$C_3$ alkyl linker, and $T_2$ is H, halo, cyano, —$OR_a$, —$NR_aR_b$, —$(NR_aR_bR_c)^+A^-$, —$C(O)NR_aR_b$, —$NR_bC(O)R_a$, —$S(O)_2R_a$, or $R_{S2}$, in which each of $R_a$ and $R_b$, independently is H or $R_{S3}$, each of $R_{S2}$ and $R_{S3}$, independently, is $C_1$-$C_6$ alkyl, or $R_a$ and $R_b$, together with the N atom to which they are attached, form a 4 to 7-membered heterocycloalkyl ring having 0 or 1 additional heteroatom, and each of $R_{S2}$, $R_{S3}$, and the 4 to 7-membered heterocycloalkyl ring formed by $R_a$ and $R_b$, is optionally, independently

26 substituted with one or more -$Q_3$-$T_3$, wherein $Q_3$ is a bond or $C_1$-$C_3$ alkyl linker and $T_3$ is selected from the group consisting of halo, $C_1$-$C_6$ alkyl, 4 to 7-membered heterocycloalkyl, $OR_d$, —$S(O)_2R_d$, and —$NR_dR_e$, each of $R_d$ and $R_e$ independently being H or $C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S.

Another subset of the compounds of Formula (I) includes those of Formula (II):

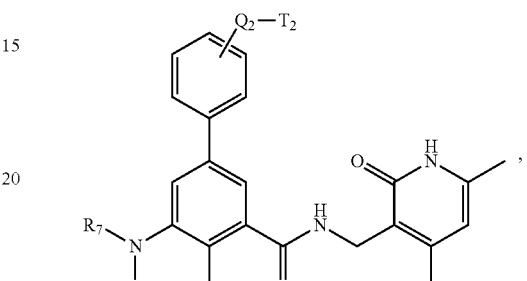

(II)

or a pharmaceutically acceptable salts or esters thereof, wherein
$Q_2$ is a bond or methyl linker;
$T_2$ is H, halo, —$OR_a$, —$NR_aR_b$, —$(NR_aR_bR_c)^+A^-$, or —$S(O)_2NR_aR_b$;
$R_7$ is piperidinyl, tetrahydropyran, cyclopentyl, or cyclohexyl, each optionally substituted with one -$Q_5$-$T_5$;
$R_8$ is ethyl and
$R_a$, $R_b$, and $R_c$ are defined herein.
For example, $Q_2$ is a bond
For example, $Q_2$ is a methyl linker
For example, $T_2$ is —$NR_aR_b$ or —$(NR_aR_bR_c)^+A^-$.

Yet another subset of the compounds of Formula (I) includes those of Formula (IIa):

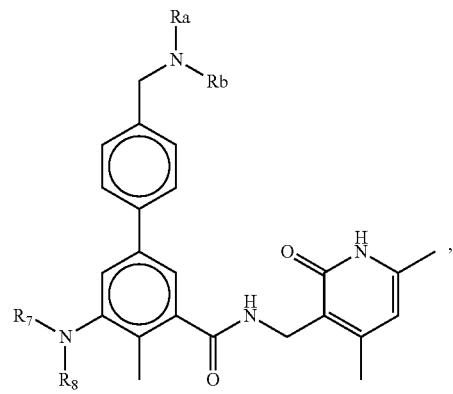

(IIa)

or a pharmaceutically acceptable salts or esters thereof, wherein $R_7$, $R_8$, $R_a$, $R_b$, and $R_c$ are defined herein.

The compounds of Formula (II) or (IIa) can include one or more of the following features:

For example, each of $R_a$ and $R_b$, independently is H or $C_1$-$C_6$ alkyl optionally substituted with one or more -$Q_3$-$T_3$.

For example, one of $R_a$ and $R_b$ is H.

For example, $R_a$ and $R_b$, together with the N atom to which they are attached, form a 4 to 7-membered heterocycloalkyl ring having 0 or 1 additional heteroatoms to the N atom (e.g., azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, morpholinyl, 1,4-diazepanyl, 1,4-oxazepanyl, 2-oxa-5-azabicyclo[2.2.1]heptanyl, 2,5-diazabicyclo[2.2.1]heptanyl, and the like) and the ring is optionally substituted with one or more $-Q_3-T_3$.

For example, $R_a$ and $R_b$, together with the N atom to which they are attached, form azetidinyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, or morpholinyl, and the ring is optionally substituted with one or more $-Q_3-T_3$.

For example, one or more $-Q_3-T_3$ are oxo.

For example, $Q_3$ is a bond or unsubstituted or substituted $C_1-C_3$ alkyl linker.

For example, $T_3$ is H, halo, 4 to 7-membered heterocycloalkyl, $C_1-C_3$ alkyl, $OR_d$, $COOR_d$, $—S(O)_2R_d$, or $—NR_dR_e$.

For example, one of $R_d$ and $R_e$ is H.

For example, $R_7$ is $C_3-C_8$ cycloalkyl or 4 to 7-membered heterocycloalkyl, each optionally substituted with one or more $-Q_5-T_5$.

For example, $R_7$ is piperidinyl, tetrahydropyran, tetrahydro-2H-thiopyranyl, cyclopentyl, cyclohexyl, pyrrolidinyl, or cycloheptyl, each optionally substituted with one or more $-Q_5-T_5$.

For example, $R_7$ is cyclopentyl cyclohexyl or tetrahydro-2H-thiopyranyl, each optionally substituted with one or more $-Q_5-T_5$.

For example, $Q_5$ is NHC(O) and $T_5$ is $C_1-C_6$ alkyl or $C_1-C_6$ alkoxy.

For example, one or more $-Q_5-T_5$ are oxo.

For example, $R_7$ is 1-oxide-tetrahydro-2H-thiopyranyl or 1,1-dioxide-tetrahydro-2H-thiopyranyl.

For example, $Q_5$ is a bond and $T_5$ is amino, mono-$C_1-C_6$ alkylamino, di-$C_1-C_6$ alkylamino.

For example, $Q_5$ is CO, $S(O)_2$, or NHC(O); and $T_5$ is $C_1-C_6$ alkyl, $C_1-C_6$ alkoxyl, $C_3-C_8$ cycloalkyl, or 4 to 7-membered heterocycloalkyl.

For example, $R_8$ is H or $C_1-C_6$ alkyl which is optionally substituted with one or more substituents selected from the group consisting of halo, hydroxyl, COOH, C(O)O—$C_1-C_6$ alkyl, cyano, $C_1-C_6$ alkoxyl, amino, mono-$C_1-C_6$ alkylamino, and di-$C_1-C_6$ alkylamino.

For example, $R_8$ is H, methyl, or ethyl.

Still another subset of compounds of Formula (I) includes those of Formula (III):

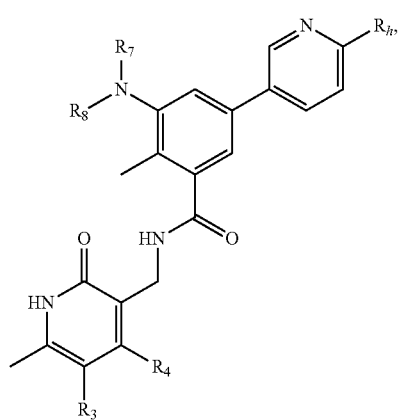

(III)

or a pharmaceutically acceptable salts or esters thereof, wherein $R_3$ is hydrogen, $C_1-C_3$ alkyl or halo;

$R_4$ is $C_1-C_3$ alkyl, $R_7$ is $C_1-C_6$ alkyl, $C_3-C_8$ cycloalkyl or 4 to 7-membered heterocycloalkyl, optionally substituted with one or more $R_s$ $R_8$ is $C_1-C_6$ alkyl;

$R_h$ is $-Q_h-T_h$, wherein $Q_h$ is a bond, a $C_1-C_3$ alkyl linker or $N(R_N)$; $T_h$ is $OR_{h1}$ or $—NR_{h1}R_{h2}$, in which $R_{h1}$ and $R_{h2}$ are independently hydrogen or $C_1-C_6$ alkyl, or one of $R_{h1}$ and $R_{h2}$ is methyl and the other is a 6-membered N-containing heterocycloalkyl optionally substituted with one or two methyl, or together with the N atom to which they are attached, $R_{h1}$ and $R_{h2}$ form a 4 to 7-membered heterocycloalkyl ring having 0 or 1 additional heteroatoms selected from oxygen and nitrogen, wherein said heterocycloalkyl ring is optionally substituted with one or more $R_i$;

$R_i$ is $C_1-C_3$ alkyl, $—NR_{N1}R_{N2}$ or a $C_3-C_8$ cycloalkyl or 5 or 6 membered heterocycle each of which cycloalkyl or heterocycle is independently optionally substituted with $R_j$;

$R_N$ is hydrogen, $C_1-C_6$ alkyl or $C_3-C_8$ cycloalkyl;

$R_j$ is $C_1-C_3$ alkyl, $—NR_{N1}R_{N2}$, or $—NC(O)R_N$;

$R_{N1}$ and $R_{N2}$ are each independently hydrogen, $C_1-C_6$ alkyl, $C_3-C_8$ cycloalkyl, 5 or 6 membered heterocycle, each of which cycloalkyl or heterocycle is independently optionally substituted with $R_j$.

For example, $R_3$ is hydrogen.

For example, $R_3$ is halogen, such as, for example, fluoro or chloro. For example, $R_3$ is fluoro.

For example $R_4$ is methyl, ethyl, propyl, or isopropyl. For example, $R_4$ is methyl. For example, $R_4$ is isopropyl.

For example, $R_7$ is 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, tetrahydro-2H-thiopyran, and morpholinyl, and the like).

For example, $R_7$ is a 5 or 6 membered cycloalkyl or heterocycloalkyl.

For example, $R_7$ is a 6 membered cycloalkyl or heterocycloalkyl.

In some embodiments, $R_7$ is piperidinyl, tetrahydropyranyl, cyclopentyl, or cyclohexyl.

In some embodiments, $R_j$ is methyl. In some embodiments, $R_j$ is $NH_2$.

For example, $R_8$ is $C_1$, $C_2$ or $C_3$ alkyl. For example, $R_8$ is methyl. For example, $R_8$ is ethyl.

In some embodiments, $Q_h$ is a bond. In others, $Q_h$ is methylene.

In some embodiments, $T_h$ is $N(CH_3)_2$.

In some embodiments, one of $R_{h1}$ and $R_{h2}$ is methyl and the other is a 6-membered N-containing heterocycloalkyl optionally substituted with one or two methyl. For example, the 6-membered N-containing heterocycloalkyl does not contain further heteroatoms in the ring. For example, the 6-membered N-containing heterocycloalkyl is not further substituted besides the one or two methyl groups.

In some embodiments, $R_{h1}$ and $R_{h2}$, together with the N to which they are attached form a 6 membered ring. For example, $T_h$ is selected from piperidine, morpholine, piperazine, and N-methyl piperazine.

For example, $T_h$ is morpholine.

In some embodiments, $R_i$ is methyl or $N(CH_3)_2$. In some embodiments, $R_i$ is $C_3-C_8$ cycloalkyl or 5 or 6 membered heterocycle. For example, $R_i$ is a 6 membered cycloalkyl or heterocycle, substituted with zero or one $R_j$.

In some embodiments, $R_N$ is H or methyl.

In certain compounds of Formula (III), compounds of formula IIIa, $R_3$ is hydrogen, $R_4$ is $CH_3$ and $Q_h$ is methylene.

In certain compounds of formula III, compounds of formula IIIb, $R_3$ is fluoro, $R_4$ is isopropyl and $Q_h$ is a bond.

In certain compounds of formula III, compounds of formula IIIc, $R_3$ is hydrogen, $R_4$ is propyl or isopropyl and $Q_h$ is methylene.

In certain compounds of formula III, compounds of formula IIId, $R_3$ is hydrogen, $R_4$ is propyl or isopropyl and $Q_h$ is a bond.

In certain compounds of formula III, compounds of Formula (IIIe),

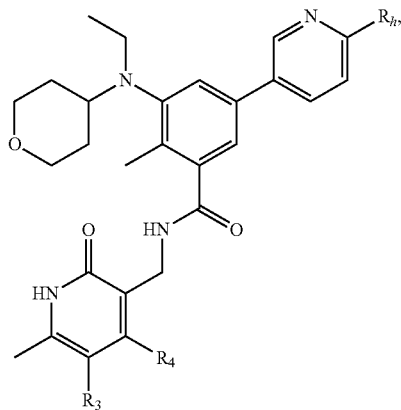

(IIIe)

wherein
$R_3$ is H or F
$R_4$ is methyl, i-propyl, or n-propyl,
$R_h$ is

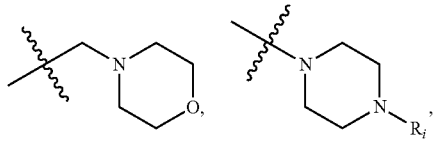

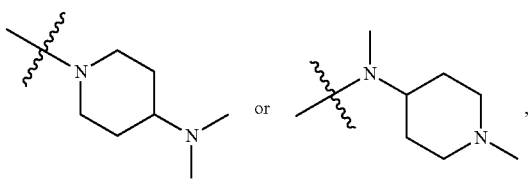

in which $R_i$ is H, methyl, or

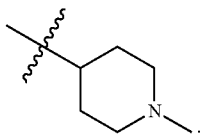 [SMILES: *C1CCN(C)CC1]

Representative compounds of the present invention include compounds listed in Table 1. In the table below, each occurrence of

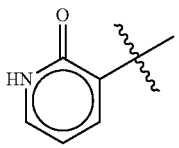

should be construed as

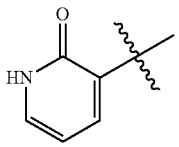

TABLE 1

| Compound Number | Structure | MS (M + 1)+ |
|---|---|---|
| 1 | 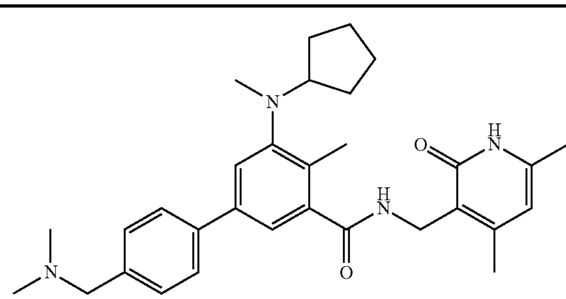 | 501.39 |

TABLE 1-continued

| Compound Number | Structure | MS (M + 1)+ |
|---|---|---|
| 2 | 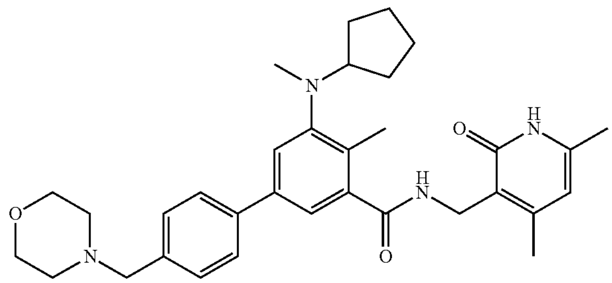 [SMILES: Cc1cc(C)c(CNC(=O)c2cc(-c3ccc(CN4CCOCC4)cc3)cc(N(C)C3CCCC3)c2C)c(=O)[nH]1] | 543.22 |
| 3 | 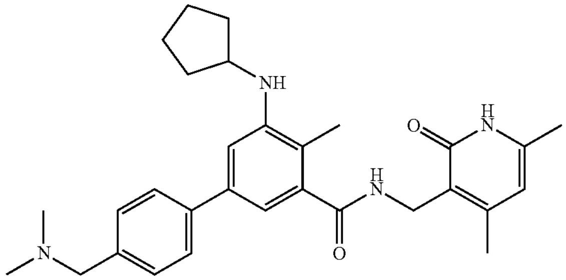 | 486.21 |
| 4 | 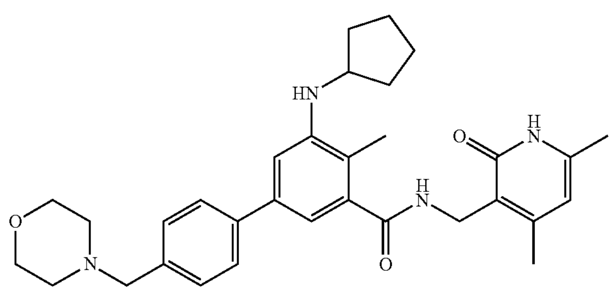 [SMILES: Cc1cc(C)c(CNC(=O)c2cc(-c3ccc(CN4CCOCC4)cc3)cc(NC3CCCC3)c2C)c(=O)[nH]1] | 529.30 |
| 5 | 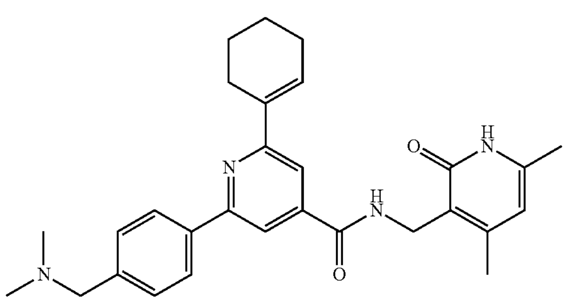 | 471.30 |
| 6 | 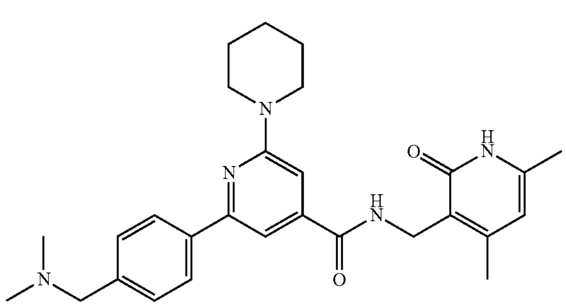 | 474.30 |

TABLE 1-continued

| Compound Number | Structure | MS (M + 1)+ |
|---|---|---|
| 7 | 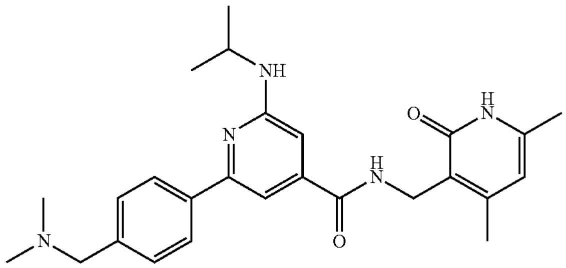 | 448.25 |
| 8 | 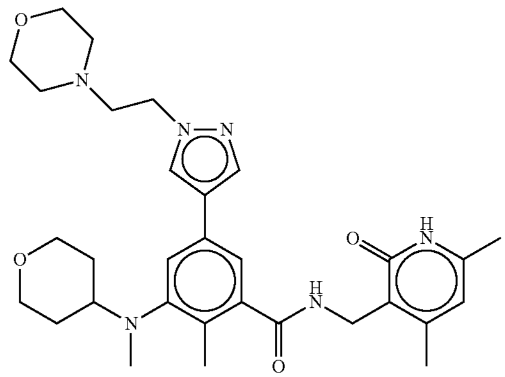 | 563 |
| 9 | 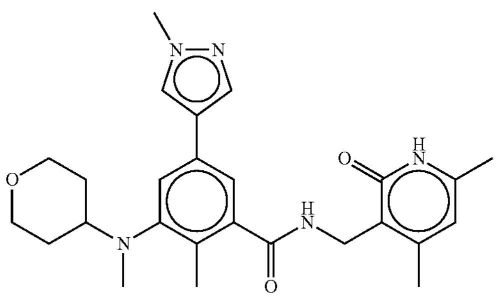 | 464.3 |
| 10 | 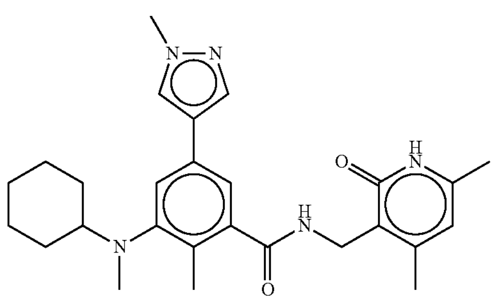 | 462.4 |
| 11 | 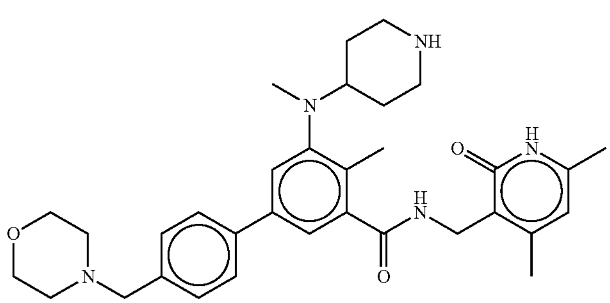 | 558.45 |

TABLE 1-continued

| Compound Number | Structure | MS (M + 1)+ |
|---|---|---|
| 12 | 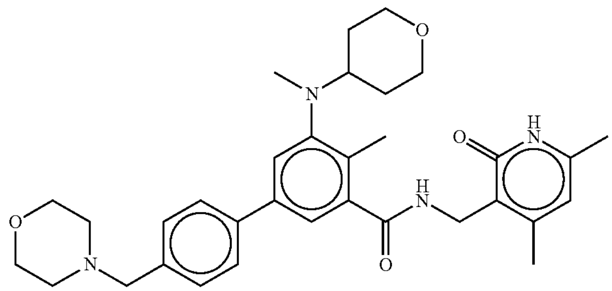 | 559.35 |
| 13 | 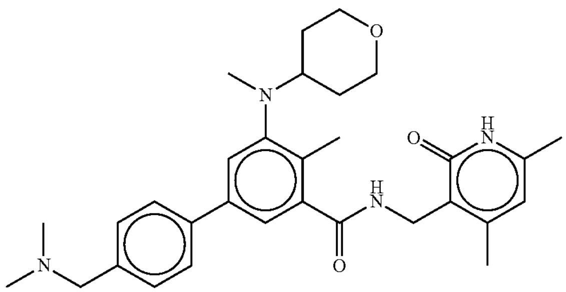 | 517.3 |
| 14 | 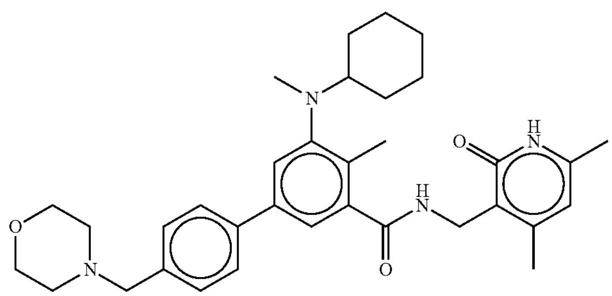 | 557.4 |
| 15 | 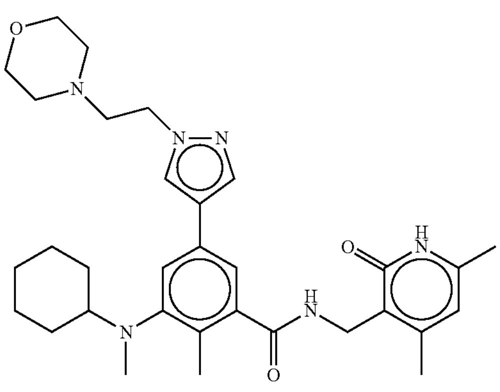 | 561.35 |
| 16 | 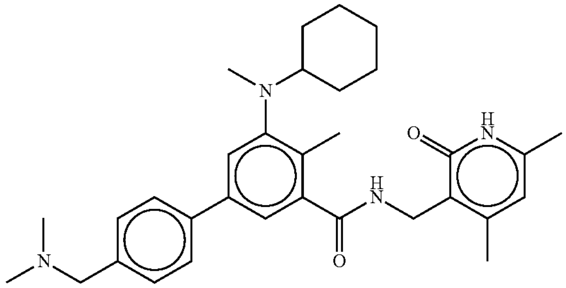 | 515.4 |

TABLE 1-continued

| Compound Number | Structure | MS (M + 1)+ |
|---|---|---|
| 17 | 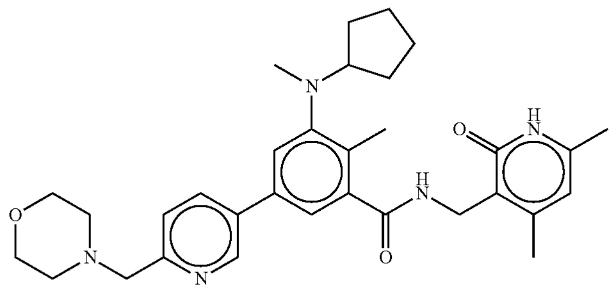 | 544.35 |
| 18 | 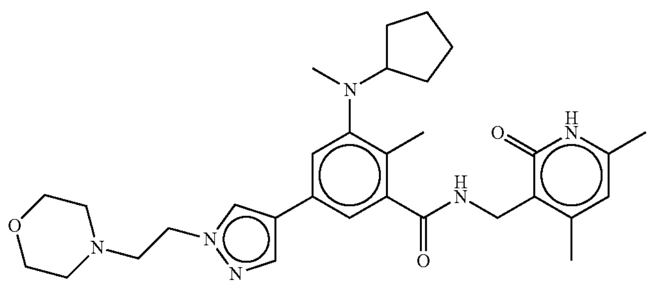 | 547.35 |
| 19 | 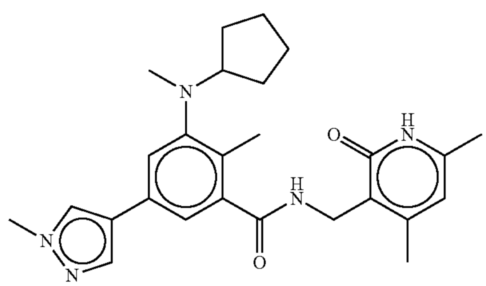 | 448.25 |
| 20 | 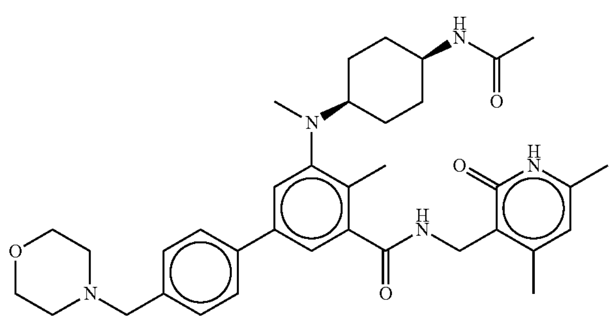 | 614.4 |
| 21 | 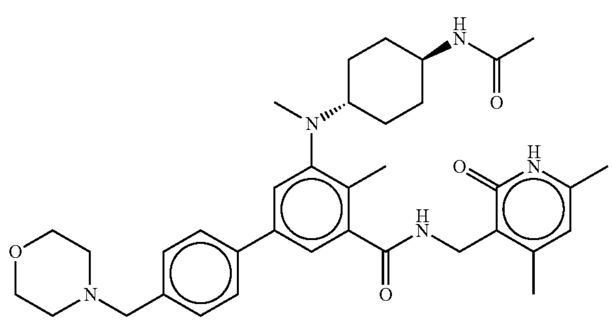 | 614.4 |

TABLE 1-continued

| Compound Number | Structure | MS (M + 1)+ |
|---|---|---|
| 22 | 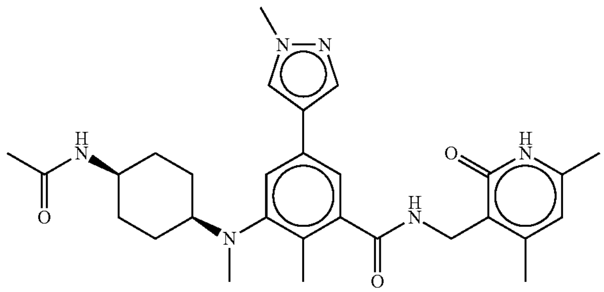 | 519.4 |
| 23 | 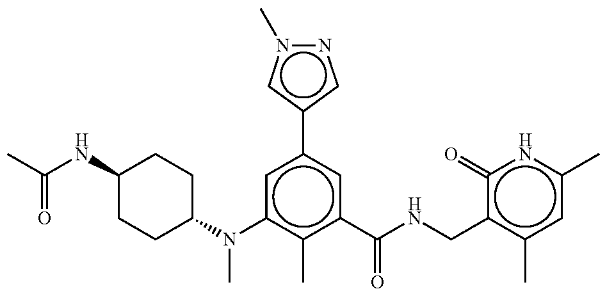 | 519.3 |
| 24 | 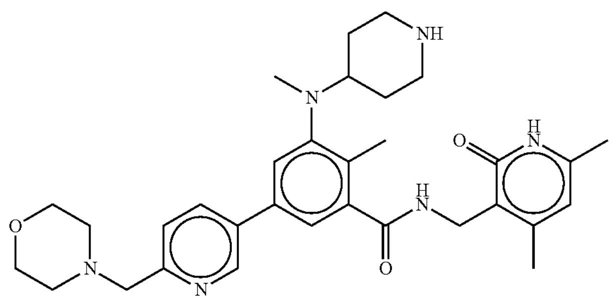 | 559.35 |
| 25 | 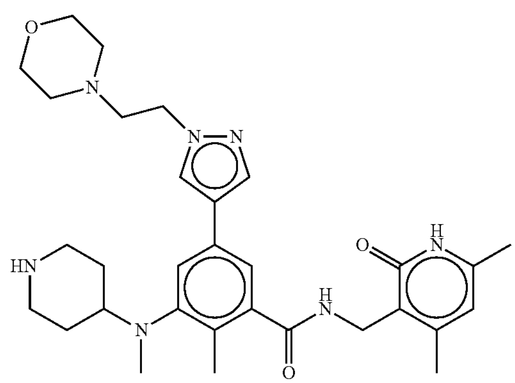 | 562.4 |
| 26 | 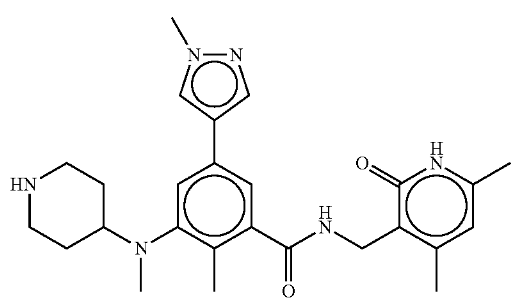 | 463.3 |

TABLE 1-continued

| Compound Number | Structure | MS (M + 1)+ |
|---|---|---|
| 27 | 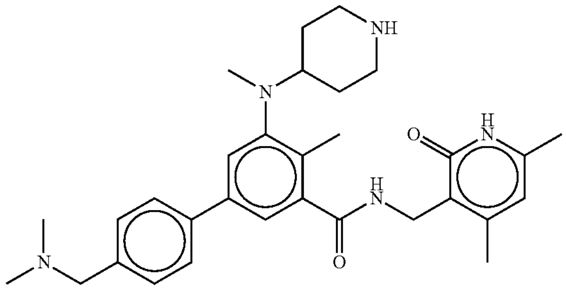 | 516.35 |
| 28 | 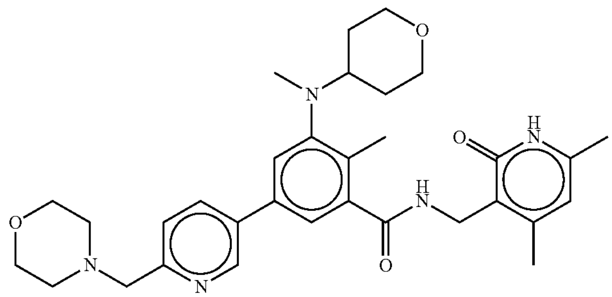 | 560.3 |
| 29 | 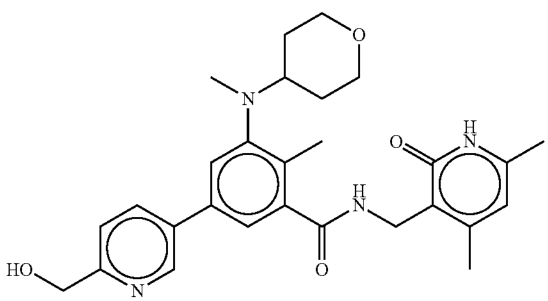 | 491.25 |
| 30 | 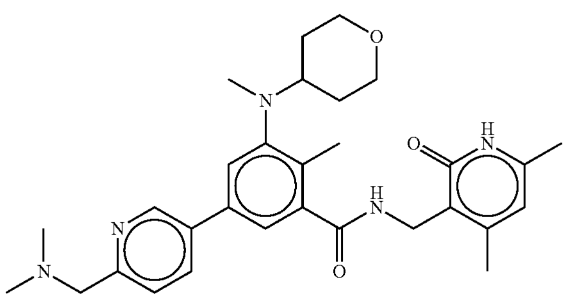 | 518.25 |
| 31 | 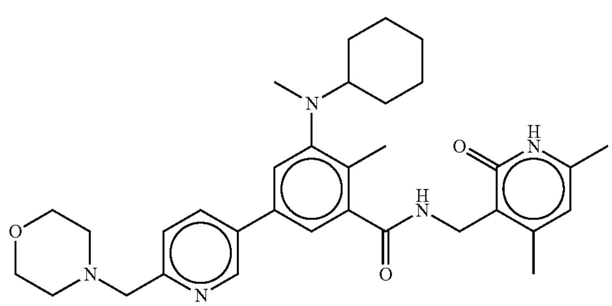 | 558.35 |

TABLE 1-continued

| Compound Number | Structure | MS (M + 1)+ |
|---|---|---|
| 32 | 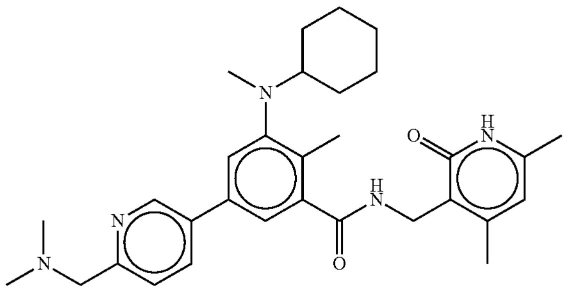 | 516.35 |
| 35 | 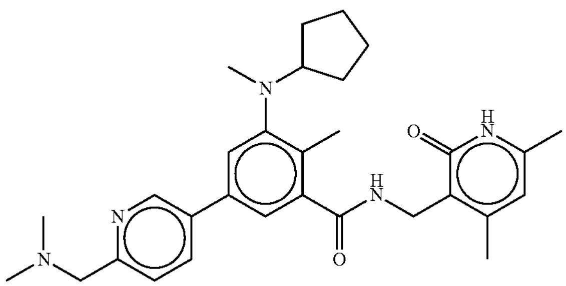 | 502.3 |
| 36 | 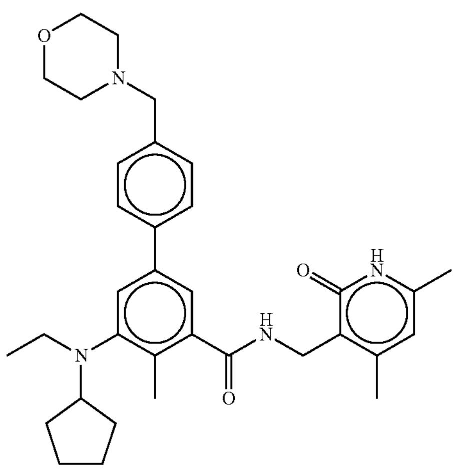 | 557.35 |
| 37 | 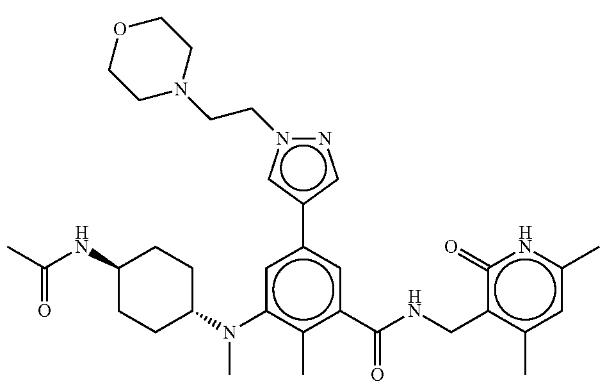 | 618.35 |

TABLE 1-continued

| Compound Number | Structure | MS (M + 1)+ |
|---|---|---|
| 38 | 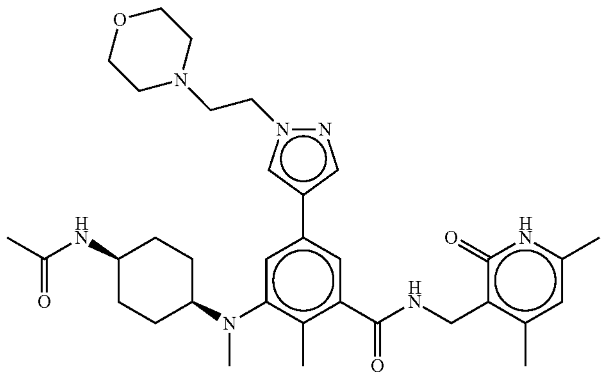 | 618.35 |
| 39 | 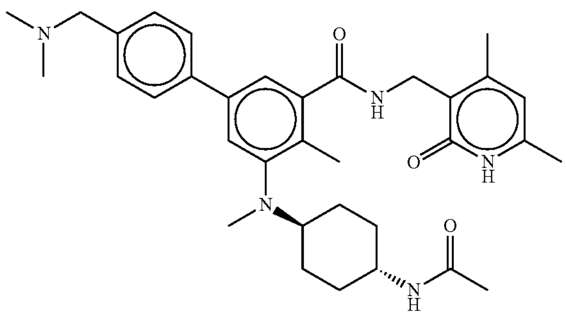 | 572.35 |
| 40 | 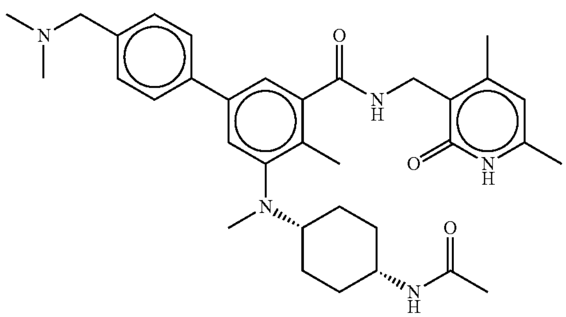 | 572.35 |
| 41 | 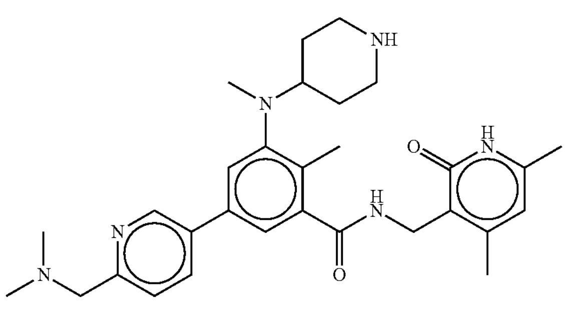 | 517.25 |

TABLE 1-continued

| Compound Number | Structure | MS (M + 1)+ |
|---|---|---|
| 42 | 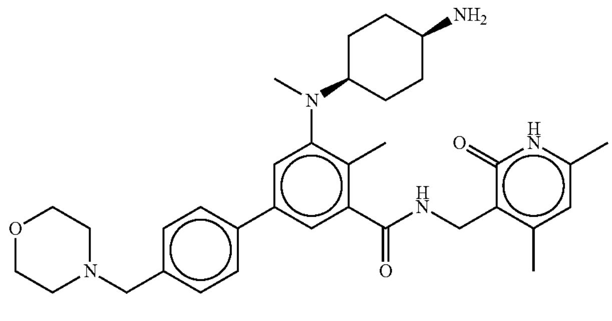 | 572.4 |
| 43 | 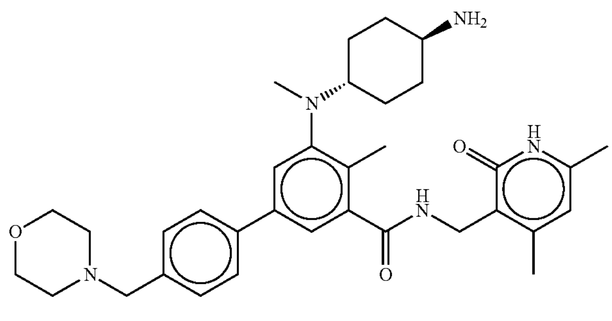 | 572.6 |
| 44 | 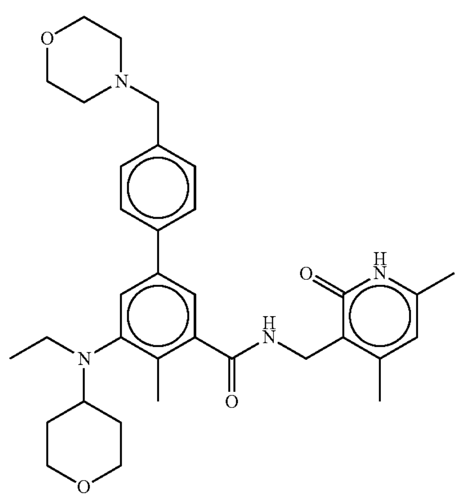 | 573.40 |
| 45 | 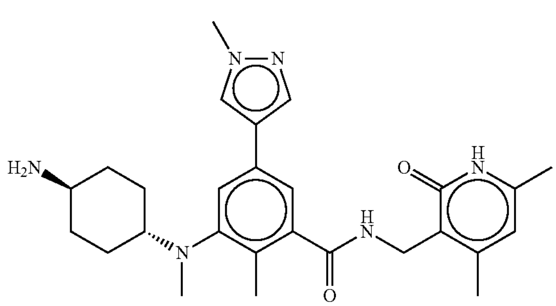 | 477.35 |

TABLE 1-continued

| Compound Number | Structure | MS (M + 1)+ |
|---|---|---|
| 46 | 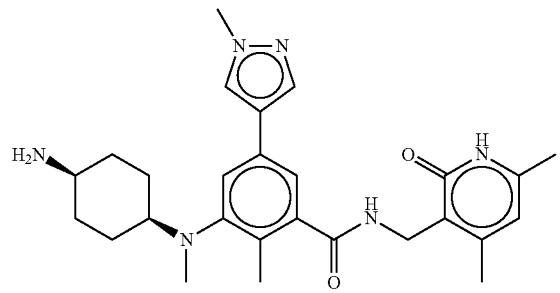 | 477.30 |
| 47 | 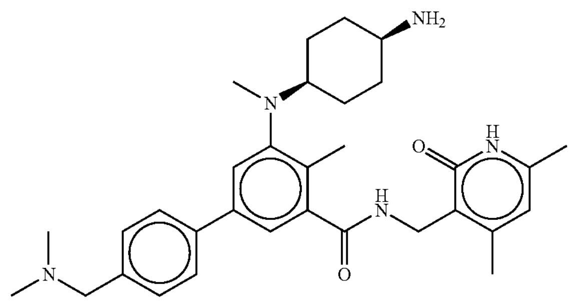 | 530.35 |
| 48 | 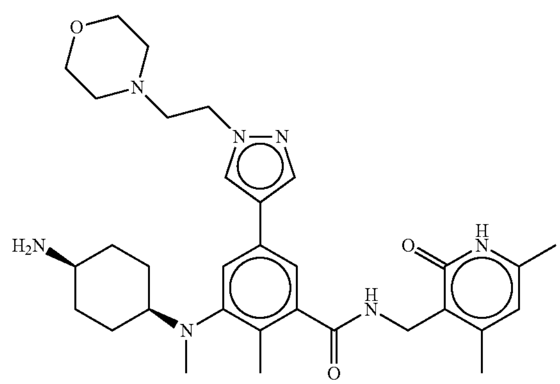 | 576.40 |
| 49 | 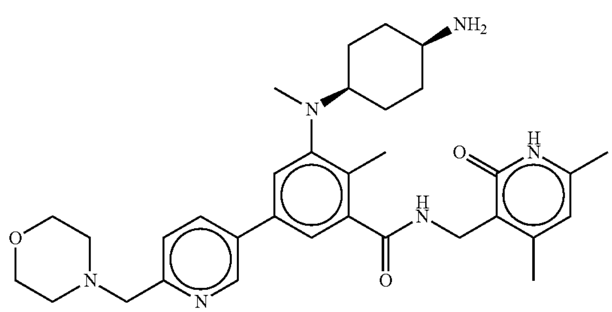 | 573.45 |
| 50 | 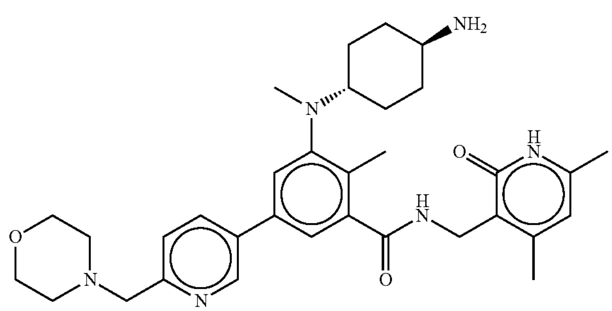 | 573.40 |

TABLE 1-continued

| Compound Number | Structure | MS (M + 1)+ |
|---|---|---|
| 51 | 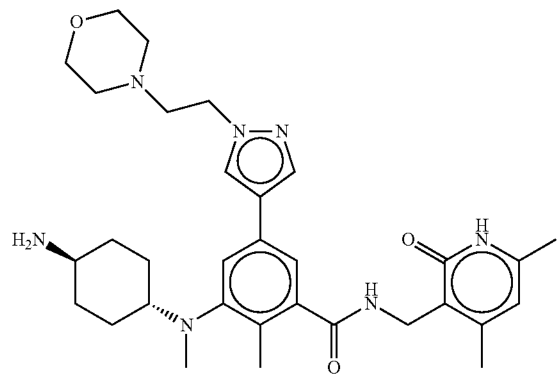 | 576.45 |
| 52 | 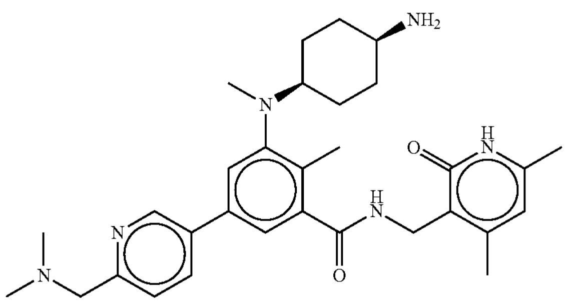 | 531.25 |
| 53 | 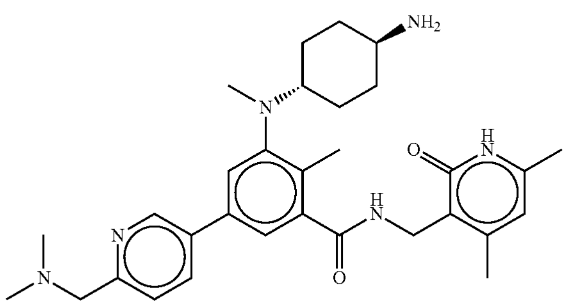 | 531.30 |
| 54 | 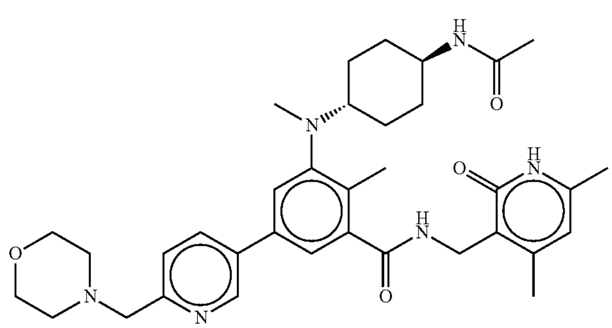 | 615.55 |

TABLE 1-continued

| Compound Number | Structure | MS (M + 1)+ |
|---|---|---|
| 55 | 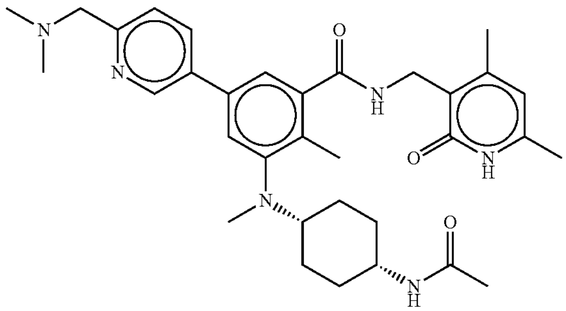 | 573.40 |
| 56 | 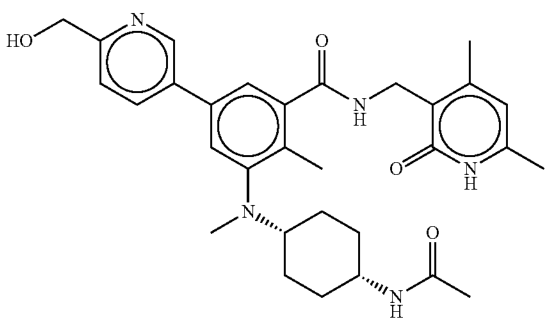 | 546.40 |
| 57 | 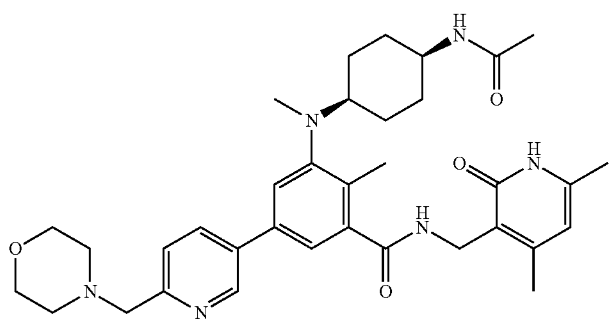 [SMILES: CC(=O)N[C@H]1CC[C@@H](N(C)c2cc(-c3ccc(CN4CCOCC4)nc3)cc(C(=O)NCc3c(C)cc(C)[nH]c3=O)c2C)CC1] | 615.40 |
| 58 | 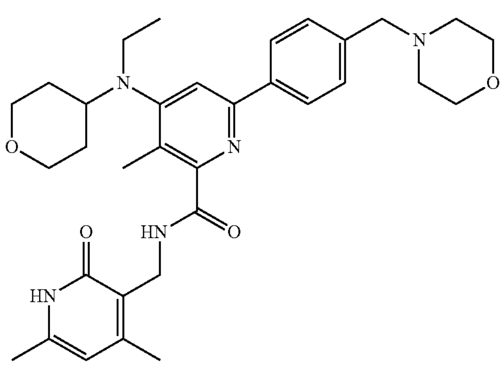 [SMILES: CCN(c1cc(-c2ccc(CN3CCOCC3)cc2)nc(C(=O)NCc2c(C)cc(C)[nH]c2=O)c1C)C1CCOCC1] | |

TABLE 1-continued

| Compound Number | Structure | MS (M + 1)+ |
|---|---|---|
| 59 | 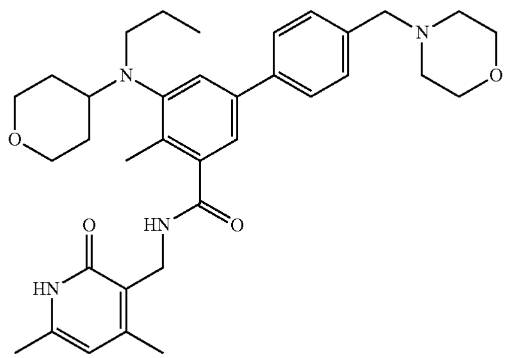 [SMILES: CCCN(c1cc(-c2ccc(CN3CCOCC3)cc2)cc(C(=O)NCc2c(C)cc(C)[nH]c2=O)c1C)C1CCOCC1] | 587.40 |
| 60 | 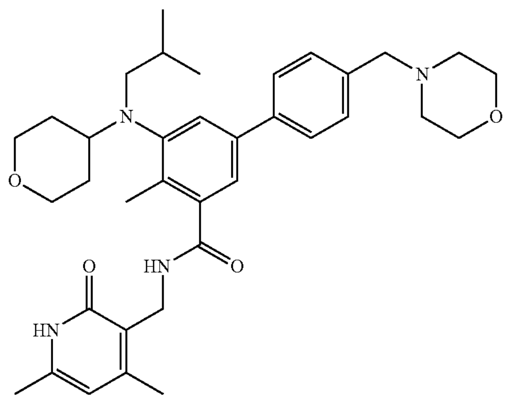 [SMILES: Cc1cc(C)c(CNC(=O)c2cc(-c3ccc(CN4CCOCC4)cc3)cc(N(CC(C)C)C3CCOCC3)c2C)c(=O)[nH]1] | 601.30 |
| 61 | 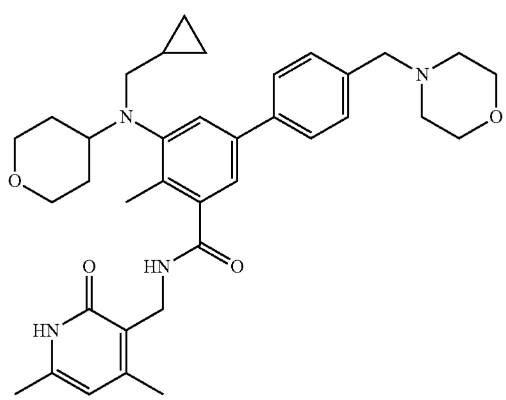 [SMILES: Cc1cc(C)c(CNC(=O)c2cc(-c3ccc(CN4CCOCC4)cc3)cc(N(CC3CC3)C3CCOCC3)c2C)c(=O)[nH]1] | 599.35 |
| 62 | 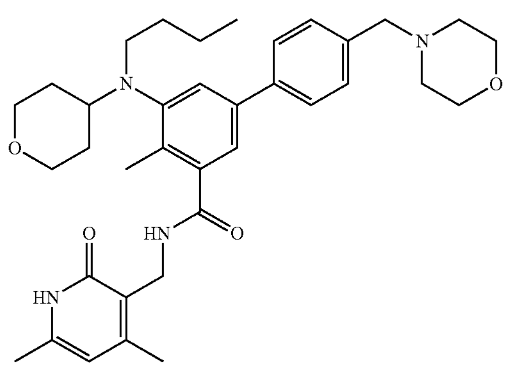 [SMILES: CCCCN(c1cc(-c2ccc(CN3CCOCC3)cc2)cc(C(=O)NCc2c(C)cc(C)[nH]c2=O)c1C)C1CCOCC1] | 601.35 |

TABLE 1-continued
| Compound Number | Structure | MS (M + 1)+ |
|---|---|---|
| 63 | 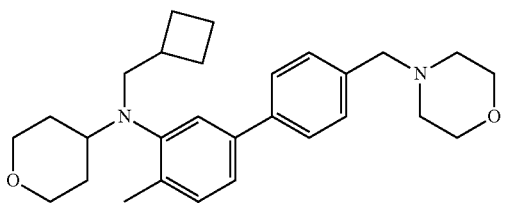 | 613.35 |
| 64 | 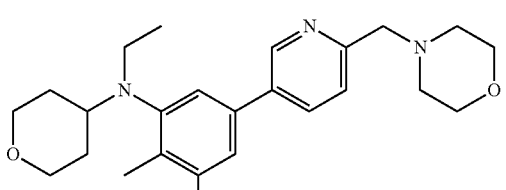 | 574.25 |
| 65 | 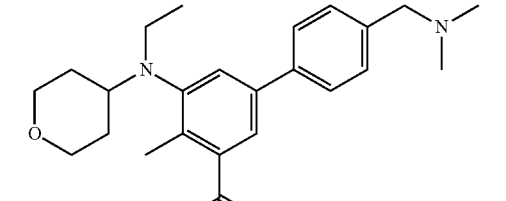 | 531.30 |
| 66 | 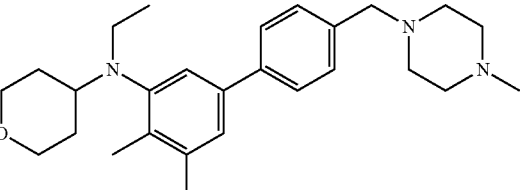 | 586.40 |

TABLE 1-continued

| Compound Number | Structure | MS (M + 1)+ |
|---|---|---|
| 67 | 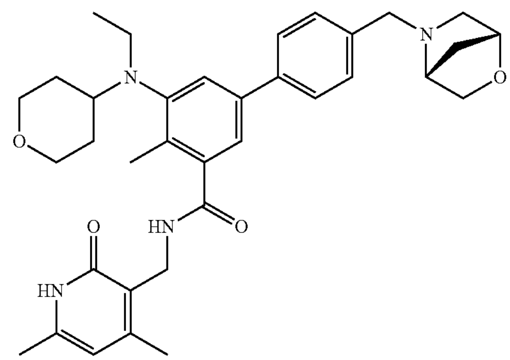 [SMILES: CCN(c1cc(-c2ccc(CN3C[C@H]4C[C@@H]3CO4)cc2)cc(C(=O)NCc2c(C)cc(C)[nH]c2=O)c1C)C1CCOCC1] | 585.25 |
| 68 | 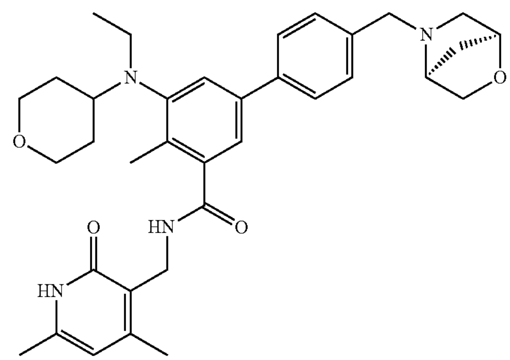 [SMILES: CCN(c1cc(-c2ccc(CN3C[C@@H]4C[C@H]3CO4)cc2)cc(C(=O)NCc2c(C)cc(C)[nH]c2=O)c1C)C1CCOCC1] | 585.35 |
| 69 | 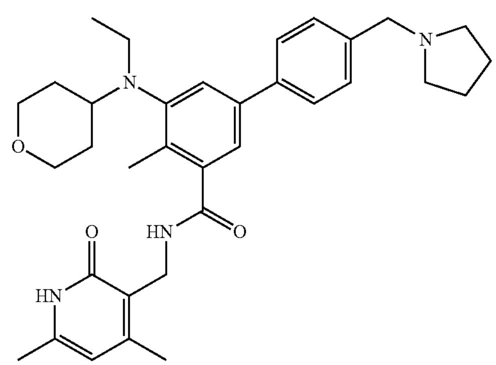 [SMILES: CCN(c1cc(-c2ccc(CN3CCCC3)cc2)cc(C(=O)NCc2c(C)cc(C)[nH]c2=O)c1C)C1CCOCC1] | 557.25 |
| 70 | 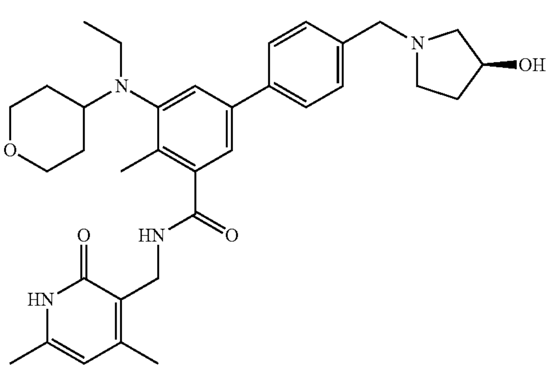 [SMILES: CCN(c1cc(-c2ccc(CN3CC[C@H](O)C3)cc2)cc(C(=O)NCc2c(C)cc(C)[nH]c2=O)c1C)C1CCOCC1] | 573.40 |

TABLE 1-continued

| Compound Number | Structure | MS (M + 1)+ |
|---|---|---|
| 71 | 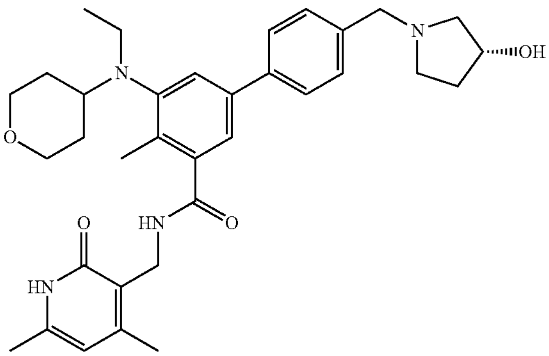 [SMILES: CCN(c1cc(-c2ccc(CN3CC[C@@H](O)C3)cc2)cc(C(=O)NCc2c(C)cc(C)[nH]c2=O)c1C)C1CCOCC1] | 573.40 |
| 72 | 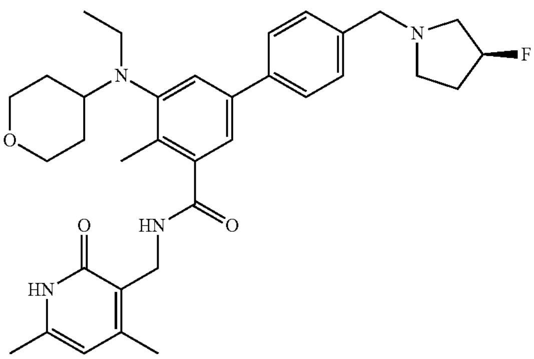 [SMILES: CCN(c1cc(-c2ccc(CN3CC[C@H](F)C3)cc2)cc(C(=O)NCc2c(C)cc(C)[nH]c2=O)c1C)C1CCOCC1] | 575.35 |
| 73 | 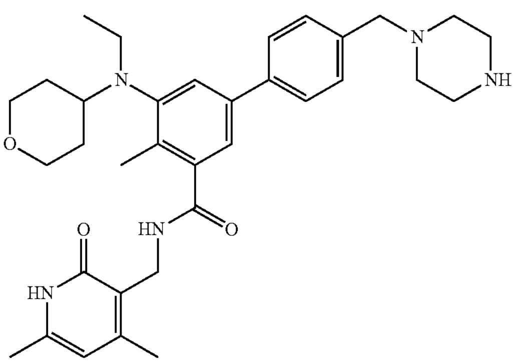 [SMILES: CCN(c1cc(-c2ccc(CN3CCNCC3)cc2)cc(C(=O)NCc2c(C)cc(C)[nH]c2=O)c1C)C1CCOCC1] | 572.10 |
| 74 | 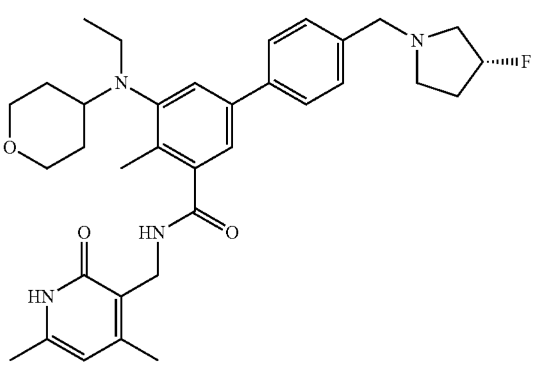 [SMILES: CCN(c1cc(-c2ccc(CN3CC[C@@H](F)C3)cc2)cc(C(=O)NCc2c(C)cc(C)[nH]c2=O)c1C)C1CCOCC1] | 575.35 |

TABLE 1-continued

| Compound Number | Structure | MS (M + 1)+ |
|---|---|---|
| 75 | 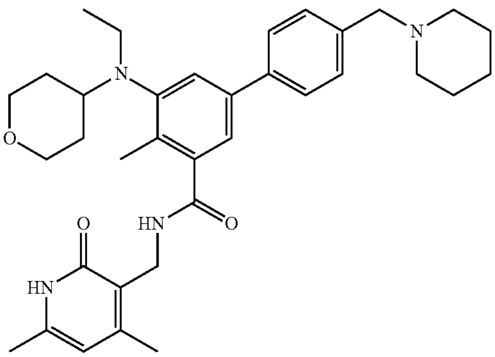 [SMILES: CCN(c1cc(-c2ccc(CN3CCCCC3)cc2)cc(C(=O)NCc2c(C)cc(C)[nH]c2=O)c1C)C1CCOCC1] | 571.25 |
| 76 | 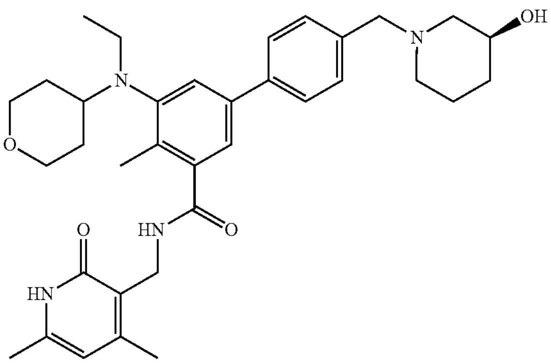 [SMILES: CCN(c1cc(-c2ccc(CN3CCC[C@H](O)C3)cc2)cc(C(=O)NCc2c(C)cc(C)[nH]c2=O)c1C)C1CCOCC1] | 587.40 |
| 77 | 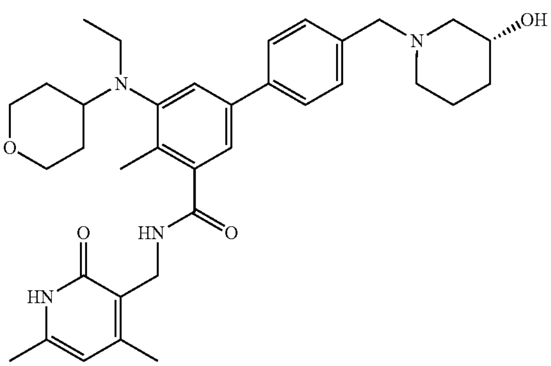 [SMILES: CCN(c1cc(-c2ccc(CN3CCC[C@@H](O)C3)cc2)cc(C(=O)NCc2c(C)cc(C)[nH]c2=O)c1C)C1CCOCC1] | 587.45 |
| 78 | 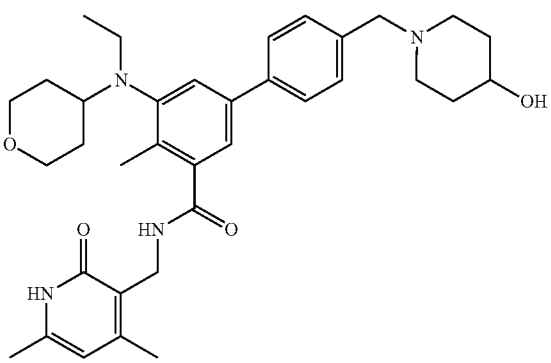 [SMILES: CCN(c1cc(-c2ccc(CN3CCC(O)CC3)cc2)cc(C(=O)NCc2c(C)cc(C)[nH]c2=O)c1C)C1CCOCC1] | 587.20 |

TABLE 1-continued

| Compound Number | Structure | MS (M + 1)+ |
|---|---|---|
| 79 | 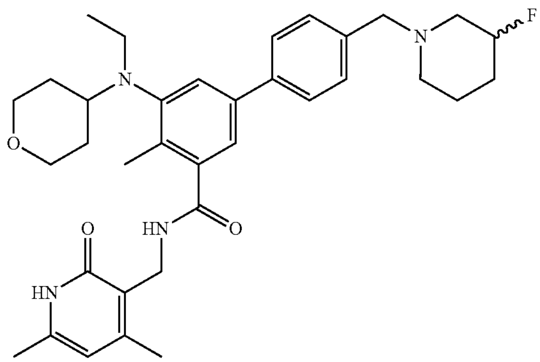 [SMILES: CCN(c1cc(-c2ccc(CN3CCCC(F)C3)cc2)cc(C(=O)NCc2c(C)cc(C)[nH]c2=O)c1C)C1CCOCC1] | 589.35 |
| 80 | 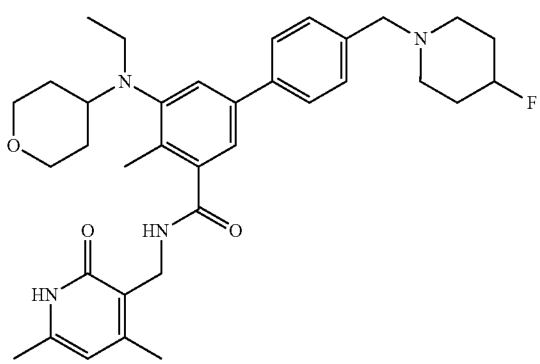 [SMILES: CCN(c1cc(-c2ccc(CN3CCC(F)CC3)cc2)cc(C(=O)NCc2c(C)cc(C)[nH]c2=O)c1C)C1CCOCC1] | 589.30 |
| 81 | 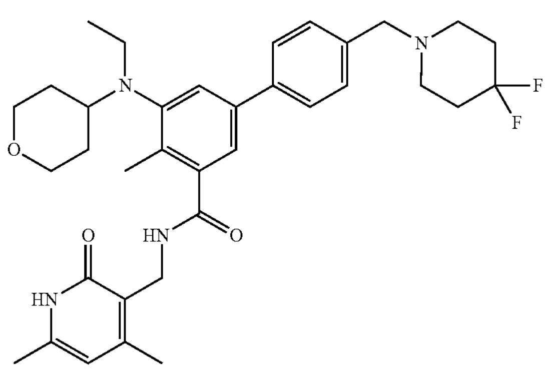 [SMILES: CCN(c1cc(-c2ccc(CN3CCC(F)(F)CC3)cc2)cc(C(=O)NCc2c(C)cc(C)[nH]c2=O)c1C)C1CCOCC1] | 607.35 |
| 82 | 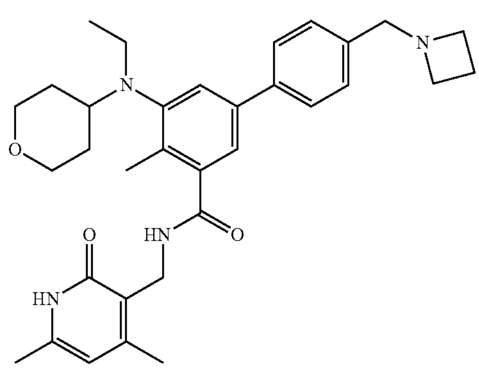 [SMILES: CCN(c1cc(-c2ccc(CN3CCC3)cc2)cc(C(=O)NCc2c(C)cc(C)[nH]c2=O)c1C)C1CCOCC1] | 543.40 |

TABLE 1-continued

| Compound Number | Structure | MS (M + 1)+ |
|---|---|---|
| 83 | 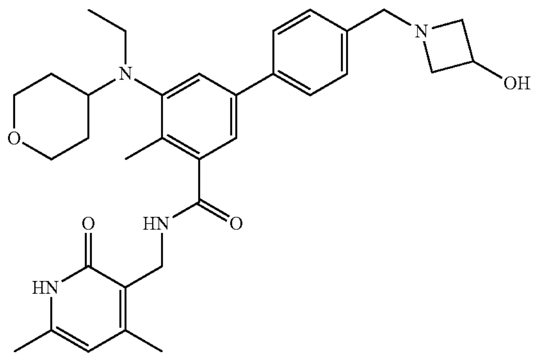 [SMILES: CCN(c1cc(-c2ccc(CN3CC(O)C3)cc2)cc(C(=O)NCc2c(C)cc(C)[nH]c2=O)c1C)C1CCOCC1] | 559.80 |
| 84 | 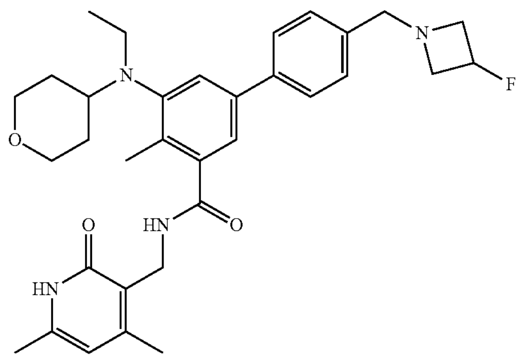 [SMILES: CCN(c1cc(-c2ccc(CN3CC(F)C3)cc2)cc(C(=O)NCc2c(C)cc(C)[nH]c2=O)c1C)C1CCOCC1] | 561.25 |
| 85 | 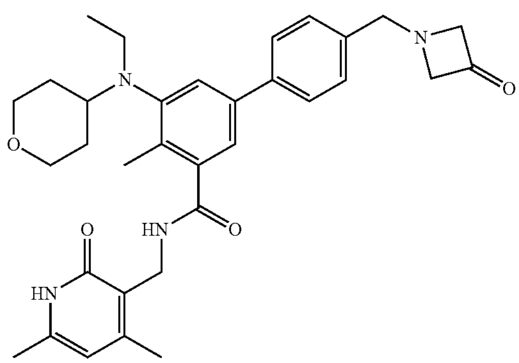 [SMILES: CCN(c1cc(-c2ccc(CN3CC(=O)C3)cc2)cc(C(=O)NCc2c(C)cc(C)[nH]c2=O)c1C)C1CCOCC1] | 561.25 |
| 86 | 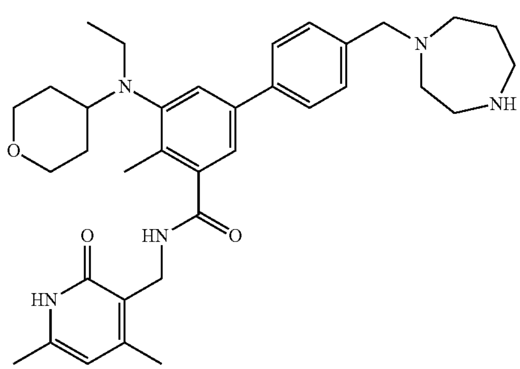 [SMILES: CCN(c1cc(-c2ccc(CN3CCCNCC3)cc2)cc(C(=O)NCc2c(C)cc(C)[nH]c2=O)c1C)C1CCOCC1] | 585.37 |

TABLE 1-continued

| Compound Number | Structure | MS (M + 1)+ |
|---|---|---|
| 87 | 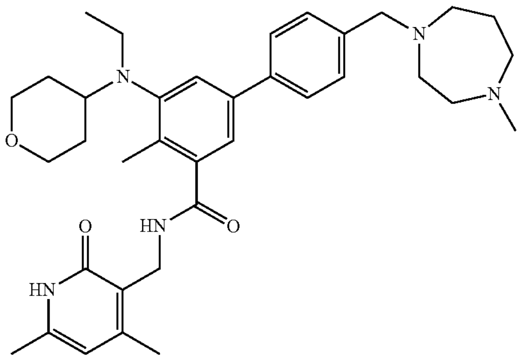 [SMILES: CCN(c1cc(-c2ccc(CN3CCCN(C)CC3)cc2)cc(C(=O)NCc2c(C)cc(C)[nH]c2=O)c1C)C1CCOCC1] | 600.30 |
| 88 | 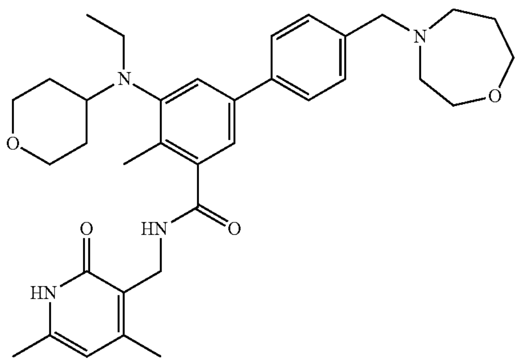 [SMILES: CCN(c1cc(-c2ccc(CN3CCCOCC3)cc2)cc(C(=O)NCc2c(C)cc(C)[nH]c2=O)c1C)C1CCOCC1] | 587.40 |
| 89 | 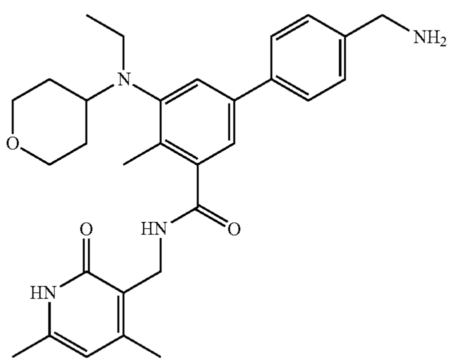 [SMILES: CCN(c1cc(-c2ccc(CN)cc2)cc(C(=O)NCc2c(C)cc(C)[nH]c2=O)c1C)C1CCOCC1] | 503.40 |
| 90 | 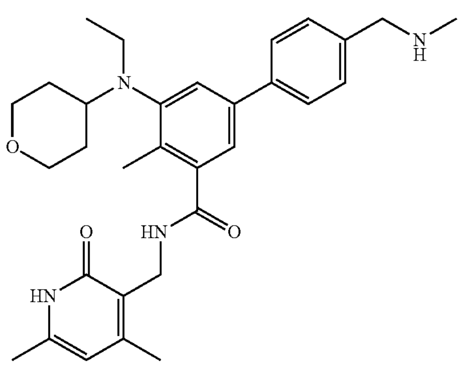 [SMILES: CCN(c1cc(-c2ccc(CNC)cc2)cc(C(=O)NCc2c(C)cc(C)[nH]c2=O)c1C)C1CCOCC1] | 517.30 |

TABLE 1-continued

| Compound Number | Structure | MS (M + 1)+ |
|---|---|---|
| 91 | 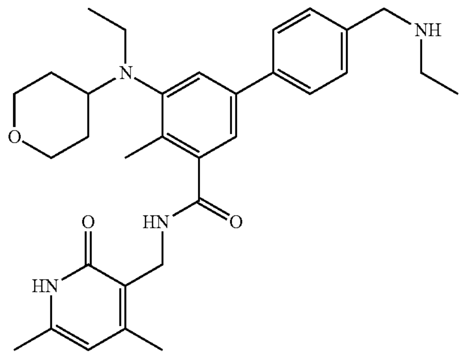 [SMILES: CCNCc1ccc(-c2cc(C(=O)NCc3c(C)cc(C)[nH]c3=O)c(C)c(N(CC)C3CCOCC3)c2)cc1] | 531.35 |
| 92 | 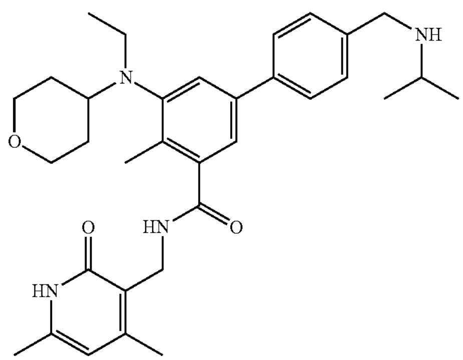 [SMILES: CCN(c1cc(-c2ccc(CNC(C)C)cc2)cc(C(=O)NCc2c(C)cc(C)[nH]c2=O)c1C)C1CCOCC1] | 545.40 |
| 93 | 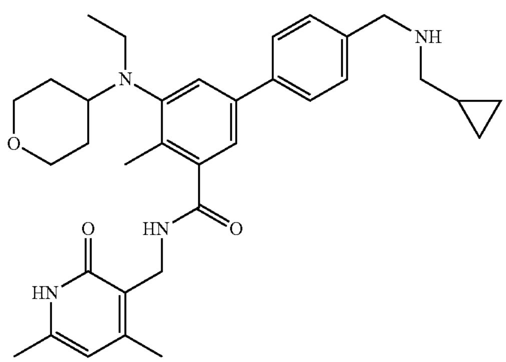 [SMILES: CCN(c1cc(-c2ccc(CNCC3CC3)cc2)cc(C(=O)NCc2c(C)cc(C)[nH]c2=O)c1C)C1CCOCC1] | 557.35 |
| 94 | 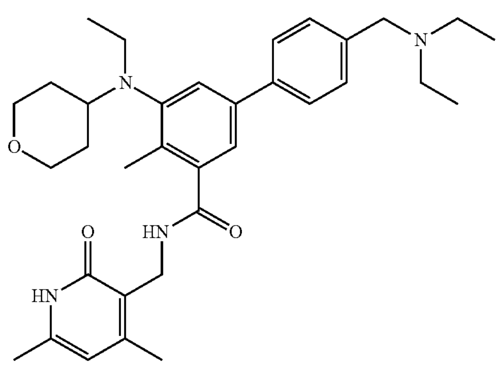 [SMILES: CCN(CC)Cc1ccc(-c2cc(C(=O)NCc3c(C)cc(C)[nH]c3=O)c(C)c(N(CC)C3CCOCC3)c2)cc1] | 559.20 |

TABLE 1-continued
| Compound Number | Structure | MS (M + 1)+ |
|---|---|---|
| 95 | 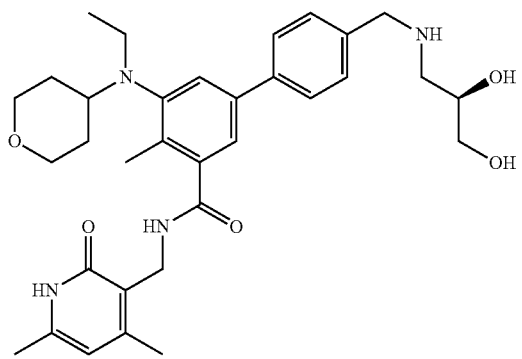 [SMILES: CCN(c1cc(-c2ccc(CNC[C@@H](O)CO)cc2)cc(C(=O)NCc2c(C)cc(C)[nH]c2=O)c1C)C1CCOCC1] | 599.35 (M + Na) |
| 96 | 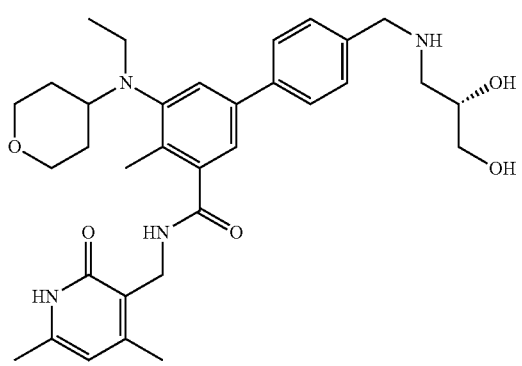 [SMILES: CCN(c1cc(-c2ccc(CNC[C@H](O)CO)cc2)cc(C(=O)NCc2c(C)cc(C)[nH]c2=O)c1C)C1CCOCC1] | 577.25 |
| 97 | 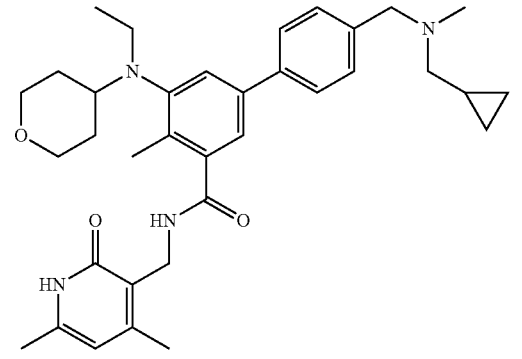 [SMILES: CCN(c1cc(-c2ccc(CN(C)CC3CC3)cc2)cc(C(=O)NCc2c(C)cc(C)[nH]c2=O)c1C)C1CCOCC1] | 571.40 |
| 98 | 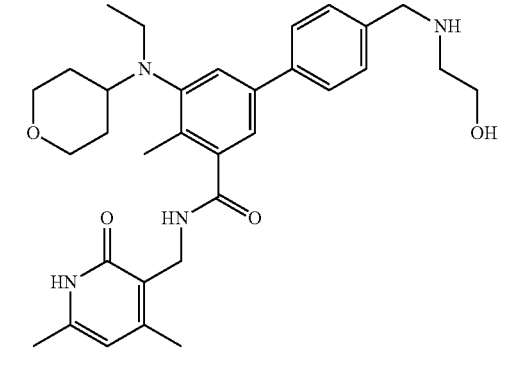 [SMILES: CCN(c1cc(-c2ccc(CNCCO)cc2)cc(C(=O)NCc2c(C)cc(C)[nH]c2=O)c1C)C1CCOCC1] | 547.35 |

TABLE 1-continued

| Compound Number | Structure | MS (M + 1)+ |
|---|---|---|
| 99 | 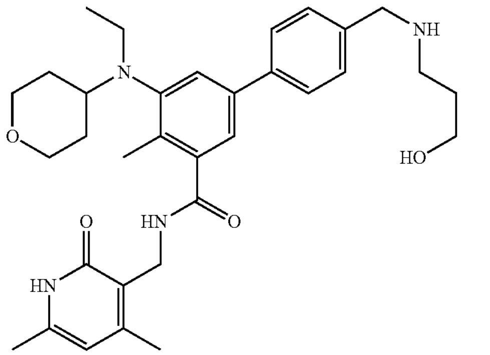 [SMILES: CCN(c1cc(-c2ccc(CNCCCO)cc2)cc(C(=O)NCc2c(C)cc(C)[nH]c2=O)c1C)C1CCOCC1] | 561.30 |
| 100 | 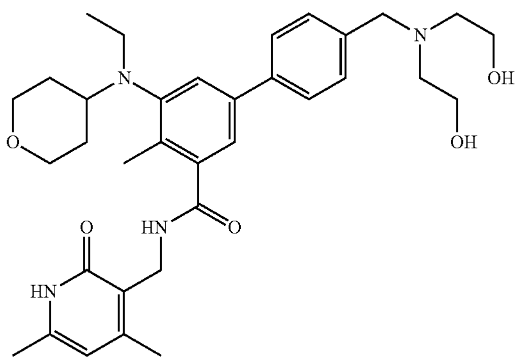 [SMILES: CCN(c1cc(-c2ccc(CN(CCO)CCO)cc2)cc(C(=O)NCc2c(C)cc(C)[nH]c2=O)c1C)C1CCOCC1] | 591.25 |
| 101 | 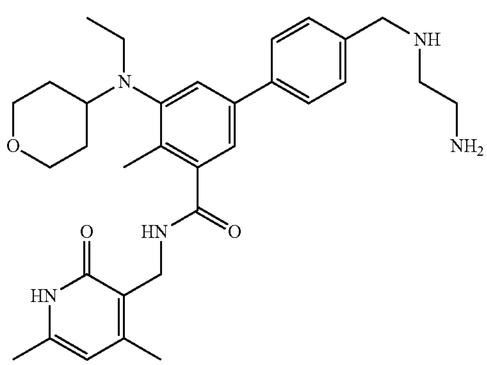 [SMILES: CCN(c1cc(-c2ccc(CNCCN)cc2)cc(C(=O)NCc2c(C)cc(C)[nH]c2=O)c1C)C1CCOCC1] | 546.35 |
| 102 | 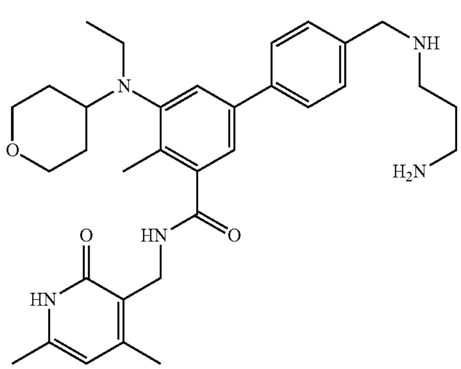 [SMILES: CCN(c1cc(-c2ccc(CNCCCN)cc2)cc(C(=O)NCc2c(C)cc(C)[nH]c2=O)c1C)C1CCOCC1] | 560.20 |

TABLE 1-continued
| Compound Number | Structure | MS (M + 1)+ |
|---|---|---|
| 103 | 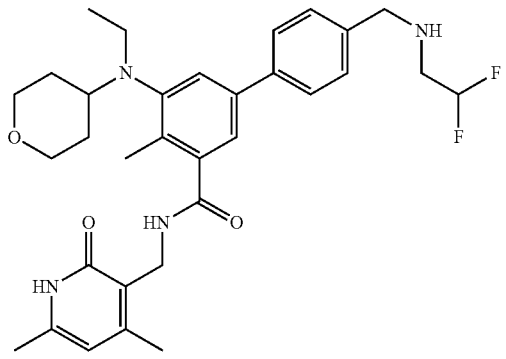 [SMILES: CCN(c1cc(-c2ccc(CNCC(F)F)cc2)cc(C(=O)NCc2c(C)cc(C)[nH]c2=O)c1C)C1CCOCC1] | 567.30 |
| 104 | 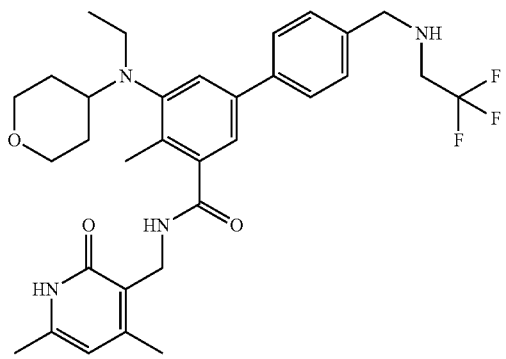 [SMILES: CCN(c1cc(-c2ccc(CNCC(F)(F)F)cc2)cc(C(=O)NCc2c(C)cc(C)[nH]c2=O)c1C)C1CCOCC1] | 585.25 |
| 105 | 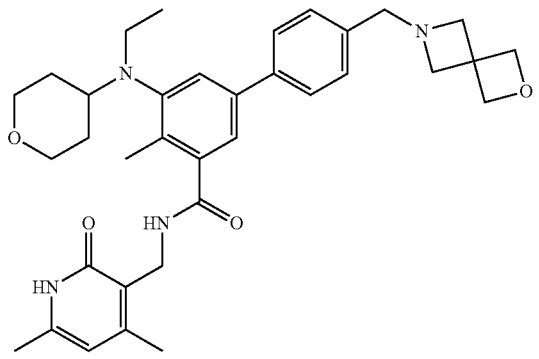 [SMILES: CCN(c1cc(-c2ccc(CN3CC4(COC4)C3)cc2)cc(C(=O)NCc2c(C)cc(C)[nH]c2=O)c1C)C1CCOCC1] | 585.40 |
| 106 | 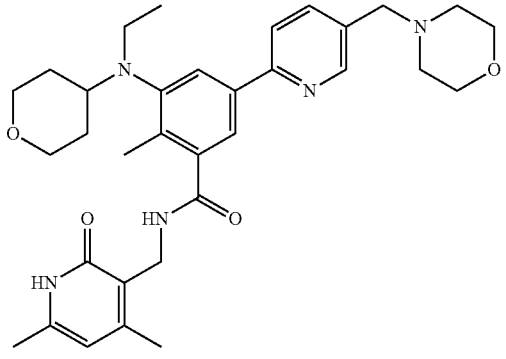 | |

TABLE 1-continued

| Compound Number | Structure | MS (M + 1)+ |
|---|---|---|
| 107 | 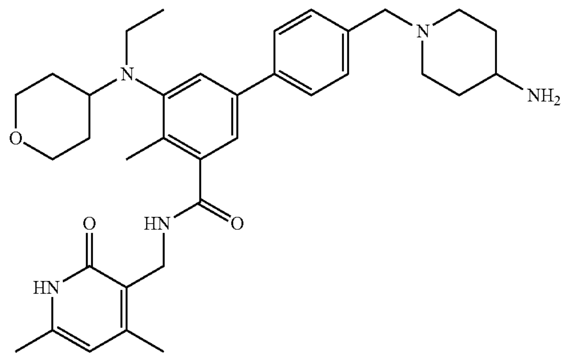 [SMILES: CCN(c1cc(-c2ccc(CN3CCC(N)CC3)cc2)cc(C(=O)NCc2c(C)cc(C)[nH]c2=O)c1C)C1CCOCC1] | |
| 108 | 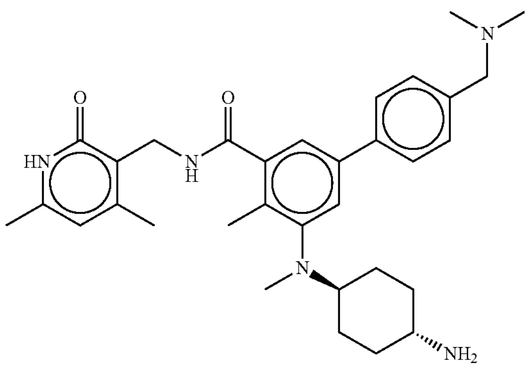 | 530.35 |
| 109 | 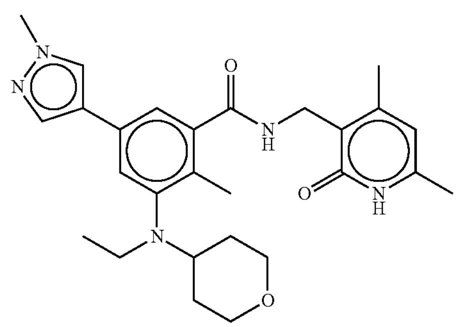 | 578.20 |
| 110 | 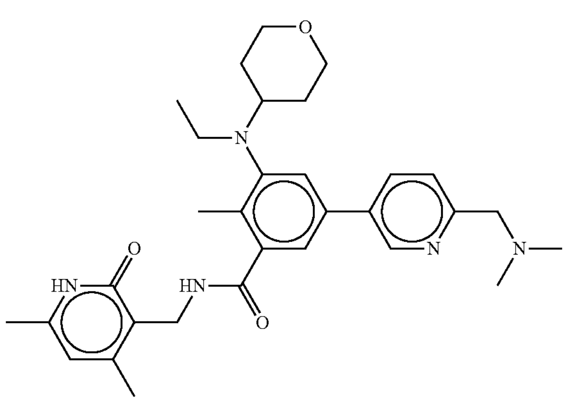 | 532.30 |

TABLE 1-continued

| Compound Number | Structure | MS (M + 1)+ |
|---|---|---|
| 111 | 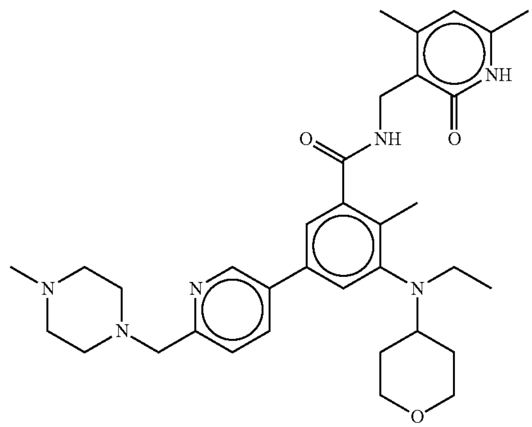 | 587.40 |
| 112 | 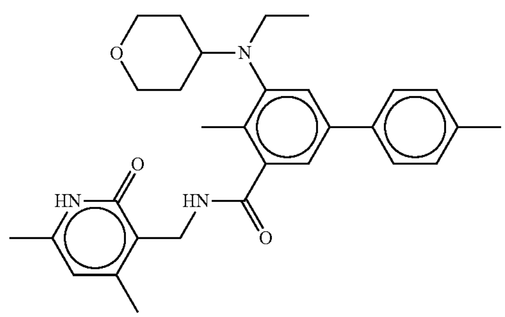 | 488.20 |
| 113 | 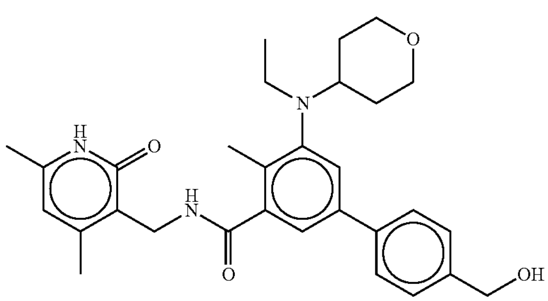 | 504.15 |
| 114 | 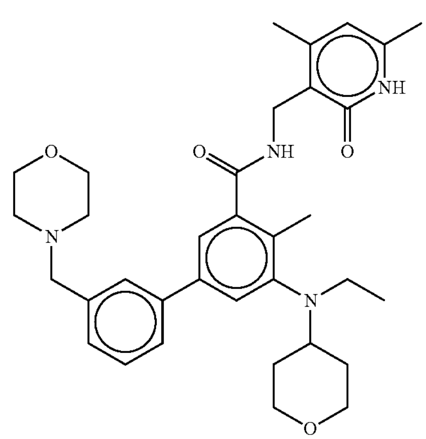 | 573.25 |

TABLE 1-continued

| Compound Number | Structure | MS (M + 1)+ |
|---|---|---|
| 115 | 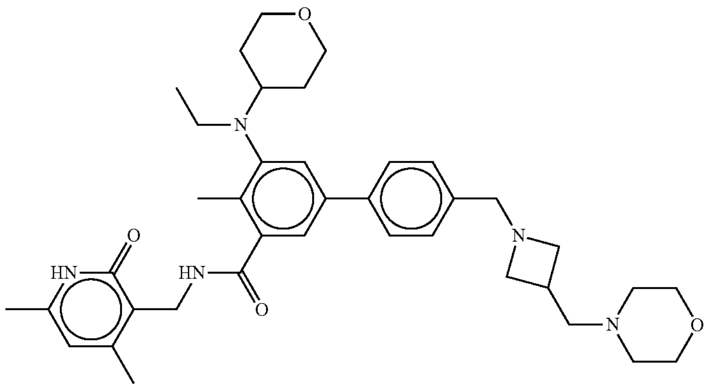 | 642.45 |
| 116 | 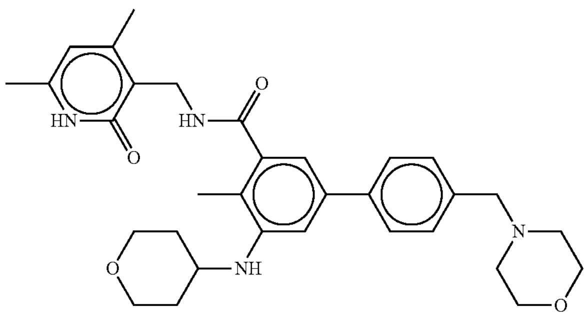 | 545.15 |
| 117 | 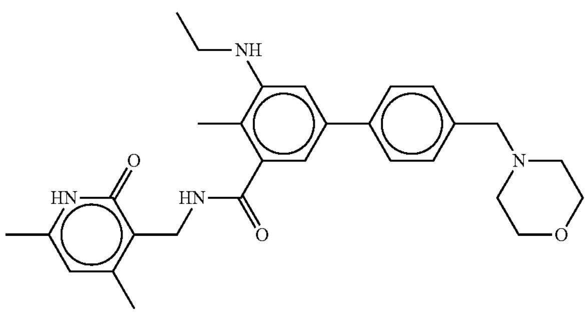 | 489.20 |
| 118 | 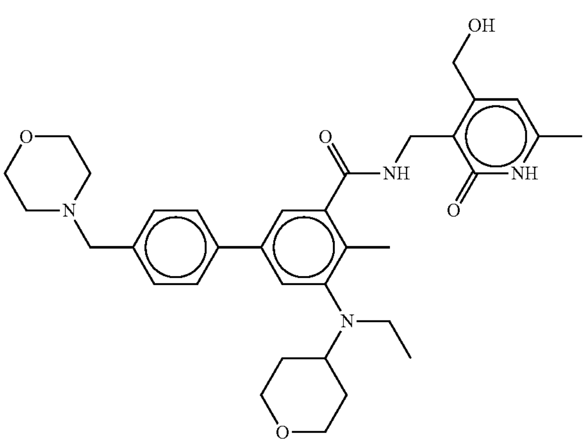 | 589.35 |

TABLE 1-continued

| Compound Number | Structure | MS (M + 1)+ |
|---|---|---|
| 119 | 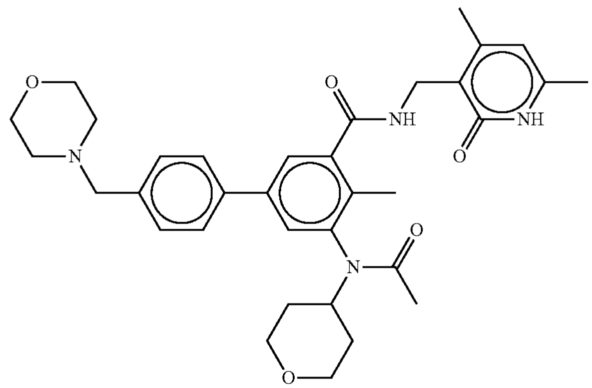 | 609.35 |
| 120 | 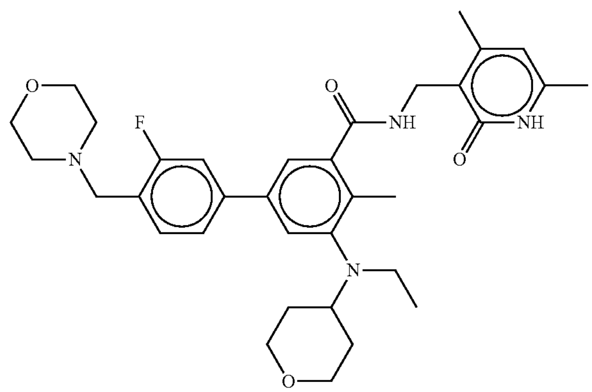 | 591.45 |
| 121 | 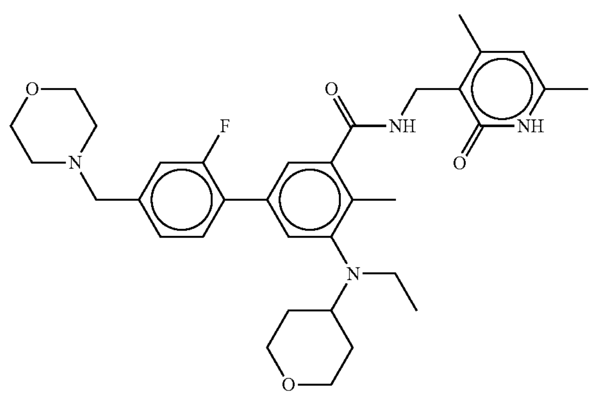 | 591.30 |
| 122 | 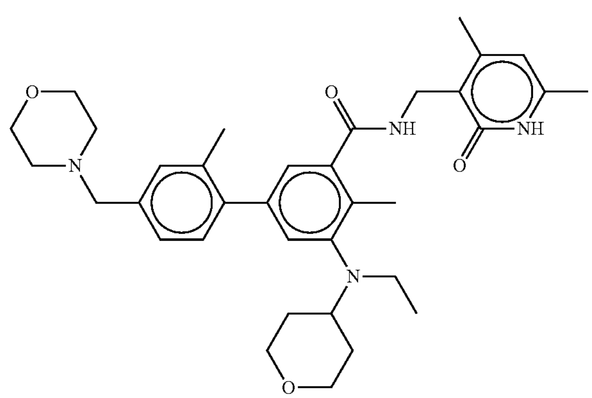 | 587.55 |

TABLE 1-continued

| Compound Number | Structure | MS (M + 1)+ |
|---|---|---|
| 123 | 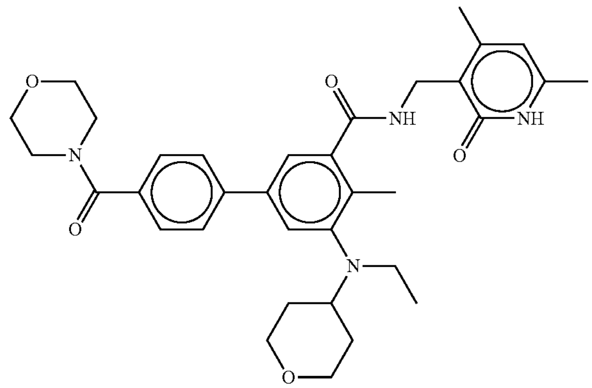 | 587.35 |
| 124 | 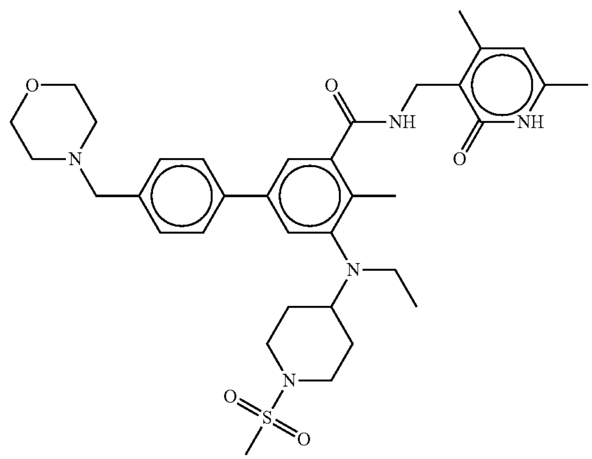 | 650.85 |
| 125 | 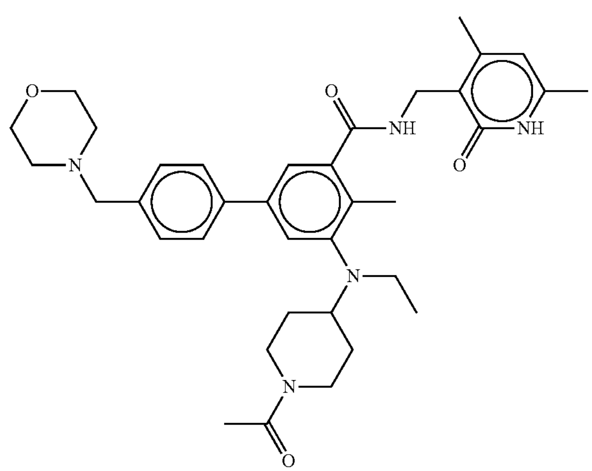 | 614.75 |

TABLE 1-continued

| Compound Number | Structure | MS (M + 1)+ |
|---|---|---|
| 126 | 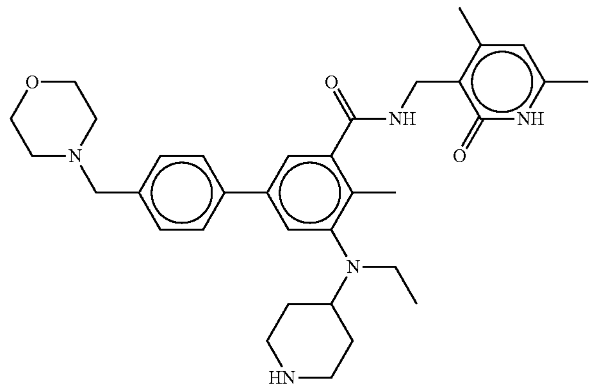 | 572.35 |
| 127 | 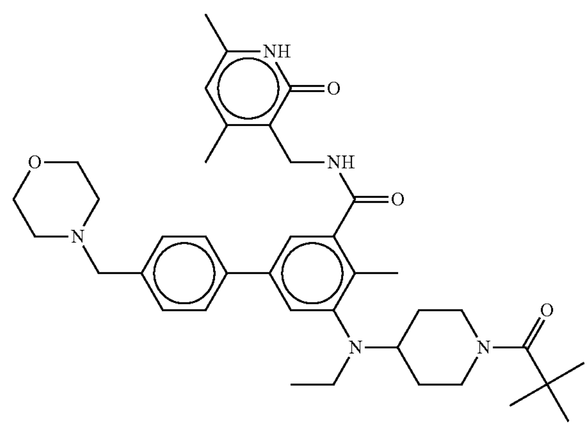 | 656.65 |
| 128 | 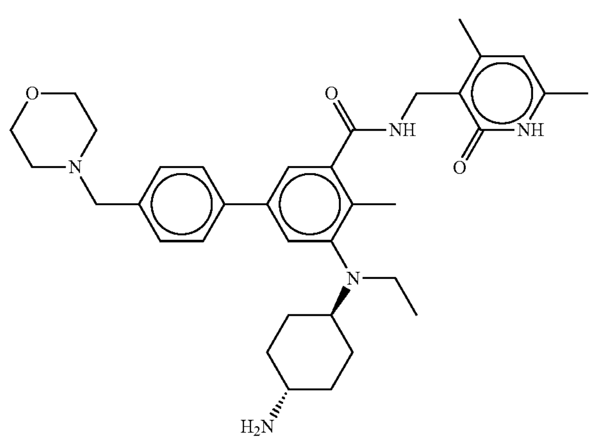 | 586.45 |

TABLE 1-continued

| Compound Number | Structure | MS (M + 1)+ |
|---|---|---|
| 129 | 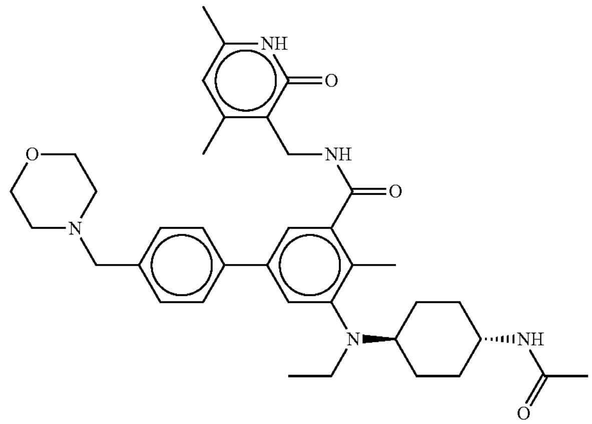 | 628.35 |
| 130 | 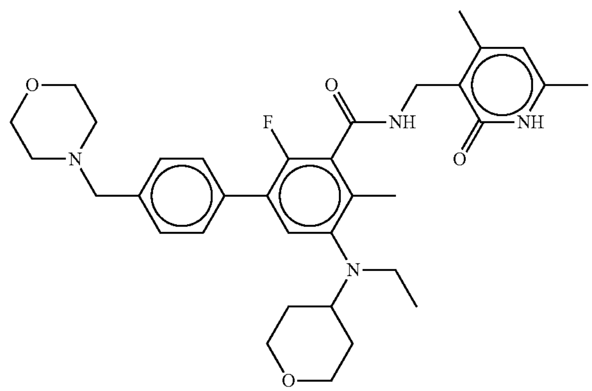 | 591.2 |
| 131 | 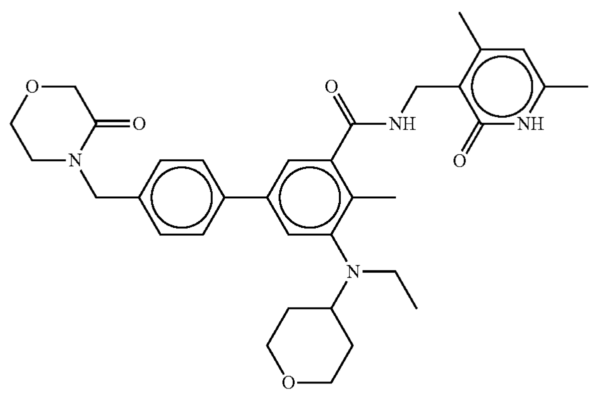 | 587.35 |
| 132 | 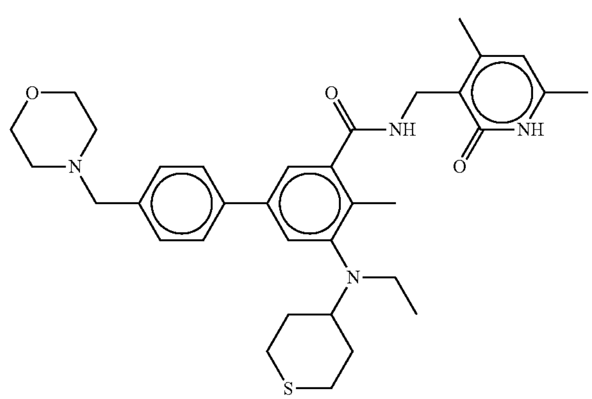 | 589.25 |

TABLE 1-continued

| Compound Number | Structure | MS (M + 1)+ |
|---|---|---|
| 133 | 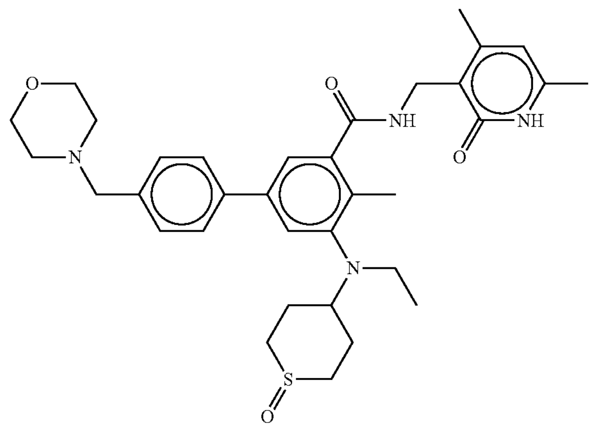 | 605.25 |
| 134 | 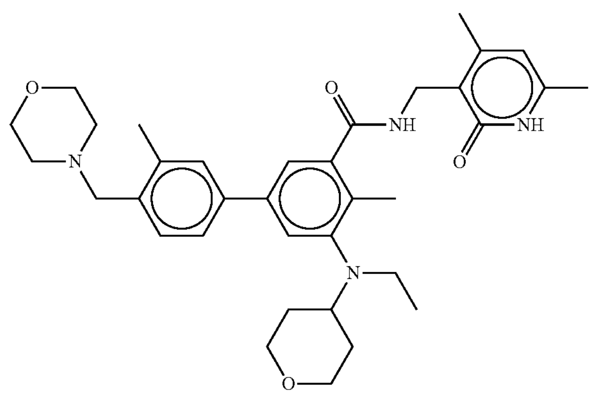 | 587.4 |
| 135 | 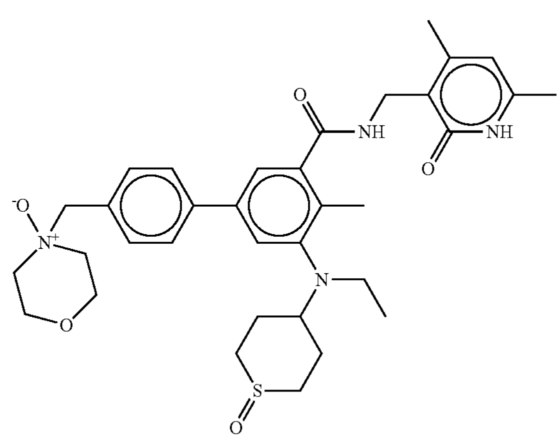 | 621.40 |

TABLE 1-continued

| Compound Number | Structure | MS (M + 1)+ |
|---|---|---|
| 136 | 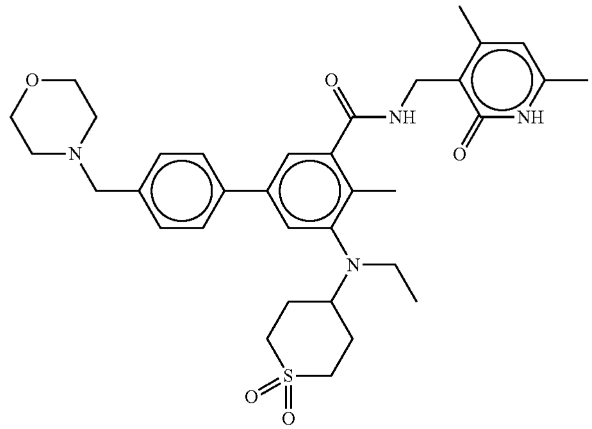 | 621.45 |
| 137 | 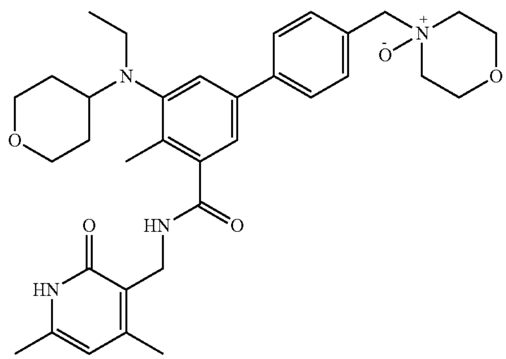 | 589.35 |
| 138 | 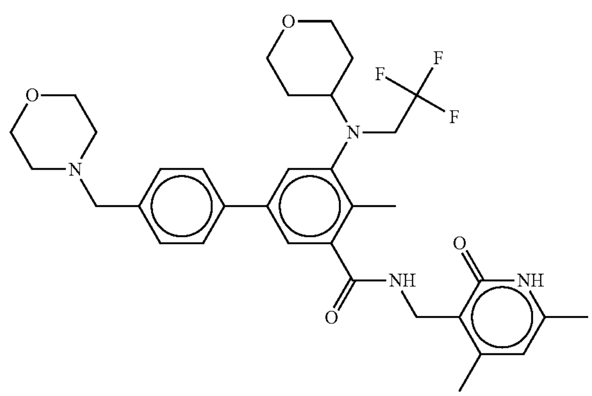 | 627.5 |
| 139 | 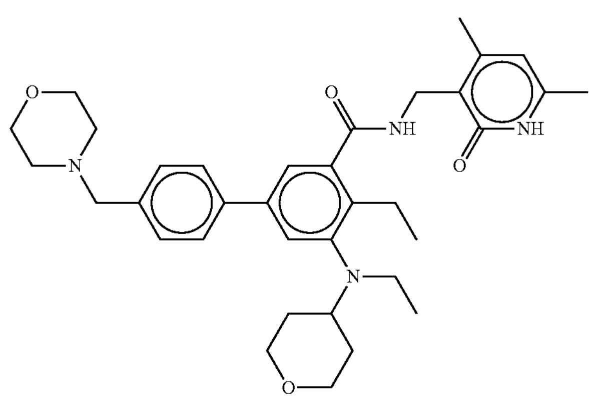 | 294.3 (M + H)/2 |

TABLE 1-continued

| Compound Number | Structure | MS (M + 1)⁺ |
|---|---|---|
| 140 | 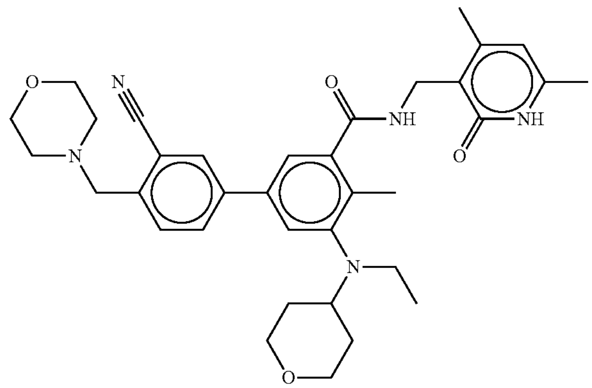 | 598.20 |
| 141 | 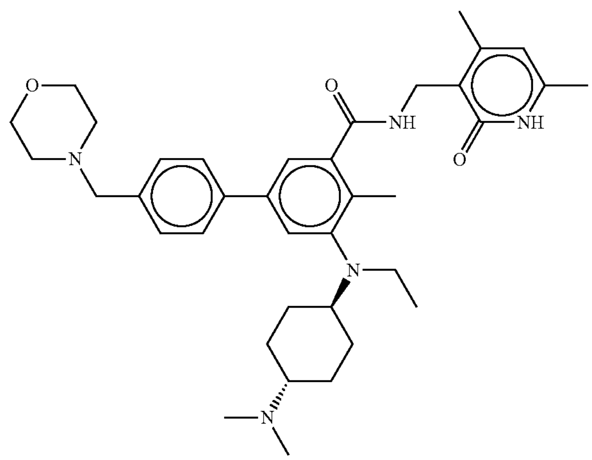 | 614.65 |
| 142 | 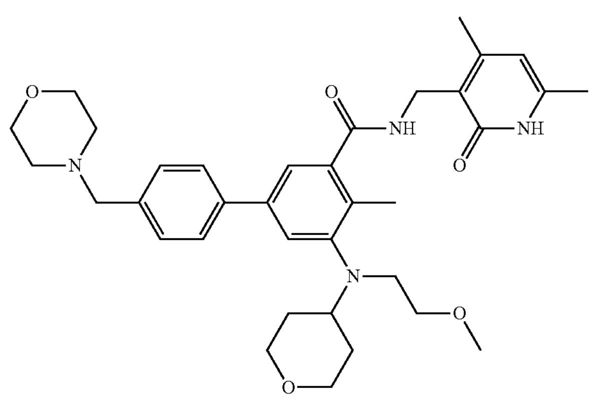 [SMILES: COCCN(c1cc(-c2ccc(CN3CCOCC3)cc2)cc(C(=O)NCc2c(C)cc(C)[nH]c2=O)c1C)C1CCOCC1] | 603.45 |

TABLE 1-continued

| Compound Number | Structure | MS (M + 1)+ |
| --- | --- | --- |
| 143 | 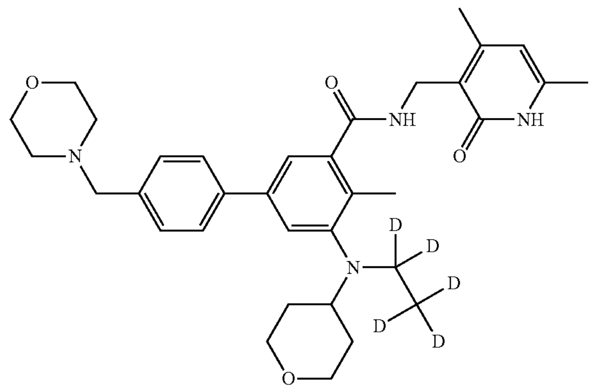 [SMILES: [2H]C([2H])([2H])C([2H])([2H])N(c1cc(-c2ccc(CN3CCOCC3)cc2)cc(C(=O)NCc2c(C)cc(C)[nH]c2=O)c1C)C1CCOCC1] | 578.35 |
| 144 | 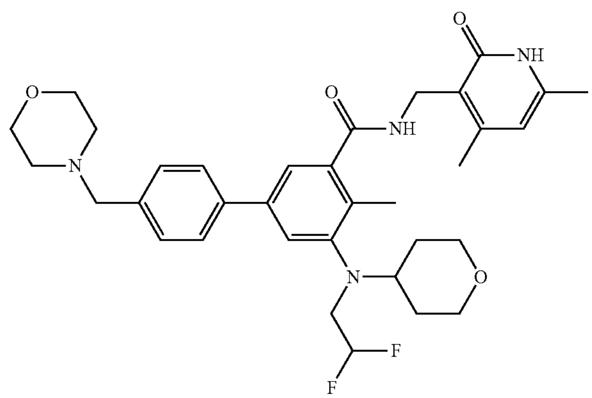 [SMILES: Cc1cc(C)c(CNC(=O)c2cc(-c3ccc(CN4CCOCC4)cc3)cc(N(CC(F)F)C3CCOCC3)c2C)c(=O)[nH]1] | 609.15 |
| 145 | 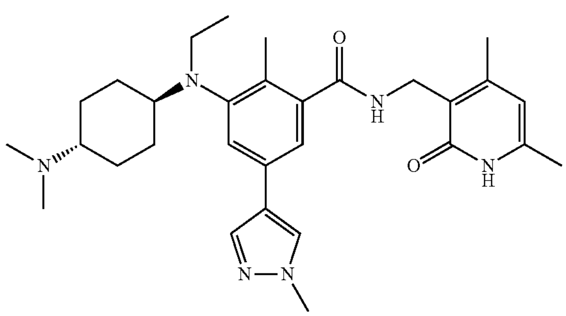 | 519.40 |
| 146 | 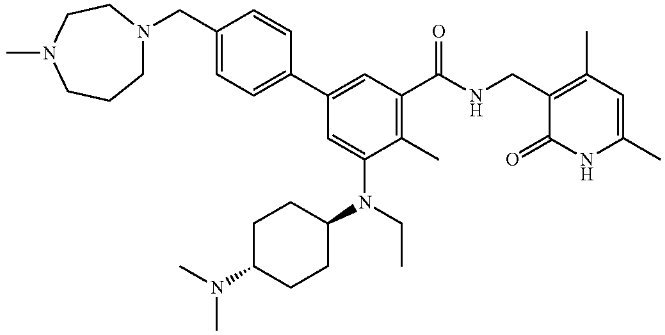 | 641.50 |

TABLE 1-continued
| Compound Number | Structure | MS (M + 1)+ |
|---|---|---|
| 147 | 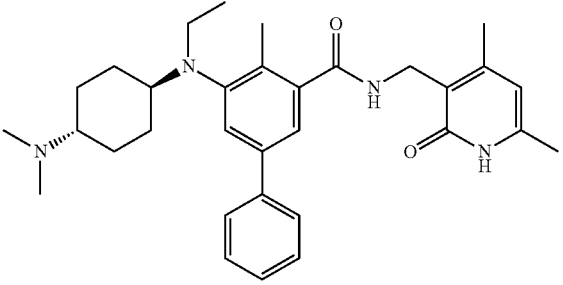 | 515.45 |
| 148 | 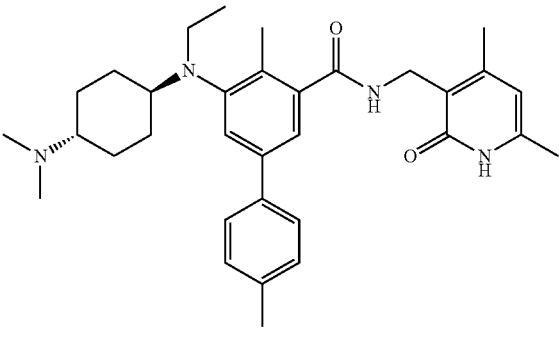 | 529.40 |
| 149 | 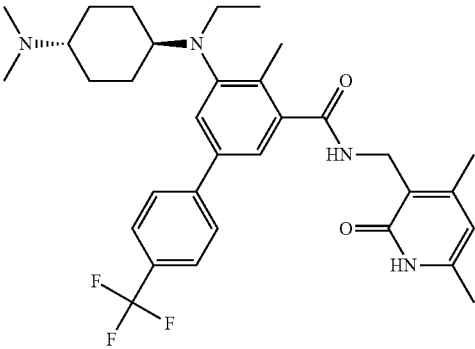 | 583.45 |
| 150 | 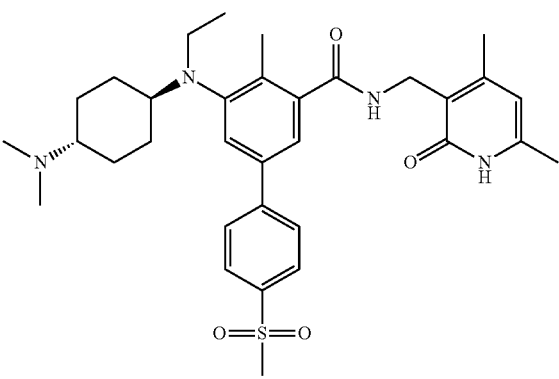 | 593.45 |

TABLE 1-continued

| Compound Number | Structure | MS (M + 1)+ |
|---|---|---|
| 151 | 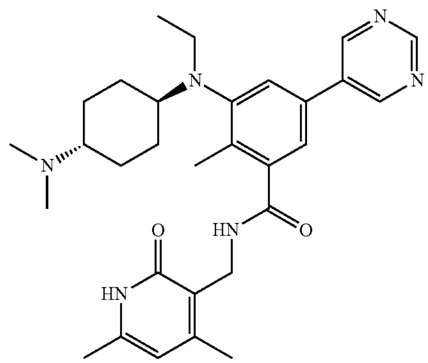 [SMILES: CCN(c1cc(-c2cncnc2)cc(C(=O)NCc2c(C)cc(C)[nH]c2=O)c1C)[C@H]1CC[C@H](N(C)C)CC1] | 517.60 |
| 152 | 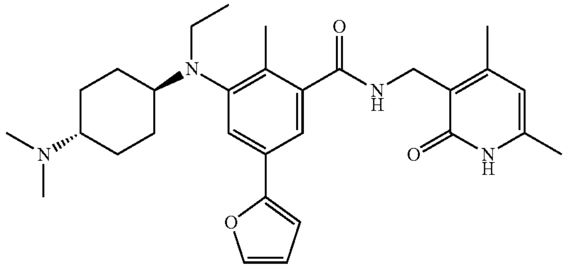 | 505.55 |
| 153 | 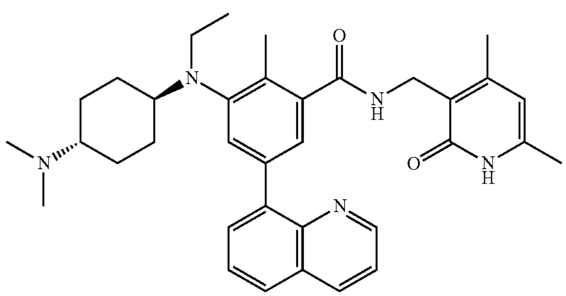 | 566.70 |
| 154 | 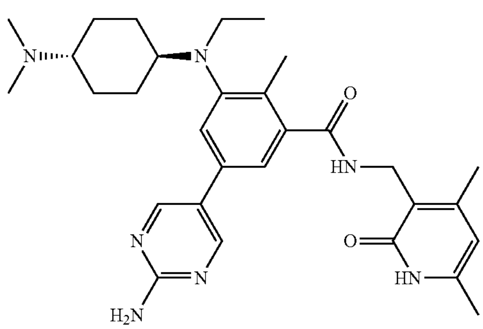 | 532.65 |
| 155 | 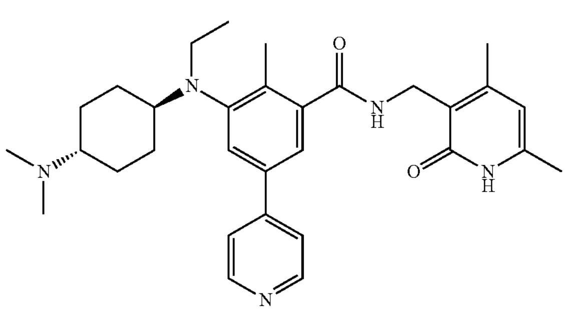 | 516.60 |

TABLE 1-continued

| Compound Number | Structure | MS (M + 1)+ |
|---|---|---|
| 156 | 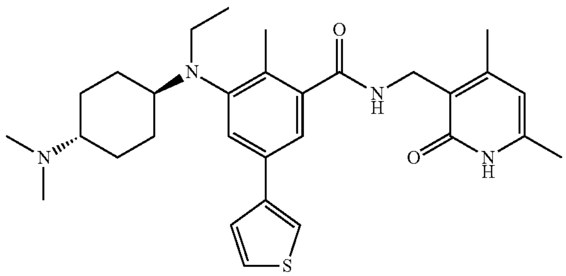 | 521.55 |
| 158 | 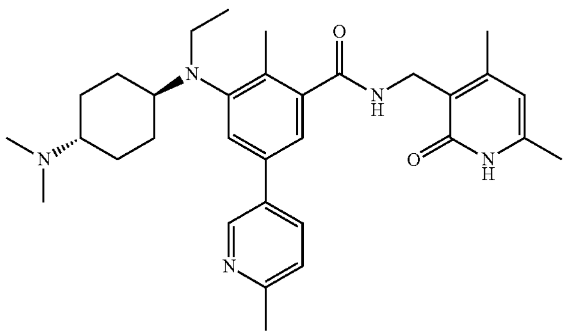 | 530.55 |
| 159 | 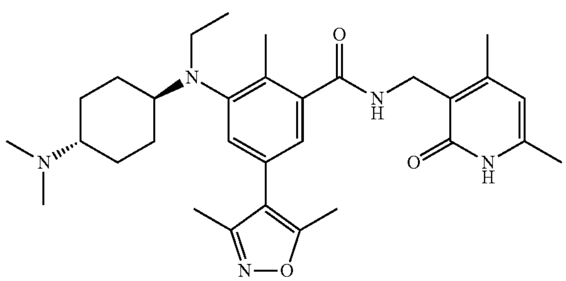 | 534.60 |
| 160 | 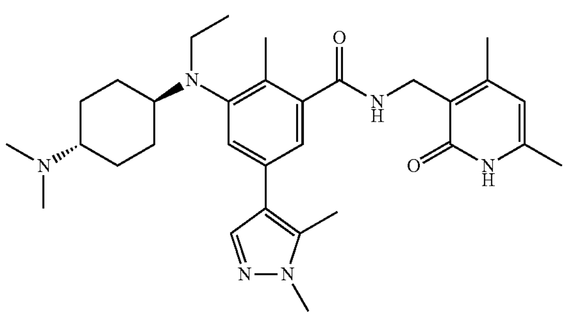 | 533.80 |
| 161 | 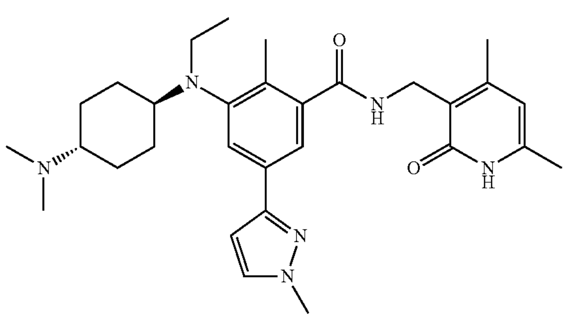 | 519.45 |

TABLE 1-continued

| Compound Number | Structure | MS (M + 1)+ |
|---|---|---|
| 162 | 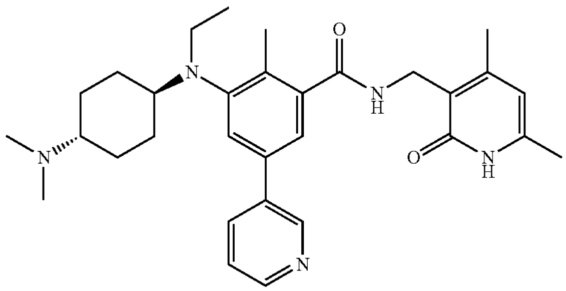 | 516.50 |
| 163 | 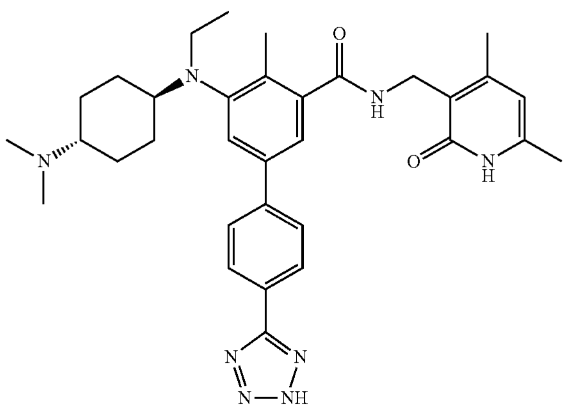 | 583.40 |
| 164 | 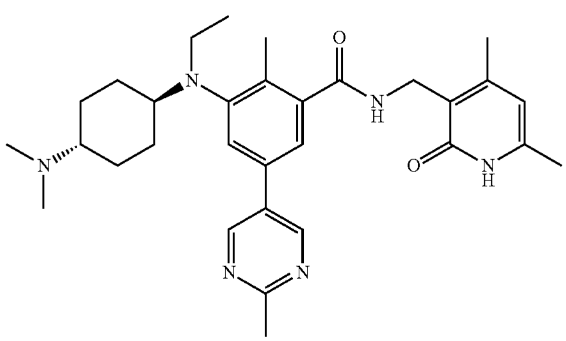 | 531.65 |
| 165 | 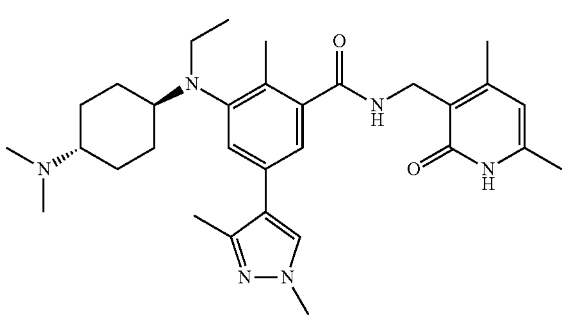 | 533.80 |

TABLE 1-continued
| Compound Number | Structure | MS (M + 1)+ |
|---|---|---|
| 166 | 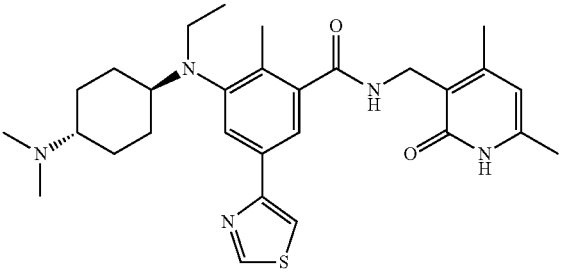 | 522.50 |
| 167 | 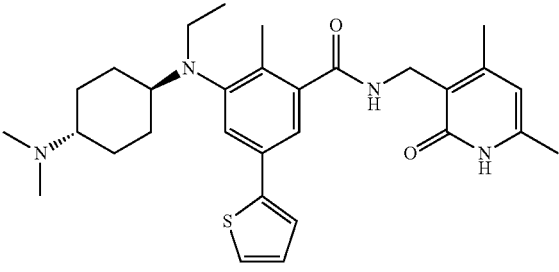 | 521.55 |
| 168 | 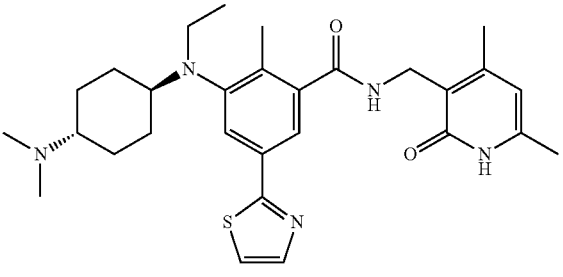 | 522.60 |
| 169 | 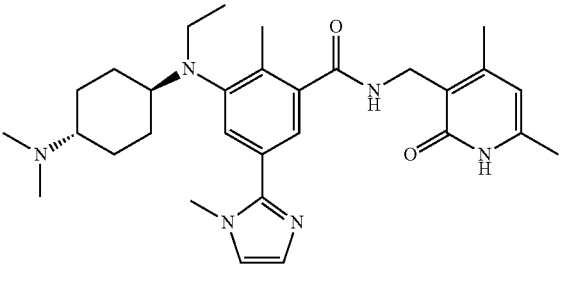 | 519.65 |
| 170 | 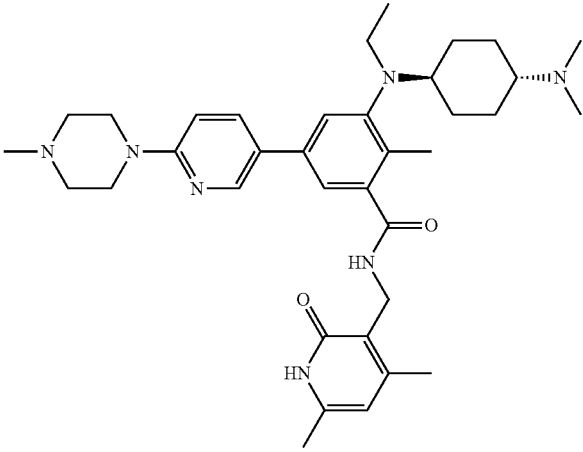 | 614.75 |

TABLE 1-continued

| Compound Number | Structure | MS (M + 1)+ |
|---|---|---|
| 171 | 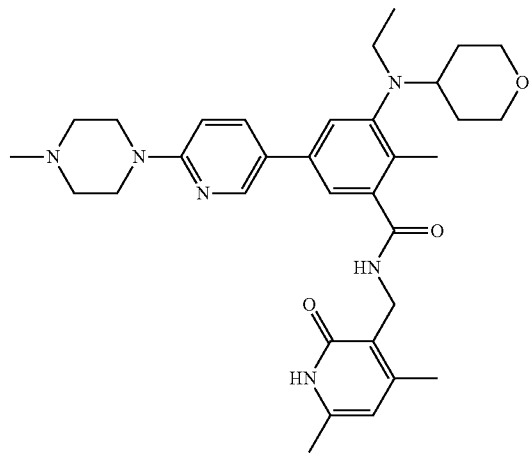 [SMILES: CCN(c1cc(-c2ccc(N3CCN(C)CC3)nc2)cc(C(=O)NCc2c(C)cc(C)[nH]c2=O)c1C)C1CCOCC1] | 573.75 |
| 172 | 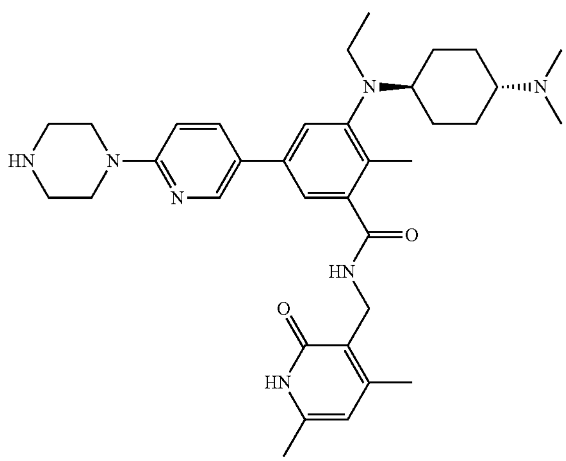 [SMILES: CCN(c1cc(-c2ccc(N3CCNCC3)nc2)cc(C(=O)NCc2c(C)cc(C)[nH]c2=O)c1C)[C@H]1CC[C@H](N(C)C)CC1] | 600.75 |
| 173 | 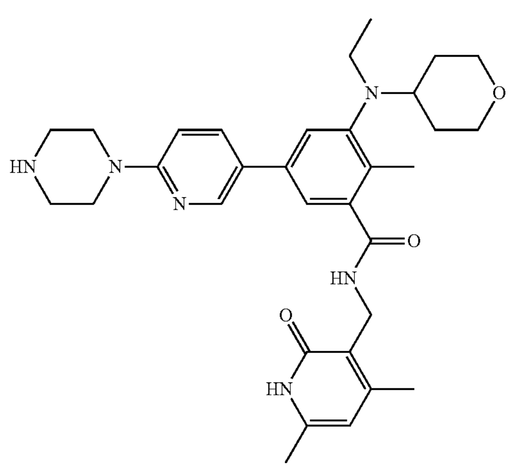 [SMILES: CCN(c1cc(-c2ccc(N3CCNCC3)nc2)cc(C(=O)NCc2c(C)cc(C)[nH]c2=O)c1C)C1CCOCC1] | 559.55 |

TABLE 1-continued

| Compound Number | Structure | MS (M + 1)+ |
|---|---|---|
| 174 | 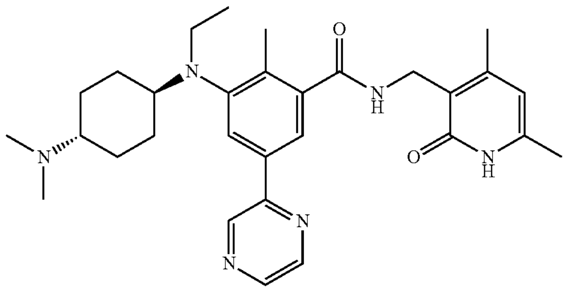 | 517.50 |
| 175 | 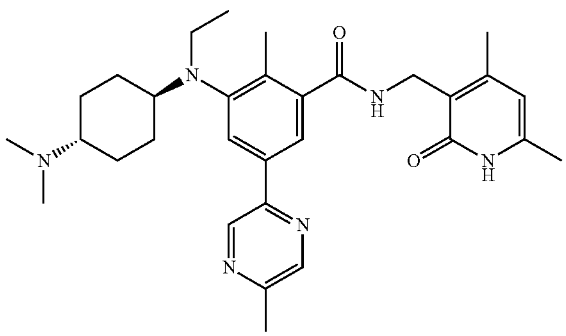 | 531.50 |
| 176 | 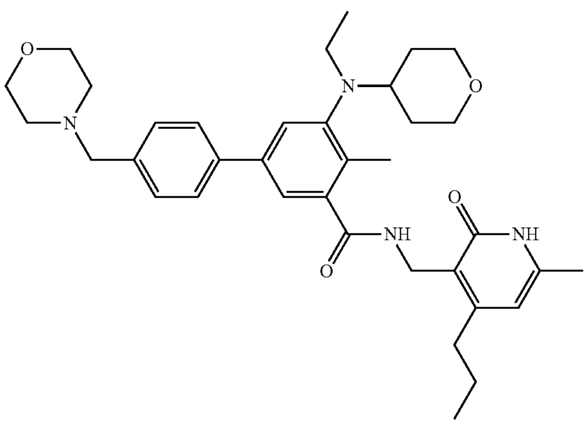 [SMILES: CCCc1cc(C)[nH]c(=O)c1CNC(=O)c1cc(-c2ccc(CN3CCOCC3)cc2)cc(N(CC)C2CCOCC2)c1C] | 601.55 |
| 177 | 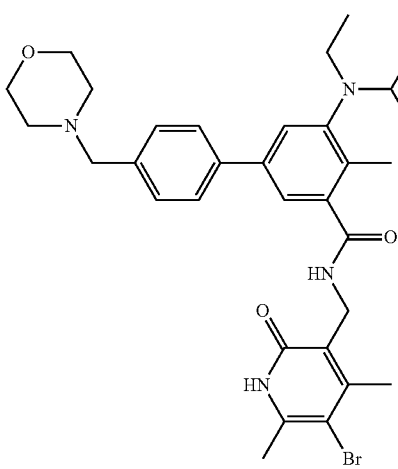 | 653.65 |

TABLE 1-continued

| Compound Number | Structure | MS (M + 1)+ |
|---|---|---|
| 178 | 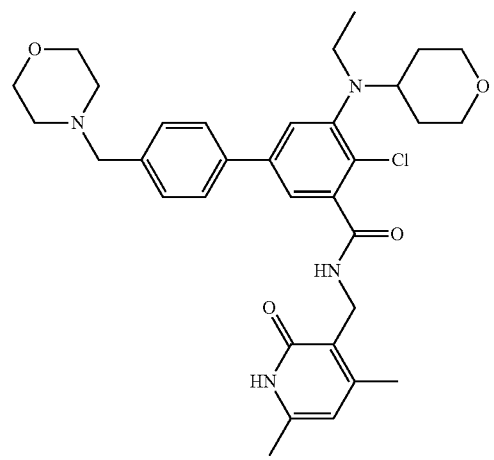 [SMILES: CCN(c1cc(-c2ccc(CN3CCOCC3)cc2)cc(C(=O)NCc2c(C)cc(C)[nH]c2=O)c1Cl)C1CCOCC1] | 593.60 |
| 179 | 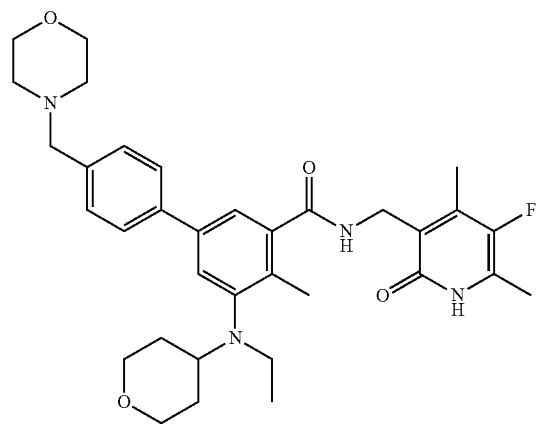 [SMILES: CCN(c1cc(-c2ccc(CN3CCOCC3)cc2)cc(C(=O)NCc2c(C)c(F)c(C)[nH]c2=O)c1C)C1CCOCC1] | 591.2 |
| 180 | 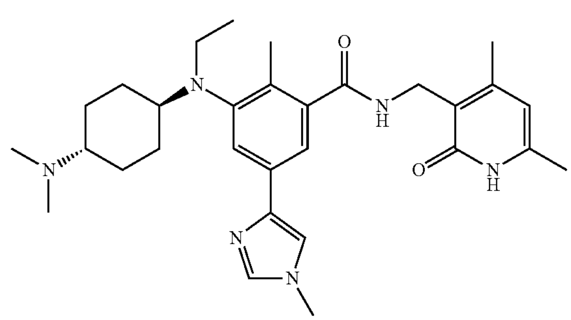 | 519.55 |

TABLE 1-continued

| Compound Number | Structure | MS (M + 1)+ |
|---|---|---|
| 181 | 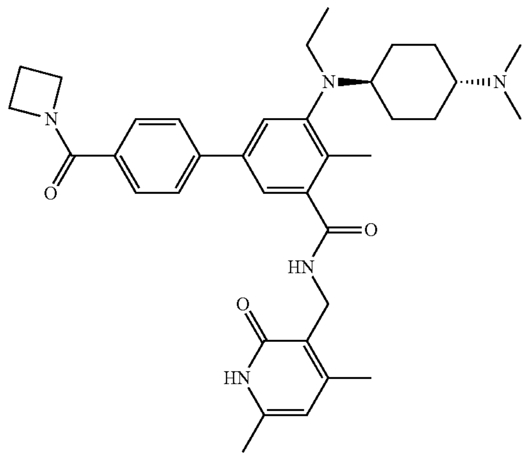 [SMILES: CCN(c1cc(-c2ccc(C(=O)N3CCC3)cc2)cc(C(=O)NCc2c(C)cc(C)[nH]c2=O)c1C)[C@H]1CC[C@H](N(C)C)CC1] | 598.60 |
| 182 | 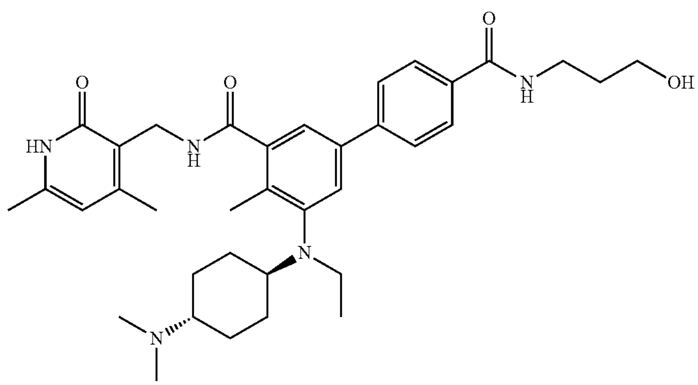 [SMILES: CCN(c1cc(-c2ccc(C(=O)NCCCO)cc2)cc(C(=O)NCc2c(C)cc(C)[nH]c2=O)c1C)[C@H]1CC[C@H](N(C)C)CC1] | 617.70 |
| 183 | 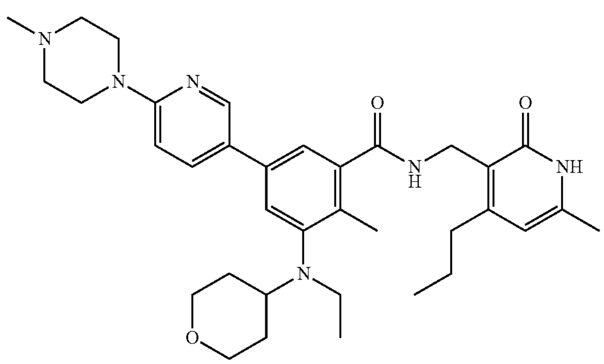 | 601.65 |
| 184 | 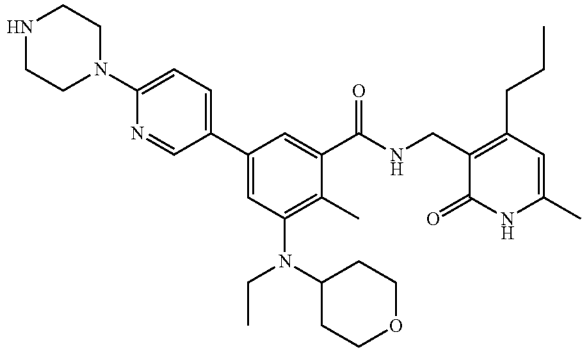 [SMILES: CCCc1cc(C)[nH]c(=O)c1CNC(=O)c1cc(-c2ccc(N3CCNCC3)nc2)cc(N(CC)C2CCOCC2)c1C] | 587.55 |

TABLE 1-continued

| Compound Number | Structure | MS (M + 1)+ |
|---|---|---|
| 185 | 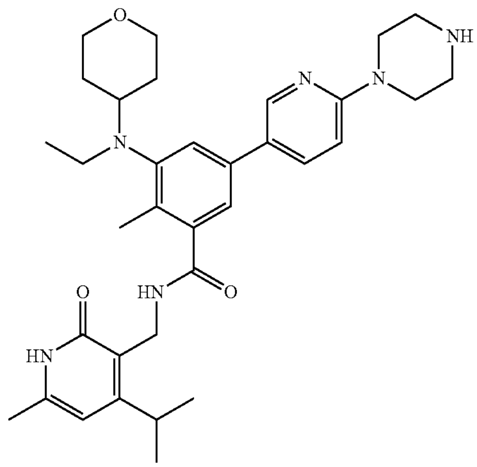 [SMILES: CCN(c1cc(-c2ccc(N3CCNCC3)nc2)cc(C(=O)NCc2c(C(C)C)cc(C)[nH]c2=O)c1C)C1CCOCC1] | 586.36 |
| 186 | 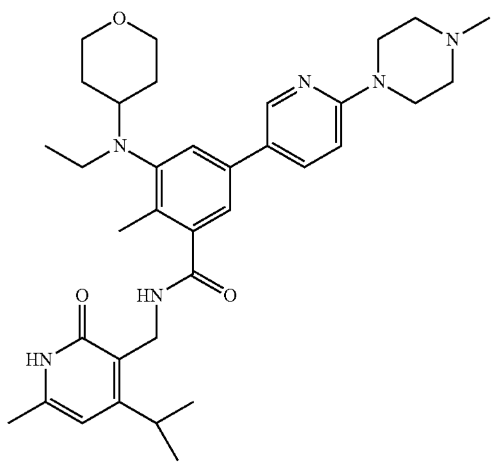 | 601.55 |
| 187 | 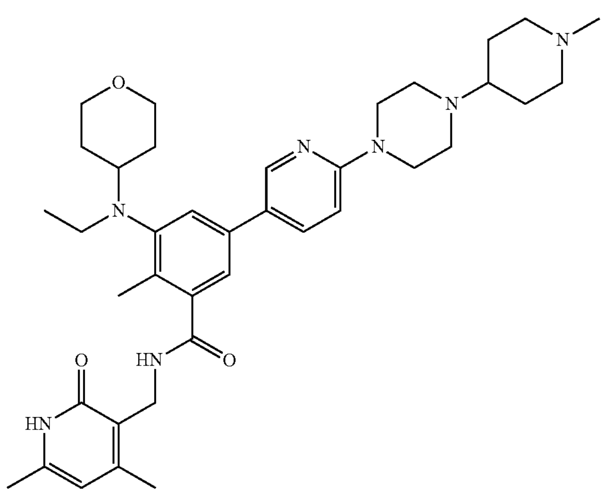 | 656.41 |

TABLE 1-continued
| Compound Number | Structure | MS (M + 1)+ |
|---|---|---|
| 188 | 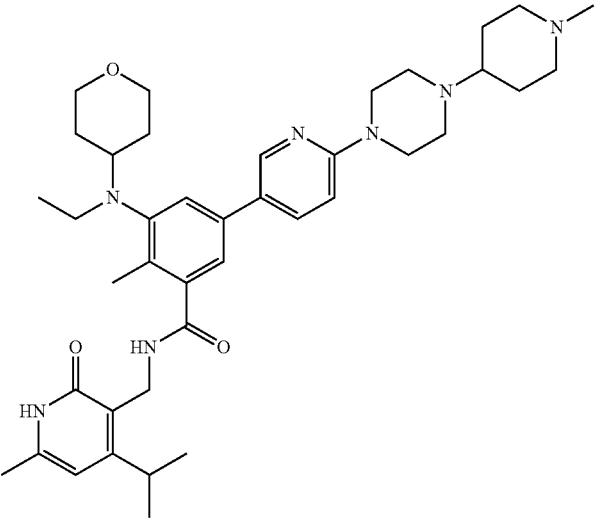 | 683.45 |
| 189 | 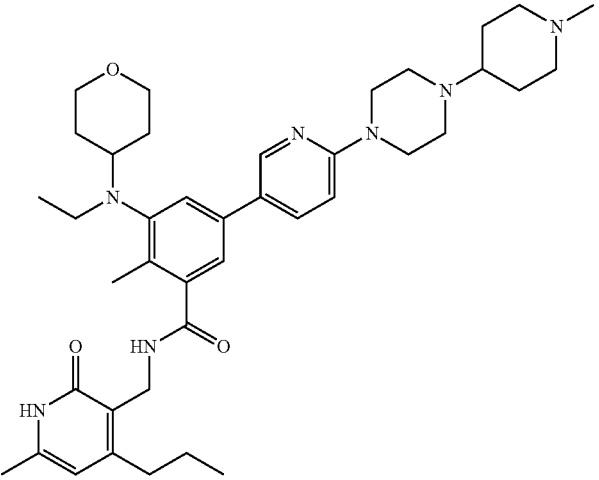 | 684.45 |
| 190 | 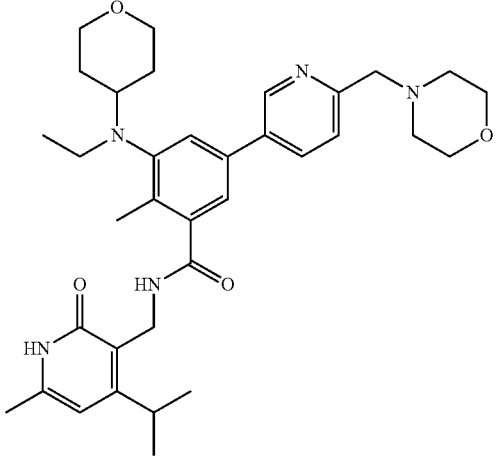 [SMILES: CCN(c1cc(-c2ccc(CN3CCOCC3)nc2)cc(C(=O)NCc2c(C(C)C)cc(C)[nH]c2=O)c1C)C1CCOCC1] | 601.36 |

TABLE 1-continued

| Compound Number | Structure | MS (M + 1)+ |
|---|---|---|
| 191 | 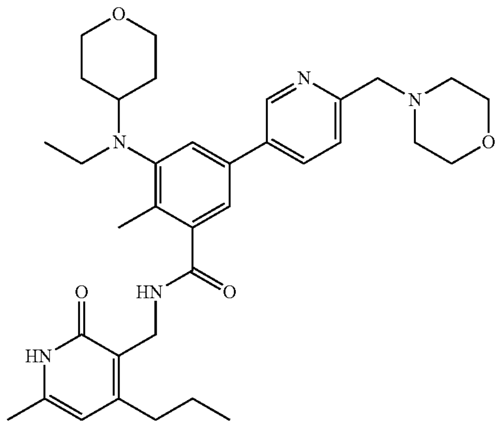 [SMILES: CCCc1cc(C)[nH]c(=O)c1CNC(=O)c1cc(-c2ccc(CN3CCOCC3)nc2)cc(N(CC)C2CCOCC2)c1C] | 602.60 |
| 192 | 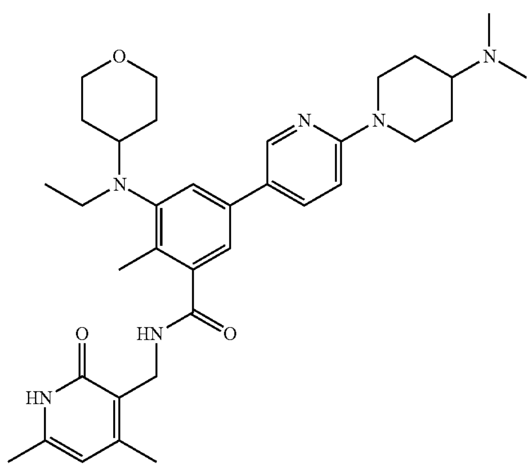 | 602.00 |
| 193 | 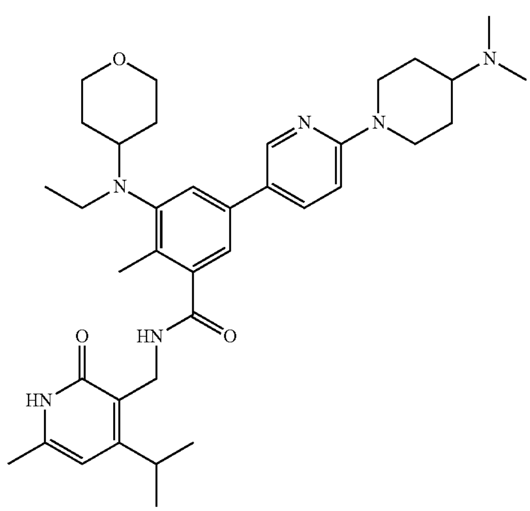 | 629.70 |

TABLE 1-continued

| Compound Number | Structure | MS (M + 1)+ |
|---|---|---|
| 194 | 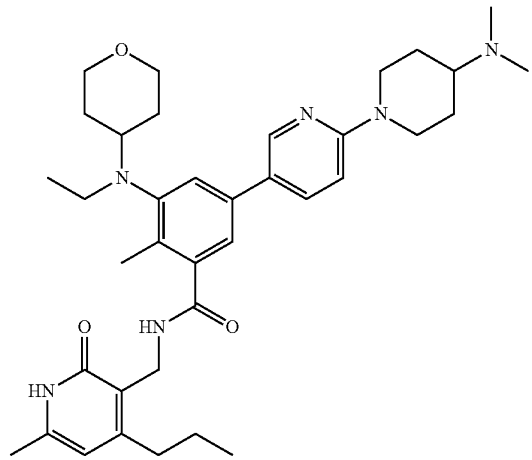 | 630.00 |
| 195 | 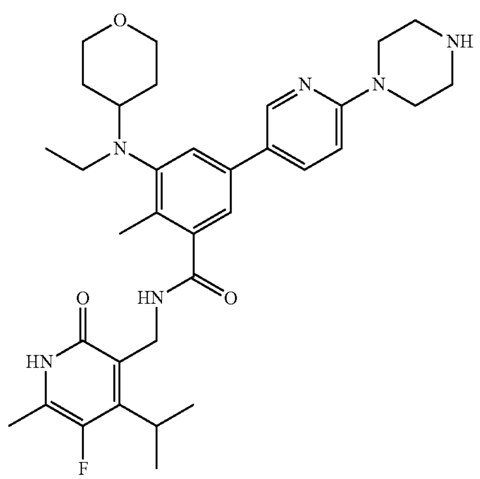 [SMILES: CCN(c1cc(-c2ccc(N3CCNCC3)nc2)cc(C(=O)NCc2c(C(C)C)c(F)c(C)[nH]c2=O)c1C)C1CCOCC1] | 605.6 |
| 196 | 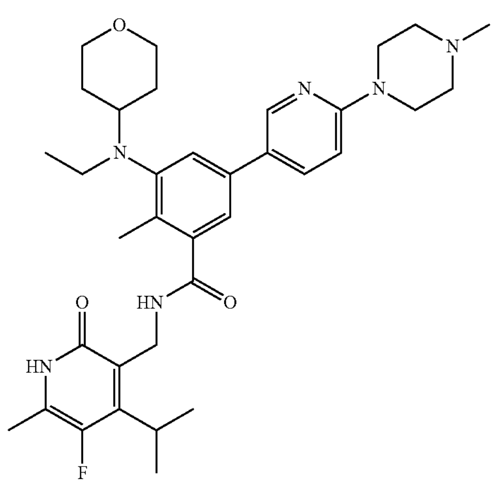 | 619.7 |

TABLE 1-continued

| Compound Number | Structure | MS (M + 1)+ |
|---|---|---|
| 197 | 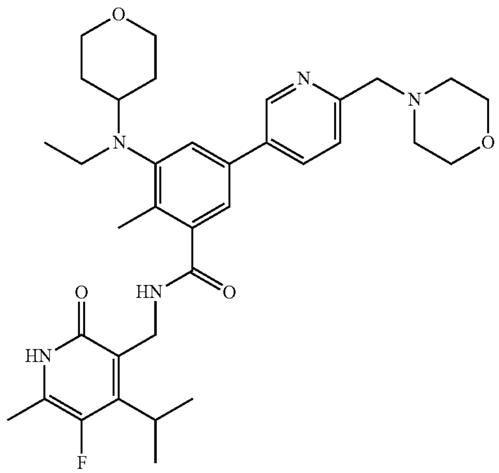 [SMILES: CCN(c1cc(-c2ccc(CN3CCOCC3)nc2)cc(C(=O)NCc2c(C(C)C)c(F)c(C)[nH]c2=O)c1C)C1CCOCC1] | 620.6 |
| 198 | 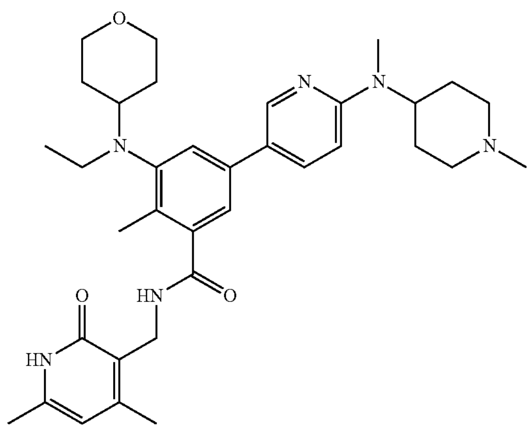 | |
| 199 | 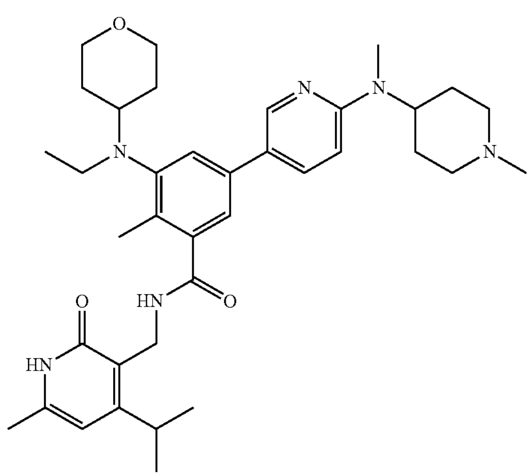 | |

| Compound Number | Structure | MS (M + 1)+ |
|---|---|---|
| 200 | 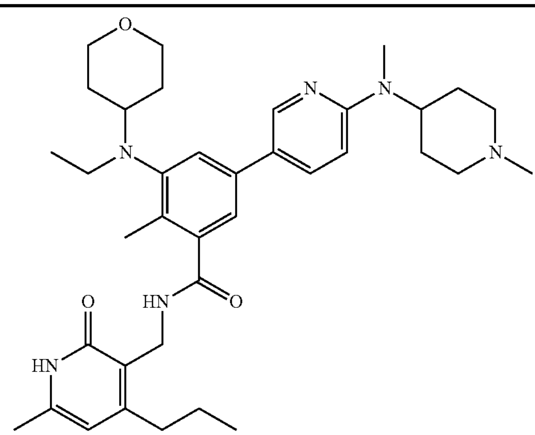 | |

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl and the like.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g. 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N—O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" or "heterocyclic group" includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or —O⁻.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxy acid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted —NH$_2$. "Alkylamino" includes groups of compounds wherein nitrogen of —NH$_2$ is bound to at least one alkyl group. Examples of alkylamino groups include benzylamino, methylamino, ethylamino, phenethylamino, etc. "Dialkylamino" includes groups wherein the nitrogen of —NH$_2$ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

Compounds of the present invention that contain nitrogens can be converted to N-oxides by treatment with an oxidizing agent (e.g., 3-chloroperoxybenzoic acid (mCPBA) and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or N$^+$—O$^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted C$_1$-C$_6$ alkyl, C$_1$-C$_6$ alkenyl, C$_1$-C$_6$ alkynyl, 3-14-membered carbocycle or 3-14-membered heterocycle) derivatives.

In the present specification, the structural formula of the compound represents a certain isomer for convenience in some cases, but the present invention includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951

(London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms, it being understood that not all isomers may have the same level of activity.

Furthermore, the structures and other compounds discussed in this invention include all atropic isomers thereof, it being understood that not all atropic isomers may have the same level of activity. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyridin-2(1H)-ones and the corresponding pyridin-2-ols, as shown below.

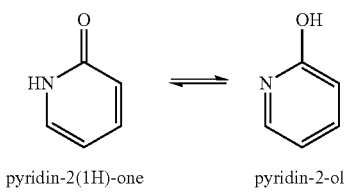 [SMILES: O=c1cccc[nH]1 ; Oc1ccccn1]

pyridin-2(1H)-one      pyridin-2-ol

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form. It will be understood that certain tautomers may have a higher level of activity than others.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The compounds of any of Formulae disclosed herein include the compounds themselves, as well as their salts, their esters, their solvates, and their prodrugs, if applicable. A salt, for example, can be formed between an anion and a positively charged group (e.g., amino) on an aryl- or heteroaryl-substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on an aryl- or heteroaryl-substituted benzene compound. Suitable cations include sodium ion, potassium ion, magnesium ion, calcium ion, and an ammonium cation such as tetramethylammonium ion. The aryl- or heteroaryl-substituted benzene compounds also include those salts containing quaternary nitrogen atoms. Examples of prodrugs include esters and other pharmaceutically acceptable derivatives, which, upon administration to a subject, are capable of providing active aryl- or heteroaryl-substituted benzene compounds.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are aryl- or heteroaryl-substituted benzene compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, Chem. Rev. 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

2. SYNTHESIS OF ARYL- OR HETEROARYL-SUBSTITUTED BENZENE COMPOUNDS

The present invention provides methods for the synthesis of the compounds of any Formula disclosed herein. The present invention also provides detailed methods for the synthesis of various disclosed compounds of the present invention according to the following schemes as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, $5^{th}$ edition, John Wiley & Sons: New York, 2001; Greene, T. W., Wuts, P. G. M., Protective Groups in Organic Synthesis, $3^{rd}$ edition, John Wiley & Sons: New York, 1999; R. Larock, Comprehensive Organic Transformations, VCH Publishers (1989); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds of this invention with any Formula disclosed herein may be prepared according to the procedures illustrated in Schemes 1-10 below, from commercially available starting materials or starting materials which can be prepared using literature procedures. The Z and R groups (such as $R_2$, $R_3$, $R_4$, $R_6$, $R_7$, $R_8$, and $R_{12}$) in Schemes 1-10 are as defined in any of Formulae disclosed herein, unless otherwise specified.

One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., Protective Groups in Organic Synthesis, $3^{rd}$ edition, John Wiley & Sons: New York, 1999.

Preferred protecting groups include, but are not limited to:
For a hydroxyl moiety: TBS, benzyl, THP, Ac
For carboxylic acids: benzyl ester, methyl ester, ethyl ester, allyl ester
For amines: Cbz, BOC, DMB
For diols: Ac (×2) TBS (×2), or when taken together acetonides
For thiols: Ac
For benzimidazoles: SEM, benzyl, PMB, DMB
For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

The following abbreviations are used throughout the specification and are defined below:
AA ammonium acetate
ACN acetonitrile
Ac acetyl
AcOH acetic acid
atm atmosphere
aq. aqueous BID or b.i.d. bis in die (twice a day)
tBuOK potassium t-butoxide
Bn benzyl
BOC tert-butoxy carbonyl
BOP (benzotriazol-1-yloxy)tris(dimethylamino)-phosphoniumhexafluorophosphate
Cbz benzyloxy carbonyl
$CDCl_3$ deuterated chloroform
$CH_2Cl_2$ dichloromethane
COMU (1-Cyano-2-ethoxy-2-oxoethylidenaminooxy)dimethyl-amino-morpholino-carbenium hexafluorophosphate
d days
DBU 1,8-diazabicyclo[5.4.0]undec-7-ene
DCE 1,2 dichloroethane
DCM dichloromethane
DEAD Diethyl azodicarboxylate
DIAD Diisopropyl azodicarboxylate
DiBAL-H diisobutyl aluminium hydride
DIPEA N,N-diisopropylethylamine (Hunig's base)
DMA Dimethylacetamide
DMAP N, N dimethyl-4-aminopyridine
DMB 2,4 dimethoxy benzyl
DMF N,NDimethylformamide
DMSO Dimethyl sulfoxide
DPPA Diphenylphosphonic azide
EA or EtOAc Ethyl acetate
EDC or EDCI N-(3-Dimethylaminopropyl)-N'-ethylcarbodiimide
$Et_2O$ diethyl ether
ELS Evaporative Light Scattering
ESI– Electrospray negative mode
ESI+ Electrospray positive mode
$Et_3N$ or TEA triethylamine
EtOH ethanol
FA formic acid
FC or FCC Flash chromatography
h hours
$H_2O$ water
HATU O-(7-Azabenzotriazol-1-yl)-N,N,N',N'-tetramethyluronium hexafluorophosphate
HOAT 1-Hydroxy-7-azabenzotriazole
HOBt 1-Hydroxybenzotriazole
HO-Su N-Hydroxysuccinimide
HCl hydrogen chloride or hydrochloric acid
HPLC High performance liquid chromatography
$K_2CO_3$ potassium carbonate
KHMDs Potassium hexamethyldisilazide
LC/MS or LC-MS Liquid chromatography mass spectrum
LDA Lithium diisopropylamide
LiHMDs Lithium hexamethyldisilazide
LG leaving group
M Molar
m/z mass/charge ratio
m-CPBA meta-chloroperbenzoic acid
MeCN Acetonitrile
MeOD d4-methanol
MeI Methyl iodide
MS3 Å 3 Å molecular sieves
$MgSO_4$ Magnesium Sulfate
min minutes
Ms Mesyl
MsCl Mesyl chloride
MsO Mesylate
MS Mass Spectrum
MWI microwave irradiation
$Na_2CO_3$ sodium carbonate $Na_2SO_4$ sodium sulfate
$NaHCO_3$ sodium bicarbonate
NaHMDs Sodium hexamethyldisilazide
NaOH sodium hydroxide
$NaHCO_3$ sodium bicarbonate
$Na_2SO_4$ sodium sulfate
NIS N-iodosuccinimide
NMR Nuclear Magnetic Resonance
o/n or O/N overnight
Pd/C Palladium on carbon
$Pd(dppf)Cl_2 \cdot DCM$ [1,1'-Bis(diphenylphosphino)ferrocene]dichloropalladium(II), complex with dichloromethane
PPAA 1-Propanephosphonic acid cyclic anhydride
$Pd(OH)_2$ Palladium dihydroxide
PE Petroleum Ether
PG protecting group
PMB para methoxybenzyl
p.o. per os (oral administration)
ppm parts per million
prep HPLC preparative High Performance Liquid Chromatography
prep TLC preparative thin layer chromatography
p-TSOH para-toluenesulfonic acid
PyBOP (Benzotriazol-1-yloxy)tripyrrolidinophosphonium hexafluorophosphate
QD or q.d. quaque die (once a day)
RBF round bottom flask
RP-HPLC Reverse phase High Performance liquid chromatography
Rt or RT Room temperature
SEM (Trimethylsilyl)ethoxymethyl
SEMCl (Trimethylsilyl)ethoxymethyl chloride
SFC Super critical chromatography
SGC silica gel chromatography
STAB Sodium triacetoxy borohydride
TBAF tetra-n-butylammonium fluoride
TBME tert-Butyl methyl ether
TEA Triethylamine
TFA trifluoroacetic acid
TfO triflate
THF tetrahydrofuran
THP tetrahydropyran
TID or t.i.d ter in die (three times a day)
TLC thin layer chromatography
TMSCl Trimethylsilyl chloride
Ts tosyl
TsOH tosic acid
UV ultraviolet Scheme 1

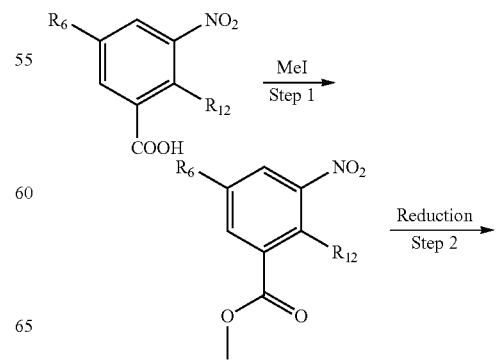

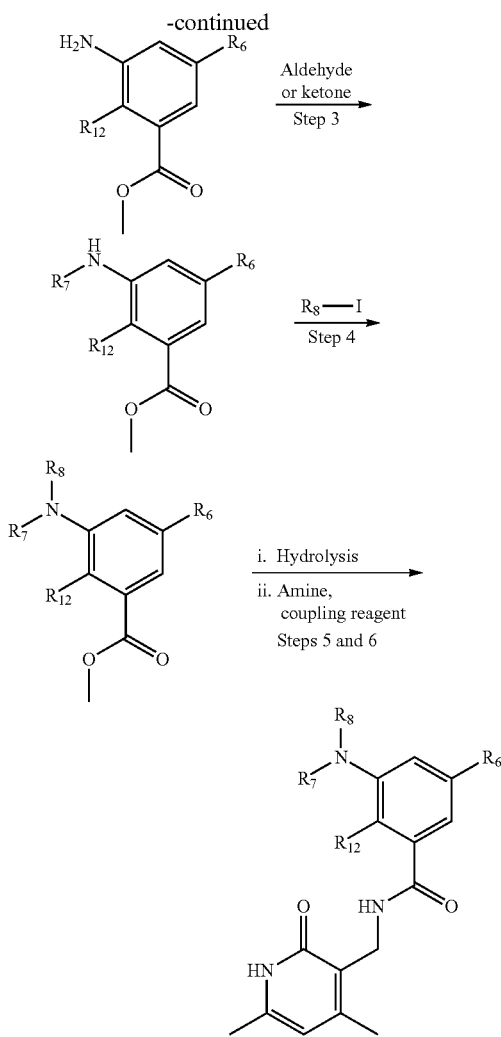

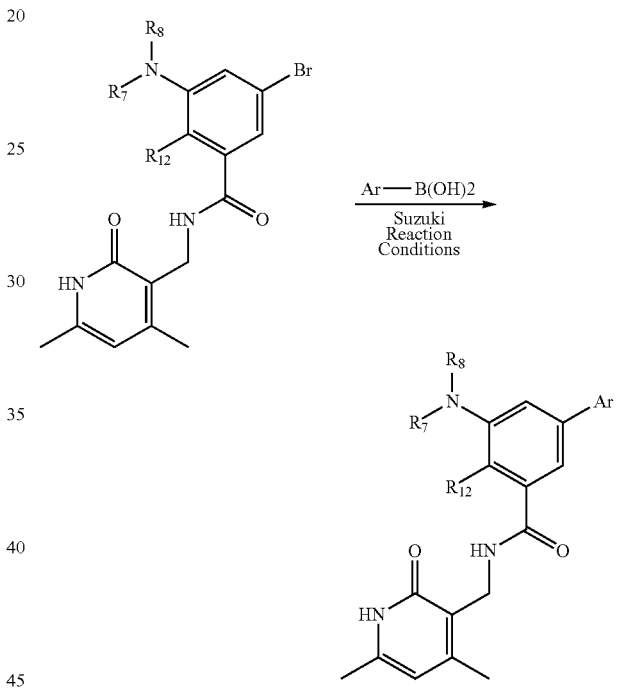

priate temperature such as 80° C. (Step 4). Alternatively, $R_8$ groups can be introduced by reductive amination with $R_8$-ketone or $R_8$-aldehyde in the presence of an appropriate reducing agent such as sodium cyanoborohydride and catalytic acid such as acetic acid in an appropriate solvent such as methanol. The ester moiety can be converted to an amide using a standard two step protocol. The ester can be hydrolyzed to the corresponding acid using a suitable base such as sodium hydroxide in a polar solvent such as ethanol (Step 5). The acid would then be subjecting to a standard amide coupling reaction whereupon the appropriate amine would be added along with a suitable amide coupling reagent such as PYBOP in a suitable solvent such as DMSO to give the desired amide (Step 6).

Scheme 1 shows the synthesis of modified aryl analogs following a general route that utilizes well-established chemistry. Substituted nitrobenzoic acids, many of which are commercially available or can be made nitrations of the appropriate substituted benzoic acids or other chemistry known to ones skilled in the art, can be converted to their methyl esters by treatment with methyliodide in a polar solvent such as DMF in the presence of an appropriate base such as sodium carbonate at an appropriate temperature such as 60° C. (Step 1). The nitro group can be reduced to an amine using an appropriate reducing agent such as iron in the presence of an acid such as ammonium chloride in a protic solvent such as ethanol at an appropriate temperature such as 80° C. (Step 2). Introduction of the $R_7$ can be done using a reductive amination with an appropriate ketone or aldehyde in the presence of an appropriate reducing agent such as sodium cyanoborohydride and catalytic acid such as acetic acid in an appropriate solvent such as methanol. A variety of $R_8$ groups can be introduced by alkylation using $R_8$-LG, where LG is a leaving group such as iodine, in the presence of a mild base such as cesium carbonate in an appropriate polar solvent such as acetonitrile at an appropriate temperature such as 80° C. (Step 4). Alternatively, $R_8$ groups can be introduced by reductive amination with $R_8$-ketone or $R_8$-aldehyde in the presence of an appropriate reducing agent such as sodium cyanoborohydride and catalytic acid such as acetic acid in an appropriate solvent such as methanol. The ester moiety can be converted to an amide using a standard two step protocol. The ester can be hydrolyzed to the corresponding acid using a suitable base such as sodium hydroxide in a polar solvent such as ethanol (Step 5). The acid would then be subjecting to a standard amide coupling reaction whereupon the appropriate amine would be added along with a suitable amide coupling reagent such as PYBOP in a suitable solvent such as DMSO to give the desired amide (Step 6).

Depending upon the nature of the $R_6$ substituent, further chemical modification could be employed to convert the $R_6$ substituent into an alternative $R_6$ substituent. A representative sampling of such modifications could include hydrogenation, protecting group removal followed by additional amide coupling reactions, palladium catalyzed coupling reactions, reductive amination reactions or alkylation reactions. For example, as depicted in Scheme 2, if $R_6$ is a bromide, alternative $R_6$ substituents could then be introduced using standard transition metal-based protocols that rely upon a leaving group such as a bromide as a connection point. The bromide would be combined with an appropriate boronic ester derivative, in the presence of a mild base and a palladium catalyst in a polar solvent such as dioxane/water, at elevated temperature to give the desired new $R_6$ substituent (i.e. Suzuki reaction). For example, as depicted in Scheme 3, if the Suzuki reaction is conducted with a boronic ester derivative bearing a formyl group further modification by reductive amination reaction with primary and secondary amines (e.g. morpholine, dimethylamine) can be conducted to introduce amine groups.

Scheme 3

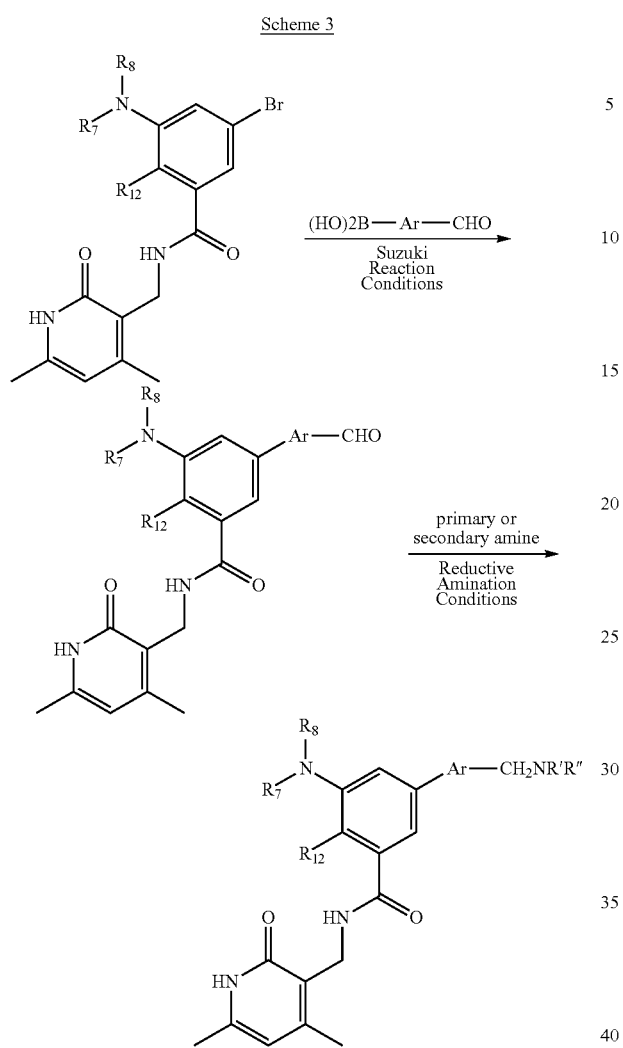

Depending upon the nature of the $R_7$ substituent, further chemical modification subsequent to Step 6 of Scheme 1 could be employed to convert the $R_7$ substituent into an alternative $R_7$ substituent. For example a protected amino group contained within $R_7$ may be subjected to deprotection reaction (e.g. Boc group cleavage) to give free amino groups. Such free amino groups may be subjected to reductive amination reactions or alkylation reactions to give substituted amines.

Scheme 4 shows the general synthesis of 2,6-disubstituted isonicotinamide compounds. Suzuki reaction in Step 1 of an aryl boronic acid compound with methyl 2,6-dichloroisonicotinate starting material can be used to introduce an aryl group which may be substituted with a functional group X that is suitable for further transformation. Such X groups include formyl or hydroxymethyl which can readily be transformed in Step 2 to various groups Y. Such Y groups include aminomethyl, monoalkylaminomethyl and dialkylaminomethyl groups. The latter can be prepared by reductive amination in the case where X is formyl or by converting X=hydroxymethyl to bromomethyl followed by alkylation with an amine. Ester hydrolysis a subsequent step gives an acid intermediate which can be coupled with appropriate 3-(aminomethyl)-pyridin-2(1H)-ones to give the penultimate 2-chloro-6-aryl-isonicotine amide intermediate. Suzuki reaction or amination reaction then gives compounds substituted in the 2-position with a Z group. In the case of an amination reaction examples of Z can be monoalkylamino or dialkylamino. In the case of a Suzuki reaction Z can be aryl, dihydroaryl or tetrahydroaryl such as cyclohexenyl.

Scheme 4

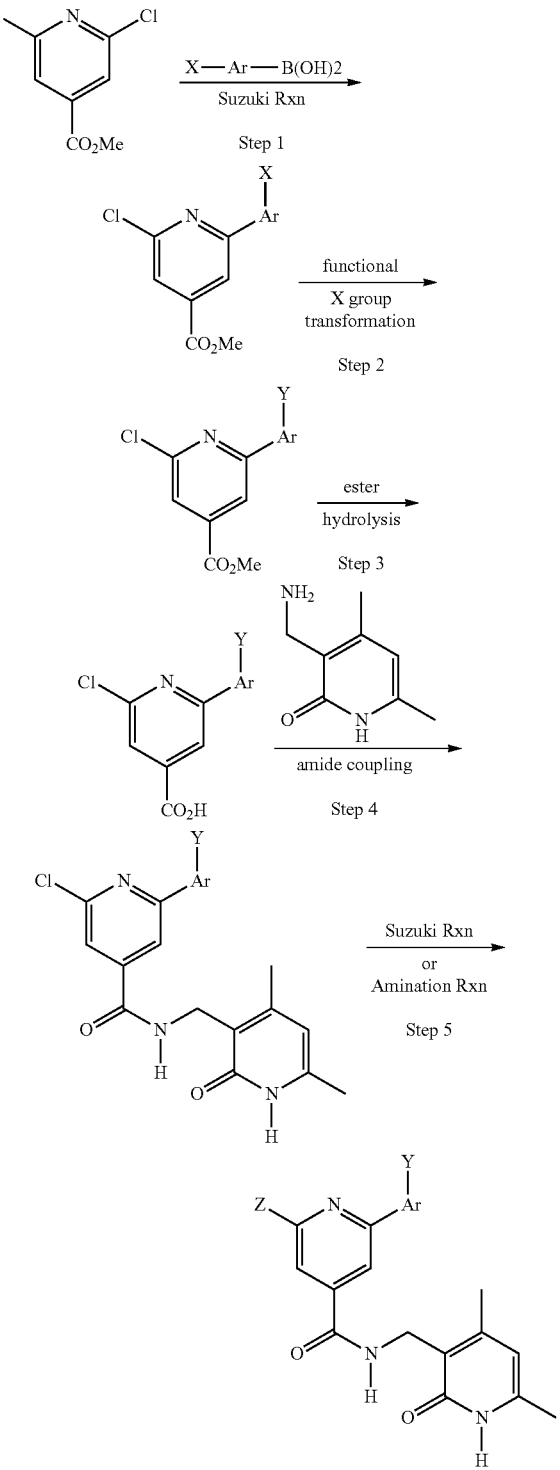

Scheme 5 shows the general synthesis of 6-aryl-3-methyl-picolinamides having monoalkylamino or dialkylamino groups in the 4-position. Starting from methyl 3-bromo-6-chloropicolinate oxidation to the N-oxide followed by chlorination with phosphorus oxychloride gives methyl 3-bromo-4,6-dichloropicolinate. The 4-chloro group can be selectively substituted with diverse mono and dialkyl amines which may also contain functional or protected functional groups that may be unmasked at a later stage. Palladium catalyzed methylation with tetramethyltin followed by ester hydrolysis and amide coupling with appropriate 3-(aminomethyl)-pyridin-2(1H)-ones yields penultimate 2-chloro pyridine intermediates. Suzuki coupling reaction group of these intermediates with aryl boronic acids results in replacement of the 2-chloro group with an aryl group. Thus, this yields 6-aryl-3-methyl-picolinamides having monoalkylamino or dialkylamino groups in the 4-position. The aryl group which may be substituted with a functional group X that remains in the final product or is converted to an another group by deprotection or functional group conversion reaction e.g. reductive amination.

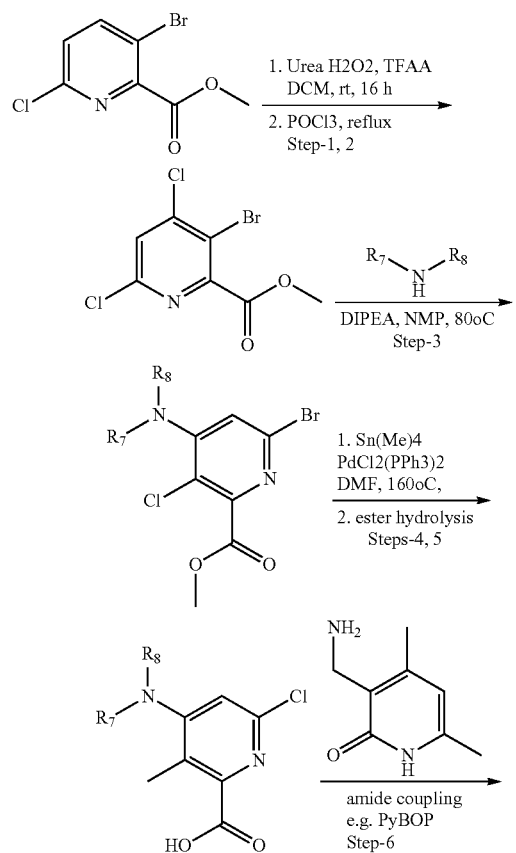

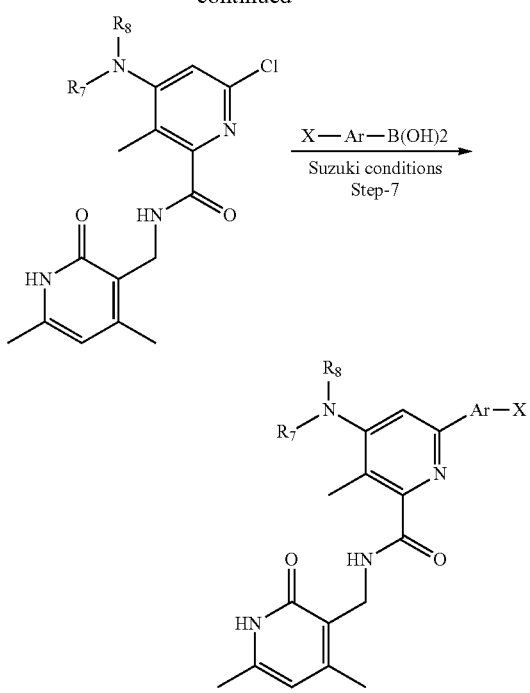

General syntheses of 3-(aminomethyl)-pyridin-2(1H)-ones intermediates for the amide coupling reaction from Scheme 1 are depicted in Scheme 6 below. In one method, a diketone can be condensed with 2-cyanoacetamide in the presence of an appropriate reagent such as piperidine acetate in a polar solvent such as ethanol to provide a cyanopyridone (Step 9). In another method, when $R_3$ is H, an appropriately substituted alkynyl ketone can be condensed with 2-cyanoacetamide in the presence of an appropriate reagent such as piperidine acetate in a polar solvent such as ethanol to provide a cyanopyridone (Step 11). The cyano group can be reduced under appropriate conditions such as hydrogenation in the presence of catalytic Raney nickel in a polar solvent such as ammonium in methanol to provide the amine (Step 10).

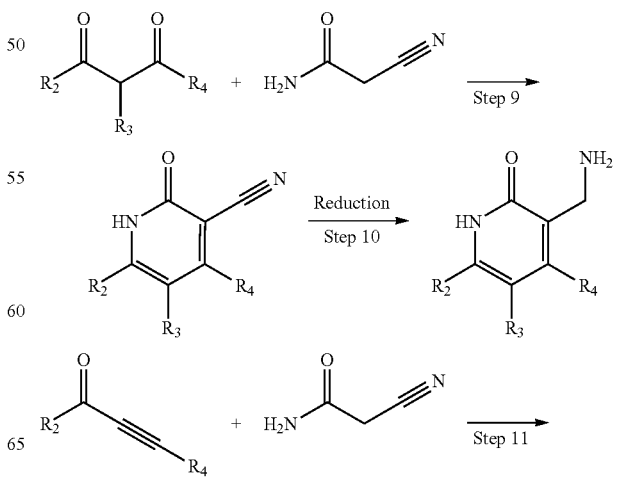

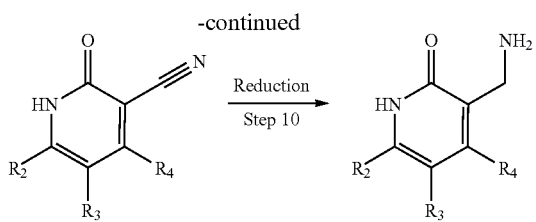

Additionally, depending upon the nature of the $R_2$, $R_3$, or $R_4$ group, further chemical modification can be employed to convert each of them independently into an alternative substituent. A representative sampling of such modifications can include hydrogenation, protecting group removal followed by additional amide coupling reactions, palladium catalyzed coupling reactions, reductive amination reactions, and alkylation reactions. Scheme 4 depicts a variant of the general synthesis route of Scheme 1 based on 2-substituted (substituent is an $R_{12}$ group) methyl 3-amino-5-bromo-benzoate starting materials. These starting materials can in turn be prepared from 2-substituted 3-nitro-benzoic acids which are commercially available or can be prepared by nitration of 2-substituted benzoic acids. Thus, bromination of 2-substituted 3-nitro-benzoic acids with a suitable reagent such as 1,3-dibromo-5,5-dimethyl-2,4-imidazolidinedione yields the appropriate 2-substituted 3-nitro-5-bromo-benzoic acids. A variety of esterification and then nitro group reduction methods can then be sequentially implemented to prepare the 2-substituted methyl 3-amino-5-bromo-benzoate starting materials from the 2-substituted 3-nitro-5-bromo-benzoic acids.

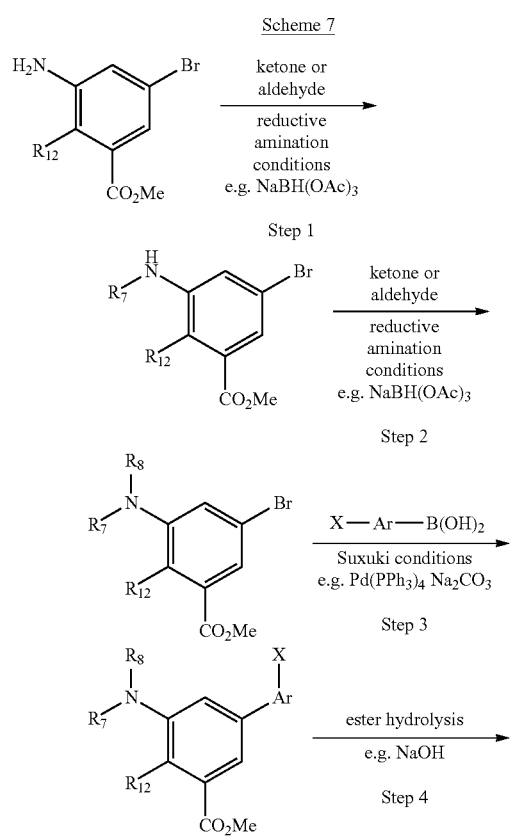

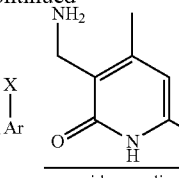

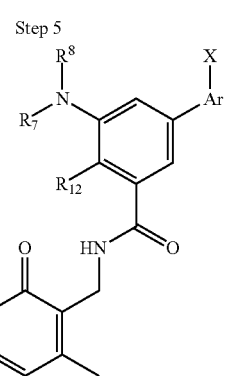

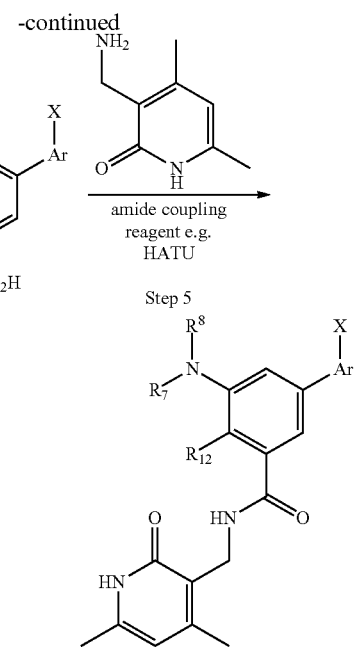

As depicted in Scheme 7 the $R_7$ group can be introduced from 2-substituted methyl 3-amino-5-bromo-benzoates in Step 1 using a reductive amination with an appropriate $R_7$-ketone or $R_7$-aldehyde in the presence of an appropriate reducing agent such as sodium cyanoborohydride and catalytic acid such as acetic acid in an appropriate solvent such as methanol. Similarly, $R_8$ groups can be introduced in Step 2 by reductive amination with $R_8$-ketone or $R_8$-aldehyde in the presence of an appropriate reducing agent such as sodium cyanoborohydride and catalytic acid such as acetic acid in an appropriate solvent such as methanol. Alternatively, a variety of $R_8$ groups can be introduced by alkylation using $R_8$-LG, where LG is a leaving group such as iodine, in the presence of a mild base such as cesium carbonate in an appropriate polar solvent such as acetonitrile at an appropriate temperature such as 80° C. In Step 3, aryl groups corresponding to $R_6$ can be introduced by Suzuki reaction of the intermediate bromide with an appropriate aryl boronic acid or ester derivative, e.g., X—Ar—B(OH)$_2$, in the presence of a mild base and a palladium catalyst in a polar solvent such as dioxane/water, at elevated temperature. The X group in X—Ar—B(OH)$_2$ may be a fully elaborated substituent on the aryl ring or may be a functional group that can be converted into another group by functional group modification. A representative sampling of such modifications could include hydrogenation, protecting group removal followed by additional amide coupling reactions, palladium catalyzed coupling reactions, reductive amination reactions or alkylation reactions. For example if the Suzuki reaction is conducted with a boronic acid derivative bearing a formyl group further modification by reductive amination reaction with primary and secondary amines (e.g. morpholine, dimethylamine) can be conducted to introduce amine groups. In Step 4 the ester moiety can be hydrolyzed to the corresponding acid using a suitable base such as sodium hydroxide in a polar solvent such as ethanol. In Step 5, the acid can be subjected to a standard amide coupling reaction whereupon the appropriate amine would be added along with a suitable amide coupling reagent such as PYBOP in a suitable solvent such as DMSO to give the desired amide. Depending upon the nature of the $R_7$ substituent, further chemical modification subsequent to Step 5 of Scheme 4 could be employed to convert the $R_7$ substituent into an alternative $R_7$ substituent. For example a protected amino group contained within $R_7$ may be subjected to deprotection reaction (e.g. Boc group cleavage) to give free amino groups. Such free amino groups may be subjected to reductive amination reactions or alkylation reactions to give substituted amines.

Scheme 8 below depicts the general synthesis of 2-monoalkylamino and 2-dialkylmino-3-substituted-6-aryl-isonicotinamides wherein the 3-substituent corresponds to $R_{12}$ and the 6-aryl group corresponds to $R_6$, Formula I In Step 1 the 3-substituent may be introduced by the method described by Epsztain J. et al. *Tetrahedron*, 1991, v. 47, 1697-16708, by metallation of 2-chloro-isonicotinanilide with n-butyllithium followed by trapping with an an alkyliodide such as methyliodide or aldehyde or other electrophilic group.

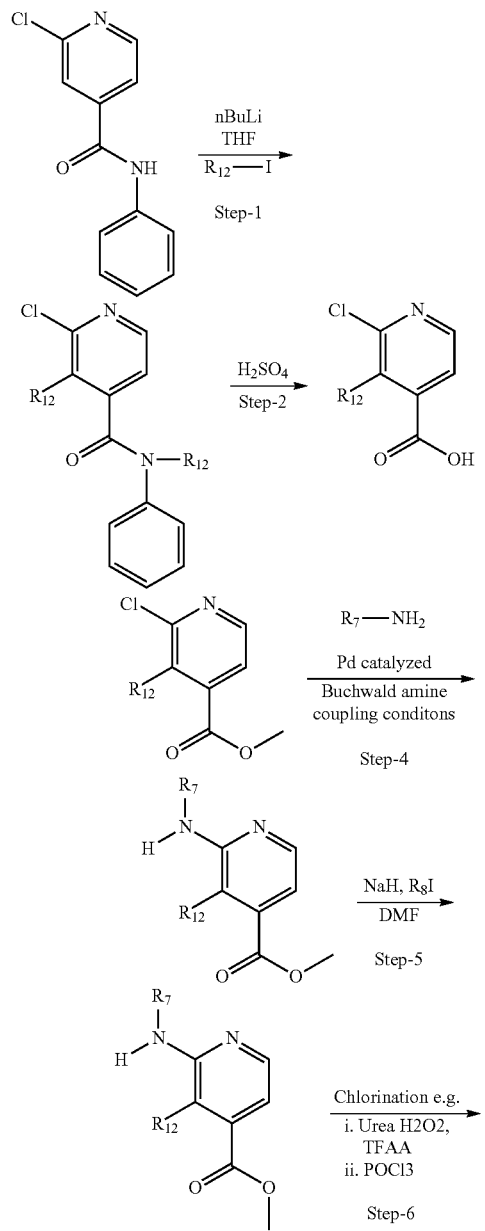

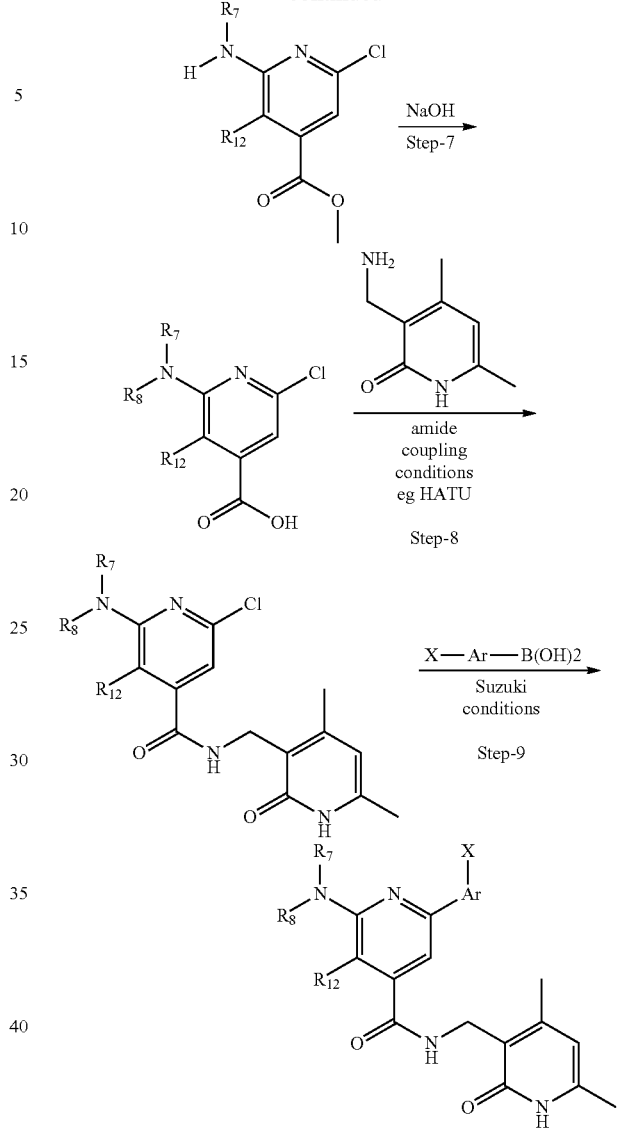

In cases where the trapping reagent yields a substituent with a functional group this group may be masked or converted into another functional group compatible with the subsequent chemical steps. In Step 2 anilide amide hydrolysis under standard acidic conditions maybe conducted followed by methyl ester synthesis under standard conditions for example as shown with methyl iodide and base gives corresponding methyl 2-chloro-3-substituted isonicotinates. In Step 4 an alkylamino group can be introduced by Buchwald coupling reaction of an $R_7NH_2$ monoalkylamine with the methyl 2-chloro-3-substituted isonicotinates. This reaction is well precedented for diverse 2-chloropyridine systems in the chemical literature. In an optional Step 5 for dialkylamino compounds $R_8$ groups can be introduced by reductive amination with $R_8$-ketone or $R_8$-aldehyde in the presence of an appropriate reducing agent such as sodium cyanoborohydride and catalytic acid such as acetic acid in an appropriate solvent such as methanol. Alternatively, a variety of $R_8$ groups can be introduced by alkylation using $R_8$-LG, where LG is a leaving group such as iodine, in the presence of a mild base such as cesium carbonate in an appropriate polar solvent such as acetonitrile at an appropriate temperature such as 80° C. In Step 6, oxidation to the N-oxide followed by chlorination with phosphorus oxychloride gives methyl 6-chloro-2-mono or dialkylamino-3-substituted isonicotinates. In Step 7 the ester moiety can be hydrolyzed to the corresponding acid using a suitable base such as sodium hydroxide in a polar solvent such as ethanol. In Step 8, the acid can be subjected to a standard amide coupling reaction whereupon the appropriate amine or substituted 3-(aminomethyl)-pyridin-2(1H)-one would be added along with a suitable amide coupling reagent such as PYBOP in a suitable solvent such as DMSO to give the desired amide. In Step 9, aryl groups corresponding to $R_6$ can be introduced by Suzuki reaction of the intermediate bromide with an appropriate aryl boronic acid or ester derivative, e.g., X—Ar—B(OH)$_2$, in the presence of a mild base and a palladium catalyst in a polar solvent such as dioxane/water, at elevated temperature. The X group in X—Ar—B(OH)$_2$ may be a fully elaborated substituent on the aryl ring or may be a functional group that can be converted into another group by functional group modification. A representative sampling of such modifications could include hydrogenation, protecting group removal followed by additional amide coupling reactions, palladium catalyzed coupling reactions, reductive amination reactions or alkylation reactions. For example if the Suzuki reaction is conducted with a boronic acid derivative bearing a formyl group further modification by reductive amination reaction with primary and secondary amines (e.g. morpholine, dimethylamine) can be conducted to introduce amine groups. Depending upon the nature of the $R_7$ substituent, further chemical modification steps may be employed to convert the $R_7$ substituent into an alternative $R_7$ substituent. For example a protected amino group contained within $R_7$ may be subjected to deprotection reaction (e.g. Boc group cleavage) to give free amino groups. Such free amino groups may be subjected to reductive amination reactions or alkylation reactions to give substituted amines.

Scheme 9

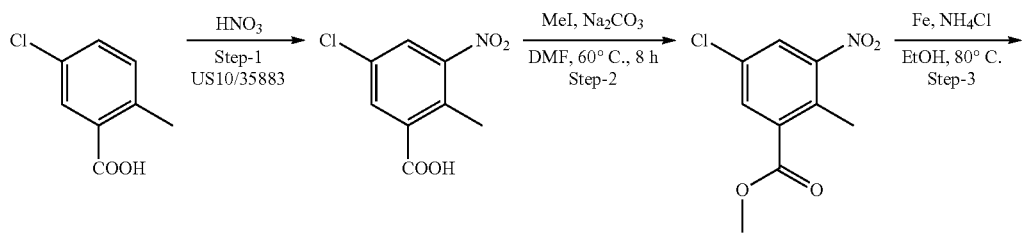

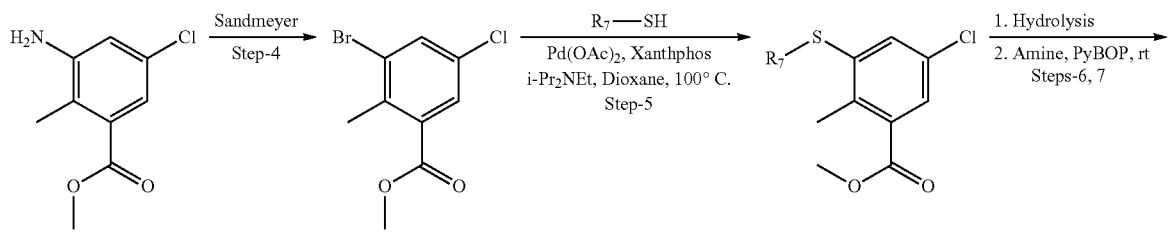

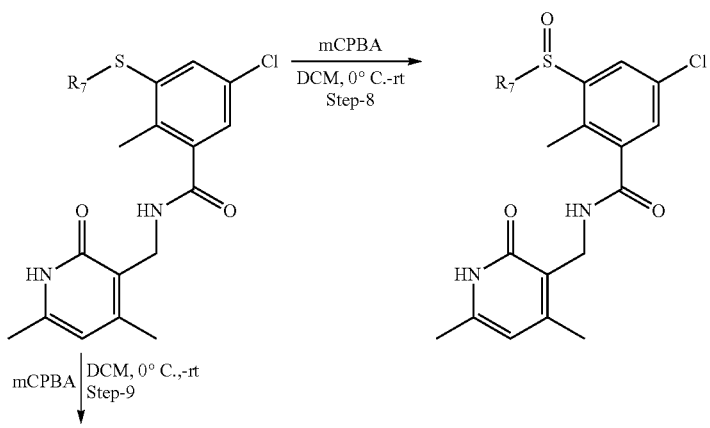

-continued

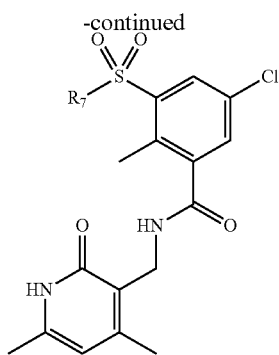

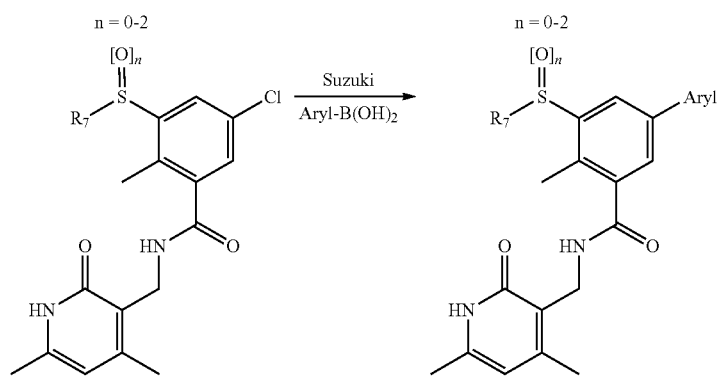

Scheme 9 depicts a synthesis of modified aryl analogs following a general route that utilizes well-established chemistry. Starting with a substituted benzoic acid such as 5-chloro-2-methylbenzoic acid, nitration using standard conditions such as treatment with conc. $H_2SO_4$ and conc. $HNO_3$ can provide the nitro analog. Esterification of the acid can be achieved using an alkylating agent such as methyl iodide in the presence of a base such as sodium carbonate in a polar solvent such as DMF. The nitro group can be reduced using conditions such iron and ammonium chloride in a protic solvent such as ethanol with heating to a temperature such as 80° C. The resulting aniline can be converted to a bromide using a Sandmeyer reaction such treatment with $CuBr_2$ and t-butyl nitrite in a solvent such as acetonitrile. A palladium catalyzed coupling of a thiol with the bromide can be achieved using a palladium source such as $Pd(OAc)_2$ with a ligand such as Xanthphos in the presence of a base such as N,N-diisopropyl ethylamine in a solvent such as 1,4-dioxane optionally heating to a temperature such as 100° C. The ester can be hydrolyzed with an aqueous base such as NaOH in water. The resulting acid can be coupled to the 3-(amino methyl)-4,6-dimethylpyridin-2(1H)-one using standard amino acid coupling conditions such as PyBOP in DMSO. The resulting thioether may be oxidized to the corresponding sulfoxide or sulfone by using the appropriate equivalents of an oxidant such as m-CPBA in a solvent such as DCM. Aryl substituents can be incorporated by using palladium couplings such as a Suzuki reaction as described above.

Scheme 10

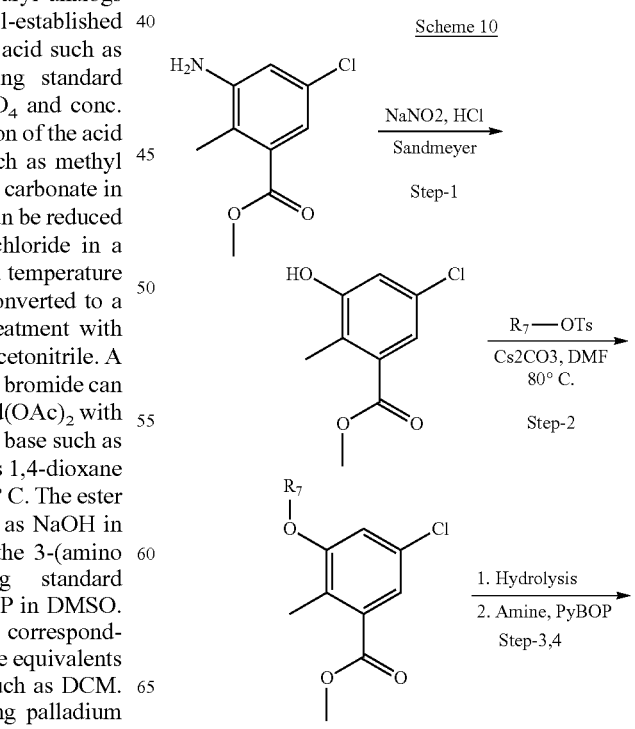

-continued

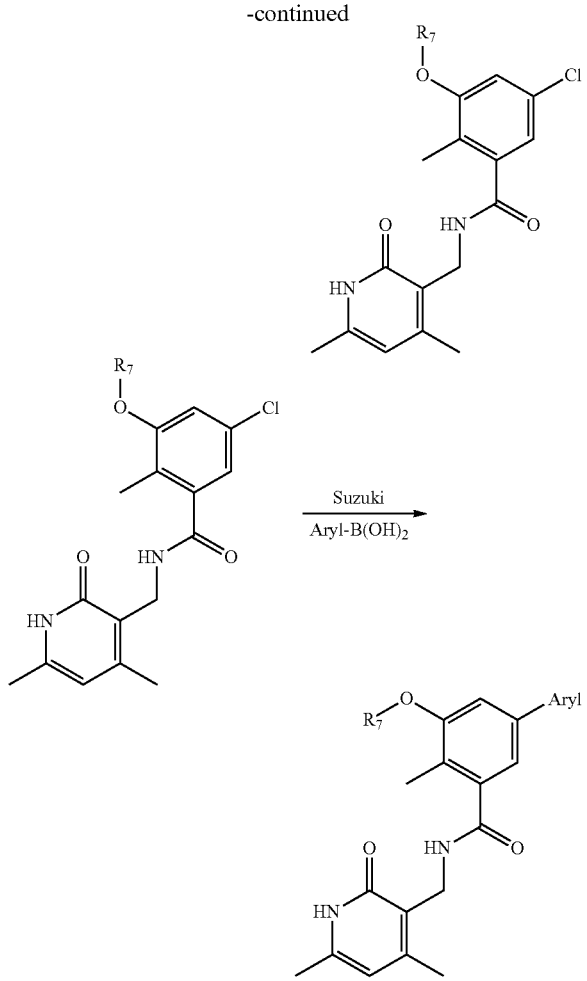

Scheme 10 depicts a synthesis of modified aryl analogs following a general route that utilizes well-established chemistry. Starting with a substituted aniline such as methyl 3-amino-5-chloro-2-methylbenzoate, the aniline can be converted to a phenol using a Sandmeyer reaction such as treatment with aqueous $NaNO_2$ solution in a aqueous acid such as 50% $H_2SO_4$. The phenol can be alkylated using an alkylating agent such as tetrahydro-2H-pyran-4-yl 4-methylbenzenesulfonate in the presence of an appropriate base such as cesium carbonate in as polar solvent such as DMF optionally heating to a temperature such as 80° C. The ester can be hydrolyzed with an aqueous base such as NaOH in water. The resulting acid can be coupled to the 3-(aminomethyl)-4,6-dimethylpyridin-2(1H)-one using standard amino acid coupling conditions such as PyBOP in DMSO. Aryl substituents can be incorporated by using palladium couplings such as a Suzuki reaction as described above.

3. METHODS OF TREATMENT

Compounds of the present invention inhibit the histone methyltransferase activity of EZH2 or a mutant thereof and, accordingly, in one aspect of the invention, certain compounds disclosed herein are candidates for treating, or preventing certain conditions and diseases. The present invention provides methods for treating conditions and diseases the course of which can be influenced by modulating the methylation status of histones or other proteins, wherein said methylation status is mediated at least in part by the activity of EZH2. Modulation of the methylation status of histones can in turn influence the level of expression of target genes activated by methylation, and/or target genes suppressed by methylation. The method includes administering to a subject in need of such treatment, a therapeutically effective amount of a compound of the present invention, or a pharmaceutically acceptable salt, prodrug, metabolite, polymorph, solvate, or stereoisomeror thereof.

The disorder in which EZH2-mediated protein methylation plays a part can be cancer or a precancerous condition. The present invention further provides the use of a compound of the present invention, or a pharmaceutically acceptable salt, ester, prodrug, metabolite, polymorph or solvate thereof in the treatment of cancer or precancer the course of which can be influenced by modulating EZH2-mediated protein methylation, or, for the preparation of a medicament useful for the treatment of such cancer or pre-cancer. Exemplary cancers that may be treated include lymphomas, including non-Hodgkin lymphoma, follicular lymphoma (FL) and diffuse large B-cell lymphoma (DLBCL); melanoma; and leukemia, including CML. Exemplary precancerous condition includes myelodysplastic syndrome (MDS; formerly known as preleukemia).

The present invention also provides methods of protecting against a disorder in which EZH2-mediated protein methylation plays a part in a subject in need thereof by administering a therapeutically effective amount of compound of the present invention, or a pharmaceutically acceptable salt, prodrug, metabolite, polymorph or solvate thereof, to a subject in need of such treatment. The disorder can be cancer, e.g., cancer in which EZH2-mediated protein methylation plays a role. The present invention also provides the use of compound of the present invention, or a pharmaceutically acceptable salt, ester, prodrug, metabolite, polymorph, solvate, or stereoisomeror thereof, for the preparation of a medicament useful for the prevention of a cell proliferative disorder associated, at least in part, with EZH2-mediated protein methylation.

The compounds of this invention can be used to modulate protein (e.g., histone) methylation, e.g., to modulate histone methyltransferase or histone demethylase enzyme activity. At least some of the compounds of the invention can be used in vivo or in vitro for modulating protein methylation. Histone methylation has been reported to be involved in aberrant expression of certain genes in cancers, and in silencing of neuronal genes in non-neuronal cells. At least some compounds described herein are suitable candidates for treating these diseases, i.e., to decrease methylation or restore methylation to roughly its level in counterpart normal cells.

Compounds that are methylation modulators may be used for modulating cell proliferation. For example, in some cases excessive proliferation may be reduced with agents that decrease methylation, whereas insufficient proliferation may be stimulated with agents that increase methylation. Accordingly, diseases that may be treated by the compounds of the invention can include hyperproliferative diseases, such as benign cell growth and malignant cell growth.

As used herein, a "subject in need thereof" is a subject having a disorder in which EZH2-mediated protein methylation plays a part, or a subject having an increased risk of developing such disorder relative to the population at large. A subject in need thereof can have a precancerous condition. Preferably, a subject in need thereof has cancer. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders that may be treated with the compounds of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. In one aspect, the methods provided herein are used to treat or alleviate a symptom of cancer or to identify suitable candidates for such purposes. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders that may be treated using one or more compounds of the present invention include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers that may be treated using one or more compounds of the present invention include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. In one aspect, compositions of the present invention may be used to treat a cancer selected from the group consisting of a hematologic cancer of the present invention or a hematologic cell proliferative disorder of the present invention, or used to identify suitable candidates for such purposes. A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. In one aspect, compositions of the present invention may be used to treat lung cancer or cell proliferative disorders of the lung, or used to identify suitable candidates for such purposes. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma," bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. Preferably, the cell proliferative disorder of the colon is colon cancer. In one aspect, compositions of the present invention may be used to treat colon cancer or cell proliferative disorders of the colon, or used to identify suitable candidates for such purposes. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present invention may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

The cell proliferative disorder of the breast can be breast cancer. In one aspect, compositions of the present invention may be used to treat breast cancer, or used to identify suitable candidates for such purposes. Breast cancer may include all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

A compound of the present invention, or a pharmaceutically acceptable salt, prodrug, metabolite, polymorph, or solvate thereof, may be used to treat breast cancer, or used to identify suitable candidates for such purposes. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich, or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the present invention, or a pharmaceutically acceptable salt, ester, prodrug, metabolite, polymorph or solvate thereof, may be used to treat or prevent a cell proliferative disorder of the breast, or to treat or prevent breast cancer, in a subject having an increased risk of developing breast cancer relative to the population at large, or used to identify suitable candidates for such purposes. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention, or a pharmaceutically acceptable salt, ester, prodrug, metabolite, polymorph or solvate thereof, that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention, or a pharmaceutically acceptable salt, ester, prodrug, metabolite, polymorph or solvate thereof. The biological or medical response can be the treatment of cancer. The biological or medical response can be treatment or prevention of a cell proliferative disorder. The biological response or effect can also include a change in cell proliferation or growth that occurs in vitro or in an animal model, as well as other biological changes that are observable in vitro. In vitro or in vivo biological assays can include, but are not limited to, enzymatic activity assays, electrophoretic mobility shift assays, reporter gene assays, in vitro cell viability assays, and the assays described herein.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention, or a pharmaceutically acceptable salt, prodrug, metabolite, polymorph or solvate thereof, is more effective than combination therapy in inducing a desired biological effect.

As used herein, "treating" or "treat" describes the management and care of a patient for the purpose of combating a disease, condition, or disorder and includes the administration of a compound of the present invention, or a pharmaceutically acceptable salt, prodrug, metabolite, polymorph or solvate thereof, to alleviate the symptoms or complications of a disease, condition or disorder, or to eliminate the disease, condition or disorder. The term "treat" can also include treatment of a cell in vitro or an animal model.

A compound of the present invention, or a pharmaceutically acceptable salt, prodrug, metabolite, polymorph or solvate thereof, can also be used to prevent a disease, condition or disorder, or used to identify suitable candidates for such purposes. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large. Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness.

Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin (see next section), some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here. However, all art-recognized signs and symptoms of cancer are contemplated and encompassed by the instant invention.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days;

more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the present invention, or a pharmaceutically acceptable salt, prodrug, metabolite, polymorph or solvate thereof, acts selectively on a cancer or precancerous cell but not on a normal cell. Preferably, a compound of the present invention, or a pharmaceutically acceptable salt, prodrug, metabolite, polymorph or solvate thereof, acts selectively to modulate one molecular target (e.g., a target protein methyltransferase) but does not significantly modulate another molecular target (e.g., a non-target protein methyltransferase). The invention also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A compound of the present invention, or a pharmaceutically acceptable salt, prodrug, metabolite, polymorph or solvate thereof, can modulate the activity of a molecular target (e.g., a target protein methyltransferase). Modulating refers to stimulating or inhibiting an activity of a molecular target. Preferably, a compound of the present invention, or a pharmaceutically acceptable salt, prodrug, metabolite, polymorph or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present invention, or a pharmaceutically acceptable salt, prodrug, metabolite, polymorph or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention, or a pharmaceutically acceptable salt, prodrug, metabolite, polymorph or solvate thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound of the present invention, or a pharmaceutically acceptable salt, prodrug, metabolite, polymorph or solvate thereof, demonstrates a minimum of a fourfold differential, preferably a tenfold differential, more preferably a fifty fold differential, in the dosage required to achieve a biological effect. Preferably, a compound of the present invention, or a pharmaceutically acceptable salt, prodrug, metabolite, polymorph or solvate thereof, demonstrates this differential across the range of inhibition, and the differential is exemplified at the $IC_{50}$, i.e., a 50% inhibition, for a molecular target of interest.

Administering a compound of the present invention, or a pharmaceutically acceptable salt, prodrug, metabolite, polymorph or solvate thereof, to a cell or a subject in need thereof can result in modulation (i.e., stimulation or inhibition) of an activity of a protein methyltransferase of interest.

The present invention provides methods to assess biological activity of a compound of the present invention, or a pharmaceutically acceptable salt, prodrug, metabolite, polymorph or solvate thereof or methods of identifying a test compound as an inhibitor of a Y641 mutant of EZH2. In one embodiment the method includes combining an isolated Y641 mutant of EZH2 with a histone substrate, a methyl group donor (such as S-adenosylmethionine (SAM)), and a test compound, wherein the histone substrate comprises a form of H3-K27 selected from the group consisting of unmethylated H3-K27, monomethylated H3-K27, dimethylated H3-K27, and any combination thereof, and performing an assay to detect methylation of H3-K27 in the histone substrate, thereby identifying the test compound as an inhibitor of the Y641 mutant of EZH2 when methylation of H3-K27 in the presence of the test compound is less than methylation of H3-K27 in the absence of the test compound. The assay to detect methylation of H3-K27 can be selected to measure the rate of methylation, the extent of methylation, or both the rate and extent of methylation.

The Y641 mutant of EZH2 is isolated as a PRC2 complex or functional equivalent thereof. As used herein, the term "isolated" means substantially separated from other components with which the complex may be found as it occurs in nature. A compound can be isolated without necessarily being purified. In one embodiment the mutant of EZH2 is isolated as a complex of a Y641 mutant of EZH2 together with EED and SUZ12. In another embodiment the mutant of EZH2 is isolated as a complex of a Y641 mutant of EZH2 together with EED, SUZ12, and RbAp48. Under appropriate conditions, a PRC2 complex or functional equivalent thereof exhibits histone methyltransferase activity for H3-K27. In one embodiment the complex is composed of recombinantly expressed component polypeptides, e.g., EZH2, EED, SUZ12, with or without RbAp48.

The isolated Y641 mutant of EZH2 is combined with a histone substrate. A histone substrate includes any suitable source of histone polypeptides or fragments thereof that can serve as substrate for EZH2. In one embodiment the histone substrate includes histones isolated from a subject. The histones can be isolated from cells of a subject using any suitable method; such methods are well known to persons skilled in the art and need not be further specified here. See, for example, Fang et al. (2004) *Methods Enzymol* 377:213-26. In accordance with the Examples below, in one embodiment the histone substrate is provided as nucleosomes. In accordance with the Examples below, in one embodiment the histone substrate is provided as avian (chicken) erythrocyte nucleosomes.

Histone substrate so provided may include an admixture of states of histone modification, including various states of H3-K27 methylation as judged by Western blotting with H3-K27 methylation state-specific antibodies. In one embodiment the histone substrate may be provided as purified full-length histone H3. Such purified full-length histone H3 may be provided as a homogeneous preparation in respect of states of H3-K27 methylation, or as an admixture of various states of H3-K27 methylation. Homogeneous preparations of isolated histone H3 in respect of states of H3-K27 methylation may be prepared in part by passage over an immunoaffinity column loaded with suitable H3-K27 methylation state-specific antibodies or by immunoprecipitation using magnetic beads coated with suitable H3-K27 methylation state-specific antibodies. Alternatively or in addition, the methylation state of H3-K27 can be characterized as part of performing the assay. For example, the starting material histone substrate might be characterized as containing 50 percent unmethylated H3-K27, 40 percent monomethylated H3-K27, 10 percent dimethylated H3-K27, and 0 percent trimethylated H3-K27.

In one embodiment the histone substrate includes a peptide library or a suitable peptide comprising one or more amino acid sequences related to histone H3, including, in particular, a sequence that encompasses H3-K27. For example, in one embodiment, the histone substrate is a peptide fragment that corresponds to amino acid residues 21-44 of histone H3. The peptide library or peptide can be prepared by peptide synthesis according to techniques well known in the art and optionally modified so as to incorporate any desired degree of methylation of lysine corresponding to H3-K27. As described in the Examples below, such peptides can also be modified to incorporate a label, such as biotin, useful in performing downstream assays. In one embodiment the label is appended to the amino (N)-terminus of the peptide(s). In one embodiment the label is appended to the carboxy (C)-terminus of the peptide(s).

Detection of methylation of H3-K27 can be accomplished using any suitable method. In one embodiment, the source of donor methyl groups includes methyl groups that are labeled with a detectable label. The detectable label in one embodiment is an isotopic label, e.g., tritium. Other types of labels may include, for example, fluorescent labels.

Detection of formation of trimethylated H3-K27 can be accomplished using any suitable method. For example, detection of formation of trimethylated H3-K27 can be accomplished using an assay to detect incorporation of labeled methyl groups, such as described above, optionally combined with a chromatographic or other method to separate labeled products by size, e.g., polyacrylamide gel electrophoresis (PAGE), capillary electrophoresis (CE), or high pressure liquid chromatography (HPLC). Alternatively or in addition, detection of formation of trimethylated H3-K27 can be accomplished using antibodies that are specific for trimethylated H3-K27.

Detection of conversion of monomethylated H3-K27 to dimethylated H3-K27 can be accomplished using any suitable method. In one embodiment the conversion is measured using antibodies specific for monomethylated H3-K27 and dimethylated H3-K27. For example, starting amounts or concentrations of monomethylated H3-K27 and dimethylated H3-K27 may be determined using appropriate antibodies specific for monomethylated H3-K27 and dimethylated H3-K27. Following the combination of enzyme, substrate, methyl group donor, and test compound, resulting amounts or concentrations of monomethylated H3-K27 and dimethylated H3-K27 may then be determined using appropriate antibodies specific for monomethylated H3-K27 and dimethylated H3-K27. The beginning and resulting amounts or concentrations of monomethylated H3-K27 and dimethylated H3-K27 can then be compared. Alternatively or in addition, beginning and resulting amounts or concentrations of monomethylated H3-K27 and dimethylated H3-K27 can then be compared to corresponding amounts of concentrations from a negative control. A negative control reaction, in which no test agent is included in the assay, can be run in parallel or as a historical control. Results of such control reaction can optionally be subtracted from corresponding results of the experimental reaction prior to or in conjunction with making the comparison mentioned above.

Because the dimethylated form of H3-K27 may be further methylated in the same assay, a reduction in the amount or concentration of monomethylated H3-K27 may not appear to correspond directly to an increase in dimethylated H3-K27. In this instance, it may be presumed, however, that a reduction in the amount or concentration of monomethylated H3-K27 is, by itself, reflective of conversion of monomethylated H3-K27 to dimethylated H3-K27.

Detection of conversion of dimethylated H3-K27 to trimethylated H3-K27 can be accomplished using any suitable method. In one embodiment the conversion is measured using antibodies specific for dimethylated H3-K27 and trimethylated H3-K27. For example, starting amounts or concentrations of dimethylated H3-K27 and trimethylated H3-K27 may be determined using appropriate antibodies specific for dimethylated H3-K27 and trimethylated H3-K27. Following the combination of enzyme, substrate, and test compound, resulting amounts or concentrations of dimethylated H3-K27 and trimethylated H3-K27 may then be determined using appropriate antibodies specific for dimethylated H3-K27 and trimethylated H3-K27. The beginning and resulting amounts or concentrations of dimethylated H3-K27 and trimethylated H3-K27 can then be compared. Alternatively or in addition, beginning and resulting amounts or concentrations of dimethylated H3-K27 and trimethylated H3-K27 can then be compared to corresponding amounts of concentrations from a negative control. A negative control reaction, in which no test agent is included in the assay, can be run in parallel or as a historical control. Results of such control reaction can optionally be subtracted from corresponding results of the experimental reaction prior to or in conjunction with making the comparison mentioned above.

A test agent is identified as an inhibitor of the Y641 mutant of EZH2 when methylation of H3-K27 with the test compound is less than methylation of H3-K27 without the test compound. In one embodiment, a test agent is identified as an inhibitor of the Y641 mutant of EZH2 when formation of trimethylated H3-K27 in the presence of the test compound is less than formation of trimethylated H3-K27 in the absence of the test compound.

The present invention also provides a method for identifying a selective inhibitor of a Y641 mutant of EZH2. In one embodiment the method includes combining an isolated Y641 mutant of EZH2 with a histone substrate, a methyl group donor (e.g., SAM), and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a test mixture; combining an isolated wild-type EZH2 with a histone substrate, a methyl group donor (e.g., SAM), and a test compound, wherein the histone substrate comprises a form of H3-K27 selected from the group consisting of monomethylated H3-K27, dimethylated H3-K27, and a combination of monomethylated H3-K27 and dimethylated H3-K27, thereby forming a control mixture; performing an assay to detect trimethylation of the histone substrate in each of the test mixture and the control mixture; calculating the ratio of (a) trimethylation with the Y641 mutant of EZH2 and the test compound (M+) to (b) trimethylation with the Y641 mutant of EZH2 without the test compound (M−); calculating the ratio of (c) trimethylation with wild-type EZH2 and the test compound (WT+) to (d) trimethylation with wild-type EZH2 without the test compound (WT−); comparing the ratio (a)/(b) with the ratio (c)/(d); and identifying the test compound as a selective inhibitor of the Y641 mutant of EZH2 when the ratio (a)/(b) is less than the ratio (c)/(d). In one embodiment the method further includes taking into account a negative control without test compound for either or both of the test mixture and the control mixture.

In some assays, immunological reagents, e.g., antibodies and antigens, are employed. Fluorescence can be utilized in the measurement of enzymatic activity in some assays. As used herein, "fluorescence" refers to a process through which a molecule emits a photon as a result of absorbing an incoming photon of higher energy by the same molecule. Specific methods for assessing the biological activity of the disclosed compounds are described in the examples.

Administering a compound of the present invention, or a pharmaceutically acceptable salt, prodrug, metabolite, polymorph or solvate thereof, to a cell or a subject in need thereof results in modulation (i.e., stimulation or inhibition) of an activity of an intracellular target (e.g., substrate). Several intracellular targets can be modulated with the compounds of the present invention, including, but not limited to, protein methyltrasferase.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

Preferably, an effective amount of a compound of the present invention, or a pharmaceutically acceptable salt, prodrug, metabolite, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, prodrug, metabolite, polymorph or solvate thereof, can induce or activate cell death selectively in cancer cells. Administering to a subject in need thereof a compound of the present invention, or a pharmaceutically acceptable salt, prodrug, metabolite, polymorph or solvate thereof, can induce or activate cell death selectively in cancer cells. Contacting a cell with a compound of the present invention, or a pharmaceutically acceptable salt, prodrug, metabolite, polymorph or solvate thereof, can induce cell death selectively in one or more cells affected by a cell proliferative disorder. Preferably, administering to a subject in need thereof a compound of the present invention, or a pharmaceutically acceptable salt, prodrug, metabolite, polymorph or solvate thereof, induces cell death selectively in one or more cells affected by a cell proliferative disorder.

One aspect of the present invention relates to a method of treating or preventing cancer (e.g., the course of which can be influenced by modulating EZH2-mediated protein methylation) by administering a compound of the present invention, or a pharmaceutically acceptable salt, prodrug, metabolite, polymorph or solvate thereof, to a subject in need thereof, where administration of the compound of the present invention, or a pharmaceutically acceptable salt, prodrug, metabolite, polymorph or solvate thereof, results in one or more of the following: prevention of cancer cell proliferation by accumulation of cells in one or more phases of the cell cycle (e.g. G1, G1/S, G2/M), or induction of cell senescence, or promotion of tumor cell differentiation; promotion of cell death in cancer cells via cytotoxicity, necrosis or apoptosis, without a significant amount of cell death in normal cells, antitumor activity in animals with a therapeutic index of at least 2. As used herein, "therapeutic index" is the maximum tolerated dose divided by the efficacious dose. The present invention also relates to a method used to identify suitable candidates for treating or preventing cancer.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3$^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18$^{th}$ edition (1990). These texts can, of course, also be referred to in making or using an aspect of the invention.

As used herein, "combination therapy" or "co-therapy" includes the administration of a compound of the present invention, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A compound of the present invention, or a pharmaceutically acceptable salt, prodrug, metabolite, analog or derivative thereof, may be administered in combination with a second chemotherapeutic agent. The second chemotherapeutic agent (also referred to as an anti-neoplastic agent or anti-proliferative agent) can be an alkylating agent; an antibiotic; an anti-metabolite; a detoxifying agent; an interferon; a polyclonal or monoclonal antibody; an EGFR inhibitor; a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase or a protein methyltransferase), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine131 tositumomab (Bexxar); alemtuzumab (Campath); ibritumomab (Zevalin; In-111; Y-90 Zevalin); gemtuzumab (Mylotarg); eculizumab (Soliris) ordenosumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur—0.4 M 5-chloro-2,4-dihydroxypyrimidine—1 M potassium oxonate) or lovastatin.

In another aspect, the second chemotherapeutic agent can be a cytokine such as G-CSF (granulocyte colony stimulating factor). In another aspect, a compound of the present invention, or a pharmaceutically acceptable salt, prodrug, metabolite, analog or derivative thereof, may be administered in combination with radiation therapy. Radiation therapy can also be administered in combination with a compound of the present invention and another chemotherapeutic agent described herein as part of a multiple agent therapy. In yet another aspect, a compound of the present invention, or a pharmaceutically acceptable salt, prodrug, metabolite, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™), CHOP (cyclophosphamide, hydroxydaunorubicin, oncovin, and prednisone or prednisolone), R-CHOP (rituximab, cyclophosphamide, hydroxydaunorubicin, oncovin, prednisone or prednisolone), or CMFP (cyclophosphamide, methotrexate, 5-fluorouracil and prednisone).

In preferred embodiments, a compound of the present invention, or a pharmaceutically acceptable salt, prodrug, metabolite, polymorph or solvate thereof, may be administered with an inhibitor of an enzyme, such as a receptor or non-receptor kinase. Receptor and non-receptor kinases are, for example, tyrosine kinases or serine/threonine kinases. Kinase inhibitors described herein are small molecules, polynucleic acids, polypeptides, or antibodies.

Exemplary kinase inhibitors include, but are not limited to, Bevacizumab (targets VEGF), BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-B, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF 1-3, PDGFR, and c-kit), Denosumab (targets RANKL, inhibits SRC), AMG888 (targets HER3), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azdl 152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

The disorder in which EZH2-mediated protein methylation plays a part can be a neurological disease. The compounds of this invention can thus also be used for treating or studying neurologic diseases such as epilepsy, schizophrenia, bipolar disorder or other psychological and/or psychiatric disorders, neuropathies, skeletal muscle atrophy, and neurodegenerative diseases, e.g., a neurodegenerative disease. Exemplary neurodegenerative diseases include: Alzheimer's, Amyotrophic Lateral Sclerosis (ALS), and Parkinson's disease. Another class of neurodegenerative diseases includes diseases caused at least in part by aggregation of poly-glutamine. Diseases of this class include: Huntington's Diseases, Spinalbulbar Muscular Atrophy (SBMA or Kennedy's Disease) Dentatorubropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataxia 6 (SCA6), Spinocerebellar Ataxia 7 (SCA7), and Spinocerebellar Ataxia 12 (SCA12).

Any other disease in which epigenetic methylation, which is mediated by EZH2, plays a role may be treatable or preventable using compounds and methods described herein, or such diseases and potential treatments thereof may be studied with the compounds described herein.

4. PHARMACEUTICAL COMPOSITIONS

The present invention also provides pharmaceutical compositions comprising a compound of any Formula disclosed herein in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound.

Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

5. EXAMPLES

General Experimental
NMR
$^1$H-NMR spectra were taken using CDCl$_3$ unless otherwise stated and were recorded at 400 or 500 MHz using a Varian or Oxford instruments magnet (500 MHz) instruments. Multiplicities indicated are s=singlet, d=doublet, t=triplet, q=quartet, quint=quintet, sxt=sextet, m=multiplet, dd=doublet of doublets, dt=doublet of triplets; br indicates a broad signal.
LCMS and HPLC
Shimadzu LC-Q, Shimadzu LCMS-2010EV or Waters Acquity Ultra Performance LC. HPLC: Products were analyzed by Shimadzu SPD-20A with 150×4.5 mm YMC ODS-M80 column or 150×4.6 mm YMC-Pack Pro C18 column at 1.0 ml/min.

Mobile phase was MeCN:H2O=3:2 (containing 0.3% SDS and 0.05% H$_3$PO$_4$), 0.05% TFA in water, 0.05% TFA in acetonitrile (gradient Initial 20%, then 0.05% TFA/MeCN to conc. to 95% in 3 min. holds for 0.5 min. at 3.51 to 4.50 min then 0.05% TFA/MeCN conc. 20%).

Alternatively the LCMS, 2 different methods were used; the one we use the most is the high pH (METCR1600) and the other one for more standard compounds (METCR1416).

0.1% Formic acid in water—Mobile phase "A" 0.1% Formic acid in acetonitrile—Mobile phase "B" utilizing Waters Atlantis dC18, 2.1 mm×100 mm, 3 μm column, with a flow rate=0.6 ml/min Column temperature=40° C.; Time (mins) % B 0.00 min 5% B. 5.0 mins 100% B, 5.4 mins 100% B and 0.42 mins 5% B 3.5 minute method refers to Atlantis dC18, 2.1 mm×50 mm, 3 m column, flow rate of 1 ml/min at 40 C. Mobile phase A Formic acid (aq.) 0.1% mobile phase B formic acid (MeCN) 0.1%, injection 3 μL, gradient 0 mins (5% organic), 2.5 min (100% organic), 2.7 mins (100% organic), 2.71 min (5% organic), 3.5 min (5% organic)

7.0 minute method refers to Atlantis dC18, 2.1 mm×100 mm, 3 μm column, flow rate of 0.6 ml/min at 40 C. Mobile phase A Formic acid (aq.) 0.1% mobile phase B formic acid (MeCN) 0.1%, injection 3 μL, gradient 0 mins (5% organic), 5 min (100% organic), 5.4 mins (100% organic), 5.42 min (5% organic), 7 min (5% organic)

Both the 3. 5 and 7 minute methods were performed on a MS18 Shimadzu LCMS-2010EV or a MS19 Shimadzu LCMS-2010EV system utilizing LC-20AB pumps and SPD-M20A PDA detectors.

Products were purified by HPLC/MS using Waters AutoPurification System with 3100 Mass Detector.

HPLC analyses may also be performed on a Shimdazu LC-2010 CHT using an YMC ODS-A, C18, (150×4.6×5 m) column at ambient temperature with a flow Rate of 1.4 ml/min. An injection volume of 10 μl is utilized and detection occurs via UV/PDA. Mobile Phase A is 0.05% TFA in water and Mobile Phase B is 0.05% TFA in acetonitrile with a gradient program of Initial 5% B to 95% B in 8 min, hold for 1.5 min, at 9.51 to 12 min B. conc. 0.5%. The diluent is the mobile phase Other Automated flash column chromatography was performed on a Biotage Isolera version 4. 10 g SNAP cartridge running at 12 ml/min or a 25 g SNAP cartridge running at 25 ml/min and detecting at 254 nm and 280 nm.

Select Nitrile reductions may be performed on a ThalesNano H-Cube® according to the conditions described in the experimental procedure.

Example 1: Synthesis of Compound 1: 5-(cyclopentyl(methyl)amino)-N-((4,6-dimethyl-2-oxo-1,2-dihydropuridin-3-yl)methyl)-4'-((dimethylamino)methyl)-4-methyl-[1,1'-biphenyl]-3-carboxamide Compound 1

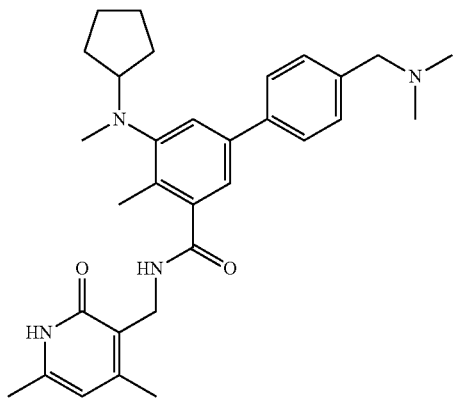

Step 1: 5-bromo-2-methyl-3-nitrobenzoic acid

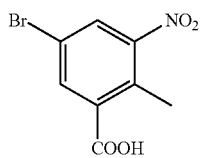

To stirred solution of 2-methyl-3-nitrobenzoic acid (50 g, 276.2 mmol) in conc. $H_2SO_4$ (200 mL), 1,3-dibromo-5,5-dimethyl-2,4-imidazolidinedione (43.4 g, 151.8 mmol) was added portion wise at room temperature and reaction mass was stirred at room temperature for 5 h. On completion, reaction mass was poured on ice cold water, solid precipitated was filtered, resulting residue was washed with water and dried under vacuum to give the desired compound (71.7 g, 100%).

Step 2: Synthesis of methyl 5-bromo-2-methyl-3-nitrobenzoate

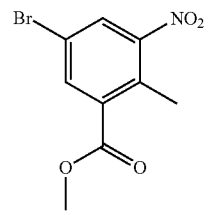

To a stirred solution of 5-bromo-2-methyl-3-nitrobenzoic acid (287 g, 1103 mmol) in DMF (150 mL), sodium carbonate (468 g, 4415 mmol) and methyl iodide (626.63 g, 4415 mmol) were added. Resulting reaction mass was heated at 60° C. for 8 h. On completion, solid precipitated was filtered, residue washed with diethyl ether (5 times). Combined organic layers were dried, concentrated under reduced pressure giving the desired crude compound (302 g, 99%).

Step 3: methyl 3-amino-5-bromo-2-methylbenzoate

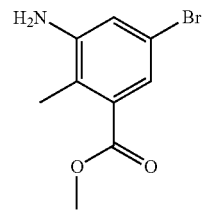

To a stirred solution of methyl 5-bromo-2-methyl-3-nitrobenzoate (150 g, 544 mmol) in ethanol (750 mL), ammonium chloride (150 g, 2777 mmol) dissolved in water (750 mL) and iron powder (93.3 g, 1636 mmol) were added under stirring. Resulting reaction mass was heated at 80° C. for 7 h. On completion, reaction mass was filtered through celite giving washing of water and ethyl acetate, filtrate was extracted with ethyl acetate. Combined organic layers were dried, concentrated under reduced pressure giving the desired compound.

Step 4: methyl 5-bromo-3-(cyclopentylamino)-2-methylbenzoate

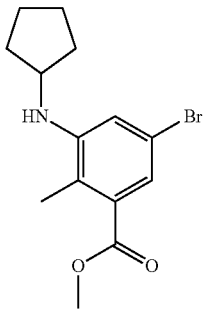 [SMILES: COC(=O)c1cc(Br)cc(NC2CCCC2)c1C]

To a stirred solution of methyl 3-amino-5-bromo-2-methylbenzoate (0.3 g, 1.33 mmol) and cyclopentanone (0.56 g, 6.6 mmol) in methanol (3 mL), acetic acid (0.159 g, 2.6 mmol) was added and reaction stirred at room temperature for 3 h. Then sodium cyanoborohydride (0.208 g, 3.3 mmol) was added and reaction stirred overnight. On completion, solvent was removed under reduced pressure to give the desired compound.

Step 5: methyl 5-bromo-3-(cyclopentyl(methyl)amino)-2-methylbenzoate

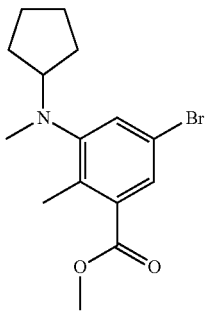 [SMILES: COC(=O)c1cc(Br)cc(N(C)C2CCCC2)c1C]

To a stirred solution of the crude methyl 5-bromo-3-(cyclopentylamino)-2-methylbenzoate (0.7 g, 2.25 mmol) in acetonitrile (15 mL), cesium carbonate (1.47 g, 4.50 mmol) and methyl iodide (1.6 g, 11.26 mmol) were added; resulting reaction mass was heated at 80° C. for 7 h. On completion, reaction mass was cooled to room temperature and filtered, residue was washed with ethyl acetate and filtrate was concentrated and then purified by column chromatography to afford the desired compound (0.6 g, 82%).

Step 6: 5-bromo-3-(cyclopentyl(methyl)amino)-N-((4,6-dimethyl-2-oxo-1,2-dihydropyridin-3-yl)methyl)-2-methylbenzamide

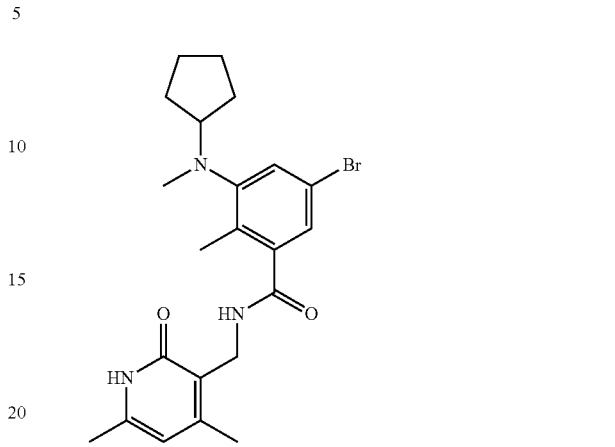

Aqueous NaOH (0.11 g, 2.75 mmol) was added to a solution of methyl 5-bromo-3-(cyclopentyl(methyl)amino)-2-methylbenzoate (0.6 g, 1.8 mmol) in MeOH (1.5 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. The combined organic layers were dried and concentrated to give the respective acid (0.5 g, 87%).

The acid (0.5 g, 1.60 mmol) was then dissolved in DMSO (3 mL) and 3-(amino methyl)-4,6-dimethylpyridin-2(1H)-one (0.49 g, 3.22 mmol) was added to it. The reaction mixture was stirred at room temperature for 15 min before PYBOP (1.25 g, 2.41 mmol) was added to it and stirring was continued for overnight. After completion of the reaction, reaction mass was poured into ice to obtain solid, this was filtered and washed with acetonitrile followed by ether to provide the desired compound (0.315 g, 44%).

Step 7: Synthesis of 5-(cyclopentyl(methyl)amino)-N-((4,6-dimethyl-2-oxo-1,2-dihydropyridin-3-yl)methyl)-4'-formyl-4-methyl-[1,1'-biphenyl]-3-carboxamide

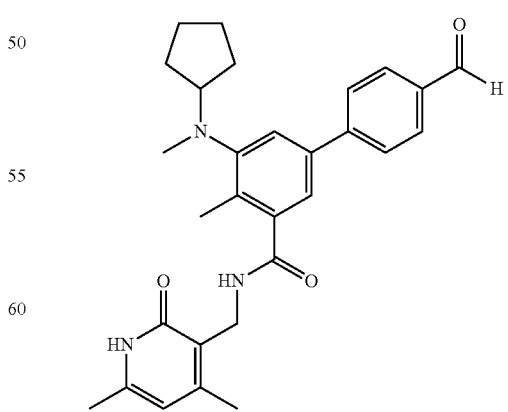

A solution of 5-bromo-3-(cyclopentyl(methyl)amino)-N-((4,6-dimethyl-2-oxo-1,2-dihydropyridin-3-yl)methyl)-2- methylbenzamide (1 equiv.), (4-formylphenyl)boronic acid (1.2 equiv.) and Pd (PPh$_3$)$_4$ (0.1 equiv.) in 1,4-dioxane (4 mL) was purged with argon for 10 min. Then, a 2 M Na$_2$CO$_3$ solution (3.6 equiv.) was added to it and argon was purged again for 10 min. The reaction mixture was stirred at 100° C. for 2 h. After completion of the reaction, water was added to it and extraction was carried out using DCM. The combined organic layers were washed with water, dried over anhydrous Na$_2$SO$_4$, filtered and concentrated under reduced pressure to afford crude material which was purified by column chromatography over silica gel (60-120 mesh size) to afford the desired compound (0.1 g, 44%).

Step 8: Synthesis of 5-(cyclopentyl(methyl)amino)-N-((4,6-dimethyl-2-oxo-1,2-dihydropuridin-3-yl)methyl)-4'-((dimethylamino)methyl)-4-methyl-[1,1'-biphenyl]-3-carboxamide

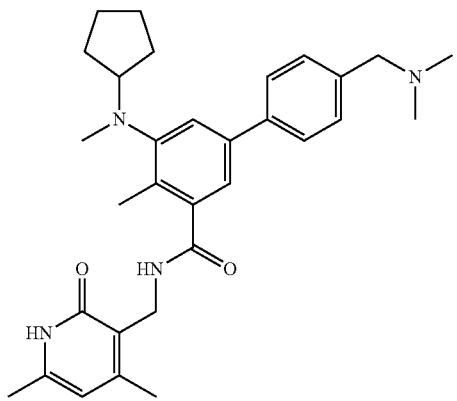

To a stirred solution of 5-(cyclopentyl(methyl)amino)-N-((4,6-dimethyl-2-oxo-1,2-dihydropyridin-3-yl)methyl)-4'-formyl-4-methyl-[1,1'-biphenyl]-3-carboxamide (0.1 g, 0.212 mmol) and N,N-dimethylamine (0.047 g, 1.06 mmol) in methanol (3 mL), acetic acid (0.1 g, 0.21 mmol) was added and reaction stirred at room temperature for 3 h. Then sodium cyanoborohydride (0.033 g, 0.53 mmol) was added and reaction stirred overnight. On completion, solvent was removed under reduced pressure and residue purified by column chromatography over silica gel to give the desired compound (0.04 g, 37%). LCMS: 501.39 (M+1)$_+$; HPLC: 90.78% (@ 254 nm) (R$_t$; 4.171; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (s, 1H), 8.17 (t, 1H), 7.57 (d, 2H, J=8 Hz), 7.33-7.37 (m, 3H), 7.17 (s, 1H), 5.85 (s, 1H), 4.27 (d, 2H, J=4.4 Hz), 3.52 (t, 1H, J=7.2 Hz), 3.04 (s, 2H), 2.54 (s, 3H), 2.23 (s, 3H), 2.19 (s, 3H), 2.15 (s, 6H), 2.09 (s, 3H), 1.70-1.72 (m, 2H), 1.61 (m, 2H), 1.43-1.50 (m, 4H).

Example 2: Synthesis of Compound 2: 5-(cyclopentyl(methyl)amino)-N-((4,6-dimethyl-2-oxo-1,2-dihydropyridin-3-yl)methyl)-4-methyl-4'-(morpholinomethyl)-[1,1'-biphenyl]-3-carboxamide Compound 2

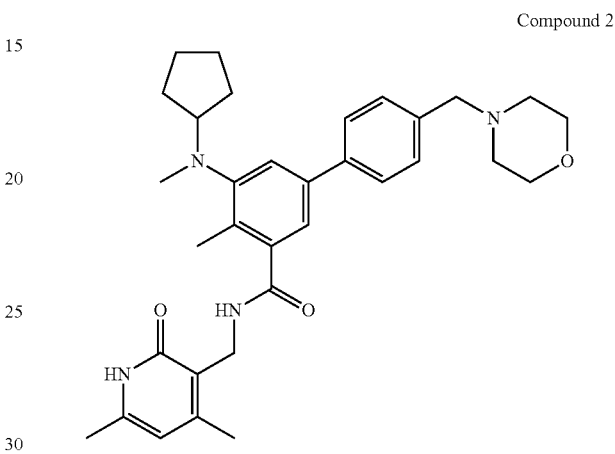

A solution of 5-bromo-3-(cyclopentyl(methyl)amino)-N-((4,6-dimethyl-2-oxo-1,2-dihydropyridin-3-yl)methyl)-2-methylbenzamide (1 equiv.), (4-(morpholinomethyl)phenyl) boronic acid (1.2 equiv.) and Pd (PPh$_3$)$_4$ (0.1 equiv.) in 1,4-dioxane (4 mL) was purged with argon for 10 min. Then, a 2 M Na$_2$CO$_3$ solution (3.6 equiv.) was added to it and argon was purged again for 10 min. The reaction mixture was stirred at 100° C. for 2 h. After completion of the reaction, water was added to it and extraction was carried out using DCM. The combined organic layers were washed with water, dried over anhydrous Na$_2$SO$_4$, filtered and concentrated under reduced pressure to afford crude material which was purified by column chromatography over silica gel (60-120 mesh size) to afford the desired compound (0.02 g, 16%). LCMS: 543.22 (M+1)$^+$; HPLC: 99.53% (@ 254 nm) (R$_t$; 4.181; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (s, 1H), 8.17 (t, 1H, J=4.4 Hz), 7.98 (s, 1H), 7.73 (d, 1H, J=7.6 Hz), 7.57 (d, 2H, J=7.6 Hz), 7.37 (s, 2H), 7.17 (s, 1H), 5.85 (s, 1H), 4.27 (d, 2H, J=4.8 Hz), 3.44-3.57 (m, 7H), 2.54 (s, 3H), 2.32-2.36 (m, 4H), 2.23 (s, 3H), 2.19 (s, 3H), 2.09 (s, 3H), 1.69-1.72 (m, 2H), 1.61 (m, 2H), 1.43-1.50 (m, 4H).

Example 3: Synthesis of 5-(cyclopentylamino)-N-((4,6-dimethyl-2-oxo-1,2-dihydropyridin-3-yl)methyl)-4'-((dimethylamino)methyl)-4-methyl-[1,1'-biphenyl]-3-carboxamide Compound 3

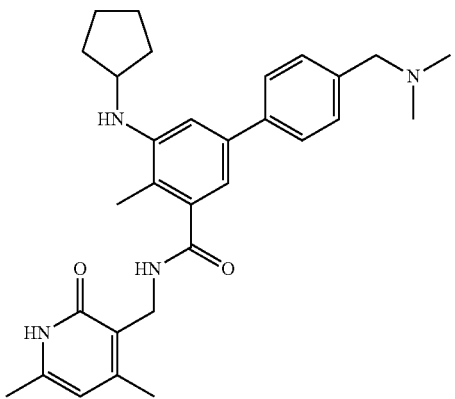

Step 1: Synthesis of 5-bromo-3-(cyclopentylamino)-N-((4,6-dimethyl-2-oxo-1,2-dihydropyridin-3-yl)methyl)-2-methylbenzamide Aqueous NaOH (0.1 g, 2.5 mmol) was added to a solution of methyl 5-bromo-3-(cyclopentylamino)-2-methylbenzoate (0.39 g, 1.25 mmol) in MeOH (5 mL) and stirred at 60° C. for 1 h. Ethanol was removed under reduced pressure, and the solution acidified using dilute HCl to pH 6 and citric acid to pH 4. The product was extracted with ethyl acetate and the combined organic layers were concentrated to give the desired acid (0.26 g, 0.82 mmol). The acid was dissolved in DMSO (3 mL) and 3-(amino methyl)-4,6-dimethylpyridin-2(1H)-one (0.25 g, 1.68 mmol) was added to the solution. The reaction mixture was stirred at room temperature for 15 min before PYBOP (0.65 g, 1.26 mmol) was added to it and stirring was continued overnight. The reaction mixture was poured onto ice to obtain a solid, and this solid was collected by filtration and washed with acetonitrile followed by ether to provide 5-bromo-3-(cyclopentylamino)-N-((4,6-dimethyl-2-oxo-1,2-dihydropyridin-3-yl)methyl)-2-methylbenzamide (0.178 g, 50%).

Step 2: Synthesis of 5-(cyclopentylamino)-N-((4,6-dimethyl-2-oxo-1,2-dihydropyridin-3-yl)methyl)-4'-formyl-4-methyl-[1,1'-biphenyl]-3-carboxamide A solution of 5-bromo-3-(cyclopentylamino)-N-((4,6-dimethyl-2-oxo-1,2-dihydropyridin-3-yl)methyl)-2-methylbenzamide (1 equiv.), (4-formylphenyl)boronic acid (1.2 equiv.) and Pd (PPh$_3$)$_4$ (0.1 equiv.) in 1,4-dioxane (4 mL) was purged with argon for 10 min. Then, 2 M Na$_2$CO$_3$ solution (3.6 equiv.) was added to it and argon was purged again for 10 min. The reaction mixture was stirred at 100° C. for 2 h. After cooling to room temperature water was added to the mixture and then product was extracted with DCM. The combined organic layers were washed with water, dried over anhydrous Na$_2$SO$_4$, filtered and concentrated under reduced pressure to afford crude material which was purified by column chromatography over silica gel (60-120 mesh size) to afford 5-(cyclopentylamino)-N-((4,6-dimethyl-2-oxo-1,2-dihydropyridin-3-yl)methyl)-4'-formyl-4-methyl-[1,1'-biphenyl]-3-carboxamide.

Step 3: 5-(cyclopentylamino)-N-((4,6-dimethyl-2-oxo-1,2-dihydropyridin-3-yl)methyl)-4'-((dimethylamino)methyl)-4-methyl-[1,1'-biphenyl]-3-carboxamide To a stirred solution of 5-(cyclopentylamino)-N-((4,6-dimethyl-2-oxo-1,2-dihydropyridin-3-yl)methyl)-4'-formyl-4-methyl-[1,1'-biphenyl]-3-carboxamide (0.11 g, 0.24 mmol) and N,N-dimethylamine (0.044 g, 1.2 mmol) in methanol (3 mL) was added acetic acid (0.014 g, 0.24 mmol) and the solution stirred at room temperature for 3 h. Then sodium cyanoborohydride (0.030 g, 0.48 mmol) was added and the solution stirred overnight. The solvent was removed under reduced pressure and the residue purified by column chromatography over silica gel to afford desired 5-(cyclopentylamino)-N-((4,6-dimethyl-2-oxo-1,2-dihydropyridin-3-yl)methyl)-4'-((dimethylamino)methyl)-4-methyl-[1,1'-biphenyl]-3-carboxamide LCMS: 486.21 (M+1)$^+$; HPLC: 99.84% (@ 254 nm) (R$_t$; 4.799; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.44 (s, 1H), 8.02-8.03 (m, 1H), 7.62 (d, 2H, J=7.6 Hz), 7.44 (s, 2H), 6.80 (s, 1H), 6.73 (s, 1H), 5.85 (s, 1H), 4.65 (d, 1H, J=6.4 Hz), 4.27 (d, 2H, J=4.4 Hz), 3.89 (d, 2H, J=5.2 Hz), 2.49 (7H merged in Solvent Peak), 1.98-2.19 (m, 11H), 1.55-1.70 (m, 6H).

Example 4: Synthesis of 5-(cyclopentylamino)-N-((4,6-dimethyl-2-oxo-1,2-dihydropyridin-3-yl)methyl)-4-methyl-4'-(morpholinomethyl)-[1,1'-biphenyl]-3-carboxamide Compound 4

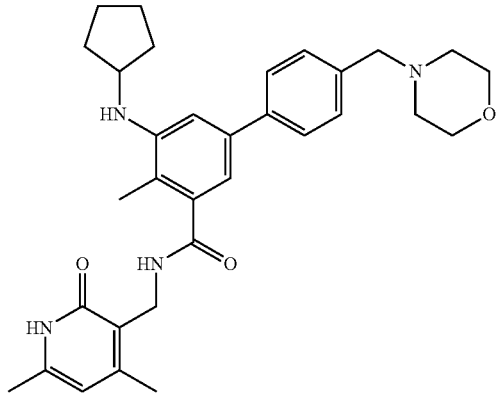

A solution of 5-bromo-3-(cyclopentylamino)-N-((4,6-dimethyl-2-oxo-1,2-dihydropyridin-3-yl)methyl)-2-methylbenzamide (1 equiv.), (4-(morpholinomethyl)phenyl)boronic acid (1.2 equiv.) and Pd (PPh$_3$)$_4$ (0.1 equiv.) in 1,4-dioxane (4 mL) was purged with argon for 10 min. Then, 2 M Na$_2$CO$_3$ solution (3.6 equiv.) was added to it and argon was purged again for 10 min. The reaction mixture was stirred at 100° C. for 2 h. After completion of the reaction, water was added to it and extraction was carried out using DCM. The combined organic layers were washed with water, dried over anhydrous Na₂SO₄, filtered and concentrated under reduced pressure to afford crude material which was purified by column chromatography over silica gel (60-120 mesh size) to afford 5-(cyclopentylamino)-N-((4,6-dimethyl-2-oxo-1,2-dihydropyridin-3-yl)methyl)-4-methyl-4'-(morpholinomethyl)-[1,1'-biphenyl]-3-carboxamide which was further purified using preparative HPLC which gave the TFA salt.

LCMS: 529.30 (M+1)+; HPLC: 99.46% (@ 254 nm) (Rt; 4.782; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); 1H NMR (DMSO-d6, 400 MHz) δ 11.46 (s, 1H), 9.90 (s, 1H), 8.06 (s, 1H), 7.72 (d, 2H, J=8 Hz), 7.55 (d, 2H, J=8 Hz), 6.83 (s, 1H), 6.76 (s, 1H), 5.86 (s, 1H), 4.37 (s, 2H), 4.27 (d, 2H, J=4 Hz), 3.89-3.98 (m, 3H), 3.28-3.31 (m, 2H), 3.14 (s, 2H), 2.19 (s, 3H), 2.10 (s, 3H), 2.05 (s, 3H), 1.98-1.99 (m, 2H), 1.70 (s, 2H), 1.55 (s, 4H).

Example 5: Synthesis of 2-(cyclohex-1-en-1-yl)-N-((4,6-dimethyl-2-oxo-1,2-dihydropyridin-3-yl)methyl)-6-(4-((dimethylamino)methyl)phenyl)isonicotinamide Compound 5

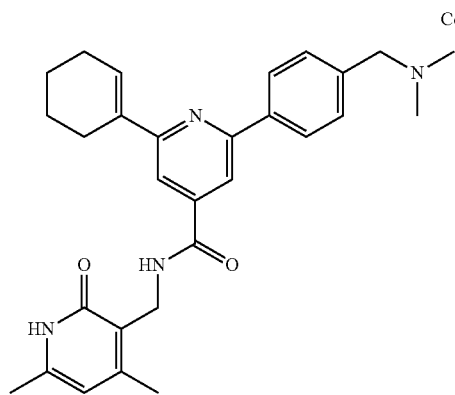

Step 1: Synthesis of methyl 2-chloro-6-(4-(hydroxymethyl)phenyl)isonicotinate

A solution of methyl 2,6-dichloroisonicotinate (1 g, 4.85 mmol), boronic acid (0.73 g, 4.8 mmol) and PdCl₂(PPh₃)₂ (0.15 g, 0.218 mmol) in THF (20 mL) was degassed for 15 min. Then Cs₂CO₃ was added and reaction mass purged again for 10 min. Reaction was heated at 70° C. for 2 h. On completion, reaction mass was concentrated and purified by column chromatography over silica gel affording methyl 2-chloro-6-(4-(hydroxymethyl)phenyl)isonicotinate (0.45 g, 33%).

Step 2: Synthesis of methyl 2-(4-(bromomethyl)phenyl)-6-chloroisonicotinate

To a solution of methyl 2-chloro-6-(4-(hydroxymethyl)phenyl)isonicotinate (0.67 g, 2.418 mmol) in DCM (10 mL), triphenyl phosphine (1 g, 3.86 mmol) and carbon tetrabromide (1.63 g, 3.87 mmol) were added at 0° C. and reaction mass stirred for overnight at rt. On completion, reaction mass was concentrated and purified by column chromatography over silica gel affording methyl 2-(4-(bromomethyl)phenyl)-6-chloroisonicotinate (0.53 g, 64%).

Step 3: Synthesis of methyl 2-chloro-6-(4-((dimethylamino)methyl)phenyl)isonicotinate To a solution of methyl 2-(4-(bromomethyl)phenyl)-6-chloroisonicotinate (0.533 g, 1.56 mmol) in THF, dimethylamine (7.8 mL, 2M solution in THF) was added and reaction mass stirred at rt for overnight. On completion, reaction mass concentrated and crude obtained was purified by column chromatography over silica gel obtaining pure methyl 2-chloro-6-(4-((dimethylamino)methyl)phenyl)isonicotinate (0.48 g, 99%).

Step 4: Synthesis of 2-chloro-N-((4,6-dimethyl-2-oxo-1,2-dihydropyridin-3-yl)methyl)-6-(4-((dimethylamino)methyl)phenyl)isonicotinamide To a solution of methyl 2-chloro-6-(4-((dimethylamino)methyl)phenyl)isonicotinate (0.48 g, 1.578 mmol) in ethanol (5 mL), NaOH (0.094 g, 2.368 mmol), dissolved in water (1 mL), was added and reaction mass heated at 60° C. for 1 h. On completion, solvent was evaporated under reduced pressure. Residue was washed with ether and acidified with 1N HCl till pH 8 and then with citric acid till pH 5-6. Aqueous layer was extracted with 20% MeOH/DCM and combined organic layers were concentrated under reduced pressure to afford the acid (0.47 g, crude) which was used in next step without further purification. To a solution of this acid (0.47 g, 1.64 mmol) in DMSO (4 mL), PyBOP (1.26 g, 2.43 mmol) was added and reaction stirred at rt for 15 min. Then 3-(aminomethyl)-4,6-dimethylpyridin-2(1H)-one (0.49 g, 3.28 mmol) was added and reaction stirred overnight. On completion, water was added and aqueous layer extracted with 20% MeOH/DCM. Combined organic layers were concentrated and residue purified by silica gel column chromatography affording 2-chloro-N-((4,6-dimethyl-2-oxo-1,2-dihydropyridin-3-yl)methyl)-6-(4-((dimethylamino)methyl)phenyl)isonicotinamide (0.3 g, 43.6%)

Step 5: Synthesis of 2-(cyclohex-1-en-1-yl)-N-((4,6-dimethyl-2-oxo-1,2-dihydropyridin-3-yl)methyl)-6-(4-((dimethylamino)methyl)phenyl)isonicotinamide To a stirred solution of 2-chloro-N-((4,6-dimethyl-2-oxo-1,2-dihydropyridin-3-yl)methyl)-6-(4-((dimethylamino)methyl)phenyl)isonicotinamide (0.11 g, 0.25 mmol), boronic acid (0.059 g, 0.27 mmol) in dioxane/water mixture (3 mL+1.5 mL), Na₂CO₃ (0.098 g, 3.6 mmol) was added and reaction mass purged with argon for 15 min. Then Pd(PPh₃)₄ (0.028 g, 0.025 mmol) was added and argon was purged again for 10 min. Reaction mass was heated at 100° C. for 3 h. On completion, reaction mass filtered through celite and celite bed washed with ethyl acetate. Combined filtrates were dried over Na₂SO₄ and solvent removed under reduced pressure to afford crude material which was purified by column over silica gel to obtain 2-(cyclohex-1-en-1-yl)-N-((4,6-dimethyl-2-oxo-1,2-dihydropyridin-3-yl)methyl)-6-(4-((dimethylamino)methyl)phenyl)isonicotinamide.

Analytical Data: LCMS: 471.30 (M+1)⁺; HPLC: 95.64% (@ 254 nm) (R$_t$; 5.661; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.52 (s, 1H), 8.79 (t, 1H), 8.13 (s, 1H), 8.10 (d, 2H, J=7.60 Hz), 7.81 (s, 1H), 7.41 (d, 2H, J=7.60 Hz), 6.90 (bs, 1H), 5.88 (s, 1H), 4.34 (d, 2H, J=4.8 Hz), 3.44 (s, 2H), 2.56 (bs, 2H), 2.26 (bs, 2H), 2.18 (s, 3H), 2.17 (s, 6H), 2.12 (s, 3H), 1.80-1.72 (m, 2H), 1.68-1.60 (m, 2H).

Example 6: Synthesis of N-((4,6-dimethyl-2-oxo-1, 2-dihydropyridin-3-yl)methyl)-2-(4-((dimethylamino)methyl)phenyl)-6-(piperidin-1-yl)isonicotinamide

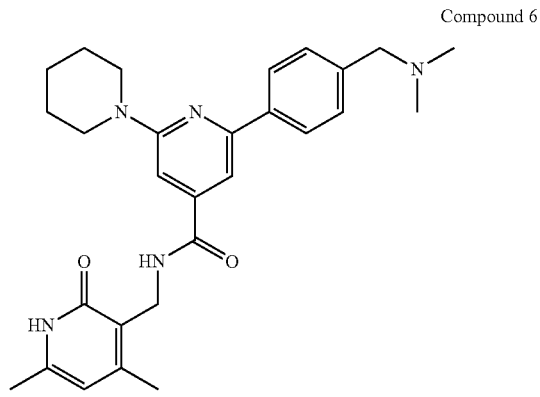

Compound 6

Step 1: Synthesis of methyl 2-chloro-6-(piperidin-1-yl)isonicotinate

A solution of methyl 2,6-dichloroisonicotinate (1 g, 4.85 mmol), piperidine (0.61 g, 7.28 mmol), K$_2$CO$_3$ (1.38 g, 9.7 mmol) in acetonitrile (20 mL) was heated at 90° C. for 20 h. After completion of reaction, reaction mass was filtered, filtrate concentrated and purified by column to obtain pure methyl 2-chloro-6-(piperidin-1-yl)isonicotinate (1.23 g, 90%).

Step 2: Synthesis of 2-chloro-N-((4,6-dimethyl-2-oxo-1,2-dihydropyridin-3-yl)methyl)-6-(piperidin-1-yl)isonicotinamide To a solution of methyl 2-chloro-6-(piperidin-1-yl)isonicotinate (1.1 g, 4.33 mmol) in ethanol (10 mL), NaOH (0.207 g, 5.196 mmol), dissolved in water (2 mL), was added and reaction mass heated at 60° C. for 1 h. On completion, solvent was evaporated under reduced pressure. Residue was washed with ether and acidified with 1N HCl till pH 8 and then with citric acid till pH 5-6. Solid obtained was filtered, washed with water and finally dried under reduced pressure to afford the acid (0.92 g, 89%) which was used in next step without further purification. To a solution of this acid (0.9 g, 3.75 mmol) in DMSO (10 mL), PyBOP (3.9 g, 7.5 mmol) was added and reaction stirred at rt for 15 min. Then 3-(aminomethyl)-4,6-dimethylpyridin-2(1H)-one (1.5 g, 10 mmol) was added and reaction stirred overnight. On completion, water was added and solid that precipitates out was filter, washed with water and dried to obtain 2-chloro-N-((4,6-dimethyl-2-oxo-1,2-dihydropyridin-3-yl) methyl)-6-(piperidin-1-yl)isonicotinamide (1 g, 74%).

Step 3: Synthesis of N-((4,6-dimethyl-2-oxo-1,2-dihydropyridin-3-yl)methyl)-2-(4-formylphenyl)-6-(piperidin-1-yl)isonicotinamide To a stirred solution of 2-chloro-N-((4,6-dimethyl-2-oxo-1,2-dihydropyridin-3-yl)methyl)-6-(piperidin-1-yl)isonicotinamide (0.6 g, 1.6 mmol), boronic acid (0.263 g, 1.76 mmol) in dioxane/water mixture (15 mL+5 mL), Na$_2$CO$_3$ (0.61 g, 5.76 mmol) was added and reaction mass purged for 15 min with argon. Then Pd(PPh$_3$)$_4$ (0.184 g, 0.16 mmol) was added and argon was purged again for 10 min. Reaction mass was heated at 100° C. for 3 h. On completion, reaction mass filtered through celite and celite bed washed with ethyl acetate. Combined filtrates were dried over Na$_2$SO$_4$ and solvent removed under reduced pressure to afford crude material which was purified by column over silica gel to obtain N-((4,6-dimethyl-2-oxo-1,2-dihydropyridin-3-yl) methyl)-2-(4-formylphenyl)-6-(piperidin-1-yl)isonicotinamide (0.5 g, 71%).

Step 4: Synthesis of N-((4,6-dimethyl-2-oxo-1,2-dihydropyridin-3-yl)methyl)-2-(4-((dimethylamino) methyl)phenyl)-6-(piperidin-1-yl)isonicotinamide To a solution of N-((4,6-dimethyl-2-oxo-1,2-dihydropyridin-3-yl)methyl)-2-(4-formylphenyl)-6-(piperidin-1-yl) isonicotinamide (0.2 g, 0.45 mmol) in methanol (12 mL), dimethyl amine (2.6 mL, 4.5 mmol, 2M solution in THF) and acetic acid (0.02 g, 0.45 mmol) were added and reaction mass stirred at rt for 90 min. Then reaction mass was cooled to 0° C. and sodium cyanoborohydride (0.056 g, 0.9 mmol) was added. Reaction stirred at 0° C. for 2 h and then stirred at rt for overnight. On completion, solvent was removed under reduced pressure, residue treated with water and extracted with ethyl acetate. Combined ethyl acetate layers were dried over sodium sulfate and concentrated under reduced pressure to afford crude material which was purified by column chromatography over silica gel obtaining N-((4, 6-dimethyl-2-oxo-1,2-dihydropyridin-3-yl)methyl)-2-(4-((dimethylamino)methyl)phenyl)-6-(piperidin-1-yl)isonicotinamide as light green solid (0.173 g, 79%).

Analytical Data: LCMS: 474.30 (M+1)$^+$; HPLC: 99.15% (@ 254 nm) (R$_t$; 5.257; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.50 (s, 1H), 8.61 (t, 1H, J=4.4 Hz), 8.03 (d, 2H, J=7.6 Hz), 7.52 (s, 1H), 7.40 (d, 2H, J=8.4 Hz), 7.13 (s, 1H), 5.87 (s, 1H), 4.32 (d, 2H, J=4 Hz), 3.63 (bs, 6H), 2.26 (bs, 6H), 2.18 (s, 3H), 2.11 (s, 3H), 1.59 (bs, 6H).

Example 7: Synthesis of N-((4,6-dimethyl-2-oxo-1, 2-dihydropyridin-3-yl)methyl)-2-(4-((dimethylamino)methyl)phenyl)-6-(isopropylamino)isonicotinamide

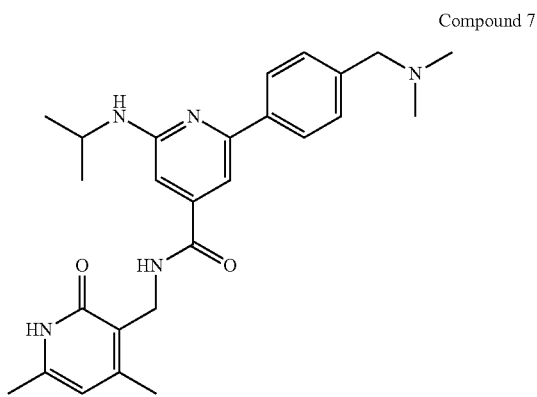

Compound 7

Step 1: Synthesis of methyl 2-chloro-6-(isopropylamino)isonicotinate

A solution of methyl 2,6-dichloroisonicotinate (1 g, 4.85 mmol), isopropyl amine (0.286 g, 4.85 mmol), $Cs_2CO_3$ (2.06 g, 6.3 mmol) in toluene (30 mL) was purged with argon for 10 min. Then, $Pd(OAc)_2$ (0.108 g, 0.485 mmol) and BINAP (0.3 g, 0.485 mmol) were added and argon was purged again for 15 min. Reaction mass was stirred at 80° C. for 6 h. On completion, reaction mass was filtered and residue washed thoroughly with ethyl acetate. Combined filtrates were concentrated and purified by column over silica gel to obtain pure methyl 2-chloro-6-(isopropylamino)isonicotinate (0.3 g, 27.27%).

Step 2: Synthesis of 2-chloro-N-((4,6-dimethyl-2-oxo-1,2-dihydropyridin-3-yl)methyl)-6-(isopropylamino)isonicotinamide To a solution of methyl 2-chloro-6-(isopropylamino) isonicotinate (0.393 g, 1.7 mmol) in ethanol (4 mL), NaOH (0.082 g, 2.06 mmol), water (0.8 mL) were added and reaction mass heated at 60° C. for 1 h. On completion, solvent was evaporated under reduced pressure. Residue was washed with ether and acidified with 1N HCl till pH 8 and then with citric acid till pH 5-6. Solid obtained was filtered, washed with water and finally dried under reduced pressure to afford the acid (0.36 g, 97%) which was used in next step without further purification. To a solution of this acid (0.36 g, 1.68 mmol) in DMSO (1.5 mL), PyBOP (1.3 g, 2.5 mmol) was added and reaction stirred at rt for 15 min. Then 3-(aminomethyl)-4,6-dimethylpyridin-2(1H)-one (0.383 g, 2.5 mmol) was added and reaction stirred overnight. On completion, water was added and aqueous layer extracted with 10% MeOH/DCM. Combined organic layers were washed with water, dried over sodium sulfate and concentrated to obtain crude 2-chloro-N-((4,6-dimethyl-2-oxo-1,2-dihydropyridin-3-yl)methyl)-6-(isopropylamino) isonicotinamide (0.58 g, 100%) which was used in next step without further purification.

Step 3: Synthesis of N-((4,6-dimethyl-2-oxo-1,2-dihydropyridin-3-yl)methyl)-2-(4-formylphenyl)-6-(isopropylamino)isonicotinamide To a stirred solution of 2-chloro-N-((4,6-dimethyl-2-oxo-1,2-dihydropyridin-3-yl)methyl)-6-(isopropylamino)isonicotinamide (0.58 g, 1.67 mmol), boronic acid (0.277 g, 1.84 mmol) in dioxane/water mixture (7 mL+3 mL), $Na_2CO_3$ (0.64 g, 6.037 mmol) was added and reaction mass purged for 15 min with argon. Then $Pd(PPh_3)_4$ (0.194 g, 0.168 mmol) was added and argon was purged again for 10 min. Reaction mass was heated at 100° C. for 3 h. On completion, reaction mass filtered through celite and celite bed washed with ethyl acetate. Combined filtrates were dried over $Na_2SO_4$ and solvent removed under reduced pressure to afford crude material which was purified by column over silica gel to obtain N-((4,6-dimethyl-2-oxo-1,2-dihydropyridin-3-yl)methyl)-2-(4-formylphenyl)-6-(isopropylamino) isonicotinamide (0.6 g, 85.7%).

Step 4: Synthesis of N-((4,6-dimethyl-2-oxo-1,2-dihydropyridin-3-yl)methyl)-2-(4-((dimethylamino) methyl)phenyl)-6-(isopropylamino)isonicotinamide To a solution of N-((4,6-dimethyl-2-oxo-1,2-dihydropyridin-3-yl)methyl)-2-(4-formylphenyl)-6-(isopropylamino) isonicotinamide (0.6 g, 1.44 mmol) in methanol (6 mL), dimethyl amine (7.1 mL, 14.33 mmol, 2M solution in THF) and acetic acid (0.086 g, 1.44 mmol) was added and reaction mass stirred at rt for 1 h. Then sodium cyanoborohydride (0.18 g, 2.8 mmol) was added reaction stirred at rt for 2 h. On completion, solvent was removed under reduced pressure, residue treated with water and extracted with ethyl acetate. Combined ethyl acetate layers were dried over sodium sulfate and concentrated under reduced pressure to afford crude material which was purified by prep HPLC obtaining target molecule Synthesis of N-((4,6-dimethyl-2-oxo-1,2-dihydropyridin-3-yl)methyl)-2-(4-((dimethylamino)methyl)phenyl)-6-(isopropylamino)isonicotinamide as light yellow solid.

Analytical Data: LCMS: 448.25 $(M+1)_+$; HPLC: 96.22% (@ 254 nm) ($R_t$; 4.170, Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR ($CD_3OD$, 400 MHz) δ 8.01 (d, 2H, J=8 Hz), 7.67 (d, 2H, J=8 Hz), 7.39 (s, 1H), 7.19 (s, 1H), 6.14 (s, 1H), 4.50 (s, 2H), 4.40 (s, 2H), 4.17-4.11 (m, 1H), 2.89 (s, 6H), 2.38 (s, 3H), 2.25 (s, 3H), 1.33 (d, 6H, J=6H).

Example 8: Synthesis of N-((4,6-dimethyl-2-oxo-1, 2-dihydropyridin-3-yl)methyl)-2-methyl-3-(methyl (tetrahydro-2H-pyran-4-yl)amino)-5-(1-(2-morpholinoethyl)-1H-pyrazol-4-yl)benzamide

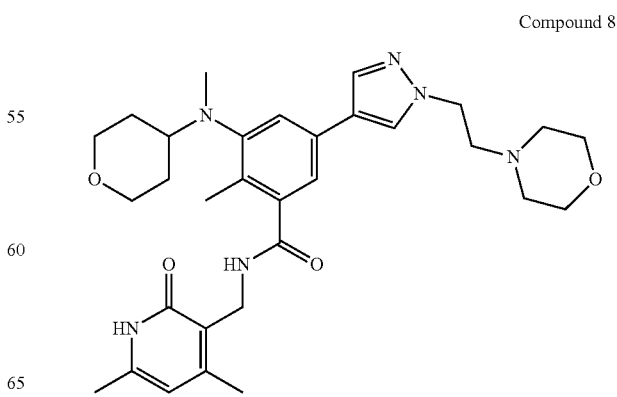

Compound 8

Step 1: Synthesis of methyl 5-bromo-2-methyl-3-((tetrahydro-2H-pyran-4-yl) amino) benzoate To a stirred solution of methyl 3-amino-5-bromo-2-methylbenzoate (2.5 g, 10.2 mmol) and dihydro-2H-pyran-4 (3H)-one (1.3 g, 13.3 mmol) in methanol (20 mL), acetic acid (0.61 g, 10.2 mmol) was added and the solution stirred at room temperature for 18 h. Then sodium cyanoborohydride (1.2 g, 20.48 mmol) was added at 0° C. and stirring was continued overnight at room temperature. Then, solvent was removed under reduced pressure and crude material was purified by column chromatography to afford methyl 5-bromo-2-methyl-3-((tetrahydro-2H-pyran-4-yl) amino) benzoate (2.2 g, 66%).

Step 2: Synthesis of methyl 5-bromo-2-methyl-3-(methyl (tetrahydro-2H-pyran-4-yl) amino) benzoate To a stirred solution of methyl 5-bromo-2-methyl-3-((tetrahydro-2H-pyran-4-yl) amino) benzoate (1.0 g, 3.15 mmol) in acetonitrile (15 mL), cesium carbonate (1.97 g, 6.10 mmol) and methyl iodide (2.15 g, 15.27 mmol) were added; resulting solution was heated at 80° C. for 20 h. The solution was cooled to room temperature, filtered, and the residue was washed with ethyl acetate. The filtrate was concentrated and the product purified by column chromatography to afford methyl 5-bromo-2-methyl-3-(methyl (tetrahydro-2H-pyran-4-yl) amino) benzoate (0.82 g, 80%).

Step 3: Synthesis of 5-bromo-N-((4,6-dimethyl-2-oxo-1,2-dihydropyridin-3-yl) methyl)-2-methyl-3-(methyl (tetrahydro-2H-pyran-4-yl) amino) benzamide Aqueous NaOH (0.19 g, 4.89 mmol) was added to a solution of methyl 5-bromo-2-methyl-3-(methyl (tetrahydro-2H-pyran-4-yl) amino) benzoate (0.82 g, 2.4 mmol) in MeOH (20 mL) and stirred at 60° C. for 1 h. Ethanol was removed under reduced pressure and the solution acidified using dilute HCl to pH 6 and citric acid to pH 4. The product was extracted with ethyl acetate and the combined organic layers were dried and concentrated to give respective acid (0.70 g). The acid was then dissolved in DMSO (3 mL) and 3-(amino methyl)-4,6-dimethylpyridin-2(1H)-one (0.74 g, 4.89 mmol) was added to it. The reaction mixture was stirred at room temperature for 15 min then PYBOP (1.9 g, 3.6 mmol) was added to it and stirring was continued for overnight. The solution was poured into ice to obtain a solid, this was filtered and washed with acetonitrile followed by purification with column chromatography to afford 5-bromo-N-((4,6-dimethyl-2-oxo-1,2-dihydropyridin-3-yl) methyl)-2-methyl-3-(methyl (tetrahydro-2H-pyran-4-yl) amino) benzamide (0.6 g, 54%).

Step 4: Synthesis of N-((4,6-dimethyl-2-oxo-1,2-dihydropyridin-3-yl)methyl)-2-methyl-3-(methyl (tetrahydro-2H-pyran-4-yl)amino)-5-(1-(2-morpholinoethyl)-1H-pyrazol-4-yl)benzamide To a stirred solution of 5-bromo-N-((4,6-dimethyl-2-oxo-1,2-dihydropyridin-3-yl) methyl)-2-methyl-3-(methyl (tetrahydro-2H-pyran-4-yl) amino) benzamide (1 equiv.) and 4-(2-(4-(4,4,5,5-tetramethyl-1,3,2-dioxaborolan-2-yl)-1H-pyrazol-1-yl)ethyl)morpholine (1.2 equiv.) in dioxane/water mixture (5 mL+1 mL), Na$_2$CO$_3$ (3.6 equiv.) was added and solution purged with argon for 15 min. Then Pd(PPh$_3$)$_4$ (0.1 equiv.) was added and argon was purged again for 10 min. The solution was heated at 100° C. for 4 h. The reaction mixture was diluted with water and extracted with 10% MeOH/DCM. Combined organic layers were dried over Na$_2$SO$_4$ and solvent removed under reduced pressure to afford crude material which was purified by column chromatography over silica gel to afford desired N-((4,6-dimethyl-2-oxo-1,2-dihydropyridin-3-yl)methyl)-2-methyl-3-(methyl(tetrahydro-2H-pyran-4-yl)amino)-5-(1-(2-morpholinoethyl)-1H-pyrazol-4-yl)benzamide (0.045 g, 36.9%).

LCMS: 563.00 (M+1)$_+$; HPLC % 99.26 (@ 254 nm) (R$_t$; 3.774; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (s, 1H), 8.17 (s, 1H), 8.06 (t, 1H, J=4.8 Hz), 7.82 (s, 1H), 7.29 (s, 1H), 7.11 (s, 1H), 5.87 (s, 1H), 4.27 (d, 2H, J=4.8 Hz), 4.21 (t, 2H, J=6.4 Hz), 3.85 (d, 2H, J=11.2 Hz), 3.54 (t, 4H), 3.23-3.26 (m, 2H), 2.99 (m, 1H), 2.72 (t, 2H, J=6.4 Hz), 2.60 (s, 3H), 2.40 (bs, 4H), 2.20 (s, 3H), 2.16 (s, 3H), 2.10 (s, 3H), 1.58-1.59 (m, 4H).

Example 9: Synthesis of N-((4,6-dimethyl-2-oxo-1,2-dihydropyridin-3-yl)methyl)-2-methyl-3-(methyl (tetrahydro-2H-pyran-4-yl)amino)-5-(1-methyl-1H-pyrazol-4-yl)benzamide

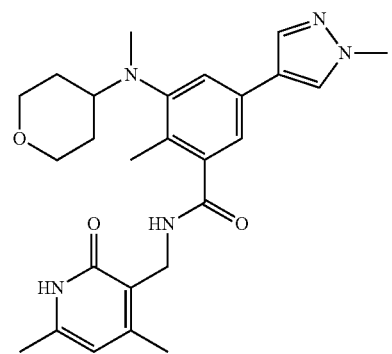

Compound 9

To a stirred solution of 5-bromo-N-((4,6-dimethyl-2-oxo-1,2-dihydropyridin-3-yl) methyl)-2-methyl-3-(methyl (tetrahydro-2H-pyran-4-yl) amino) benzamide (1 equiv.) and 1-methyl-4-(4,4,5,5-tetramethyl-1,3,2-dioxaborolan-2-yl)-1H-pyrazole (1.2 equiv.) in dioxane/water mixture (5 mL+1 mL), Na$_2$CO$_3$ (3.6 equiv.) was added and solution purged with argon for 15 min. Then Pd(PPh$_3$)$_4$ (0.1 equiv.) was added and argon was purged again for 10 min. The solution was heated at 100° C. for 4 h. The reaction mixture was diluted with water and extracted with 10% MeOH/DCM. Combined organic layers were dried over Na$_2$SO$_4$ and solvent removed under reduced pressure to afford crude material which was purified by column chromatography over silica gel to afford desired N-((4,6-dimethyl-2-oxo-1,2-dihydropyridin-3-yl)methyl)-2-methyl-3-(methyl(tetrahydro-2H-pyran-4-yl)amino)-5-(1-methyl-1H-pyrazol-4-yl)benzamide (0.02 g, 20%).

LCMS: 464.30 (M+1)$^+$; HPLC % 97.80 (@ 254 nm) (R$_t$; 4.286; Method: Column: YMC ODS-A 150 mm×4.6 mm×5µ; Mobile Phase: A; 0.05% TFA in water/B; 0.05%

TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (s, 1H), 8.12 (s, 1H), 8.06 (t, 1H), 7.81 (s, 1H), 7.28 (s, 1H), 7.10 (s, 1H), 5.85 (s, 1H), 4.27 (d, 2H, J=4.8 Hz), 3.83-3.86 (m, 5H), 3.23-3.29 (m, 2H), 2.99 (m, 1H), 2.59 (s, 3H), 2.20 (s, 3H), 2.16 (s, 3H), 2.10 (s, 3H), 1.58 (m, 4H).

Example 10: Synthesis of 3-(cyclohexyl(methyl) amino)-N-((4,6-dimethyl-2-oxo-1,2-dihydropyridin-3-yl)methyl)-2-methyl-5-(1-methyl-1H-pyrazol-4-yl) benzamide

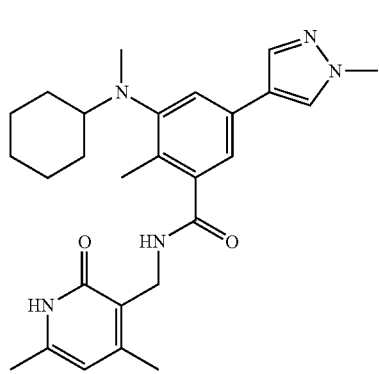

Compound 10

Step 1: Synthesis of methyl 5-bromo-3-(cyclohexylamino)-2-methylbenzoate

To a stirred solution of methyl 3-amino-5-bromo-2-methylbenzoate (5.0 g, 20.6 mmol) and cyclohexanone (4.03 g, 41.2 mmol) in methanol (50 mL), acetic acid (0.247 g, 20.6 mmol) was added and reaction stirred at room temperature for 3 h. Then sodium cyanoborohydride (1.55 g, 24.6 mmol) was added and reaction stirred overnight. On completion, solvent was removed under reduced pressure and crude material was purified by column chromatography to afford methyl 5-bromo-3-(cyclohexylamino)-2-methylbenzoate (2.75 g, 41%).

Step 2: Synthesis of methyl 5-bromo-3-(cyclohexyl (methyl) amino)-2-methylbenzoate To a stirred solution of methyl 5-bromo-3-(cyclohexylamino)-2-methylbenzoate (2.75 g, 8.45 mmol) in acetonitrile (25 mL), cesium carbonate (5.45 g, 16.9 mmol) and methyl iodide (6 g, 42.3 mmol) were added; resulting solution was heated at 80° C. for 20 h. On completion, the solution was cooled to room temperature and filtered, and the residue was washed with ethyl acetate. The filtrate was concentrated and then purified by column chromatography to afford methyl 5-bromo-3-(cyclohexyl (methyl) amino)-2-methylbenzoate (2.5 g, 87%).

Step 3: Synthesis of 5-bromo-3-(cyclohexyl (methyl) amino)-N-((4,6-dimethyl-2-oxo-1,2-dihydropyridin-3-yl) methyl)-2-methylbenzamide Aqueous NaOH (0.55 g, 14.7 mmol) was added to a solution of methyl 5-bromo-3-(cyclohexyl (methyl) amino)-2-methylbenzoate (2.5 g, 7.35 mmol) in MeOH (15 mL) and stirred at 60° C. for 1 h. After completion of the reaction, ethanol was removed under reduced pressure and acidified using dilute HCl to pH 6 and citric acid to pH 4. The product was extracted with ethyl acetate. Combined organic layers were dried and concentrated to give the respective acid (2.5 g, 87%). The acid was then dissolved in DMSO (20 mL) and 3-(amino methyl)-4,6-dimethylpyridin-2(1H)-one (2.34 g, 15.1 mmol) was added to it. The reaction mixture was stirred at room temperature for 15 min before PYBOP (5.85 g, 11.05 mmol) was added to it and stirring was continued for overnight. Then the reaction was poured into ice to obtain a solid which was collected by filtration and washed with acetonitrile. Column purification on silica provided 5-bromo-3-(cyclohexyl (methyl) amino)-N-((4,6-dimethyl-2-oxo-1,2-dihydropyridin-3-yl) methyl)-2-methylbenzamide (1.5 g, 44.19%).

Step 4: Synthesis of 3-(cyclohexyl(methyl)amino)-N-((4,6-dimethyl-2-oxo-1,2-dihydropyridin-3-yl) methyl)-2-methyl-5-(1-methyl-1H-pyrazol-4-yl)benzamide To a stirred solution of 5-bromo-3-(cyclohexyl (methyl) amino)-N-((4,6-dimethyl-2-oxo-1,2-dihydropyridin-3-yl) methyl)-2-methylbenzamide (1 equiv.) and 1-methyl-4-(4,4,5,5-tetramethyl-1,3,2-dioxaborolan-2-yl)-1H-pyrazole (1.2 equiv.) in dioxane/water mixture (5 mL+1 mL), Na$_2$CO$_3$ (3.6 equiv.) was added and solution purged with argon for 15 min. Then Pd (PPh$_3$)$_4$ (0.1 equiv.) was added and argon was purged again for 10 min. The reaction was heated at 100° C. for 4 h. After cooling, the reaction mixture was diluted with water and extracted with 10% MeOH/DCM. The combined organic layers were dried over Na$_2$SO$_4$ and the solvent removed under reduced pressure to afford crude product. Purification by column chromatography over silica gel afforded the title compound (0.02 g, 20%).

LCMS: 462.40 (M+1)$_+$; HPLC % 88.48 (@ 254 nm) (R$_t$; 4.683; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (s, 1H), 8.11 (s, 1H), 8.06 (t, 1H), 7.79 (s, 1H), 7.22 (s, 1H), 7.06 (s, 1H), 5.85 (s, 1H), 4.26 (d, 2H, J=4 Hz), 3.83 (s, 3H), 2.71 (t, 1H), 2.60 (s, 3H), 2.20 (s, 3H), 2.14 (s, 3H), 2.10 (s, 3H), 1.69 (m, 4H), 1.53-1.55 (m, 1H), 1.39-1.41 (m, 2H), 1.06-1.19 (m, 3H).

Example 11: Synthesis of N-((4,6-dimethyl-2-oxo-1,2-dihydropyridin-3-yl)methyl)-4-methyl-5-(methyl (piperidin-4-yl)amino)-4'-(morpholinomethyl)-[1,1'-biphenyl]-3-carboxamide

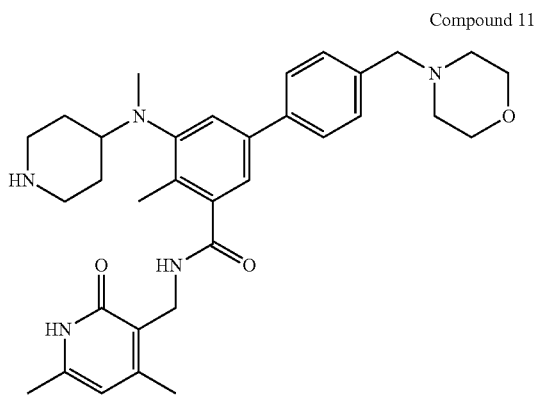 [SMILES: Cc1cc(C)c(CNC(=O)c2cc(-c3ccc(CN4CCOCC4)cc3)cc(N(C)C3CCNCC3)c2C)c(=O)[nH]1]

Compound 11

Step 1: Synthesis of tert-butyl 4-((5-bromo-3-(methoxycarbonyl) amino) piperidine-1-carboxylate To a stirred solution of methyl 3-amino-5-bromo-2-methylbenzoate (5.0 g, 20.6 mmol) and tert-butyl 4-oxopiperidine-1-carboxylate (8.2 g, 41.1 mmol) in methanol (50 mL), acetic acid (1.2 g, 20.6 mmol) was added and the reaction stirred at room temperature for 8 h. Then sodium cyanoborohydride (1.55 g, 24.6 mmol) was added at 0° C. and the reaction stirred overnight at room temperature. The solvent was removed under reduced pressure and the product was purified by column chromatography on silica gel to afford tert-butyl 4-((5-bromo-3-(methoxycarbonyl) amino) piperidine-1-carboxylate (5.0 g, 57%).

Step 2: Synthesis of tert-butyl 4-((5-bromo-3-(methoxycarbonyl)-2-methylphenyl (methyl) amino) piperidine-1-carboxylate To a stirred solution of tert-butyl 4-((5-bromo-3-(methoxycarbonyl) amino) piperidine-1-carboxylate (3.0 g, 7.06 mmol) in acetonitrile (25 mL), cesium carbonate (4.57 g, 14.1 mmol) and methyl iodide (5.0 g, 35.2 mmol) were added. The reaction was heated to 80° C. for 20 h. Then the reaction was cooled to room temperature and filtered, washing with ethyl acetate. The filtrate was concentrated and the product purified by column chromatography on silica gel to afford tert-butyl 4-((5-bromo-3-(methoxycarbonyl)-2-methylphenyl (methyl) amino) piperidine-1-carboxylate (2.5 g, 81%).

Step 3: Synthesis of tert-butyl 4-((5-bromo-3-(((4,6-dimethyl-2-oxo-1,2-dihydropyridin-3-yl) methyl) carbamoyl)-2-methylphenyl) (methyl) amino) piperidin-1-carboxylate Aqueous NaOH (0.37 g, 9.38 mmol) was added to a solution of tert-butyl 4-((5-bromo-3-(methoxycarbonyl)-2-methylphenyl (methyl) amino) piperidine-1-carboxylate (2.0 g, 4.69 mmol) in MeOH (20 mL) and stirred at 60° C. for 1 h. After completion of the reaction, ethanol was removed under reduced pressure and the solution acidified using dilute HCl to pH 6 and citric acid to pH 4. The product was extracted using ethyl acetate. The combined organic layers were dried and concentrated to give the respective acid (1.7 g, 90%). The acid was then dissolved in DMSO (10 mL) and 3-(amino methyl)-4,6-dimethylpyridin-2(1H)-one (1.42 g, 9.38 mmol) was added to it. The reaction mixture was stirred at room temperature for 15 min before PYBOP (3.66 g, 7.04 mmol) was added to it and stirring was continued for overnight. After completion, reaction mass was poured into ice to obtain solid, this was filtered and washed with acetonitrile followed by purification with column chromatography to afford tert-butyl 4-((5-bromo-3-(((4,6-dimethyl-2-oxo-1,2-dihydropyridin-3-yl) methyl) carbamoyl)-2-methylphenyl) (methyl) amino) piperidin-1-carboxylate (1.3 g, 50%).

Step 4: Synthesis of tert-butyl 4-((5-(((4,6-dimethyl-2-oxo-1,2-dihydropyridin-3-yl)methyl)carbamoyl)-4-methyl-4'-(morpholinomethyl)-[1,1'-biphenyl]-3-yl)(methyl)amino)piperidine-1-carboxylate To a stirred solution of tert-butyl 4-((5-bromo-3-(((4,6-dimethyl-2-oxo-1,2-dihydropyridin-3-yl) methyl) carbamoyl)-2-methylphenyl) (methyl) amino) piperidin-1-carboxylate (1 equiv.) and 4-(4-(4,4,5,5-tetramethyl-1,3,2-dioxaborolan-2-yl)benzyl)morpholine (1.2 equiv.) in dioxane/water mixture (5 mL+1 mL), $Na_2CO_3$ (3.6 equiv.) was added and solution purged with argon for 15 min. Then $Pd(PPh_3)_4$ (0.1 equiv.) was added and argon was purged again for 10 min. The reaction was heated at 100° C. for 5 h. After cooling, the reaction mixture was diluted with water, and the product was extracted with 10% MeOH/DCM. The combined organic layers were dried over $Na_2SO_4$ and the solvent removed under reduced pressure to afford crude product which was purified by column chromatography over silica gel to afford tert-butyl 4-((5-(((4,6-dimethyl-2-oxo-1,2-dihydropyridin-3-yl)methyl)carbamoyl)-4-methyl-4'-(morpholinomethyl)-[1,1'-biphenyl]-3-yl)(methyl)amino) piperidine-1-carboxylate

Step 5: Synthesis of N-((4,6-dimethyl-2-oxo-1,2-dihydropyridin-3-yl)methyl)-4-methyl-5-(methyl (piperidin-4-yl)amino)-4'-(morpholinomethyl)-[1,1'-biphenyl]-3-carboxamide A stirred solution of tert-butyl 4-((5-(((4,6-dimethyl-2-oxo-1,2-dihydropyridin-3-yl)methyl)carbamoyl)-4-methyl-4'-(morpholinomethyl)-[1,1'-biphenyl]-3-yl)(methyl)amino) piperidine-1-carboxylate (1 mmol) in DCM (5 mL) was cooled to 0° C. and TFA (2 mL) was added to it. The reaction was stirred at room temperature for 1 h. On completion, the solution was concentrated to dryness. The residue was purified by solvent washings to afford the title compound (0.07 g, 86%).

LCMS: 558.45 $(M+1)_+$; HPLC % 98.81 (@ 254 nm) ($R_t$; 4.009; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.45 (s, 1H), 10.1 (bs, 1H), 8.51 (d, 1H), 8.16 (t, 2H), 7.77 (d, 2H, J=8 Hz), 7.57 (d, 2H, J=8 Hz), 7.42 (s, 1H), 7.26 (s, 1H), 5.86 (s, 1H), 4.33 (bs, 2H), 4.29 (d, 2H, J=19.2 HZ), 3.96 (m, 2H), 3.25 (m, 4H), 3.15 (m, 4H), 2.89-2.91 (m, 2H), 2.64 (s, 3H), 2.26 (s, 3H), 2.20 (s, 3H), 2.10 (s, 3H), 1.81 (m, 4H).

Example 12: Synthesis of N-((4,6-dimethyl-2-oxo-1,2-dihydropyridin-3-yl)methyl)-4-methyl-5-(methyl(tetrahydro-2H-pyran-4-yl)amino)-4'-(morpholinomethyl)-[1,1'-biphenyl]-3-carboxamide Compound 12

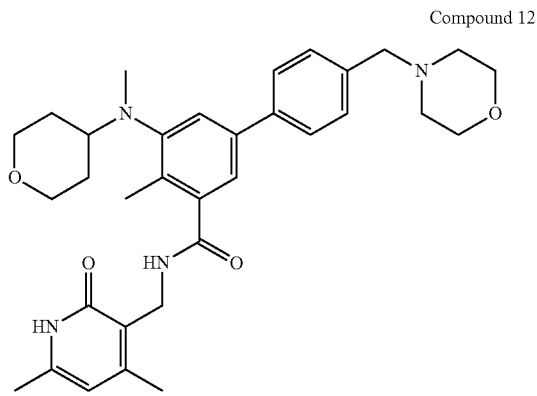 [SMILES: Cc1cc(C)c(CNC(=O)c2cc(-c3ccc(CN4CCOCC4)cc3)cc(N(C)C3CCOCC3)c2C)c(=O)[nH]1]

To a stirred solution of 5-bromo-N-((4,6-dimethyl-2-oxo-1,2-dihydropyridin-3-yl) methyl)-2-methyl-3-(methyl (tetrahydro-2H-pyran-4-yl) amino) benzamide (1 equiv.) and 4-(4-(4,4,5,5-tetramethyl-1,3,2-dioxaborolan-2-yl)benzyl) morpholine (1.2 equiv.) in dioxane/water mixture (5 mL+1 mL), $Na_2CO_3$ (3.6 equiv.) was added and solution purged with argon for 15 min. Then $Pd(PPh_3)_4$ (0.1 equiv.) was added and argon was purged again for 10 min. The solution was heated at 100° C. for 4 h. The reaction mixture was diluted with water and extracted with 10% MeOH/DCM. Combined organic layers were dried over $Na_2SO_4$ and solvent removed under reduced pressure to afford crude material which was purified by column chromatography over silica gel to afford the title compound (0.065 g, 55%). LCMS: 559.35 $(M+1)^+$; HPLC % 99.26 (@ 254 nm) ($R_t$: 3.983; Method: Column: YMC ODS-A 150 mm×4.6 mm×5μ; Mobile Phase: A; 0.05% TFA in water/B; 0.05% TFA in acetonitrile; Inj. Vol: 10 L, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.45 (s, 1H), 8.15 (t, 1H), 7.58 (d, 2H, J=8 Hz), 7.36 (d, 3H, J=8.4 Hz), 7.18 (s, 1H), 5.85 (s, 1H), 4.28 (d, 2H, J=4.8 Hz), 3.84 (d, 2H, J=11.2 Hz), 3.57 (m, 3H), 3.48 (m, 3H), 3.24 (m, 2H), 3.40 (m, 1H), 2.63 (s, 3H), 2.36 (m, 4H), 2.23 (s, 3H), 2.20 (s, 3H), 2.10 (s, 3H), 1.60 (m, 4H).

Example 13: Synthesis of N-((4,6-dimethyl-2-oxo-1,2-dihydropyridin-3-yl)methyl)-4'-((dimethylamino)methyl)-4-methyl-5-(methyl(tetrahydro-2H-pyran-4-yl)amino)-[1,1'-biphenyl]-3-carboxamide Compound 13

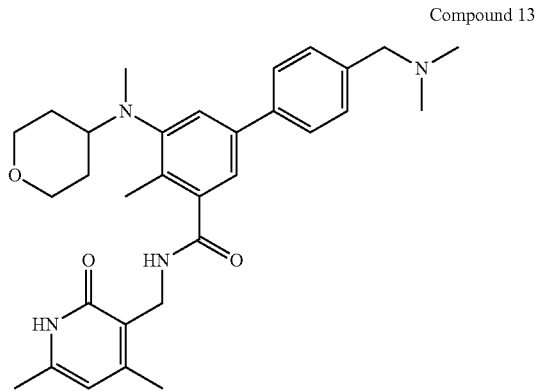

To a stirred solution of 5-bromo-N-((4,6-dimethyl-2-oxo-1,2-dihydropyridin-3-yl) methyl)-2-methyl-3-(methyl (tetrahydro-2H-pyran-4-yl) amino) benzamide (1 equiv.) and N,N-dimethyl-1-(4-(4,4,5,5-tetramethyl-1,3,2-dioxaborolan-2-yl)phenyl)methanamine (1.2 equiv.) in dioxane/water mixture (5 mL+1 mL), $Na_2CO_3$ (3.6 equiv.) was added and solution purged with argon for 15 min. Then $Pd(PPh_3)_4$ (0.1 equiv.) was added and argon was purged again for 10 min. The solution was heated at 100° C. for 4 h. The reaction mixture was diluted with water and extracted with 10% MeOH/DCM. Combined organic layers were dried over $Na_2SO_4$ and solvent removed under reduced pressure to afford crude material which was purified by column chromatography over silica gel to afford the title compound (0.01 g, 9%). LCMS: 517.30 (M+1)+; HPLC % 98.12 (@ 254 nm) ($R_t$: 3.972; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.45 (s, 1H), 8.16 (t, 1H), 7.58 (d, 2H, J=8 Hz), 7.34-7.36 (m, 2H), 7.18 (s, 1H), 5.85 (s, 1H), 4.28 (d, 2H, J=4 Hz), 3.84 (d, 2H, J=10.8 Hz), 3.42 (s, 2H), 3.02 (m, 2H), 2.66 (m, 1H), 2.63 (s, 3H), 2.50 (3H merged in solvent peak), 2.23 (s, 3H), 2.20 (s, 3H), 2.16 (s, 3H), 2.10 (s, 3H), 1.60 (m, 4H).

Example 14: Synthesis of 5-(cyclohexyl(methyl)amino)-N-((4,6-dimethyl-2-oxo-1,2-dihydropyridin-3-yl)methyl)-4-methyl-4'-(morpholinomethyl)-[1,1'-biphenyl]-3-carboxamide Compound 14

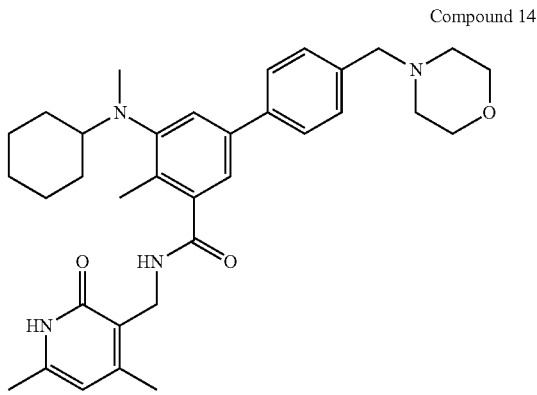 [SMILES: Cc1cc(C)c(CNC(=O)c2cc(-c3ccc(CN4CCOCC4)cc3)cc(N(C)C3CCCCC3)c2C)c(=O)[nH]1]

To a stirred solution of 5-bromo-3-(cyclohexyl(methyl)amino)-N-((4,6-dimethyl-2-oxo-1,2-dihydropyridin-3-yl) methyl)-2-methylbenzamide (1 equiv.) and (4-(morpholinomethyl) phenyl)boronic acid (1.2 equiv.) in dioxane/water mixture (5 mL+1 mL), $Na_2CO_3$ (3.6 equiv.) was added and the solution was purged with argon for 15 min. Then Pd (PPh$_3$)$_4$ (0.1 equiv.) was added and solution was purged again for 10 min. Reaction mixture was heated at 100° C. for 4 h. On completion, the mixture was diluted with water and extracted with 10% MeOH/DCM. Combined organic layers were dried over $Na_2SO_4$ and solvent removed under reduced pressure to afford crude material which was purified by column chromatography over silica gel to afford the title compound (0.070 g, 29% yield). LCMS: 557.40 $(M+1)^+$; HPLC % 98.83 (@ 254 nm) ($R_t$: 4.303; Method: Column: YMC ODS-A 150 mm×4.6 mm×5μ; Mobile Phase: A; 0.05% TFA in water/B; 0.05% TFA in acetonitrile; Inj. Vol:

10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (s, 1H), 8.15 (t, 1H, J=4 Hz), 7.56 (d, 2H, J=7.6 Hz), 7.36 (d, 2H, J=8 Hz), 7.28 (s, 1H), 7.13 (s, 1H), 5.85 (s, 1H), 4.28 (d, 2H, J=4.4 Hz), 3.57 (m, 4H), 3.48 (s, 2H), 2.74 (t, 1H), 2.64 (s, 3H), 2.36 (m, 4H), 2.20 (s, 6H), 2.10 (s, 3H), 1.69-1.71 (m, 3H), 1.53-1.56 (m, 2H), 1.41-1.44 (m, 2H), 1.10-1.23 (m, 3H).

Example 15: Synthesis of 3-(Cyclohexyl(methyl) amino)-N-((4,6-dimethyl-2-oxo-1,2-dihydropyridin-3-yl)methyl)-2-methyl-5-(1-(2-morpholinoethyl)-1H-pyrazol-4-yl)benzamide Compound 15

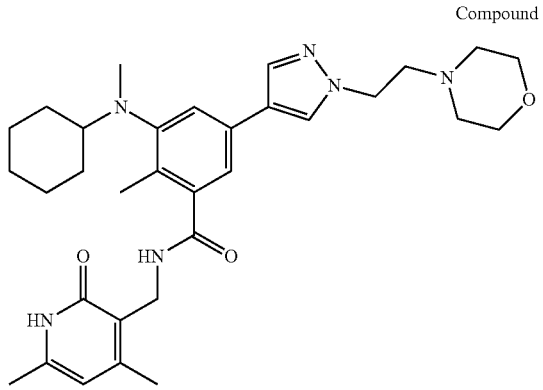

To a stirred solution of 5-bromo-3-(cyclohexyl(methyl) amino)-N-((4,6-dimethyl-2-oxo-1,2-dihydropyridin-3-yl) methyl)-2-methylbenzamide (1 equiv.) and (1-(2-morpholinoethyl)-1H-pyrazol-4-yl)boronic acid (1.2 equiv.) in dioxane/water mixture (5 mL+1 mL), Na$_2$CO$_3$ (3.6 equiv.) was added and the solution was purged with argon for 15 min. Then Pd (PPh$_3$)$_4$ (0.1 equiv.) was added and solution was purged again for 10 min. Reaction mixture was heated at 100° C. for 4 h. On completion, the mixture was diluted with water and extracted with 10% MeOH/DCM. Combined organic layers were dried over Na$_2$SO$_4$ and solvent removed under reduced pressure to afford crude material which was purified by column chromatography over silica gel to afford the title compound (0.06 g, 25% yield). LCMS: 561.35 (M+1)$^+$; HPLC % 96.87 (@ 254 nm) (R$_t$; 4.209; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.44 (s, 1H), 8.15 (s, 1H), 8.06 (t, 1H), 7.81 (s, 1H), 7.22 (s, 1H), 7.06 (s, 1H), 5.85 (s, 1H), 4.28 (d, 2H, J=4.8 Hz), 4.21 (t, 2H, J=6 Hz), 3.54 (m, 4H), 2.72 (t, 2H, J=6.8 Hz), 2.61 (s, 3H), 2.40 (m, 4H), 2.20 (s, 3H), 2.14 (s, 3H), 2.10 (s, 3H), 1.70 (m, 4H), 1.53-1.56 (m, 3H), 1.10-1.23 (m, 4H).

Example 16: Synthesis of 5-(Cyclohexyl(methyl) amino)-N-((4,6-dimethyl-2-oxo-1,2-dihydropyridin-3-yl)methyl)-4'-((dimethylamino)methyl)-4-methyl-[1,1'-biphenyl]-3-carboxamide Compound 16

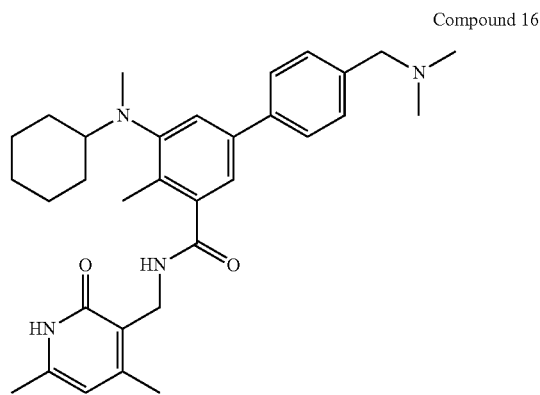

To a stirred solution of 5-bromo-3-(cyclohexyl(methyl) amino)-N-((4,6-dimethyl-2-oxo-1,2-dihydropyridin-3-yl) methyl)-2-methylbenzamide (1 equiv.) and (4-((dimethylamino) methyl)phenyl)boronic acid (1.2 equiv.) in dioxane/water mixture (5 mL+1 mL), Na$_2$CO$_3$ (3.6 equiv.) was added and the solution was purged with argon for 15 min. Then Pd (PPh$_3$)$_4$ (0.1 equiv.) was added and solution was purged again for 10 min. Reaction mixture was heated at 100° C. for 4 h. On completion, the mixture was diluted with water and extracted with 10% MeOH/DCM. Combined organic layers were dried over Na$_2$SO$_4$ and solvent removed under reduced pressure to afford crude material which was purified by column chromatography over silica gel to afford the title compound (0.065 g, 29% yield). LCMS: 515.40 (M+1)$^+$; HPLC % 96.73 (@ 254 nm) (R$_t$; 4.362; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (s, 1H), 8.16 (t, 1H), 7.64 (d, 2H, J=6.8 Hz), 7.45 (d, 2H), 7.30 (s, 1H), 7.16 (s, 1H), 5.85 (s, 1H), 4.28 (d, 2H, J=4.4 Hz), 2.75 (t, 1H), 2.65 (s, 3H), 2.32-2.42 (m, 6H), 2.20 (s, 6H), 2.10 (s, 3H), 1.69 (m, 4H), 1.53-1.56 (m, 1H), 1.42-1.45 (m, 2H), 1.10-1.23 (m, 4H). [1H merged in solvent peak].

Example 17: Synthesis of 3-(Cyclopentyl(methyl) amino)-N-((4,6-dimethyl-2-oxo-1,2-dihydropyridin-3-yl)methyl)-2-methyl-5-(6-(morpholinomethyl) pyridin-3-yl)benzamide Compound 17

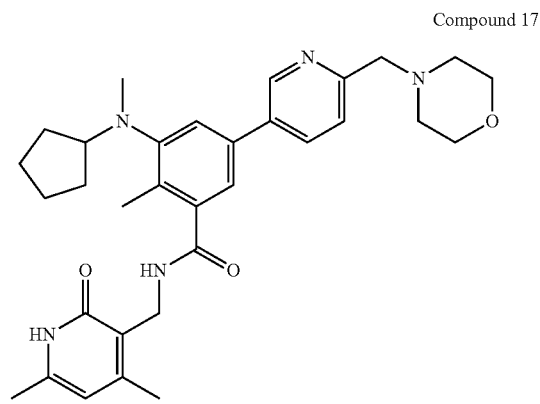 [SMILES: Cc1cc(C)c(CNC(=O)c2cc(-c3ccc(CN4CCOCC4)nc3)cc(N(C)C3CCCC3)c2C)c(=O)[nH]1]

Step 1: Synthesis of 3-(cyclopentyl(methyl)amino)-N-((4,6-dimethyl-2-oxo-1,2-dihydropyridin-3-yl)methyl)-5-(6-formylpyridin-3-yl)-2-methylbenzamide To a stirred solution of 5-bromo-3-(cyclopentyl(methyl)amino)-N-((4,6-dimethyl-2-oxo-1,2-dihydropyridin-3-yl)methyl)-2-methylbenzamide (0.5 g, 1.12 mmol) and (6-formylpyridin-3-yl)boronic acid (0.39 g, 1.68 mmol) in dioxane/water mixture (15 mL+3 mL), $Na_2CO_3$ (0.42 g, 4.09 mmol) was added and solution purged with argon for 15 min. Then $Pd(PPh_3)_4$ (0.130 g, 0.112 mmol) was added the mixture was purged again for 10 min. Reaction mass was heated at 100° C. for 4 h. On completion, reaction mixture was diluted with water and extracted with 10% MeOH/DCM. Combined organic layers were dried over $Na_2SO_4$ and solvent removed under reduced pressure to afford crude material which was purified by column chromatography over silica gel to afford the title compound (0.35 g, 66% yield).

Step 2: Synthesis of 3-(cyclopentyl(methyl)amino)-N-((4,6-dimethyl-2-oxo-1,2-dihydropyridin-3-yl)methyl)-2-methyl-5-(6-(morpholinomethyl)pyridin-3-yl)benzamide To a stirred solution of compound 3-(cyclopentyl(methyl)amino)-N-((4,6-dimethyl-2-oxo-1,2-dihydropyridin-3-yl)methyl)-5-(6-formylpyridin-3-yl)-2-methylbenzamide (1 equiv.) and morpholine (5 equiv.) in methanol (10 mL), acetic acid (2 equiv.) was added and reaction stirred at room temperature for 18 h. Then sodium cyanoborohydride (2.5 equiv.) was added at 0° C. and reaction stirred overnight at room temperature. On completion, solvent was removed under reduced pressure and crude material was purified by column chromatography to afford compound and crude material which was purified by preparative HPLC giving the title compound as a TFA salt, (0.022 g, 22%). LCMS: 544.35 $(M+1)^+$; HPLC % 98.42 (@ 254 nm) ($R_t$; 4.143; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.45 (s, 1H), 8.75 (s, 1H), 8.17 (t, 1H), 8.01 (d, 1H, J=7.6) 7.50 (d, 1H, J=7.6 Hz), 7.42 (s, 1H), 7.22 (s, 1H), 7.06 (s, 1H), 5.85 (s, 1H), 4.28 (d, 2H), 3.59-3.61 (m, 8H), 3.35-3.37 (m, 2H), 2.66 (s, 1H), 2.55 (s, 3H), 2.24 (s, 3H), 2.19 (s, 3H), 2.10 (s, 3H), 1.72 (m, 2H), 1.61 (m, 2H), 1.48 (m, 4H).

Example 18: Synthesis of 3-(Cyclopentyl(methyl)amino)-N-((4,6-dimethyl-2-oxo-1,2-dihydropyridin-3-yl)methyl)-2-methyl-5-(1-(2-morpholinoethyl)-1H-pyrazol-4-yl)benzamide

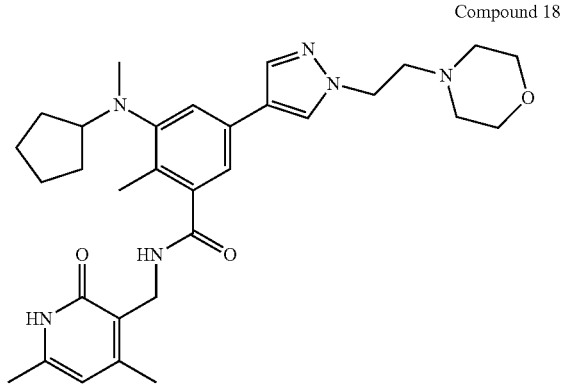 [SMILES: Cc1cc(C)c(CNC(=O)c2cc(-c3cnn(CCN4CCOCC4)c3)cc(N(C)C3CCCC3)c2C)c(=O)[nH]1]

Compound 18

A solution of 5-bromo-3-(cyclopentyl(methyl)amino)-N-((4,6-dimethyl-2-oxo-1,2-dihydropyridin-3-yl)methyl)-2-methylbenzamide (1 equiv.), (1-(2-morpholinoethyl)-1H-pyrazol-4-yl)boronic acid (1.2 equiv.) and Pd $(PPh_3)_4$ (0.1 equiv.) in 1,4-dioxane (4 mL) was purged with argon for 10 min. Then, 2 M $Na_2CO_3$ solution (3.6 equiv.) was added to it and the mixture was purged again for 10 min. The reaction mixture was stirred at 100° C. for 2 h. After reaction completion, water was added to it and extraction was carried out using DCM. The combined organic layers were washed with water, dried over anhydrous $Na_2SO_4$, filtered and concentrated under reduced pressure to afford crude material which was purified by column chromatography over silica gel (60-120 mesh size) to afford 3 the title compound (0.08 g, 66%). LCMS: 547.35 $(M+1)^+$; HPLC % 97.60 (@ 254 nm) ($R_t$; 4.071; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.44 (s, 1H), 8.17 (s, 1H), 8.05 (t, 1H), 7.81 (s, 1H), 7.30 (s, 1H), 7.10 (s, 1H), 5.85 (s, 1H), 4.26 (d, 2H, J=4 Hz), 4.20 (d, 2H, J=6.4 Hz), 3.49-3.53 (m, 6H), 2.72 (t, 2H), 2.40 (bs, 6H), 2.20 (s, 3H), 2.17 (s, 3H), 2.10 (s, 3H), 1.61-1.70 (m, 4H), 1.42-1.50 (m, 4H).

Example 19: Synthesis of 3-(Cyclopentyl(methyl)amino)-N-((4,6-dimethyl-2-oxo-1,2-dihydropyridin-3-yl)methyl)-2-methyl-5-(1-methyl-1H-pyrazol-4-yl)benzamide

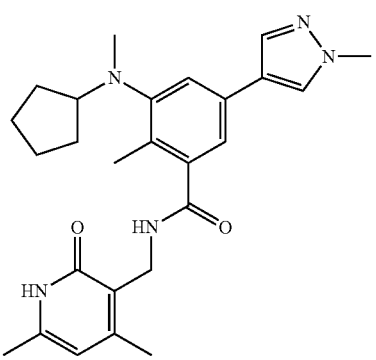

Compound 19

A solution of 5-bromo-3-(cyclopentyl(methyl)amino)-N-((4,6-dimethyl-2-oxo-1,2-dihydropyridin-3-yl)methyl)-2-methylbenzamide (1 equiv.), (1-methyl-1H-pyrazol-4-yl)boronic acid (1.2 equiv.) and Pd $(PPh_3)_4$ (0.1 equiv.) in 1,4-dioxane (4 mL) was purged with argon for 10 min. Then, 2 M $Na_2CO_3$ solution (3.6 equiv.) was added to it and the mixture was purged again for 10 min. The reaction mixture was stirred at 100° C. for 2 h. After reaction completion, water was added and extraction was carried out using DCM. The combined organic layers were washed with water, dried over anhydrous $Na_2SO_4$, filtered and concentrated under reduced pressure to afford crude material which was purified by column chromatography over silica gel (60-120 mesh size) to afford the title compound (0.07 g, 70%) LCMS: 448.25 $(M+1)^+$; HPLC % 98.34 (@ 254 nm) ($R_t$; 4.578; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate:

1.4 mL/min.; Gradient: 5% B to 95% B in 8 min, Hold for 1.5 min, 9.51-12 min 5% B); $^1$H NMR (DMSO-$d_6$, 400 MHz) δ 11.44 (s, 1H), 8.11 (s, 1H), 8.05 (t, 1H), 7.80 (s, 1H), 7.29 (s, 1H), 7.09 (s, 1H), 5.85 (s, 1H), 4.26 (d, 2H, J=3.2 Hz), 3.83 (s, 3H), 3.49 (m, 1H), 2.20 (s, 3H), 2.16 (s, 3H), 2.10 (s, 3H), 1.69 (m, 2H), 1.60 (m, 2H), 1.42-1.49 (m, 4H). [3H merged in solvent peak].

Example 20: Synthesis of 5-(((1s,4s)-4-acetamido-cyclohexyl)(methyl)amino)-N-((4,6-dimethyl-2-oxo-1,2-dihydropyridin-3-yl)methyl)-4-methyl-4'-(morpholinomethyl)-[1,1'-biphenyl]-3-carboxamide Compound 20

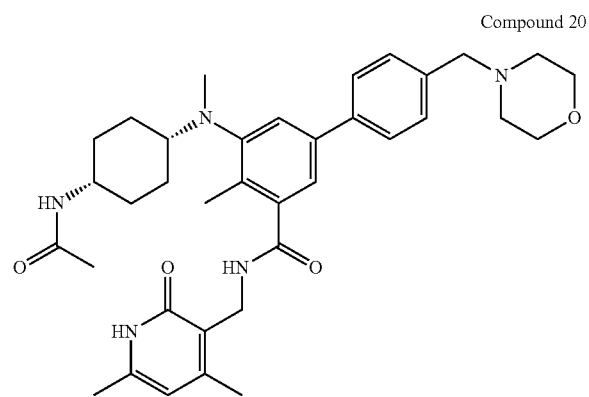 [SMILES: CC(=O)N[C@H]1CC[C@@H](N(C)c2cc(-c3ccc(CN4CCOCC4)cc3)cc(C(=O)NCc3c(C)cc(C)[nH]c3=O)c2C)CC1]

Step 1: Synthesis of 5-bromo-2-methyl-3-nitrobenzoic acid

To a stirred solution of 2-methyl-3-nitrobenzoic acid (50 g, 276.2 mmol) in conc. $H_2SO_4$ (200 mL) was added 1,3-dibromo-5,5-dimethyl-2,4-imidazolidinedione (43.4 g, 151.8 mmol) portion wise at room temperature and the reaction mixture was stirred at room temperature for 5 h. On completion, the reaction mixture was poured onto ice cold water, the resulting precipitate was filtered, the residue was washed with water and dried under vacuum to give 5-bromo-2-methyl-3-nitrobenzoic acid (71.7 g, 99.9%) which was used directly in the next step.

Step 2: Synthesis of methyl 5-bromo-2-methyl-3-nitrobenzoate

To a stirred solution of 5-bromo-2-methyl-3-nitrobenzoic acid (287 g, 1103 mmol) in DMF (150 mL) was added sodium carbonate (468 g, 4415 mmol) and methyl iodide (626.63 g, 4415 mmol). The resulting reaction mixture was heated at 60° C. for 8 h. On completion, the precipitated solid was collected by filtration, the residue washed with diethyl ether (5 times). The combined organic layers were dried, concentrated under reduced pressure to give methyl 5-bromo-2-methyl-3-nitrobenzoate (302 g, 99%) which was used directly in the next step.

Step 3: Synthesis of methyl 3-amino-5-bromo-2-methylbenzoate

To a stirred solution of methyl 5-bromo-2-methyl-3-nitrobenzoate (150 g, 544 mmol) in ethanol (750 mL) was added ammonium chloride (150 g, 2777 mmol) dissolved in water (750 mL) and iron powder (93.3 g, 1636 mmol) with stirring. The resulting reaction mixture was heated at 80° C. for 7 h. On completion, the reaction mixture was filtered through celite; the residue was washed with water and ethyl acetate, filtrate was extracted with ethyl acetate. The combined organic layers were dried, concentrated under reduced pressure to give methyl 3-amino-5-bromo-2-methylbenzoate which was used directly in the next step.

Step 4: Synthesis of methyl 5-bromo-3-((4-((tert-butoxycarbonyl)-amino)-cyclohexyl)-amino)-2-methylbenzoate To a stirred solution of methyl 3-amino-5-bromo-2-methylbenzoate (5 g, 20.57 mmol) and tert-butyl (4-oxocyclohexyl)carbamate (5.6 g, 26.7 mmol) in methanol (50 mL) was added acetic acid (1.2 g, 20.57 mmol) and the reaction mixture stirred at room temperature for 8 h. Then sodium cyanoborohydride (1.6 g, 26.74 mmol) was added at 0° C. and the reaction stirred overnight. On completion, solvent was removed under reduced pressure and the crude material was purified by column chromatography twice eluting with ethyl acetate: hexane to afford methyl 5-bromo-3-((4-((tert-butoxycarbonyl)-amino)-cyclohexyl)-amino)-2-methylbenzoate 4 g (44%) of non-polar isomer (cis isomer, contaminated with starting) and 3 g (33%) of pure polar isomer (trans isomer).

Step 5: Synthesis of methyl 5-bromo-3-((1s,4s)-(4-((tert-butoxycarbonyl)-amino)-cyclohexyl)-(methyl)-amino)-2-methylbenzoate To a stirred solution of the cis isomer of methyl 5-bromo-3-((4-((tert-butoxycarbonyl) amino) cyclohexyl) amino)-2-methylbenzoate (4 g, 9.09 mmol) in acetonitrile (50 mL) was added cesium carbonate (5.9 g, 18.18 mmol) and methyl iodide (6.45 g, 45.45 mmol). The resulting reaction mixture was heated at 80° C. for 7 h. On completion, the reaction mixture was cooled to room temperature and filtered, the residue was washed with ethyl acetate and the filtrate concentrated then purified by column chromatography to give 4.0 g (44%) of the less-polar cis-isomer, methyl 5-bromo-3-(((1s,4s)-4-((tert-butoxycarbonyl)-amino)-cyclohexyl)-amino)-2-methylbenzoate) and 3.0 g (33%) of more polar trans-isomer, methyl5-bromo-3-(((1r,4r)-4-((tert-butoxycarbonyl)-amino)-cyclohexyl)-amino)-2-methylbenzoate.

Step 6: Synthesis of tert-butyl (1s,4s)-(4-((5-bromo-3-(((4,6-dimethyl-2-oxo-1,2-dihydropyridin-3-yl)methyl)-carbamoyl)-2-methylphenyl)-(methyl)-amino)-cyclohexyl)carbamate Aqueous NaOH (0.23 g, 5.72 mmol) was added to a solution of methyl 5-bromo-3-(((1s,4s)-4-((tert-butoxycarbonyl)-amino)-cyclohexyl)-(methyl)-amino)-2-methylbenzoate (1.3 g, 2.86 mmol) in MeOH (20 mL) and stirred at 60° C. for 1 h. After completion of the reaction, ethanol was removed under reduced pressure and acidified using dilute HCl up to pH 6 and adjusted to pH 4 with citric acid. Extraction was carried out using ethyl acetate. The combined organic layers were dried concentrated to give the crude acid (1.13 g, 90.1%).

The acid (1.13 g, 2.57 mmol) was then dissolved in DMSO (10 mL) and 3-(amino methyl)-4,6-dimethylpyridin-2(1H)-one (0.87 g, 5.72 mmol) was added. The reaction mixture was stirred at room temperature for 15 min before PYBOP (2.23 g, 4.28 mmol) was added and stirring was continued overnight. After completion of the reaction, the reaction mixture was poured into ice to obtain a solid, this was filtered and washed with acetonitrile followed by purification with column chromatography to afford tert-butyl (1s,4s)-(4-((5-bromo-3-(((4,6-dimethyl-2-oxo-1,2-dihydropyridin-3-yl)methyl)-carbamoyl)-2-methylphenyl)-(methyl)-amino)-cyclohexyl)carbamate (0.8 g, 48.7%).

Step 7: Synthesis of 3-(((1s,4s)-4-aminocyclohexyl)-(methyl)-amino)-5-bromo-N-((4,6-dimethyl-2-oxo-1,2-dihydropyridin-3-yl)-methyl)-2-methylbenzamide To a stirred solution of tert-butyl (4-((5-bromo-3-(((4,6-dimethyl-2-oxo-1,2-dihydropyridin-3-yl)methyl)-carbamoyl)-2-methylphenyl)-(methyl)-amino)-cyclohexyl)-carbamate (0.8 g, 1.39 mmol) in DCM (25 mL) at 0° C. was added TFA (5 mL). The reaction mixture was stirred at room temperature for 1 h. On completion, the reaction mixture was concentrated to dryness. The residue was basified with aqueous sodium bicarbonate to pH 8 and the aqueous layer extracted with 20% MeOH/DCM. The combined organic layers were dried over sodium sulfate and concentrated to afford 3-(((1s,4s)-4-aminocyclohexyl)-(methyl)-amino)-5-bromo-N-((4,6-dimethyl-2-oxo-1,2-dihydropyridin-3-yl)-methyl)-2-methylbenzamide (600 mg, 90.9%).

Step 8: Synthesis of 3-((1s,4s)-(4-acetamidocyclohexyl)-(methyl)-amino)-5-bromo-N-((4,6-dimethyl-2-oxo-1,2-dihydropyridin-3-yl)-methyl)-2-methylbenzamide To a stirred solution of 3-((4-aminocyclohexyl)-(methyl)-amino)-5-bromo-N-((4,6-dimethyl-2-oxo-1,2-dihydropyridin-3-yl)-methyl)-2-methylbenzamide (0.275, 0.580 mmol) in DMF (5 mL), was added EDCl.HCl (0.168 g, 0.870 mmol), HOBt (0.078 g, 0.58 mmol) and acetic acid (0.07 g, 1.16 mmol), the reaction mixture was stirred at room temperature for 18 h. On completion, water was added and the organics extracted with 10% MeOH/DCM. The combined organic layers were dried, concentrated giving crude material which then purified by column chromatography to afford 3-(((1s,4s)-4-acetamidocyclohexyl)-(methyl)-amino)-5-bromo-N-((4,6-dimethyl-2-oxo-1,2-dihydropyridin-3-yl)-methyl)-2-methylbenzamide (0.25 g, 83.6%).

Step 9: Synthesis of 5-(((1s,4s)-4-acetamidocyclohexyl)(methyl)amino)-N-((4,6-dimethyl-2-oxo-1,2-dihydropyridin-3-yl)methyl)-4-methyl-4'-(morpholinomethyl)-[1,1'-biphenyl]-3-carboxamide To a stirred solution of 3-((4-acetamidocyclohexyl)-(methyl)-amino)-5-bromo-N-((4,6-dimethyl-2-oxo-1,2-dihydropyridin-3-yl)-methyl)-2-methylbenzamide (1 equiv.) and 4-(4-(4,4,5,5-tetramethyl-1,3,2-dioxaborolan-2-yl) benzyl) morpholine (1.2 equiv.) in dioxane/water mixture (5 mL+1 mL) was added $Na_2CO_3$ (3.6 equiv.) and the solution purged with argon for 15 min. Then $Pd(PPh_3)_4$ (0.1 equiv.) was added and argon was purged again for 10 min. The reaction mixture was heated at 100° C. for 4 h. On completion, the reaction mixture was diluted with water and extracted with 10% MeOH/DCM. The combined organic layers were dried over $Na_2SO_4$ and the solvent removed under reduced pressure to afford crude material which was purified by column chromatography over silica gel to afford the title compound (0.06 g, 50.8%). LCMS: 614.40 (M+1)$^+$; HPLC % 99.44 (@ 254 nm) ($R_t$: 3.948; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.45 (s, 1H), 8.17 (t, 1H), 7.76 (d, 1H, J=7.2 Hz), 7.55 (d, 2H, J=7.6 Hz), 7.36 (d, 3H, J=8 Hz), 7.16 (s, 1H), 5.85 (s, 1H), 4.28 (d, 2H, J=4.4 Hz), 3.71 (bs, 1H), 3.57 (m, 4H), 3.47 (s, 2H), 2.98 (m, 1H), 2.59 (s, 3H), 2.36 (m, 4H), 2.26 (s, 3H), 2.20 (s, 3H), 2.10 (s, 3H), 1.74-1.81 (m, 5H), 1.49-1.56 (m, 3H), 1.40-1.48 (m, 3H).

Example 21: 5-(((1r,4r)-4-acetamidocyclohexyl)(methyl)amino)-N-((4,6-dimethyl-2-oxo-1,2-dihydropyridin-3-yl)methyl)-4-methyl-4'-(morpholinomethyl)-[1,1'-biphenyl]-3-carboxamide prepared in analogous fashion as example 20 from trans-isomer, methyl 5-bromo-3-(((1r,4r)-4-((tert-butoxycarbonyl)-amino)-cyclohexyl)-amino)-2-methylbenzoate intermediate described in Example 20

Compound 21

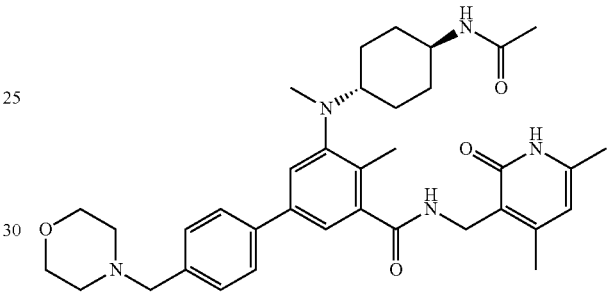

Analytical Data of 1258-Trans: LCMS: 614.40 (M+1)$^+$; HPLC % 99.64 (@ 254 nm) ($R_t$: 3.917; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.45 (s, 1H), 8.16 (t, 1H), 7.76 (d, 1H, J=7.6 Hz), 7.57 (d, 2H, J=7.2 Hz), 7.36 (d, 2H, J=7.6 Hz), 7.29 (s, 1H), 7.14 (s, 1H), 5.85 (s, 1H), 4.28 (d, 2H), 3.57 (bs, 5H), 3.48 (m, 2H), 2.71 (m, 1H), 2.64 (s, 3H), 2.36 (m, 4H), 2.20 (s, 6H), 2.10 (s, 3H), 1.68-1.81 (m, 7H), 1.51-1.53 (m, 2H), 1.10-1.13 (m, 2H).

Example 22: Synthesis of 3-(((1s,4s)-4-acetamidocyclohexyl)(methyl)amino)-N-((4,6-dimethyl-2-oxo-1,2-dihydropyridin-3-yl)methyl)-2-methyl-5-(1-methyl-1H-pyrazol-4-yl)benzamide Compound 22

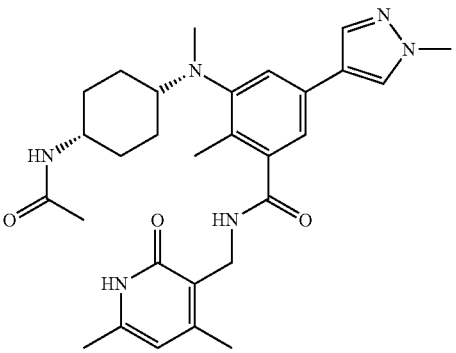

To a stirred solution of 3-(((1s,4s)-4-acetamidocyclohexyl)-(methyl)-amino)-5-bromo-N-((4,6-dimethyl-2-oxo-1,2-dihydropyridin-3-yl)-methyl)-2-methylbenzamide (1 equiv.) and 1-methyl-4-(4,4,5,5-tetramethyl-1,3,2-dioxaborolan-2-yl)-1H-pyrazole (1.2 equiv.) in dioxane/water mixture (5 mL+1 mL) was added $Na_2CO_3$ (3.6 equiv.) and the solution purged with argon for 15 min. Then $Pd(PPh_3)_4$ (0.1 equiv.) was added and argon was purged again for 10 min. The reaction mixture was heated at 100° C. for 4 h. On completion, the reaction mixture was diluted with water and extracted with 10% MeOH/DCM. The combined organic layers were dried over $Na_2SO_4$ and the solvent removed under reduced pressure to afford crude material which was purified by column chromatography over silica gel to afford the title compound (0.02 g, 20%). LCMS: 519.40 $(M+1)^+$; HPLC % 96.24 (@ 254 nm) ($R_t$: 4.247; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.44 (s, 1H), 8.10 (s, 1H), 8.07 (t, 1H), 7.79 (s, 1H), 7.75 (d, 1H, J=7.2 Hz), 7.27 (s, 1H), 7.09 (s, 1H), 5.86 (s, 1H), 4.27 (d, 2H, J=4.8 Hz), 3.83 (s, 3H), 3.69 (bs, 1H), 2.96 (m, 1H), 2.56 (s, 3H), 2.20 (s, 6H), 2.10 (s, 3H), 1.81 (s, 3H), 1.74-1.76 (m, 2H), 1.54 (m, 2H), 1.36-1.46 (m 4H).

Example 23 Synthesis of 3-(((1r,4r)-4-acetamidocyclohexyl)(methyl)amino)-N-((4,6-dimethyl-2-oxo-1,2-dihydropyridin-3-yl)methyl)-2-methyl-5-(1-methyl-1H-pyrazol-4-yl)benzamide Compound 23

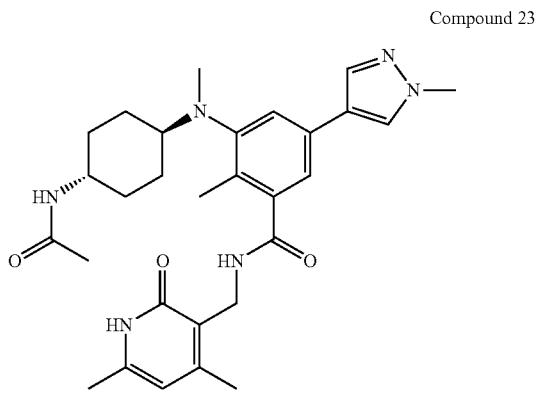 [SMILES: CC(=O)N[C@H]1CC[C@H](N(C)c2cc(-c3cnn(C)c3)cc(C(=O)NCc3c(C)cc(C)[nH]c3=O)c2C)CC1]

Prepared in prepared in analogous fashion as example 22 (0.06 g, 40%). LCMS: 519.30 $(M+1)^+$; HPLC % 98.21 (@ 254 nm) ($R_t$: 4.155; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.45 (s, 1H), 8.12 (s, 1H), 8.07 (t, 1H), 7.80 (s, 1H), 7.66 (d, 1H, J=7.2 Hz), 7.23 (s, 1H), 7.07 (s, 1H), 5.86 (s, 1H), 4.26 (d, 2H, J=2.8 Hz), 3.83 (s, 3H), 3.44 (m, 1H), 2.66-2.69 (m, 1H), 2.61 (s, 3H), 2.20 (s, 3H), 2.13 (s, 3H), 2.10 (s, 3H), 1.78-1.80 (m, 2H), 1.74 (s, 3H), 1.67-1.70 (m, 2H), 1.48-1.51 (m 2H), 1.10-1.13 (m, 2H).

Example 24: Synthesis of N-((4,6-dimethyl-2-oxo-1,2-dihydropyridin-3-yl)methyl)-2-methyl-3-(methyl (piperidin-4-yl)amino)-5-(6-(morpholinomethyl) pyridin-3-yl)benzamide Compound 24

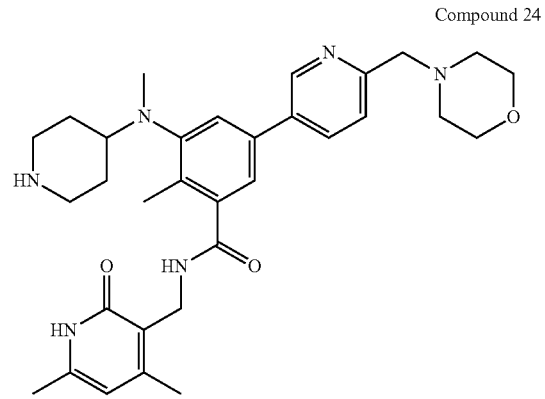 [SMILES: Cc1cc(C)c(CNC(=O)c2cc(-c3ccc(CN4CCOCC4)nc3)cc(N(C)C3CCNCC3)c2C)c(=O)[nH]1]

Step 1: Synthesis of tert-butyl 4-((3-(((4,6-dimethyl-2-oxo-1,2-dihydropyridin-3-yl) methyl) carbamoyl)-5-(6-formylpyridin-3-yl)-2-methylphenyl) (methyl) amino) piperidine-1-carboxylate Tert-butyl 4-((5-bromo-3-(((4,6-dimethyl-2-oxo-1,2-dihydropyridin-3-yl) methyl) carbamoyl)-2-methylphenyl) (methyl) amino) piperidin-1-carboxylate (0.5 g, 0.892 mmol), (6-formylpyridin-3-yl)boronic acid (0.31 g, 1.33 mmol) and $Pd(PPh_3)_4$ (0.103 g, 0.082 mmol) in 1,4-dioxane (10 mL) was purged with argon for 10 min. Then, 2 M $Na_2CO_3$ solution (0.34 g, 3.21 mmol) was added to it and again argon was purged through it for 10 min. The reaction mixture was stirred at 100° C. for 2 h. After completion of the reaction, water was added to it and extraction was carried out using 5% MeOH in DCM. The combined organic layers were washed with water, dried over anhydrous $Na_2SO_4$, filtered and concentrated under reduced pressure to afford crude material which was purified by column chromatography over silica gel (60-120 mesh size) to afford tert-butyl 4-((3-(((4,6-dimethyl-2-oxo-1,2-dihydropyridin-3-yl) methyl)carbamoyl)-5-(6-formylpyridin-3-yl)-2-methylphenyl)(methyl)amino)piperidine-1-carboxylate (0.40 g, 87.9%).

Step 2: Synthesis of N-((4,6-dimethyl-2-oxo-1,2-dihydropyridin-3-yl)methyl)-2-methyl-3-(methyl (piperidin-4-yl)amino)-5-(6-(morpholinomethyl) pyridin-3-yl)benzamide To a stirred solution of tert-butyl 4-((3-(((4,6-dimethyl-2-oxo-1,2-dihydropyridin-3-yl)methyl)carbamoyl)-5-(6-formylpyridin-3-yl)-2-methylphenyl)(methyl)amino)piperidine-1-carboxylate (1 equiv.) and morpholine (5 equiv.) in methanol (5 mL for 0.3 mmol), acetic acid (1 equiv.) was added and reaction stirred at room temperature for 4 h. Then reducing agent $NaBH_3CN$ (1 equiv.) was added and reaction stirred overnight. On completion, solvent was removed under reduced pressure and residue purified by column chromatography over silica gel affording desired tert-butyl 4-((3-(((4,6-dimethyl-2-oxo-1,2-dihydropyridin-3-yl) methyl)carbamoyl)-2-methyl-5-(6-(morpholinomethyl)pyridin-3-yl)phenyl)(methyl)amino)piperidine-1-carboxylate. This compound was then dissolved in DCM (5 mL) and cooled to 0° C. TFA (2 mL) was added to it. Reaction mixture was stirred at room temperature for 1 h. On completion, reaction was concentrated to dryness. Residue was purified by solvent washings to afford the title compound (0.1 g, 65.78%). LCMS: 559.35 (M+1)+; HPLC: 95.60% (@ 254 nm) ($R_t$: 3.906; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.45 (s, 1H), 8.96 (s, 1H), 8.67 (m, 1H), 8.22 (d, 2H, J=8 Hz), 8.17 (t, 1H), 7.61 (d, 1H, J=8 Hz), 7.48 (s, 1H), 7.32 (s, 1H), 5.87 (s, 1H), 4.52 (s, 2H), 4.29 (d, 2H, J=4.4 Hz), 3.84 (bs, 4H), 3.26 (bs, 6H), 3.16 (t, 1H), 2.89-2.91 (m, 2H), 2.64 (s, 3H), 2.26 (s, 3H), 2.21 (s, 3H), 2.10 (s, 3H), 1.81 (bs, 4H).

Example 25: Synthesis of N-((4,6-dimethyl-2-oxo-1,2-dihydropyridin-3-yl)methyl)-2-methyl-3-(methyl (piperidin-4-yl)amino)-5-(1-(2-morpholinoethyl)-1H-pyrazol-4-yl)benzamide

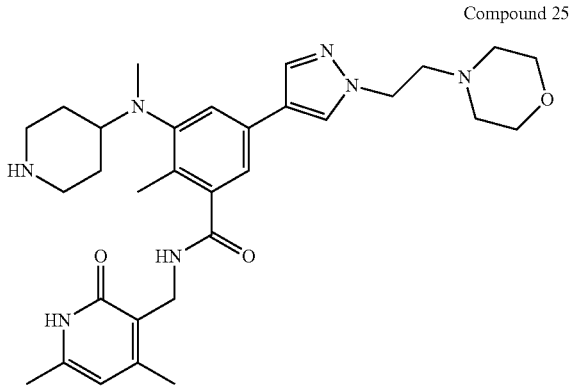 [SMILES: Cc1cc(C)c(CNC(=O)c2cc(-c3cnn(CCN4CCOCC4)c3)cc(N(C)C3CCNCC3)c2C)c(=O)[nH]1]

Compound 25

To a stirred solution of tert-butyl 4-((5-bromo-3-(((4,6-dimethyl-2-oxo-1,2-dihydropyridin-3-yl) methyl) carbamoyl)-2-methylphenyl) (methyl) amino) piperidin-1-carboxylate (1 equiv.) and 4-(2-(4-(4,4,5,5-tetramethyl-1,3,2-dioxaborolan-2-yl)-1H-pyrazol-1-yl)ethyl)morpholine (1.2 equiv.) in dioxane/water mixture (5 mL+1 mL), $Na_2CO_3$ (3.6 equiv.) was added and solution purged with argon for 15 min. Then Pd(PPh$_3$)$_4$ (0.1 equiv.) was added and argon was purged again for 10 min. The reaction was heated at 100° C. for 5 h. After cooling, the reaction mixture was diluted with water, and the product was extracted with 10% MeOH/DCM. The combined organic layers were dried over $Na_2SO_4$ and the solvent removed under reduced pressure to afford crude product which was purified by column chromatography over silica gel to afford tert-butyl 4-((3-(((4,6-dimethyl-2-oxo-1,2-dihydropyridin-3-yl)methyl)carbamoyl)-2-methyl-5-(1-(2-morpholinoethyl)-1H-pyrazol-4-yl)phenyl)(methyl)amino)piperidine-1-carboxylate. A stirred solution of this compound (1 mmol) in DCM (5 mL) was cooled to 0° C. and TFA (2 mL) was added to it. The reaction was stirred at room temperature for 1 h. On completion, the solution was concentrated to dryness. The residue was purified by solvent washings to afford the title compound (0.06 g, 89%). LCMS: 562.40 (M+1)+; HPLC: 99.01% (@ 254 nm) ($R_t$: 3.838; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (s, 1H), 8.52 (s, 1H), 8.26 (s, 1H), 8.23 (m, 1H), 8.05 (t, 1H), 8.00 (s, 1H), 7.34 (s, 1H), 7.16 (s, 1H), 5.87 (s, 1H), 4.53 (t, 2H), 4.27 (d, 2H, J=3.6 Hz), 3.25 (m, 4H), 3.10-3.16 (m, 4H), 2.87 (m, 2H), 2.60 (s, 3H), 2.20 (s, 3H), 2.18 (s, 3H), 2.11 (s, 3H), 1.79 (bs, 4H). [5H merged in solvent peak]

Example 26: Synthesis of N-((4,6-dimethyl-2-oxo-1,2-dihydropyridin-3-yl)methyl)-2-methyl-3-(methyl (piperidin-4-yl)amino)-5-(1-methyl-1H-pyrazol-4-yl)benzamide

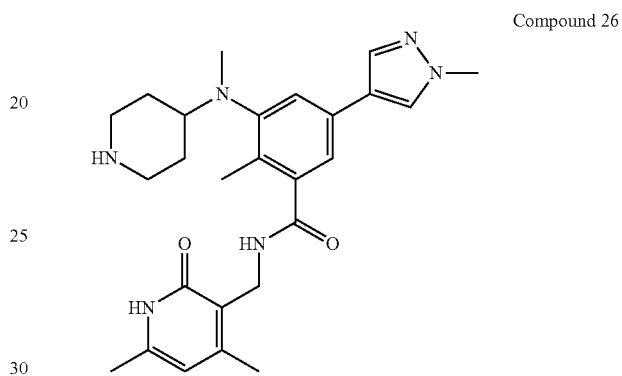

Compound 26

To a stirred solution of tert-butyl 4-((5-bromo-3-(((4,6-dimethyl-2-oxo-1,2-dihydropyridin-3-yl) methyl) carbamoyl)-2-methylphenyl) (methyl) amino) piperidin-1-carboxylate (1 equiv.) and 1-methyl-4-(4,4,5,5-tetramethyl-1,3,2-dioxaborolan-2-yl)-1H-pyrazole (1.2 equiv.) in dioxane/water mixture (5 mL+1 mL), $Na_2CO_3$ (3.6 equiv.) was added and solution purged with argon for 15 min. Then Pd(PPh$_3$)$_4$ (0.1 equiv.) was added and argon was purged again for 10 min. The reaction was heated at 100° C. for 5 h. After cooling, the reaction mixture was diluted with water, and the product was extracted with 10% MeOH/DCM. The combined organic layers were dried over $Na_2SO_4$ and the solvent removed under reduced pressure to afford crude product which was purified by column chromatography over silica gel to afford tert-butyl 4-((3-(((4,6-dimethyl-2-oxo-1,2-dihydropyridin-3-yl)methyl)carbamoyl)-2-methyl-5-(1-methyl-1H-pyrazol-4-yl)phenyl)(methyl)amino)piperidine-1-carboxylate. A stirred solution of this compound (1 mmol) in DCM (5 mL) was cooled to 0° C. and TFA (2 mL) was added to it. The reaction was stirred at room temperature for 1 h. On completion, the solution was concentrated to dryness. The residue was purified by solvent washings to afford the title compound (0.07 g, 87%). LCMS: 463.30 (M+1)+; HPLC: 98.02% (@ 254 nm) ($R_t$: 4.145; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (s, 1H), 8.47 (bs, 1H), 8.12 (s, 2H), 8.05 (s, 1H), 7.83 (s, 1H), 7.32 (s, 1H), 7.14 (s, 1H), 5.86 (s, 1H), 4.28 (m, 2H), 3.84 (s, 3H), 3.24-3.27 (m, 2H), 3.11 (bs, 1H), 2.87-2.89 (m, 2H), 2.59 (s, 3H), 2.20 (s, 3H), 2.18 (s, 3H), 2.10 (s, 3H), 1.77-1.80 (m, 4H).

Example 27: Synthesis of N-((4,6-dimethyl-2-oxo-1,2-dihydropyridin-3-yl)methyl)-4'-((dimethylamino)methyl)-4-methyl-5-(methyl(piperidin-4-yl)amino)-[1,1'-biphenyl]-3-carboxamide

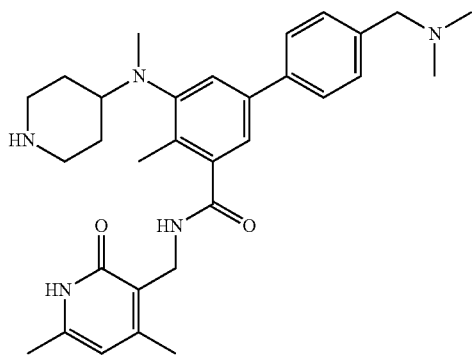

Compound 27

To a stirred solution of tert-butyl 4-((5-bromo-3-(((4,6-dimethyl-2-oxo-1,2-dihydropyridin-3-yl) methyl) carbamoyl)-2-methylphenyl) (methyl) amino) piperidin-1-carboxylate (1 equiv.) and N,N-dimethyl-1-(4-(4,4,5,5-tetramethyl-1,3,2-dioxaborolan-2-yl)phenyl)methanamine (1.2 equiv.) in dioxane/water mixture (5 mL+1 mL), Na$_2$CO$_3$ (3.6 equiv.) was added and solution purged with argon for 15 min. Then Pd(PPh$_3$)$_4$ (0.1 equiv.) was added and argon was purged again for 10 min. The reaction was heated at 100° C. for 5 h. After cooling, the reaction mixture was diluted with water, and the product was extracted with 10% MeOH/DCM. The combined organic layers were dried over Na$_2$SO$_4$ and the solvent removed under reduced pressure to afford crude product which was purified by column chromatography over silica gel to afford tert-butyl 4-((5-(((4,6-dimethyl-2-oxo-1,2-dihydropyridin-3-yl)methyl)carbamoyl)-4'-((dimethylamino)methyl)-4-methyl-[1,1'-biphenyl]-3-yl)(methyl)amino)piperidine-1-carboxylate. A stirred solution of this compound (1 mmol) in DCM (5 mL) was cooled to 0° C. and TFA (2 mL) was added to it. The reaction was stirred at room temperature for 1 h. On completion, the solution was concentrated to dryness. The residue was purified by solvent washings to afford the title compound (0.06 g, 90%). LCMS: 516.35 (M+1)$^+$; HPLC: 98.28% (@ 254 nm) (R$_t$; 3.930; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (s, 1H), 9.82 (bs, 1H), 8.51 (bs, 1H), 8.17 (s, 2H), 7.77 (d, 2H, J=7.2 Hz), 7.55 (d, 2H, J=7.6 Hz), 7.43 (s, 1H), 7.27 (s, 1H), 5.86 (s, 1H), 4.30 (m, 4H), 3.25 (4H merged in solvent peak), 2.88-2.91 (m, 1H), 2.75 (s, 6H), 2.64 (s, 3H), 2.25 (s, 3H), 2.20 (s, 3H), 2.10 (s, 3H), 1.81 (m, 4H).

Example 28: Synthesis of N-((4,6-dimethyl-2-oxo-1,2-dihydropyridin-3-yl)methyl)-2-methyl-3-(methyl(tetrahydro-2H-pyran-4-yl)amino)-5-(6-(morpholinomethyl)pyridin-3-yl)benzamide

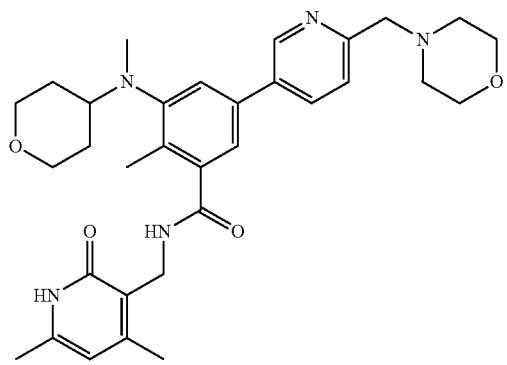

Compound 28

Step 1: N-((4,6-dimethyl-2-oxo-1,2-dihydropyridin-3-yl)methyl)-5-(6-formylpyridin-3-yl)-2-methyl-3-(methyl (tetrahydro-2H-pyran-4-yl)amino)benzamide To a stirred solution of 5-bromo-N-((4,6-dimethyl-2-oxo-1,2-dihydropyridin-3-yl) methyl)-2-methyl-3-(methyl (tetrahydro-2H-pyran-4-yl) amino) benzamide (0.4 g, 0.86 mmol) and (6-formylpyridin-3-yl)boronic acid (0.3 g, 1.29 mmol) in dioxane/water mixture (10 mL+2 mL), Na$_2$CO$_3$ (0.32 g, 3.09 mmol) was added and solution purged with argon for 15 min. Then Pd(PPh$_3$)$_4$ (0.092 g, 0.086 mmol) was added and argon was purged again for 10 min. The reaction mixture was heated at 100° C. for 6 h. On completion, reaction mixture was diluted with water and extracted with 10% MeOH/DCM. Combined organic layers were dried over Na$_2$SO$_4$ and solvent removed under reduced pressure to afford crude material which was purified by column chromatography over silica gel to afford N-((4,6-dimethyl-2-oxo-1,2-dihydropyridin-3-yl)methyl)-5-(6-formylpyridin-3-yl)-2-methyl-3-(methyl(tetrahydro-2H-pyran-4-yl)amino)benzamide (0.28 g, 66%).

Step 2: N-((4,6-dimethyl-2-oxo-1,2-dihydropyridin-3-yl)methyl)-2-methyl-3-(methyl(tetrahydro-2H-pyran-4-yl)amino)-5-(6-(morpholinomethyl)pyridin-3-yl)benzamide To a stirred solution of N-((4,6-dimethyl-2-oxo-1,2-dihydropyridin-3-yl)methyl)-5-(6-formylpyridin-3-yl)-2-methyl-3-(methyl(tetrahydro-2H-pyran-4-yl)amino)benzamide (1 equiv.) and morpholine (5 equiv.) in methanol (10 mL), acetic acid (2 equiv.) was added and reaction stirred at room temperature for 18 h. Then sodium cyanoborohydride (2.5 equiv.) was added at 0° C. and reaction stirred overnight at room temperature. On completion, solvent was removed under reduced pressure and crude material was purified by column chromatography to afford the title compound (0.08 g, 70%). LCMS: 560.30 (M+1)$^+$; HPLC: 99.22% (@ 254 nm) (R$_t$; 3.944; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (s, 1H), 8.76 (s, 1H), 8.17 (t, 1H), 8.02 (d, 1H, J=7.6 Hz), 7.50 (d, 1H, J=8 Hz), 7.41 (s, 1H), 7.23 (s, 1H), 5.85 (s, 1H), 4.28 (d, 2H, J=4.8 Hz), 3.85 (d, 2H, J=11.2 Hz), 3.61 (s, 3H), 3.59-3.60 (m, 3H), 3.24-3.29 (m, 2H), 3.02-3.05 (m, 1H), 2.64 (s, 3H), 2.42 (bs, 4H), 2.24 (s, 3H), 2.20 (s, 3H), 2.10 (s, 3H), 1.61 (bs, 4H).

Example 29: Synthesis of N-((4,6-dimethyl-2-oxo-1,2-dihydropyridin-3-yl)methyl)-5-(6-(hydroxymethyl)pyridin-3-yl)-2-methyl-3-(methyl(tetrahydro-2H-pyran-4-yl)amino)benzamide Compound 29

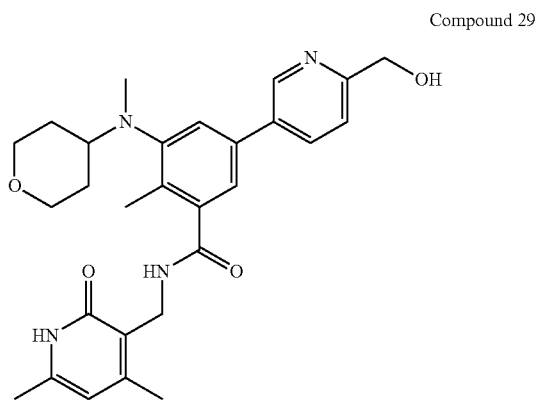 [SMILES: Cc1cc(C)c(CNC(=O)c2cc(-c3ccc(CO)nc3)cc(N(C)C3CCOCC3)c2C)c(=O)[nH]1]

To a stirred solution of N-((4,6-dimethyl-2-oxo-1,2-dihydropyridin-3-yl)methyl)-5-(6-formylpyridin-3-yl)-2-methyl-3-(methyl(tetrahydro-2H-pyran-4-yl)amino)benzamide (1 equiv.) and dimethylamine (5 equiv.) in methanol (10 mL), acetic acid (2 equiv.) was added and reaction stirred at room temperature for 18 h. Then sodium cyanoborohydride (2.5 equiv.) was added at 0° C. and reaction stirred overnight at room temperature. On completion, solvent was removed under reduced pressure and crude material was purified by column chromatography to afford the title compound. LCMS: 491.25 (M+1)$^+$; HPLC: 99.58% (@254 nm) (R$_t$; 3.984; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.47 (s, 1H), 8.75 (s, 1H), 8.19 (t, 1H), 8.05 (d, 1H, J=8.4 Hz), 7.52 (d, 1H, J=8.4 Hz), 7.41 (s, 1H), 7.24 (s, 1H), 5.86 (s, 1H), 5.44 (t, 1H, J=5.6 Hz), 4.59 (d, 2H, J=5.6 Hz), 4.28 (d, 2H, J=4 Hz), 3.85 (d, 2H, J=10.4 Hz), 3.32 (2H merged in solvent peak), 3.03 (m, 1H), 2.64 (s, 3H), 2.24 (s, 3H), 2.20 (s, 3H), 2.10 (s, 3H), 1.61 (bs, 4H).

Example 30: Synthesis of N-((4,6-dimethyl-2-oxo-1,2-dihydropyridin-3-yl)methyl)-5-(6-((dimethylamino)methyl)pyridin-3-yl)-2-methyl-3-(methyl(tetrahydro-2H-pyran-4-yl)amino)benzamide Compound 30

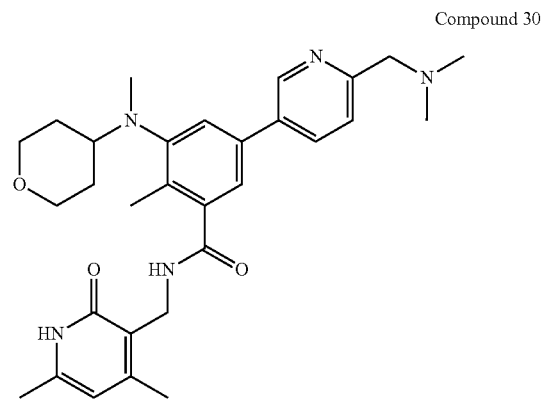 [SMILES: Cc1cc(C)c(CNC(=O)c2cc(-c3ccc(CN(C)C)nc3)cc(N(C)C3CCOCC3)c2C)c(=O)[nH]1]

To a stirred solution of N-((4,6-dimethyl-2-oxo-1,2-dihydropyridin-3-yl)methyl)-5-(6-formylpyridin-3-yl)-2-methyl-3-(methyl(tetrahydro-2H-pyran-4-yl)amino)benzamide (1 equiv.) and dimethylamine (5 equiv.) in methanol (10 mL), acetic acid (2 equiv.) was added and reaction stirred at room temperature for 18 h. Then sodium cyanoborohydride (2.5 equiv.) was added at 0° C. and reaction stirred overnight at room temperature. On completion, solvent was removed under reduced pressure and crude material was purified by column chromatography to afford the title compound (0.03 g, 26%). LCMS: 518.25 (M+1)$^+$; HPLC: 89.16% (@ 254 nm) (R$_t$; 3.982; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (s, 1H), 8.81 (s, 1H), 8.18 (t, 1H), 8.08 (d, 1H, J=8 Hz), 7.52 (d, 1H, J=8 Hz), 7.43 (s, 1H), 7.26 (s, 1H), 5.86 (s, 1H), 4.28 (d, 2H, J=4.8 Hz), 3.83-3.86 (m, 4H), 3.32 (2H merged in solvent peak), 3.03 (m, 1H), 2.64 (s, 3H), 2.50 (3H merged in solvent peak), 2.40 (bs, 3H), 2.24 (s, 3H), 2.21 (s, 3H), 2.10 (s, 3H), 1.60 (bs, 4H).

Example 31: Synthesis of 3-(Cyclohexyl(methyl) amino)-N-((4,6-dimethyl-2-oxo-1,2-dihydropyridin-3-yl)methyl)-2-methyl-5-(6-(morpholinomethyl) pyridin-3-yl)benzamide Compound 31

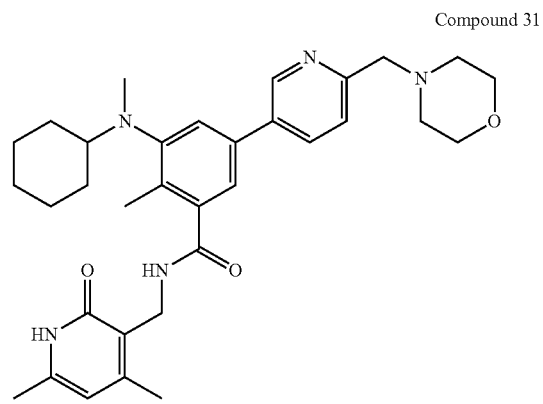 [SMILES: Cc1cc(C)c(CNC(=O)c2cc(-c3ccc(CN4CCOCC4)nc3)cc(N(C)C3CCCCC3)c2C)c(=O)[nH]1]

Step 1: Synthesis of 3-(cyclohexyl(methyl)amino)-N-((4,6-dimethyl-2-oxo-1,2-dihydropyridin-3-yl)methyl)-5-(6-formylpyridin-3-yl)-2-methylbenzamide To a stirred solution of bromo compound 5-bromo-3-(cyclohexyl(methyl)amino)-N-((4,6-dimethyl-2-oxo-1,2-dihydropyridin-3-yl)methyl)-2-methylbenzamide (0.6 g, 1.30 mmol) and (6-formylpyridin-3-yl)boronic acid (0.450 g, 1.95 mmol) in dioxane/water mixture (8 mL+2 mL), $Na_2CO_3$ (0.498 g, 4.5 mmol) was added and solution purged with argon for 15 min. Then Pd $(PPh_3)_4$ (0.15 g, 0.129 mmol) was added and the mixture was purged again for 10 min. Reaction mass was heated at 100° C. for 4 h. On completion, reaction mixture was diluted with water and extracted with 10% MeOH/DCM. Combined organic layers were dried over $Na_2SO_4$ and solvent removed under reduced pressure to afford crude material which was purified by column chromatography over silica gel to afford 3-(cyclohexyl(methyl)amino)-N-((4,6-dimethyl-2-oxo-1,2-dihydropyridin-3-yl)methyl)-5-(6-formylpyridin-3-yl)-2-methylbenzamide (0.525 g, 83%).

Step 2: Synthesis of 3-(cyclohexyl(methyl)amino)-N-((4,6-dimethyl-2-oxo-1,2-dihydropyridin-3-yl)methyl)-2-methyl-5-(6-(morpholinomethyl)pyridin-3-yl)benzamide To a stirred solution of compound 3-(cyclohexyl(methyl)amino)-N-((4,6-dimethyl-2-oxo-1,2-dihydropyridin-3-yl)methyl)-5-(6-formylpyridin-3-yl)-2-methylbenzamide (1 equiv.) and morpholine (5 equiv.) in methanol (10 mL), acetic acid (2 equiv.) was added and reaction stirred at room temperature for 8 h. Then sodium cyanoborohydride (2.5 equiv.) was added at 0° C. and reaction stirred overnight at room temperature. On completion, solvent was removed under reduced pressure and crude material was purified by column chromatography to afford 3-(cyclohexyl(methyl)amino)-N-((4,6-dimethyl-2-oxo-1,2-dihydropyridin-3-yl)methyl)-2-methyl-5-(6-(morpholinomethyl)pyridin-3-yl)benzamide (0.089 g, 53% yield). LCMS: 558.35 $(M+1)^+$; HPLC: 96.52% (@ 254 nm) $(R_t: 4.375$; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (s, 1H), 8.75 (s, 1H), 8.18 (t, 1H), 8.01 (d, 1H, J=6.8 Hz), 7.49 (d, 1H, J=8 Hz), 7.33 (s, 1H), 7.18 (s, 1H), 5.85 (s, 1H), 4.28 (d, 2H, J=3.6 Hz), 3.59-3.61 (m, 6H), 2.75 (m, 1H), 2.65 (s, 3H), 2.43 (bs, 4H), 2.21 (s, 3H), 2.20 (s, 3H), 2.10 (s, 3H), 1.70 (bs, 4H), 1.53-1.56 (m, 1H), 1.42-1.44 (m, 1H), 1.09-1.23 (m, 4H).

Example 32: Synthesis of 3-(Cyclohexyl(methyl)amino)-N-((4,6-dimethyl-2-oxo-1,2-dihydropyridin-3-yl)methyl)-5-(6-((dimethylamino)methyl)pyridin-3-yl)-2-methylbenzamide

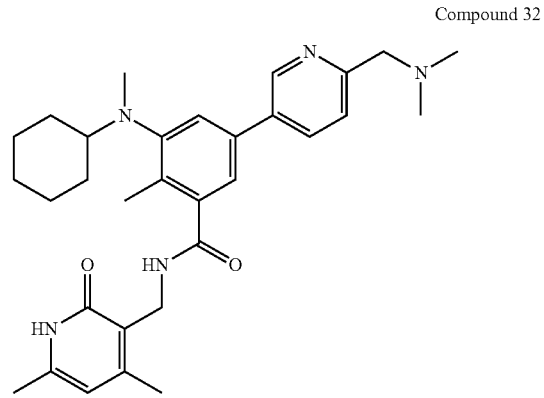 [SMILES: Cc1cc(C)c(CNC(=O)c2cc(-c3ccc(CN(C)C)nc3)cc(N(C)C3CCCCC3)c2C)c(=O)[nH]1]

Compound 32

To a stirred solution of compound 3-(cyclohexyl(methyl)amino)-N-((4,6-dimethyl-2-oxo-1,2-dihydropyridin-3-yl)methyl)-5-(6-formylpyridin-3-yl)-2-methylbenzamide (1 equiv.) and dimethylamine (5 equiv.) in methanol (10 mL), acetic acid (2 equiv.) was added and reaction stirred at room temperature for 8 h. Then sodium cyanoborohydride (2.5 equiv.) was added at 0° C. and reaction stirred overnight at room temperature. On completion, solvent was removed under reduced pressure and crude material was purified by column chromatography to afford the title compound (0.017 g, 11% yield). LCMS: 516.35 $(M+1)^+$; HPLC: 90.32% (@254 nm) $(R_t: 4.203$; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.45 (s, 1H), 8.78 (s, 1H), 8.18 (t, 1H), 8.05 (d, 1H, J=6 Hz), 7.50 (d, 1H, J=8.4 Hz), 7.34 (s, 1H), 7.20 (s, 1H), 5.86 (s, 1H), 4.28 (d, 2H, J=4.8 Hz), 3.75 (bs, 2H), 2.75 (m, 1H), 2.65 (s, 3H), 2.34 (bs, 6H), 2.22 (s, 3H), 2.20 (s, 3H), 2.10 (s, 3H), 1.69-1.71 (m, 4H), 1.54-1.56 (m, 2H), 1.42-1.45 (m, 2H), 1.08-1.23 (m, 2H).

Example 35: Synthesis of 3-(Cyclopentyl(methyl)amino)-N-((4,6-dimethyl-2-oxo-1,2-dihydropyridin-3-yl)methyl)-5-(6-((dimethylamino)methyl)pyridin-3-yl)-2-methylbenzamide

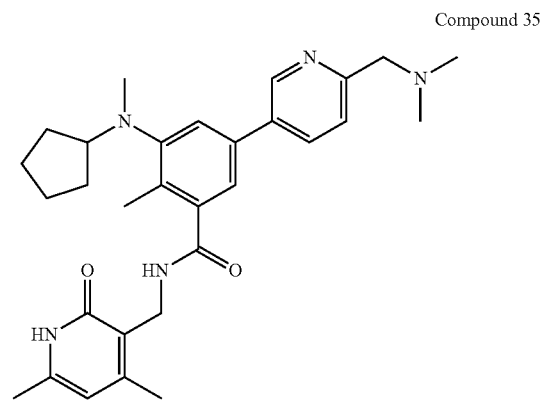

Compound 35

To a stirred solution of compound 3-(cyclopentyl(methyl) amino)-N-((4,6-dimethyl-2-oxo-1,2-dihydropyridin-3-yl) methyl)-5-(6-formylpyridin-3-yl)-2-methylbenzamide (1 equiv.) and dimethylamine (5 equiv.) in methanol (10 mL), acetic acid (2 equiv.) was added and reaction stirred at room temperature for 18 h. Then sodium cyanoborohydride (2.5 equiv.) was added at 0° C. and reaction stirred overnight at room temperature. On completion, solvent was removed under reduced pressure and crude material was purified by column chromatography to afford compound and crude material which was purified by preparative HPLC giving the title compound as a TFA salt, (0.12 g, 57%). LCMS: 502.30 (M+1)$^+$; HPLC: 99.07% (@ 254 nm) (R$_t$: 4.059; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.50 (s, 1H), 10.04 (bs, 1H), 8.96 (s, 1H), 8.22 (m, 2H), 7.57-7.61 (m, 1H), 7.35 (s, 1H), 5.87 (s, 1H), 4.49 (s, 2H), 4.28 (d, 2H, J=2 Hz), 3.65 (bs, 1H), 2.83 (s, 6H), 2.65 (s, 3H), 2.28 (s, 3H), 2.12 (s, 3H), 2.10 (s, 3H), 1.73 (bs, 2H), 1.63 (bs, 2H), 1.50 (m, 4H).

Example 36: Synthesis of N-((4,6-dimethyl-2-oxo-1,2-dihydropyridin-3-yl)methyl)-4'-((dimethylamino)methyl)-4-methyl-5-(methyl(piperidin-4-yl)amino)-[1,1'-biphenyl]-3-carboxamide Compound 36

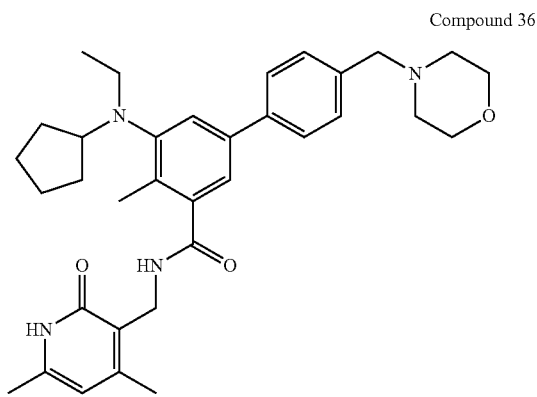 [SMILES: CCN(c1cc(-c2ccc(CN3CCOCC3)cc2)cc(C(=O)NCc2c(C)cc(C)[nH]c2=O)c1C)C1CCCC1]

Step 1: Synthesis of methyl 5-bromo-3-(cyclopentylamino)-2-methylbenzoate

To a stirred solution of methyl 3-amino-5-bromo-2-methylbenzoate (5 g, 20.57 mmol) and cyclopentanone (8.64 g, 102.8 mmol) in methanol (30 mL), acetic acid (2.46 g, 41.1 mmol) was added and reaction stirred at room temperature for 3 h. Then sodium cyanoborohydride (3.23 g, 51.4 mmol) was added and reaction stirred overnight. On completion, solvent was removed under reduced pressure and crude material was purified by column chromatography to afford methyl 5-bromo-3-(cyclopentylamino)-2-methylbenzoate (4 g, 78.2%).

Step 2: Synthesis of methyl 5-bromo-3-(cyclopentyl (ethyl) amino)-2-methylbenzoate To a stirred solution of 5-bromo-3-(cyclopentylamino)-2-methylbenzoate (2 g, 6.43 mmol) in DMF (15 mL), cesium carbonate (4.18 g, 12.8 mmol) and ethyl iodide (5.01 g, 32.15 mmol) were added; the resulting reaction mixture was heated at 80° C. for 18 h. On completion, the reaction mixture was cooled to room temperature and filtered, residue was washed with ethyl acetate and filtrate was concentrated to afford desired crude compound, which was purified by column chromatography at afford methyl 5-bromo-3-(cyclopentyl(ethyl)amino)-2-methylbenzoate (0.7 g, 32.1%).

Step 3: Synthesis of 5-bromo-3-(cyclopentyl (ethyl) amino)-N-((4,6-dimethyl-2-oxo-1,2-dihydropyridin-3-yl) methyl)-2-methylbenzamide Aqueous NaOH (0.126 g, 3.09 mmol) was added to a solution of methyl 5-bromo-3-(cyclopentyl (ethyl) amino)-2-methylbenzoate (0.7 g, 2.06 mmol) in ethanol (5 mL) and stirred at 60° C. for 1 h. After completion of the reaction, ethanol was removed under reduced pressure and the aqueous layer acidified using dilute HCl to pH 6 and citric acid to pH 4. The product was extracted using ethyl acetate. Combined organic layers were dried and concentrated to give the crude acid (0.5 g, 75%). The acid (0.5 g, 1.53 mmol) was then dissolved in DMSO (5 mL) and 3-(amino methyl)-4,6-dimethylpyridin-2(1H)-one (0.467 g, 3.07 mmol) was added to it. The reaction mixture was stirred at room temperature for 15 min before PYBOP (1.19 g, 2.30 mmol) was added to it and stirring was continued for overnight. After completion of the reaction, the reaction mixture was poured into ice, extracted with 10% MeOH/DCM. Combined organic layers were dried and concentrated, then the product was purified by column chromatography to afford 5-bromo-3-(cyclopentyl (ethyl) amino)-N-((4,6-dimethyl-2-oxo-1,2-dihydropyridin-3-yl) methyl)-2-methylbenzamide (0.3 g, 42%).

Step 4: Synthesis of 5-(cyclopentyl (ethyl) amino)-N-((4,6-dimethyl-2-oxo-1,2-dihydropyridin-3-yl) methyl)-4-methyl-4'-(morpholinomethyl)-[1,1'-biphenyl]-3-carboxamide To a stirred solution of 5-bromo-3-(cyclopentyl (ethyl) amino)-N-((4,6-dimethyl-2-oxo-1,2-dihydropyridin-3-yl) methyl)-2-methylbenzamide (0.3 g, 0.653 mmol) and (4-(morpholinomethyl) phenyl) boronic acid (0.216 g, 0.98 mmol) in dioxane/water mixture (5 mL+1 mL), Na$_2$CO$_3$ (0.249 g, 2.35 mmol) was added and solution purged with argon for 15 min. Then Pd (PPh$_3$)$_4$ (0.075 g, 0.065 mmol) was added and argon was purged again for 10 min. The reaction mixture was heated at 100° C. for 3 h. On completion, the reaction mixture was diluted with water and extracted with 10% MeOH/DCM. Combined organic layers were dried over Na$_2$SO$_4$ and solvent removed under reduced pressure to afford crude material which was purified by column chromatography over silica gel to afford the title compound (0.15 g, 41%). LCMS: 557.35 (M+1)$^+$; HPLC: 99.13% (@ 254 nm) (R$_t$: 4.128; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.44 (s, 1H), 8.17 (t, 1H), 7.57 (d, 2H, J=8 Hz), 7.41 (s, 1H), 7.37 (d, 2H, J=8 Hz), 7.20 (s, 1H), 5.85 (s, 1H), 4.28 (d, 2H, J=4.8 Hz), 3.56-3.57 (m, 4H), 3.48 (s, 3H), 3.00-3.02 (m, 2H), 2.36 (m, 4H), 2.24 (s, 3H), 2.20 (s, 3H), 2.10 (s, 3H), 1.69-1.70 (m, 2H), 1.60 (m, 2H), 1.47-1.48 (m, 4H), 0.81 (t, 3H, J=6.4 Hz).

Example 37: Synthesis of 3-(((1r,4r)-4-acetamido-cyclohexyl)(methyl)amino)-N-((4,6-dimethyl-2-oxo-1,2-dihydropyridin-3-yl)methyl)-2-methyl-5-(1-(2-morpholinoethyl)-1H-pyrazol-4-yl)benzamide Compound 37

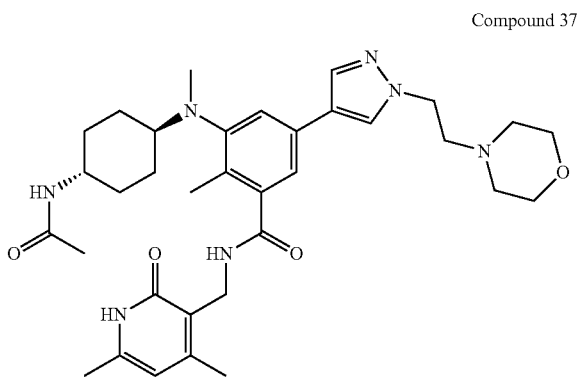 [SMILES: CC(=O)N[C@H]1CC[C@H](N(C)c2cc(-c3cnn(CCN4CCOCC4)c3)cc(C(=O)NCc3c(C)cc(C)[nH]c3=O)c2C)CC1]

To a stirred solution of 3-(((1r,4r)-4-acetamidocyclohexyl)-(methyl)-amino)-5-bromo-N-((4,6-dimethyl-2-oxo-1,2-dihydropyridin-3-yl)-methyl)-2-methylbenzamide (1 equiv.) and 4-(2-(4-(4,4,5,5-tetramethyl-1,3,2-dioxaborolan-2-yl)-1H-pyrazol-1-yl)ethyl)morpholine (1.2 equiv.) in dioxane/water mixture (5 mL+1 mL) was added $Na_2CO_3$ (3.6 equiv.) and the solution purged with argon for 15 min. Then $Pd(PPh_3)_4$ (0.1 equiv.) was added and argon was purged again for 10 min. The reaction mixture was heated at 100° C. for 4 h. On completion, the reaction mixture was diluted with water and extracted with 10% MeOH/DCM. The combined organic layers were dried over $Na_2SO_4$ and the solvent removed under reduced pressure to afford crude material which was purified by column chromatography over silica gel to afford the title compound (0.050 g, 28%). LCMS: 618.35 (M+1)+; HPLC: 95.34% (@ 254 nm) ($R_t$: 3.760; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.47 (s, 1H), 8.17 (s, 1H), 8.09 (t, 1H), 7.82 (s, 1H), 7.67 (d, 1H, J=7.2 Hz), 7.23 (s, 1H), 7.08 (s, 1H), 5.86 (s, 1H), 4.26 (d, 2H, J=3.2 Hz), 4.21 (t, 2H, J=6 Hz), 3.44-3.53 (m, 5H), 2.72 (t, 3H, J=5.6 Hz), 2.61 (s, 3H), 2.40 (m, 4H), 2.20 (s, 3H), 2.13 (s, 3H), 2.10 (s, 3H), 1.67-1.88 (m, 7H), 1.46-1.55 (m, 2H), 1.07-1.15 (m, 2H).

Example 38: Synthesis of 3-(((1s,4s)-4-acetamido-cyclohexyl)(methyl)amino)-N-((4,6-dimethyl-2-oxo-1,2-dihydropyridin-3-yl)methyl)-2-methyl-5-(1-(2-morpholinoethyl)-1H-pyrazol-4-yl)benzamide Compound 38

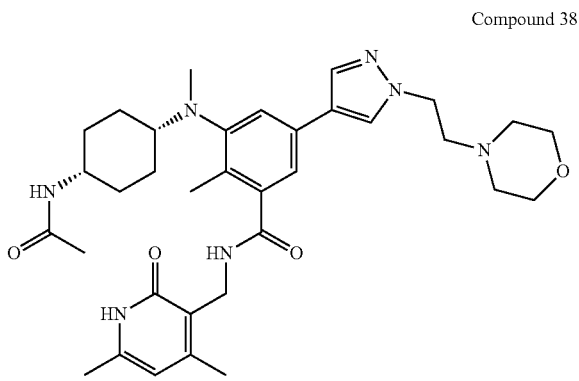 [SMILES: CC(=O)N[C@H]1CC[C@@H](N(C)c2cc(-c3cnn(CCN4CCOCC4)c3)cc(C(=O)NCc3c(C)cc(C)[nH]c3=O)c2C)CC1]

Prepare in the analogous fashion as compound 37 (0.020 g, 11%). LCMS: 618.35 (M+1)+; HPLC: 99.00% (@ 254 nm) ($R_t$: 3.732; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (s, 1H), 8.16 (s, 1H), 8.09 (t, 1H), 7.82 (s, 1H), 7.77 (d, 1H, J=7.2 Hz), 7.28 (s, 1H), 7.09 (s, 1H), 5.86 (s, 1H), 4.45 (bs, 1H), 4.27 (d, 2H, J=4 Hz), 4.22 (s, 2H), 3.70 (bs, 1H), 3.54 (m, 4H), 2.97 (m, 1H), 2.67-2.72 (m, 2H), 2.56 (s, 3H), 2.42 (m, 3H), 2.20 (s, 6H), 2.10 (s, 3H), 1.74-1.81 (m, 5H), 1.55 (m, 2H), 1.39-1.41 (m, 4H).

Example 39: Synthesis of 5-(((1r,4r)-4-acetamido-cyclohexyl)(methyl)amino)-N-((4,6-dimethyl-2-oxo-1,2-dihydropyridin-3-yl)methyl)-4'-((dimethyl-amino)methyl)-4-methyl-[1,1'-biphenyl]-3-carboxamide Compound 39

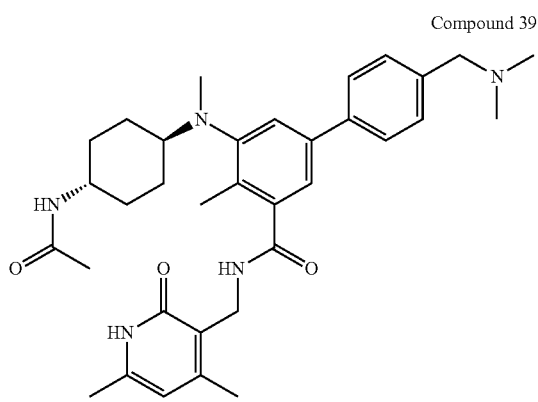 [SMILES: CC(=O)N[C@H]1CC[C@H](N(C)c2cc(-c3ccc(CN(C)C)cc3)cc(C(=O)NCc3c(C)cc(C)[nH]c3=O)c2C)CC1]

To a stirred solution of 3-(((1r,4r)-4-acetamidocyclohexyl)-(methyl)-amino)-5-bromo-N-((4,6-dimethyl-2-oxo-1,2-dihydropyridin-3-yl)-methyl)-2-methylbenzamide (1 equiv.) and N,N-dimethyl-1-(4-(4,4,5,5-tetramethyl-1,3,2-dioxaborolan-2-yl)phenyl)methanamine (1.2 equiv.) in dioxane/water mixture (5 mL+1 mL) was added $Na_2CO_3$ (3.6 equiv.) and the solution purged with argon for 15 min. Then $Pd(PPh_3)_4$ (0.1 equiv.) was added and argon was purged again for 10 min. The reaction mixture was heated at 100° C. for 4 h. On completion, the reaction mixture was diluted with water and extracted with 10% MeOH/DCM. The combined organic layers were dried over $Na_2SO_4$ and the solvent removed under reduced pressure to afford crude material which was purified by column chromatography over silica gel to afford the title compound (0.05 g, 30%). LCMS: 572.35 (M+1)+; HPLC: 96.88% (@ 254 nm) ($R_t$: 3.900; Method: Column: YMC ODS-A 150 mm×4.6 mm×5µ; Mobile Phase: A; 0.05% TFA in water/B; 0.05% TFA in acetonitrile; Inj. Vol: 10 L, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (s, 1H), 8.18 (t, 1H), 7.67 (d, 1H, J=6.8 Hz), 7.57 (d, 2H, J=7.6 Hz), 7.34 (d, 2H, J=7.6 Hz), 7.30 (s, 1H), 7.14 (s, 1H), 5.85 (s, 1H), 4.27 (d, 2H, J=3.6 Hz), 3.39 (m, 3H), 2.72 (m, 1H), 2.64 (s, 3H), 2.20 (s, 6H), 2.15 (s, 6H), 2.10 (s, 3H), 1.78-1.81 (m, 2H), 1.74 (s, 3H), 1.68 (m, 2H), 1.51-1.56 (m, 2H), 1.08-1.23 (m, 2H).

Example 40: Synthesis of 5-(((1s,4s)-4-acetamido-cyclohexyl)(methyl)amino)-N-((4,6-dimethyl-2-oxo-1,2-dihydropyridin-3-yl)methyl)-4'-((dimethylamino)methyl)-4-methyl-[1,1'-biphenyl]-3-carboxamide Compound 40

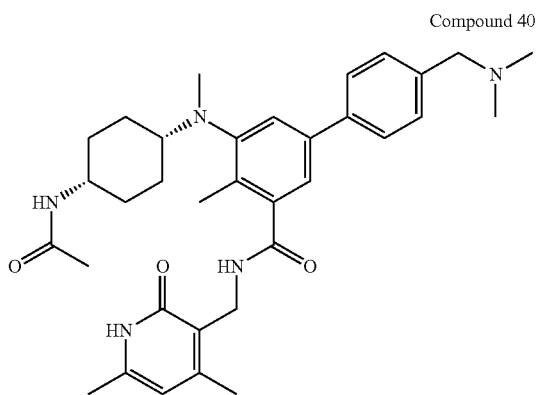 [SMILES: CC(=O)N[C@H]1CC[C@@H](N(C)c2cc(-c3ccc(CN(C)C)cc3)cc(C(=O)NCc3c(C)cc(C)[nH]c3=O)c2C)CC1]

Prepared in the analogous fashion as Example 39 (0.06 g, 36%). LCMS: 572.35 (M+1)+; HPLC: 94.79% (@ 254 nm) (R$_t$: 3.936; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.47 (s, 1H), 8.19 (t, 1H), 7.78 (d, 1H, J=7.2 Hz), 7.56 (d, 2H, J=8 Hz), 7.33-7.35 (m, 3H), 7.17 (s, 1H), 5.86 (s, 1H), 4.28 (d, 2H, J=3.6 Hz), 3.70 (bs, 1H), 3.37-3.40 (m, 2H), 2.98 (m, 1H), 2.59 (s, 3H), 2.26 (s, 3H), 2.20 (m, 3H), 2.15 (s, 6H), 2.10 (s, 3H), 1.81 (s, 3H), 1.74 (m, 2H), 1.55 (m, 2H), 1.40-1.48 (m, 4H).

Example 41: Synthesis of N-((4,6-dimethyl-2-oxo-1,2-dihydropyridin-3-yl)methyl)-5-(6-((dimethylamino)methyl)pyridin-3-yl)-2-methyl-3-(methyl(piperidin-4-yl)amino)benzamide Compound 41

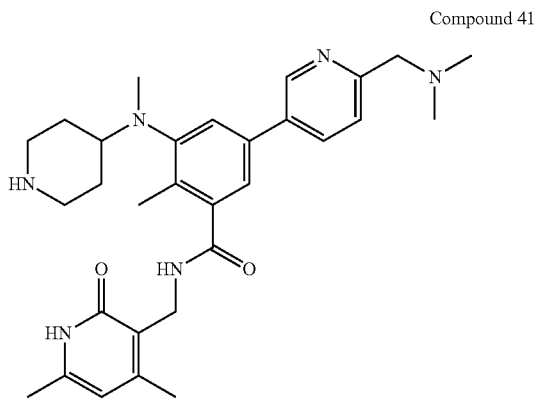 [SMILES: Cc1cc(C)c(CNC(=O)c2cc(-c3ccc(CN(C)C)nc3)cc(N(C)C3CCNCC3)c2C)c(=O)[nH]1]

To a stirred solution of tert-butyl 4-((3-(((4,6-dimethyl-2-oxo-1,2-dihydropyridin-3-yl)methyl)carbamoyl)-5-(6-formylpyridin-3-yl)-2-methylphenyl)(methyl)amino)piperidine-1-carboxylate (1 equiv.) and morpholine (5 equiv.) in methanol (5 mL for 0.3 mmol), acetic acid (1 equiv.) was added and reaction stirred at room temperature for 4 h. Then reducing agent NaBH$_3$CN (1 equiv.) was added and reaction stirred overnight. On completion, solvent was removed under reduced pressure and residue purified by column chromatography over silica gel affording desired tert-butyl 4-((3-(((4,6-dimethyl-2-oxo-1,2-dihydropyridin-3-yl)methyl)carbamoyl)-5-(6-((dimethylamino)methyl)pyridin-3-yl)-2-methylphenyl)(methyl)amino)piperidine-1-carboxylate. This compound was then dissolved in DCM (5 mL) and cooled to 0° C. TFA (2 mL) was added to it. The reaction mixture was stirred at room temperature for 1 h. On completion, reaction was concentrated to dryness. Residue was purified by solvent washings to afford the title compound (0.06 g, 40%). LCMS: 517.25 (M+1)+; HPLC: 99.07% (@ 254 nm) (R$_t$: 3.913; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.48 (s, 1H), 10.08 (bs, 1H), 8.97 (s, 1H), 8.57 (bs, 1H), 8.23 (d, 2H, J=7.6 Hz), 8.18 (s, 1H), 7.60 (d, 1H, J=8 Hz), 7.50 (s, 1H), 7.34 (s, 1H), 5.87 (s, 1H), 4.49 (d, 2H), 4.30 (s, 2H), 3.25 (d, 2H), 3.16 (s, 1H), 2.89 (m, 2H), 2.83 (s, 6H), 2.64 (s, 3H), 2.26 (s, 3H), 2.21 (s, 3H), 2.10 (s, 3H), 1.81 (bs, 4H).

Example 42: Synthesis of 5-(((1s,4s)-4-aminocyclohexyl)(methyl)amino)-N-((4,6-dimethyl-2-oxo-1,2-dihydropyridin-3-yl)methyl)-4-methyl-4'-(morpholinomethyl)-[1,1'-biphenyl]-3-carboxamide Compound 42

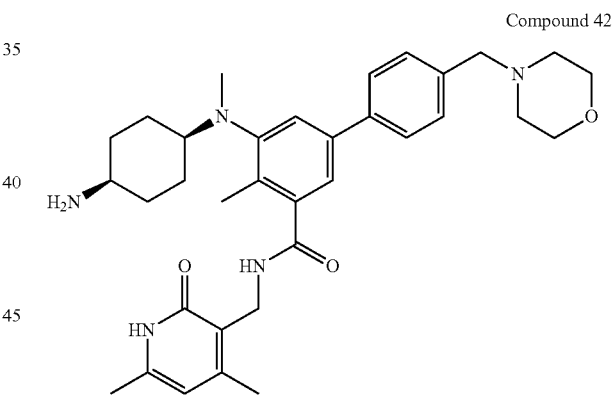

Step 1: Synthesis of methyl 5-bromo-3-(((1s,4s)-4-((tert-butoxycarbonyl)amino)cyclohexyl)(methyl)-amino)-2-methylbenzoate To a stirred solution of the less polar cis isomer, methyl 5-bromo-3-(((1s,4s)-4-((tert-butoxycarbonyl)amino)cyclohexyl)amino)-2-methylbenzoate, (4 g, 9.09 mmol) in acetonitrile (50 mL), cesium carbonate (5.9 g, 18.18 mmol) and methyl iodide (6.45 g, 45.45 mmol) were added. The resulting reaction mixture was heated at 80° C. for 7 h. The reaction mixture was cooled to room temperature and filtered, with the collected solids being washed with ethyl acetate. The filtrate was concentrated to afford desired product which purified by column chromatography giving methyl 5-bromo-3-(((1s,4s)-4-((tert-butoxycarbonyl)amino)cyclohexyl)(methyl)-amino)-2-methylbenzoate (1.4 g, 34.14%).

Step 2: Synthesis of tert-butyl ((1s,4s)-4-((5-bromo-3-(((4,6-dimethyl-2-oxo-1,2-dihydropyridin-3-yl)methyl)carbamoyl)-2-methylphenyl)(methyl)amino)cyclohexyl)carbamate Aqueous NaOH (0.23 g, 5.72 mmol) was added to a solution of methyl 5-bromo-3-(((1s,4s)-4-((tert-butoxycarbonyl)amino)cyclohexyl)(methyl)-amino)-2-methylbenzoate (1.3 g, 2.86 mmol) in MeOH (20 mL) and stirred at 60° C. for 1 h. The ethanol was removed under reduced pressure and the mixture acidified to pH with dilute HCl and to pH 4 with citric acid. The mixture was extracted with ethyl acetate. The combined organic extracts were dried and concentrated giving respective acid (1.13 g, 90.1%).

The acid (1.13 g, 2.57 mmol) was then dissolved in DMSO (10 mL) and 3-(amino methyl)-4,6-dimethylpyridin-2(1H)-one (0.87 g, 5.72 mmol) was added to it. The reaction mixture was stirred at room temperature for 15 min before PyBOP (2.23 g, 4.28 mmol) was added. Stirring was then continued overnight. The reaction, reaction mixture was poured into ice water. The resulting precipitate was filtered, washed with acetonitrile and purified by column chromatography to afford tert-butyl ((1s,4s)-4-((5-bromo-3-(((4,6-dimethyl-2-oxo-1,2-dihydropyridin-3-yl)methyl)carbamoyl)-2-methylphenyl)(methyl)amino)cyclohexyl)carbamate (0.8 g, 48.7%).

Step 3: Synthesis of tert-butyl ((1s,4s)-4-((5-(((4,6-dimethyl-2-oxo-1,2-dihydropyridin-3-yl)methyl)-carbamoyl)-4-methyl-4'-(morpholinomethyl)-[1,1'-biphenyl]-3-yl)(methyl)amino)-cyclohexyl)carbamate To a stirred solution of tert-butyl ((1s,4s)-4-((5-bromo-3-(((4,6-dimethyl-2-oxo-1,2-dihydropyridin-3-yl)methyl)carbamoyl)-2-methylphenyl)(methyl)amino)cyclohexyl)-carbamate (1 equiv.) and 4-(4-(4,4,5,5-tetramethyl-1,3,2-dioxaborolan-2-yl)benzyl)morpholine (1.2 equiv.) in dioxane/water mixture (5 mL+1 mL), Na$_2$CO$_3$ (3.6 equiv.) was added. The solution was then purged with argon for 15 min. Pd(PPh$_3$)$_4$ (0.1 equiv.) was added and the reaction mixture again purged with argon for 10 min. The reaction mixture was heated at 100° C. for 4 h. The reaction mixture was diluted with water and extracted with 10% MeOH/DCM. The combined extracts were dried over Na$_2$SO$_4$ and the solvent removed under reduced pressure to afford the crude product which was purified by column chromatography over silica gel to afford tert-butyl ((1s,4s)-4-((5-(((4,6-dimethyl-2-oxo-1,2-dihydropyridin-3-yl)methyl)-carbamoyl)-4-methyl-4'-(morpholinomethyl)-[1,1'-biphenyl]-3-yl)(methyl)amino)-cyclohexyl)carbamate (0.08 g, 45.71%).

Step 4: Synthesis of 5-(((1s,4s)-4-aminocyclohexyl)(methyl)amino)-N-((4,6-dimethyl-2-oxo-1,2-dihydropyridin-3-yl)methyl)-4-methyl-4'-(morpholinomethyl)-[1,1'-biphenyl]-3-carboxamide A stirred solution of tert-butyl ((1s,4s)-4-((5-(((4,6-dimethyl-2-oxo-1,2-dihydropyridin-3-yl)methyl)-carbamoyl)-4-methyl-4'-(morpholinomethyl)-[1,1'-biphenyl]-3-yl)(methyl)amino)-cyclohexyl)carbamate (0.08 g) in DCM (5 mL) was cooled to 0° C. and TFA (2 mL) was added. The reaction mixture was stirred at room temperature for 1 h. The reaction was concentrated to dryness yielding the title compound as a TFA salt (0.06 g, 88.2%). LCMS: 572.40 (M+1)$^+$; HPLC: 95.39% (@ 254 nm) (R$_t$: 3.719; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (s, 1H), 10.05 (bs, 1H), 8.19 (t, 1H), 7.74-7.78 (m, 4H), 7.56 (d, 2H, J=6.8 Hz), 7.46 (s, 1H), 7.24 (s, 1H), 5.87 (s, 1H), 4.38 (bs, 2H), 4.29 (d, 2H, J=4.4 Hz), 3.95 (m, 2H), 3.60-3.63 (m, 2H), 3.27-3.30 (m, 2H), 3.13-3.19 (m, 4H), 2.54 (s, 3H), 2.30 (s, 3H), 2.21 (s, 3H), 2.10 (s, 3H), 1.86 (m, 2H), 1.59-1.64 (m, 4H), 1.49-1.51 (m, 2H).

Example 43: Synthesis of 5-(((1r,4r)-4-acetamidocyclohexyl)(methyl)amino)-N-((4,6-dimethyl-2-oxo-1,2-dihydropyridin-3-yl)methyl)-4-methyl-4'-(morpholinomethyl)-[1,1'-biphenyl]-3-carboxamide

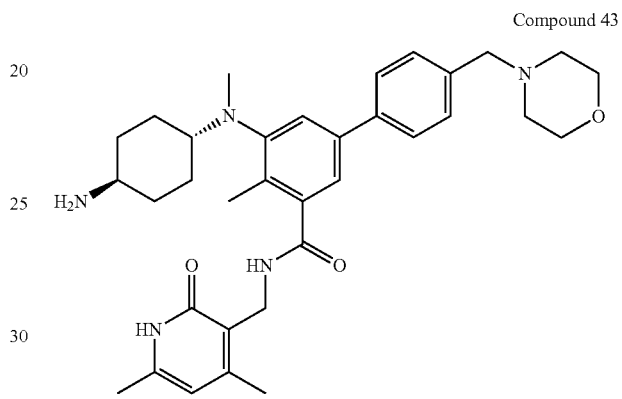

Compound 43

Step 1: Synthesis of 5-bromo-2-methyl-3-nitrobenzoic acid

To stirred solution of 2-methyl-3-nitrobenzoic acid (50 g, 276.2 mmol) in conc. H$_2$SO$_4$ (200 mL), 1,3-dibromo-5,5-dimethyl-2,4-imidazolidinedione (43.4 g, 151.8 mmol) was added portionwise at room temperature and the reaction mixture stirred at room temperature for 5 h. The reaction mixture was poured into ice cold water; the solid which precipitated was filtered, washed with water and dried under vacuum giving the desired compound, 5-bromo-2-methyl-3-nitrobenzoic acid (71.7 g, 99.9%) which was used as is in further reactions.

Step 2: Synthesis of methyl 5-bromo-2-methyl-3-nitrobenzoate

To a stirred solution of 5-bromo-2-methyl-3-nitrobenzoic acid (287 g, 1103 mmol) in DMF (150 mL), sodium carbonate (468 g, 4415 mmol) and methyl iodide (626.63 g, 4415 mmol) were added. The reaction mixture was then heated at 60° C. for 8 h. The precipitated solids were filtered and washed with diethyl ether (5 times). The combined organic filtrates were dried, concentrated under reduced pressure giving desired compound methyl 5-bromo-2-methyl-3-nitrobenzoate (302 g, 99%) which was used as is in further reactions

Step 3: Synthesis of methyl 3-amino-5-bromo-2-methylbenzoate

To a stirred solution of methyl 5-bromo-2-methyl-3-nitrobenzoate (150 g, 544 mmol) in ethanol (750 mL), ammonium chloride (150 g, 2777 mmol) dissolved in water (750 mL) and iron powder (93.3 g, 1636 mmol) were added under stirring. The resulting reaction mixture was heated at 80° C. for 7 h. The reaction mixture was filtered through Celite and the collected solids washed with water and ethyl acetate. The filtrate was extracted with ethyl acetate and the extract dried, concentrated under reduced pressure to give the desired compound methyl 3-amino-5-bromo-2-methylbenzoate which was used as is in further reactions.

Step 4: Synthesis of methyl 5-bromo-3-((4-((tert-butoxycarbonyl)amino)cyclohexyl)amino)-2-methylbenzoate To a stirred solution of methyl 3-amino-5-bromo-2-methylbenzoate (5.0 g, 20.6 mmol) and tert-butyl (4-oxocyclohexyl)carbamate (5.6 g, 26.7 mmol) in methanol (50 mL), acetic acid (1.2 g, 20.57 mmol) was added and reaction mixture stirred at room temperature for 8 h. Then sodium cyanoborohydride (1.6 g, 26.74 mmol) was added at 0° C. and the reaction stirred overnight. The solvent was removed under reduced pressure and the crude material purified by column chromatography (twice) eluting with ethyl acetate/hexane to afford 4 g (44%) of less-polar cis isomer, methyl 5-bromo-3-(((1s,4s)-4-((tert-butoxycarbonyl)amino)cyclohexyl)amino)-2-methylbenzoate (contaminated with some starting material) and 3 g (33%) of the more polar pure trans isomer, methyl 5-bromo-3-(((1r,4r)-4-((tert-butoxycarbonyl)amino)cyclohexyl)amino)-2-methylbenzoate.

Step 5: Synthesis of methyl 5-bromo-3-(((1r,4r)-4-((tert-butoxycarbonyl)amino)cyclohexyl)(methyl)-amino)-2-methylbenzoate To a stirred solution of the more polar trans isomer, methyl 5-bromo-3-(((1r,4r)-4-((tert-butoxycarbonyl)amino)cyclohexyl)amino)-2-methylbenzoate, (3 g, 6.81 mmol) in acetonitrile (40 mL), cesium carbonate (4.4 g, 13.62 mmol) and methyl iodide (4.83 g, 34.05 mmol) were added The resulting reaction mixture was heated at 80° C. for 7 h. The reaction mixture was cooled to room temperature and filtered and the solids washed with ethyl acetate. The filtrate was concentrated to afford the desired crude compound which purified by column chromatography giving methyl 5-bromo-3-(((1r,4r)-4-((tert-butoxycarbonyl)amino)cyclohexyl)(methyl)amino)-2-methylbenzoate (1.3 g, 43.33%).

Step 6: Synthesis of tert-butyl ((1r,4r)-4-((5-bromo-3-(((4,6-dimethyl-2-oxo-1,2-dihydropyridin-3-yl) methyl)carbamoyl)-2-methylphenyl)(methyl)amino) cyclohexyl)carbamate Aqueous NaOH (0.23 g, 5.72 mmol) was added to a solution of methyl 5-bromo-3-(((1r,4r)-4-((tert-butoxycarbonyl)amino)cyclohexyl)(methyl)amino)-2-methylbenzoate (1.3 g, 2.86 mmol) in MeOH (20 mL) and stirred at 60° C. for 1 h. After completion of the reaction, the methanol was removed under reduced pressure and the residue acidified to pH 6 with dilute HCl and to pH 4 with citric acid. The acidified mixture was extracted with ethyl acetate. The combined organic extracts were dried and concentrated giving the respective acid (1 g, 83%).

The above acid (1 g, 2.27 mmol) was dissolved in DMSO (5 mL) and 3-(aminomethyl)-4,6-dimethylpyridin-2(1H)-one (0.65 g, 4.54 mmol) was added. The reaction mixture was stirred at room temperature for 15 min before PyBOP (1.7 g, 3.4 mmol) was added. Stirring was continued overnight. The reaction mixture was poured into ice water. The resulting precipitate was filtered, washed with acetonitrile and purified by column chromatography to afford compound tert-butyl ((1r,4r)-4-((5-bromo-3-(((4,6-dimethyl-2-oxo-1,2-dihydropyridin-3-yl)methyl)carbamoyl)-2-methylphenyl) (methyl)amino)-cyclohexyl)carbamate (0.7 g, 53.8%).

Step 7: Synthesis of tert-butyl ((1r,4r)-4-((5-(((4,6-dimethyl-2-oxo-1,2-dihydropyridin-3-yl)methyl)-carbamoyl)-4-methy-4'-(morpholinomethyl)-[1,1'-biphenyl]-3-yl)(methyl)amino)-cyclohexyl) carbamate To a stirred solution of tert-butyl ((1r,4r)-4-((5-bromo-3-(((4,6-dimethyl-2-oxo-1,2-dihydropyridin-3-yl)methyl)carbamoyl)-2-methylphenyl)(methyl)amino)-cyclohexyl)carbamate (1 equiv.) and 4-(4-(4,4,5,5-tetramethyl-1,3,2-dioxaborolan-2-yl)benzyl)morpholine (1.2 equiv.) in dioxane/water mixture (5 mL+1 mL), Na$_2$CO$_3$ (3.6 equiv.) was added and solution purged with argon for 15 min. Then Pd(PPh$_3$)$_4$ (0.1 equiv.) was added and the reaction flask was purged again for 10 min. with argon. The reaction mixture was heated at 100° C. for 4 h. The reaction mixture was diluted with water and extracted with 10% MeOH/DCM. The combined organic extracts were dried over Na$_2$SO$_4$ and the solvent removed under reduced pressure to afford the crude product which was purified by column chromatography over silica gel to afford tert-butyl ((1r,4r)-4-((5-(((4,6-dimethyl-2-oxo-1,2-dihydropyridin-3-yl)methyl)carbamoyl)-4-methyl-4'-(morpholinomethyl)-[1,1'-biphenyl]-3-yl) (methyl)amino)cyclohexyl)carbamate (0.07 g, 40%)

Step 8: Synthesis of 5-(((1r,4r)-4-aminocyclohexyl) (methyl)amino)-N-((4,6-dimethyl-2-oxo-1,2-dihydropyridin-3-yl)methyl)-4-methyl-4'-(morpholinomethyl)-[1,1'-biphenyl]-3-carboxamide A stirred solution of tert-butyl ((1r,4r)-4-((5-(((4,6-dimethyl-2-oxo-1,2-dihydropyridin-3-yl)methyl)carbamoyl)-4-methyl-4'-(morpholinomethyl)-[1,1'-biphenyl]-3-yl) (methyl)amino)cyclohexyl)carbamate (0.07 g) in DCM (5 mL) was cooled to 0° C. and TFA (2 mL) was added. The reaction mixture was stirred at room temperature for 1 h. The reaction was concentrated to dryness yielding the title compound as a TFA salt (0.05 g, 84.74%). LCMS: 572.60 (M+1)$^+$; HPLC: 88.92% (@ 254 nm) (R$_t$: 3.546; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (s, 1H), 10.05 (bs, 1H), 8.16 (t, 1H), 7.74-7.76 (m, 4H), 7.56 (d, 2H, J=7.6 Hz), 7.34 (s, 1H), 7.21 (s, 1H), 5.86 (s, 1H), 4.38 (bs, 2H), 4.28 (d, 2H, J=4.4 Hz), 3.95 (m, 2H), 3.63 (m, 2H), 3.27 (m, 1H), 3.12 (m, 2H), 2.97 (m, 2H), 2.74 (t, 1H), 2.66 (s, 3H), 2.20 (s, 6H), 2.10 (s, 3H), 1.93-1.95 (m, 2H), 1.74-1.77 (m, 2H), 1.54-1.57 (m, 2H), 1.28-1.31 (m, 2H).

Example 44: Synthesis of N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide Compound 44

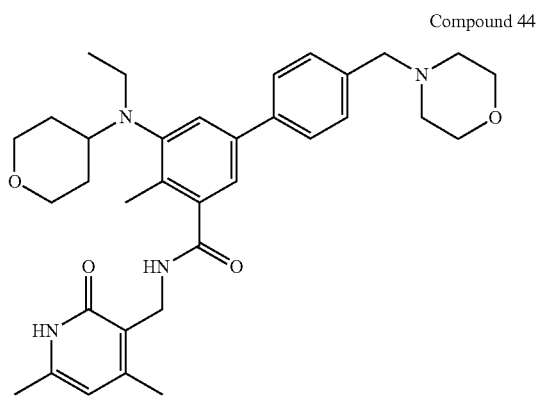 [SMILES: CCN(c1cc(-c2ccc(CN3CCOCC3)cc2)cc(C(=O)NCc2c(C)cc(C)[nH]c2=O)c1C)C1CCOCC1]

Step 1: Synthesis of 5-bromo-2-methyl-3-nitrobenzoic acid

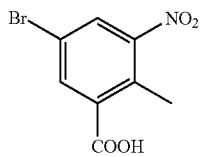

To stirred solution of 2-methyl-3-nitrobenzoic acid (100 g, 552 mmol) in conc. H$_2$SO$_4$ (400 mL), 1,3-dibromo-5,5-dimethyl-2,4-imidazolidinedione (88 g, 308 mmol) was added in a portion wise manner at room temperature and the reaction mixture was then stirred at room temperature for 5 h. The reaction mixture was poured onto ice cold water, the precipitated solid was filtered off, washed with water and dried under vacuum to afford the desired compound as a solid (140 g, 98%). The isolated compound was taken directly into the next step. $^1$H NMR (DMSO-d$_6$, 400 MHz) δ 8.31 (s, 1H), 8.17 (s, 1H), 2.43 (s, 3H).

Step 2: Synthesis of methyl 5-bromo-2-methyl-3-nitrobenzoate

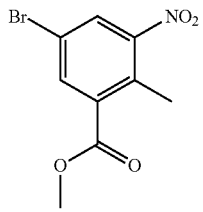

To a stirred solution of 5-bromo-2-methyl-3-nitrobenzoic acid (285 g, 1105 mmol) in DMF (2.8 L) at room temperature was added sodium carbonate (468 g, 4415 mmol) followed by addition of methyl iodide (626.6 g, 4415 mmol). The resulting reaction mixture was heated at 60° C. for 8 h. After completion (monitored by TLC), the reaction mixture was filtered (to remove sodium carbonate) and washed with ethyl acetate (1 L×3). The combined filtrate was washed with water (3 L×5) and the aqueous phase was back extracted with ethyl acetate (1 L×3). The combined organic layers were dried over anhydrous sodium sulfate, filtered and concentrated under reduced pressure to afford the title compound as a solid (290 g, 97% yield). The isolated compound was taken directly into the next step. $^1$H NMR (CDCl$_3$, 400 MHz) δ 8.17 (s, 1H), 7.91 (s, 1H), 3.96 (s, 3H), 2.59 (s, 3H).

Step 3: Synthesis of methyl 3-amino-5-bromo-2-methylbenzoate

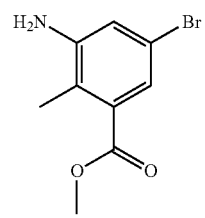

To a stirred solution of methyl 5-bromo-2-methyl-3-nitrobenzoate (290 g, 1058 mmol) in ethanol (1.5 L) was added aqueous ammonium chloride (283 g, 5290 mmol dissolved in 1.5 L water). The resulting mixture was stirred at 80° C. to which iron powder (472 g, 8451 mmol) was added in a portion wise manner. The resulting reaction mixture was heated at 80° C. for 12 h. Upon completion as determined by TLC, the reaction mixture was hot filtered over Celite® and the celite bed was washed with methanol (5 L) followed by washing with 30% MeOH in DCM (5 L). The combined filtrate was concentrated in-vacuo, the residue obtained was diluted with aqueous sodium bicarbonate solution (2 L) and extracted with ethyl acetate (5 L×3). The combined organic layers were dried over anhydrous sodium sulfate, filtered and concentrated under reduced pressure to afford the title compound as a solid (220 g, 85%). The compound was taken directly into the next step. $^1$H NMR (CDCl$_3$, 400 MHz) δ 7.37 (s, 1H), 6.92 (s, 1H), 3.94 (s, 3H), 3.80 (bs, 2H), 2.31 (s, 3H).

Step 4: Synthesis of methyl 5-bromo-2-methyl-3-((tetrahydro-2H-pyran-4-yl) amino) benzoate

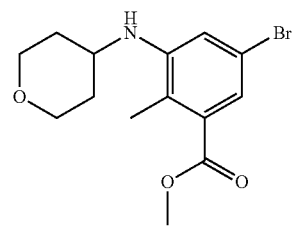 [SMILES: COC(=O)c1cc(Br)cc(NC2CCOCC2)c1C]

To a stirred solution of methyl 3-amino-5-bromo-2-methylbenzoate (15 g, 61.5 mmol) and dihydro-2H-pyran-4(3)-one (9.2 g, 92 mmol) in dichloroethane (300 mL) was added acetic acid (22 g, 369 mmol) and the reaction mixture stirred at room temperature for 15 minutes, then the reaction mixture was cooled to 0° C. and sodium triacetoxyborohydride (39 g, 184 mmol) was added. The reaction mixture was stirred overnight at room temperature. Upon completion of the reaction as determined by TLC, aqueous sodium bicarbonate solution was added to the reaction mixture until a pH of 7-8 was obtained. The organic phase was separated and the aqueous phase was extracted with ethyl acetate. The combined organic layers were dried over anhydrous sodium sulfate, filtered and concentrated under reduced pressure. The crude compound was purified by column chromatography (100-200 mesh silica gel) eluting with ethyl acetate: hexane to afford the desired compound as a solid (14 g, 69%). $^1$H NMR (DMSO-$d_6$, 400 MHz) δ 7.01 (s, 1H), 6.98 (s, 1H), 5.00 (d, 1H, J=7.6 Hz), 3.84-3.87 (m, 2H), 3.79 (s, 3H), 3.54-3.56 (m, 1H), 3.43 (t, 2H, J=12 Hz), 2.14 (s, 3H), 1.81-1.84 (m, 2H), 1.47-1.55 (m, 2H).

Step 5: Synthesis of methyl 5-bromo-3-(ethyl (tetrahydro-2H-pyran-4-yl) amino)-2-methylbenzoate

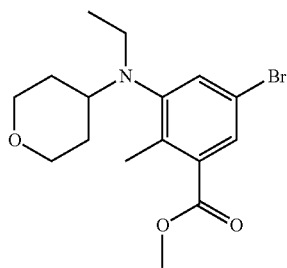 [SMILES: CCN(c1cc(Br)cc(C(=O)OC)c1C)C1CCOCC1]

To a stirred solution of methyl 5-bromo-2-methyl-3-((tetrahydro-2H-pyran-4-yl) amino) benzoate (14 g, 42.7 mmol) in dichloroethane (150 mL) was added acetaldehyde (3.75 g, 85.2 mmol) and acetic acid (15.3 g, 256 mmol). The resulting reaction mixture was stirred at room temperature for 15 minutes. The mixture was cooled to 0° C. and sodium triacetoxyborohydride (27 g, 128 mmol) was added. The reaction mixture was stirred at room temperature for 3 hours. Upon completion of the reaction as determined by TLC, aqueous sodium bicarbonate solution was added to the reaction mixture until a pH 7-8 was obtained, the organic phase was separated and the aqueous phase was extracted with ethyl acetate. The combined organic layers were dried over anhydrous sodium sulfate, filtered and concentrated under reduced pressure. The crude compound was purified by column chromatography (100-200 mesh silica gel) eluting with ethyl acetate: hexane to afford the desired compound as a viscous liquid (14 g, 93%). $^1$H NMR (DMSO-$d_6$, 400 MHz) δ 7.62 (s, 1H), 7.52 (s, 1H), 3.80 (bs, 5H), 3.31 (t, 2H), 2.97-3.05 (m, 2H), 2.87-2.96 (m, 1H), 2.38 (s, 3H), 1.52-1.61 (m, 2H), 1.37-1.50 (m, 2H), 0.87 (t, 3H, J=6.8 Hz).

Step 6: Synthesis of 5-bromo-N-((4,6-dimethyl-2-oxo-1,2-dihydropyridin-3-yl) methyl)-3-(ethyl (tetrahydro-2H-pyran-4-yl) amino)-2-methylbenzamide

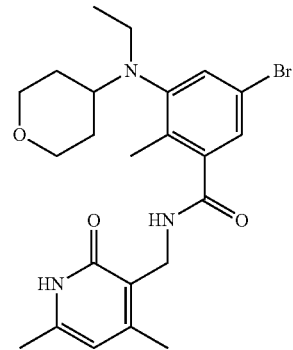 [SMILES: CCN(c1cc(Br)cc(C(=O)NCc2c(C)cc(C)[nH]c2=O)c1C)C1CCOCC1]

To a stirred solution of 5-bromo-3-(ethyl (tetrahydro-2H-pyran-4-yl) amino)-2-methylbenzoate (14 g, 39.4 mmol) in ethanol (100 mL) was added aqueous NaOH (2.36 g, 59.2 mmol in 25 mL water) and the resulting mixture was stirred at 60° C. for 1 h. Upon completion of the reaction as determined by TLC, the solvent was removed under reduced pressure and the residue obtained was acidified with 1N HCl until a pH 7 was obtained and then aqueous citric acid solution was added until a pH 5-6 was obtained. The aqueous layer was extracted with 10% MeOH in DCM (200 mL×3), the combined organic layers were dried over anhydrous sodium sulfate, filtered and concentrated under reduced pressure to give the respective acid (14 g, 100%).

The above acid (14 g, 40.9 mmol) was then dissolved in DMSO (70 mL) and 3-(amino methyl)-4,6-dimethylpyridin-2(1H)-one (12.4 g, 81.9 mmol) was added to it. The reaction mixture was stirred at room temperature for 15 minutes, then PYBOP (31.9 g, 61.4 mmol) was added and stirring was continued for overnight at room temperature. Upon completion of the reaction as determined by TLC, the reaction mixture was poured onto ice-cold water (700 mL), stirred for 30 minutes and the precipitated solid was collected by filtration, washed with water (500 mL) and air dried. The solid obtained was stirred with acetonitrile (75 mL×2), filtered and air dried. The solid obtained was again stirred with 5% MeOH in DCM (100 mL), filtered and dried completely under vacuum to afford the title compound as a solid (14 g, 74%). $^1$H NMR (DMSO-$d_6$, 400 MHz) δ 11.47 (s, 1H), 8.23 (t, 1H), 7.30 (s, 1H), 7.08 (s, 1H), 5.85 (s, 1H), 4.23 (d, 2H, J=4.4 Hz), 3.81 (d, 2H, J=10.4 Hz), 3.20-3.26 (m, 2H), 3.00-3.07 (m, 1H), 2.91-2.96 (m, 2H), 2.18 (s, 3H), 2.14 (s, 3H), 2.10 (s, 3H), 1.58-1.60 (m, 2H), 1.45-1.50 (m, 2H), 0.78 (t, 3H, J=6.8 Hz).

Step 7: Synthesis of N-((4,6-dimethyl-2-oxo-1,2-dihydropyridin-3-yl) methyl)-5-(ethyl (tetrahydro-2H-pyran-4-yl) amino)-4-methyl-4'-(morpholinomethyl)-[1,1'-biphenyl]-3-carboxamide

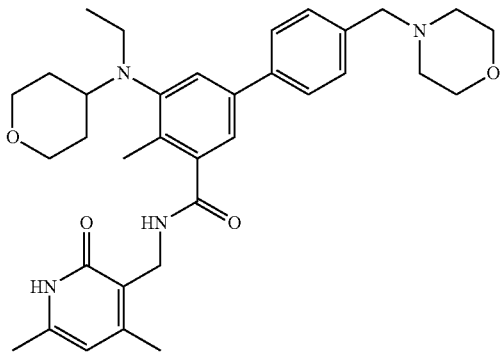

To a stirred solution of 5-bromo-N-((4,6-dimethyl-2-oxo-1,2-dihydropyridin-3-yl) methyl)-3-(ethyl (tetrahydro-2H-pyran-4-yl) amino)-2-methylbenzamide (14 g, 29.5 mmol) in dioxane/water mixture (70 mL/14 mL) was added 4-(4-(4,4,5,5-tetramethyl-1,3,2-dioxaborolan-2-yl) benzyl) morpholine (13.4 g, 44.2 mmol) followed by addition of $Na_2CO_3$ (11.2 g, 106.1 mmol). The solution was purged with argon for 15 minutes and then Pd (PPh$_3$)$_4$ (3.40 g, 2.94 mmol) was added and the solution was again purged with argon for a further 10 min. The reaction mixture was heated at 100° C. for 4 h. After completion (monitored by TLC), the reaction mixture was diluted with water and extracted with 10% MeOH/DCM. The combined organic layers were dried over anhydrous sodium sulphate, filtered and concentrated under reduced pressure. The crude compound was purified by column chromatography (100-200 mesh silica gel) eluting with methanol: DCM to the title compound as a solid (12 g, 71%). Analytical Data: LCMS: 573.35 (M+1)$^+$; HPLC: 99.5% (@ 254 nm) (R$_t$; 3.999; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.46 (s, 1H), 8.19 (t, 1H), 7.57 (d, 2H, J=7.2 Hz), 7.36-7.39 (m, 3H), 7.21 (s, 1H), 5.85 (s, 1H), 4.28 (d, 2H, J=2.8 Hz), 3.82 (d, 2H, J=9.6 Hz), 3.57 (bs, 4H), 3.48 (s, 2H), 3.24 (t, 2H, J=10.8 Hz), 3.07-3.09 (m, 2H), 3.01 (m, 1H), 2.36 (m, 4H), 2.24 (s, 3H), 2.20 (s, 3H), 2.10 (s, 3H), 1.64-1.67 (m, 2H), 1.51-1.53 (m, 2H), 0.83 (t, 3H, J=6.4 Hz).

Step 8: Synthesis of N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide trihydrochloride

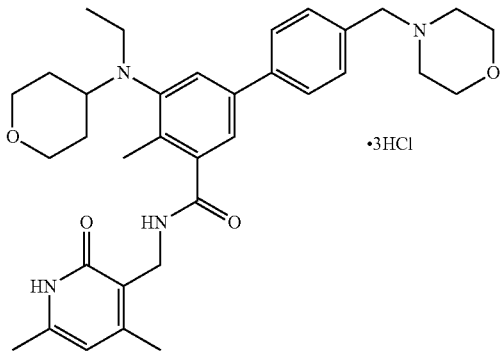 [SMILES: CCN(c1cc(-c2ccc(CN3CCOCC3)cc2)cc(C(=O)NCc2c(C)cc(C)[nH]c2=O)c1C)C1CCOCC1 ; "·3HCl"]

N-((4,6-dimethyl-2-oxo-1,2-dihydropyridin-3-yl) methyl)-5-(ethyl (tetrahydro-2H-pyran-4-yl) amino)-4-methyl-4'-(morpholinomethyl)-[1,1'-biphenyl]-3-carboxamide (12 g, 21.0 mmol) was dissolved in methanolic HCl (200 mL) and stirred at room temperature for 3 h. After three hours of stirring, the reaction mixture was concentrated under reduced pressure. The solid obtained was stirred with ether (100 mL×2) to afford the desired salt as a solid (11 g, 77%). Analytical Data of the tri-HCl salt: LCMS: 573.40 (M+1)$^+$; HPLC: 99.1% (@ 254 nm) (R$_t$; 3.961; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (D$_2$O 400 MHz) δ 7.92 (bs, 1H) 7.80 (s, 1H), 7.77 (d, 2H, J=8 Hz), 7.63 (s, 1H), 7.61 (s, 1H), 6.30 (s, 1H), 4.48 (s, 2H), 4.42 (s, 2H), 4.09-4.11 (m, 4H), 3.95-3.97 (m, 2H), 3.77 (t, 3H, J=10.4 Hz), 3.44-3.47 (m, 3H), 3.24-3.32 (m, 3H), 2.42 (s, 3H), 2.35 (s, 3H), 2.26 (s, 3H), 2.01 (m, 2H), 1.76 (m, 2H), 1.04 (t, 3H, J=6.8 Hz).

Example 45: Synthesis of 3-(((1r,4r)-4-aminocyclohexyl)(methyl)amino)-N-((4,6-dimethyl-2-oxo-1,2-dihydropyridin-3-yl)methyl)-2-methyl-5-(1-methyl-1H-pyrazol-4-yl)benzamide

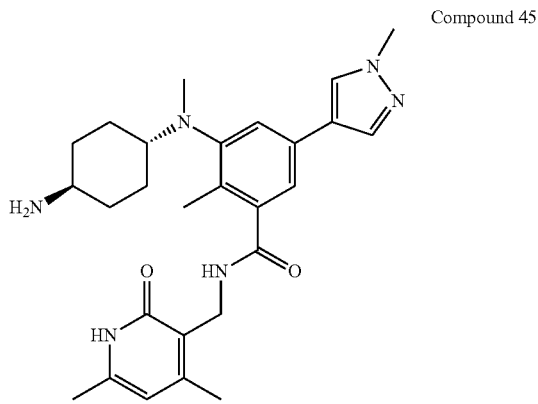 [SMILES: Cc1cc(C)c(CNC(=O)c2cc(-c3cnn(C)c3)cc(N(C)[C@H]3CC[C@H](N)CC3)c2C)c(=O)[nH]1]

Compound 45

Step 1: Synthesis of tert-butyl ((1r,4r)-4-((3-(((4,6-dimethyl-2-oxo-1,2-dihydropyridin-3-yl)methyl) carbamoyl)-2-methyl-5-(1-methyl-1H-pyrazol-4-yl) phenyl)(methyl)amino)cyclohexyl)carbamate To a stirred solution of tert-butyl ((1r,4r)-4-((5-bromo-3-(((4,6-dimethyl-2-oxo-1,2-dihydropyridin-3-yl)methyl)carbamoyl)-2-methylphenyl)(methyl)amino)-cyclohexyl)carbamate (1 equiv.) and 1-methyl-4-(4,4,5,5-tetramethyl-1,3,2-dioxaborolan-2-yl)-1H-pyrazole (1.2 equiv.) in dioxane/water mixture (5 mL+1 mL), Na$_2$CO$_3$ (3.6 equiv.) was added and solution purged with argon for 15 min. Then Pd(PPh$_3$)$_4$ (0.1 equiv.) was added and the reaction flask was purged again for 10 min. with argon. The reaction mixture was heated at 100° C. for 4 h. The reaction mixture was diluted with water and extracted with 10% MeOH/DCM. The combined organic extracts were dried over Na$_2$SO$_4$ and the solvent removed under reduced pressure to afford the crude product which was purified by column chromatography over silica gel to afford tert-butyl ((1r,4r)-4-((3-(((4,6-dimethyl-2-oxo-1,2-dihydropyridin-3-yl)methyl)carbamoyl)-2- methyl-5-(1-methyl-1H-pyrazol-4-yl)phenyl)(methyl) amino)cyclohexyl)carbamate (0.07 g, 46.6%)

Step 2: Synthesis of 3-(((1r,4r)-4-aminocyclohexyl) (methyl)amino)-N-((4,6-dimethyl-2-oxo-1,2-dihydropyridin-3-yl)methyl)-2-methyl-5-(1-methyl-1H-pyrazol-4-yl)benzamide A stirred solution of tert-butyl ((1r,4r)-4-((3-(((4,6-dimethyl-2-oxo-1,2-dihydropyridin-3-yl)methyl)carbamoyl)-2-methyl-5-(1-methyl-1H-pyrazol-4-yl)phenyl)(methyl) amino)cyclohexyl)carbamate (0.07 g) in DCM (5 mL) was cooled to 0° C. and TFA (2 mL) was added. The reaction mixture was stirred at room temperature for 1 h. The reaction was concentrated to dryness yielding the title compound as a TFA salt (0.07 g, 98.59%). LCMS: 477.35 (M+1)$^+$; HPLC: 99.16% (@ 254 nm) (R$_t$; 3.796; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (s, 1H), 8.12 (s, 1H), 8.08 (t, 1H), 7.82 (s, 1H), 7.74 (m, 3H), 7.28 (s, 1H), 7.11 (s, 1H), 5.86 (s, 1H), 4.26 (d, 2H, J=4.4 Hz), 3.84 (s, 3H), 2.96 (bs, 1H), 2.73 (bs, 1H), 2.63 (s, 3H), 2.20 (s, 3H), 2.14 (s, 3H), 2.10 (s, 3H), 1.92-1.95 (m, 2H), 1.74-1.77 (m, 2H), 1.48-1.57 (m, 2H), 1.23-1.32 (m, 2H).

Example 46: Synthesis of 3-(((1s,4s)-4-aminocyclohexyl)(methyl)amino)-N-((4,6-dimethyl-2-oxo-1,2-dihydropyridin-3-yl)methyl)-2-methyl-5-(1-methyl-1H-pyrazol-4-yl)benzamide Compound 46

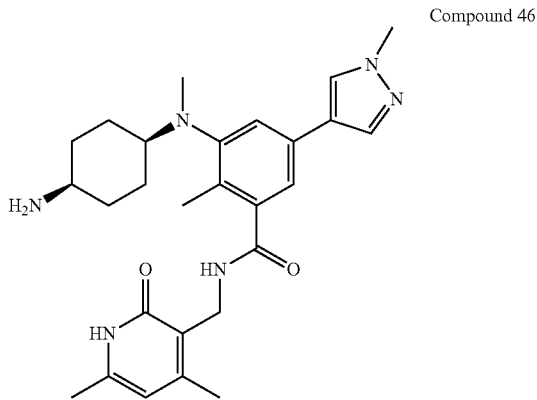 [SMILES: Cc1cc(C)c(CNC(=O)c2cc(-c3cnn(C)c3)cc(N(C)[C@H]3CC[C@@H](N)CC3)c2C)c(=O)[nH]1]

Step 1: Synthesis of tert-butyl ((1s,4s)-4-((3-(((4,6-dimethyl-2-oxo-1,2-dihydropyridin-3-yl)methyl) carbamoyl)-2-methyl-5-(1-methyl-1H-pyrazol-4-yl) phenyl)(methyl)amino)cyclohexyl)carbamate To a stirred solution of tert-butyl ((1s,4s)-4-((5-bromo-3-(((4,6-dimethyl-2-oxo-1,2-dihydropyridin-3-yl)methyl)carbamoyl)-2-methylphenyl)(methyl)amino)cyclohexyl)-carbamate (1 equiv.) and 1-methyl-4-(4,4,5,5-tetramethyl-1,3,2-dioxaborolan-2-yl)-1H-pyrazole (1.2 equiv.) in dioxane/water mixture (5 mL+1 mL), Na$_2$CO$_3$ (3.6 equiv.) was added. The solution was then purged with argon for 15 min. Pd(PPh$_3$)$_4$ (0.1 equiv.) was added and the reaction mixture again purged with argon for 10 min. The reaction mixture was heated at 100° C. for 4 h. The reaction mixture was diluted with water and extracted with 10% MeOH/DCM. The combined extracts were dried over Na$_2$SO$_4$ and the solvent removed under reduced pressure to afford the crude product which was purified by column chromatography over silica gel to afford tert-butyl ((1s,4s)-4-((3-(((4,6-dimethyl-2-oxo-1,2-dihydropyridin-3-yl)methyl)carbamoyl)-2-methyl-5-(1-methyl-1H-pyrazol-4-yl)phenyl)(methyl) amino)cyclohexyl)carbamate (0.05 g, 33.3%).

Step 2: Synthesis of 3-(((1s,4s)-4-aminocyclohexyl) (methyl)amino)-N-((4,6-dimethyl-2-oxo-1,2-dihydropyridin-3-yl)methyl)-2-methyl-5-(1-methyl-1H-pyrazol-4-yl)benzamide A stirred solution of tert-butyl ((1s,4s)-4-((3-(((4,6-dimethyl-2-oxo-1,2-dihydropyridin-3-yl)methyl)carbamoyl)-2-methyl-5-(1-methyl-1H-pyrazol-4-yl)phenyl)(methyl) amino)cyclohexyl)carbamate (0.05 g) in DCM (5 mL) was cooled to 0° C. and TFA (2 mL) was added. The reaction mixture was stirred at room temperature for 1 h. The reaction was concentrated to dryness yielding the title compound as a TFA salt (0.03 g, 73.1%). LCMS: 477.30 (M+1)$^+$; HPLC: 98.76% (@ 254 nm) (R$_t$; 3.862; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (s, 1H), 8.08-8.12 (m, 2H), 7.76-7.81 (m, 4H), 7.33 (s, 1H), 7.12 (s, 1H), 5.86 (s, 1H), 4.27 (d, 2H, J=4 Hz), 3.83 (s, 3H), 3.16 (m, 2H), 2.50 (3H merged in solvent peak), 2.22 (s, 3H), 2.20 (s, 3H), 2.10 (s, 3H), 1.84 (m, 2H), 1.57-1.63 (m, 4H), 1.47-1.50 (m, 2H).

Example 47: Synthesis of 5-(((1s,4s)-4-aminocyclohexyl)(methyl)amino)-N-((4,6-dimethyl-2-oxo-1,2-dihydropyridin-3-yl)methyl)-4'-((dimethylamino) methyl)-4-methyl-[1,1'-biphenyl]-3-carboxamide Compound 47

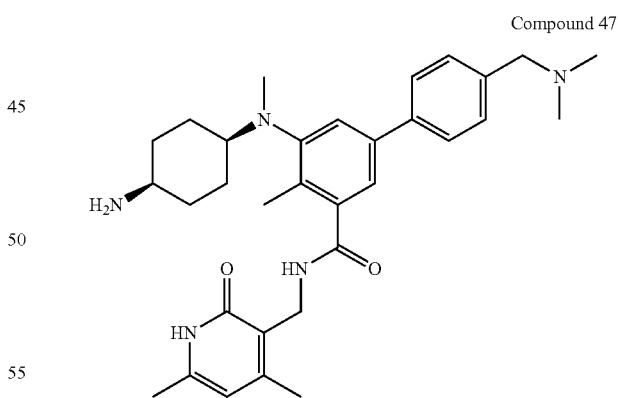

Step 1: Synthesis of tert-butyl ((1s,4s)-4-((5-(((4,6-dimethyl-2-oxo-1,2-dihydropyridin-3-yl)methyl) carbamoyl)-4'-((dimethylamino)methyl)-4-methyl-[1,1'-biphenyl]-3-yl)(methyl)amino)cyclohexyl) carbamate To a stirred solution of tert-butyl ((1s,4s)-4-((5-bromo-3-(((4,6-dimethyl-2-oxo-1,2-dihydropyridin-3-yl)methyl)carbamoyl)-2-methylphenyl)(methyl)amino)cyclohexyl)-carbamate (1 equiv.) and N,N-dimethyl-1-(4-(4,4,5,5-tetramethyl-1,3,2-dioxaborolan-2-yl)phenyl)methanamine (1.2 equiv.) in dioxane/water mixture (5 mL+1 mL), Na₂CO₃ (3.6 equiv.) was added. The solution was purged then with argon for 15 min. Pd(PPh₃)₄ (0.1 equiv.) was added and the reaction mixture again purged with argon for 10 min. The reaction mixture was heated at 100° C. for 4 h. The reaction mixture was diluted with water and extracted with 10% MeOH/DCM. The combined extracts were dried over Na₂SO₄ and the solvent removed under reduced pressure to afford the crude product which was purified by column chromatography over silica gel to afford tert-butyl ((1s,4s)-4-((5-(((4,6-dimethyl-2-oxo-1,2-dihydropyridin-3-yl)methyl)carbamoyl)-4'-((dimethylamino)methyl)-4-methyl-[1,1'-biphenyl]-3-yl)(methyl)amino)cyclohexyl)carbamate (0.100 g, 61%).

Step 2: Synthesis of 5-(((1s,4s)-4-aminocyclohexyl)(methyl)amino)-N-((4,6-dimethyl-2-oxo-1,2-dihydropyridin-3-yl)methyl)-4'-((dimethylamino)methyl)-4-methyl-[1,1'-biphenyl]-3-carboxamide A stirred solution of tert-butyl ((1s,4s)-4-((5-(((4,6-dimethyl-2-oxo-1,2-dihydropyridin-3-yl)methyl)carbamoyl)-4'-((dimethylamino)methyl)-4-methyl-[1,1'-biphenyl]-3-yl)(methyl)amino)cyclohexyl)carbamate (0.10 g) in DCM (5 mL) was cooled to 0° C. and TFA (2 mL) was added. The reaction mixture was stirred at room temperature for 1 h. The reaction was concentrated to dryness yielding the title compound as a TFA salt (0.05 g, 59.5%). LCMS: 530.35 (M+1)⁺; HPLC: 97.13% (@ 254 nm) (R$_t$: 3.672; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d₆, 400 MHz) δ 11.44 (s, 1H), 9.47 (bs, 1H), 8.17 (t, 1H), 7.74-7.76 (m, 4H), 7.55 (d, 2H, J=7.6 Hz), 7.44 (s, 1H), 7.25 (s, 1H), 5.86 (s, 1H), 4.30 (m, 4H), 3.12 (m, 2H), 2.74 (s, 6H), 2.54 (s, 3H), 2.30 (s, 3H), 2.12 (s, 3H), 2.10 (s, 3H), 1.84 (bs, 2H), 1.59-1.63 (m, 4H), 1.48 (m, 2H).

Example 48: Synthesis of 3-(((1s,4s)-4-aminocyclohexyl)(methyl)amino)-N-((4,6-dimethyl-2-oxo-1,2-dihydropyridin-3-yl)methyl)-2-methyl-5-(1-(2-morpholinoethyl)-1H-pyrazol-4-yl)benzamide Compound 48

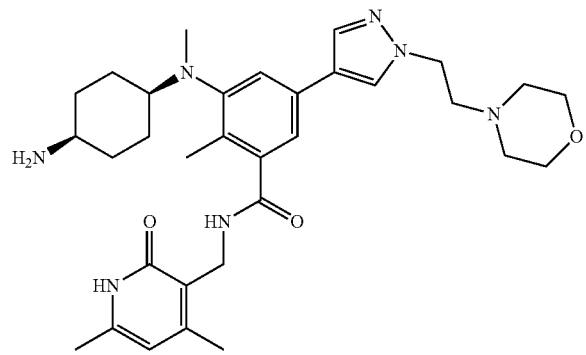

Step 1: Synthesis of tert-butyl ((1s,4s)-4-((3-(((4,6-dimethyl-2-oxo-1,2-dihydropyridin-3-yl)methyl)carbamoyl)-2-methyl-5-(1-(2-morpholinoethyl)-1H-pyrazol-4-yl)phenyl)(methyl)amino)cyclohexyl)carbamate To a stirred solution of tert-butyl ((1s,4s)-4-((5-bromo-3-(((4,6-dimethyl-2-oxo-1,2-dihydropyridin-3-yl)methyl)carbamoyl)-2-methylphenyl)(methyl)amino)cyclohexyl)-carbamate (1 equiv.) and 4-(2-(4-(4,4,5,5-tetramethyl-1,3,2-dioxaborolan-2-yl)-1H-pyrazol-1-yl)ethyl)morpholine (1.2 equiv.) in dioxane/water mixture (5 mL+1 mL), Na₂CO₃ (3.6 equiv.) was added. The solution was purged then with argon for 15 min. Pd(PPh₃)₄ (0.1 equiv.) was added and the reaction mixture again purged with argon for 10 min. The reaction mixture was heated at 100° C. for 4 h. The reaction mixture was diluted with water and extracted with 10% MeOH/DCM. The combined extracts were dried over Na₂SO₄ and the solvent removed under reduced pressure to afford the crude product which was purified by column chromatography over silica gel to afford tert-butyl ((1r,4r)-4-((3-(((4,6-dimethyl-2-oxo-1,2-dihydropyridin-3-yl)methyl)carbamoyl)-2-methyl-5-(1-(2-morpholinoethyl)-1H-pyrazol-4-yl)phenyl)(methyl)amino)cyclohexyl)carbamate (0.120 g, 75.4%).

Step 2: Synthesis of 3-(((1s,4s)-4-aminocyclohexyl)(methyl)amino)-N-((4,6-dimethyl-2-oxo-1,2-dihydropyridin-3-yl)methyl)-2-methyl-5-(1-(2-morpholinoethyl)-1H-pyrazol-4-yl)benzamide A stirred solution of tert-butyl ((1s,4s)-4-((3-(((4,6-dimethyl-2-oxo-1,2-dihydropyridin-3-yl)methyl)carbamoyl)-2-methyl-5-(1-(2-morpholinoethyl)-1H-pyrazol-4-yl)phenyl)(methyl)amino)cyclohexyl)carbamate (0.10 g) in DCM (5 mL) was cooled to 0° C. and TFA (2 mL) was added. The reaction mixture was stirred at room temperature for 1 h. The reaction was concentrated to dryness yielding the title compound as a TFA salt (0.06 g, 58.82%). LCMS: 576.40 (M+1)⁺; HPLC: 96.89% (@ 254 nm) (R$_t$: 3.481; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d₆, 400 MHz) δ 11.45 (s, 1H), 8.25 (s, 1H), 8.08 (t, 1H), 7.79 (s, 1H), 7.74-7.79 (m, 3H), 7.34 (s, 1H), 7.15 (s, 1H), 5.86 (s, 1H), 4.51 (bs, 2H), 4.27 (d, 2H, J=4.4 Hz), 3.16 (m, 6H), 2.50 (3H merged in solvent peak), 2.23 (s, 3H), 2.21 (s, 3H), 2.11 (s, 3H), 1.84 (bs, 2H), 1.57-1.63 (m, 4H), 1.47-1.49 (m, 2H). [3H merged in solvent peak].

Example 49: Synthesis of 3-(((1s,4s)-4-aminocyclohexyl)(methyl)amino)-N-((4,6-dimethyl-2-oxo-1,2-dihydropyridin-3-yl)methyl)-2-methyl-5-(6-(morpholinomethyl)pyridin-3-yl)benzamide Compound 49

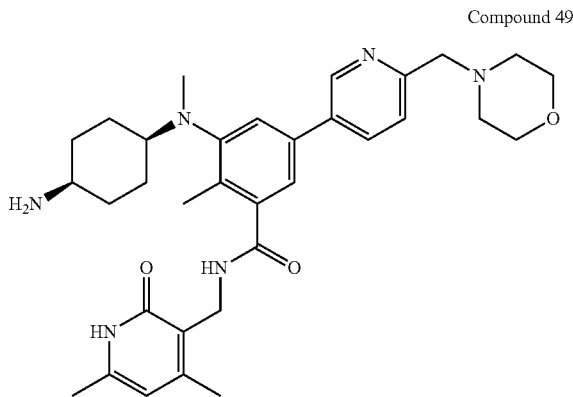 [SMILES: Cc1cc(C)c(CNC(=O)c2cc(-c3ccc(CN4CCOCC4)nc3)cc(N(C)[C@H]3CC[C@@H](N)CC3)c2C)c(=O)[nH]1]

Step 1: Synthesis of tert-butyl ((1s,4s)-4-((3-(((4,6-dimethyl-2-oxo-1,2-dihydropyridin-3-yl)methyl)carbamoyl)-5-(6-formylpyridin-3-yl)-2-methylphenyl)(methyl)-amino)cyclohexyl)carbamate To a stirred solution of tert-butyl ((1s,4s)-4-((5-bromo-3-(((4,6-dimethyl-2-oxo-1,2-dihydropyridin-3-yl)methyl)carbamoyl)-2-methylphenyl)(methyl)amino)-cyclohexyl)carbamate (0.5 g, 8.71 mmol) and (6-formylpyridin-3-yl)boronic acid (0.264 g, 1.13 mmol) in dioxane/water mixture (10 mL+2 mL), $Na_2CO_3$ (0.333 g, 2.8 mmol) was added. The solution was then purged with argon for 15 min. Pd (PPh$_3$)$_4$ (0.1 g, 0.086 mmol) was added and the solution again purged with argon for 10 min. The reaction mixture was heated at 100° C. for 4 h. The reaction mixture was diluted with water and extracted with 10% MeOH/DCM. The combined extracts were dried over $Na_2SO_4$ and the solvent removed under reduced pressure to afford the crude product which was purified by column chromatography over silica gel to afford tert-butyl ((1s,4s)-4-((3-(((4,6-dimethyl-2-oxo-1,2-dihydropyridin-3-yl)methyl)carbamoyl)-5-(6-formylpyridin-3-yl)-2-methylphenyl)(methyl)amino)cyclohexyl)carbamate (0.3 g, 57.3%).

Step 2: Synthesis of tert-butyl ((1s,4s)-4-((3-(((4,6-dimethyl-2-oxo-1,2-dihydropyridin-3-yl)methyl)carbamoyl)-2-methyl-5-(6-(morpholinomethyl)pyridin-3-yl)phenyl)(methyl)amino)cyclohexyl)carbamate To a stirred solution of tert-butyl ((1s,4s)-4-((3-(((4,6-dimethyl-2-oxo-1,2-dihydropyridin-3-yl)methyl)carbamoyl)-5-(6-formylpyridin-3-yl)-2-methylphenyl)(methyl)amino)cyclohexyl)carbamate (1 equiv.) and morpholine (5 equiv.) in methanol (10 mL), acetic acid (2 equiv.) was added. The reaction mixture was stirred at room temperature for 18 h. Sodium cyanoborohydride (2.5 equiv.) was then added at 0° C. and the reaction mixture stirred overnight at room temperature. The solvent was removed under reduced pressure and the crude product was purified by column chromatography to afford tert-butyl ((1s,4s)-4-((3-(((4,6-dimethyl-2-oxo-1,2-dihydropyridin-3-yl)methyl)carbamoyl)-2-methyl-5-(6-(morpholinomethyl)pyridin-3-yl)phenyl)(methyl)amino)cyclohexyl)carbamate.

Step 3: Synthesis of 3-(((1s,4s)-4-aminocyclohexyl)(methyl)amino)-N-((4,6-dimethyl-2-oxo-1,2-dihydropyridin-3-yl)methyl)-2-methyl-5-(6-(morpholinomethyl)pyridin-3-yl)benzamide A stirred solution of tert-butyl ((1s,4s)-4-((3-(((4,6-dimethyl-2-oxo-1,2-dihydropyridin-3-yl)methyl)carbamoyl)-2-methyl-5-(6-(morpholinomethyl)pyridin-3-yl)phenyl)(methyl)amino)cyclohexyl)carbamate in DCM (5 mL) was cooled to 0° C. and TFA (2 mL) was added. The reaction mixture was stirred at room temperature for 1 h. The reaction was concentrated to dryness and the product purified by solvent washings to afford the title compound as a TFA salt (0.1 g, 94.33%). LCMS: 573.45 (M+1)$^+$; HPLC: 98.94% (@ 254 nm) (R$_t$; 3.618; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.47 (s, 1H), 8.94 (s, 1H), 8.19-8.21 (m, 2H), 7.80 (s, 3H), 7.60 (d, 1H, J=8 Hz), 7.49 (s, 1H), 7.31 (s, 1H), 5.86 (s, 1H), 4.52 (bs, 2H), 4.29 (d, 2H, J=4.4 Hz), 3.83 (bs, 4H), 3.27 (m, 4H), 3.14-3.21 (m, 2H), 2.55 (s, 3H), 2.30 (s, 3H), 2.21 (s, 3H), 2.10 (s, 3H), 1.87 (bs, 2H), 1.59-1.64 (m, 4H), 1.49-1.51 (m, 2H).

Example 50: Synthesis of 3-(((1r,4r)-4-aminocyclohexyl)(methyl)amino)-N-((4,6-dimethyl-2-oxo-1,2-dihydropyridin-3-yl)methyl)-2-methyl-5-(6-(morpholinomethyl)pyridin-3-yl)benzamide Compound 50

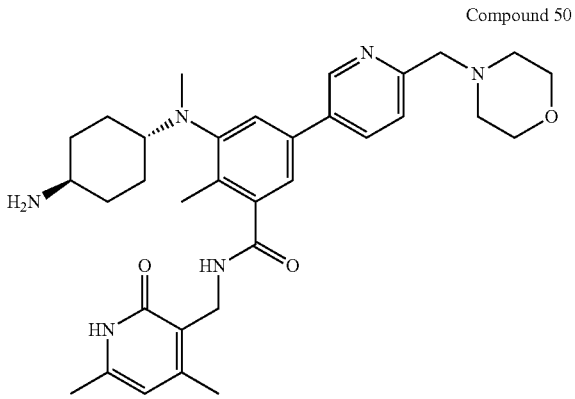 [SMILES: Cc1cc(C)c(CNC(=O)c2cc(-c3ccc(CN4CCOCC4)nc3)cc(N(C)[C@H]3CC[C@H](N)CC3)c2C)c(=O)[nH]1]

Step 1: Synthesis of tert-butyl ((1r,4r)-4-((3-(((4,6-dimethyl-2-oxo-1,2-dihydropyridin-3-yl)methyl)carbamoyl)-5-(6-formylpyridin-3-yl)-2-methylphenyl)(methyl)amino)-cyclohexyl)carbamate To a stirred solution of tert-butyl ((1r,4r)-4-((5-bromo-3-(((4,6-dimethyl-2-oxo-1,2-dihydropyridin-3-yl)methyl)carbamoyl)-2-methylphenyl)(methyl)amino)cyclohexyl)-carbamate (0.4 g, 0.696 mmol) and (6-formylpyridin-3-yl)boronic acid (0.21 g, 0.906 mmol) in dioxane/water mixture (8 mL+2 mL), $Na_2CO_3$ (0.332 g, 3.13 mmol) was added. The reaction solution was then purged with argon for 15 min. Pd (PPh$_3$)$_4$ (0.080 g, 0.069 mmol) was added and argon purging was again performed for 10 min. The reaction mixture was heated at 100° C. for 4 h. The reaction mixture was diluted with water and extracted with 10% MeOH/DCM. The combined organic layers were dried over Na₂SO₄ and the solvent removed under reduced pressure to afford crude product which was purified by column chromatography over silica gel to afford tert-butyl ((1r,4r)-4-((3-(((4,6-dimethyl-2-oxo-1,2-dihydropyridin-3-yl)methyl)carbamoyl)-5-(6-formylpyridin-3-yl)-2-methylphenyl)(methyl)amino)-cyclohexyl)carbamate (0.28 g, 66.98%).

Step 2: Synthesis of tert-butyl ((1r,4r)-4-((3-(((4,6-dimethyl-2-oxo-1,2-dihydropyridin-3-yl)methyl)carbamoyl)-2-methyl-5-(6-(morpholinomethyl)pyridin-3-yl)phenyl)(methyl)-amino)cyclohexyl) carbamate To a stirred solution of tert-butyl ((1r,4r)-4-((3-(((4,6-dimethyl-2-oxo-1,2-dihydropyridin-3-yl)methyl)carbamoyl)-5-(6-formylpyridin-3-yl)-2-methylphenyl)(methyl)amino)-cyclohexyl)carbamate (1 equiv.) and morpholine (5 equiv.) in methanol (10 mL), acetic acid (2 equiv.) was added. The reaction was stirred at room temperature for 18 h. Sodium cyanoborohydride (2.5 equiv.) was then added at 0° C. and reaction stirred overnight at room temperature. The solvent was removed under reduced pressure and crude material was purified by column chromatography to afford tert-butyl ((1r,4r)-4-((3-(((4,6-dimethyl-2-oxo-1,2-dihydropyridin-3-yl)methyl)-carbamoyl)-2-methyl-5-(6-(morpholinomethyl)pyridin-3-yl)phenyl)(methyl)-amino)cyclohexyl)carbamate.

Step 3: Synthesis of 3-(((1r,4r)-4-aminocyclohexyl)(methyl)amino)-N-((4,6-dimethyl-2-oxo-1,2-dihydropyridin-3-yl)methyl)-2-methyl-5-(6-(morpholinomethyl)pyridin-3-yl)benzamide A stirred solution of tert-butyl ((1r,4r)-4-((3-(((4,6-dimethyl-2-oxo-1,2-dihydropyridin-3-yl)methyl)-carbamoyl)-2-methyl-5-(6-(morpholinomethyl)pyridin-3-yl)phenyl)(methyl)-amino)cyclohexyl)carbamate in DCM (5 mL) was cooled to 0° C. and TFA (2 mL) was added to it. Reaction mass was stirred at room temperature for 1 h. The reaction mixture was concentrated to dryness and the solid product purified by solvent washings to afford the title compound as a TFA salt (0.07 g, 82.3%). LCMS: 573.40 (M+1)⁺; HPLC: 91.56% (@ 254 nm) (R$_t$: 3.591; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d₆, 400 MHz) δ 11.46 (s, 1H), 8.95 (s, 1H), 8.19-8.22 (m, 2H), 7.78 (bs, 3H), 7.61 (d, 1H, J=8 Hz), 7.40 (s, 1H), 7.27 (s, 1H), 5.86 (s, 1H), 4.52 (bs, 2H), 4.28 (d, 2H, J=3.2 Hz), 3.84 (bs, 4H), 3.27 (bs, 4H), 2.97 (bs, 1H), 2.75 (m, 1H), 2.66 (s, 3H), 2.21 (s, 3H), 2.20 (s, 3H), 2.10 (s, 3H), 1.93 (m, 2H), 1.74-1.76 (m, 2H), 1.54-1.57 (m, 2H), 1.28-1.31 (m, 2H).

Example 51: Synthesis of 3-(((1r,4r)-4-aminocyclohexyl)(methyl)amino)-N-((4,6-dimethyl-2-oxo-1,2-dihydropyridin-3-yl)methyl)-2-methyl-5-(1-(2-morpholinoethyl)-1H-pyrazol-4-yl)benzamide Compound 51

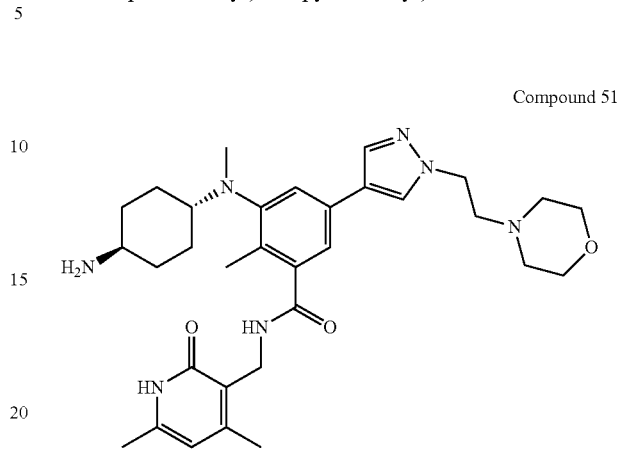

Step 1: Synthesis of tert-butyl ((1r,4r)-4-((3-(((4,6-dimethyl-2-oxo-1,2-dihydropyridin-3-yl)methyl)carbamoyl)-2-methyl-5-(1-(2-morpholinoethyl)-1H-pyrazol-4-yl)phenyl)(methyl)amino)cyclohexyl) carbamate To a stirred solution of tert-butyl ((1r,4r)-4-((5-bromo-3-(((4,6-dimethyl-2-oxo-1,2-dihydropyridin-3-yl)methyl)carbamoyl)-2-methylphenyl)(methyl)amino)-cyclohexyl)carbamate (1 equiv.) and 4-(2-(4-(4,4,5,5-tetramethyl-1,3,2-dioxaborolan-2-yl)-1H-pyrazol-1-yl)ethyl)morpholine (1.2 equiv.) in dioxane/water mixture (5 mL+1 mL), Na₂CO₃ (3.6 equiv.) was added and solution purged with argon for 15 min. Then Pd(PPh₃)₄ (0.1 equiv.) was added and the reaction flask was purged again for 10 min. with argon. The reaction mixture was heated at 100° C. for 4 h. The reaction mixture was diluted with water and extracted with 10% MeOH/DCM. The combined organic extracts were dried over Na₂SO₄ and the solvent removed under reduced pressure to afford the crude product which was purified by column chromatography over silica gel to afford tert-butyl ((1r,4r)-4-((3-(((4,6-dimethyl-2-oxo-1,2-dihydropyridin-3-yl)methyl)carbamoyl)-2-methyl-5-(1-(2-morpholinoethyl)-1H-pyrazol-4-yl)phenyl)(methyl)amino)cyclohexyl)carbamate (0.08 g, 45.45%)

Step 2: Synthesis of 3-(((1r,4r)-4-aminocyclohexyl)(methyl)amino)-N-((4,6-dimethyl-2-oxo-1,2-dihydropyridin-3-yl)methyl)-2-methyl-5-(1-(2-morpholinoethyl)-1H-pyrazol-4-yl)benzamide A stirred solution of tert-butyl ((1r,4r)-4-((3-(((4,6-dimethyl-2-oxo-1,2-dihydropyridin-3-yl)methyl)carbamoyl)-2-methyl-5-(1-(2-morpholinoethyl)-1H-pyrazol-4-yl)phenyl)(methyl)amino)cyclohexyl)carbamate (0.08 g) in DCM (5 mL) was cooled to 0° C. and TFA (2 mL) was added. The reaction mixture was stirred at room temperature for 1 h. The reaction was concentrated to dryness the title compound as a TFA salt (0.07 g, 86.41%). LCMS: 576.45 (M+1)⁺; HPLC: 98.26% (@ 254 nm) (R$_t$: 3.413; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (s, 1H), 8.26 (s, 1H), 8.08 (t, 1H), 7.99 (s, 1H), 7.75 (m, 3H), 7.28 (s, 1H), 7.13 (s, 1H), 5.87 (s, 1H), 4.53 (t, 2H), 4.27 (d, 2H, J=3.6 Hz), 2.97-3.16 (m, 4H), 2.67-2.71 (m, 1H), 2.62 (s, 3H), 2.20 (s, 3H), 2.14 (s, 3H), 2.11 (s, 3H), 1.92-1.94 (m, 2H), 1.72 (m, 2H), 1.52-1.55 (m, 2H), 1.23-1.29 (m, 2H).

Example 52: Synthesis of 3-(((1s,4s)-4-aminocyclohexyl)(methyl)amino)-N-((4,6-dimethyl-2-oxo-1,2-dihydropyridin-3-yl)methyl)-5-(6-((dimethylamino)methyl)pyridin-3-yl)-2-methylbenzamide

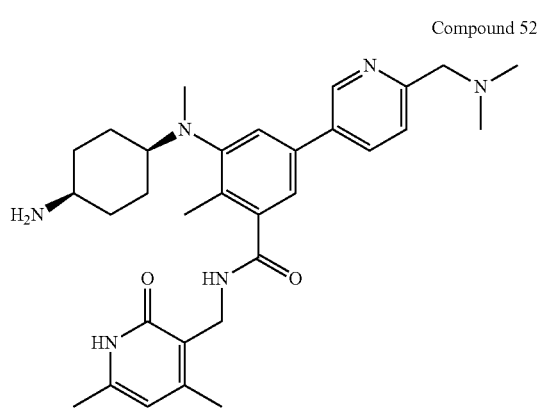 [SMILES: Cc1cc(C)c(CNC(=O)c2cc(-c3ccc(CN(C)C)nc3)cc(N(C)[C@H]3CC[C@@H](N)CC3)c2C)c(=O)[nH]1]

Compound 52

Step 1: Synthesis of tert-butyl ((1s,4s)-4-((3-(((4,6-dimethyl-2-oxo-1,2-dihydropyridin-3-yl)methyl)-carbamoyl)-5-(6-((dimethylamino)methyl)pyridin-3-yl)-2-methylphenyl)(methyl)amino)-cyclohexyl)carbamate To a stirred solution of tert-butyl ((1s,4s)-4-((3-(((4,6-dimethyl-2-oxo-1,2-dihydropyridin-3-yl)methyl)carbamoyl)-5-(6-formylpyridin-3-yl)-2-methylphenyl)-(methyl)amino)cyclohexyl)carbamate (1 equiv.) and dimethylamine (5 equiv.) in methanol (10 mL), acetic acid (2 equiv.) was added. The reaction mixture was stirred at room temperature for 18 h. Sodium cyanoborohydride (2.5 equiv.) was then added at 0° C. and the reaction mixture stirred overnight at room temperature. The solvent was removed under reduced pressure and the crude product was purified by column chromatography to afford tert-butyl ((1s,4s)-4-((3-(((4,6-dimethyl-2-oxo-1,2-dihydropyridin-3-yl)methyl)carbamoyl)-5-(6-((dimethylamino)methyl)pyridin-3-yl)-2-methylphenyl)(methyl)amino)cyclohexyl)carbamate.

Step 2: Synthesis of 3-(((1s,4s)-4-aminocyclohexyl)(methyl)amino)-N-((4,6-dimethyl-2-oxo-1,2-dihydropyridin-3-yl)methyl)-5-(6-((dimethylamino)methyl)pyridin-3-yl)-2-methylbenzamide A stirred solution of tert-butyl ((1s,4s)-4-((3-(((4,6-dimethyl-2-oxo-1,2-dihydropyridin-3-yl)methyl)carbamoyl)-5-(6-((dimethylamino)methyl)pyridin-3-yl)-2-methylphenyl)(methyl)amino)cyclohexyl)carbamate in DCM (5 mL) was cooled to 0° C. and TFA (2 mL) was added. The reaction mixture was stirred at room temperature for 1 h. The reaction was concentrated to dryness and the product purified by solvent washings to the title compound as a TFA salt (0.07 g, 93.3%). LCMS: 531.25 (M+1)$^+$; HPLC: 97.59% (@ 254 nm) (R$_t$: 3.680; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (s, 1H), 10.01 (s, 1H), 8.95 (s, 1H), 8.20 (d, 2H, J=5.2 Hz), 7.80 (bs, 3H), 7.59 (d, 1H, J=8 Hz), 7.51 (s, 1H), 7.32 (s, 1H), 5.87 (s, 1H), 4.48 (bs, 2H), 4.29 (d, 2H, J=4.4 Hz), 3.21 (m, 1H), 3.14-3.16 (m, 1H), 2.83 (s, 6H), 2.55 (s, 3H), 2.31 (s, 3H), 2.21 (s, 3H), 2.10 (s, 3H), 1.86 (bs, 2H), 1.59-1.64 (m, 4H), 1.49-1.51 (m, 2H).

Example 53: Synthesis of 3-(((1r,4r)-4-aminocyclohexyl)(methyl)amino)-N-((4,6-dimethyl-2-oxo-1,2-dihydropyridin-3-yl)methyl)-5-(6-((dimethylamino)methyl)pyridin-3-yl)-2-methylbenzamide

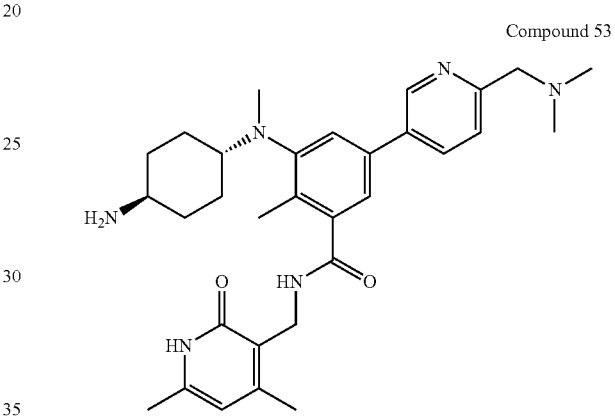

Compound 53

Step 1: Synthesis of tert-butyl ((1r,4r)-4-((3-(((4,6-dimethyl-2-oxo-1,2-dihydropyridin-3-yl)methyl)carbamoyl)-5-(6-((dimethylamino)methyl)pyridin-3-yl)-2-methylphenyl)(methyl)amino)cyclohexyl)carbamate To a stirred solution of tert-butyl ((1r,4r)-4-((3-(((4,6-dimethyl-2-oxo-1,2-dihydropyridin-3-yl)methyl)carbamoyl)-5-(6-formylpyridin-3-yl)-2-methylphenyl)(methyl)amino)-cyclohexyl)carbamate (1 equiv.) and dimethylamine (5 equiv.) in methanol (10 mL), acetic acid (2 equiv.) was added. The reaction was stirred at room temperature for 18 h. Sodium cyanoborohydride (2.5 equiv.) was then added at 0° C. and reaction stirred overnight at room temperature. The solvent was removed under reduced pressure and crude material was purified by column chromatography to afford tert-butyl ((1r,4r)-4-((3-(((4,6-dimethyl-2-oxo-1,2-dihydropyridin-3-yl)methyl)carbamoyl)-5-(6-((dimethylamino)methyl)pyridin-3-yl)-2-methylphenyl)(methyl)amino)cyclohexyl)carbamate.

Step 2: Synthesis of 3-(((1r,4r)-4-aminocyclohexyl)(methyl)amino)-N-((4,6-dimethyl-2-oxo-1,2-dihydropyridin-3-yl)methyl)-5-(6-((dimethylamino)methyl)pyridin-3-yl)-2-methylbenzamide A stirred solution of tert-butyl ((1r,4r)-4-((3-(((4,6-dimethyl-2-oxo-1,2-dihydropyridin-3-yl)methyl)carbamoyl)-5-(6-((dimethylamino)methyl)pyridin-3-yl)-2-methylphenyl)(methyl)amino)cyclohexyl)carbamate in DCM (5 mL) was cooled to 0° C. and TFA (2 mL) was added to it. Reaction mass was stirred at room temperature for 1 h. The reaction mixture was concentrated to dryness and the solid product purified by solvent washings to afford the title compound as a TFA salt (0.05 g, 66.6%). LCMS: 531.30 (M+1)⁺; HPLC: 97.59% (@ 254 nm) (R$_t$: 3.564; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d₆, 400 MHz) δ 11.46 (s, 1H), 10.01 (s, 1H), 8.95 (s, 1H), 8.20 (bs, 2H), 7.78 (bs, 2H), 7.59 (d, 1H, J=6 Hz), 7.41 (s, 1H), 7.28 (s, 1H), 5.86 (s, 1H), 4.48 (bs, 2H), 4.29 (m, 2H), 2.97 (bs, 2H), 2.83 (s, 6H), 2.66 (s, 3H), 2.21 (s, 6H), 2.10 (s, 3H), 1.93 (m, 2H), 1.74 (m, 2H), 1.55-1.57 (m, 2H), 1.28-1.31 (m, 2H).

Example 54: Synthesis of 3-(((1r,4r)-4-acetamidocyclohexyl)(methyl)amino)-N-((4,6-dimethyl-2-oxo-1,2-dihydropyridin-3-yl)methyl)-2-methyl-5-(6-(morpholinomethyl)pyridin-3-yl)benzamide Compound 54

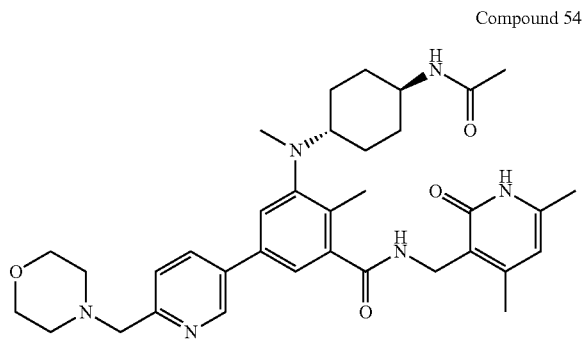 [SMILES: CC(=O)N[C@H]1CC[C@H](N(C)c2cc(-c3ccc(CN4CCOCC4)nc3)cc(C(=O)NCc3c(C)cc(C)[nH]c3=O)c2C)CC1]

Compound 54 was prepared with the method similar to that described in Example 57.

Analytical Data of: LCMS: 615.55 (M+1)⁺; HPLC: 98.75% (@ 254 nm) (R$_t$: 3.854; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d₆, 400 MHz) δ 11.46 (s, 1H), 8.75 (s, 1H), 8.18 (t, 1H), 8.02 (d, 1H, J=8 Hz), 7.67 (d, 1H, J=7.2 Hz), 7.49 (d, 1H, J=8 Hz), 7.35 (s, 1H), 7.19 (s, 1H), 5.86 (s, 1H), 4.28 (d, 2H, J=4.4 Hz), 3.59-3.61 (m, 4H), 3.47-3.55 (m, 2H), 2.76 (t, 2H, J=4 Hz), 2.65 (s, 3H), 2.42 (bs, 4H), 2.21 (s, 3H), 2.20 (s, 3H), 2.10 (s, 3H), 1.78-1.90 (m, 2H), 1.68-1.74 (m, 5H), 1.48-1.57 (m, 2H), 1.03-1.23 (m, 2H).

Example 55: Synthesis of 3-(((1s,4s)-4-acetamidocyclohexyl)(methyl)amino)-N-((4,6-dimethyl-2-oxo-1,2-dihydropyridin-3-yl)methyl)-5-(6-((dimethylamino)methyl)pyridin-3-yl)-2-methylbenzamide Compound 55

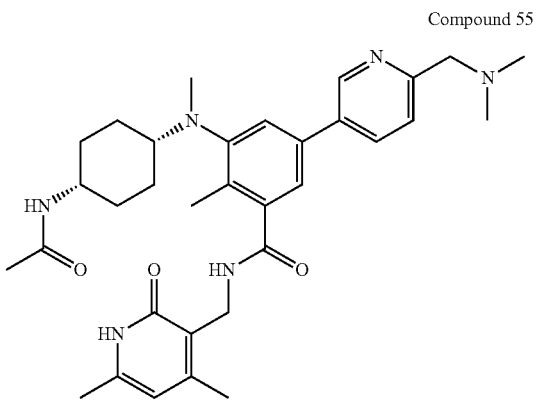 [SMILES: CC(=O)N[C@H]1CC[C@@H](N(C)c2cc(-c3ccc(CN(C)C)nc3)cc(C(=O)NCc3c(C)cc(C)[nH]c3=O)c2C)CC1]

Step 1: Synthesis of 3-(((1s,4s)-4-acetamidocyclohexyl)(methyl)amino)-N-((4,6-dimethyl-2-oxo-1,2-dihydropyridin-3-yl)methyl)-5-(6-formylpyridin-3-yl)-2-methylbenzamide 3-(((1s,4s)-4-acetamidocyclohexyl)(methyl)amino)-5-bromo-N-((4,6-dimethyl-2-oxo-1,2-dihydropyridin-3-yl)methyl)-2-methylbenzamide (0.65 g, 1.25 mmol) and (6-formylpyridin-3-yl)boronic acid (0.38 g, 1.63 mmol) in dioxane/water mixture (10 mL+2 mL) was added Na₂CO₃ (0.48 g, 4.53 mmol) and the solution purged with argon for 15 min. Then Pd(PPh₃)₄ (0.14 g, 0.12 mmol) was added and argon was purged again for 10 min. The reaction mixture was heated at 100° C. for 4 h. On completion, the reaction mixture was diluted with water and extracted with 10% MeOH/DCM. The combined organic layers were dried over Na₂SO₄ and solvent removed under reduced pressure to afford crude material which was purified by column chromatography over silica gel to afford cis-isomer 3-((4-acetamidocyclohexyl)-(methyl)amino)-N-((4,6-dimethyl-2-oxo-1,2-dihydropyridin-3-yl)methyl)-5-(6-formylpyridin-3-yl)-2-methylbenzamide (0.35 g, 51.16%).

Step 2: Synthesis of

To a stirred solution of 3-(((1s,4s)-4-acetamidocyclohexyl)(methyl)amino)-N-((4,6-dimethyl-2-oxo-1,2-dihydropyridin-3-yl)methyl)-5-(6-formylpyridin-3-yl)-2-methylbenzamide (1 equiv.) and dimethylamine (5 equiv.) in 5 mL for 0.3 mmol; MeOH was added acetic acid (2 equiv.) and the reaction stirred at room temperature. Then NaBH₃CN (1.5 equiv.) was added and the reaction stirred overnight. On completion, the solvent was removed under reduced pressure and the residue purified by column chromatography over silica gel or as specified affording the title compound (0.006 g, 3.2%). LCMS: 573.40 (M+1)⁺; HPLC: 95.52% (@ 254 nm) (R$_t$: 3.899; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d₆, 400 MHz) δ 11.47 (s, 1H), 8.88 (s, 1H), 8.20 (t, 1H), 8.14 (d, 1H, J=7.6 Hz), 7.78 (d, 1H, J=7.2 Hz), 7.55 (d, 1H, J=8 Hz), 7.44 (s, 1H), 7.26 (s, 1H), 5.86 (s, 1H), 4.28 (d, 2H, J=3.2 Hz), 4.26 (bs, 1H), 3.71 (bs, 1H), 3.01 (bs, 1H), 2.61-2.66 (m, 8H), 2.28 (s, 3H), 2.21 (s, 3H), 2.10 (s, 3H), 1.81 (m, 5H), 1.56 (m, 2H), 1.40-1.46 (m, 2H), 1.23 (m, 2H). [2H merged in solvent peak].

Example 56: Synthesis of 3-(((1s,4s)-4-acetamido-cyclohexyl)(methyl)amino)-N-((4,6-dimethyl-2-oxo-1,2-dihydropyridin-3-yl)methyl)-5-(6-(hydroxymethyl)pyridin-3-yl)-2-methylbenzamide Compound 56

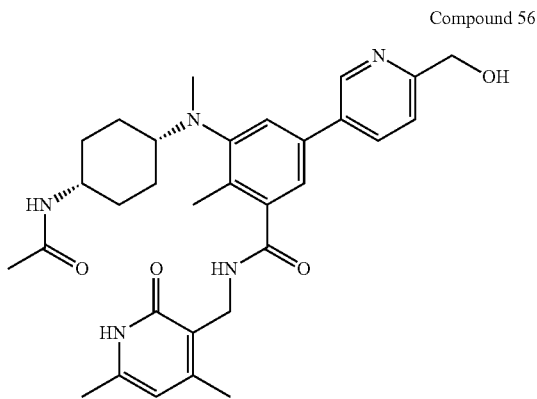 [SMILES: CC(=O)N[C@H]1CC[C@@H](N(C)c2cc(-c3ccc(CO)nc3)cc(C(=O)NCc3c(C)cc(C)[nH]c3=O)c2C)CC1]

Compound 56 was prepared in the same reaction as compound 55. LCMS: 546.40 (M+1)+; HPLC: 99.40% (@ 254 nm) (R$_t$: 3.845; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.47 (s, 1H), 8.74 (s, 1H), 8.20 (t, 1H), 8.04 (d, 1H, J=8 Hz), 7.77 (d, 1H, J=7.2 Hz), 7.52 (d, 1H, J=7.6 Hz), 7.40 (s, 1H), 7.22 (s, 1H), 5.86 (s, 1H), 5.45 (t, 1H, J=5.2 Hz), 4.59 (d, 2H, J=5.6 Hz), 4.27 (d, 2H, J=4 Hz), 3.71 (bs, 1H), 3.00 (bs, 1H), 2.60 (s, 3H), 2.27 (s, 3H), 2.21 (s, 3H), 2.10 (s, 3H), 1.81 (m, 5H), 1.56 (m, 2H), 1.40-1.48 (m, 4H).

Example 57: Synthesis of 3-(((1s,4s)-4-acetamido-cyclohexyl)(methyl)amino)-N-((4,6-dimethyl-2-oxo-1,2-dihydropyridin-3-yl)methyl)-2-methyl-5-(6-(morpholinomethyl)pyridin-3-yl)benzamide Compound 57

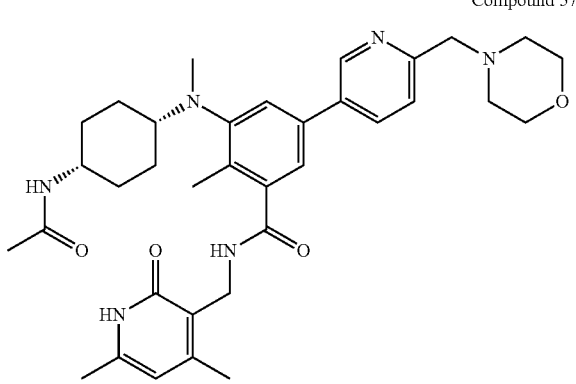

To a stirred solution of 3-(((1s,4s)-4-acetamidocyclohexyl)(methyl)amino)-N-((4,6-dimethyl-2-oxo-1,2-dihydropyridin-3-yl)methyl)-5-(6-formylpyridin-3-yl)-2-methylbenzamide (1 equiv.) and morpholine (5 equiv.) in 5 mL for 0.3 mmol; MeOH was added acetic acid (2 equiv.) and the reaction stirred at room temperature. Then NaBH$_3$CN (1.5 equiv.) was added and the reaction stirred overnight. On completion, the solvent was removed under reduced pressure and the residue purified by column chromatography over silica gel or as specified affording the title compound (0.08 g, 43%). LCMS: 615.40 (M+1)+; HPLC: 99.64% (@ 254 nm) (R$_t$: 3.900; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (s, 1H), 8.75 (s, 1H), 8.19 (t, 1H), 8.01 (d, 1H, J=7.6 Hz), 7.77 (d, 1H, J=7.2 Hz), 7.50 (d, 1H, J=8 Hz), 7.40 (s, 1H), 7.21 (s, 1H), 5.86 (s, 1H), 4.28 (d, 2H, J=4.4 Hz), 3.71 (bs, 1H), 3.59-3.61 (m, 4H), 3.50 (t, 1H, J=4.4 Hz), 3.00 (bs, 1H), 2.68 (t, 1H, J=4.4 Hz), 2.60 (s, 3H), 2.42 (bs, 4H), 2.27 (s, 3H), 2.20 (s, 3H), 2.10 (s, 3H), 1.81 (m, 5H), 1.56 (m, 2H), 1.40-1.45 (m, 2H), 1.16-1.29 (m, 2H).

Example 59: Synthesis of N-((4,6-dimethyl-2-oxo-1,2-dihydropyridin-3-yl)methyl)-4-methyl-4'-(morpholinomethyl)-5-(propyl(tetrahydro-2H-pyran-4-yl)amino)-[1,1'-biphenyl]-3-carboxamide Compound 59

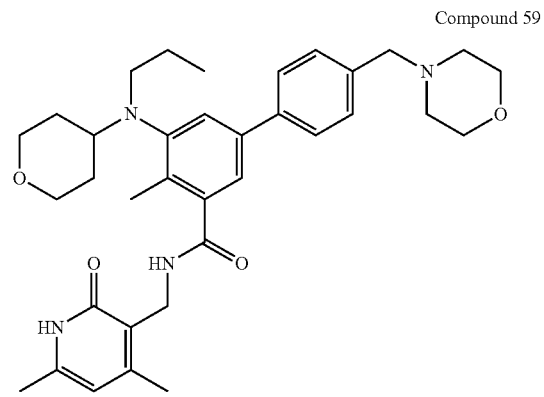 [SMILES: CCCN(c1cc(-c2ccc(CN3CCOCC3)cc2)cc(C(=O)NCc2c(C)cc(C)[nH]c2=O)c1C)C1CCOCC1]

Step 1: Synthesis of methyl 5-bromo-2-methyl-3-((tetrahydro-2H-pyran-4-yl)amino)benzoate To a stirred solution of methyl 3-amino-5-bromo-2-methylbenzoate (15 g, 61.5 mmol) and dihydro-2H-pyran-4(3)-one (9.2 g, 92 mmol) in dichloroethane (300 mL) was added acetic acid (22 g, 369 mmol) and the reaction mixture stirred at room temperature for 15 minutes, upon which the reaction mixture was cooled to 0° C. and sodium triacetoxyborohydride (39 g, 183.96 mmol) was added. The reaction mixture was stirred overnight at room temperature. Aqueous sodium bicarbonate was then added to the reaction mixture adjusting the pH to 7-8. The organic phase was separated and the aqueous phase extracted with ethyl acetate. The combined extracts were dried over anhydrous sodium sulfate, filtered and concentrated under reduced pressure. The crude product was purified by column chromatography (100-200 mesh silica gel) eluting with ethyl acetate: hexane to afford methyl 5-bromo-2-methyl-3-((tetrahydro-2H-pyran-4-yl)amino) benzoate as an off-white solid (14 g, 69%).

Step 2: Synthesis of methyl 5-bromo-2-methyl-3-(propyl(tetrahydro-2H-pyran-4-yl)amino)benzoate To a stirred solution of 5-bromo-2-methyl-3-((tetrahydro-2H-pyran-4-yl)amino)benzoate (1 g, 3.04 mmol) and propionaldehyde (0.354 g, 6.09 mmol) in dichloroethane (10 mL), acetic acid (1.12 g, 18.2 mmol) was added. The reaction mixture was stirred at room temperature for 10 minutes. Then sodium triacetoxyborohydride (1.94 g, 9.14 mmol) was added at 0° C. and the reaction mixture stirred at room temperature for 2 h. The solvent was then removed under reduced pressure and water added to the residue. The mixture was extracted with DCM. The combined extracts were dried over sodium sulfate, filtered and concentrated under reduced pressure to give the crude product which was purified by column chromatography to afford methyl 5-bromo-2-methyl-3-(propyl(tetrahydro-2H-pyran-4-yl)amino)benzoate (0.96 g, 85.7%).

Step 3: Synthesis of 5-bromo-N-((4,6-dimethyl-2-oxo-1,2-dihydropyridin-3-yl)methyl)-2-methyl-3-(propyl(tetrahydro-2H-pyran-4-yl)amino)benzamide Aqueous NaOH (0.156 g, 3.8 mmol) was added to a solution of 5-bromo-2-methyl-3-(propyl(tetrahydro-2H-pyran-4-yl)amino)benzoate (0.96 g, 2.59 mmol) in ethanol (5 mL). The reaction mixture was stirred at 60° C. for 1 h. The ethanol was then removed under reduced pressure and the residue acidified to pH 6 using dilute HCl and to pH 4 with citric acid. The mixture was extracted with ethyl acetate. The combined extracts were dried, filtered and concentrated giving the respective acid (0.8 g, 86.67%).

The above acid (0.8 g, 2.24 mmol) was dissolved in DMSO (5 mL) and 3-(amino methyl)-4,6-dimethylpyridin-2(1H)-one (0.683 g, 4.49 mmol) was added. The reaction mixture was stirred at room temperature for 15 min before PyBOP (1.75 g, 3.36 mmol) was added to it and stirring was continued for overnight. The reaction mixture was poured into ice water and extracted with 10% MeOH/DCM. The combined extracts were dried, filtered, and concentrated to obtain the crude product which purified by solvent washings to afford 5-bromo-N-((4,6-dimethyl-2-oxo-1,2-dihydropyridin-3-yl)methyl)-2-methyl-3-(propyl(tetrahydro-2H-pyran-4-yl)amino)benzamide (0.9 g, 81.8%).

Step 4: Synthesis of N-((4,6-dimethyl-2-oxo-1,2-dihydropyridin-3-yl)methyl)-4-methyl-4'-(morpholinomethyl)-5-(propyl(tetrahydro-2H-pyran-4-yl)amino)-[1,1'-biphenyl]-3-carboxamide To a stirred solution of 5-bromo-N-((4,6-dimethyl-2-oxo-1,2-dihydropyridin-3-yl)methyl)-2-methyl-3-(propyl(tetrahydro-2H-pyran-4-yl)amino)benzamide (0.2 g, 0.412 mmol) and 4-(4-(4,4,5,5-tetramethyl-1,3,2-dioxaborolan-2-yl)benzyl)morpholine (0.148 g, 0.488 mmol) in dioxane/water mixture (5 mL+1 mL), Na$_2$CO$_3$ (0.108 g, 1.01 mmol) was added and reaction mixture purged with argon for 15 min. Pd(PPh$_3$)$_4$ (0.048 g, 0.042 mmol) was then added and the reaction mixture again purged with argon for 10 min. The reaction mixture was heated at 100° C. for 2 h. The reaction mixture was diluted with water and extracted with 10% MeOH/DCM. The combined extracts were dried over Na$_2$SO$_4$ and solvent removed under reduced pressure to afford crude product which was purified by column chromatography over silica gel to afford the title compound (0.20 g, 83.68%). LCMS: 587.40 (M+1)$^+$; HPLC: 98.68% (@ 254 nm) (R$_t$: 4.257; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (s, 1H), 8.19 (t, 1H, J=4.8 Hz), 7.56 (d, 2H, J=8 Hz), 7.38 (t, 3H, J=8 Hz), 7.19 (s, 1H), 5.85 (s, 1H), 4.28 (d, 2H, J=4.4 Hz), 3.82-3.85 (m, 2H), 3.57 (m, 4H), 3.48 (s, 2H), 3.23 (t, 2H, J=10.8 Hz), 2.94-3.02 (m, 3H), 2.36 (bs, 4H), 2.24 (s, 3H), 2.20 (s, 3H), 2.10 (s, 3H), 1.56-1.65 (m, 4H), 1.20-1.25 (m, 2H), 0.76 (t, 3H, J=6.8 Hz).

Example 60: Synthesis of N-((4,6-dimethyl-2-oxo-1,2-dihydropyridin-3-yl)methyl)-5-(isobutyl(tetrahydro-2H-pyran-4-yl)amino)-4-methyl-4'-(morpholinomethyl)-[1,1'-biphenyl]-3-carboxamide

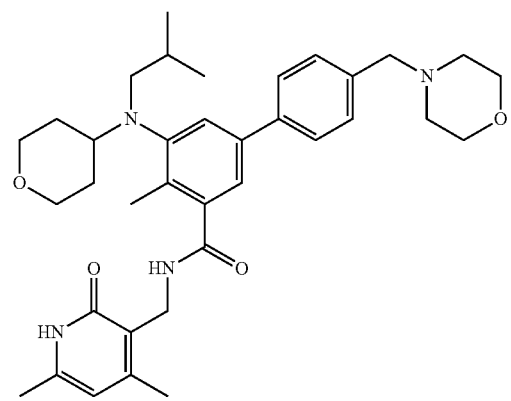

Compound 60

Step 1: Synthesis of methyl 5-bromo-3-(isobutyl (tetrahydro-2H-pyran-4-yl)amino)-2-methylbenzoate To a stirred solution of methyl 5-bromo-2-methyl-3-((tetrahydro-2H-pyran-4-yl)amino)benzoate (1 g, 3.04 mmol) and isobutyraldehyde (1.09 g, 15.24 mmol) in methanol (15 mL), acetic acid (0.456 g, 7.6 mmol) was added. The reaction mixture was stirred at room temperature for 8 h. Sodium cyanoborohydride (0.522 g, 7.56 mmol) was then added at 0° C. and the reaction mixture stirred overnight at room temperature. The solvent was then removed under reduced pressure and crude product purified by column chromatography to afford methyl 5-bromo-3-(isobutyl(tetrahydro-2H-pyran-4-yl)amino)-2-methylbenzoate (0.52 g, 54.33%).

Step 2: Synthesis of 5-bromo-N-((4,6-dimethyl-2-oxo-1,2-dihydropyridin-3-yl)methyl)-3-(isobutyl (tetrahydro-2H-pyran-4-yl)amino)-2-methylbenzamide Aqueous NaOH (0.104 g, 2.61 mmol) was added to a solution of methyl 5-bromo-3-(isobutyl(tetrahydro-2H-pyran-4-yl)amino)-2-methylbenzoate (0.5 g, 1.30 mmol) in ethanol (15 mL) and stirred at 60° C. for 1 h. The ethanol was then removed under reduced pressure and acidified to pH 6 with dilute HCl and to pH 4 with citric acid. The mixture was extracted with ethyl acetate. The combined extracts were dried and concentrated giving the respective acid (0.375 g, 76.9%).

The above acid (0.350 g, 9.45 mmol) was then dissolved in DMSO (5 mL) and 3-(amino methyl)-4,6-dimethylpyridin-2(1H)-one (0.283 g, 18.9 mmol) was added. The reaction mixture was stirred at room temperature for 15 min before PyBOP (0.737 g, 14.17 mmol) was added. The reaction mixture was stirred overnight. The reaction mixture was poured into ice water and the resulting precipitate was collected and purified by solvent washings giving 5-bromo-N-((4,6-dimethyl-2-oxo-1,2-dihydropyridin-3-yl)methyl)-3-(isobutyl(tetrahydro-2H-pyran-4-yl)amino)-2-methylbenzamide (0.2 g, 42.01%).

Step 3: Synthesis of N-((4,6-dimethyl-2-oxo-1,2-dihydropyridin-3-yl)methyl)-5-(isobutyl(tetrahydro-2H-pyran-4-yl)amino)-4-methyl-4'-(morpholinomethyl)-[1,1'-biphenyl]-3-carboxamide To a stirred solution of 5-bromo-N-((4,6-dimethyl-2-oxo-1,2-dihydropyridin-3-yl)methyl)-3-(isobutyl(tetrahydro-2H-pyran-4-yl)amino)-2-methylbenzamide (0.14 g, 0.277 mmol) and 4-(4-(4,4,5,5-tetramethyl-1,3,2-dioxaborolan-2-yl)benzyl)morpholine (0.100 g, 0.333 mmol) in dioxane/water mixture (5 mL+1 mL), Na$_2$CO$_3$ (0.108 g, 1.01 mmol) was added and solution purged with argon for 15 min. Pd(PPh$_3$)$_4$ (0.032 g, 0.027 mmol) was then added and the reaction mixture again purged with argon for 10 min. The reaction mixture was heated at 100° C. for 2 h. The reaction mixture was then diluted with water and extracted with 10% MeOH/DCM. The combined extracts were dried over Na$_2$SO$_4$ and the solvent removed under reduced pressure to afford the crude product which was purified by preparative HPLC to afford the title compound as a TFA salt (0.039 g, 23.49%). LCMS: 601.30 (M+1)$^+$; HPLC: 99.88% (@ 254 nm) (R$_t$; 5.225; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (s, 1H), 9.83 (bs, 1H), 8.20 (t, 1H), 7.73 (d, 2H, J=8 Hz), 7.56 (d, 2H, J=8 Hz), 7.43 (s, 1H), 7.21 (s, 1H), 5.86 (s, 1H), 4.39 (bs, 2H), 4.28 (d, 2H, J=4.4 Hz), 3.95-3.98 (m, 2H), 3.85-3.87 (m, 2H), 3.62 (t, 2H, J=11.2 Hz), 3.15-3.31 (m, 9H), 2.84 (m, 1H), 2.26 (s, 3H), 2.21 (s, 3H), 2.10 (s, 3H), 1.62 (bs, 2H), 1.37-1.40 (m, 2H), 0.80 (d, 6H, J=6 Hz).

Example 61: Synthesis of 5-((cyclopropylmethyl)(tetrahydro-2H-pyran-4-yl)amino)-N-((4,6-dimethyl-2-oxo-1,2-dihydropyridin-3-yl)methyl)-4-methyl-4'-(morpholinomethyl)-[1,1'-biphenyl]-3-carboxamide

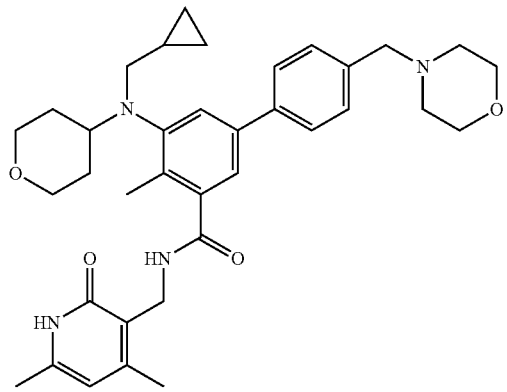

Compound 61

Step 1: Synthesis of methyl 5-bromo-3-((cyclopropylmethyl)(tetrahydro-2H-pyran-4-yl)amino)-2-methylbenzoate To a stirred solution of methyl 5-bromo-2-methyl-3-((tetrahydro-2H-pyran-4-yl)amino)benzoate (1 g, 3.04 mmol) and cyclopropanecarbaldehyde (1.06 g, 15.24 mmol) in methanol (15 mL), acetic acid (0.456 g, 7.6 mmol) was added The reaction mixture was stirred at room temperature for 8 h. Sodium cyanoborohydride (0.488 g, 7.62 mmol) was then added at 0° C. and reaction mixture stirred overnight at room temperature. The solvent was then removed under reduced pressure and the crude product purified by column chromatography to afford methyl 5-bromo-3-((cyclopropylmethyl)(tetrahydro-2H-pyran-4-yl)amino)-2-methylbenzoate (0.275 g, 23.70%).

Step 2: Synthesis of 5-bromo-3-((cyclopropylmethyl)(tetrahydro-2H-pyran-4-yl)amino)-N-((4,6-dimethyl-2-oxo-1,2-dihydropyridin-3-yl)methyl)-2-methylbenzamide Aqueous NaOH (0.056 g, 1.45 mmol) was added to a solution of methyl 5-bromo-3-((cyclopropylmethyl)(tetrahydro-2H-pyran-4-yl)amino)-2-methylbenzoate (0.275 g, 0.943 mmol) in ethanol (5 mL) and stirred at 60° C. for 1 h. The ethanol was then removed under reduced pressure and acidified to pH 6 with dilute HCl and to pH 4 with citric acid. The mixture was extracted with ethyl acetate. The combined extracts were dried and concentrated giving the respective acid (0.25 g, 93.28%).

The above acid (0.250 g, 0.68 mmol) was dissolved in DMSO (3 mL) and 3-(aminomethyl)-4,6-dimethylpyridin-2(1H)-one (0.155 g, 1.02 mmol) was added. The reaction mixture was stirred at room temperature for 15 min before PyBOP (0.708 g, 1.36 mmol) was added. The reaction mixture was stirred overnight. The reaction mixture was poured into ice water and the resulting precipitate collected and purified by solvent washings giving 5-bromo-3-((cyclopropylmethyl)(tetrahydro-2H-pyran-4-yl)amino)-N-((4,6-dimethyl-2-oxo-1,2-dihydropyridin-3-yl)methyl)-2-methylbenzamide (0.25 g, 73.31%).

Step 3: Synthesis of 5-((cyclopropylmethyl)(tetrahydro-2H-pyran-4-yl)amino)-N-((4,6-dimethyl-2-oxo-1,2-dihydropyridin-3-yl)methyl)-4-methyl-4'-(morpholinomethyl)-[1,1'-biphenyl]-3-carboxamide To a stirred solution of 5-bromo-3-((cyclopropylmethyl)(tetrahydro-2H-pyran-4-yl)amino)-N-((4,6-dimethyl-2-oxo-1,2-dihydropyridin-3-yl)methyl)-2-methylbenzamide (0.25 g, 0.499 mmol) and 4-(4-(4,4,5,5-tetramethyl-1,3,2-dioxaborolan-2-yl)benzyl)morpholine (0.181 g, 0.598 mmol) in dioxane/water mixture (5 mL+1 mL), Na$_2$CO$_3$ (0.19 g, 1.79 mmol) was added and solution purged with argon for 15 min. Pd (PPh$_3$)$_4$ (0.057 g, 0.049 mmol) was then added and the reaction mixture again purged with argon for 10 min. The reaction mixture was heated at 100° C. for 2 h. The reaction mixture was diluted with water and extracted with 10% MeOH/DCM. The combined extracts were dried over Na$_2$SO$_4$ and the solvent removed under reduced pressure to afford the crude product which was purified by preparative HPLC to afford the title compound as a TFA salt (0.085 g, 28.52%). LCMS: 599.35 (M+1)$^+$; HPLC: 99.21% (@ 254 nm) (R$_t$; 4.191; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.51 (s, 1H), 9.83 (bs, 1H), 8.20 (s, 1H), 7.77 (d, 2H, J=6.4 Hz), 7.53-7.58 (m, 3H), 7.28 (s, 1H), 5.87 (s, 1H), 4.39 (bs, 2H), 4.29 (d, 2H, J=4.4 Hz), 3.95-3.98 (m, 2H), 3.59-3.65 (m, 2H), 3.31-3.21 (m, 5H), 3.05-3.16 (m, 3H), 2.93 (m, 2H), 2.32 (m, 4H), 2.21 (s, 3H), 2.10 (s, 3H), 1.65 (bs, 2H), 1.50 (m, 2H), 0.66 (bs, 1H), 0.28 (d, 2H, J=7.2 Hz).

Example 62: Synthesis of 5-(butyl(tetrahydro-2H-pyran-4-yl)amino)-N-((4,6-dimethyl-2-oxo-1,2-dihydropyridin-3-yl)methyl)-4-methyl-4'-(morpholinomethyl)-[1,1'-biphenyl]-3-carboxamide

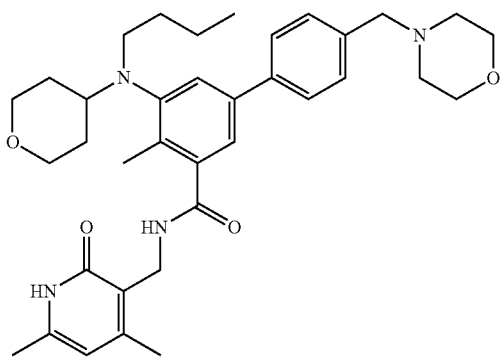

Compound 62

Compound 62 was prepared with the method similar to that described in Example 61.

Analytical Data of TFA salt: LCMS: 601.35 (M+1)$^+$; HPLC: 99.41% (@ 254 nm) (R$_t$; 4.482; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.47 (s, 1H), 9.89 (bs, 1H), 8.22 (t, 1H), 7.75 (d, 2H, J=8 Hz), 7.57 (d, 2H, J=8 Hz), 7.44 (s, 1H), 7.25 (s, 1H), 5.86 (s, 1H), 4.39 (bs, 2H), 4.28 (d, 2H, J=4.4 Hz), 3.95-3.98 (m, 3H), 3.83-3.86 (m, 4H), 3.21-3.30 (m, 4H), 3.08-3.11 (m, 4H), 2.24 (s, 3H), 2.21 (s, 3H), 2.10 (s, 3H), 1.62 (m, 4H), 1.20 (m, 4H), 0.79 (t, 3H, J=6.4 Hz).

Example 63: Synthesis of 5-((cyclobutylmethyl)(tetrahydro-2H-pyran-4-yl)amino)-N-((4,6-dimethyl-2-oxo-1,2-dihydropyridin-3-yl)methyl)-4-methyl-4'-(morpholinomethyl)-[1,1'-biphenyl]-3-carboxamide

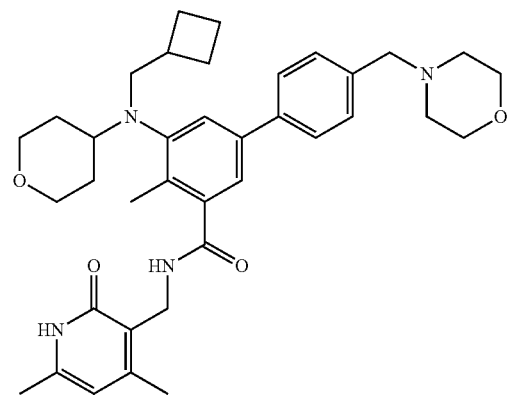

Compound 63

Compound 63 was prepared with the method similar to that described in Example 61.

Analytical Data: LCMS: 613.35 (M+1)$^+$; HPLC: 99.25% (@ 254 nm) (R$_t$; 4.586; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.18 (t, 1H), 7.56 (d, 2H, J=7.6 Hz), 7.41 (s, 1H), 7.37 (d, 2H, J=8 Hz), 7.20 (s, 1H), 5.85 (s, 1H), 4.45 (m, 2H), 4.28 (d, 2H, J=4 Hz), 3.83-3.85 (m, 2H), 3.57 (m, 3H), 3.48 (s, 2H), 3.19-3.22 (m, 2H), 3.08 (bs, 2H), 2.86 (m, 1H), 2.36 (m, 4H), 2.20 (s, 6H), 2.10 (s, 3H), 1.70-1.78 (m, 4H), 1.56-1.63 (m, 6H).

Example 64: Synthesis of N-((4,6-dimethyl-2-oxo-1,2-dihydropyridin-3-yl) methyl)-3-(ethyl (tetrahydro-2H-pyran-4-yl) amino)-2-methyl-5-(6-(morpholinomethyl) pyridin-3-yl) benzamide

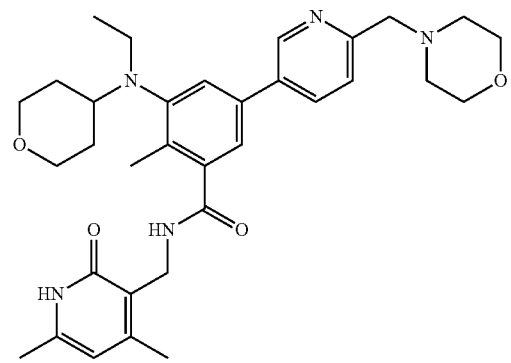

Compound 64

Step 1: Synthesis of N-((4,6-dimethyl-2-oxo-1,2-dihydropyridin-3-yl) methyl)-3-(ethyl (tetrahydro-2H-pyran-4-yl) amino)-5-(6-formylpyridin-3-yl)-2-methylbenzamide To a stirred solution of 5-bromo-N-((4,6-dimethyl-2-oxo-1,2-dihydropyridin-3-yl) methyl)-3-(ethyl (tetrahydro-2H-pyran-4-yl) amino)-2-methylbenzamide (1 g, 2.15 mmol) and (6-formylpyridin-3-yl) boronic acid (0.539 g, 2.31 mmol) in dioxane/water mixture (15 mL+3 mL), $Na_2CO_3$ (0.82 g, 7.74 mmol) was added and solution purged with argon for 15 min. Then Pd $(PPh_3)_4$ (0.288 g, 0.25 mmol) was added and argon was purged again for 10 min. Reaction mass was heated at 80° C. for 2 h. On completion, reaction mixture was diluted with water and extracted with 10% MeOH/DCM. Combined organic layers were dried over $Na_2SO_4$ and solvent removed under reduced pressure to afford crude material which was purified by column chromatography over silica gel to afford the desired compound (0.60 g, 57%).

Step 2: Synthesis of N-((4,6-dimethyl-2-oxo-1,2-dihydropyridin-3-yl) methyl)-3-(ethyl (tetrahydro-2H-pyran-4-yl) amino)-2-methyl-5-(6-(morpholinomethyl) pyridin-3-yl) benzamide To a stirred solution of N-((4,6-dimethyl-2-oxo-1,2-dihydropyridin-3-yl) methyl)-3-(ethyl (tetrahydro-2H-pyran-4-yl) amino)-5-(6-formylpyridin-3-yl)-2-methylbenzamide (0.2 g, mmol) in dichloroethane (3 mL) was added morpholine (5 equiv.) in 5 mL MeOH and acetic acid (2 equiv.) and the mixture was stirred at room temperature for 15 minutes. Then $NaBH_3CN$ (1.5 equiv.) was added and the reaction stirred at room temperature for 16 hours. After completion (monitored by TLC), aqueous sodium bicarbonate was added to the reaction mixture till pH 7-8, the organic phase was separated and the aqueous phase was extracted with ethyl acetate. The combined organic layers were dried over anhydrous sodium sulfate, filtered and concentrated under reduced pressure. The crude compound was purified by column chromatography (100-200 mesh silica gel) eluting with ethyl acetate: hexane to afford the title compound as an off-white solid. LCMS: 574.25 (M+1)$^+$; HPLC: 97.17% (@ 254 nm) ($R_t$: 3.906; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.46 (s, 1H), 8.75 (s, 1H), 8.20 (t, 1H), 8.01 (d, 1H, J=7.2 Hz), 7.50 (d, 1H, J=7.6 Hz), 7.46 (s, 1H), 7.27 (s, 1H), 5.85 (s, 1H), 4.28 (d, 2H, J=3.6 Hz), 3.81-3.83 (m, 2H), 3.59-3.61 (m, 6H), 3.22-3.30 (m, 2H), 3.08-3.10 (m, 2H), 3.03 (m, 1H), 2.43 (s, 4H), 2.25 (s, 3H), 2.20 (s, 3H), 2.10 (s, 3H), 1.65-1.67 (m, 2H), 1.51-1.53 (m, 2H), 0.83 (t, 3H, J=6.4 Hz).

Example 65: Synthesis of N-((4,6-dimethyl-2-oxo-1,2-dihydropyridin-3-yl)methyl)-4'-((dimethylamino)methyl)-5-(ethyl(tetrahydro-2H-pyran-4-yl) amino)-4-methyl-[1,1'-biphenyl]-3-carboxamide

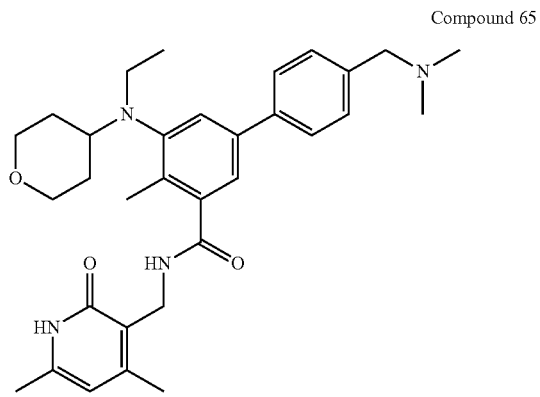 [SMILES: CCN(c1cc(-c2ccc(CN(C)C)cc2)cc(C(=O)NCc2c(C)cc(C)[nH]c2=O)c1C)C1CCOCC1]

Compound 65

Step 1: Synthesis of methyl 5-bromo-3-(ethyl(tetrahydro-2H-pyran-4-yl)amino)-2-methylbenzoate To a stirred solution of methyl 5-bromo-2-methyl-3-((tetrahydro-2H-pyran-4-yl)amino)benzoate (14 g, 42.68 mmol) and acetaldehyde (3.75 g, 85.36 mmol) in dichloroethane (150 mL), acetic acid (15.36 g, 256.08 mmol) was added and the reaction stirred at room temperature for 20 minutes. Sodium triacetoxyborohydride (27.01 g, 128.04 mmol) was then added at 0° C. and the reaction mixture stirred at room temperature for 2 h. The solvent was then removed under reduced pressure and water added to the residue. The mixture was extracted with DCM. The combined extracts were dried over sodium sulfate and concentrated under reduced pressure to give the crude product was purified by column chromatography to afford methyl 5-bromo-3-(ethyl(tetrahydro-2H-pyran-4-yl)amino)-2-methylbenzoate (14 g, 93.33%).

Step 2: Synthesis of 5-bromo-N-((4,6-dimethyl-2-oxo-1,2-dihydropyridin-3-yl)methyl)-3-(ethyl(tetrahydro-2H-pyran-4-yl)amino)-2-methylbenzamide Aqueous NaOH (2.36 g, 59.15 mmol) was added to a solution of methyl 5-bromo-3-(ethyl(tetrahydro-2H-pyran-4-yl)amino)-2-methylbenzoate (14 g, 39.43 mmol) in ethanol (100 mL) and stirred at 60° C. for 1 h. The ethanol was then removed under reduced pressure and acidified to pH 6 with dilute HCl and to pH 4 with citric acid. The mixture was extracted with ethyl acetate. The combined extracts were dried and concentrated giving the respective acid (13.9 g, 100%).

The above acid (10 g, 29.23 mmol) was dissolved in DMSO (25 mL) and 3-(aminomethyl)-4,6-dimethylpyridin-2(1H)-one (8.8 g, 58 mmol) and triethylamine (5.6 g, 58.4 mmol) was added. The reaction mixture was stirred at room temperature for 15 min before PyBOP (22 g, 43.8 mmol) was added. The reaction mixture was overnight. The reaction mixture was poured into ice water and extracted with 10% MeOH/DCM. The combined extracts were dried and concentrated to obtain the crude product which purified by solvent washings to afford 5-bromo-N-((4,6-dimethyl-2- oxo-1,2-dihydropyridin-3-yl)methyl)-3-(ethyl(tetrahydro-2H-pyran-4-yl)amino)-2-methylbenzamide (14 g, 73.68%).

Step 3: Synthesis of N-((4,6-dimethyl-2-oxo-1,2-dihydropyridin-3-yl)methyl)-4'-((dimethylamino) methyl)-5-(ethyl(tetrahydro-2H-pyran-4-yl)amino)-4-methyl-[1,1'-biphenyl]-3-carboxamide To a stirred solution of 5-bromo-N-((4,6-dimethyl-2-oxo-1,2-dihydropyridin-3-yl)methyl)-3-(ethyl(tetrahydro-2H-pyran-4-yl)amino)-2-methylbenzamide (0.2 g, 0.42 mmol) and (4-((dimethylamino)methyl)phenyl)boronic acid (0.15 g, 0.505 mmol) in dioxane/water mixture (5 mL+1 mL), Na$_2$CO$_3$ (0.16 g, 1.51 mmol) was added and the solution purged with argon for 15 min. Pd (PPh$_3$)$_4$ (0.048 g, 0.042 mmol) was the added and the reaction mixture again purged with argon for 10 min. The reaction mixture was heated at 100° C. for 2 h. The reaction mixture was then diluted with water and extracted with 10% MeOH/DCM. The combined extracts were dried over Na$_2$SO$_4$ and the solvent removed under reduced pressure to afford the crude product which was purified by column chromatography over silica gel to afford the title compound (0.120 g, 53.8%). LCMS: 531.30 (M+1)$^+$; HPLC: 94.88% (@ 254 nm) (R$_t$: 3.949; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (s, 1H), 8.19 (t, 1H, J=4.4 Hz), 7.61 (d, 2H, J=8 Hz), 7.39-7.41 (m, 3H), 7.23 (s, 1H), 5.86 (s, 1H), 4.28 (d, 2H, J=4.8 Hz), 3.62-3.84 (m, 4H), 3.22-3.38 (m, 2H), 3.02-3.06 (m, 3H), 2.30 (bs, 6H), 2.24 (s, 3H), 2.20 (s, 3H), 2.10 (s, 3H), 1.64-1.67 (m, 2H), 1.51-1.53 (m, 2H), 0.83 (t, 3H, J=6.8 Hz).

Example 66: Synthesis of N-((4,6-dimethyl-2-oxo-1,2-dihydropyridin-3-yl)methyl)-5-(ethyl(tetrahydro-2H-pyran-4-yl)amino)-4-methyl-4'-((4-methylpiperazin-1-yl)methyl)-[1,1'-biphenyl]-3-carboxamide Compound 66

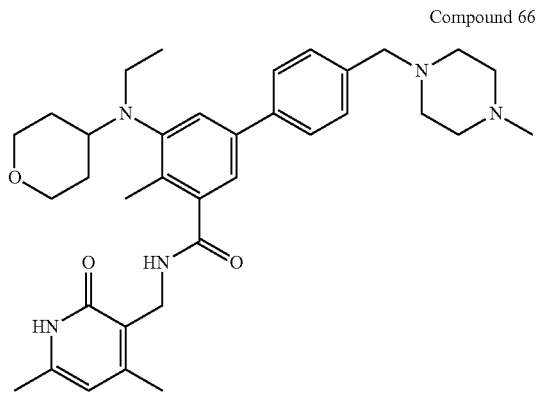 [SMILES: CCN(c1cc(-c2ccc(CN3CCN(C)CC3)cc2)cc(C(=O)NCc2c(C)cc(C)[nH]c2=O)c1C)C1CCOCC1]

To a stirred solution of 5-bromo-N-((4,6-dimethyl-2-oxo-1,2-dihydropyridin-3-yl)methyl)-3-(ethyl(tetrahydro-2H-pyran-4-yl)amino)-2-methylbenzamide (0.2 g, 0.42 mmol) and (4-((4-methylpiperazin-1-yl)methyl)phenyl)boronic acid (0.159 g, 0.505 mmol) in dioxane/water mixture (5 mL+1 mL), Na$_2$CO$_3$ (0.16 g, 1.51 mmol) was added and the solution purged with argon for 15 min. Pd (PPh$_3$)$_4$ (0.048 g, 0.042 mmol) was then added and the reaction mixture again purged with argon for 10 min. The reaction mixture was heated at 100° C. for 2 h. The reaction mixture was then diluted with water and extracted with 10% MeOH/DCM. The combined extracts were dried over Na$_2$SO$_4$ and the solvent removed under reduced pressure to afford the crude product which was purified by preparative HPLC to afford the title compound as a TFA salt (0.110 g, 44.7%). LCMS: 586.40 (M+1)$^+$; HPLC: 96.03% (@ 254 nm) (R$_t$; 3.803; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (s, 1H), 8.23 (t, 1H), 7.69 (d, 2H, J=7.6 Hz), 7.47 (t, 3H, J=8 Hz), 7.29 (s, 1H), 5.87 (s, 1H), 4.28 (d, 4H, J=4 Hz), 3.93 (s, 3H), 3.83-3.86 (m, 2H), 3.43 (m, 2H), 3.16-3.27 (m, 8H), 2.81 (s, 3H), 2.26 (s, 3H), 2.21 (s, 3H), 2.10 (s, 3H), 1.66 (m, 2H), 1.57 (m, 2H), 0.84 (t, 3H, J=6 Hz).

Example 67: Synthesis of 4'-((1R,4R)-2-oxa-5-azabicyclo[2.2.1]heptan-5-ylmethyl)-N-((4,6-dimethyl-2-oxo-1,2-dihydropyridin-3-yl) methyl)-5-(ethyl (tetrahydro-2H-pyran-4-yl) amino)-4-methyl-[1,1'-biphenyl]-3-carboxamide (0.1 g, 28%)

Compound 67

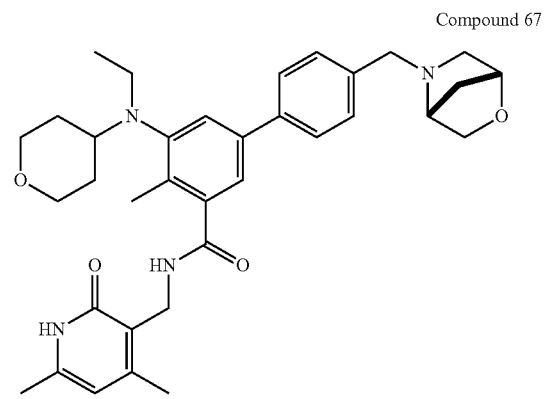

Step 1: Synthesis of methyl 5-bromo-3-(ethyl (tetrahydro-2H-pyran-4-yl) amino)-2-methylbenzoate To a stirred solution of methyl 5-bromo-2-methyl-3-((tetrahydro-2H-pyran-4-yl) amino) benzoate (14 g, 43 mmol) and acetaldehyde (3.75 g, 85.4 mmol) in dichloroethane (150 mL), was added acetic acid (15.36 g, 256 mmol). After stirring at room temperature for 20 minutes, sodium triacetoxyborohydride (27.0 g, 128 mmol) was added at 0° C. The mixture was stirred at room temperature for 2 h. and quenched with aqueous sodium bicarbonate. The organic phase was separated and the aqueous phase was extracted with dichloromethane. The combined organic layers were dried over sodium sulphate and concentrated under reduced pressure to give crude material which was purified by column chromatography over silica gel to afford methyl 5-bromo-3-(ethyl (tetrahydro-2H-pyran-4-yl) amino)-2-methylbenzoate (14 g, 93%).

Step 2: Synthesis of 5-bromo-N-((4,6-dimethyl-2-oxo-1,2-dihydropyridin-3-yl) methyl)-3-(ethyl (tetrahydro-2H-pyran-4-yl) amino)-2-methylbenzamide To a stirred solution of methyl 5-bromo-3-(ethyl (tetrahydro-2H-pyran-4-yl) amino)-2-methylbenzoate (14 g, 39 mmol) in ethanol (100 mL) was added aqueous NaOH (2.36 g, 59.1 mmol). After stirring 60° C. for 1 h, ethanol was removed under reduced pressure and acidified to pH 4 using dilute HCl followed by citric acid buffer solution. The mixture was extracted with ethyl acetate, and the combined organic layers were dried and concentrated to afford the corresponding acid (13.9 g).

To a stirred solution of the above acid (10 g, 29 mmol), 3-(amino methyl)-4,6-dimethylpyridin-2(1H)-one (8.8 g, 58 mmol) and triethylamine (5.6 g, 58 mmol) in DMSO (25 mL) was added PYBOP (22 g, 44 mmol) at 0° C. After stirring overnight at room temperature, the mixture was poured onto ice and extracted with 10% MeOH/CH$_2$Cl$_2$. The combined organic layers were dried and concentrated under reduced pressure to obtain crude. Trituration of the crude material with solvent afforded 5-bromo-N-((4,6-dimethyl-2-oxo-1,2-dihydropyridin-3-yl) methyl)-3-(ethyl (tetrahydro-2H-pyran-4-yl) amino)-2-methylbenzamide (14 g, 73%).

Step 3: Synthesis of N-((4,6-dimethyl-2-oxo-1,2-dihydropyridin-3-yl) methyl)-5-(ethyl (tetrahydro-2H-pyran-4-yl) amino)-4'-formyl-4-methyl-[1,1'-biphenyl]-3-carboxamide To a stirred solution of 5-bromo-N-((4,6-dimethyl-2-oxo-1,2-dihydropyridin-3-yl) methyl)-3-(ethyl (tetrahydro-2H-pyran-4-yl) amino)-2-methylbenzamide (5.0 g, 10 mmol) and (4-formylphenyl) boronic acid (2.35 g, 15.8 mmol) in dioxane/water (30 mL/10 mL) was added Na$_2$CO$_3$ (4.01 g, 37.9 mmol). The solution was purged with argon for 15 min., Pd(PPh$_3$)$_4$ (1.21 g, 1.05 mmol) and the mixture was heated at 100° C. for 2 h. The mixture was allowed to cool to room temperature, diluted with water and extracted with 10% MeOH/CH$_2$Cl$_2$. The combined organic layers were dried over sodium sulphate and the solvent removed under reduced pressure. The resulting crude material was purified by column chromatography over silica gel to afford N-((4,6-dimethyl-2-oxo-1,2-dihydropyridin-3-yl)methyl)-5-(ethyl (tetrahydro-2H-pyran-4-yl) amino)-4'-formyl-4-methyl-[1,1'-biphenyl]-3-carboxamide (3.5 g, 66%).

The Following Reductive Amination Procedure was Used to Synthesize Compounds 67 Through 105

To a stirred solution of N-((4,6-dimethyl-2-oxo-1,2-dihydropyridin-3-yl) methyl)-5-(ethyl (tetrahydro-2H-pyran-4-yl) amino)-4'-formyl-4-methyl-[1,1'-biphenyl]-3-carboxamide (1.0 mmol) the requisite amine (3.0 mmol) in dichloroethane (10 mL), was added acetic acid (6.0 mmol). After stirring at room temperature for 20 minutes, sodium triacetoxyborohydride (0.63 g, 3.0 mmol) was added at 0° C. The mixture was stirred at room temperature for 2 h. and quenched with aqueous sodium bicarbonate. The organic phase was separated and the aqueous phase extracted with dichloromethane. The combined organic layers were dried over sodium sulfate and concentrated under reduced pressure to give crude material which was purified by column chromatography over silica gel or by RP-HPLC to afford the product in free base or trifluoroacetate salt form.

Analytical Data of 4'-((1R,4R)-2-oxa-5-azabicyclo[2.2.1] heptan-5-ylmethyl)-N-((4,6-dimethyl-2-oxo-1,2-dihydropyridin-3-yl) methyl)-5-(ethyl (tetrahydro-2H-pyran-4-yl) amino)-4-methyl-[1,1'-biphenyl]-3-carboxamide: LCMS: 585.25 (M+1)$^+$; HPLC: 99.65% (@254 nm) (R$_t$; 4.019; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.19 (t, 1H), 7.55 (d, 2H, J=7.6 Hz), 7.39-7.41 (m, 3H), 7.21 (s, 1H), 5.85 (s, 1H), 4.35 (s, 2H), 4.28 (d, 2H, J=4.4 Hz), 3.93 (d, 2H, J=7.2 Hz), 3.82 (d, 2H, J=9.6 Hz), 3.72 (d, 2H, J=4.4 Hz), 3.44-3.53 (m, 3H), 3.22-3.27 (m, 1H), 3.01-3.09 (m, 2H), 2.73 (d, 1H, J=9.2 Hz), 2.23 (s, 3H), 2.20 (s, 3H), 2.10 (s, 3H), 1.79-1.82 (m, 1H), 1.51-1.67 (m, 5H), 0.82 (t, 3H, J=6.8 Hz).

Example 68: 4'-((1S,4S)-2-oxa-5-azabicyclo[2.2.1] heptan-5-ylmethyl)-N-((4,6-dimethyl-2-oxo-1,2-dihydropyridin-3-yl) methyl)-5-(ethyl (tetrahydro-2H-pyran-4-yl) amino)-4-methyl-[1,1'-biphenyl]-3-carboxamide (0.15 g, 43%)

Compound 68

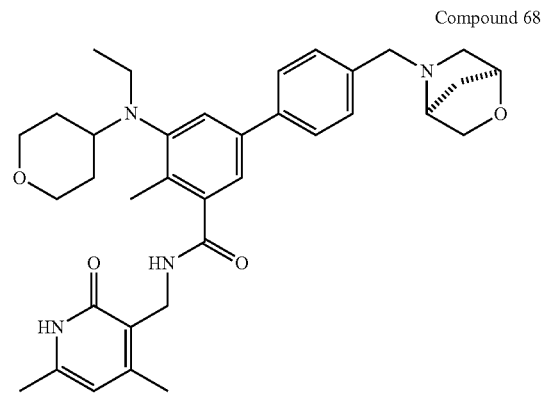

Analytical Data: LCMS: 585.35 (M+1)$^+$; HPLC: 98.99% (@ 254 nm) (R$_t$; 3.95; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (bs, 1H), 8.18 (s, 1H), 7.56-7.54 (m, 2H), 7.41-7.39 (m, 3H), 7.21 (s, 1H), 5.87 (s, 1H), 4.34 (s, 1H), 4.28 (d, 2H, J=4.4 Hz),3.93 (d, 1H, J=7.6 Hz), 3.83-3.81 (m, 2H), 3.74-3.72 (m, 2H), 3.52 (d, 1H, J=6.8 Hz), 3.44 (s, 1H), 3.28-3.22 (m, 2H), 3.09-3.08 (m, 3H), 2.73 (d, 1H J=10 Hz), 2.41 (d, 1H J=10 Hz), 2.24 (s, 3H), 2.20 (s, 3H), 2.10 (s, 3H), 1.79 (m, 1H), 1.67-1.51 (m, 5H). 0.83 (t, 3H J=6.8 Hz).

Example 69: N-((4,6-dimethyl-2-oxo-1,2-dihydro-pyridin-3-yl) methyl)-5-(ethyl (tetrahydro-2H-pyran-4-yl) amino)-4-methyl-4'-(pyrrolodin-1-ylm-ethyl)-[1,1'-biphenyl]-3-carboxamide (0.19 g)

Compound 69

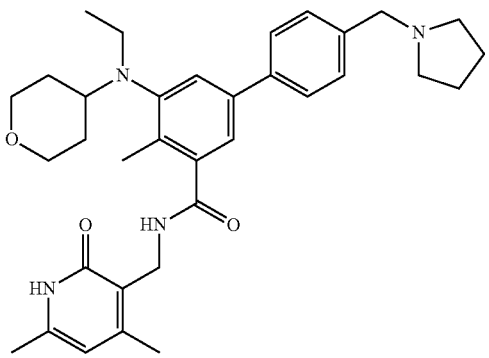

Analytical Data: LCMS: 557.25 (M+1)$^+$; HPLC: 97.70% (@ 254 nm) (R$_t$; 4.075; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (s, 1H), 8.19 (t, 1H, J=4.4 Hz), 7.55 (d, 2H, J=8 Hz), 7.38 (d, 2H, J=6.4 Hz), 7.35 (s, 1H), 7.21 (s, 1H), 5.85 (s, 1H), 4.28 (d, 2H, J=4.4 Hz), 3.81-3.84 (m, 2H), 3.58 (s, 2H), 3.22-3.27 (m, 2H), 3.06-3.09 (m, 2H), 2.99-3.04 (m, 1H), 2.43 (bs, 4H), 2.24 (s, 3H), 2.20 (s, 3H), 2.10 (s, 3H), 1.64-1.69 (m, 6H), 1.51-1.56 (m, 2H), 0.83 (t, 3H, J=6.8 Hz).

Example 70: (S)—N-((4,6-dimethyl-2-oxo-1,2-dihydropyridin-3-yl) methyl)-5-(ethyl (tetrahydro-2H-pyran-4-yl) amino)-4'-(3-hydroxypyrrolodin-1-ylm-ethyl)-4-methyl-[1,1'-biphenyl]-3-carboxamide TFA salt, (0.15 g, 44%)

Compound 70

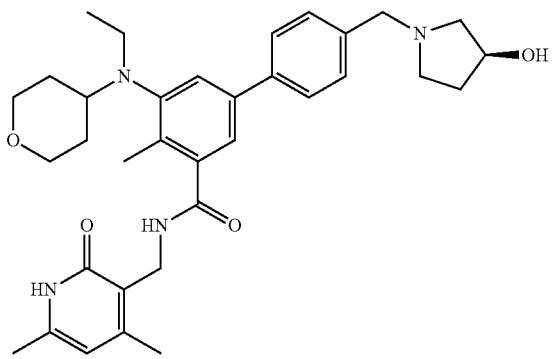

Analytical Data: LCMS: 573.40 (M+1)$^+$; HPLC: 97.97% (@ 254 nm) (R$_t$; 3.965; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.47 (s, 1H), 10.03-10.30 (m, 1H), 8.23 (s, 1H), 7.75 (d, 2H, J=7.2 Hz), 7.60 (d, 2H, J=8 Hz), 7.52 (s, 1H), 7.32 (s, 1H), 5.87 (s, 1H), 4.45-4.46 (m, 2H), 4.39-4.40 (m, 2H), 4.29 (d, 2H, J=5.2 Hz), 3.83-3.86 (m, 2H), 3.43-3.55 (m, 2H), 3.01-3.36 (m, 6H), 2.32-2.37 (m, 2H), 2.27 (s, 3H), 2.21 (s, 3H), 2.11 (s, 3H), 1.67 (m, 2H), 1.58 (m, 2H), 0.84 (t, 3H, J=6.4 Hz).

Example 71: (R)—N-((4,6-dimethyl-2-oxo-1,2-dihydropyridin-3-yl) methyl)-5-(ethyl (tetrahydro-2H-pyran-4-yl) amino)-4'-(3-hydroxypyrrolodin-1-ylm-ethyl)-4-methyl-[1,1'-biphenyl]-3-carboxamide, (0.125 g, 55%)

Compound 71

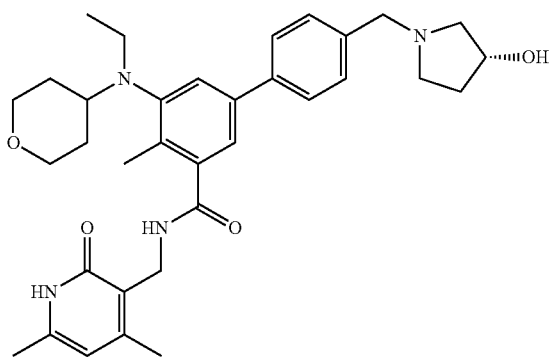

Analytical Data: LCMS: 573.40 (M+1)$^+$; HPLC: 96.12% (@ 254 nm) (R$_t$; 3.921; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.18 (t, 1H), 7.56 (d, 2H, J=7.6 Hz), 7.39 (s, 1H), 7.36 (d, 2H, J=8 Hz), 7.21 (s, 1H), 5.85 (s, 1H), 4.68 (s, 1H), 4.28 (d, 2H, J=4 Hz), 4.19 (bs, 1H), 3.81-3.84 (m, 2H), 3.56-3.59 (m, 2H), 3.22-3.25 (m, 2H), 3.08-3.09 (m, 2H), 3.01 (m, 1H), 2.57-2.67 (m, 2H), 2.32 (m, 2H), 2.24 (s, 3H), 2.20 (s, 3H), 2.10 (s, 3H), 1.97-2.00 (m, 1H), 1.64-1.67 (m, 2H), 1.51-1.53 (m, 3H), 0.83 (t, 3H, J=6.4 Hz).

Example 72: (S)—N-((4,6-dimethyl-2-oxo-1,2-dihydropyridin-3-yl) methyl)-5-(ethyl (tetrahydro-2H-pyran-4-yl) amino)-4'-(3-fluoropyrrolodin-1-ylm-ethyl)-4-methyl-[1,1'-biphenyl]-3-carboxamide (0.05 g)

Compound 72

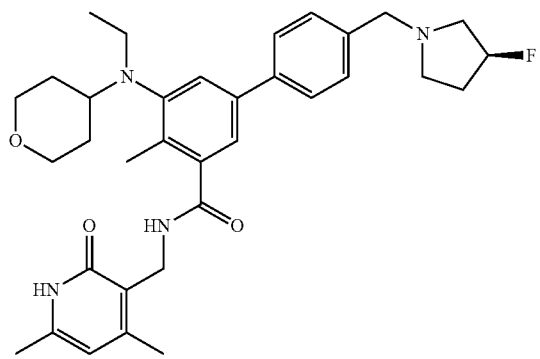

Analytical Data: LCMS: 575.35 (M+1)+; HPLC: 98.44% (@ 254 nm) (R$_t$: 4.081; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.18 (t, 1H), 7.56 (d, 2H, J=7.6 Hz), 7.39 (s, 1H), 7.34 (d, 2H, J=8 Hz), 7.21 (s, 1H), 5.85 (s, 1H), 5.09-5.25 (m, 1H), 4.28 (d, 2H, J=4 Hz), 3.81-3.86 (m, 2H), 3.65 (s, 2H), 3.53-3.55 (m, 2H), 3.17-3.25 (m, 2H), 3.07-3.16 (m, 7H), 2.24 (s, 3H), 2.20 (s, 3H), 2.10 (s, 3H), 1.64-1.67 (m, 2H), 1.51-1.53 (m, 2H), 0.83 (t, 3H, J=6.8 Hz).

Example 73: N-((4,6-dimethyl-2-oxo-1,2-dihydropyridin-3-yl) methyl)-5-(ethyl (tetrahydro-2H-pyran-4-yl) amino)-4-methyl-4'-(piperazin-1-ylmethyl)-[1,1'-biphenyl]-3-carboxamide TFA salt, (0.18 g, 50%)

Compound 73

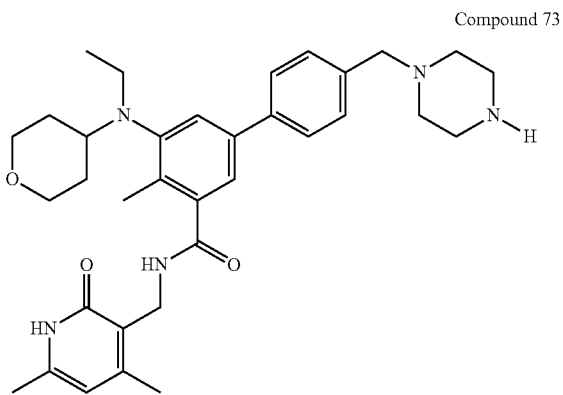

Analytical Data: LCMS: 572.10 (M+1)+; HPLC: 96.61% (@ 254 nm) (R$_t$: 3.736; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (s, 1H), 8.81 (bs, 2H), 8.20 (s, 1H), 7.66 (d, 2H, J=7.2 Hz), 7.47 (d, 2H, J=7.6 Hz), 7.42 (m, 1H), 7.25 (s, 1H), 5.86 (s, 1H), 4.28 (d, 2H, J=4 Hz), 3.82-3.85 (m, 4H), 3.11-3.27 (m, 9H), 2.88 (m, 4H), 2.25 (s, 3H), 2.20 (s, 3H), 2.10 (s, 3H), 1.65 (m, 2H), 1.53-1.55 (m, 2H), 0.83 (t, 3H, J=6 Hz).

Example 74: (R)—N-((4,6-dimethyl-2-oxo-1,2-dihydropyridin-3-yl) methyl)-5-(ethyl (tetrahydro-2H-pyran-4-yl) amino)-4'-(3-fluoropyrrolodin-1-ylmethyl)-4-methyl-[1,1'-biphenyl]-3-carboxamide, (0.07 g, 31%)

Compound 74

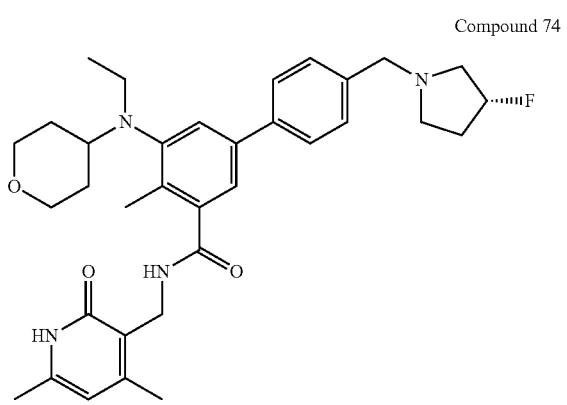 [SMILES: CCN(c1cc(-c2ccc(CN3CC[C@@H](F)C3)cc2)cc(C(=O)NCc2c(C)cc(C)[nH]c2=O)c1C)C1CCOCC1]

Analytical Data: LCMS: 575.35 (M+1)+; HPLC: 97.53% (@ 254 nm) (R$_t$: 4.079; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.18 (t, 1H), 7.57 (d, 2H, J=7.6 Hz), 7.38 (d, 2H, J=4.4 Hz), 7.36 (s, 1H), 7.22 (s, 1H), 5.85 (s, 1H), 5.12-5.26 (m, 1H), 4.28 (d, 2H, J=4 Hz), 3.81-3.84 (m, 2H), 3.63 (s, 2H), 3.22-3.25 (m, 2H), 3.08-3.09 (m, 2H), 3.02 (m, 1H), 2.73-2.83 (m, 2H), 2.32 (m, 1H), 2.24 (s, 3H), 2.20 (s, 3H), 2.10 (s, 3H), 1.89 (m, 1H), 1.64-1.67 (m, 2H), 1.51-1.53 (m, 2H), 0.83 (t, 3H, J=7.2 Hz).

Example 75: N-((4,6-dimethyl-2-oxo-1,2-dihydropyridin-3-yl) methyl)-5-(ethyl (tetrahydro-2H-pyran-4-yl) amino)-4-methyl-4'-(piperidin-1-ylmethyl)-[1,1'-biphenyl]-3-carboxamide, (0.1 g, 88%)

Compound 75

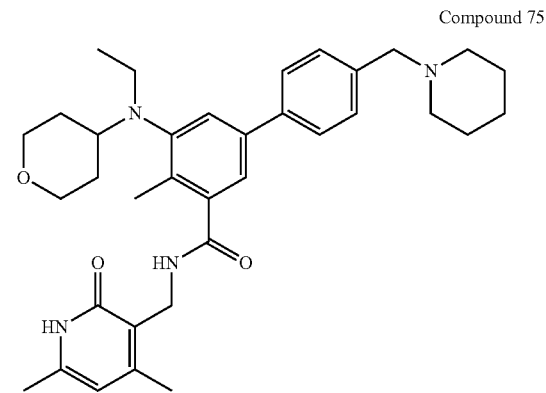 [SMILES: CCN(c1cc(-c2ccc(CN3CCCCC3)cc2)cc(C(=O)NCc2c(C)cc(C)[nH]c2=O)c1C)C1CCOCC1]

Analytical Data: LCMS: 571.25 (M+1)+; HPLC: 98.25% (@ 254 nm) (R$_t$: 4.147; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (s, 1H), 8.19 (t, 1H, J=5.2 Hz), 7.55 (d, 2H, J=8 Hz), 7.39 (s, 1H), 7.34 (d, 2H, J=8 Hz), 7.21 (s, 1H), 5.85 (s, 1H), 4.28 (d, 2H, J=4.4 Hz), 3.82-3.83 (m, 2H), 3.43 (s, 2H), 3.24 (t, 2H, J=11.2 Hz), 3.06-3.09 (m, 2H), 2.99-3.01 (m, 1H), 2.32 (bs, 4H), 2.24 (s, 3H), 2.20 (s, 3H), 2.10 (s, 3H), 1.64-1.67 (m, 2H), 1.47-1.56 (m, 6H), 1.38-1.39 (m, 2H), 0.83 (t, 3H, J=7.2 Hz).

Example 76: (S)—N-((4,6-dimethyl-2-oxo-1,2-dihydropyridin-3-yl) methyl)-5-(ethyl (tetrahydro-2H-pyran-4-yl) amino)-4'-((3-hydroxypiperidin-1-yl) methyl)-4-methyl-[1,1'-biphenyl]-3-carboxamide, (0.25 g, 71.4%)

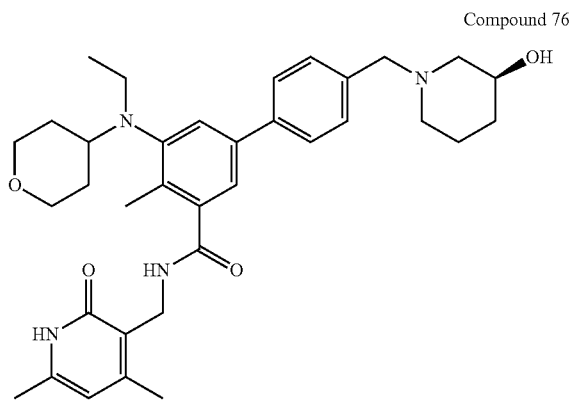 [SMILES: CCN(c1cc(-c2ccc(CN3CCC[C@H](O)C3)cc2)cc(C(=O)NCc2c(C)cc(C)[nH]c2=O)c1C)C1CCOCC1]

Compound 76

Analytical Data: LCMS: 587.40 (M+1)⁺; HPLC: 97.63% (@ 254 nm) (R_t; 3.997; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.18 (t, 1H, J-4.8 Hz), 7.56 (d, 2H, J=8 Hz), 7.39 (s, 1H), 7.34 (d, 2H, J=8 Hz), 7.21 (s, 1H), 5.85 (s, 1H), 4.55 (d, 1H, J=4.8 Hz), 4.28 (d, 2H, J=4.4 Hz), 3.81-3.84 (m, 2H), 3.51-3.54 (m, 2H), 3.43-3.45 (m, 1H), 3.06-3.09 (m, 3H), 2.99-3.01 (m, 2H), 2.79 (d, 1H, J=6.8 Hz), 2.65 (d, 1H, J=10.8 Hz), 2.24 (s, 3H), 2.20 (s, 3H), 2.10 (s, 3H), 1.78-1.88 (m, 2H), 1.58-1.71 (m, 2H), 1.39-1.51 (m, 4H), 1.04-1.10 (m, 1H), 0.83 (t, 3H, J=6.8 Hz).

Example 77: (R)—N-((4,6-dimethyl-2-oxo-1,2-dihydropyridin-3-yl) methyl)-5-(ethyl (tetrahydro-2H-pyran-4-yl) amino)-4'-((3-hydroxypiperidin-1-yl) methyl)-4-methyl-[1,1'-biphenyl]-3-carboxamide, (0.11 g, 48.6%)

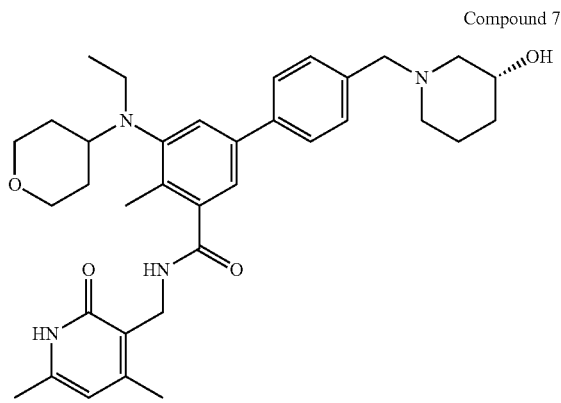

Compound 77

Analytical Data: LCMS: 587.45 (M+1)⁺; HPLC: 98.65% (@ 254 nm) (R_t; 3.976; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.44 (s, 1H), 8.18 (t, 1H), 7.56 (d, 2H, J=7.6 Hz), 7.39 (s, 1H), 7.35 (d, 2H, J=8 Hz), 7.21 (s, 1H), 5.85 (s, 1H), 4.28 (d, 2H, J=4.4 Hz), 3.81-3.84 (m, 2H), 3.40-3.54 (m, 3H), 3.22-3.25 (m, 2H), 3.08-3.09 (m, 2H), 3.02 (m, 1H), 2.78-2.80 (m, 2H), 2.66 (m, 2H), 2.24 (s, 3H), 2.20 (s, 3H), 2.10 (s, 3H), 1.80-1.86 (m, 3H), 1.53-1.67 (m, 3H), 1.40-1.51 (m, 3H), 1.04-1.06 (m, 1H), 0.83 (t, 3H, J=6.8 Hz).

Example 78: N-((4,6-dimethyl-2-oxo-1,2-dihydropyridin-3-yl) methyl)-5-(ethyl (tetrahydro-2H-pyran-4-yl) amino)-4'-((4-hydroxypiperidin-1-yl) methyl)-4-methyl-[1,1'-biphenyl]-3-carboxamide, (0.2 g, 57%)

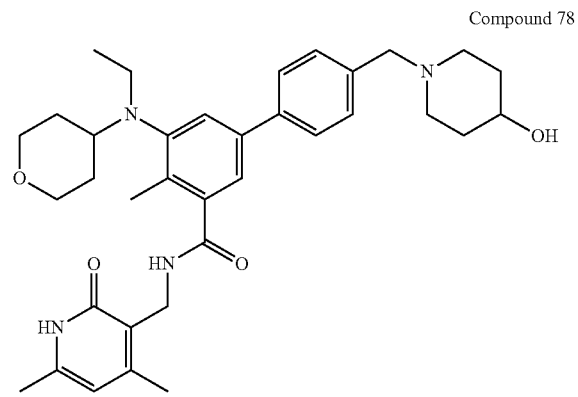 [SMILES: CCN(c1cc(-c2ccc(CN3CCC(O)CC3)cc2)cc(C(=O)NCc2c(C)cc(C)[nH]c2=O)c1C)C1CCOCC1]

Compound 78

Analytical Data: LCMS: 587.20 (M+1)⁺; HPLC: 99.89% (@ 254 nm) (R_t; 1.456; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.46 (s, 1H), 8.19 (t, 1H, J=4.4 Hz), 7.56 (d, 2H, J=8 Hz), 7.39 (s, 1H), 7.34 (d, 2H, J=8 Hz), 7.21 (s, 1H), 5.85 (s, 1H), 4.53 (d, 1H, J=3.6 Hz), 4.28 (d, 2H, J=4.4 Hz), 3.81-3.84 (m, 2H), 3.44 (s, 3H), 3.22-3.27 (m, 2H), 3.07-3.09 (m, 2H), 3.01-3.06 (m, 1H), 2.66 (m, 2H), 2.24 (s, 3H), 2.20 (s, 3H), 2.10 (s, 3H), 2.00-2.04 (m, 2H), 1.64-1.67 (m, 4H), 1.51-1.53 (m, 2H), 1.36-1.39 (m, 2H), 0.83 (t, 3H, J=7.2 Hz).

Example 79: N-((4,6-dimethyl-2-oxo-1,2-dihydro-pyridin-3-yl) methyl)-5-(ethyl (tetrahydro-2H-pyran-4-yl) amino)-4'-((3-fluoropiperidin-1-yl) methyl)-4-methyl-[1,1'-biphenyl]-3-carboxamide, (0.2 g, 56%)

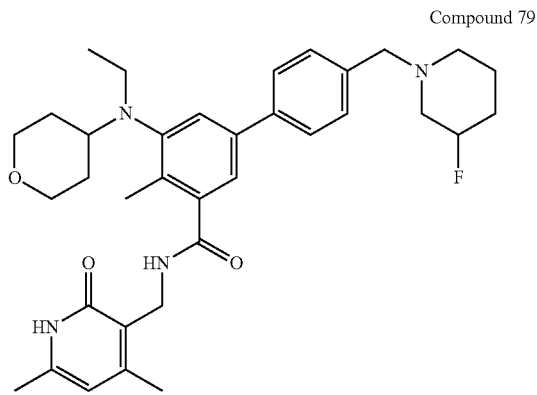 [SMILES: CCN(c1cc(-c2ccc(CN3CCCC(F)C3)cc2)cc(C(=O)NCc2c(C)cc(C)[nH]c2=O)c1C)C1CCOCC1]

Compound 79

Analytical Data: LCMS: 589.35 (M+1)$^+$; HPLC: 96.06% (@ 254 nm) (R$_t$; 4.092; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.18 (t, 1H), 7.57 (d, 2H, J=7.2 Hz), 7.40 (s, 1H), 7.35 (d, 2H, J=7.2 Hz), 7.22 (s, 1H), 5.85 (s, 1H), 4.56-4.68 (m, 1H), 4.28 (d, 2H), 3.81-3.84 (m, 2H), 3.52 (s, 2H), 3.22-3.28 (m, 3H), 3.08-3.09 (m, 2H), 3.02 (m, 1H), 2.65-2.72 (m, 1H), 2.39 (m, 2H), 2.24 (s, 3H), 2.20 (s, 3H), 2.10 (s, 3H), 1.78-1.81 (m, 2H), 1.64-1.68 (m, 2H), 1.50-1.53 (m, 4H), 0.83 (t, 3H).

Example 80: N-((4,6-dimethyl-2-oxo-1,2-dihydro-pyridin-3-yl) methyl)-5-(ethyl (tetrahydro-2H-pyran-4-yl) amino)-4'-((4-fluoropiperidin-1-yl) methyl)-4-methyl-[1,1'-biphenyl]-3-carboxamide, (0.09 g, 25%)

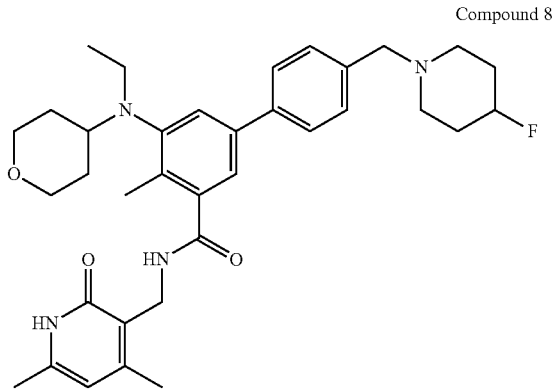

Compound 80

Analytical Data: LCMS: 589.30 (M+1)$^+$; HPLC: 95.46% (@ 254 nm) (R$_t$; 4.156; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.18 (t, 1H), 7.56 (d, 2H), 7.39 (s, 1H), 7.37 (d, 2H), 7.21 (s, 1H), 5.85 (s, 1H), 4.62-4.74 (m, 1H), 4.28 (d, 2H, J=3.2 Hz), 3.81-3.84 (m, 2H), 3.49 (s, 2H), 3.22-3.25 (m, 3H), 3.08-3.09 (m, 3H), 3.02 (m, 1H), 2.32 (m, 2H), 2.24 (s, 3H), 2.20 (s, 3H), 2.10 (s, 3H), 1.82-1.85 (m, 2H), 1.64-1.67 (m, 4H), 1.51-1.53 (m, 2H), 0.83 (t, 3H, J=6.4 Hz).

Example 81: 4'-((4,4-difluoropiperidin-1-yl)methyl)-N-((4,6-dimethyl-2-oxo-1,2-dihydropyridin-3-yl) methyl)-5-(ethyl (tetrahydro-2H-pyran-4-yl) amino)-4-methyl-[1,1'-biphenyl]-3-carboxamide, (0.1 g, 27%)

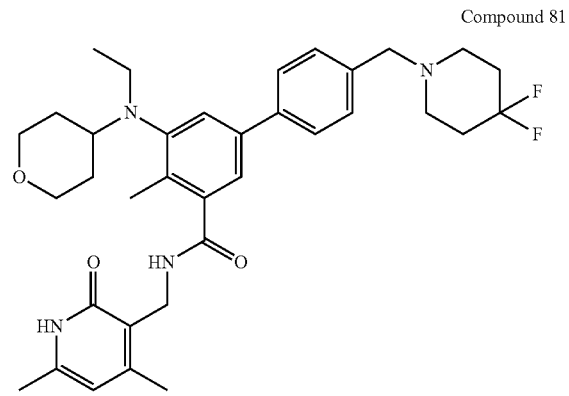 [SMILES: CCN(c1cc(-c2ccc(CN3CCC(F)CC3)cc2)cc(C(=O)NCc2c(C)cc(C)[nH]c2=O)c1C)C1CCOCC1]

Compound 81

Analytical Data: LCMS: 607.35 (M+1)$^+$; HPLC: 95.48% (@ 254 nm) (R$_t$; 4.237; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.46 (s, 1H), 8.19 (t, 1H), 7.58 (d, 2H, J=8 Hz), 7.38 (d, 2H, J=3.6 Hz), 7.36 (s, 1H), 7.21 (s, 1H), 5.85 (s, 1H), 4.28 (d, 2H, J=4.4 Hz), 3.81-3.84 (m, 2H), 3.56 (s, 2H), 3.22-3.27 (m, 2H), 3.08-3.09 (m, 2H), 2.99-3.01 (m, 1H), 2.24 (s, 3H), 2.20 (s, 3H), 2.10 (s, 3H), 1.90-1.99 (m, 4H), 1.64-1.67 (m, 2H), 1.48-1.56 (m, 2H), 0.83 (t, 3H, J=6.4 Hz). [4H merged in solvent peak].

Example 82: 4'-(azetidin-1-ylmethyl)-N-((4,6-dimethyl-2-oxo-1,2-dihydropyridin-3-yl) methyl)-5-(ethyl (tetrahydro-2H-pyran-4-yl) amino)-4-methyl-[1,1'-biphenyl]-3-carboxamide Compound 82

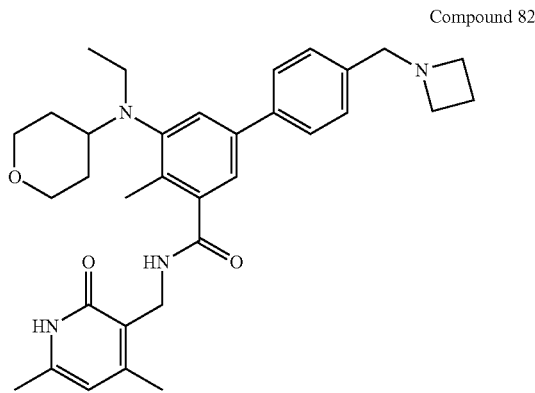 [SMILES: CCN(c1cc(-c2ccc(CN3CCC3)cc2)cc(C(=O)NCc2c(C)cc(C)[nH]c2=O)c1C)C1CCOCC1]

Analytical Data: LCMS: 543.40 (M+1)$^+$; HPLC: 96.50% (@ 254 nm) (R$_t$; 4.010; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.19 (t, 1H, J=4.4 Hz), 7.54 (d, 2H, J=8 Hz), 7.38 (s, 1H), 7.32 (d, 2H, J=8 Hz), 7.20 (s, 1H), 5.85 (s, 1H), 4.28 (d, 2H, J=4.4 Hz), 3.81-3.84 (m, 2H), 3.52 (s, 2H), 3.22-3.27 (m, 2H), 2.98-3.11 (m, 7H), 2.23 (s, 3H), 2.20 (s, 3H), 2.10 (s, 3H), 1.94-2.01 (m, 2H), 1.64-1.67 (m, 2H), 1.51-1.56 (m, 2H), 0.82 (t, 3H, J=7.2 Hz).

Example 83: N-((4,6-dimethyl-2-oxo-1,2-dihydropyridin-3-yl) methyl)-5-(ethyl (tetrahydro-2H-pyran-4-yl) amino)-4'-((3-hydroxyazetidin-1-yl) methyl)-4-methyl-[1,1'-biphenyl]-3-carboxamide Compound 83

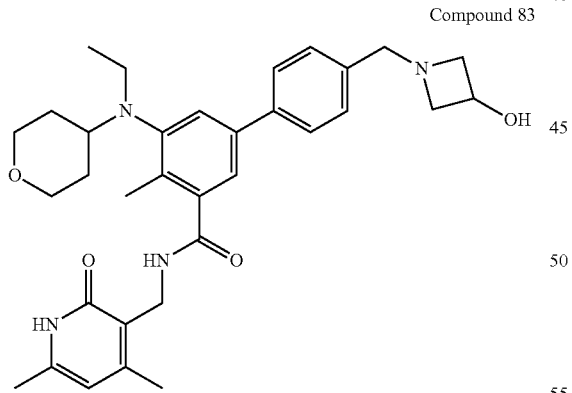

Analytical Data: LCMS: 559.80 (M+1)$^+$; HPLC: 96.10% (@ 254 nm) (R$_t$; 3.917; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.18 (t, 1H), 7.54 (d, 2H, J=8 Hz), 7.38 (s, 1H), 7.31 (d, 2H, J=4.4 Hz), 7.20 (s, 1H), 5.85 (s, 1H), 5.28 (d, 1H, J=6.4 Hz), 4.28 (d, 2H, J=4.4 Hz), 4.17-4.19 (m, 1H), 3.81-3.84 (m, 2H), 3.56 (s, 2H), 3.48 (t, 2H, J=6.4 Hz), 3.22-3.27 (m, 2H), 3.06-3.09 (m, 2H), 3.01 (m, 1H), 2.75 (t, 2H, J=6.8 Hz), 2.24 (s, 3H), 2.20 (s, 3H), 2.10 (s, 3H), 1.64-1.67 (m, 2H), 1.51-1.53 (m, 2H), 0.82 (t, 3H, J=7.2 Hz).

Example 84: N-((4,6-dimethyl-2-oxo-1,2-dihydropyridin-3-yl) methyl)-5-(ethyl (tetrahydro-2H-pyran-4-yl) amino)-4'-((3-fluoroazetidin-1-yl) methyl)-4-methyl-[1,1'-biphenyl]-3-carboxamide Compound 84

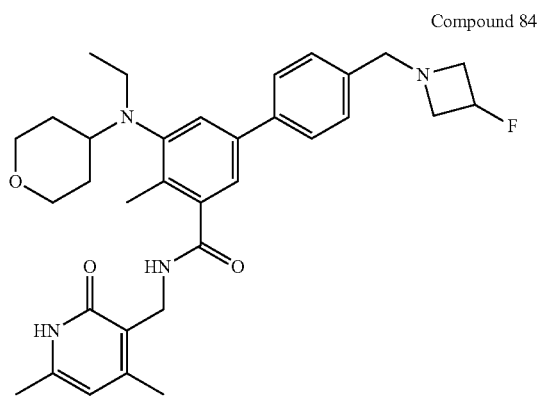 [SMILES: CCN(c1cc(-c2ccc(CN3CC(F)C3)cc2)cc(C(=O)NCc2c(C)cc(C)[nH]c2=O)c1C)C1CCOCC1]

Analytical Data: LCMS: 561.25 (M+1)$^+$; HPLC: 97.99% (@ 254 nm) (R$_t$; 4.021; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.18 (t, 1H), 7.57 (d, 2H, J=7.2 Hz), 7.37-7.40 (m, 3H), 7.22 (s, 1H), 5.85 (s, 1H), 5.27 (m, 1H), 4.28 (d, 2H, J=4.4 Hz), 3.81-3.84 (m, 2H), 3.63 (s, 2H), 3.22-3.27 (m, 2H), 3.08-3.09 (m, 2H), 3.01 (m, 1H), 2.77 (m, 2H), 2.24 (s, 3H), 2.20 (s, 3H), 2.15 (s, 3H), 1.65-1.67 (m, 2H), 1.51-1.53 (m, 2H), 1.04-1.06 (m, 1H), 0.83 (t, 3H, J=7.2 Hz) [2H merged in solvent peak].

Example 86: 4'-((1,4-diazepan-1-yl)methyl)-N-((4,6-dimethyl-2-oxo-1,2-dihydropyridin-3-yl) methyl)-5-(ethyl (tetrahydro-2H-pyran-4-yl) amino)-4-methyl-[1,1'-biphenyl]-3-carboxamide Compound 86

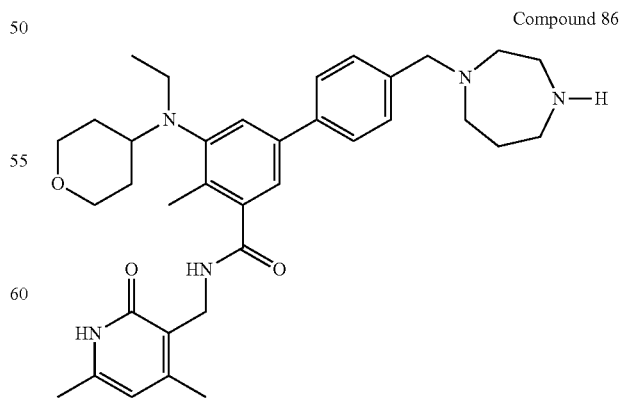

Analytical Data: LCMS: 585.37 (M+1)$^+$; HPLC: 87.74% (@ 254 nm) (R$_t$; 3.715; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.47 (s, 1H), 8.18 (t, 1H), 7.57 (d, 2H, J=6.8 Hz), 7.39 (m, 3H), 7.21 (s, 1H), 5.85 (s, 1H), 4.29 (d, 2H), 3.81-3.84 (m, 2H), 3.66 (s, 2H), 3.08-3.09 (m, 3H), 3.02 (bs, 4H), 2.96 (m, 3H), 2.64-2.66 (m, 4H), 2.24 (s, 3H), 2.20 (s, 3H), 2.10 (s, 3H), 1.78 (m, 2H), 1.64-1.67 (m, 2H), 1.51-1.53 (m, 2H), 0.83 (t, 3H).

Example 87: N-((4,6-dimethyl-2-oxo-1,2-dihydro-pyridin-3-yl) methyl)-5-(ethyl (tetrahydro-2H-pyran-4-yl) amino)-4-methyl-4'-((4-methyl-1,4-diazepan-1-yl)methyl)-[1,1'-biphenyl]-3-carboxamide Compound 87

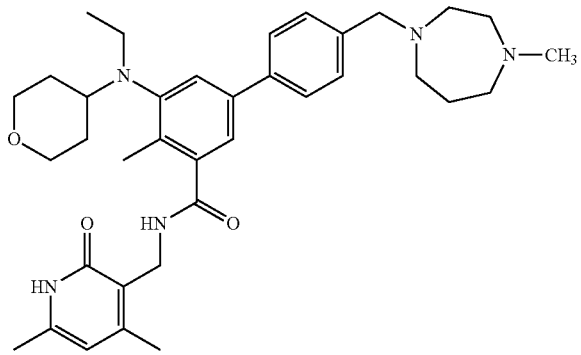

Analytical Data: LCMS: 600.30 (M+1)$^+$; HPLC: 99.46% (@ 254 nm) (R$_t$: 3.713; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.44 (s, 1H), 8.17 (t, 1H), 7.56 (d, 2H, J=8 Hz), 7.38 (d, 2H, J=5.6 Hz), 7.36 (s, 1H), 7.21 (s, 1H), 5.85 (s, 1H), 4.28 (d, 2H, J=5.2 Hz), 3.81-3.84 (m, 2H), 3.61 (s, 2H), 3.09-3.28 (m, 3H), 3.06-3.09 (m, 2H), 3.02 (m, 1H), 2.59-2.65 (m, 5H), 2.56 (t, 2H, J=6 Hz), 2.24 (s, 6H), 2.20 (s, 3H), 2.10 (s, 3H), 1.64-1.72 (m, 4H), 1.51-1.53 (m, 2H), 0.83 (t, 3H, J=6.4 Hz).

Example 88: 4'-((1,4-oxazepan-4-yl)methyl)-N-((4,6-dimethyl-2-oxo-1,2-dihydropyridin-3-yl) methyl)-5-(ethyl (tetrahydro-2H-pyran-4-yl) amino)-4-methyl-[1,1'-biphenyl]-3-carboxamide Compound 88

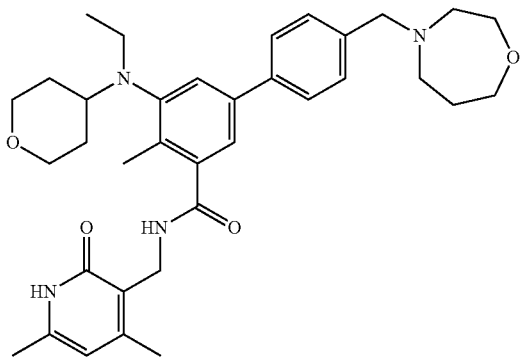

Analytical Data: LCMS: 587.40 (M+1)$^+$; HPLC: 96.85% (@ 254 nm) (R$_t$: 4.055; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.18 (t, 1H, J=4.8 Hz), 7.56 (d, 2H, J=8 Hz), 7.37-7.39 (m, 3H), 7.21 (s, 1H), 5.85 (s, 1H), 4.28 (d, 2H, J=4.4 Hz), 3.81-3.84 (m, 2H), 3.69 (t, 3H, J=6 Hz), 3.64 (s, 1H), 3.59-3.61 (m, 2H), 3.22-3.27 (m, 2H), 2.99-3.09 (m, 3H), 2.59-2.64 (m, 4H), 2.24 (s, 3H), 2.20 (s, 3H), 2.10 (s, 3H), 1.77-1.83 (m, 2H), 1.64-1.67 (m, 2H), 1.48-1.56 (m, 2H), 0.83 (t, 3H, J=7.2 Hz).

Example 89: 4'-(aminomethyl)-N-((4,6-dimethyl-2-oxo-1,2-dihydropyridin-3-yl) methyl)-5-(ethyl (tetrahydro-2H-pyran-4-yl) amino)-4-methyl-[1,1'-biphenyl]-3-carboxamide Compound 89

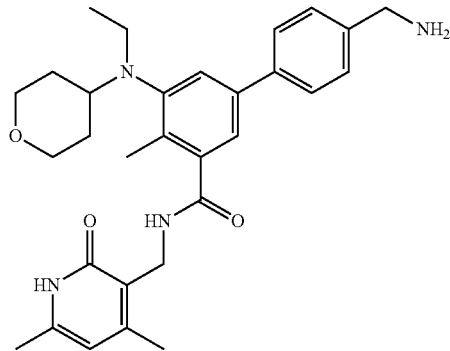

Analytical Data: LCMS: 503.40 (M+1)$^+$; HPLC: 79.83% (@ 254 nm) (R$_t$: 3.846; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.19 (t, 1H), 7.63 (d, 2H, J=8.4 Hz), 7.47 (d, 2H, J=8 Hz), 7.39 (s, 1H), 7.23 (s, 1H), 5.86 (s, 1H), 4.28 (d, 2H, J=4.4 Hz), 3.92 (s, 2H), 3.81-3.84 (m, 2H), 3.22-3.32 (m, 2H), 3.08-3.10 (m, 2H), 3.01 (m, 1H), 2.24 (s, 3H), 2.20 (s, 3H), 2.10 (s, 3H), 1.65-1.67 (m, 2H), 1.51-1.56 (m, 2H), 0.83 (t, 3H, J=6.8 Hz).

Example 90: N-((4,6-dimethyl-2-oxo-1,2-dihydro-pyridin-3-yl) methyl)-5-(ethyl (tetrahydro-2H-pyran-4-yl) amino)-4-methyl-4'-((methylamino) methyl)-[1,1'-biphenyl]-3-carboxamide Compound 90

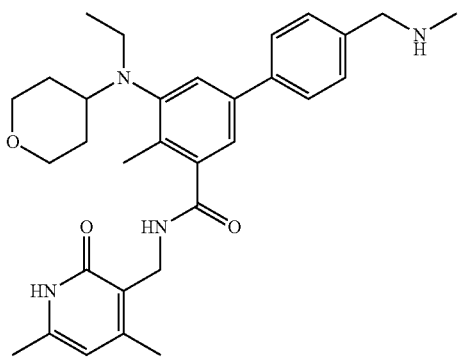

Analytical Data: LCMS: 517.30 (M+1)+; HPLC: 98.05% (@ 254 nm) (R$_t$; 3.886; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.51 (s, 1H), 8.19 (t, 1H, J=4.4 Hz), 7.55 (d, 2H, J=8 Hz), 7.38 (d, 2H), 7.36 (s, 1H), 7.21 (s, 1H), 5.85 (s, 1H), 4.28 (d, 2H, J=4.4 Hz), 3.81-3.84 (m, 2H), 3.66 (s, 2H), 3.11-3.25 (m, 3H), 3.04-3.09 (m, 2H), 2.99-3.01 (m, 1H), 2.26 (s, 3H), 2.24 (s, 3H), 2.20 (s, 3H), 2.10 (s, 3H), 1.65-1.67 (m, 2H), 1.48-1.56 (m, 2H), 0.83 (t, 3H, J=6.8 Hz).

Example 91: N-((4,6-dimethyl-2-oxo-1,2-dihydro-pyridin-3-yl) methyl)-5-(ethyl (tetrahydro-2H-pyran-4-yl) amino)-4-methyl-4'-((ethylamino) methyl)-[1,1'-biphenyl]-3-carboxamide Compound 91

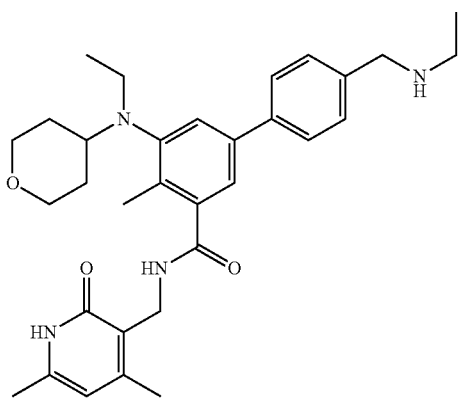

Analytical Data: LCMS: 531.35 (M+1)+; HPLC: 98.28% (@ 254 nm) (R$_t$; 3.977; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.18 (t, 1H, J=4.8 Hz), 7.55 (d, 2H, J=8 Hz), 7.39 (s, 1H), 7.37 (d, 2H, J=2 Hz), 7.21 (s, 1H), 5.85 (s, 1H), 4.28 (d, 2H, J=6 Hz), 3.81-3.84 (m, 2H), 3.71 (s, 2H), 3.22-3.28 (m, 2H), 3.01-3.11 (m, 3H), 2.52-2.55 (m, 2H), 2.24 (s, 3H), 2.20 (s, 3H), 2.10 (s, 3H), 1.65-1.67 (m, 2H), 1.50-1.53 (m, 2H), 1.03 (t, 3H, J=7.2 Hz), 0.83 (t, 3H, J=6.8 Hz).

Example 92: N-((4,6-dimethyl-2-oxo-1,2-dihydro-pyridin-3-yl) methyl)-5-(ethyl (tetrahydro-2H-pyran-4-yl) amino)-4-methyl-4'-((isopropylamino) methyl)-[1,1'-biphenyl]-3-carboxamide TFA salt Compound 92

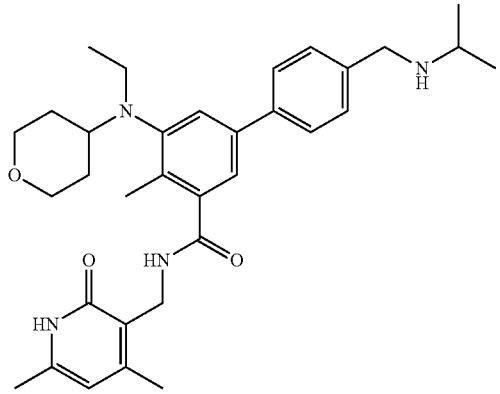

Analytical Data of TFA salt: LCMS: 545.40 (M+1)+; HPLC: 94.74% (@ 254 nm) (R$_t$; 4.081; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.47 (s, 1H), 8.66 (bs, 1H), 8.20 (s, 1H), 7.74 (d, 2H, J=7.6 Hz), 7.57 (d, 2H, J=7.6 Hz), 7.43 (s, 1H), 7.27 (s, 1H), 5.86 (s, 1H), 4.28 (d, 2H, J=4.4 Hz), 4.19 (t, 2H), 3.82-3.85 (m, 2H), 3.25 (t, 2H, J=10.8 Hz), 3.09-3.22 (m, 3H), 2.25 (s, 3H), 2.21 (s, 3H), 2.10 (s, 3H), 1.65 (m, 2H), 1.53-1.55 (m, 3H), 1.28 (d, 6H, J=6.4 Hz), 0.83 (t, 3H, J=6.8 Hz).

Example 93: 4'-((cyclopropylmethyl)amino) methyl)-N-((4,6-dimethyl-2-oxo-1,2-dihydropyridin-3-yl) methyl)-5-(ethyl (tetrahydro-2H-pyran-4-yl) amino)-4-methyl-[1,1'-biphenyl]-3-carboxamide Compound 93

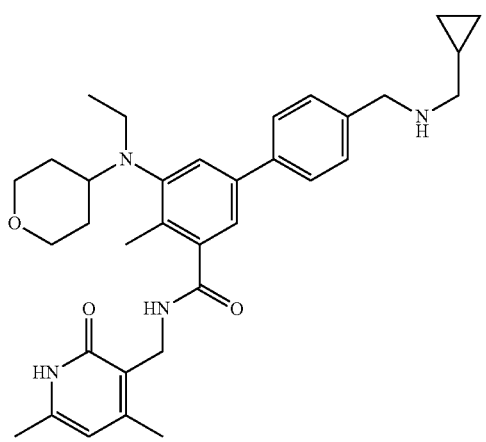

Analytical Data: LCMS: 557.35 (M+1)⁺; HPLC: 96.44% (@ 254 nm) (R$_t$; 4.182; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d6, 400 MHz) δ 11.45 (s, 1H), 8.19 (t, 1H), 7.55 (d, 2H, J=7.2 Hz), 7.37-7.39 (m, 3H), 7.21 (s, 1H), 5.85 (s, 1H), 4.28 (d, 2H, J=4.4 Hz), 3.81-3.84 (m, 2H), 3.73 (s, 2H), 3.22-3.24 (m, 3H), 3.06-3.09 (m, 2H), 3.01 (m, 1H), 2.36 (d, 2H, J=6.8 Hz), 2.23 (s, 3H), 2.20 (s, 3H), 2.10 (s, 3H), 1.64-1.67 (m, 2H), 1.51-1.56 (m, 2H), 0.81-0.084 (m, 4H), 0.38-0.39 (m, 2H), 0.07-0.08 (m, 2H).

Example 94: 4'-((diethyl)amino)methyl)-N-((4,6-dimethyl-2-oxo-1,2-dihydropyridin-3-yl) methyl)-5-(ethyl (tetrahydro-2H-pyran-4-yl) amino)-4-methyl-[1,1'-biphenyl]-3-carboxamide

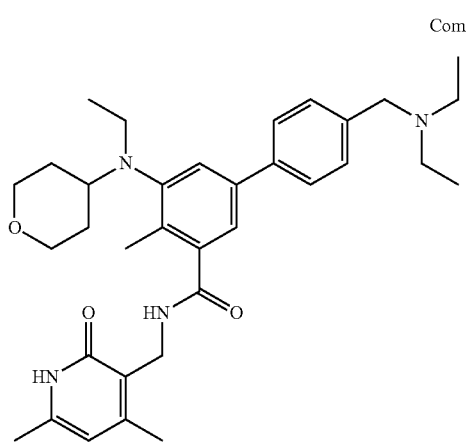

Compound 94

Analytical Data: LCMS: 559.20 (M+1)⁺; HPLC: 98.33% (@ 254 nm) (R$_t$; 4.126; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d6, 400 MHz) δ 11.47 (s, 1H), 8.19 (t, 1H, J=5.2 Hz), 7.55 (d, 2H, J=8 Hz), 7.38 (d, 2H, J=5.2 Hz), 7.36 (s, 1H), 7.21 (s, 1H), 5.85 (s, 1H), 4.28 (d, 2H, J=4.4 Hz), 3.81-3.83 (m, 2H), 3.54 (s, 2H), 3.22-3.37 (m, 2H), 3.06-3.11 (m, 2H), 2.99-3.01 (m, 1H), 2.43-2.47 (m, 4H), 2.24 (s, 3H), 2.20 (s, 3H), 2.10 (s, 3H), 1.64-1.67 (m, 2H), 1.48-1.56 (m, 2H), 0.98 (t, 6H, J=7.2 Hz), 0.83 (t, 3H, J=6.8 Hz).

Example 95: (R)-4'-(((2,3-dihydroxypropyl)amino) methyl)-N-((4,6-dimethyl-2-oxo-1,2-dihydropyridin-3-yl) methyl)-5-(ethyl (tetrahydro-2H-pyran-4-yl) amino)-4-methyl-[1,1'-biphenyl]-3-carboxamide

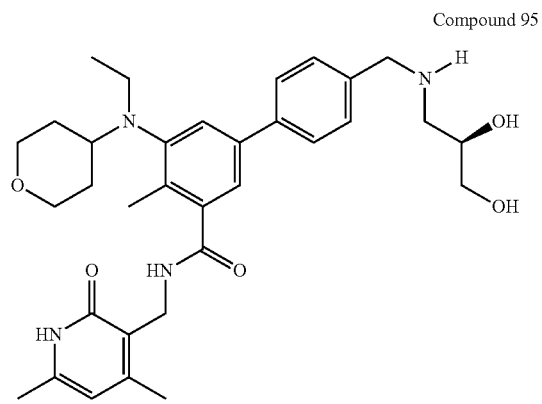 [SMILES: CCN(c1cc(-c2ccc(CNC[C@@H](O)CO)cc2)cc(C(=O)NCc2c(C)cc(C)[nH]c2=O)c1C)C1CCOCC1]

Compound 95

Analytical Data: LCMS: 599.35 (M+1)⁺; HPLC: 93.58% (@ 254 nm) (R$_t$; 3.808; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d6, 400 MHz) δ 11.45 (s, 1H), 8.18 (t, 1H, J=4.8 Hz), 7.56 (d, 2H, J=8 Hz), 7.37-7.39 (m, 3H), 7.16 (s, 1H), 5.85 (s, 1H), 4.51-4.56 (m, 2H), 4.28 (d, 2H, J=4.8 Hz), 3.81-3.84 (m, 2H), 3.73 (s, 2H), 3.55 (m, 1H), 3.11-3.25 (m, 3H), 3.01-3.09 (m, 3H), 2.56-2.61 (m, 1H), 2.41-2.46 (m, 2H), 2.24 (s, 3H), 2.20 (s, 3H), 2.15 (s, 3H), 1.65-1.67 (m, 2H), 1.48-1.56 (m, 2H), 0.83 (t, 3H, J=6.8 Hz).

Example 96: (S)-4'-(((2,3-dihydroxypropyl)amino) methyl)-N-((4,6-dimethyl-2-oxo-1,2-dihydropyridin-3-yl) methyl)-5-(ethyl (tetrahydro-2H-pyran-4-yl) amino)-4-methyl-[1,1'-biphenyl]-3-carboxamide

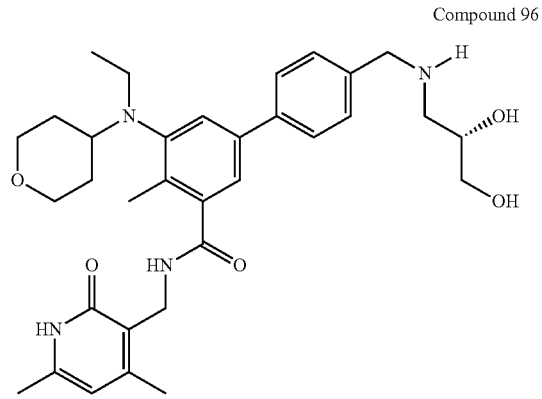 [SMILES: CCN(c1cc(-c2ccc(CNC[C@H](O)CO)cc2)cc(C(=O)NCc2c(C)cc(C)[nH]c2=O)c1C)C1CCOCC1]

Compound 96

Analytical Data: LCMS: 577.25 (M+1)⁺; HPLC: 96.96% (@ 254 nm) (R$_t$; 3.812; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d6, 400 MHz) δ 11.45 (s, 1H), 8.19 (t, 1H, J=4.8 Hz), 7.55 (d, 2H, J=8 Hz), 7.37-7.39 (m, 3H), 7.21 (s, 1H), 5.85 (s, 1H), 4.55 (m, 3H), 4.28 (d, 2H, J=4.8 Hz), 3.81-3.83 (m, 2H), 3.72 (s, 2H), 3.55 (bs, 1H), 3.22-3.28 (m, 3H), 3.01-3.11 (m, 3H), 2.57-2.60 (m, 1H), 2.41-2.45 (m, 2H), 2.24 (s, 3H), 2.20 (s, 3H), 2.10 (s, 3H), 1.64-1.67 (m, 2H), 1.51-1.56 (m, 2H), 0.83 (t, 3H, J=7.2 Hz).

Example 97: 4'-(((cyclopropylmethyl)(methyl)amino)methyl)-N-((4,6-dimethyl-2-oxo-1,2-dihydropyridin-3-yl)methyl)-5-(ethyl(tetrahydro-2H-pyran-4-yl)amino)-4-methyl-[1,1'-biphenyl]-3-carboxamide

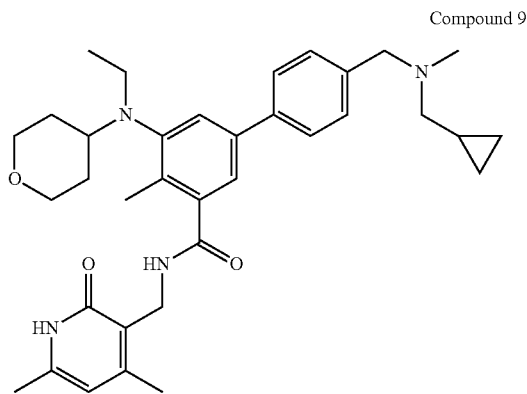

Compound 97

Analytical Data: LCMS: 571.40 (M+1)⁺; HPLC: 99.80% (@ 254 nm) (R$_t$; 4.243; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d6, 400 MHz) δ 11.45 (s, 1H), 8.18 (t, 1H, J=4.8 Hz), 7.57 (d, 2H, J=8 Hz), 7.40 (s, 1H), 7.37 (d, 2H, J=8 Hz), 7.22 (s, 1H), 5.85 (s, 1H), 4.28 (d, 2H, J=4.4 Hz), 3.81-3.83 (m, 2H), 3.53 (s, 2H), 3.11-3.25 (m, 2H), 2.99-3.09 (m, 3H), 2.25-2.32 (m, 2H), 2.24 (s, 3H), 2.20 (s, 6H), 2.10 (s, 3H), 1.65-1.67 (m, 2H), 1.48-1.56 (m, 2H), 0.88 (m, 1H), 0.83 (t, 3H, J=7.2 Hz), 0.46-0.47 (m, 2H), 0.081 (m, 2H).

Example 98: N-((4,6-dimethyl-2-oxo-1,2-dihydropyridin-3-yl) methyl)-5-(ethyl (tetrahydro-2H-pyran-4-yl) amino)-4-methyl-4'-(((2-hydroxyethyl)amino)methyl)-[1,1'-biphenyl]-3-carboxamide

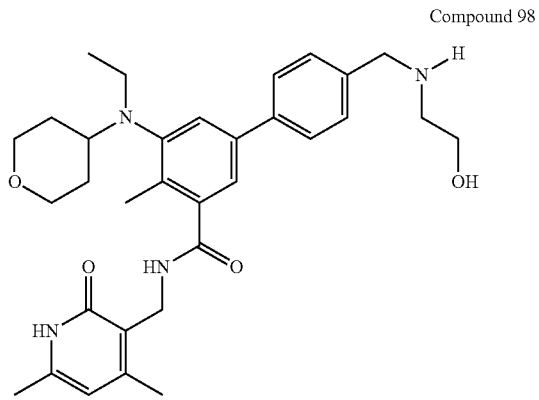 [SMILES: CCN(c1cc(-c2ccc(CNCCO)cc2)cc(C(=O)NCc2c(C)cc(C)[nH]c2=O)c1C)C1CCOCC1]

Compound 98

Analytical Data: LCMS: 547.35 (M+1)⁺; HPLC: 96.46% (@ 254 nm) (R$_t$; 3.862; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d₆, 400 MHz) δ 11.44 (s, 1H), 8.19 (t, 1H, J=4.4 Hz), 7.55 (d, 2H, J=8 Hz), 7.38 (d, 2H, J=4.4 Hz), 7.37 (s, 1H), 7.21 (s, 1H), 5.85 (s, 1H), 4.47 (bs, 2H), 4.28 (d, 2H, J=3.6 Hz), 3.81-3.83 (m, 2H), 3.72 (s, 2H), 3.46 (m, 2H), 3.22-3.27 (m, 2H), 3.07-3.09 (m, 2H), 3.01-3.06 (m, 1H), 2.55-2.57 (m, 2H), 2.23 (s, 3H), 2.20 (s, 3H), 2.10 (s, 3H), 1.64-1.67 (m, 2H), 1.51-1.53 (m, 2H), 0.83 (t, 3H, J=6.8 Hz).

Example 99: N-((4,6-dimethyl-2-oxo-1,2-dihydropyridin-3-yl) methyl)-5-(ethyl (tetrahydro-2H-pyran-4-yl) amino)-4-methyl-4'-(((3-hydroxypropyl)amino)methyl)-[1,1'-biphenyl]-3-carboxamide

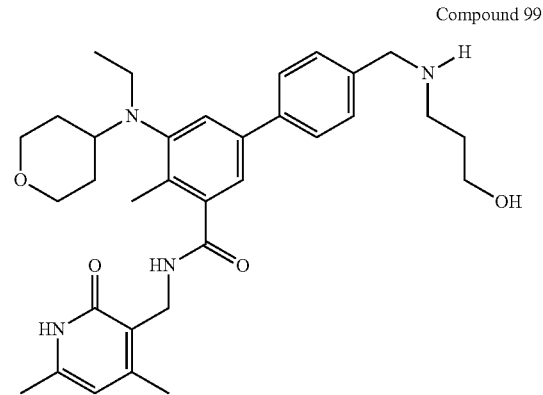 [SMILES: CCN(c1cc(-c2ccc(CNCCCO)cc2)cc(C(=O)NCc2c(C)cc(C)[nH]c2=O)c1C)C1CCOCC1]

Compound 99

Analytical Data: LCMS: 561.30 (M+1)⁺; HPLC: 96.82% (@ 254 nm) (R$_t$; 3.911; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d6, 400 MHz) δ 11.47 (s, 1H), 8.19 (t, 1H), 7.55 (d, 2H, J=7.6 Hz), 7.39 (d, 2H), 7.37 (s, 1H), 7.21 (s, 1H), 5.85 (s, 1H), 4.46 (bs, 1H), 4.28 (d, 2H, J=4.4 Hz), 3.81-3.83 (m, 2H), 3.69 (s, 2H), 3.45 (t, 2H, J=6.4 Hz), 3.22-3.27 (m, 2H), 3.07-3.09 (m, 2H), 3.01-3.06 (m, 1H), 2.23 (s, 3H), 2.20 (s, 3H), 2.14 (s, 3H), 1.64-1.67 (m, 2H), 1.51-1.61 (m, 4H), 0.83 (t, 3H, J=6.8 Hz) [1H merged in solvent peak].

Example 100: 4'-((bis(2-hydroxyethyl)amino)
methyl)-N-((4,6-dimethyl-2-oxo-1,2-dihydropyridin-
3-yl) methyl)-5-(ethyl (tetrahydro-2H-pyran-4-yl)
amino)-4-methyl-[1,1'-biphenyl]-3-carboxamide
TFA salt Compound 100

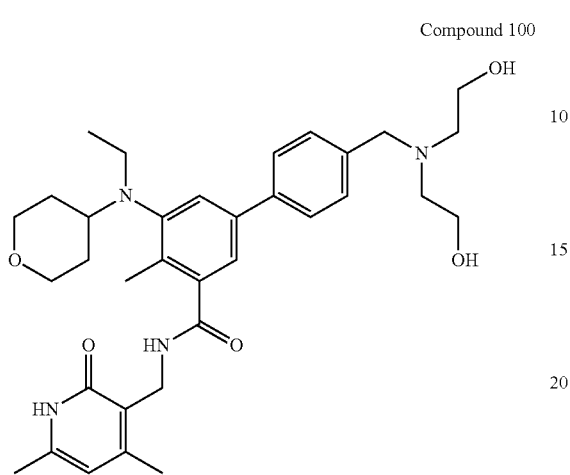

Analytical Data TFA salt: LCMS: 591.25 (M+1)+; HPLC: 99.00% (@ 254 nm) (R$_t$: 3.860; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.47 (s, 1H), 9.38 (s, 1H), 8.25 (s, 1H), 7.77 (d, 2H, J=3.2 Hz), 7.65 (s, 2H), 7.63 (s, 1H), 7.33 (s, 1H), 5.87 (s, 1H), 4.46 (s, 2H), 4.29 (d, 2H, J=4.8 Hz), 3.78-3.90 (m, 6H), 3.18-3.28 (m, 9H), 2.27 (s, 3H), 2.21 (s, 3H), 2.10 (s, 3H), 1.58-1.67 (m, 4H), 0.85 (t, 3H, J=6.8 Hz).

Example 101: 4'-(((2-aminoethyl)amino)methyl)-N-
((4,6-dimethyl-2-oxo-1,2-dihydropyridin-3-yl)
methyl)-5-(ethyl (tetrahydro-2H-pyran-4-yl) amino)-
4-methyl-[1,1'-biphenyl]-3-carboxamide Compound 101

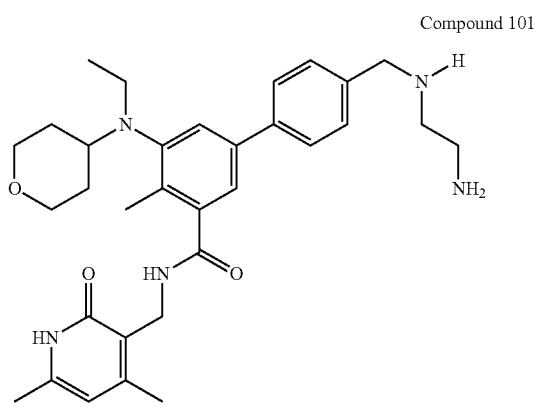 [SMILES: CCN(c1cc(-c2ccc(CNCCN)cc2)cc(C(=O)NCc2c(C)cc(C)[nH]c2=O)c1C)C1CCOCC1]

Analytical Data: LCMS: 546.35 (M+1)+; HPLC: 93.12% (@ 254 nm) (R$_t$: 3.721; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.47 (s, 1H), 9.19 (bs, 1H), 8.20 (t, 1H), 7.99 (bs, 2H), 7.74 (d, 2H, J=8 Hz), 7.57 (d, 2H, J=8 Hz), 7.42 (s, 1H), 7.26 (s, 1H), 5.86 (s, 1H), 4.26-4.29 (m, 3H), 3.82-3.84 (m, 2H), 3.11-3.27 (m, 8H), 3.03 (s, 2H), 2.24 (s, 3H), 2.21 (s, 3H), 2.10 (s, 3H), 1.64-1.67 (m, 2H), 1.55 (m, 2H), 0.83 (t, 3H, J=6 Hz).

Example 102: 4'-(((3-aminopropyl)amino)methyl)-
N-((4,6-dimethyl-2-oxo-1,2-dihydropyridin-3-yl)
methyl)-5-(ethyl (tetrahydro-2H-pyran-4-yl) amino)-
4-methyl-[1,1'-biphenyl]-3-carboxamide TFA salt Compound 102

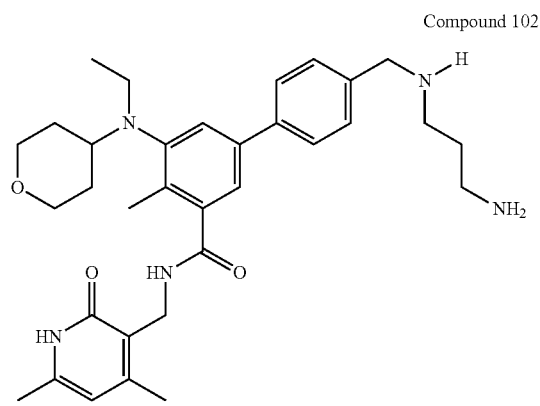 [SMILES: CCN(c1cc(-c2ccc(CNCCCN)cc2)cc(C(=O)NCc2c(C)cc(C)[nH]c2=O)c1C)C1CCOCC1]

Analytical Data TFA salt: LCMS: 560.20 (M+1)+; HPLC: 98.90% (@ 254 nm) (R$_t$: 3.611; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.48 (s, 1H), 8.93 (bs, 2H), 8.20 (t, 1H), 7.79 (bs, 2H), 7.73 (d, 2H, J=8 Hz), 7.55 (d, 2H, J=8 Hz), 7.43 (s, 1H), 7.27 (s, 1H), 5.87 (s, 1H), 4.28 (d, 2H, J=4.4 Hz), 4.19 (m, 2H), 3.81-3.85 (m, 2H), 3.25 (t, 2H, J=11.2 Hz), 3.11-3.16 (m, 3H), 3.01 (m, 3H), 2.87-2.88 (m, 1H), 2.24 (s, 3H), 2.21 (s, 3H), 2.10 (s, 3H), 1.89-1.92 (m, 2H), 1.65-1.68 (m, 2H), 1.53-1.55 (m, 2H), 0.83 (t, 3H, J=6.8 Hz).

Example 103: 4'-(((2,2-difluoroethyl)amino)
methyl)-N-((4,6-dimethyl-2-oxo-1,2-dihydropyridin-
3-yl) methyl)-5-(ethyl (tetrahydro-2H-pyran-4-yl)
amino)-4-methyl-[1,1'-biphenyl]-3-carboxamide Compound 103

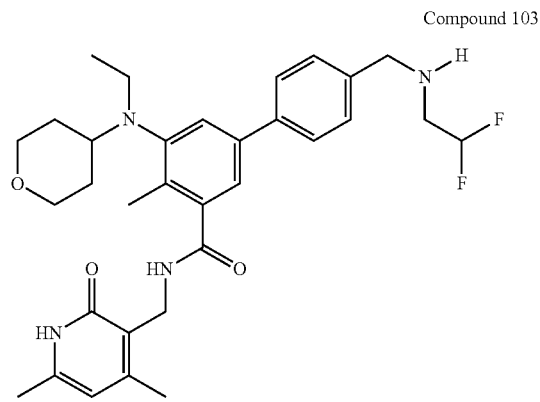 [SMILES: CCN(c1cc(-c2ccc(CNCC(F)F)cc2)cc(C(=O)NCc2c(C)cc(C)[nH]c2=O)c1C)C1CCOCC1]

Analytical Data: LCMS: 567.30 (M+1)⁺; HPLC: 92.86% (@ 254 nm) (R$_t$: 3.984; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.46 (s, 1H), 8.19 (t, 1H), 7.57 (d, 2H, J=7.2 Hz), 7.38-7.40 (m, 3H), 7.21 (s, 1H), 6.01 (t, 1H), 5.85 (s, 1H), 4.28 (d, 2H, J=4.4 Hz), 3.81-3.84 (m, 2H), 3.77 (s, 2H), 3.22-3.28 (m, 2H), 3.06-3.09 (m, 2H), 3.01 (m, 1H), 2.84 (t, 2H), 2.24 (s, 3H), 2.20 (s, 3H), 2.10 (s, 3H), 1.65-1.67 (m, 2H), 1.51-1.53 (m, 2H), 0.83 (t, 3H, J=6.8 Hz).

Example 104: N-((4,6-dimethyl-2-oxo-1,2-dihydropyridin-3-yl) methyl)-5-(ethyl (tetrahydro-2H-pyran-4-yl) amino)-4-methyl-4'-(((2,2,2-trifluoroethyl)amino)methyl)-[1,1'-biphenyl]-3-carboxamide Compound 104

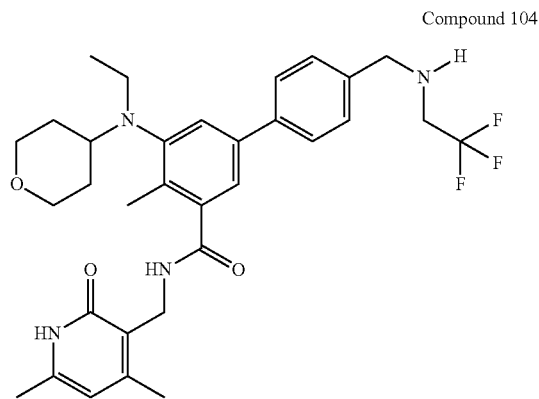 [SMILES: CCN(c1cc(-c2ccc(CNCC(F)(F)F)cc2)cc(C(=O)NCc2c(C)cc(C)[nH]c2=O)c1C)C1CCOCC1]

Analytical Data: LCMS: 585.25 (M+1)⁺; HPLC: 99.52% (@ 254 nm) (R$_t$: 4.175; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.46 (s, 1H), 8.19 (t, 1H), 7.58 (d, 2H, J=8 Hz), 7.39-7.40 (m, 3H), 7.21 (s, 1H), 5.85 (s, 1H), 4.28 (d, 2H, J=4.4 Hz), 3.80-3.83 (m, 4H), 2.93-3.27 (m, 8H), 2.24 (s, 3H), 2.20 (s, 3H), 2.10 (s, 3H), 1.64-1.67 (m, 2H), 1.51-1.53 (m, 2H), 0.83 (t, 3H, J=6.8 Hz).

Example 105: 4'-(2-oxa-6-azaspiro[3.3]heptan-6-ylmethyl)-N-((4,6-dimethyl-2-oxo-1,2-dihydropyridin-3-yl) methyl)-5-(ethyl (tetrahydro-2H-pyran-4-yl) amino)-4-methyl-[1,1'-biphenyl]-3-carboxamide Compound 105

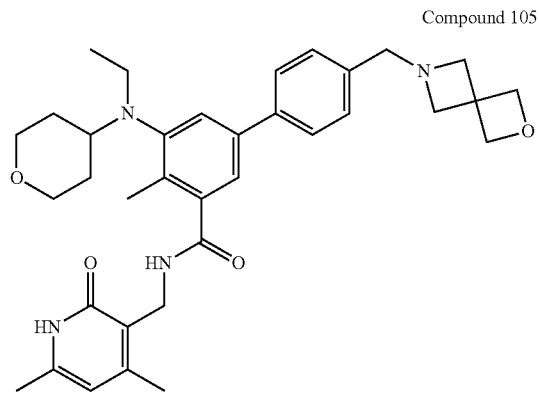 [SMILES: CCN(c1cc(-c2ccc(CN3CC4(COC4)C3)cc2)cc(C(=O)NCc2c(C)cc(C)[nH]c2=O)c1C)C1CCOCC1]

Analytical Data: LCMS: 585.40 (M+1)⁺; HPLC: 99.67% (@ 254 nm) (R$_t$: 3.99; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (bs, 1H), 8.18 (s, 1H), 7.55-7.54 (m, 2H), 7.38 (s, 1H), 7.31-7.29 (m, 2H), 7.20 (s, 1H), 5.85 (s, 1H), 4.60 (s, 3H), 4.28 (d, 2H, J=4.8 Hz), 3.83-3.81 (m, 2H), 3.53 (s, 2H), 3.83-3.81 (m, 2H), 3.32 (2 Protons merged in solvent peak), 3.24-3.22 (m, 4H), 3.09-3.01 (m, 3H), 2.24 (s, 3H), 2.20 (s, 3H), 2.10 (s, 3H), 1.67-1.64 (m, 2H), 1.53-1.51 (m, 2H), 0.83 (t, 3H J=6.4 Hz).

Example 108: Synthesis of 5-(((1r,4r)-4-aminocyclohexyl)(methyl)amino)-N-((4,6-dimethyl-2-oxo-1, 2-dihydropyridin-3-yl)methyl)-4'-((dimethylamino) methyl)-4-methyl-[1,1'-biphenyl]-3-carboxamide Compound 108

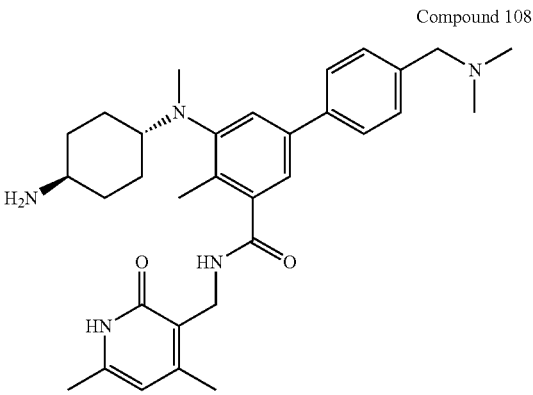 [SMILES: Cc1cc(C)c(CNC(=O)c2cc(-c3ccc(CN(C)C)cc3)cc(N(C)[C@H]3CC[C@H](N)CC3)c2C)c(=O)[nH]1]

Step 1: Synthesis of tert-butyl ((1r,4r)-4-((5-(((4,6-dimethyl-2-oxo-1,2-dihydropyridin-3-yl)methyl) carbamoyl)-4'-((dimethylamino)methyl)-4-methyl-[1,1'-biphenyl]-3-yl)(methyl)amino)cyclohexyl) carbamate To a stirred solution of tert-butyl ((1r,4r)-4-((5-bromo-3-(((4,6-dimethyl-2-oxo-1,2-dihydropyridin-3-yl)methyl)carbamoyl)-2-methylphenyl)(methyl)amino)-cyclohexyl)carbamate (1 equiv.) and N,N-dimethyl-1-(4-(4,4,5,5-tetramethyl-1,3,2-dioxaborolan-2-yl)phenyl)methanamine (1.2 equiv.) in dioxane/water mixture (5 mL+1 mL), Na$_2$CO$_3$ (3.6 equiv.) was added and solution purged with argon for 15 min. Then Pd(PPh$_3$)$_4$ (0.1 equiv.) was added and the reaction flask was purged again for 10 min. with argon. The reaction mixture was heated at 100° C. for 4 h. The reaction mixture was diluted with water and extracted with 10% MeOH/DCM. The combined organic extracts were dried over Na$_2$SO$_4$ and the solvent removed under reduced pressure to afford the crude product which was purified by column chromatography over silica gel to afford tert-butyl ((1r,4r)-4-((5-(((4,6-dimethyl-2-oxo-1,2-dihydropyridin-3-yl)methyl)carbamoyl)-4'-((dimethylamino) methyl)-4-methyl-[1,1'-biphenyl]-3-yl)(methyl)amino)cyclohexyl)carbamate (0.08 g, 48.78%)

Step 2: Synthesis of 5-(((1r,4r)-4-aminocyclohexyl) (methyl)amino)-N-((4,6-dimethyl-2-oxo-1,2-dihydropyridin-3-yl)methyl)-4'-((dimethylamino) methyl)-4-methyl-[1,1'-biphenyl]-3-carboxamide A stirred solution of tert-butyl ((1r,4r)-4-((5-(((4,6-dimethyl-2-oxo-1,2-dihydropyridin-3-yl)methyl)carbamoyl)-4'-

((dimethylamino)methyl)-4-methyl-[1,1'-biphenyl]-3-yl) (methyl)amino)cyclohexyl)carbamate (0.08 g) in DCM (5 mL) was cooled to 0° C. and TFA (2 mL) was added. The reaction mixture was stirred at room temperature for 1 h. The reaction was concentrated to dryness yielding the title compound as a TFA salt (0.06 g, 89.55%). LCMS: 530.35 (M+1)$^+$; HPLC: 89.74% (@ 254 nm) (R$_t$; 3.557; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (s, 1H), 9.74 (bs, 1H), 8.17 (t, 1H), 7.74-7.76 (m, 4H), 7.55 (d, 2H, J=7.6 Hz), 7.36 (s, 1H), 7.22 (s, 1H), 5.86 (s, 1H), 4.28-4.31 (m, 4H), 2.97 (bs, 1H), 2.74 (d, 6H, J=4.4 Hz), 2.66 (s, 3H), 2.20 (d, 6H, J=2 Hz), 2.10 (s, 3H), 1.92-1.95 (m, 2H), 1.74-1.77 (m, 2H), 1.52-1.57 (m, 2H), 1.28-1.30 (m, 2H) [1H merged in solvent peak].

Example 109: Synthesis of N-((4,6-dimethyl-2-oxo-1,2-dihydropyridin-3-yl)methyl)-3-(ethyl(tetrahydro-2H-pyran-4-yl)amino)-2-methyl-5-(1-methyl-1H-pyrazol-4-yl)benzamide

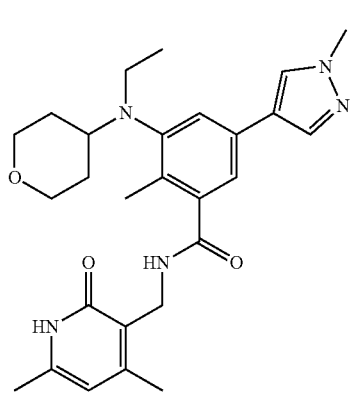

Compound 109

To a stirred solution of 5-bromo-N-((4,6-dimethyl-2-oxo-1,2-dihydropyridin-3-yl)methyl)-3-(ethyl(tetrahydro-2H-pyran-4-yl)amino)-2-methylbenzamide (0.2 g, 0.42 mmol) and (1-methyl-1H-pyrazol-4-yl)boronic acid (0.105 g, 0.505 mmol) in dioxane/water mixture (5 mL+1 mL), Na$_2$CO$_3$ (0.16 g, 1.51 mmol) was added and solution purged with argon for 15 min. Pd (PPh$_3$)$_4$ (0.048 g, 0.042 mmol) was then added and the reaction mixture again purged with argon for 10 min. The reaction mixture was heated at 100° C. for 2 h. The reaction mixture was then diluted with water and extracted with 10% MeOH/DCM. The combined extracts were dried over Na$_2$SO$_4$ and the solvent removed under reduced pressure to afford the crude product which was purified by column chromatography to afford the title compound (0.100 g, 50%). LCMS: 478.20 (M+1)$^+$; HPLC: 95.82% (@ 254 nm) (R$_t$; 4.322; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (s, 1H), 8.12 (s, 1H), 8.10 (t, 1H), 7.81 (s, 1H), 7.33 (s, 1H), 7.13 (s, 1H), 5.86 (s, 1H), 4.27 (d, 2H, J=4.8 Hz), 3.81-3.83 (m, 5H), 3.21-3.26 (m, 2H), 2.98-3.08 (m, 3H), 2.20 (s, 3H), 2.17 (s, 3H), 2.10 (s, 3H), 1.63-1.66 (m, 2H), 1.48-1.52 (m, 2H), 0.86 (t, 3H, J=7.2 Hz).

Example 110: Synthesis of N-((4,6-dimethyl-2-oxo-1,2-dihydropyridin-3-yl)methyl)-5-(6-((dimethylamino)methyl)pyridin-3-yl)-3-(ethyl(tetrahydro-2H-pyran-4-yl)amino)-2-methylbenzamide

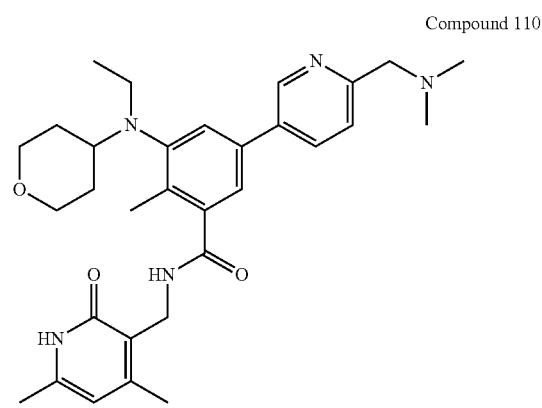 [SMILES: CCN(c1cc(-c2ccc(CN(C)C)nc2)cc(C(=O)NCc2c(C)cc(C)[nH]c2=O)c1C)C1CCOCC1]

Compound 110

Step 1: Synthesis of N-((4,6-dimethyl-2-oxo-1,2-dihydropyridin-3-yl)methyl)-3-(ethyl(tetrahydro-2H-pyran-4-yl)amino)-5-(6-formylpyridin-3-yl)-2-methylbenzamide To a stirred solution of 5-bromo-N-((4,6-dimethyl-2-oxo-1,2-dihydropyridin-3-yl)methyl)-3-(ethyl(tetrahydro-2H-pyran-4-yl)amino)-2-methylbenzamide (1 g, 2.15 mmol) and (6-formylpyridin-3-yl) boronic acid (0.539 g, 2.31 mmol) in dioxane/water mixture (15 mL+3 mL), Na$_2$CO$_3$ (0.82 g, 7.74 mmol) was added and solution purged with argon for 15 min. Then Pd (PPh$_3$)$_4$ (0.288 g, 0.25 mmol) was added and argon was purged again for 10 min. Reaction mass was heated at 80° C. for 2 h. On completion, reaction mixture was diluted with water and extracted with 10% MeOH/DCM. Combined organic layers were dried over Na$_2$SO$_4$ and solvent removed under reduced pressure to afford crude material which was purified by column chromatography over silica gel to afford the desired compound (0.60 g, 57%).

Step 2: Synthesis of N-((4,6-dimethyl-2-oxo-1,2-dihydropyridin-3-yl)methyl)-5-(6-((dimethylamino)methyl)pyridin-3-yl)-3-(ethyl(tetrahydro-2H-pyran-4-yl)amino)-2-methylbenzamide To a stirred solution of N-((4,6-dimethyl-2-oxo-1,2-dihydropyridin-3-yl)methyl)-3-(ethyl(tetrahydro-2H-pyran-4-yl)amino)-5-(6-formylpyridin-3-yl)-2-methylbenzamide (0.102 g, 0.203 mmol) and dimethylamine (0.044 g, 2M 0.507 mL, 1.01 mmol) in dichloroethane (3 mL), acetic acid (0.073 g, 1.021 mmol) was added and reaction stirred at room temperature for 20 minutes. Then sodium triacetoxyborohydride (0.129 g, 0.609 mmol) was added at 0° C. and reaction stirred for 4 h at room temperature. On completion, solvent was removed under reduced pressure and water was added, extraction was carried out using 10% MeOH/DCM. Combined organic layers were dried over sodium sulphate and concentrated under reduced pressure giving crude material which was purified by column chromatography to afford the title compound (0.08 g, 75%). LCMS: 532.30 (M+1)+; HPLC: 97.53% (@ 254 nm) (R,: 3.878; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.46 (s, 1H), 8.75 (d, 1H, J=1.2 Hz), 8.20 (t, 1H, J=4.8 Hz), 8.02 (d, 1H, J=6.4 Hz), 7.49 (s, 1H), 7.47 (s, 1H), 7.27 (s, 1H), 5.87 (s, 1H), 4.28 (d, 2H, J=4.8 Hz), 3.81-3.84 (m, 2H), 3.56 (s, 2H), 3.22-3.24 (m, 2H), 3.02-3.12 (m, 3H), 2.25 (s, 3H), 2.21 (s, 6H), 2.20 (s, 3H), 2.10 (s, 3H), 1.65-1.67 (m, 2H), 1.50-1.56 (m, 2H), 0.82 (t, 3H, J=6.8 Hz).

Example 111: Synthesis of N-((4,6-dimethyl-2-oxo-1,2-dihydropyridin-3-yl) methyl)-3-(ethyl (tetrahydro-2H-pyran-4-yl) amino)-2-methyl-5-(6-((4-methylpiperazin-1-yl) methyl) pyridin-3-yl) benzamide

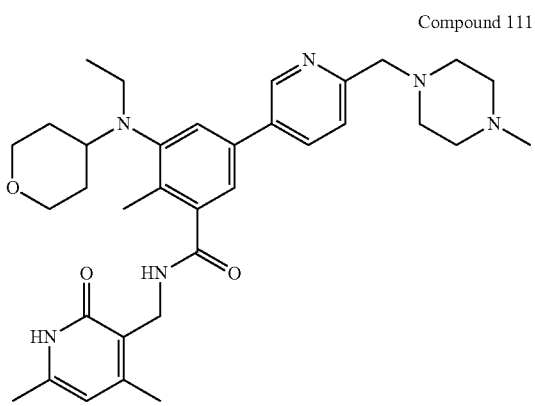 [SMILES: CCN(c1cc(-c2ccc(CN3CCN(C)CC3)nc2)cc(C(=O)NCc2c(C)cc(C)[nH]c2=O)c1C)C1CCOCC1]

Compound 111

Step 1a: Synthesis of N-((4,6-dimethyl-2-oxo-1,2-dihydropyridin-3-yl) methyl)-3-(ethyl (tetrahydro-2H-pyran-4-yl) amino)-5-(6-formylpyridin-3-yl)-2-methylbenzamide

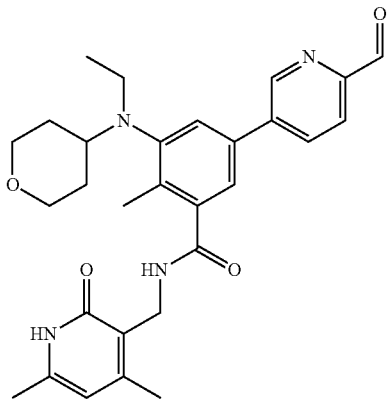 [SMILES: CCN(c1cc(-c2ccc(C=O)nc2)cc(C(=O)NCc2c(C)cc(C)[nH]c2=O)c1C)C1CCOCC1]

To a stirred solution of 5-bromo-N-((4,6-dimethyl-2-oxo-1,2-dihydropyridin-3-yl) methyl)-3-(ethyl (tetrahydro-2H-pyran-4-yl) amino)-2-methylbenzamide (1 g, 2.15 mmol) and (6-formylpyridin-3-yl) boronic acid (0.539 g, 2.31 mmol) in dioxane/water mixture (15 mL+3 mL), Na$_2$CO$_3$ (0.82 g, 7.74 mmol) was added and solution purged with argon for 15 min. Then Pd (PPh$_3$)$_4$ (0.288 g, 0.25 mmol) was added and argon was purged again for 10 min. Reaction mass was heated at 80° C. for 2 h. On completion, reaction mixture was diluted with water and extracted with 10% MeOH/DCM. Combined organic layers were dried over Na$_2$SO$_4$ and solvent removed under reduced pressure to afford crude material which was purified by column chromatography over silica gel to afford the desired compound (0.60 g, 57%).

Step 1b: N-((4,6-dimethyl-2-oxo-1,2-dihydropyridin-3-yl)methyl)-3-(ethyl(tetrahydro-2H-pyran-4-yl)amino)-5-(6-(hydroxymethyl)pyridin-3-yl)-2-methylbenzamide

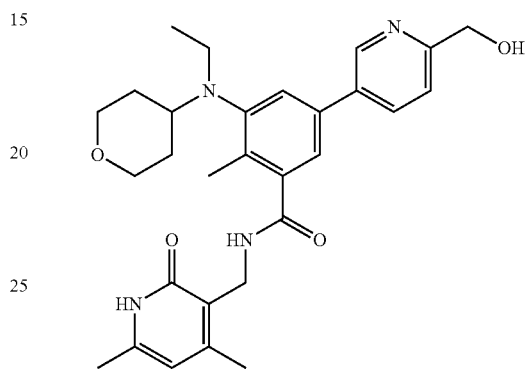

When the above reaction was repeated on a 1.5 g scale, N-((4,6-dimethyl-2-oxo-1,2-dihydropyridin-3-yl)methyl)-3-(ethyl(tetrahydro-2H-pyran-4-yl)amino)-5-(6-(hydroxymethyl)pyridin-3-yl)-2-methylbenzamide was isolated (0.350 g, 22%).

Step 2: Synthesis of 5-(6-(bromomethyl) pyridin-3-yl)-N-((4,6-dimethyl-2-oxo-1,2-dihydropyridin-3-yl) methyl)-3-(ethyl (tetrahydro-2H-pyran-4-yl) amino)-2-methylbenzamide

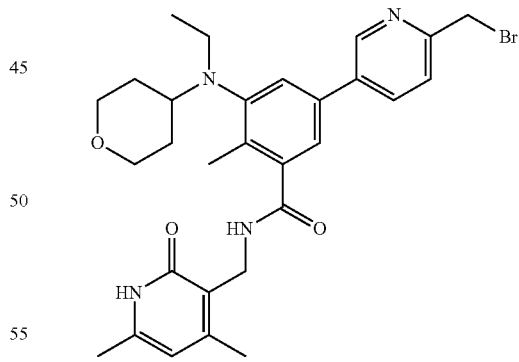

To a stirred solution of N-((4,6-dimethyl-2-oxo-1,2-dihydropyridin-3-yl)methyl)-3-(ethyl(tetrahydro-2H-pyran-4-yl) amino)-5-(6-(hydroxymethyl)pyridin-3-yl)-2-methylbenzamide (0.35 g, 0.694 mmol) in DCM (5 mL), triphenyl phosphine (0.361 g, 1.38 mmol) was added and stirred it at room temperature for 10 min. Finally CBr$_4$ (0.318 g, 1.38 mmol) was added portion wise to it and resulting solution was stirred at room temperature for 18 h. On completion, water was added to the reaction mass and extraction was carried out using DCM. Combined organic layers were dried over sodium sulphate, concentrated under reduced pressure to give crude material which then column purification gave desired compound (0.35 g, 89%).

Step 3: Synthesis of N-((4,6-dimethyl-2-oxo-1,2-dihydropyridin-3-yl) methyl)-3-(ethyl (tetrahydro-2H-pyran-4-yl) amino)-2-methyl-5-(6-((4-methyl-piperazin-1-yl) methyl) pyridin-3-yl) benzamide To stirred solution of 5-(6-(bromomethyl) pyridin-3-yl)-N-((4,6-dimethyl-2-oxo-1,2-dihydropyridin-3-yl) methyl)-3-(ethyl (tetrahydro-2H-pyran-4-yl) amino)-2-methylbenzamide (0.175 g, 0.309 mmol) dissolved in THF (2 mL), was added 1-methyl-piperazine (0.309 g, 1.54 mmol) at room temperature and stirred at the same temperature for 18 h. On completion, water was added to the reaction mass and extraction was carried out using DCM. Combined organic layers were dried over sodium sulphate and concentrated under reduced pressure giving crude material which then purified by preparative HPLC to give the title compound as a TFA salt (0.028 g, 15%). LCMS: 587.40 (M+1)$^+$; HPLC: 98.05% (@ 254 nm) (R$_t$: 3.831; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.46 (s, 1H), 8.89 (s, 1H), 8.21 (d, 2H, J=7.6 Hz), 7.59 (d, 2H, J=7.6 Hz), 7.35 (s, 1H), 5.87 (s, 1H), 4.29 (d, 2H, J=4 Hz), 3.96-4.04 (m, 2H), 3.83-3.86 (m, 2H), 3.16-3.43 (m, 13H), 2.81 (s, 3H), 2.27 (s, 3H), 2.21 (s, 3H), 2.10 (s, 3H), 1.67 (m, 2H), 1.56 (m, 2H), 0.84 (t, 3H, J=6.4 Hz).

Example 112: Synthesis of N-((4,6-dimethyl-2-oxo-1,2-dihydropyridin-3-yl)methyl)-5-(ethyl(tetrahydro-2H-pyran-4-yl)amino)-4,4'-dimethyl-[1,1'-biphenyl]-3-carboxamide

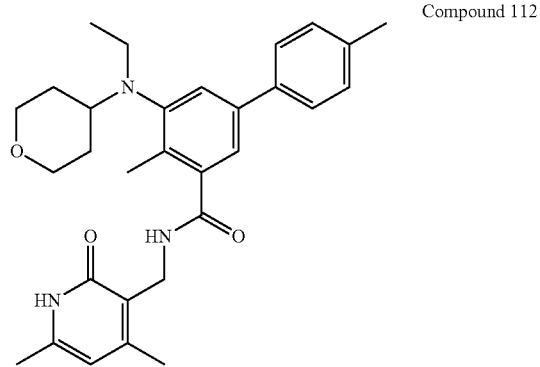 [SMILES: CCN(c1cc(-c2ccc(C)cc2)cc(C(=O)NCc2c(C)cc(C)[nH]c2=O)c1C)C1CCOCC1]

Compound 112

To a stirred solution 5-bromo-N-((4,6-dimethyl-2-oxo-1, 2-dihydropyridin-3-yl) methyl)-3-(ethyl (tetrahydro-2H-pyran-4-yl) amino)-2-methylbenzamide (200 mg, 0.42 mmol) and p-tolyl boronic acid (86 mg, 0.63 mmol) in dioxane (3 mL), aqueous 2M Na$_2$CO$_3$ solution (0.75 mL, 1.51 mmol) was added and solution was purged with argon for 15 min. Then Pd(PPh$_3$)$_4$ (48 mg, 0.04 mmol) was added and argon was purged again for 15 min. Reaction mass was heated at 100° C. for 2 h. On completion, reaction mixture was diluted with water and extracted with 10% MeOH/DCM (3 times). Combined organic layer was dried over sodium sulphate. Removal of the solvent under reduced pressure followed by column chromatographic purification afforded the title compound (150 mg, 73%). LCMS: 488.20 (M+1)$^+$; HPLC: 99.33% (@ 254 nm) (R$_t$: 5.393; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.46 (s, 1H), 8.19 (t, 1H), 7.51 (d, 2H, J=8 Hz), 7.37 (s, 1H), 7.25 (d, 2H, J=8 Hz), 7.19 (s, 1H), 5.85 (s, 1H), 4.28 (d, 2H, J=4.4 Hz), 3.81-3.83 (m, 2H), 3.22-3.27 (m, 2H), 3.07-3.09 (m, 2H), 3.01 (m, 1H), 2.33 (s, 3H), 2.23 (s, 3H), 2.20 (s, 3H), 2.10 (s, 3H), 1.64-1.67 (m, 2H), 1.51-1.55 (m, 2H), 0.82 (t, 3H, J=6.8 Hz).

Example 113: Synthesis of N-((4,6-dimethyl-2-oxo-1,2-dihydropyridin-3-yl)methyl)-5-(ethyl(tetrahydro-2H-pyran-4-yl)amino)-4'-(hydroxymethyl)-4-methyl-[1,1'-biphenyl]-3-carboxamide

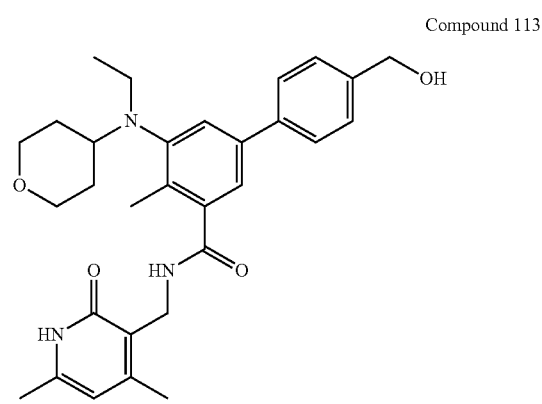 [SMILES: CCN(c1cc(-c2ccc(CO)cc2)cc(C(=O)NCc2c(C)cc(C)[nH]c2=O)c1C)C1CCOCC1]

Compound 113

To a stirred solution of 5-bromo-N-((4,6-dimethyl-2-oxo-1,2-dihydropyridin-3-yl)methyl)-3-(ethyl(tetrahydro-2H-pyran-4-yl)amino)-2-methylbenzamide (200 mg, 0.42 mmol) and 4-(hydroxymethyl)phenylboronic acid (96 mg, 0.63 mmol) in dioxane (2.5 mL), aqueous 2M Na$_2$CO$_3$ solution (0.75 mL, 1.51 mmol) was added and solution was purged with argon for 15 min. Then Pd(PPh$_3$)$_4$ (48 mg, 0.04 mmol) was added and argon was purged again for 15 min. Reaction mass was heated at 100° C. for 4 h. On completion, reaction mixture was diluted with water and extracted with 10% MeOH/DCM (3 times). Combined organic layer was dried over sodium sulphate. Removal of the solvent under reduced pressure followed by column chromatographic purification afforded the title compound (130 mg, 62%). LCMS: 504.15 (M+1)$^+$; HPLC: 98.86% (@ 254 nm) (R$_t$: 4.240; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.19 (t, 1H), 7.57 (d, 2H, J=7.2 Hz), 7.39 (s, 1H), 7.37 (d, 2H), 7.21 (s, 1H), 5.85 (s, 1H), 5.20 (t, 1H, J=5.2 Hz), 4.52 (d, 2H, J=5.6 Hz), 4.28 (d, 2H, J=3.6 Hz), 3.81-3.84 (m, 2H), 3.22-3.32 (m, 2H), 3.08-3.09 (m, 2H), 3.01 (m, 1H), 2.24 (s, 3H), 2.20 (s, 3H), 2.10 (s, 3H), 1.65-1.67 (m, 2H), 1.51-1.53 (m, 2H), 0.83 (t, 3H, J=6.4 Hz).

Example 114: Synthesis of N-((4,6-dimethyl-2-oxo-1,2-dihydropyridin-3-yl)methyl)-5-(ethyl(tetrahydro-2H-pyran-4-yl)amino)-4-methyl-3'-(morpholinomethyl)-[1,1'-biphenyl]-3-carboxamide Compound 114

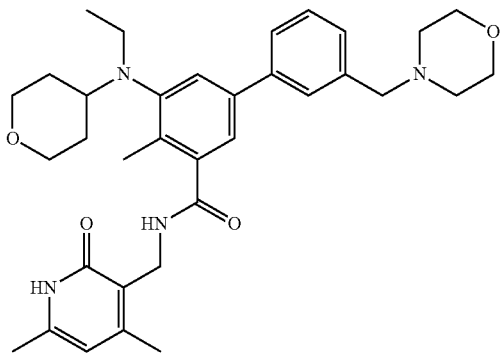

Step 1: Synthesis of N-((4,6-dimethyl-2-oxo-1,2-dihydropyridin-3-yl)methyl)-5-(ethyl(tetrahydro-2H-pyran-4-yl)amino)-3'-formyl-4-methyl-[1,1'-biphenyl]-3-carboxamide To a stirred solution of 5-bromo-N-((4,6-dimethyl-2-oxo-1,2-dihydropyridin-3-yl)methyl)-3-(ethyl(tetrahydro-2H-pyran-4-yl)amino)-2-methylbenzamide (400 mg, 0.84 mmol) and (3-formylphenyl)boronic acid (189 mg, 1.26 mmol) in dioxane (2 mL), aqueous 2M Na$_2$CO$_3$ solution (1.5 mL, 3.03 mmol) was added and solution was purged with argon for 15 min. Then Pd(PPh$_3$)$_4$ (97 mg, 0.08 mmol) was added and argon was purged again for 15 min. Reaction mass was heated at 100° C. for 4 h. On completion, reaction mixture was diluted with water and extracted with 10% MeOH/DCM (3 times). Combined organic layer was dried over sodium sulphate. Removal of the solvent under reduced pressure followed by column chromatographic purification afforded the title compound (270 mg, 64%).

Step 2: Synthesis of N-((4,6-dimethyl-2-oxo-1,2-dihydropyridin-3-yl)methyl)-5-(ethyl(tetrahydro-2H-pyran-4-yl)amino)-4-methyl-3'-(morpholinomethyl)-[1,1'-biphenyl]-3-carboxamide To a stirred solution of N-((4,6-dimethyl-2-oxo-1,2-dihydropyridin-3-yl)methyl)-5-(ethyl(tetrahydro-2H-pyran-4-yl)amino)-3'-formyl-4-methyl-[1,1'-biphenyl]-3-carboxamide (270 mg, 0.53 mmol) and morpholine (94 mg, 1.07 mmol) in dichloroethane (5 mL), acetic acid (194 mg, 3.23 mmol) was added and reaction stirred at room temperature for 30 minutes. Then sodium triacetoxyborohydride (343 mg, 1.61 mmol) was added to the reaction mixture at 0° C., allowed to attain room temperature and stirring continued for overnight. On completion, reaction mixture was diluted with dichloromethane, washed with water, saturated aqueous sodium bicarbonate solution and dried over sodium sulphate. Removal of the solvent under reduced pressure followed by column chromatographic purification afforded the title compound (200 mg, 65%). LCMS: 573.25 (M+1)$^+$; HPLC: 90.21% (@ 254 nm) (R$_t$; 4.048; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.20 (t, 1H), 7.52 (s, 1H), 7.49 (d, 2H, J=7.6 Hz), 7.39 (d, 1H, J=5.6 Hz), 7.29 (d, 1H, J=7.2 Hz), 7.20 (s, 1H), 5.85 (s, 1H), 4.28 (d, 2H, J=4.4 Hz), 3.82-3.84 (m, 2H), 3.56 (m, 4H), 3.52 (s, 2H), 3.22-3.30 (m, 2H), 3.08-3.10 (m, 2H), 3.01 (m, 1H), 2.37 (s, 4H), 2.24 (s, 3H), 2.20 (s, 3H), 2.10 (s, 3H), 1.65-1.67 (m, 2H), 1.51-1.54 (m, 2H), 0.83 (t, 3H, J=6.4 Hz).

Example 115: N-((4,6-dimethyl-2-oxo-1,2-dihydropyridin-3-yl)methyl)-5-(ethyl(tetrahydro-2H-pyran-4-yl)amino)-4-methyl-4'-((3-(morpholinomethyl)azetidin-1-yl)methyl)-[1,1'-biphenyl]-3-carboxamide Compound 115

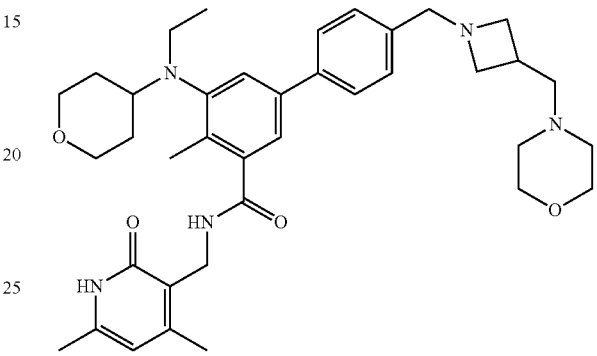

Compound 115 was prepared with the method similar to that described in Example 67. Analytical Data: LCMS: 642.45 (M+1)$^+$; HPLC: 93.13% (@ 254 nm) (R$_t$; 3.803; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.18 (t, 1H), 7.54 (d, 2H, J=7.6 Hz), 7.38 (s, 1H), 7.31 (d, 2H, J=7.6 Hz), 7.20 (s, 1H), 5.85 (s, 1H), 4.28 (d, 2H, J=4 Hz), 3.81-3.83 (m, 2H), 3.52-3.53 (m, 6H), 3.22-3.24 (m, 2H), 3.07-3.09 (m, 2H), 3.01 (m, 1H), 2.79 (s, 2H), 2.56-2.58 (m, 2H), 2.29 (m, 2H), 2.28 (s, 3H), 2.23 (s, 3H), 2.20 (s, 3H), 2.10 (s, 3H), 1.64-1.67 (m, 2H), 1.51-1.53 (m, 2H), 0.82 (t, 3H, J=6.8 Hz).

Example 116: Synthesis of N-((4,6-dimethyl-2-oxo-1,2-dihydropyridin-3-yl)methyl)-4-methyl-4'-(morpholinomethyl)-5-((tetrahydro-2H-pyran-4-yl)amino)-[1,1'-biphenyl]-3-carboxamide Compound 116

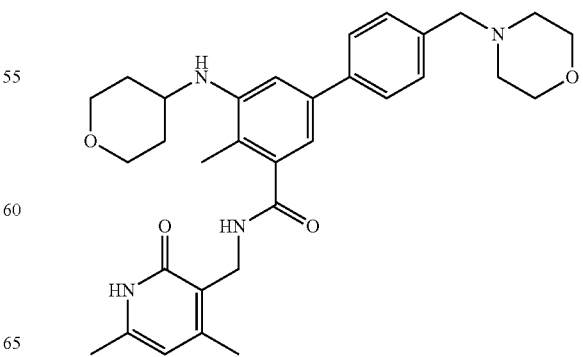

Step 1: Synthesis of methyl 4-methyl-4'-(morpholinomethyl)-5-((tetrahydro-2H-pyran-4-yl)amino)-[1,1'-biphenyl]-3-carboxylate To a stirred solution of methyl 5-bromo-2-methyl-3-((tetrahydro-2H-pyran-4-yl)amino)benzoate (600 mg, 1.83 mmol) and 4-[4-(4,4,5,5-tetramethyl-1,3,2-dioxaborolan-2-yl)benzyl]morpholine (833 mg, 2.75 mmol) in dioxane (9 mL), aqueous 2M Na$_2$CO$_3$ solution (3.30 mL, 6.60 mmol) was added and solution was purged with argon for 15 min. Then Pd(PPh$_3$)$_4$ (211 mg, 0.18 mmol) was added and argon was purged again for 15 min. Reaction mass was heated at 100° C. for 4 h. On completion, reaction mixture was diluted with water and extracted with 10% MeOH/DCM (3 times). Combined organic layer was dried over sodium sulphate. Removal of the solvent under reduced pressure followed by column chromatographic purification afforded the title compound (500 mg, 77%).

Step 2: Synthesis of N-((4,6-dimethyl-2-oxo-1,2-dihydropyridin-3-yl)methyl)-4-methyl-4'-(morpholinomethyl)-5-((tetrahydro-2H-pyran-4-yl)amino)-[1,1'-biphenyl]-3-carboxamide Aqueous NaOH (73 m g, 1.76 mmol) was added to a stirred solution of methyl 4-methyl-4'-(morpholinomethyl)-5-((tetrahydro-2H-pyran-4-yl)amino)-[1,1'-biphenyl]-3-carboxylate (500 mg, 1.17 mmol) in ethanol (10 mL) and stirring continued at 60° C. for 1 h. After completion, ethanol was removed under reduced pressure and acidified using dilute HCl up to pH 6. Aqueous layer was extracted ethyl acetate (5 times) and the combined organic layer was dried over sodium sulphate. Removal of the solvent under reduced pressure afforded respective acid (350 mg, 72.4%).

To an stirred ice cooled solution of above acid (200 mg, 0.48 mmol) in DMF (10 mL) EDCI (139 mg, 0.73 mmol) and triethylamine (0.17 mL, 1.21 mmol) were added. Then after 15 minutes interval of stirring at 0° C., HOBT (78 mg, 0.58 mmol) followed by 3-(amino methyl)-4,6-dimethylpyridin-2(1H)-one (148 mg, 0.97 mmol) were added. Reaction mixture was allowed to attain room temperature and stirring continued for overnight. On completion, the reaction mass was poured into ice, extracted with 10% MeOH/DCM (5 times). Combined organic layer was washed with water and dried over sodium sulphate. Removal of the solvent under reduced pressure followed by solvent washings afforded the title compound (50 mg, 19%). LCMS: 545.15 (M+1)$^+$; HPLC: 95.86% (@ 254 nm) (R$_t$: 4.382; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.03 (m, 1H), 7.71 (bs, 1H), 7.54 (d, 1H, J=7.6 Hz), 7.34 (d, 2H, J=7.6 Hz), 6.85 (s, 1H), 6.70 (s, 1H), 5.83 (d, 2H, J=7.6 Hz), 4.58 (d, 1H, J=7.6 Hz), 4.26 (d, 2H, J=4 Hz), 4.04 (d, 2H, J=4.8 Hz), 3.85-3.88 (m, 2H), 3.62 (m, 1H), 3.57 (t, 2H), 3.41-3.47 (m, 3H), 2.32-2.36 (m, 4H), 2.19 (s, 3H), 2.11 (s, 3H), 2.05 (s, 3H), 1.88-1.91 (m, 2H), 1.50-1.52 (m, 2H).

Example 117: Synthesis of N-((4,6-dimethyl-2-oxo-1,2-dihydropyridin-3-yl)methyl)-5-(ethylamino)-4-methyl-4'-(morpholinomethyl)-[1,1'-biphenyl]-3-carboxamide

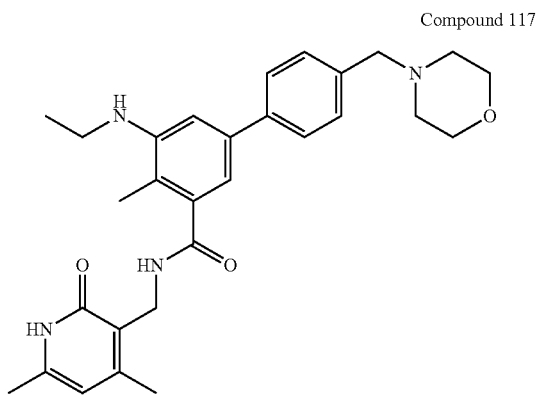 [SMILES: CCNc1cc(-c2ccc(CN3CCOCC3)cc2)cc(C(=O)NCc2c(C)cc(C)[nH]c2=O)c1C]

Compound 117

Step 1: Synthesis of methyl 5-bromo-3-(ethylamino)-2-methylbenzoate

To a stirred solution of methyl 3-amino-5-bromo-2-methylbenzoate (1.0 g, 4.09 mmol) and acetaldehyde (180 mg, 4.09 mmol) in dichloroethane (10 mL), acetic acid (1.47 g, 24.58 mmol) was added and reaction stirred at room temperature for 30 minutes. Then sodium triacetoxyborohydride (2.6 g, 12.29 mmol) was added at 0° C., allowed to attain room temperature and stirring continued for 2 h. On completion, reaction mixture was diluted with dichloromethane, washed with water, saturated aqueous sodium bicarbonate solution and dried over sodium sulphate. Removal of the solvent under reduced pressure followed by column chromatographic purification afforded the desired compound (600 mg, 55%).

Step 2: Synthesis of methyl 5-(ethylamino)-4-methyl-4'-(morpholinomethyl)-[1,1'-biphenyl]-3-carboxylate To a stirred solution of methyl 5-bromo-3-(ethylamino)-2-methylbenzoate (600 mg, 2.2 mmol) and 4-[4-(4,4,5,5-tetramethyl-1,3,2-dioxaborolan-2-yl)benzyl]morpholine (1.0 g, 3.3 mmol) in dioxane (5 mL), aqueous 2M Na$_2$CO$_3$ solution (3.96 mL, 7.93 mmol) was added and solution was purged with argon for 15 min. Then Pd(PPh$_3$)$_4$ (255 mg, 0.22 mmol) was added and argon was purged again for 15 min. Reaction mass was heated at 100° C. for 4 h. On completion, reaction mixture was diluted with water and extracted with 10% MeOH/DCM (3 times). Combined organic layer was dried over sodium sulphate. Removal of the solvent under reduced pressure followed by column chromatographic purification afforded the desired compound (800 mg, 98%).

Step 3: Synthesis of 5-(ethylamino)-4-methyl-4'-(morpholinomethyl)-[1,1'-biphenyl]-3-carboxylic acid Aqueous NaOH (130 mg, 3.25 mmol) was added to a stirred solution of compound 6 (800 mg, 2.17 mmol) in ethanol (10 mL) and stirring continued at 60° C. for 1 h. After completion, ethanol was removed under reduced pressure and acidified using dilute HCl up to pH-6. Aqueous layer was extracted ethyl acetate (5 times) and the combined organic layer was dried over sodium sulphate. Removal of the solvent under reduced pressure afforded the desired compound (700 mg, 91%). LCMS: 355.05 (M+1)+; HPLC: 89.74% (@ 254 nm) ($R_t$; 3.854; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (CD$_3$OD, 400 MHz) δ 8.24 (s, 1H), 7.88 (s, 1H), 7.84 (d, 2H, J=8 Hz), 7.71 (d, 2H, J=8.4 Hz), 4.45 (s, 2H), 4.06 (d, 2H, J=11.2 Hz), 3.79 (t, 2H, J=12 Hz), 3.53 (q, 2H, J=7.2 Hz), 3.40-3.43 (m, 2H), 3.22-3.31 (m, 2H), 2.66 (s, 3H), 1.45 (t, 3H, J=7.2 Hz).

Step 4: Synthesis of N-((4,6-dimethyl-2-oxo-1,2-dihydropyridin-3-yl)methyl)-5-(ethylamino)-4-methyl-4'-(morpholinomethyl)-[1,1'-biphenyl]-3-carboxamide 5-(Ethylamino)-4-methyl-4'-(morpholinomethyl)-[1,1'-biphenyl]-3-carboxylic acid (300 mg, 0.84 mmol) was dissolved in DMSO (2 mL) and 3-(amino methyl)-4,6-dimethylpyridin-2(1H)-one (257 mg, 1.69 mmol) was added to it. After 15 minutes stirring at room temperature PyBOP (660 mg, 1.26 mmol) was added to the reaction mixture and stirring was continued for overnight. After completion, the reaction mass was poured into ice, extracted with 10% MeOH/DCM (5 times). Combined organic layer was washed with water and dried over sodium sulphate. Removal of the solvent under reduced pressure followed by solvent washings afforded the title compound (100 mg, 24%). LCMS: 489.20 (M+1)+; HPLC: 96.41% (@ 254 nm) ($R_t$; 4.060; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.46 (s, 1H), 9.90 (s, 1H), 8.06 (t, 1H), 7.73 (d, 2H, J=7.6 Hz), 7.55 (d, 2H, J=7.2 Hz), 6.80 (d, 2H, J=7.6 Hz), 5.86 (s, 1H), 4.38 (s, 2H), 4.27 (d, 2H, J=4 Hz), 3.95 (m, 2H), 3.62-3.65 (m, 2H), 3.28-3.31 (m, 2H), 3.20-3.24 (m, 2H), 3.14-3.19 (m, 2H), 2.20 (s, 3H), 2.10 (s, 3H), 2.06 (s, 3H), 1.21 (t, 3H, J=6.8 Hz).

Example 118: Synthesis 5-(ethyl(tetrahydro-2H-pyran-4-yl)amino)-N-((4-(hydroxymethyl)-6-methyl-2-oxo-1,2-dihydropyridin-3-yl)methyl)-4-methyl-4'-(morpholinomethyl)-[1,1'-biphenyl]-3-carboxamide Compound 118

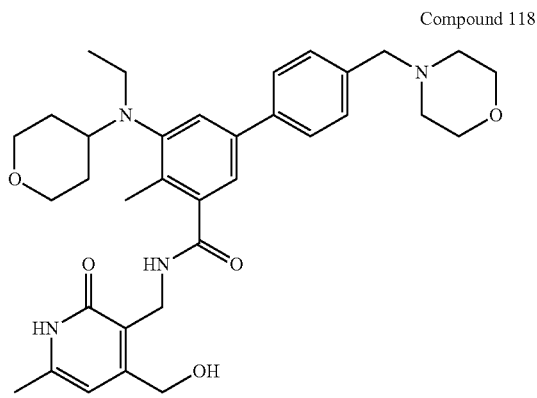 [SMILES: CCN(c1cc(-c2ccc(CN3CCOCC3)cc2)cc(C(=O)NCc2c(CO)cc(C)[nH]c2=O)c1C)C1CCOCC1]

Step 1: Synthesis of tert-butyldimethyl(prop-2-yn-1-yloxy)silane

To an ice cooled stirred solution of prop-2-yn-1-ol (10.0 g, 178.3 mmol) and imidazole (18.2 mg, 267.5 mmol) in dichloroethane (500 mL), was added TBDMSCl (40.24 g, 267.5 mmol) and stirring continued at 0° C. for 1.5 h. On completion, saturated aqueous ammonium chloride solution was added to the reaction mixture and extracted with ethyl acetate (3 times). Combined organic layer was dried over sodium sulphate. Removal of the solvent under reduced pressure followed by solvent washings afforded the desired compound (20 g, 67%).

Step 2: Synthesis of 5-((tert-butyldimethylsilyl)oxy)pent-3-yn-2-one

To a stirred solution of tert-butyldimethyl(prop-2-yn-1-yloxy)silane (20.0 g, 116.9 mmol) in THF (400 mL) at −78° C. was added n-BuLi (90 mL, 140.0 mmol) and the reaction mixture was allowed to attain room temperature with in 2 h. Then the reaction mixture was cooled to −78° C. and borontrifluoride etherate (18 mL, 140.0 mmol) was added. After 10 minutes stirring acetic anhydride (15 mL, 153.0 mmol) was added and the reaction mixture was allowed to attain room temperature with in 2.5 h. Reaction was quenched with aqueous 1N NaOH solution and extracted with ethyl acetate (3 times). Combined organic layer was dried over sodium sulphate. Removal of the solvent under reduced pressure followed by solvent washings afforded C (13 g, 52%).

Step 3: Synthesis of 4-(((tert-butyldimethylsilyl)oxy)methyl)-6-methyl-2-oxo-1,2-dihydropyridine-3-carbonitrile To a stirred solution of compound 5-((tert-butyldimethylsilyl)oxy)pent-3-yn-2-one (13.0 g, 61.0 mmol) and cyanoacetamide (6.2 g, 73.2 mmol) in a mixture of ethanol and water (9:1) (270 mL) at room temperature was added piperidineacetate (catalytic) and the reaction mixture was heated to reflux for 5 h. After removal of solvent water was added and the solid product was filtered. The solid product on washing with water followed by ether and hexane afforded the desired compound (5.5 g, 32%).

Step 4: Synthesis of 3-(aminomethyl)-4-(((tert-butyldimethylsilyl)oxy)methyl)-6-methylpyridin-2(1H)-one To a stirred solution of 4-(((tert-butyldimethylsilyl)oxy) methyl)-6-methyl-2-oxo-1,2-dihydropyridine-3-carbonitrile (5.5 g, 19.7 mmol) in methanol (100 mL) and ammonia (30 mL) was added Raney nickel (quantitative) and the reaction mixture was stirred in presence of hydrogen under balloon pressure for 14 h. On completion, reaction mixture was filtered through celite and washed with methanol. Removal of the solvent under reduced pressure afforded the desired compound (3.5 g, 63%).

Step 5: Synthesis of 5-bromo-3-(ethyl(tetrahydro-2H-pyran-4-yl)amino)-N-((4-(hydroxymethyl)-6-methyl-2-oxo-1,2-dihydropyridin-3-yl)methyl)-2-methylbenzamide Aqueous NaOH (70 mg, 1.7 mmol) was added to a stirred solution of methyl 5-bromo-3-(ethyl(tetrahydro-2H-pyran- 4-yl)amino)-2-methylbenzoate (400 mg, 1.1 mmol) in ethanol (60 mL) and stirring continued at 60° C. for 1 h. After completion, ethanol was removed under reduced pressure and acidified using dilute HCl up to pH~6. Aqueous layer was extracted ethyl acetate (5 times) and the combined organic layer was dried over sodium sulphate. Removal of the solvent under reduced pressure afforded respective acid (320 mg, 83.55%).

The above acid (400 mg, 1.1 mmol) was then dissolved in DMSO (4 mL) and 3-(aminomethyl)-4-(((tert-butyldimethylsilyl)oxy)methyl)-6-methylpyridin-2(1H)-one (525 mg, 1.7 mmol) was added to it. After 15 minutes stirring at room temperature PyBOP (900 mg, 1.6 mmol) was added to the reaction mixture and stirring was continued for overnight. After completion, the reaction mass was poured into ice, extracted with 10% MeOH/DCM (5 times). Combined organic layer was washed with water and dried over sodium sulphate. Removal of the solvent under reduced pressure followed by solvent washings afforded the desired compound (230 mg, 40%).

Step 6: Synthesis 5-(ethyl(tetrahydro-2H-pyran-4-yl)amino)-N-((4-(hydroxymethyl)-6-methyl-2-oxo-1,2-dihydropyridin-3-yl)methyl)-4-methyl-4'-(morpholinomethyl)-[1,1'-biphenyl]-3-carboxamide To a stirred solution of 5-bromo-3-(ethyl(tetrahydro-2H-pyran-4-yl)amino)-N-((4-(hydroxymethyl)-6-methyl-2-oxo-1,2-dihydropyridin-3-yl)methyl)-2-methylbenzamide (250 mg, 0.5 mmol) and 4-[4-(4,4,5,5-tetramethyl-1,3,2-dioxaborolan-2-yl)benzyl]morpholine (230 mg, 7.6 mmol) in dioxane (5 mL), aqueous 2M Na$_2$CO$_3$ solution (0.9 mL, 1.8 mmol) was added and solution was purged with argon for 15 min. Then Pd (PPh$_3$)$_4$ (57 mg, 0.05 mmol) was added and argon was purged again for 15 min. Reaction mass was heated at 100° C. for 4 h. On completion, reaction mixture was diluted with water and extracted with 10% MeOH/DCM (3 times). Combined organic layer was dried over sodium sulphate. Removal of the solvent under reduced pressure followed by column chromatographic purification afforded the title compound (60 mg, 25%). LCMS: 589.35 (M+1)$^+$; HPLC: 95.58% (@ 254 nm) (R$_t$: 3.524; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.54 (s, 1H), 8.22 (t, 1H), 7.57 (d, 2H, J=7.6 Hz), 7.38 (d, 2H, J=5.6 Hz), 7.36 (s, 1H), 7.21 (s, 1H), 6.16 (s, 1H), 5.28 (m, 1H), 4.52 (d, 2H, J=4.8 Hz), 4.25 (d, 2H, J=3.6 Hz), 3.81-3.83 (m, 2H), 3.57 (m, 4H), 3.48 (s, 2H), 3.01-3.09 (m, 3H), 2.36 (m, 4H), 2.23 (s, 3H), 2.15 (s, 3H), 1.64-1.67 (m, 2H), 1.51-1.53 (m, 2H), 1.23 (m, 2H), 0.82 (t, 3H, J=6.4 Hz).

Example 119: Synthesis of N-((4,6-dimethyl-2-oxo-1,2-dihydropyridin-3-yl)methyl)-4-methyl-4'-(morpholinomethyl)-5-(N-(tetrahydro-2H-pyran-4-yl)acetamido)-[1,1'-biphenyl]-3-carboxamide

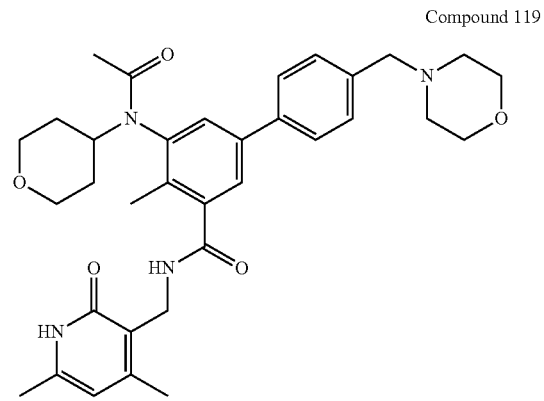 [SMILES: CC(=O)N(c1cc(-c2ccc(CN3CCOCC3)cc2)cc(C(=O)NCc2c(C)cc(C)[nH]c2=O)c1C)C1CCOCC1]

Compound 119

Step 1: Synthesis of methyl 5-bromo-2-methyl-3-(N-(tetrahydro-2H-pyran-4-yl)acetamido) benzoate A solution of methyl 5-bromo-2-methyl-3-((tetrahydro-2H-pyran-4-yl)amino)benzoate (520 mg, 1.58 mmol) was heated at 70° C. in Acetic 3 ml of anhydride for 6 h. The reaction mixture was cooled to room temperature and quenched with sat. NaHCO$_3$ and extracted with ethyl acetate. The organic layer was dried over Na$_2$SO$_4$, concentrated and purified by silica gel (100-200) column chromatography to get the target compound (400 mg, 68%).

Step 2: Synthesis of 5-bromo-N-((4,6-dimethyl-2-oxo-1,2-dihydropyridin-3-yl)methyl)-2-methyl-3-(N-(tetrahydro-2H-pyran-4-yl)acetamido)benzamide A mixture of methyl 5-bromo-2-methyl-3-(N-(tetrahydro-2H-pyran-4-yl)acetamido) benzoate (400 mg, 1.08 mmol) and NaOH (47 mg, 1.13 mmol) in 5 ml of ethanol:water (2:1) was heated at 70° C. for 2 h. The reaction mixture was concentrated to dryness and the crude material dissolved in water, pH was adjusted to 5 to 6 by slow addition of HCl and extracted with 10% MeOH in DCM. The organic layer was dried over Na$_2$SO$_4$, concentrated under reduced pressure to afford 400 mg of acid.

The crude acid (400 mg, 1.23 mmol), 3-(aminomethyl)-4,6-dimethylpyridin-2(1H)-one (370 mg, 2.46 mmol), PyBOP (960 mg, 1.85 mmol) and triethyl amine (0.17 ml, 1.23) mixture was stirred in 2 ml of DMSO at room temperature overnight. The reaction mixture was diluted with water and compound was extracted in 10% MeOH in DCM, dried over Na$_2$SO$_4$, concentrated and crude was purified by silica gel (100-200) column chromatography to get 5-bromo-N-((4,6-dimethyl-2-oxo-1,2-dihydropyridin-3-yl)methyl)-2-methyl-3-(N-(tetrahydro-2H-pyran-4-yl)acetamido)benzamide (95 mg, 17.3%).

Step 3: Synthesis of N-((4,6-dimethyl-2-oxo-1,2-dihydropyridin-3-yl)methyl)-4-methyl-4'-(morpholinomethyl)-5-(N-(tetrahydro-2H-pyran-4-yl)acetamido)-[1,1'-biphenyl]-3-carboxamide A solution of 5-bromo-N-((4,6-dimethyl-2-oxo-1,2-dihydropyridin-3-yl)methyl)-2-methyl-3-(N-(tetrahydro-2H- pyran-4-yl)acetamido)benzamide (50 mg, 0.10 mmol), (4-(morpholinomethyl)phenyl)boronic acid (41 mg, 0.13 mmol), sodium carbonate (27 mg, 0.25 mmol) in 3 ml of dioxane was degassed with argon for 20 min, Pd(PPh$_3$) (12 mg, 0.0012 mmol) was added to the mixture and heated to 100° C. for overnight. The reaction was cooled to room temperature and diluted with water, before extraction with 10% MeOH in DCM, the organic layers were dried over Na$_2$SO$_4$, concentrated and the resulting crude product purified by silica gel (100-200) chromatography to obtain the title compound (26 mg, 23%).

LCMS: 609.35 (M+23)$^+$; HPLC: 97.81% (@ 254 nm) (R$_t$: 4.407; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.48 (bs, 1H), 8.41 (t, 1H), 7.67-7.69 (m, 2H), 7.39-7.56 (m, 4H), 5.87 (s, 1H), 4.54-4.57 (m, 1H), 4.30-4.31 (d, 2H, J=4 Hz), 3.77-3.85 (m, 2H), 3.50-3.58 (m, 6H), 2.37 (m, 4H), 2.22 (s, 3H), 2.16 (s, 3H), 2.11 (s, 3H), 1.88-1.91 (m, 1H), 1.51-1.65 (m, 6H), 2 protons merged in solvent peak.

Example 120: Synthesis of N-((4,6-dimethyl-2-oxo-1,2-dihydropyridin-3-yl)methyl)-5-(ethyl(tetrahydro-2H-pyran-4-yl)amino)-3'-fluoro-4-methyl-4'-(morpholinomethyl)-[1,1'-biphenyl]-3-carboxamide Compound 120

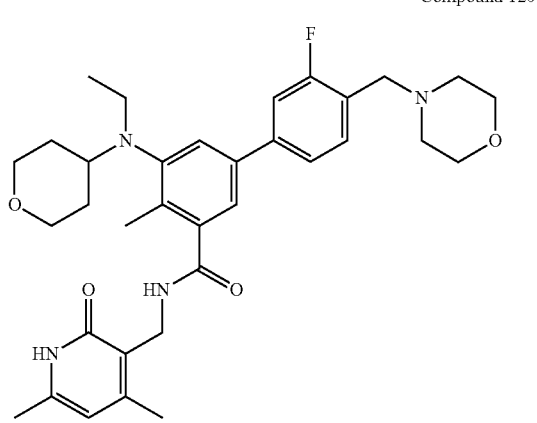

Step 1: Synthesis of N-((4,6-dimethyl-2-oxo-1,2-dihydropyridin-3-yl)methyl)-5-(ethyl(tetrahydro-2H-pyran-4-yl)amino)-3'-fluoro-4'-formyl-4-methyl-[1,1'-biphenyl]-3-carboxamide To a stirred solution of 5-bromo-N-((4,6-dimethyl-2-oxo-1,2-dihydropyridin-3-yl)methyl)-3-(ethyl(tetrahydro-2H-pyran-4-yl)amino)-2-methylbenzamide (300 mg, 0.63 mmol) and (3-fluoro-4-formylphenyl)boronic acid (160 mg, 0.94 mmol) in dioxane (6 mL), aqueous 2M Na$_2$CO$_3$ solution (1.15 mL, 2.3 mmol) was added and solution was purged with argon for 15 min. Then Pd(PPh$_3$)$_4$ (72 mg, 0.06 mmol) was added and argon was purged again for 15 min. Reaction mass was heated at 100° C. for 4 h. On completion, reaction mixture was diluted with water and extracted with 10% MeOH/DCM (3 times). Combined organic layer was dried over sodium sulphate. Removal of the solvent under reduced pressure followed by column chromatographic purification afforded the title compound (288 mg, 88%).

Step 2: Synthesis of N-((4,6-dimethyl-2-oxo-1,2-dihydropyridin-3-yl)methyl)-5-(ethyl(tetrahydro-2H-pyran-4-yl)amino)-3'-fluoro-4-methyl-4'-(morpholinomethyl)-[1,1'-biphenyl]-3-carboxamide To a stirred solution of N-((4,6-dimethyl-2-oxo-1,2-dihydropyridin-3-yl)methyl)-5-(ethyl(tetrahydro-2H-pyran-4-yl)amino)-3'-fluoro-4'-formyl-4-methyl-[1,1'-biphenyl]-3-carboxamide (285 mg, 0.55 mmol) and morpholine (149 mg, 1.64 mmol) in dichloroethane (5 mL), acetic acid (0.2 mL, 3.29 mmol) was added and reaction stirred at room temperature for 30 minutes. Then sodium triacetoxyborohydride (349 mg, 1.64 mmol) was added to the reaction mixture at 0° C., allowed to attain room temperature and stirring continued for overnight. On completion, reaction mixture was diluted with dichloromethane, washed with water, saturated aqueous sodium bicarbonate solution and dried over sodium sulphate. Removal of the solvent under reduced pressure followed by column chromatographic and prep. HPLC purification afforded the title compound (70 mg, 20%). LCMS: 591.45 (M+1)$^+$; HPLC: 98.96% (@ 254 nm) (R$_t$: 4.034; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.5 (bs, 1H), 10.1 (bs, 1H), 8.24 (s, 1H), 7.66-7.73 (m, 3H), 7.54 (s, 1H), 7.36 (s, 1H), 5.88 (s, 1H), 4.44 (s, 2H), 4.30 (m, 5H), 3.96 (m, 2H), 3.66-3.86 (m, 6H), 3.17-3.34 (m, 4H), 2.27 (s, 3H), 2.22 (s, 3H), 2.11 (s, 3H), 1.57-1.67 (m, 4H), 0.84 (t, 3H, J=6 Hz).

Example 121: Synthesis of N-((4,6-dimethyl-2-oxo-1,2-dihydropyridin-3-yl)methyl)-5-(ethyl(tetrahydro-2H-pyran-4-yl)amino)-2'-fluoro-4-methyl-4'-(morpholinomethyl)-[1,1'-biphenyl]-3-carboxamide Compound 121

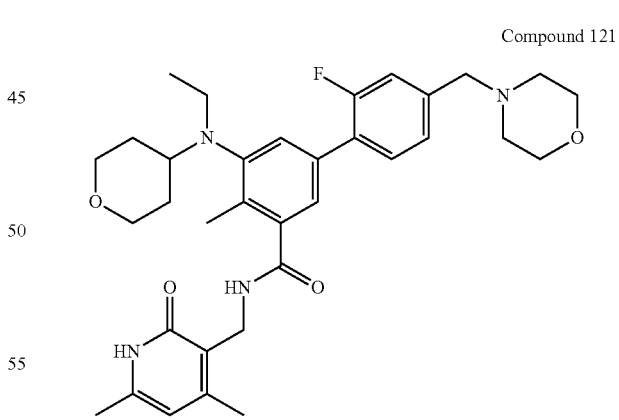

Step 1: Synthesis of N-((4,6-dimethyl-2-oxo-1,2-dihydropyridin-3-yl)methyl)-5-(ethyl(tetrahydro-2H-pyran-4-yl)amino)-2'-fluoro-4'-formyl-4-methyl-[1,1'-biphenyl]-3-carboxamide To a stirred solution of 5-bromo-N-((4,6-dimethyl-2-oxo-1,2-dihydropyridin-3-yl)methyl)-3-(ethyl(tetrahydro-2H-pyran-4-yl)amino)-2-methylbenzamide (300 mg, 0.62 mmol) and (2-fluoro-4-formylphenyl)boronic acid (158 mg, 0.94 mmol) in dioxane (3 mL), aqueous 2M Na$_2$CO$_3$ solution (1.13 mL, 2.26 mmol) was added and solution was purged with argon for 15 min. Then Pd(PPh$_3$)$_4$ (72 mg, 0.06 mmol) was added and argon was purged again for 15 min. Reaction mass was heated at 100° C. for 4 h. On completion, reaction mixture was diluted with water and extracted with 10% MeOH/DCM (3 times). Combined organic layer was dried over sodium sulphate. Removal of the solvent under reduced pressure followed by column chromatographic purification afforded the desired compound (300 mg, 91%).

Step 2: Synthesis of N-((4,6-dimethyl-2-oxo-1,2-dihydropyridin-3-yl)methyl)-5-(ethyl(tetrahydro-2H-pyran-4-yl)amino)-2'-fluoro-4-methyl-4'-(morpholinomethyl)-[1,1'-biphenyl]-3-carboxamide To a stirred solution of N-((4,6-dimethyl-2-oxo-1,2-dihydropyridin-3-yl)methyl)-5-(ethyl(tetrahydro-2H-pyran-4-yl)amino)-2'-fluoro-4'-formyl-4-methyl-[1,1'-biphenyl]-3-carboxamide (300 mg, 0.57 mmol) and morpholine (100 mg, 1.15 mmol) in dichloroethane (4 mL), acetic acid (207 mg, 3.46 mmol) was added and reaction stirred at room temperature for 30 minutes. Then sodium triacetoxyborohydride (367 mg, 1.73 mmol) was added to the reaction mixture at 0° C., allowed to attain room temperature and stirring continued for overnight. On completion, reaction mixture was diluted with dichloromethane, washed with water, saturated aqueous sodium bicarbonate solution and dried over sodium sulphate. Removal of the solvent under reduced pressure followed by column chromatographic purification afforded the title compound (300 mg, 87.97%).

LCMS: 591.30 (M+1)$^+$; HPLC: 96.03% (@ 254 nm) (R$_t$; 4.077; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (bs, 1H), 8.17 (t, 1H), 7.47 (t, 1H, J=8 Hz), 7.30 (s, 1H), 7.21-7.23 (m, 2H), 7.10 (s, 1H), 5.85 (s, 1H), 4.28 (d, 2H, J=4.4 Hz), 3.81-3.84 (m, 2H), 3.50-3.59 (m, 6H), 3.22-3.25 (m, 2H), 3.00-3.06 (m, 3H), 2.38 (m, 4H), 2.25 (s, 3H), 2.19 (s, 3H), 2.10 (s, 3H), 1.51-1.66 (m, 4H), 0.83 (t, 3H, J=6.8 Hz).

Example 122: Synthesis of N-((4,6-dimethyl-2-oxo-1,2-dihydropyridin-3-yl)methyl)-5-(ethyl(tetrahydro-2H-pyran-4-yl)amino)-2',4-dimethyl-4'-(morpholinomethyl)-[1,1'-biphenyl]-3-carboxamide Compound 122

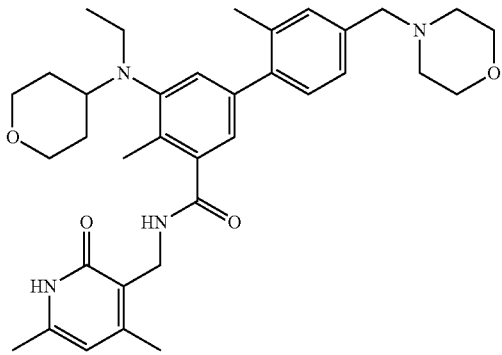

Step 1: Synthesis of N-((4,6-dimethyl-2-oxo-1,2-dihydropyridin-3-yl)methyl)-5-(ethyl(tetrahydro-2H-pyran-4-yl)amino)-4'-formyl-2',4-dimethyl-[1,1'-biphenyl]-3-carboxamide To a stirred solution of 5-bromo-N-((4,6-dimethyl-2-oxo-1,2-dihydropyridin-3-yl)methyl)-3-(ethyl(tetrahydro-2H-pyran-4-yl)amino)-2-methylbenzamide (400 mg, 0.84 mmol) and 3-methyl-4-(4,4,5,5-tetramethyl-1,3,2-dioxaborolan-2-yl)benzaldehyde (310 mg, 1.26 mmol) in dioxane (2 mL), aqueous 2M Na$_2$CO$_3$ solution (1.5 mL, 3.03 mmol) was added and solution was purged with argon for 15 min. Then Pd(PPh$_3$)$_4$ (97 mg, 0.08 mmol) was added and argon was purged again for 15 min. Reaction mass was heated at 100° C. for 4 h. On completion, reaction mixture was diluted with water and extracted with 10% MeOH/DCM (3 times). Combined organic layer was dried over sodium sulphate. Removal of the solvent under reduced pressure followed by column chromatographic purification afforded the desired compound (300 mg, 69.28%).

Step 2: Synthesis of N-((4,6-dimethyl-2-oxo-1,2-dihydropyridin-3-yl)methyl)-5-(ethyl(tetrahydro-2H-pyran-4-yl)amino)-2',4-dimethyl-4'-(morpholinomethyl)-[1,1'-biphenyl]-3-carboxamide To a stirred solution of N-((4,6-dimethyl-2-oxo-1,2-dihydropyridin-3-yl)methyl)-5-(ethyl(tetrahydro-2H-pyran-4-yl)amino)-4'-formyl-2',4-dimethyl-[1,1'-biphenyl]-3-carboxamide (410 mg, 0.79 mmol) and morpholine (210 mg, 2.38 mmol) in dichloroethane (10 mL), acetic acid (280 mg, 4.77 mmol) was added and reaction stirred at room temperature for 30 minutes. Then sodium triacetoxyborohydride (580 mg, 2.71 mmol) was added to the reaction mixture at 0° C., allowed to attain room temperature and stirring continued for overnight. On completion, reaction mixture was diluted with dichloromethane, washed with water, saturated aqueous sodium bicarbonate solution and dried over sodium sulphate. Removal of the solvent under reduced pressure followed by column chromatographic purification afforded the title compound (125 mg, 26.76%).

LCMS: 587.55 (M+1)$^+$; HPLC: 97.23% (@ 254 nm) (R$_t$; 4.065; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (bs, 1H), 9.91 (bs, 1H), 8.17 (bs, 1H), 7.32-7.42 (m, 3H), 7.15 (bs, 1H), 6.92 (bs, 1H), 5.86 (s, 1H), 4.27-4.35 (m, 4H), 3.86 (m, 2H), 3.64-3.67 (m, 3H), 3.12-3.32 (m, 10H), 2.33 (bs, 6H), 2.19 (s, 3H), 2.10 (s, 3H), 1.55-1.64 (m, 4H), 0.84 (t, 3H, J=6 Hz), 2 protons merged in solvent peak.

Example 123: Synthesis of N-((4,6-dimethyl-2-oxo-1,2-dihydropyridin-3-yl)methyl)-5-(ethyl(tetrahydro-2H-pyran-4-yl)amino)-4-methyl-4'-(morpholine-4-carbonyl)-[1,1'-biphenyl]-3-carboxamide Compound 123

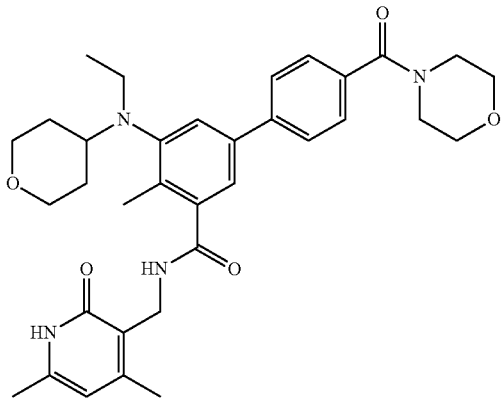

To a stirred solution of 5-bromo-N-((4,6-dimethyl-2-oxo-1,2-dihydropyridin-3-yl)methyl)-3-(ethyl(tetrahydro-2H-pyran-4-yl)amino)-2-methylbenzamide (300 mg, 0.63 mmol) and morpholino(4-(4,4,5,5-tetramethyl-1,3,2-dioxaborolan-2-yl)phenyl)methanone (260 mg, 0.82 mmol) in dioxane (10 mL), aqueous 2M Na$_2$CO$_3$ solution (1.13 mL, 2.27 mmol) was added and solution was purged with argon for 15 min. Then Pd(PPh$_3$)$_4$ (72 mg, 0.06 mmol) was added and argon was purged again for 15 min. Reaction mass was heated at 100° C. for 4 h. On completion, reaction mixture was diluted with water and extracted with 10% MeOH/DCM (3 times). Combined organic layer was dried over sodium sulphate. Removal of the solvent under reduced pressure followed by column chromatographic purification afforded the title compound (250 mg, 68%). LCMS: 587.35 (M+1)$^+$; HPLC: 93.85% (@ 254 nm) (R$_t$: 4.535; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.46 (bs, 1H), 8.21 (t, 1H), 7.69-7.71 (m, 2H), 7.45-7.49 (m, 3H), 7.26 (s, 1H), 5.86 (s, 1H), 4.29 (d, 2H, J=4 Hz), 3.82-3.84 (m, 2H), 3.48-3.60 (m, 8H), 3.23-3.25 (m, 2H), 3.09-3.11 (m, 3H), 2.26 (s, 3H), 2.21 (s, 3H), 2.11 (s, 3H), 1.52-1.68 (m, 4H), 0.83 (t, 3H, J=6.8 Hz).

Example 124: Synthesis of N-((4,6-dimethyl-2-oxo-1,2-dihydropyridin-3-yl)methyl)-5-(ethyl(1-(methylsulfonyl)piperidin-4-yl)amino)-4-methyl-4'-(morpholinomethyl)-[1,1'-biphenyl]-3-carboxamide Compound 124

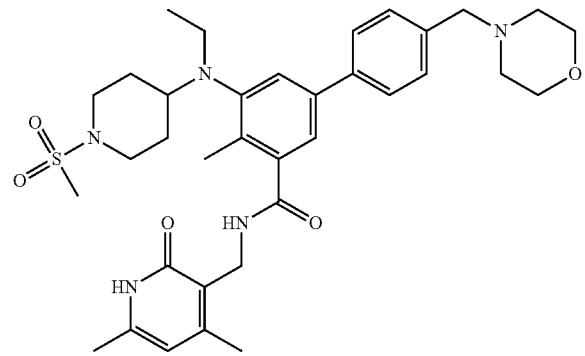

To stirred solution of N-((4,6-dimethyl-2-oxo-1,2-dihydropyridin-3-yl)methyl)-5-(ethyl(piperidin-4-yl)amino)-4-methyl-4'-(morpholinomethyl)-[1,1'-biphenyl]-3-carboxamide (0.2 g, 0.35 mmol) in DCM (8 mL) was added triethyl amine (0.106 g, 1.04 mmol) and mesyl chloride (0.08 g, 0.69 mmol) at 0° C. The resulting reaction mixture was stirred at room temperature for 2 h. After completion, water was added to the reaction mixture and extracted with 10% MeOH/DCM. Combined organic layers were dried over sodium sulphate and concentrated under reduced pressure giving crude material which was then dissolved in methanol (10 mL) and added NaOH (0.021 g, 0.52 mmol). This mixture was stirred at room temperature for 15 h. After completion, extraction was carried out using 20% MeOH/DCM. Combined organic layers were dried over sodium sulfate, concentrated and crude material was purified by solvent washing giving the title compound (0.1 g, 45.45%).

LCMS: 650.85 (M+1)$^+$; HPLC: 95.37% (@ 254 nm) (R$_t$: 4.258; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (bs, 1H), 8.18 (t, 1H), 7.57-7.59 (m, 3H), 7.37-7.39 (m, 2H), 7.22 (s, 1H), 5.86 (s, 1H), 4.29 (d, 2H, J=4.4 Hz), 3.58 (m, 4H), 3.48-3.52 (m, 4H), 3.09-3.11 (m, 2H), 2.94 (m, 1H), 2.82 (s, 3H), 2.67-2.72 (m, 2H), 2.36 (m, 4H), 2.24 (s, 3H), 2.21 (s, 3H), 2.10 (s, 3H), 1.81-1.83 (m, 2H), 1.59-1.61 (m, 2H), 0.84 (t, 3H, J=6 Hz).

Example 125: Synthesis of 5-((1-acetylpiperidin-4-yl)(ethyl)amino)-N-((4,6-dimethyl-2-oxo-1,2-dihydropyridin-3-yl)methyl)-4-methyl-4'-(morpholinomethyl)-[1,1'-biphenyl]-3-carboxamide Compound 125

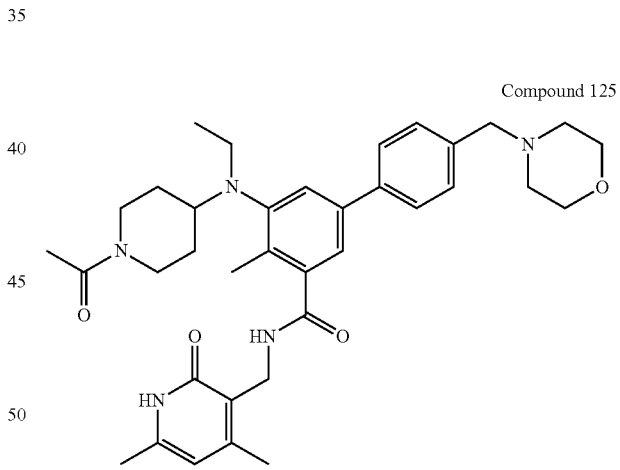

To a stirred solution of N-((4,6-dimethyl-2-oxo-1,2-dihydropyridin-3-yl)methyl)-5-(ethyl(piperidin-4-yl)amino)-4-methyl-4'-(morpholinomethyl))-[1,1'-biphenyl]-3-carboxamide (0.25 g, 0.44 mmol) and acetic acid (0.052 g, 0.86 mmol) in DMF (3 mL), EDCI (0.123 g, 0.64 mmol) and HOBt (0.087 g, 0.64 mmol) was added followed by the addition of triethylamine (0.108 g, 1.06 mmol) and reaction was stirred at room temperature for overnight. After completion of the reaction, water was added to it and extraction was carried out using 10% MeOH/DCM. The combined organic layers were washed with water, dried over anhydrous Na$_2$SO$_4$, filtered and concentrated under reduced pressure to afford crude material which was purified by column chromatography to give the title compound (0.1 g, 37.31%).

LCMS: 614.75 (M+1)⁺; HPLC: 97.57% (@ 254 nm) (R$_t$: 4.140; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (bs, 1H), 8.19 (t, 1H), 7.57 (d, 2H, J=7.2 Hz), 7.37-7.39 (m, 3H), 7.22 (s, 1H), 5.86 (s, 1H), 4.29 (d, 2H, J=4.4 Hz), 3.78 (m, 1H), 3.49-3.58 (m, 6H), 2.99-3.08 (m, 4H), 2.36 (m, 4H), 2.24 (s, 3H), 2.21 (s, 3H), 2.10 (s, 3H), 1.97 (s, 3H), 1.74 (m, 2H), 1.31-1.52 (m, 2H), 0.83 (t, 3H, J=6.8 Hz), 2 protons merged in solvent peak.

Example 126: Synthesis of N-((4,6-dimethyl-2-oxo-1,2-dihydropyridin-3-yl)methyl)-5-(ethyl(piperidin-4-yl)amino)-4-methyl-4'-(morpholinomethyl)-[1,1'-biphenyl]-3-carboxamide

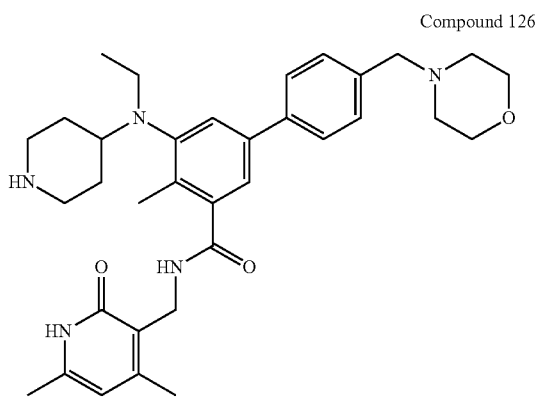 [SMILES: CCN(c1cc(-c2ccc(CN3CCOCC3)cc2)cc(C(=O)NCc2c(C)cc(C)[nH]c2=O)c1C)C1CCNCC1]

Compound 126

Step 1: Synthesis of tert-butyl 4-((5-bromo-3-(methoxycarbonyl)-2-methylphenyl)amino)piperidine-1-carboxylate To a stirred solution of methyl 3-amino-5-bromo-2-methylbenzoate (4.5 g, 18.44 mmol) and tert-butyl 4-oxopiperidine-1-carboxylate (11.01 g, 55.33 mmol) in dichloroethane (50 mL), acetic acid (6.64 g, 110.6 mmol) was added and reaction stirred at room temperature for 10 min. Then sodium triacetoxyborohydride (11.72 g, 55.28 mmol) was added at 0° C. and reaction stirred overnight at room temperature. On completion, solvent was removed under reduced pressure and crude material was purified by column chromatography to afford the desired compound (5.2 g, 66.24%).

Step 2: Synthesis of tert-butyl 4-((5-bromo-3-(methoxycarbonyl)-2-methylphenyl)(ethyl)-amino)-piperidine-1-carboxylate To a stirred solution of tert-butyl 4-((5-bromo-3-(methoxycarbonyl)-2-methylphenyl)amino)piperidine-1-carboxylate (5 g, 11.70 mmol) and acetaldehyde (1.58 g, 35.12 mmol) in dichloroethane (60 mL), acetic acid (4.24 g, 70.66 mmol) was added and reaction stirred at room temperature for 10 min. Then sodium triacetoxyborohydride (7.44 g, 35.09 mmol) was added at 0° C. and reaction stirred at room temperature for 2 h. On completion, the reaction was quenched with aqueous sodium bicarbonate, organic phase was separated and aqueous phase was extracted with dichloromethane. Combined organic layers were dried over sodium sulphate and concentrated under reduced pressure to give crude material was purified by column chromatography to afford the desired product (5 g, 93.45%).

Step 3: Synthesis of tert-butyl 4-((5-bromo-3-(((4,6-dimethyl-2-oxo-1,2-dihydropyridin-3-yl)methyl) carbamoyl)-2-methyl-phenyl)(ethyl)amino)piperidine-1-carboxylate Aqueous NaOH (0.7 g, 17.50 mmol) was added to a solution of tert-butyl 4-((5-bromo-3-(methoxycarbonyl)-2-methylphenyl)amino)piperidine-1-carboxylate (5 g, 10.94 mmol) in ethanol (50 mL) and stirred at 60° C. for 1 h. After completion of the reaction, ethanol was removed under reduced pressure and acidified using dilute HCl up to pH 6 and adjusted using citric acid to pH 4. Extraction was carried out using ethyl acetate. Combined organic layers were dried concentrated giving respective acid (4.8 g, 99.17%).

The above acid (4.8 g, 10.90 mmol) was then dissolved in DMSO (20 mL) and 3-(amino methyl)-4,6-dimethylpyridin-2(1H)-one (3.32 g, 21.81 mmol) was added to it. The reaction mixture was stirred at room temperature for 15 min before PYBOP (8.50 g, 16.35 mmol) was added to it and stirring was continued for overnight. On completion, reaction mixture was diluted with water and extracted with 10% MeOH/DCM. Combined organic layers were dried over Na$_2$SO$_4$ and solvent removed under reduced pressure to afford crude material which was purified by column chromatography over silica gel to afford tert-butyl 4-((5-bromo-3-(((4,6-dimethyl-2-oxo-1,2-dihydropyridin-3-yl)methyl) carbamoyl)-2-methyl-phenyl)(ethyl)amino)piperidine-1-carboxylate (4.4 g, 70.96%).

Step 4: Synthesis of tert-butyl 4-((5-(((4,6-dimethyl-2-oxo-1,2-dihydropyridin-3-yl)methyl)carbamoyl)-4-methyl-4'-(morpholinomethyl)-[1,1'-biphenyl]-3-yl)(ethyl)amino)piperidine-1-carboxylate To a stirred solution of tert-butyl 4-((5-bromo-3-(((4,6-dimethyl-2-oxo-1,2-dihydropyridin-3-yl)methyl)carbamoyl)-2-methyl-phenyl)(ethyl)amino)piperidine-1-carboxylate (2 g, 3.47 mmol) and 4-(morpholinomethyl)-phenyl) boronic acid (1.58 g, 5.21 mmol) in dioxane/water mixture, Na$_2$CO$_3$ (1.32 g, 12.45 mmol) was added and solution purged with argon for 15 min. Then Pd (PPh$_3$)$_4$ (0.4 g, 0.35 mmol) was added and argon was purged again for 10 min. The reaction mixture was heated at 90° C. for 3.5 h. On completion, reaction mixture was diluted with water and extracted with 10% MeOH/DCM. Combined organic layers were dried over Na$_2$SO$_4$ and solvent removed under reduced pressure to afford crude material which was purified by column chromatography over silica gel to afford desired compound (1.6 g, 68.66%).

Step 5: Synthesis of N-((4,6-dimethyl-2-oxo-1,2-dihydropyridin-3-yl)methyl)-5-(ethyl(piperidin-4-yl) amino)-4-methyl-4'-(morpholinomethyly)-[1,1'-biphenyl]-3-carboxamide tert-Butyl 4-((5-(((4,6-dimethyl-2-oxo-1,2-dihydropyridin-3-yl)methyl)carbamoyl)-4-methyl-4'-(morpholinomethyl)-[1,1'-biphenyl]-3-yl)(ethyl)amino)piperidine-1-carboxylate (1.3 g, 0.1.93 mmol) was taken in DCM (20 mL), to it TFA (10 mL) was added at 0° C. and stirred at rt for 2 h. On completion of reaction, solvent was removed under reduced pressure, reaction was quenched with aqueous sodium bicarbonate and extracted with 10% MeOH/DCM. Combined organic layers were dried over sodium sulphate and concentrated under reduced pressure to obtain crude; which then purified by acetonitrile washing to give the title compound (0.9 g, 81.81%).

LCMS: 572.35 (M+1)+; HPLC: 96.59% (@ 254 nm) (R$_t$: 3.964; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 8.19 (t, 1H), 7.57 (d, 2H, J=8 Hz), 7.38 (m, 3H), 7.21 (s, 1H), 5.86 (s, 1H), 4.29 (d, 2H, J=4 Hz), 3.48-3.57 (m, 8H), 2.98-3.10 (m, 4H), 2.88 (m, 1H), 2.36 (m, 4H), 2.24 (s, 3H), 2.21 (s, 3H), 2.11 (s, 3H), 1.70-1.73 (m, 2H), 1.48-1.51 (m, 2H), 0.84 (t, 3H, J=6.8 Hz).

Example 127: Synthesis of N-((4,6-dimethyl-2-oxo-1,2-dihydropyridin-3-yl)methyl)-5-(ethyl(1-pivaloylpiperidin-4-yl)amino)-4-methyl-4'-(morpholinomethyl)-[1,1'-biphenyl]-3-carboxamide

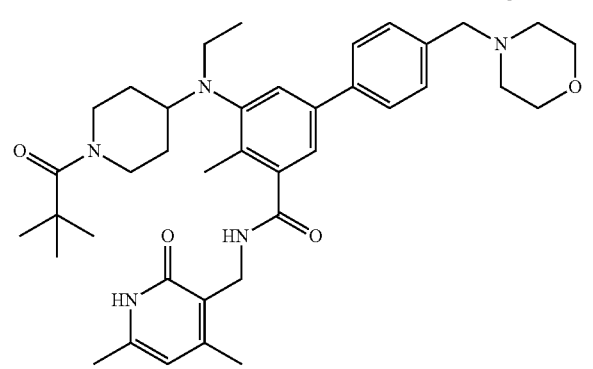

Compound 127

N-((4,6-dimethyl-2-oxo-1,2-dihydropyridin-3-yl) methyl)-5-(ethyl(piperidin-4-yl)amino)-4-methyl-4'-(morpholinomethyl)-[1,1'-biphenyl]-3-carboxamide (0.2 g, 0.34 mmol) was dissolved in DMSO (2 mL) and pivalic acid (0.107 g, 1.04 mmol) and triethyl amine (0.106 g, 1.04 mmol) was added to it. The reaction mixture was stirred at room temperature for 15 min before PYBOP (0.27 g, 0.52 mmol) was added to it and stirring was continued for overnight. After completion of the reaction, reaction mixture was poured into ice, extracted with 10% MeOH/DCM. Combined organic layers were dried, concentrated to obtain crude; which then purified by column chromatography to afford the title compound (0.14 g, 60.86%).

LCMS: 656.65 (M+1)+; HPLC: 97.51% (@ 254 nm) (R$_t$: 4.555; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (bs, 1H), 8.18 (t, 1H), 7.57 (d, 2H, J=7.2), 7.37-7.40 (m, 3H), 7.21 (s, 1H), 5.86 (s, 1H), 4.21-4.29 (m, 4H), 3.49-3.58 (m, 6H), 3.06-3.08 (m, 3H), 2.73-2.79 (m, 2H), 2.37 (m, 4H), 2.24 (s, 3H), 2.21 (s, 3H), 2.11 (s, 3H), 1.75-1.78 (m, 2H), 1.38-1.41 (m, 2H), 1.17 (s, 9H), 0.83 (t, 3H, J=7.2 Hz).

Example 128: Synthesis of 5-(((1r,4r)-4-aminocyclohexyl)(ethyl)amino)-N-((4,6-dimethyl-2-oxo-1,2-dihydropyridin-3-yl)methyl)-4-methyl-4'-(morpholinomethyl)-[1,1'-biphenyl]-3-carboxamide

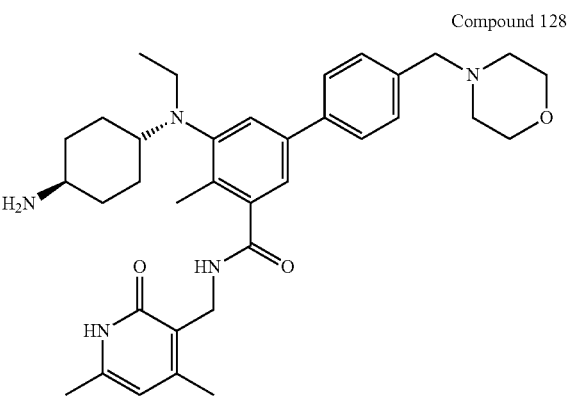

Compound 128

Step 1: Synthesis of methyl 5-bromo-3-(((1r,4r)-4-((tert-butoxycarbonyl)amino)cyclohexyl)amino)-2-methylbenzoate To a stirred solution of methyl 3-amino-5-bromo-2-methylbenzoate (5 g, 20.57 mmol) and tert-butyl (4-oxocyclohexyl)carbamate (5.6 g, 26.74 mmol) in dichloroethane (50 mL), acetic acid (7.4 g, 123.33 mmol) was added and reaction stirred at room temperature for 10 min. Then sodium triacetoxyborohydride (13 g, 61.72 mmol) was added at 0° C. and reaction stirred overnight at room temperature. On completion, the reaction was quenched with aqueous sodium bicarbonate, organic phase was separated and aqueous phase was extracted with dichloromethane. Combined organic layers were dried over sodium sulphate and concentrated under reduced pressure to give crude material was purified by column chromatography to afford the title compound (3.5 g, 38.88%).

Step 2: Synthesis of methyl 5-bromo-3-(((1r,4r)-4-((tert-butoxycarbonyl)-amino)cyclohexyl)-(ethyl)-amino)-2-methylbenzoate To a stirred solution of methyl 5-bromo-3-(((1r,4r)-4-((tert-butoxycarbonyl)amino)cyclohexyl)amino)-2-methylbenzoate (1.4 g, 3.18 mmol) and acetaldehyde (0.419 g, 9.52 mmol) in dichloroethane (20 mL), acetic acid (1.14 g, 19.0 mmol) was added and reaction stirred at room temperature for 10 min. Then sodium triacetoxyborohydride (2 g, 9.43 mmol) was added at 0° C. and reaction stirred at room temperature for 2 h. On completion, the reaction was quenched with aqueous sodium bicarbonate, organic phase was separated and aqueous phase was extracted with dichloromethane. Combined organic layers were dried over sodium sulphate and concentrated under reduced pressure to give crude material was purified by column chromatography to afford the title compound (1.25 g, 84.45%).

Step 3: Synthesis of tert-butyl ((1r,4r)-4-((5-bromo-3-(((4,6-dimethyl-2-oxo-1,2-dihydropyridin-3-yl) methyl)carbamoyl)-2-methylphenyl)(ethyl)amino) cyclohexyl)carbamate Aqueous NaOH (0.16 g, 4.0 mmol) was added to a solution of methyl 5-bromo-3-(((1r,4r)-4-((tert-butoxycarbonyl)-amino)cyclohexyl)-(ethyl)-amino)-2-methylbenzoate (1.25 g, 2.67 mmol) in ethanol (10 mL) and stirred at 60° C. for 1 h. After completion of the reaction, ethanol was removed under reduced pressure and acidified using dilute HCl up to pH 6 and adjusted using citric acid to pH 4. Extraction was carried out using ethyl acetate. Combined organic layers were dried concentrated giving respective acid (1.1 g, 90%).

The above acid (1.1 g, 2.42 mmol) was then dissolved in DMSO (10 mL) and 3-(amino methyl)-4,6-dimethylpyridin-2(1H)-one (0.736 g, 4.84 mmol) was added to it. The reaction mixture was stirred at room temperature for 15 min before PYBOP (1.88 g, 3.61 mmol) was added to it and stirring was continued for overnight. On completion, the reaction mixture was diluted with water and extracted with 10% MeOH/DCM. Combined organic layers were dried over $Na_2SO_4$ and solvent removed under reduced pressure to afford crude material which was purified by column chromatography over silica gel to afford the title compound (0.75 g, 53.57%).

Step 4: Synthesis of tert-butyl ((1r,4r)-4-((5-(((4,6-dimethyl-2-oxo-1,2-dihydropyridin-3-yl)-methyl)-carbamoyl)-4-methyl-4'-(morpholinomethyl)-[1,1'-biphenyl]-3-yl)-(ethyl)-amino)-cyclohexyl)-carbamate To a stirred solution of tert-butyl ((1r,4r)-4-((5-bromo-3-(((4,6-dimethyl-2-oxo-1,2-dihydropyridin-3-yl)methyl)carbamoyl)-2-methylphenyl)(ethyl)amino)cyclohexyl)carbamate (0.7 g, 1.19 mmol) and (4-(morpholinomethyl)phenyl)-boronic acid (0.489 g, 1.78 mmol) in dioxane/water mixture, $Na_2CO_3$ (0.454 g, 4.28 mmol) was added and solution purged with argon for 15 min. Then Pd (PPh$_3$)$_4$ (0.137 g, 0.119 mmol) was added and argon was purged again for 10 min. The reaction mixture was heated at 90° C. for 3.5 h. On completion, the reaction mixture was diluted with water and extracted with 10% MeOH/DCM. Combined organic layers were dried over $Na_2SO_4$ and solvent removed under reduced pressure to afford crude material which was purified by column chromatography over silica gel to afford the title compound (0.55 g, 67.48%).

Step 5: Synthesis of 5-(((1r,4r)-4-aminocyclohexyl) (ethyl)amino)-N-((4,6-dimethyl-2-oxo-1,2-dihydropyridin-3-yl)methyl)-4-methyl-4'-(morpholinomethyl)-[1,1'-biphenyl]-3-carboxamide tert-Butyl ((1r,4r)-4-((5-(((4,6-dimethyl-2-oxo-1,2-dihydropyridin-3-yl)-methyl)-carbamoyl)-4-methyl-4'-(morpholinomethyl)-[1,1'-biphenyl]-3-yl)-(ethyl)-amino)-cyclohexyl)-carbamate (0.55 g, 0.80 mmol) was taken in DCM (10 mL), to it, TFA (3 mL) was added at 0° C. and stirred at room temperature overnight. On completion of reaction, solvent was removed under reduced pressure, and the reaction quenched with aqueous sodium bicarbonate and extracted with dichloromethane. Combined organic layers were dried over sodium sulphate and concentrated under reduced pressure to obtain crude product which then purified by acetonitrile washing to give the title compound (0.42 g, 89.36%).

LCMS: 586.45 (M+1)$^+$; HPLC: 98.38% (@ 254 nm) (R$_t$: 3.667; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 8.18 (t, 1H), 7.56 (d, 2H, J=7.6), 7.35-7.38 (m, 3H), 7.18 (s, 1H), 5.86 (s, 1H), 4.29 (d, 2H, J=3.2 Hz), 3.58 (m, 4H), 3.49 (m, 2H), 3.09-3.10 (m, 2H), 2.63-2.66 (m, 2H), 2.37 (m, 4H), 2.21 (s, 3H), 2.20 (s, 3H), 2.11 (s, 3H), 1.75-1.78 (m, 4H), 1.40-1.43 (m, 2H), 1.05-1.08 (m, 2H), 0.83 (t, 3H, J=6.4 Hz).

Example 129: Synthesis of 5-(((1r,4r)-4-acetamidocyclohexyl)(ethyl)amino)-N-((4,6-dimethyl-2-oxo-1,2-dihydropyridin-3-yl)methyl)-4-methyl-4'-(morpholinomethyl)-[1,1'-biphenyl]-3-carboxamide

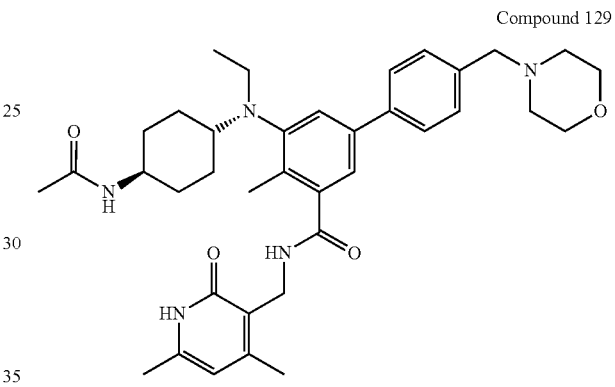

Compound 129

To a stirred solution of 5-(((1r,4r)-4-aminocyclohexyl) (ethyl)amino)-N-((4,6-dimethyl-2-oxo-1,2-dihydropyridin-3-yl)methyl)-4-methyl-4'-(morpholinomethyl)-[1,1'-biphenyl]-3-carboxamide (0.25 g, 0.42 mmol) and acetic acid (0.151 g, 0.85 mmol) in DMF (3 mL), EDCI (0.123 g, 0.64 mmol) and HOBt (0.057 g, 0.42 mmol) was added followed by the addition of triethylamine (0.064 g, 0.63 mmol) and reaction was stirred at room temperature overnight. After completion of the reaction, water was added to it and extraction was carried out using 10% MeOH/DCM. The combined organic layers were washed with water, dried over anhydrous $Na_2SO_4$, filtered and concentrated under reduced pressure to afford crude material which was purified by column chromatography to give the title compound (0.11 g, 41.04%).

LCMS: 628.35 (M+1)$^+$; HPLC: 98.79% (@ 254 nm) (R$_t$: 3.902; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (bs, 1H), 8.18 (t, 1H), 7.56-7.66 (m, 3H), 7.36-7.38 (m, 3H), 7.18 (s, 1H), 5.86 (s, 1H), 4.29 (d, 2H, J=4 Hz), 3.99 (m, 1H), 3.48-3.58 (m, 6H), 3.10-3.11 (m, 2H), 2.67 (m, 1H), 2.37 (m, 4H), 2.22 (s, 3H), 2.21 (s, 3H), 2.11 (s, 3H), 1.74-1.79 (m, 6H), 1.43-1.46 (m, 2H), 1.08-1.11 (m, 2H), 0.81-0.94 (t, 4H).

Example 130: Synthesis of N-((4,6-dimethyl-2-oxo-1,2-dihydropyridin-3-yl)methyl)-5-(ethyl(tetrahydro-2H-pyran-4-yl)amino)-2-fluoro-4-methyl-4'-(morpholinomethyl)-[1,1'-biphenyl]-3-carboxamide

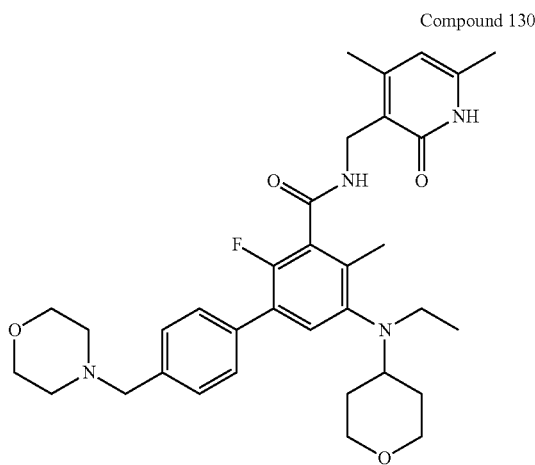 [SMILES: CCN(c1cc(-c2ccc(CN3CCOCC3)cc2)c(F)c(C(=O)NCc2c(C)cc(C)[nH]c2=O)c1C)C1CCOCC1]

Compound 130

Step 1: 6-fluoro-2-methyl-3-nitrobenzoic acid

A solution of 2-fluoro-6-methylbenzoic acid (2 g, 12.98 mmol) in concentrated $H_2SO_4$ (15.77 ml, 295.85 mmol) was cooled to −5° C. in an acetone/ice bath in air. A mixture of concentrated nitric acid (1.08 ml, 16.87 mmol) and concentrated $H_2SO_4$ (1 ml, 18.76 mmol) was added dropwise to the reaction mixture at −5 to 0° C. over 15 minutes. The pale yellow reaction mixture was stirred at −5 to 0° C. for 30 minutes before being poured onto ice (100 g). The resulting precipitate was filtered and dissolved in EtOAc (50 ml) and the organic phase was washed with deionized water (25 ml) followed by brine (25 ml). The organic phase was dried over $MgSO_4$, filtered and concentrated under reduced pressure to give 2 g (77%) of 6-fluoro-2-methyl-3-nitrobenzoic acid as a white solid. LC-MS 99%, 1.31 min (3 minute LC-MS method), m/z=198.0, $^1$H NMR (500 MHz, Chloroform-d) δ ppm 8.04 (dd, J=9.1, 5.0 Hz, 1H), 7.16 (t, J=8.6 Hz, 1H), 2.63 (s, 3H).

Step 2: Synthesis of 3-bromo-2-fluoro-6-methyl-5-nitrobenzoic acid

To a solution of 6-fluoro-2-methyl-3-nitrobenzoic acid (100 mg, 0.5 mmol) in concentrated $H_2SO_4$ (0.5 ml, 9.38 mmol) was added 1,3-dibromo-5,5-dimethylimidazolidine-2,4-dione (79 mg, 0.28 mmol) at room temperature and under nitrogen. The reaction mixture was stirred for 6 hours during which time a precipitate formed. The reaction mixture was added slowly to deionized water (3 ml) and the resulting precipitate was filtered. The solid was washed with deionized water (2 ml) and air dried for 2 hours to give 123 mg (88%) of 3-bromo-2-fluoro-6-methyl-5-nitrobenzoic acid as a pale yellow solid. LC-MS 94%, 1.61 min (3 minute LC-MS method), m/z=275.9/277.9 (ES−), $^1$H NMR (500 MHz, Chloroform-d) δ ppm 8.25 (d, J=6.2 Hz, 1H), 2.58 (s, 3H).

Step 3: Synthesis of methyl 3-bromo-2-fluoro-6-methyl-5-nitrobenzoate

To a solution of 3-bromo-2-fluoro-6-methyl-5-nitrobenzoic acid (2.41 g, 8.67 mmol) in N,N-Dimethylformamide (25 ml) at room temperature and under nitrogen was added $K_2CO_3$ (2.4 g, 17.34 mmol) followed by iodomethane (0.7 ml, 11.27 mmol). The reaction mixture was stirred at room temperature for 2 hours before being diluted with deionized water (100 ml) and extracted with EtOAc (3×50 ml). The combined organic phases were washed with saturated $NaHCO_3$(aq) (50 ml) and then dried over $MgSO_4$, filtered and concentrated under reduced pressure. The residue was purified twice by FCC (50 g silica, Isolute cartridge, gradient of eluents; 98:2 Heptane:EtOAc to 9:1 Heptane:EtOAc) to give 2.43 g (89%) of methyl 3-bromo-2-fluoro-6-methyl-5-nitrobenzoate as a white solid. LC-MS 99%, 2.18 min (3 minute LC-MS method), m/z=no ionization, $^1$H NMR (500 MHz, Chloroform-d) δ ppm 8.22 (d, J=6.2 Hz, 1H), 4.00 (s, 3H), 2.48 (s, 3H).

Step 4: Synthesis of methyl 3-amino-5-bromo-6-fluoro-2-methylbenzoate

To a solution of methyl 3-bromo-2-fluoro-6-methyl-5-nitrobenzoate (2.43 g, 8.32 mmol) in Methanol (80 ml) at room temperature was added ammonium chloride (4.37 g, 83.2 mmol) followed by deionized Water (40 ml). The mixture was heated to 70° C. in air before the addition of iron (2.79 g, 49.92 mmol). The reaction turned brown over the 2.5 hours it was stirred at 70° C. This mixture was allowed to cool to room temperature and was filtered through Kieselgel. The filter pad was washed with MeOH (80 ml) and the filtrate concentrated under reduced pressure. The residue was dissolved in saturated $NaHCO_3$(aq) (50 ml) and EtOAc (150 ml). The phases were separated and the organic phase was washed with saturated $NaHCO_3$(aq) (50 ml) before being dried over $MgSO_4$, filtered and concentrated under reduced pressure. The residue was purified by FCC (50 g silica, Isolute cartridge, gradient of eluents; 95:5 Heptane:EtOAc to 7:3 Heptane:EtOAc) to give 2.23 g (95%, 77% corrected yields) of methyl 3-amino-5-bromo-6-fluoro-2-methylbenzoate as a yellow oil. The material was taken through the next step without further purification. LC-MS 81%, 1.87 min (3 minute LC-MS method), m/z=261.9/263.9, $^1$H NMR (500 MHz, Chloroform-d) δ ppm 6.89 (d, J=6.0 Hz, 1H), 3.94 (s, 3H), 3.60 (s, 2H), 2.08 (s, 3H).

Step 5: Synthesis of methyl 3-bromo-2-fluoro-6-methyl-5-[(oxan-4-yl)amino]benzoate To a solution of methyl 3-amino-5-bromo-6-fluoro-2-methylbenzoate (2.23 g, 8.08 mmol) in 1,2-Dichloroethane (32 ml) at room temperature and under nitrogen was added oxan-4-one (1.49 ml, 16.17 mmol) followed by acetic acid (2.78 ml, 48.5 mmol). This solution was stirred for 5 minutes before the addition of sodium triacetoxyborohydride (5.14 g, 24.25 mmol) at room temperature. After stirring for 5.5 hours there was no unreacted starting material present by LCMS. Deionized water (32 ml) was added and the mixture was neutralized with solid $NaHCO_3$. The phases were separated and the aqueous layer was extracted with EtOAc (2×32 ml). The combined organic extracts were dried over $MgSO_4$, filtered and concentrated under reduced pressure. The residue was purified by FCC (50 g silica, Isolute cartridge, gradient of eluents; 95:5 Heptane:EtOAc to 6:4 Heptane:EtOAc) to give 2.3 g (82%) of methyl 3-bromo-2-fluoro-6-methyl-5-[(oxan-4-yl)amino]benzoate as a off-white solid. LC-MS 99%, 2.13 min (3 minute LC-MS method), m/z=245.9/247.9, $^1$H NMR (500 MHz, Chloroform-d) δ ppm 6.78 (d, J=5.9 Hz, 1H), 4.01 (dt, J=11.9, 3.4 Hz, 2H), 3.93 (s, 3H), 3.53 (td, J=11.7, 2.1 Hz, 2H), 3.49-3.42 (m, 1H), 3.34 (s, 1H), 2.04 (s, 5H), 1.48 (qd, J=11.0, 4.2 Hz, 2H).

Step 6: Synthesis of methyl 3-bromo-5-[ethyl(oxan-4-yl)amino]-2-fluoro-6-methylbenzoate To a solution of methyl 3-bromo-2-fluoro-6-methyl-5-[(oxan-4-yl)amino]benzoate (500 mg, 1.44 mmol) in 1,2-Dichloroethane (15 ml) at room temperature and under nitrogen was added acetaldehyde (0.81 ml, 14.44 mmol) followed by acetic acid (0.5 ml, 8.67 mmol). This solution was stirred for 5 minutes before the addition of sodium triacetoxyborohydride (3.06 g, 14.44 mmol) at room temperature. After stirring for 2 hours deionized water (20 ml) was added and the mixture was neutralized with solid NaHCO₃. The phases were separated and the aqueous layer was extracted with EtOAc (2×20 ml). The combined organic extracts were dried over MgSO₄, filtered and concentrated under reduced pressure. The residue was purified by FCC (10 g silica, Isolute cartridge, gradient of eluents; 95:5 Heptane:EtOAc to 85:15 Heptane:EtOAc) to give 519 mg (96%) of methyl 3-bromo-5-[ethyl(oxan-4-yl)amino]-2-fluoro-6-methylbenzoate as a pale yellow oil that solidified upon standing. LC-MS 94%, 2.45 min (3 minute LC-MS method), m/z=373.9/375.9, ¹H NMR (500 MHz, Chloroform-d) δ ppm 7.33 (d, J=6.6 Hz, 1H), 3.95 (s, 5H), 3.32 (td, J=11.7, 2.1 Hz, 2H), 3.00 (q, J=7.1 Hz, 2H), 2.88 (tt, J=10.9, 4.0 Hz, 1H), 2.25 (s, 3H), 1.73-1.54 (m, 4H), 0.85 (t, J=7.1 Hz, 3H).

Step 7: Synthesis of 3-bromo-5-[ethyl(oxan-4-yl)amino]-2-fluoro-6-methylbenzoic acid To a solution of methyl 3-bromo-5-[ethyl(oxan-4-yl)amino]-2-fluoro-6-methylbenzoate (519 mg, 1.39 mmol) in Tetrahydrofuran (13 ml) and MeOH (4 ml) was added 4M NaOH (13.87 ml). The reaction mixture was stirred at 50° C. in air for 72 hours. The reaction mixture was acidified to pH 2-3 with 6M HCl and extracted with DCM (5×15 ml). The combined organic extracts were dried over MgSO₄, filtered and concentrated under reduced pressure to give 526 mg (95%) of 3-bromo-5-[ethyl(oxan-4-yl)amino]-2-fluoro-6-methylbenzoic acid as a beige foam. LC-MS 88%, 1.77 min (3 minute LC-MS method), m/z=359.9/361.9, ¹H NMR (500 MHz, Chloroform-d) δ ppm 7.43-7.31 (m, 1H), 4.00 (d, J=11.3 Hz, 2H), 3.41-3.29 (m, 2H), 3.16-2.91 (m, 3H), 2.40 (s, 3H), 1.84-1.59 (m, 4H), 0.99-0.82 (m, 3H).

Step 8: Synthesis of 3-bromo-N-[(4,6-dimethyl-2-oxo-1,2-dihydropyridin-3-yl)methyl]-5-[ethyl(oxan-4-yl)amino]-2-fluoro-6-methylbenzamide To a solution of 3-bromo-5-[ethyl(oxan-4-yl)amino]-2-fluoro-6-methylbenzoic acid (200 mg, 0.56 mmol) in N,N-Dimethylformamide (2 ml) at room temperature and under nitrogen was added PyBOP (346.72 mg, 0.67 mmol) followed by N-ethyl-N-(propan-2-yl)propan-2-amine (145 μl, 0.83 mmol) and 3-(aminomethyl)-4,6-dimethyl-1,2-dihydropyridin-2-one (89%, 104 mg, 0.61 mmol). After stirring for 1 hour at room temperature no starting material was observed by LCMS. EtOAc (20 ml) was added to the reaction mixture and this was then washed with deionized water (5 ml) followed by saturated NaHCO₃(aq) (3×5 ml). The organic phase was dried over MgSO₄, filtered and concentrated under reduced pressure. The residue was then purified by FCC (5 g silica, Isolute cartridge, gradient of eluents; 100% DCM to 97:3 DCM:MeOH) to give 112 mg (41%) of 3-bromo-N-[(4,6-dimethyl-2-oxo-1,2-dihydropyridin-3-yl)methyl]-5-[ethyl(oxan-4-yl)amino]-2-fluoro-6-methylbenzamide as a pale yellow solid. LC-MS 97%, 1.85 min (3 minute LC-MS method), m/z=494.0/496.0, ¹H NMR (500 MHz, Chloroform-d) δ ppm 11.66 (s, 1H), 7.23 (d, J=6.5 Hz, 1H), 5.95 (s, 1H), 4.65-4.43 (m, 2H), 3.93 (d, J=11.0 Hz, 2H), 3.38-3.22 (m, 2H), 2.97 (q, J=7.0 Hz, 2H), 2.91-2.79 (m, 1H), 2.37 (s, 3H), 2.24-2.11 (m, 6H), 1.72-1.53 (m, 4H), 0.83 (t, J=7.0 Hz, 3H).

Step 9: Synthesis of N-((4,6-dimethyl-2-oxo-1,2-dihydropyridin-3-yl)methyl)-5-(ethyl(tetrahydro-2H-pyran-4-yl)amino)-2-fluoro-4-methyl-4'-(morpholinomethyl)-[1,1'-biphenyl]-3-carboxamide To a solution of 3-bromo-N-[(4,6-dimethyl-2-oxo-1,2-dihydropyridin-3-yl)methyl]-5-[ethyl(oxan-4-yl)amino]-2-fluoro-6-methylbenzamide (112 mg, 0.23 mmol) in 1,4-Dioxane (2 ml) and Water (1 ml) was added 4-[4-(4,4,5,5-tetramethyl-1,3,2-dioxaborolan-2-yl)benzyl]morpholine (103 mg, 0.34 mmol) followed by Na₂CO₃ (84.04 mg, 0.79 mmol). The solution was purged with nitrogen for 5 minutes before the addition of palladium-triphenylphosphine (1:4) (26 mg, 0.02 mmol). The yellow mixture was then purged with nitrogen for 5 minutes before being heated to 100° C. After 4 hours LCMS indicated no unreacted starting material was present. The darken reaction mixture was diluted with deionized water (5 ml) and extracted with 10% MeOH in DCM (5×5 ml). The combined organic extracts were dried over MgSO₄, filtered and concentrated under reduced pressure. The residue was purified by FCC (5 g silica, Isolute cartridge, gradient of eluents; 99:1 DCM:MeOH to 95:5 DCM:MeOH) to give 69 mg (52%) of the title compound as an off-white solid. LC-MS 97%, 2.70 min (7 minute LC-MS method), m/z=591.2, ¹H NMR (500 MHz, Chloroform-d) δ ppm 12.10 (br s, 1H), 7.53-7.30 (m, 4H), 7.13 (d, J=7.4 Hz, 1H), 7.07 (br s, 1H), 5.88 (s, 1H), 4.55 (br s, 2H), 3.93 (d, J=11.2 Hz, 2H), 3.73-3.69 (m, 4H), 3.52 (s, 2H), 3.30 (t, J=10.8 Hz, 2H), 3.02 (q, J=6.9 Hz, 2H), 2.92 (ddd, J=14.6, 10.7, 3.7 Hz, 1H), 2.46 (s, 4H), 2.35 (s, 3H), 2.26 (s, 3H), 2.12 (s, 3H), 1.79-1.43 (m, 4H), 0.86 (t, J=7.0 Hz, 3H).

Example 131: Synthesis of N-((4,6-dimethyl-2-oxo-1,2-dihydropyridin-3-yl)methyl)-5-(ethyl(tetrahydro-2H-pyran-4-yl)amino)-4-methyl-4'-((3-oxomorpholino)methyl)-[1,1'-biphenyl]-3-carboxamide Compound 131

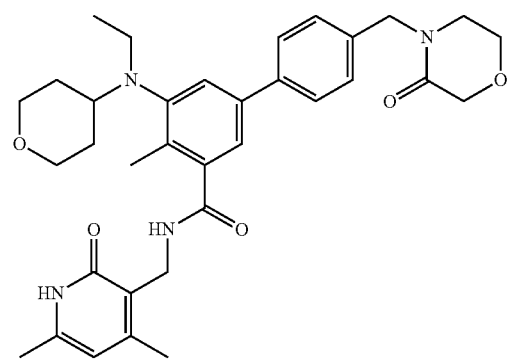

Step 1: Synthesis of 4'-(bromomethyl)-N-((4,6-dimethyl-2-oxo-1,2-dihydropyridin-3-yl)methyl)-5-(ethyl(tetrahydro-2H-pyran-4-yl)amino)-4-methyl-[1,1'-biphenyl]-3-carboxamide To an ice cooled stirred solution of N-((4,6-dimethyl-2-oxo-1,2-dihydropyridin-3-yl)methyl)-5-(ethyl(tetrahydro-2H-pyran-4-yl)amino)-4'-(hydroxymethyl)-4-methyl-[1,1'-biphenyl]-3-carboxamide (450 mg, 0.89 mmol) in DCM (10 mL) was added triphenyl phosphine (469 mg, 1.78 mmol) and carbon tetrabromide (741 mg, 2.25 mmol). Reaction mixture was allowed to attain room temperature and stirring continued for 16 h. On completion, removal of the solvent under reduced pressure followed by column chromatographic purification afforded compound 8 (300 mg, 59%).

Step 2: Synthesis of N-((4,6-dimethyl-2-oxo-1,2-dihydropyridin-3-yl)methyl)-5-(ethyl(tetrahydro-2H-pyran-4-yl)amino)-4-methyl-4'-((3-oxomorpholino)methyl)-[1,1'-biphenyl]-3-carboxamide To an ice cooled stirred solution of 4'-(bromomethyl)-N-((4,6-dimethyl-2-oxo-1,2-dihydropyridin-3-yl)methyl)-5-(ethyl(tetrahydro-2H-pyran-4-yl)amino)-4-methyl-[1,1'-biphenyl]-3-carboxamide (250 mg, 0.44 mmol) and morpholin-3-one (67 mg, 0.66 mmol) in DMF (30 mL) was added sodium hydride (27 mg, 0.66 mmol). After 10 minutes, ice was removed and stirring continued for 16 h at room temperature. On completion, water was added and extracted with DCM (3 times). Combined organic layer was dried over sodium sulphate. Removal of the solvent under reduced pressure followed by column chromatographic and prep. HPLC purification afforded the title compound (75 mg, 29%). LCMS: 587.35 (M+1)$^+$; HPLC: 98.69% (@ 254 nm) (R$_t$; 4.604; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.50 (bs, 1H), 8.25 (m, 1H), 7.65 (m, 2H), 7.37-7.35 (m, 3H), 5.87 (s, 1H), 4.59 (m, 2H), 4.29 (d, 2H), 4.12 (s, 2H), 3.82 (m, 4H), 3.28 (m, 4H), 3.17-3.09 (m, 2H), 2.32-2.28 (m, 4H), 2.22 (s, 3H), 2.11 (s, 3H), 1.57 (m, 4H), 0.86 (t, 3H).

Example 132: Synthesis of N-((4,6-dimethyl-2-oxo-1,2-dihydropyridin-3-yl)methyl)-5-(ethyl(tetrahydro-2H-thiopyran-4-yl)amino)-4-methyl-4'-(morpholinomethyl)-[1,1'-biphenyl]-3-carboxamide Compound 132

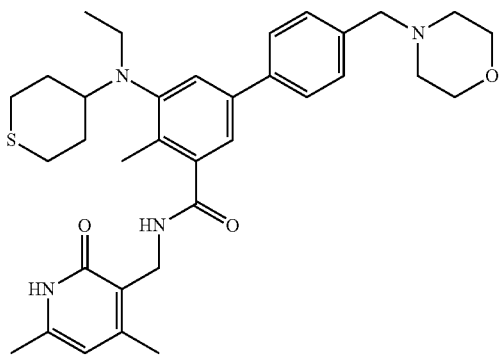

Step 1: Synthesis of methyl 5-bromo-2-methyl-3-((tetrahydro-2H-thiopyran-4-yl)amino) benzoate To a stirred solution of methyl 3-amino-5-bromo-2-methylbenzoate (2.5 g, 10.24 mmol) and dihydro-2H-thiopyran-4(3H)-one (1.42 g, 12.29 mmol) in dichloroethane (50 mL), acetic acid (3.6 ml, 61.47 mmol) was added and reaction stirred at room temperature for 10 min. The reaction mixture was cooled to 0° C. and sodium triacetoxyborohydride (6.5 g, 30.73 mmol) was added and stirred at room temperature overnight. The reaction mixture was neutralized with sat. NaHCO$_3$ and compound was extracted in DCM, dried over Na$_2$SO$_4$, concentrated under reduced pressure. Column chromatography purification of crude gave methyl 5-bromo-2-methyl-3-((tetrahydro-2H-thiopyran-4-yl)amino) benzoate (2.5 g, 71.0%).

Step 2: Synthesis of methyl 5-bromo-3-(ethyl(tetrahydro-2H-thiopyran-4-yl)amino)-2-methylbenzoate To a stirred solution of methyl 5-bromo-2-methyl-3-((tetrahydro-2H-thiopyran-4-yl)amino) benzoate (2.5 g, 5.83 mmol) and acetaldehyde (513 mg, 11.66 mmol) in dichloroethane (50 mL), acetic acid (2.0 ml, 34.9 mmol) was added and reaction was stirred at room temperature for 20 minutes. The reaction mixture was cooled to 0° C. and sodium triacetoxyborohydride (3.7 g, 17.49 mmol) was added and stirred at room temperature for overnight. The mixture was neutralized with sat. NaHCO$_3$ and compound was extracted in DCM, dried over Na$_2$SO$_4$, concentrated under reduced pressure. The crude material was purified by column chromatography to afford methyl 5-bromo-3-(ethyl(tetrahydro-2H-thiopyran-4-yl)amino)-2-methylbenzoate (2.0 g, 74.0%).

Step 3: Synthesis of 5-bromo-N-((4,6-dimethyl-2-oxo-1,2-dihydropyridin-3-yl)methyl)-3-(ethyl(tetrahydro-2H-thiopyran-4-yl)amino)-2-methylbenzamide A mixture of methyl 5-bromo-3-(ethyl(tetrahydro-2H-thiopyran-4-yl)amino)-2-methylbenzoate (2.0 g, 5.39 mol) and NaOH (0.323 g, 8.08 mol) in 3 ml of ethanol:water (2:1) was heated at 70° C. for 2 h. reaction mixture was concentrated to dryness and crude was partitioned between water and DCM, organic layer was dried over Na$_2$SO$_4$, concentrated under reduced pressure to afford 1.8 g of acid.

The crude acid (1.8 g, 5.04 mmol), 3-(aminomethyl)-4,6-dimethylpyridin-2(1H)-one (1.53 mg, 10.08 mmol) and PyBOP (3.9 g, 7.56 mmol) mixture was stirred in 3 ml of DMSO at room temperature overnight. The reaction mixture was diluted with water and compound was extracted in DCM. Organic layer was dried over Na$_2$SO$_4$, concentrated under reduced pressure and purified by silica gel (100-200 mesh) column chromatography (eluted at 4% MeOH in DCM) to yield 5-bromo-N-((4,6-dimethyl-2-oxo-1,2-dihydropyridin-3-yl)methyl)-3-(ethyl(tetrahydro-2H-thiopyran-4-yl)amino)-2-methylbenzamide (1.5 g, 60.7%).

Step 4: Synthesis of N-((4,6-dimethyl-2-oxo-1,2-dihydropyridin-3-yl)methyl)-5-(ethyl(tetrahydro-2H-thiopyran-4-yl)amino)-4-methyl-4'-(morpholinomethyl)-[1,1'-biphenyl]-3-carboxamide A solution of 5-bromo-N-((4,6-dimethyl-2-oxo-1,2-dihydropyridin-3-yl)methyl)-3-(ethyl(tetrahydro-2H-thiopyran-4-yl)amino)-2-methylbenzamide (800 mg, 1.629 mmol), 4-(4-(4,4,5,5-tetramethyl-1,3,2-dioxaborolan-2-yl)benzyl)morpholine (740 mg, 2.443 mmol), sodium carbonate (621 mg, 5.86 mmol) in 20 ml of dioxane was degassed with argon for 20 min, Pd(PPh₃) (188 mg, 0.16 mmol) was added to the mixture and heated to 100° C. overnight. The reaction was cooled to room temperature and diluted with water, compound was extracted in 10% MeOH in DCM, dried over Na₂SO₄, concentrated and crude was purified by silica gel (100-200) chromatography to obtain the title compound (700 mg, 73.0%).

LCMS: 589.25 (M+1)⁺; HPLC: 96.75% (@ 254 nm) ($R_t$; 4.869; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (D20, 400 MHz) δ 7.78-7.89 (m, 4H), 7.64-7.66 (m, 2H), 6.33 (s, 1H), 4.52 (s, 2H), 4.45 (s, 2H), 4.13 (d, J=13.2 Hz, 2H), 3.77-3.89 (m, 5H), 3.49 (d, J=12.0 Hz, 2H), 3.30-3.33 (m, 2H), 2.73-2.82 (m, 5H), 2.44, 2.38, 2.30 (3s, 9H), 1.89 (m, 2H), 1.06 (t, J=7.2 Hz, 3H).

Example 133: Synthesis of N-((4,6-dimethyl-2-oxo-1,2-dihydropyridin-3-yl)methyl)-5-(ethyl(1-oxidotetrahydro-2H-thiopyran-4-yl)amino)-4-methyl-4'-(morpholinomethyl)-[1,1'-biphenyl]-3-carboxamide Compound 133

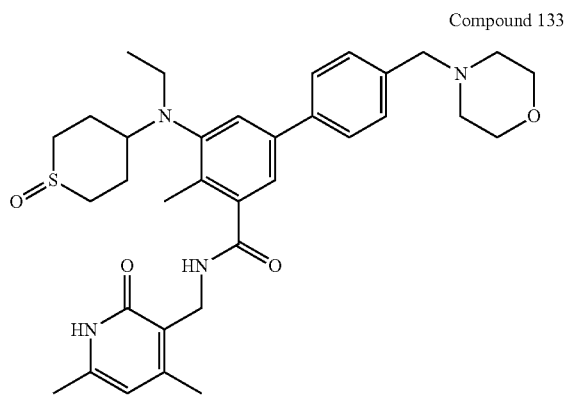 [SMILES: CCN(c1cc(-c2ccc(CN3CCOCC3)cc2)cc(C(=O)NCc2c(C)cc(C)[nH]c2=O)c1C)C1CCS(=O)CC1]

To a cooled solution of N-((4,6-dimethyl-2-oxo-1,2-dihydropyridin-3-yl)methyl)-5-(ethyl(tetrahydro-2H-thiopyran-4-yl)amino)-4-methyl-4'-(morpholinomethyl)-[1,1'-biphenyl]-3-carboxamide (200 mg, 0.34 mmol) in 2 ml of DCM, m-CPBA (70 mg, 0.41 mmol) was added at 0° C. and stirred at room temperature for 2 h (monitored by TLC). The reaction was quenched with sat. NaHCO₃, compound was extracted in DCM, dried over Na₂SO₄, concentrated under reduced pressure and purified by silica gel (100-200) column chromatography to obtain the title compound (60 mg, 29.3%).

LCMS: 605.25 (M+1)⁺; HPLC: 44.06% & 54.42% (@ 254 nm) ($R_t$; 4.092&4.448; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d6, 400 MHz) δ 11.45 (s, 1H), 8.18 (t, 1H), 7.59-7.57 (m, 2H), 7.39-7.37 (m, 3H), 7.23-7.21 (m, 1H), 5.86 (s, 1H), 4.29 (d, 2H, J=4 Hz), 3.58 (m, 3H), 3.48 (m, 3H), 3.18-2.86 (m, 5H), 2.67-2.59 (m, 4H), 2.37-2.33 (m, 4H), 2.25 (s, 3H), 2.21 (s, 3H), 2.10 (s, 3H), 1.77 (m, 2H), 0.85 (t, 3H).

Example 134: N-((4,6-dimethyl-2-oxo-1,2-dihydropyridin-3-yl)methyl)-5-(ethyl(tetrahydro-2H-pyran-4-yl)amino)-3',4-dimethyl-4'-(morpholinomethyl)-[1,1'-biphenyl]-3-carboxamide Compound 134

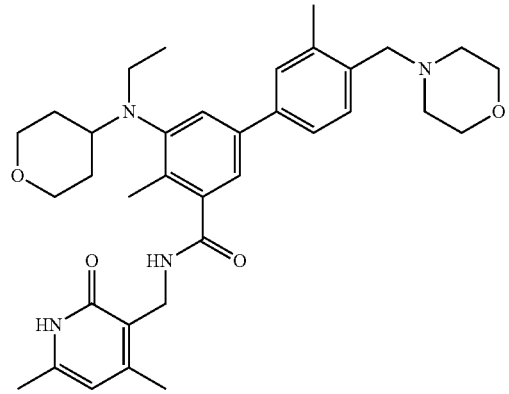

Compound 134 was prepared with the method similar to that described in Example 131. Analytical Data: LCMS: 587.4 (M+1)⁺; HPLC: 98.76% (@ 254 nm) ($R_t$; 4.11; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d6, 400 MHz) δ 11.45 (bs, 1H), 8.17 (bs, 1H), 7.41-7.20 (m, 5H), 5.85 (s, 1H), 4.28 (d, J=4 Hz, 2H), 3.82 (d, J=10 Hz, 2H), 3.55 (m, 4H), 3.44 (bs, 2H), 3.27-3.22 (m, 2H), 3.09-3.01 (m, 3H), 2.39 (m, 7H), 2.23 (s, 3H), 2.20 (s, 3H), 2.10 (s, 3H), 1.67-1.51 (m, 4H), 0.83 (t, J=6.8 Hz, 3H).

Example 135: 4-((3'-(((4,6-dimethyl-2-oxo-1,2-dihydropyridin-3-yl)methyl)carbamoyl)-5'-(ethyl(1-oxidotetrahydro-2H-thiopyran-4-yl)amino)-4'-methyl-[1,1'-biphenyl]-4-yl)methyl)morpholine 4-oxide Compound 135

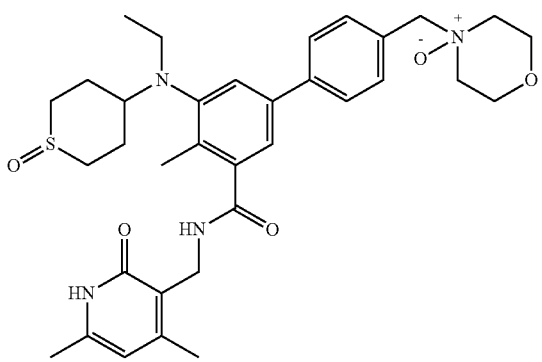

During above mentioned prep HPLC purification, 4-((3'-(((4,6-Dimethyl-2-oxo-1,2-dihydropyridin-3-yl)methyl)carbamoyl)-5'-(ethyl(1-oxidotetrahydro-2H-thiopyran-4-yl)amino)-4'-methyl-[1,1'-biphenyl]-4-yl)methyl)morpholine 4-oxide was also isolated. LCMS: 621.40 (M+1)+; HPLC: 98.69% (@ 254 nm) (R$_t$: 4.157; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 12.18 (s, 1H), 11.45 (s, 1H), 8.20 (t, 1H), 7.79 (d, 2H, J=6.8 Hz), 7.62 (d, 2H, J=6.8 Hz), 7.45 (s, 1H), 7.27 (s, 2H), 5.86 (s, 1H), 4.89 (s, 2H), 4.30 (d, 2H, J=4 Hz), 4.00-3.80 (m, 7H), 3.19 (m, 2H), 3.00-2.85 (m, 4H), 2.70-2.60 (m, 2H), 2.30 (bs, 2H), 2.26 (s, 3H), 2.21 (s, 3H), 2.10 (s, 3H), 1.75 (m, 2H), 0.87 (t, 3H, J=6 Hz).

Example 136: Synthesis of N-((4,6-dimethyl-2-oxo-1,2-dihydropyridin-3-yl)methyl)-5-((1,1-dioxidotetrahydro-2H-thiopyran-4-yl)(ethyl)amino)-4-methyl-4'-(morpholinomethyl)-[1,1'-biphenyl]-3-carboxamide

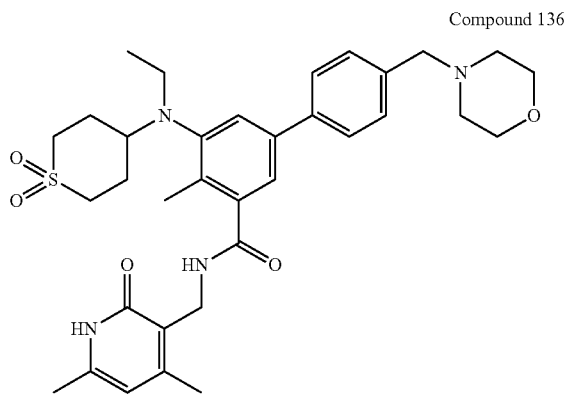 [SMILES: CCN(c1cc(-c2ccc(CN3CCOCC3)cc2)cc(C(=O)NCc2c(C)cc(C)[nH]c2=O)c1C)C1CCS(=O)(=O)CC1]

Compound 136

To a cooled solution of compound N-((4,6-dimethyl-2-oxo-1,2-dihydropyridin-3-yl)methyl)-5-(ethyl(tetrahydro-2H-thiopyran-4-yl)amino)-4-methyl-4'-(morpholinomethyl)-[1,1'-biphenyl]-3-carboxamide (200 mg, 0.34 mmol) in 2 ml of DCM, m-CPBA (117 mg, 0.68 mmol) was added at 0° C. and stirred at room temperature for 2 hours (monitored by TLC). The reaction was quenched with saturated NaHCO$_3$ and extracted with in DCM, dried over Na$_2$SO$_4$ and concentrated under reduced pressure. After column chromatography, the title compound was obtained as the TFA salt after further purification by prep. HPLC (80 mg, 38.1%).

LCMS: 621.45 (M+1)+; HPLC: 99.93% (@ 254 nm) (R$_t$: 4.522; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 12.22 (s, 1H), 11.45 (s, 1H), 8.20 (t, 1H), 7.78 (d, 2H, J=8 Hz), 7.61 (d, 2H, J=8 Hz), 7.43 (s, 1H), 7.28 (s, 1H), 5.86 (s, 1H), 4.89 (s, 2H), 4.29 (d, 2H, J=4.4 Hz), 4.00-3.80 (m, 7H), 3.32 (m, 2H), 3.04 (m, 4H), 2.65-2.55 (m, 2H), 2.26 (s, 3H), 2.21 (s, 3H), 2.17 (m, 2H), 2.10 (s, 3H), 1.78 (m, 2H), 0.83 (t, 3H, J=6.4&7.2 Hz).

Example 137: Synthesis of N-((4,6-dimethyl-2-oxo-1,2-dihydropyridin-3-yl)methyl)-5-(ethyl(tetrahydro-2H-pyran-4-yl)amino)-4,4'-dimethyl-[1,1'-biphenyl]-3-carboxamide

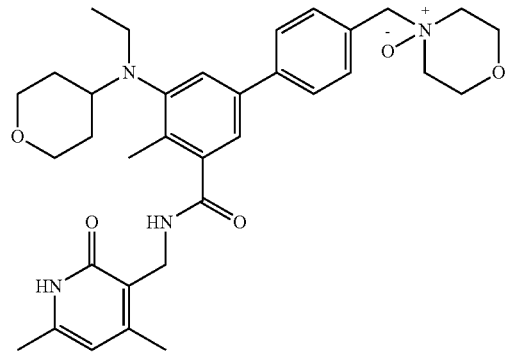

Compound 137

To a stirred solution of N-((4,6-dimethyl-2-oxo-1,2-dihydropyridin-3-yl)methyl)-5-(ethyl(tetrahydro-2H-pyran-4-yl)amino)-4,4'-dimethyl-[1,1'-biphenyl]-3-carboxamide (200 mg, 0.35 mmol) in dichloromethane at room temperature, m-CPBA (60 mg, 0.35 mmol) was added and stirring continued for overnight at room temperature. On completion, reaction was quenched by addition of saturated aqueous sodium bicarbonate solution and extracted with 10% MeOH/DCM (3 times). Combined organic layer was dried over sodium sulphate. Removal of the solvent under reduced pressure followed by solvent washing afforded the title compound (120 mg, 58%). LCMS: 589.35 (M)+; HPLC: 95.56% (@ 254 nm) (R$_t$: 4.143; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.5 (bs, 1H), 8.22 (t, 1H), 7.66-7.60 (m, 4H), 7.42 (s, 1H), 7.21 (s, 1H), 5.85 (s, 1H), 4.34-4.28 (m, 4H), 4.12-4.07 (m, 2H), 3.83-3.81 (m, 2H), 3.62-3.60 (m, 2H), 3.42-3.39 (m, 2H), 3.33-3.22 (m, 2H), 3.16-3.08 (m, 3H), 2.65-2.62 (m, 2H), 2.25-2.10 (m, 9H), 1.67-1.51 (m, 4H), 0.83 (t, 3H, J=6.8 Hz).

Example 138: Synthesis of N-((4,6-dimethyl-2-oxo-1,2-dihydropyridin-3-yl)methyl)-4-methyl-4'-(morpholinomethyl)-5-((tetrahydro-2H-pyran-4-yl)(2,2,2-trifluoroethyl)amino)-[1,1'-biphenyl]-3-carboxamide

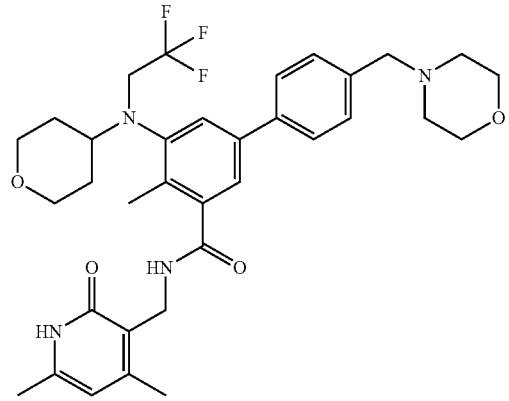

Compound 138

Step 1: Synthesis of 5-bromo-2-methyl-3-nitrobenzoic acid

A solution of 5-bromo-2-methylbenzoic acid (5.0 g, 23 mmol) in concentrated $H_2SO_4$ (27 ml, 512 mmol) was cooled to 5° C. in an acetone/ice bath. A mixture of concentrated nitric acid (1.9 ml, 30 mmol) and concentrated $H_2SO_4$ (2.8 ml, 52 mmol) was added dropwise to the reaction mixture at −5 to 0° C. over 15 minutes. The yellow reaction mixture was stirred at −5 to 0° C. for 2 hours during which time a yellow precipitate formed. The reaction mixture was poured onto ice (150 g) and the precipitate was then collected by filtration. The precipitate was air dried to give the title compound (5.5 g, 52%) as a pale yellow solid. LC-MS 57%, 1.82 min (3.5 minute LC-MS method), no ionization; $^1$H NMR (500 MHz, DMSO-$d_6$) δ ppm 8.29 (s, 1H) 8.13 (d, J=1.58 Hz, 1H) 2.43 (s, 3H).

Step 2: Synthesis of methyl 5-bromo-2-methyl-3-nitrobenzoate

To a solution of 5-bromo-2-methyl-3-nitrobenzoic acid (5.5 g, 21 mmol) in DMF (42 ml) under nitrogen, was added $Na_2CO_3$ (3.4 g, 32 mmol) followed by iodomethane (2.0 ml, 32 mmol). The reaction mixture was stirred at room temperature for 2 hours. The mixture was diluted with deionized water (150 ml) and extracted with EtOAc (4×50 ml). The combined organic phases were washed with saturated $NaHCO_3$ (aq) (2×50 ml), dried over $MgSO_4$, filtered and concentrated in-vacuo to give the title compound (6.3 g, 61%) as a yellow oil. LC-MS 57%, 2.20 min (3.5 minute LC-MS method), no ionization; $^1$H NMR (500 MHz, Chloroform-d) δ ppm 7.38 (d, J=2.05 Hz, 1H) 7.23 (d, J=2.05 Hz, 1H) 3.20 (s, 3H) 1.82 (s, 3H).

Step 3: Synthesis of methyl 3-amino-5-bromo-2-methylbenzoate

To a solution of methyl 5-bromo-2-methyl-3-nitrobenzoate (6.3 g, 21 mmol) in methanol (150 ml) was added ammonium chloride (11.0 g, 209 mmol) followed by deionized water (75 ml). The mixture was heated to 70° C. before the addition of iron (7.0 g, 125 mmol). The reaction mixture was stirred at 70° C. for 2 hours, before being allowed to cool to room temperature and filtered through Kieselgel. The filter pad was washed with MeOH (150 ml) and the filtrate concentrated in-vacuo. The residue was dissolved in saturated $NaHCO_3$ (aq) (50 ml) and EtOAc (150 ml). The phases were separated and the organic phase was washed with saturated $NaHCO_3$ (aq) (3×50 ml), dried over $MgSO_4$, filtered and concentrated in-vacuo. The residue was purified by flash column chromatography (50 g silica Isolute cartridge, 5-20% EtOAc:Heptanes) to give the title compound (3.0 g, 51%) as a thick pale yellow oil. LC-MS 87%, 1.89 min (3.5 minute LC-MS method), m/z=243.9, 244.9, 245.9, 246.9; $^1$H NMR (500 MHz, Chloroform-d) δ ppm 7.34 (d, J=1.89 Hz, 1H) 6.95 (d, J=1.89 Hz, 1H) 3.88 (s, 3H) 3.80 (br. s., 2H) 2.29 (s, 3H).

Step 4: Synthesis of methyl 5-bromo-2-methyl-3-[(oxan-4-yl)amino]benzoate

To a solution of methyl 3-amino-5-bromo-2-methylbenzoate (3.0 g, 12 mmol) in 1,2-Dichloroethane (48 ml) under nitrogen, was added oxan-4-one (2.3 ml, 25 mmol) followed by acetic acid (4.2 ml, 74 mmol). The reaction mixture was stirred for 5 minutes before the addition of sodium triacetoxyborohydride (7.8 g, 37 mmol). After stirring for 64 hours, deionized water (100 ml) was added and the mixture was neutralized with solid $NaHCO_3$. The phases were separated and the aqueous layer was extracted with EtOAc (4×50 ml). The combined organic extracts were dried over $MgSO_4$, filtered and concentrated in-vacuo. The residue was purified by flash column chromatography (50 g silica, Isolute cartridge, 10-30% EtOAc:Heptanes) to give the title compound (3.5 g 85%) as a white solid. LC-MS 99.8%, 2.18 min (3.5 minute LC-MS method), m/z=327.9, 328.9, 329.9, 330.9; $^1$H NMR (500 MHz, Chloroform-d) δ ppm 7.24 (d, J=1.73 Hz, 1H) 6.85 (d, J=1.58 Hz, 1H) 4.03 (dt, J=11.82, 3.31 Hz, 2H) 3.88 (s, 3H) 3.66 (br.s., 1H) 3.56 (td, J=11.55, 1.97 Hz, 2H) 3.47-3.55 (m, 1H) 2.24 (s, 3H) 2.06 (d, J=13.56 Hz, 2H) 1.47-1.60 (m, 2H).

Step 5: Synthesis of methyl 5-bromo-2-methyl-3-[(oxan-4-yl)(2,2,2-trifluoroethyl)amino]benzoate In a 2 necked 100 ml RBF, containing methyl 5-bromo-2-methyl-3-[(oxan-4-yl)amino]benzoate (500 mg, 1.5 mmol) and TFA (15 ml), was added sodium tetrahydroborate (1.0 g, 26 mmol) portionwise over 5 minutes. The reaction mixture was stirred at room temperature for 2 hours and then heated to 50° C. for 3 hours and treated with a further aliquot of $NaBH_4$ (300 mg) over 25 minutes. The reaction mixture was then heated to 60° C. for 2 hours and left to stir at room temperature for 17 hours. The reaction mixture was treated with TFA (5 ml) and $NaBH_4$ (200 mg) and heated back up to 60° C. for 3.5 hours. A further aliquot of $NaBH_4$ (200 mg) was added over 15 minutes, along with TFA (5 ml) and heating continued for a further 3 hours, before being left to stand at room temperature overnight. The reaction mixture was poured over ice (75 ml) and stirred until the ice had melted. The reaction mixture was then basified by the addition of 6M NaOH (aq) (40 ml) and re-adjusted to pH 7 using 1M HCl (aq) (40 ml). The resulting white suspension was collected by filtration, the solid washed with water (20 ml) and dried in-vacuo at 40° C. for 3 hours to give the title compound (577 mg, 91%) as a white solid. LC-MS 98.2%, 2.42 min (3.5 minute LC-MS method), m/z=409.90, 410.9, 411.90, 412.9; $^1$H NMR (500 MHz, Chloroform-d) δ ppm 7.80 (d, J=1.73 Hz, 1H) 7.41 (d, J=1.73 Hz, 1H) 4.01 (dd, J=11.51, 4.10 Hz, 2H) 3.91 (s, 3H) 3.64 (d, J=5.20 Hz, 2H) 3.32 (t, J=11.82 Hz, 2H) 2.99 (tt, J=11.43, 3.63 Hz, 1H) 2.48 (s, 3H) 1.80 (dd, J=12.53, 1.50 Hz, 2H) 1.54-1.62 (m, 2H).

Step 6: Synthesis of 5-bromo-2-methyl-3-[(oxan-4-yl)(2,2,2-trifluoroethyl)amino]benzoic acid To a stirred solution of methyl 5-bromo-2-methyl-3-[(oxan-4-yl)(2,2,2-trifluoroethyl)amino]benzoate (572 mg, 1.4 mmol) in a mixture of THF (14 ml) and MeOH (2.1 ml), was added 4M NaOH (aq) (13.9 ml). The reaction mixture was stirred at 50° C. for 5.5 hours and then stirred at room temperature for 17 hours. THF was removed by concentrating in-vacuo and the aqueous residue was acidified to pH 4 with 6M HCl (aq) (9.5 ml). The resulting suspension was allowed to stand at room temperature for 20 minutes before collecting the solid by filtration. The solid cake was washed with water (20 ml) and dried under high vacuum for 2 hours to give the title compound (507 mg, 90%) as a white solid. LC-MS 98%, 2.04 min (3.5 minute LC-MS method), m/z=395.9, 396.9, 397.9, 398.9; $^1$H NMR (500 MHz, Chloroform-d) δ ppm 7.97 (d, J=1.73 Hz, 1H) 7.48 (d, J=1.73 Hz, 1H) 4.02 (dd, J=11.35, 3.94 Hz, 2H) 3.65 (br. s, 2H) 3.33 (t, J=11.59 Hz, 2H) 3.00 (tt, J=11.49, 3.80 Hz, 1H) 2.55 (s, 3H) 1.82 (d, J=11.98 Hz, 2H) 1.55-1.69 (m, 2H). OH not visible.

Step 7: Synthesis of 5-bromo-N-[(4,6-dimethyl-2-oxo-1,2-dihydropyridin-3-yl)methyl]-2-methyl-3-[(oxan-4-yl)(2,2,2-trifluoroethyl)amino]benzamide A stirred solution of methyl 5-bromo-2-methyl-3-[(oxan-4-yl)(2,2,2-trifluoroethyl)amino]benzoate (250 mg, 0.63 mmol) in dry DMF (3.0 ml) at 0° C. under a balloon of nitrogen, was treated with HATU (288 mg, 0.76 mmol) and DIPEA (220 μl, 1.3 mmol) dropwise. The resulting solution was stirred for 5 minutes and then treated with 3-(aminomethyl)-4,6-dimethyl-1,2-dihydropyridin-2-one (89%, 119 mg, 0.69 mmol). The resulting suspension was stirred at 0° C. for 20 minutes and then stirred at room temperature for 16.5 hours. The reaction mixture was treated with 3-(aminomethyl)-4,6-dimethyl-1,2-dihydropyridin-2-one (30 mg). Stirring was continued for further 23 hours and the reaction mixture was then partitioned between water (30 ml) and CH$_2$Cl$_2$ (20 ml). The layers were separated and the aqueous phase was extracted with CH$_2$Cl$_2$ (3×20 ml). The combined organics were washed with a saturated solution of NaHCO$_3$ (aq) (50 ml), water (60 ml), brine (2×40 ml), dried over MgSO$_4$, filtered and concentrated in-vacuo. The crude residue was purified by flash column chromatography (10 g SNAP cartridge, Isolera, 0-10% MeOH/CH$_2$Cl$_2$) and triturated from ether (10 ml) with sonication. The resulting precipitate was collected by filtration and dried in-vacuo to give the title compound (249 mg, 74%) as a white solid. LC-MS 100%, 4.08 min (7 minute LC-MS method), m/z=530.0, 531.0, 532.0, 533.0; $^1$H NMR (500 MHz, Acetone) δ 10.67 (s, 1H), 7.55 (d, J=1.8 Hz, 2H), 7.27 (d, J=1.9 Hz, 1H), 5.90 (s, 1H), 4.40 (d, J=5.5 Hz, 2H), 3.90 (dd, J=11.2, 4.6 Hz, 4H), 3.28 (t, J=11.6 Hz, 2H), 3.07-2.97 (m, 1H), 2.32 (s, 3H), 2.29 (s, 3H), 2.24 (s, 3H), 1.76 (dd, J=12.3, 1.6 Hz, 2H), 1.61 (qd, J=12.0, 4.5 Hz, 2H).

Step 8: Synthesis of N-((4,6-dimethyl-2-oxo-1,2-dihydropyridin-3-yl)methyl)-4-methyl-4'-(morpholinomethyl)-5-((tetrahydro-2H-pyran-4-yl)(2,2,2-trifluoroethyl)amino)-[1,1'-biphenyl]-3-carboxamide In a 2 necked RBF, 5-bromo-N-[(4,6-dimethyl-2-oxo-1,2-dihydropyridin-3-yl)methyl]-2-methyl-3-[(oxan-4-yl)(2,2,2-trifluoroethyl)amino]benzamide (200 mg, 0.38 mmol), 4-[4-(4,4,5,5-tetramethyl-1,3,2-dioxaborolan-2-yl)benzyl]morpholine (126 mg, 0.41 mmol) in 1,4-dioxane (3.0 ml) was treated with a solution containing Na$_2$CO$_3$ (140 mg, 1.3 mmol) in water (1.0 ml). Nitrogen was bubbled through the mixture using a long needle for 5 minutes before the addition of palladium-triphenylphosphane (1:4) (44 mg, 0.04 mmol). Nitrogen was bubbled through the yellow suspension for a further 5 minutes before heating the reaction mixture to 100° C. for 5.5 hours. The reaction mixture was diluted with water (10 ml) and 10% MeOH in CH$_2$Cl$_2$ (10 ml). The layers were separated and the aqueous phase was extracted with 10% MeOH in CH$_2$Cl$_2$ (3×15 ml). The combined organic extracts were washed with brine (40 ml), dried over MgSO$_4$, filtered and concentrated in-vacuo. The crude residue was purified by column chromatography (10 g SNAP cartridge, Isolera, 0-4% MeOH:CH$_2$Cl$_2$) to give the title compound (193 mg, 82%) as an off white powder. LC-MS 100%, 3.34 min (7 minute LC-MS method), m/z=627.5; $^1$H NMR (500 MHz, Acetone) δ 10.76 (s, 1H), 7.65 (d, J=1.5 Hz, 1H), 7.60 (d, J=8.2 Hz, 2H), 7.57 (t, J=5.6 Hz, 1H), 7.43 (d, J=1.5 Hz, 1H), 7.39 (d, J=8.1 Hz, 2H), 5.91 (s, 1H), 4.44 (d, J=5.5 Hz, 2H), 3.97 (s, 2H), 3.90 (dd, J=11.4, 4.1 Hz, 2H), 3.61 (t, J=4.6 Hz, 4H), 3.50 (s, 2H), 3.29 (t, J=11.5 Hz, 2H), 3.06 (tt, J=11.4, 3.8 Hz, 1H), 2.39 (d, J=5.0 Hz, 7H), 2.34 (s, 3H), 2.22 (s, 3H), 1.82 (dd, J=12.3, 1.7 Hz, 2H), 1.70-1.56 (m, 2H).

Example 139: Synthesis of N-((4,6-dimethyl-2-oxo-1,2-dihydropyridin-3-yl)methyl)-4-ethyl-5-(ethyl(tetrahydro-2H-pyran-4-yl)amino)-4'-(morpholinomethyl)-[1,1'-biphenyl]-3-carboxamide

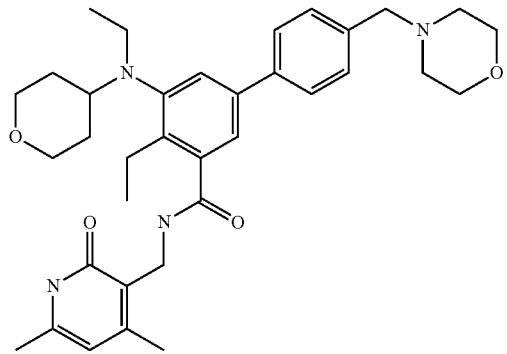

Compound 139

Step 1: Synthesis of methyl 5-chloro-2-[2-(trimethylsilyl)ethynyl]benzoate

To a solution of methyl 2-bromo-5-chlorobenzoate (14.8 g, 59 mmol) in TEA (124 ml, 889.82 mmol) was added copper(I) iodide (338 mg, 1.78 mmol) and triphenylphosphine (778 mg, 2.97 mmol) at room temperature and under nitrogen. This mixture had nitrogen bubbled through it for 10 minutes before the addition of ethynyl(trimethyl)silane (12.45 ml, 89 mmol) and Pd(OAc)$_2$ (266 mg, 1.19 mmol). The reaction mixture was stirred at 50° C. for 20 hours before being concentrated under reduced pressure. The residue was dissolved in deionized water (50 ml) and EtOAc (50 ml) and filtered through Celite. The filter cake was washed with EtOAc (50 ml) before the phases were separated and the aqueous layer was extracted with EtOAc (2×50 ml). The combined organic extracts were dried over MgSO$_4$, filtered and concentrated under reduced pressure. The residue was purified by FCC (10 g silica, Isolute cartridge, gradient of eluents; 99:1 Heptane:EtOAc to 85:15 Heptane:EtOAc) to give 16.2 g (102.4%) of methyl 5-chloro-2-[2-(trimethylsilyl)ethynyl]benzoate as an orange oil that solidified upon standing. Sample contained heptane. LC-MS 91%, 2.57 min (3 minute LC-MS method), m/z=267.4/268.9, $^1$H NMR (500 MHz, Chloroform-d) δ ppm 7.89 (d, J=2.2 Hz, 1H), 7.51 (d, J=8.3 Hz, 1H), 7.41 (dd, J=8.3, 2.3 Hz, 1H), 3.92 (s, 3H), 0.27 (s, 9H).

Step 2: Synthesis of methyl 5-chloro-2-ethynylbenzoate

To a solution of methyl 5-chloro-2-[2-(trimethylsilyl)ethynyl]benzoate (10 g, 37.5 mmol) in Methanol (150 ml) was added K$_2$CO$_3$ (10.36 g, 75 mmol) at room temperature and in air. The reaction mixture was stirred for 1 hour before being concentrated under reduced pressure. The residue was dissolved in deionized water (50 ml) and EtOAc (50 ml).

The phases were separated and the aqueous layer was extracted with EtOAc (2×50 ml). The combined organic extracts were dried over MgSO$_4$, filtered and concentrated under reduced pressure. The residue was purified by FCC (50 g silica, Isolute cartridge, gradient of eluents; 95:5 Heptane:EtOAc to 9:1 Heptane:EtOAc) to give 5.75 g (55.2%) of methyl 5-chloro-2-ethynylbenzoate as an orange oil that solidified upon standing. This material contained 30% of ethyl ester which was suitable for use without any further purification. LC-MS 38%, 1.98 min (3 minute LC-MS method), m/z=195.0/196.9, $^1$H NMR (500 MHz, Chloroform-d) δ ppm 7.93 (d, J=2.2 Hz, 1H), 7.55 (d, J=8.3 Hz, 1H), 7.45 (dd, J=8.3, 2.3 Hz, 1H), 3.94 (s, 3H), 3.43 (s, 1H).

Step 3: Synthesis of methyl 5-chloro-2-ethylbenzoate

To a solution of methyl 5-chloro-2-ethynylbenzoate (5.34 g, 27.44 mmol) in Ethyl acetate (135 ml) was added Pd/C (10%) (50% water, 2.92 g, 1.37 mmol). The reaction mixture was stirred under a hydrogen atmosphere at room temperature for 3 hours. LCMS indicated the reaction had gone to completion and the mixture was filtered through Celite. The filter cake washed with EtOAc (50 ml) and the filtrate was concentrated under reduced pressure to give 5.12 g (93.9%) of methyl 5-chloro-2-ethylbenzoate as a brown oil which was suitable for use without any further purification. LC-MS 56%, 2.21 min (3 minute LC-MS method), m/z=198.9/200.9, $^1$H NMR (500 MHz, Chloroform-d) δ ppm 7.84 (d, J=2.3 Hz, 1H), 7.39 (dd, J=8.3, 2.3 Hz, 1H), 7.21 (d, J=8.3 Hz, 1H), 3.90 (s, 3H), 2.94 (q, J=7.5 Hz, 2H), 1.21 (t, J=7.5 Hz, 3H).

Step 4: Synthesis of methyl 5-chloro-2-ethyl-3-nitrobenzoate

A solution of methyl 5-chloro-2-ethylbenzoate (5.12 g, 25.77 mmol) in concentrated H$_2$SO$_4$ (31 ml, 587 mmol) was cooled to −5° C. in an acetone/ice bath in air. A mixture of concentrated nitric acid (2.15 ml, 33.51 mmol) and concentrated H$_2$SO$_4$ (2 ml, 37.52 mmol) was added dropwise to the reaction mixture at −5 to 0° C. over 15 minutes. The pale yellow reaction mixture was stirred at −5 to 0° C. for 1 hour before being poured onto ice (500 ml) and this was extracted with EtOAc (3×100 ml). The combined organic phases was washed with deionized water (100 ml) and then brine (100 ml). The organic phase was dried over MgSO$_4$, filtered and concentrated under reduced pressure. LCMS and NMR showed ~30% hydrolysis of the ester. The crude material was dissolved in Methanol (30 ml) and cooled to 0° C. under nitrogen where SOCl$_2$ (2.25 ml, 30.93 mmol) was added slowly. The reaction mixture was then heated to reflux for 6 hours before being concentrated under reduced pressure to give 6.18 g (98.4%) of methyl 5-chloro-2-ethyl-3-nitrobenzoate as an orange oil. Product contained 1:1 mixture of 3-nitro:6-nitro isomers along with some ethyl ester which was suitable for use without any further purification.

Step 5: Synthesis of methyl 3-amino-5-chloro-2-ethylbenzoate

To a solution of methyl 5-chloro-2-ethyl-3-nitrobenzoate (6.18 g, 25.36 mmol) in Methanol (250 ml) at room temperature was added ammonium chloride (13.31 g, 253.65 mmol) followed by deionized Water (125 ml). The mixture was heated to 70° C. in air before the addition of iron (8.5 g, 152.19 mmol). The reaction turned to a dark color over the 2.5 hours it was stirred at 70° C. This mixture was allowed to cool to room temperature and was filtered through Kieselgel. The filter pad was washed with MeOH (250 ml) and the filtrate concentrated under reduced pressure. The residue was dissolved in saturated NaHCO$_3$(aq) (50 ml) and EtOAc (150 ml). The phases were separated and the organic phase was washed with saturated NaHCO$_3$(aq) (2×50 ml) before being dried over MgSO$_4$, filtered and concentrated under reduced pressure. The residue was purified by FCC (50 g silica, Isolute cartridge, gradient of eluents; 95:5 Heptane:EtOAc to 75:25 Heptane:EtOAc) to give 2.42 g (22%, 7% corrected yields) of methyl 3-amino-5-chloro-2-ethylbenzoate as a yellow oil. The product contains ~25% ethyl ester and possible ~15% 4-nitro products. The material was taken through the next step without further purification. LC-MS 31%, 2.00 min (3 minute LC-MS method), m/z=295.0, $^1$H NMR (500 MHz, Chloroform-d) δ ppm 7.17 (d, J=2.1 Hz, 1H), 6.79 (d, J=2.1 Hz, 1H), 3.87 (s, 3H), 3.86-3.81 (m, 2H), 2.74 (q, J=7.5 Hz, 2H), 1.20 (t, J=7.5 Hz, 3H).

Step 6: Synthesis of methyl 5-chloro-2-ethyl-3-[(oxan-4-yl)amino]benzoate

To a solution of methyl 3-amino-5-chloro-2-ethylbenzoate (1.5 g, 7.02 mmol) in 1,2-Dichloroethane (28 ml) at room temperature and under nitrogen was added oxan-4-one (1.3 ml, 14.04 mmol) followed by acetic acid (2.41 ml, 42.12 mmol). This solution was stirred for 5 minutes before the addition of sodium triacetoxyborohydride (4.46 g, 21.06 mmol) at room temperature. After stirring for 20 hours, deionized water (28 ml) was added and the mixture was neutralized with solid NaHCO$_3$. The phases were separated and the aqueous layer was extracted with EtOAc (2×28 ml). The combined organic extracts were dried over MgSO$_4$, filtered and concentrated under reduced pressure. The residue was purified by FCC (50 g silica, Isolute cartridge, gradient of eluents; 95:5 Heptane:EtOAc to 8:2 Heptane:EtOAc) to give 1.76 g (84%, 50% corrected yields) of methyl 5-chloro-2-ethyl-3-[(oxan-4-yl)amino]benzoate as a white solid. Product contains ~25% ethyl ester. The material was taken through the next step without further purification. LC-MS 60%, 2.27 min (3 minute LC-MS method), m/z=298.0/300.0, $^1$H NMR (500 MHz, Chloroform-d) δ ppm 7.07 (d, J=2.0 Hz, 1H), 6.71 (d, J=1.9 Hz, 1H), 4.01 (dt, J=11.8, 3.4 Hz, 2H), 3.87 (s, 3H), 3.82-3.76 (m, 1H), 3.64-3.47 (m, 3H), 2.79-2.63 (m, 2H), 2.06 (d, J=13.2 Hz, 2H), 1.55-1.46 (m, 2H), 1.18 (t, J=7.5 Hz, 3H).

Step 7: Synthesis of 5-chloro-2-ethyl-3-[ethyl(oxan-4-yl)amino]benzoic Acid

To a solution of methyl 5-chloro-2-ethyl-3-[(oxan-4-yl)amino]benzoate (350 mg, 1.18 mmol) in DCE (10 ml) at room temperature and under nitrogen was added acetaldehyde (0.66 ml, 11.75 mmol) followed by acetic acid (0.4 ml, 7.05 mmol). This solution was stirred for 5 minutes before the addition of sodium triacetoxyborohydride (2.49 g, 11.75 mmol) at room temperature. After stirring for 23 h further acetaldehyde (0.66 ml, 11.75 mmol) was added followed sodium triacetoxyborohydride (2.49 g, 11.75 mmol). After stirring for a further 3 hours deionized water (15 ml) was added and the mixture was neutralized with solid NaHCO$_3$. The phases were separated and the aqueous layer was extracted with EtOAc (2×15 ml). The combined organic extracts were dried over MgSO$_4$, filtered and concentrated under reduced pressure. The residue was purified by FCC (10 g silica, Isolute cartridge, gradient of eluents; 99:1

Heptane:EtOAc to 85:15 Heptane:EtOAc) to afford the title compound (317 mg) as a 2:1 mixture of methyl and ethyl esters that were used in the next stage.

To the mixture of esters was added THF (10 ml) and 4M NaOH (9.7 ml, 38.9 mmol) and the reaction was stirred at 50° C. for 27 hours, after which time MeOH (5 ml) was added to the reaction mixture and this was stirred for a further 21H at 50° C. The reaction mixture was acidified to pH 2-3 with 6M HCl and extracted with DCM (5×10 ml). The combined organic extracts were dried over $MgSO_4$, filtered and concentrated under reduced pressure to afford the title compound as orange crystals (289 mg, 79% over two steps). LC-MS 100%, 2.09 min (3.5 minute LC-MS method), m/z=312.0/314.0, 1H NMR (500 MHz, Chloroform-d) δ 7.73 (d, J=1.7 Hz, 1H), 7.29 (d, J=1.8 Hz, 1H), 3.99 (d, J=11.0 Hz, 2H), 3.38-3.29 (m, 2H), 3.20-3.03 (m, 4H), 3.02-2.91 (m, 1H), 1.78-1.61 (m, 4H), 1.13 (t, J=7.4 Hz, 3H), 0.91 (t, J=7.0 Hz, 3H).

Step 8: Synthesis of N-((4,6-dimethyl-2-oxo-1,2-dihydropyridin-3-yl)methyl)-4-ethyl-5-(ethyl(tetrahydro-2H-pyran-4-yl)amino)-4'-(morpholinomethyl)-[1,1'-biphenyl]-3-carboxamide To a solution of 5-chloro-2-ethyl-3-[ethyl(oxan-4-yl)amino]benzoic acid (191 mg, 0.61 mmol) in DMF (3 ml) at 0° C. was added HATU (280 mg, 0.74 mmol) followed by DIPEA (213 μl, 1.26 mmol) and 3-(aminomethyl)-4,6-dimethyl-1,2-dihydropyridin-2-one (89%, 115 mg, 0.67 mmol). The reaction was stirred at room temperature for 3 h after which the reaction was poured onto deionized water (50 ml) and the resultant solid was filtered and washed with water. The aqueous phase was washed with DCM (3×50 ml), the combined organics were washed with brine (30 m), dried with $MgSO_4$, filtered and evaporated to give an oil. The solid and oil were combined an purified using a 10 g isolate column eluting with 0% to 3% MeOH in DCM and evaporated followed by purification using a 10 g Isolute eluting with 0% to 3% MeOH in EtOAc to afford the title compound as an off-white solid (234 mg, 79%). LC-MS 92%, 1.78 min (3.5 minute LC-MS method), m/z=446.2/448. To a stirred solution of 5-chloro-N-[(4,6-dimethyl-2-oxo-1,2-dihydropyridin-3-yl)methyl]-2-ethyl-3-[ethyl(oxan-4-yl)amino] benzamide (117 mg, 0.26 mmol) in a degassed mixture of diglyme (4 ml) and MeOH (2 ml) which was bubbled with nitrogen gas was added 2'-(dicyclohexylphosphanyl)-N,N-dimethylbiphenyl-2-amine (21 mg, 0.05 mmol), palladium diacetate (5.89 mg, 0.03 mmol), caesium fluoride (120 mg, 0.79 mmol) and 4-[4-(4,4,5,5-tetramethyl-1,3,2-dioxaborolan-2-yl)benzyl]morpholine (119 mg, 0.39 mmol). The nitrogen bubbling continued for 10 min and then the reaction was heated to 70° C. for 16 h after which time further 4-[4-(4,4,5,5-tetramethyl-1,3,2-dioxaborolan-2-yl)benzyl]morpholine (119 mg, 0.39 mmol) was added and heating continued for 6 h. The reaction was then cooled to room temperature and filtered through Keiselguhr, the cake being washed with MeOH. Distilled water (20 ml) was added to the filtrate which was then extracted with EtOAc (3×50 ml), the combined organics were then washed with brine (2×50 ml), dried with $MgSO_4$, filtered and evaporated. The resultant residue was purified using a 25 g Isolute column eluting with a gradient of 0% to 10% MeOH in DCM to afford the title compound as a pale yellow solid (32 mg, 21%). LC-MS 99%, 2.72 min (7 minute LC-MS method), m/z=294.3 (M+H/2), 1H NMR (500 MHz, Acetone-d6) δ 10.80 (s, 1H), 7.60-7.54 (m, 3H), 7.51 (s, 1H), 7.39 (d, J=7.9 Hz, 2H), 7.36 (d, J=1.4 Hz, 1H), 5.92 (s, 1H), 4.45 (d, J=5.6 Hz, 2H), 3.88 (d, J=8.0 Hz, 2H), 3.66-3.56 (m, 4H), 3.51 (s, 2H), 3.29 (t, J=11.2 Hz, 2H), 3.17 (q, J=7.0 Hz, 2H), 3.09 (t, J=11.2 Hz, 1H), 2.98 (q, J=7.4 Hz, 2H), 2.41 (s, 4H), 2.36 (s, 3H), 2.22 (s, 3H), 1.76 (d, J=11.2 Hz, 2H), 1.65-1.56 (m, 2H), 1.08 (t, J=7.4 Hz, 3H), 0.91 (t, J=7.0 Hz, 3H).

Example 140: Synthesis of 3'-cyano-N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide

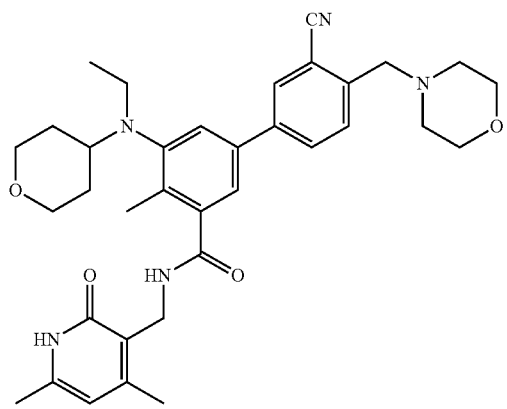

Compound 140

Step 1: Synthesis of 5-bromo-2-(morpholinomethyl)benzonitrile

To a stirred solution of 5-bromo-2-formylbenzonitrile (200 mg, 0.95 mmol) and morpholine (248 mg, 2.85 mmol) in dichloroethane (10 mL), acetic acid (342 mg, 5.7 mmol) was added and reaction stirred at room temperature for 30 minutes. Then sodium triacetoxyborohydride (604 mg, 2.85 mmol) was added to the reaction mixture at 0° C., allowed to attain room temperature and stirring continued for overnight. On completion, reaction mixture was diluted with dichloromethane, washed with water, saturated aqueous sodium bicarbonate solution and dried over sodium sulphate. Removal of the solvent under reduced pressure followed by column chromatographic purification afforded the desired compound (150 mg, 56%).

Step 2: Synthesis of N-((4,6-dimethyl-2-oxo-1,2-dihydropyridin-3-yl)methyl)-3-(ethyl(tetrahydro-2H-pyran-4-yl)amino)-2-methyl-5-(4,4,5,5-tetramethyl-1,3,2-dioxaborolan-2-yl)benzamide To a stirred mixture of 5-bromo-N-((4,6-dimethyl-2-oxo-1,2-dihydropyridin-3-yl)methyl)-3-(ethyl(tetrahydro-2H-pyran-4-yl)amino)-2-methylbenzamide (1.0 g, 2.1 mmol), bispinacolato diboron (2.67 g, 10.5 mmol) and potassium acetate (610 mg, 6.31 mmol) in dioxane (10 mL) was purged with argon for 15 min. Then 1,1'-bis(diphenylphosphino) ferrocene-palladium(II)dichloride dichloromethane complex (85 mg, 0.10 mmol) was added and argon was purged again for 15 min. Reaction mass was heated at 80° C. for 7 h. On completion, reaction mixture was diluted with water and extracted with 10% MeOH/DCM (3 times). Combined organic layer was dried over sodium sulphate. Removal of the solvent under reduced pressure followed by column chromatographic purification afforded the desired compound (250 mg, 27%).

Step 3: Synthesis of 3'-cyano-N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide To a stirred solution of 5-bromo-2-(morpholinomethyl) benzonitrile (190 mg, 0.68 mmol) and N-((4,6-dimethyl-2-oxo-1,2-dihydropyridin-3-yl)methyl)-3-(ethyl(tetrahydro-2H-pyran-4-yl)amino)-2-methyl-5-(4,4,5,5-tetramethyl-1,3,2-dioxaborolan-2-yl)benzamide (200 mg, 0.45 mmol) in dioxane (6 mL), aqueous 2M $Na_2CO_3$ solution (0.81 mL, 1.63 mmol) was added and solution was purged with argon for 15 min. Then $Pd(PPh_3)_4$ (52 mg, 0.04 mmol) was added and argon was purged again for 15 min. Reaction mass was heated at 100° C. for 4 h. On completion, reaction mixture was diluted with water and extracted with 10% MeOH/DCM (3 times). Combined organic layer was dried over sodium sulphate. Removal of the solvent under reduced pressure followed by column chromatographic purification afforded the title compound (16 mg, 6%). LCMS: 598.20 (M+1)+; HPLC: 89.15% (@ 254 nm) ($R_t$: 4.039; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (bs, 1H), 8.20 (t, 1H), 8.15 (s, 1H), 7.94 (d, 1H, J=6.8 Hz), 7.63 (d, 1H, J=8.4 Hz), 7.51 (s, 1H), 7.31 (s, 1H), 5.86 (s, 1H), 4.29 (m, 2H), 3.84-3.82 (m, 2H), 3.66-3.58 (m, 6H), 3.32 (m, 5H), 3.11-3.03 (m, 4H), 2.25 (s, 3H), 2.21 (s, 3H), 2.11 (s, 3H), 1.65-1.51 (m, 4H), 0.82 (t, 3H, J=6 Hz).

Example 141: N-((4,6-dimethyl-2-oxo-1,2-dihydropyridin-3-yl)methyl)-5-(((1r,4r)-4-(dimethylamino)cyclohexyl)(ethyl)amino)-4-methyl-4'-(morpholinomethyl)-[1,1'-biphenyl]-3-carboxamide Compound 141

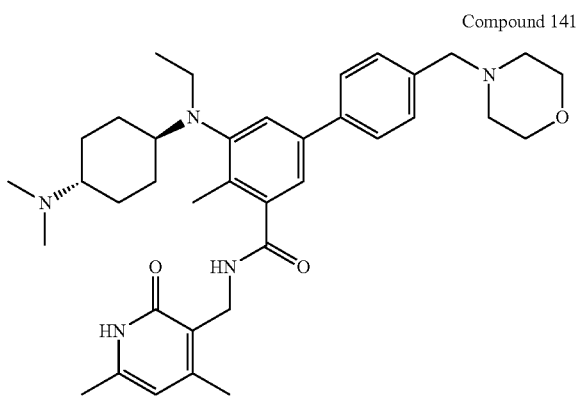 [SMILES: CCN(c1cc(-c2ccc(CN3CCOCC3)cc2)cc(C(=O)NCc2c(C)cc(C)[nH]c2=O)c1C)[C@H]1CC[C@H](N(C)C)CC1]

Step 1: 5-bromo-2-methyl-3-nitrobenzoic acid

To stirred solution of 2-methyl-3-nitrobenzoic acid (100 g, 552.48 mmol) in conc. $H_2SO_4$ (400 mL), 1,3-dibromo-5,5-dimethyl-2,4-imidazolidinedione (87.98 g, 307.70 mmol) was added in a portion-wise manner at room temperature. The reaction mixture was then stirred at room temperature for 5 h. The reaction mixture was poured into ice cold water, the precipitated solid collected by filtration, washed with water and dried under vacuum to afford desired 5-bromo-2-methyl-3-nitrobenzoic acid as off-white solid (140 g, 97.90% yield). $^1$H NMR (DMSO-$d_6$, 400 MHz) δ 8.31 (s, 1H), 8.17 (s, 1H), 2.43 (s, 3H).

Step 2: methyl 5-bromo-2-methyl-3-nitrobenzoate

To a stirred solution of 5-bromo-2-methyl-3-nitrobenzoic acid (285 g, 1104.65 mmol) in DMF (2.8 L) was added sodium carbonate (468 g, 4415.09 mmol) followed by addition of methyl iodide (626.63 g, 4415 mmol) at room temperature. The resulting reaction mixture was stirred at 60° C. for 8 h. The reaction mixture was then filtered to remove suspended solids which were washed well with ethyl acetate (3×1 L). The combined filtrates were washed well with water (5×3 L) and the aqueous phase back extracted with ethyl acetate (3×1 L). The combined organic extracts dried over anhydrous sodium sulfate, filtered and concentrated under reduced pressure to afford methyl 5-bromo-2-methyl-3-nitrobenzoate as an off-white solid (290 g, 97% yield). $^1$H NMR (CDCl$_3$, 400 MHz) δ 8.17 (s, 1H), 7.91 (s, 1H), 3.96 (s, 3H), 2.59 (s, 3H).

Step 3: methyl 3-amino-5-bromo-2-methylbenzoate

To a stirred solution of methyl 5-bromo-2-methyl-3-nitrobenzoate (290 g, 1058.39 mmol) in ethanol (1.5 L) was added aqueous ammonium chloride (283 g, 5290 mmol dissolved in 1.5 L water). The resulting mixture was stirred and heated at 80° C. followed by addition of iron powder (472 g, 8451 mmol) in portions at 80° C. The resulting reaction mixture was heated at 80° C. for 12 h. The reaction mixture was then hot filtered through Celite® and the Celite® bed washed well methanol (5 L) and then with 30% MeOH in DCM (5 L). The combined filtrates were concentrated in vacuo and the residue obtained was diluted with aqueous bicarbonate (2 L) and extracted with ethyl acetate (3×5 L). The combined organic layers were dried over anhydrous sodium sulfate, filtered and concentrated under reduced pressure to afford methyl 3-amino-5-bromo-2-methylbenzoate as a brown solid (220 g, 89.41% yield).

A portion of the product (5 g) was dissolved in hot ethanol (20 mL), insoluble residue filtered off and mother liquor concentrated to obtain methyl 3-amino-5-bromo-2-methylbenzoate (3.5 g, 70% yield) with HPLC purity 93.81% as light brown solid. $^1$H NMR (CDCl$_3$, 400 MHz) δ 7.37 (s, 1H), 6.92 (s, 1H), 3.94 (s, 3H), 3.80 (bs, 2H), 2.31 (s, 3H).

Step 4: methyl 5-bromo-3-(((1r,4r)-4-((tert-butoxycarbonyl)amino)cyclohexyl)amino)-2-methylbenzoate To a stirred solution of methyl 3-amino-5-bromo-2-methylbenzoate (5 g, 20.5 mmol) and tert-butyl (4-oxocyclohexyl)carbamate (5.69 g, 26.7 mmol) in dichloroethane (50 mL), acetic acid (7.4 g, 123 mmol) was added and the reaction was stirred at room temperature for 10 minutes. Sodium triacetoxyborohydride (13.1 g, 61.7 mmol) was then added at 0° C. and reaction was stirred at room temperature for 16 hours. The reaction was quenched with aqueous sodium bicarbonate, the organic phase separated and the aqueous phase extracted with dichloromethane. The combined organic layers were dried over anhydrous sodium sulfate and concentrated in vacuo. The crude product was purified by silica gel column chromatography (100-200 mesh size) eluting with 10% ethyl acetate in hexane to afford 3.5 g of the more polar (trans) isomer, methyl 5-bromo-3-(((1r,4r)-4-((tert-butoxycarbonyl)amino)cyclohexyl) amino)-2-methylbenzoate, as solid (38.46%). $^1$H NMR (CDCl$_3$, 400 MHz) δ 7.21 (s, 1H), 6.80 (s, 1H), 4.41 (bs, 1H), 3.85 (s, 3H), 3.60 (m, 1H), 3.45 (m, 1H), 3.20 (m, 1H), 2.22 (s, 3H), 2.15 (bs, 2H), 2.05 (bs, 2H), 1.45 (s, 9H), 1.30 (m, 4H).

Step 5: methyl 5-bromo-3-(((1r,4r)-4-((tert-butoxycarbonyl)amino)cyclohexyl)-(ethyl)amino)-2-methylbenzoate To a stirred solution of methyl 5-bromo-3-(((1r,4r)-4-((tert-butoxycarbonyl)amino)-cyclohexyl)(ethyl)amino)-2-methylbenzoate (55 g, 0.124 mol) and acetaldehyde (11 g, 0.25 mol) in dichloroethane (550 mL), acetic acid (44.64 g, 0.744 mol) was added and the reaction mixture stirred at room temperature for 10 minutes. Sodium triacetoxyborohydride (79 g, 0.372 mol) was then added at 0° C. and the reaction mixture was stirred at room temperature for 16 hours. The reaction was quenched with aqueous sodium bicarbonate, the organic phase separated and the aqueous phase extracted with dichloromethane. The combined extracts were dried over anhydrous sodium sulfate and concentrated in-vacuo. The crude compound was purified by silica gel column chromatography (100-200 mesh size) eluting with 10% ethyl acetate in hexane to afford 44 g of methyl 5-bromo-3-(((1r,4r)-4-((tert-butoxycarbonyl)amino) cyclohexyl)-(ethyl)amino)-2-methylbenzoate (75.2%) as solid. $^1$H NMR (DMSO-d6, 400 MHz) δ 7.55 (s, 1H), 7.45 (s, 1H), 6.65 (d, 1H), 3.80 (s, 3H), 3.15 (bs, 1H), 3.05 (q, 2H), 2.60 (m, 1H), 2.30 (s, 3H), 1.75 (m, 4H), 1.40 (m, 2H), 1.35 (s, 9H), 1.10 (m, 2H), 0.80 (t, 3H).

Step 6: tert-butyl ((1r,4r)-4-((5-bromo-3-(((4,6-dimethyl-2-oxo-1,2-dihydropyridin-3-yl)methyl)carbamoyl)-2-methylphenyl)(ethyl)amino)cyclohexyl)carbamate Aqueous NaOH (3.5 g, 0.08 mol in 10 mL H$_2$O) was added to a solution of methyl 5-bromo-3-(((1r,4r)-4-((tert-butoxycarbonyl)amino)cyclohexyl)-(ethyl)amino)-2-methylbenzoate (25 g, 0.053 mol) in EtOH (100 mL) and stirred at 60° C. for 1 h. The ethanol was then removed under reduced pressure and acidified to pH 8 with dilute HCl and to pH 6 with citric acid. The mixture was extracted with 10% methanol in DCM (3×200 mL). The combined organic layers were dried and concentrated giving the respective acid (24.2 g, 99.0%). $^1$H NMR (DMSO-d6, 400 MHz) δ 13.13 (s, 1H), 7.54 (s, 1H), 7.43 (s, 1H), 6.68 (d, 1H), 3.14 (bs, 1H), 3.03 (q, 2H), 2.56 (m, 1H), 2.33 (s, 3H), 1.80-1.65 (m, 4H), 1.40 (m, 2H), 1.35 (s, 9H), 1.10 (m, 2H), 0.77 (t, 3H).

The acid (24 g, 0.053 mol) was dissolved in DMSO (100 mL) and 3-(aminomethyl)-4,6-dimethylpyridin-2(1H)-one (16 g, 0.106 mol) and triethylamine (5.3 g, 0.053 mol) was added. The reaction mixture was stirred at room temperature for 15 min before PyBop (41 g, 0.079 mmol) was added and stirring was then continued for overnight at room temperature. The reaction mixture was poured into ice water (1 L). The resulting precipitate was collected by filtration, washed well with water (2×1 L) and dried. The product obtained was further purified by washings with acetonitrile (3×200 mL) and DCM (100 mL) to afford tert-butyl ((1r,4r)-4-((5-bromo-3-(((4,6-dimethyl-2-oxo-1,2-dihydropyridin-3-yl) methyl)carbamoyl)-2-methylphenyl)(ethyl)amino)cyclohexyl)-carbamate (24 g, 77%). $^1$H NMR (DMSO-d6, 400 MHz) δ 11.47 (s, 1H), 8.24 (t, 1H), 7.25 (s, 1H), 7.04 (s, 1H), 6.67 (d, 1H), 5.85 (s, 1H), 4.24 (d, 2H), 3.13 (bs, 1H), 3.01 (q, 2H), 2.53 (m, 1H), 2.18 (s, 3H), 2.10 (s, 6H), 1.80-1.65 (m, 4H), 1.40 (m, 2H), 1.35 (s, 9H), 1.10 (m, 2H), 0.77 (t, 3H).

Step 7: tert-butyl ((1r,4r)-4-((5-(((4,6-dimethyl-2-oxo-1,2-dihydropyridin-3-yl)methyl)carbamoyl)-4-methyl-4'-(morpholinomethyl)-[1,1'-biphenyl]-3-yl) (ethyl)amino)cyclohexyl)carbamate To a stirred solution of tert-butyl ((1r,4r)-4-((5-bromo-3-(((4,6-dimethyl-2-oxo-1,2-dihydropyridin-3-yl)methyl)carbamoyl)-2-methylphenyl)(ethyl)amino)cyclohexyl)-carbamate (24 g, 0.041 mol) and 4-(4-(4,4,5,5-tetramethyl-1,3,2-dioxaborolan-2-yl)benzyl)morpholine (18 g, 0.061 mol) in dioxane/water mixture (160 mL+40 mL), Na$_2$CO$_3$ (15 g, 0.15 mol) was added and solution purged with argon for 15 min. Pd(PPh$_3$)$_4$ (4.7 g, 0.041 mol) was then added and the reaction mixture again purged with argon for 10 min. The reaction mixture was heated at 100° C. for 4 h. The reaction mixture was then diluted with 10% MeOH/DCM (500 mL) and filtered. The filtrate was concentrated, diluted with water (500 mL) and extracted with 10% MeOH in DCM (3×500 mL). The combined organic layers were dried over Na$_2$SO$_4$ and solvent removed under reduced pressure. The crude product was purified by silica gel column chromatography (100-200 mesh) eluting with 7% MeOH in DCM to afford tert-butyl ((1r,4r)-4-((5-(((4,6-dimethyl-2-oxo-1,2-dihydropyridin-3-yl)methyl)carbamoyl)-4-methyl-4'-(morpholinomethyl)-[1,1'-biphenyl]-3-yl)(ethyl)amino)cyclohexyl) carbamate (20 g, 71.43%). $^1$H NMR (DMSO-d6, 400 MHz) δ 11.46 (s, 1H), 8.20 (t, 1H), 7.56 (d, 2H), 7.36 (m, 3H), 7.17 (s, 1H), 6.66 (d, 1H), 5.85 (s, 1H), 4.28 (d, 2H), 3.57 (bs, 4H), 3.48 (s, 2H), 3.20-3.05 (m, 3H), 2.62 (m, 1H), 2.36 (bs, 4H), 2.20 (s, 6H), 2.10 (s, 3H), 1.75 (m, 4H), 1.42 (m, 2H), 1.35 (s, 9H), 1.10 (m, 2H), 0.82 (t, 3H).

Step 8: 5-(((1r,4r)-4-aminocyclohexyl)(ethyl) amino)-N-((4,6-dimethyl-2-oxo-1,2-dihydropyridin-3-yl)methyl)-4-methyl-4'-(morpholinomethyl)-[1,1'-biphenyl]-3-carboxamide To a stirred solution of tert-butyl ((1r,4r)-4-((5-(((4,6-dimethyl-2-oxo-1,2-dihydropyridin-3-yl)methyl)carbamoyl)-4-methyl-4'-(morpholinomethyl)-[1,1'-biphenyl]-3-yl) (ethyl)amino)cyclohexyl)carbamate (20 g, 0.03 mol) in DCM (200 mL) at 0° C., TFA (75 mL) was added and reaction was stirred for 2 h at room temperature. The reaction mixture was then concentrated to dryness and the residue basified with aqueous saturated bicarbonate solution (300 mL) to pH 8. The mixture was extracted with 20% methanol in DCM (4×200 m). The combined extracts were dried over Na$_2$SO$_4$ and the solvent removed under reduced pressure to afford 5-(((1r,4r)-4-aminocyclohexyl)(ethyl) amino)-N-((4,6-dimethyl-2-oxo-1,2-dihydropyridin-3-yl) methyl)-4-methyl-4'-(morpholinomethyl)-[1,1'-biphenyl]-3-carboxamide (15.5 g, 91%) which was used as is in the next reaction. $^1$H NMR (DMSO-d6, 400 MHz) δ 8.18 (bs, 1H), 7.57 (d, 2H), 7.38 (m, 3H), 7.20 (s, 1H), 5.85 (s, 1H), 4.29 (d, 2H), 3.57 (bs, 4H), 3.48 (s, 2H), 3.31 (bs, 2H), 3.10 (m, 2H), 2.91 (m, 1H), 2.67 (m, 1H), 2.36 (bs, 4H), 2.21 (s, 3H), 2.20 (s, 3H), 2.10 (s, 3H), 1.90 (m, 2H), 1.83 (m, 2H), 1.45 (m, 2H), 1.23 (m, 2H), 0.83 (t, 3H).

Step 9: N-((4,6-dimethyl-2-oxo-1,2-dihydropyridin-3-yl)methyl)-5-(((1r,4r)-4-(dimethylamino)cyclohexyl)(ethyl)amino)-4-methyl-4'-(morpholinomethyl)-[1,1'-biphenyl]-3-carboxamide To a stirred solution of 5-(((1r,4r)-4-aminocyclohexyl)(ethyl)amino)-N-((4,6-dimethyl-2-oxo-1,2-dihydropyridin-3-yl)methyl)-4-methyl-4'-(morpholinomethyl)-[1,1'-biphenyl]-3-carboxamide (14 g, 0.023 mol) in dichloromethane (150 mL) was added aqueous 35% formaldehyde solution (2.4 g, 0.080 mol) at 0° C. After stirring for 20 min, Na(OAc)$_3$BH (12.2 g, 0.057 mol) was added and stirring continued for 2 h at 0° C. Water (100 mL) was then added to the reaction mixture and the mixture extracted with 20% methanol in DCM (3×200 mL). The combined extracts were dried over Na$_2$SO$_4$ and the solvent removed under reduced pressure. The crude product was purified by basic alumina column chromatography eluting with 6-7% MeOH in DCM to afford the title compound (10 g, 63.6%). LCMS: 614.65 (M+1)+; HPLC: 98.88% (@ 210-370 nm) (R$_t$; 3.724; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.17 (t, 1H), 7.56 (d, 2H, J=8 Hz), 7.36 (m, 3H), 7.17 (s, 1H), 5.85 (s, 1H), 4.29 (d, 2H, J=4.4 Hz), 3.57 (bs, 4H), 3.48 (s, 2H), 3.09 (q, 2H), 2.66 (m, 1H), 2.36 (bs, 4H), 2.21 (s, 3H), 2.20 (s, 3H), 2.11 (s, 9H), 1.79 (m, 4H), 1.36 (m, 2H), 1.11 (m, 2H), 0.82 (t, 3H, J=6.4&6.8 Hz).

Example 142: Synthesis of N-((4,6-dimethyl-2-oxo-1,2-dihydropyridin-3-yl)methyl)-5-((2-methoxyethyl)(tetrahydro-2H-pyran-4-yl)amino)-4-methyl-4'-(morpholinomethyl)-[1,1'-biphenyl]-3-carboxamide Compound 142

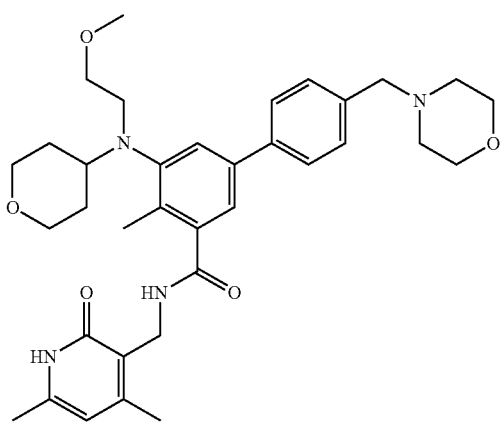

Step 1: Synthesis of methyl 5-bromo-3-((2-methoxyethyl)(tetrahydro-2H-pyran-4-yl)amino)-2-methylbenzoate To a stirred solution of methyl 5-bromo-2-methyl-3-((tetrahydro-2H-pyran-4-yl)amino)benzoate (400 mg, 1.22 mmol) and 2-methoxyacetaldehyde (1.3 mg, 17.56 mmol) in 7 ml of dichloroethane, acetic acid (0.42 mL, 7.33 mmol) was added and stirred at room temperature for 20 minutes. The reaction mixture was cooled to 0° C. and sodium triacetoxyborohydride (777 mg, 3.66 mmol) was added and stirred at room temperature for 2 h. The reaction mixture was then neutralized with sat. NaHCO$_3$ and extracted with DCM, and the organic layer was dried over Na$_2$SO$_4$, concentrated under reduced pressure to get 260 mg of crude product.

Step 2: Synthesis of 5-bromo-N-((4,6-dimethyl-2-oxo-1,2-dihydropyridin-3-yl)methyl)-3-((2-methoxyethyl)(tetrahydro-2H-pyran-4-yl)amino)-2-methylbenzamide A mixture of methyl 5-bromo-3-((2-methoxyethyl)(tetrahydro-2H-pyran-4-yl)amino)-2-methylbenzoate (260 mg, 0.67 mmol) and NaOH (40 mg, 1.01 mmol) in 5 ml of ethanol:water (2:1) was heated at 70° C. for 2 h. The reaction mixture was concentrated to dryness and the crude dissolved in water, pH was adjusted to 5 to 6 by slow addition of HCl and compound was extracted in 10% MeOH in DCM. Organic layer was dried over Na$_2$SO$_4$, concentrated under reduced pressure to afford 230 mg of acid.

The crude acid (230 mg, 0.62 mmol), 3-(aminomethyl)-4,6-dimethylpyridin-2(1H)-one (188 mg, 1.24 mmol), PyBOP (483 mg, 0.93 mmol) and triethyl amine (0.17 ml, 1.238) mixture was stirred in 3 ml of DMSO at rt for overnight. The reaction mixture was diluted with water and compound was extracted in 10% MeOH in DCM, dried over Na$_2$SO$_4$, concentrated and crude was purified by silica gel (100-200) column chromatography to get 5-bromo-N-((4,6-dimethyl-2-oxo-1,2-dihydropyridin-3-yl)methyl)-3-((2-methoxyethyl)(tetrahydro-2H-pyran-4-yl)amino)-2-methylbenzamide (110 mg, 35%).

Step 3: Synthesis N-((4,6-dimethyl-2-oxo-1,2-dihydropyridin-3-yl)methyl)-5-((2-methoxyethyl)(tetrahydro-2H-pyran-4-yl)amino)-4-methyl-4'-(morpholinomethyl)-[1,1'-biphenyl]-3-carboxamide A solution of 5-bromo-N-((4,6-dimethyl-2-oxo-1,2-dihydropyridin-3-yl)methyl)-3-((2-methoxyethyl)-2H-pyran-4-yl)amino)-2-methylbenzamide (110 mg, 0.21 mmol), (4-(morpholinomethyl)phenyl)boronic acid (99 mg, 0.33 mmol), sodium carbonate (83 mg, 0.78 mmol) in 4 ml of dioxane was degassed with argon for 20 min, Pd(PPh$_3$) (25 mg, 0.02 mmol) was added to the mixture and heated to 100° C. for overnight. The reaction was cooled to room temperature and diluted with water, compound was extracted in 10% MeOH in DCM, dried over Na$_2$SO$_4$, concentrated and crude product purified by silica gel (100-200) chromatography to obtain the title compound (50 mg 38%).

LCMS: 603.45 (M+1)+; HPLC: 99.60% (@ 254 nm) (R$_t$; 4.492; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (bs, 1H), 8.20 (t, 1H), 7.58 (d, 2H, J=7.2 Hz), 7.47 (s, 1H), 7.37 (d, 2H, J=7.2 Hz), 7.23 (s, 1H), 5.86 (s, 1H), 4.29 (d, 2H, J=3.6 Hz), 3.82-3.85 (m, 2H), 3.49-3.58 (m, 6H), 3.15-3.3.23 (m, 9H), 2.98 (m, 1H), 2.36 (m, 4H), 2.23 (s, 3H), 2.21 (s, 3H), 2.11 (s, 3H), 1.51-1.68 (m, 4H).

Example 143: N-((4,6-dimethyl-2-oxo-1,2-dihydropyridin-3-yl)methyl)-5-(ethyl-d5 (tetrahydro-2H-pyran-4-yl)amino)-4-methyl-4'-(morpholinomethyl)-[1,1'-biphenyl]-3-carboxamide Compound 143

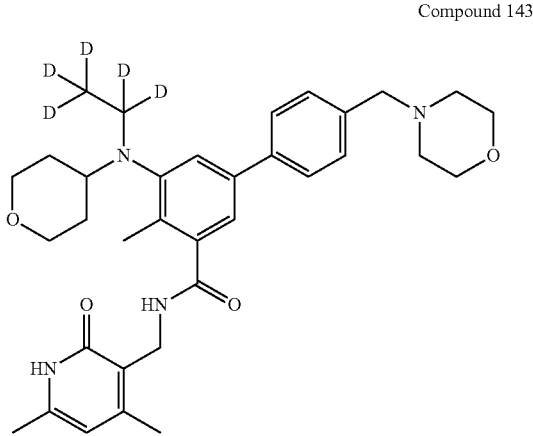 [SMILES: [2H]C([2H])([2H])C([2H])([2H])N(c1cc(-c2ccc(CN3CCOCC3)cc2)cc(C(=O)NCc2c(C)cc(C)[nH]c2=O)c1C)C1CCOCC1]

Step 1: Synthesis of methyl 5-bromo-3-(ethyl-d$_5$ (tetrahydro-2H-pyran-4-yl) amino)-2-methylbenzoate To a stirred solution of compound methyl 5-bromo-2-methyl-3-((tetrahydro-2H-pyran-4-yl)amino)benzoate (Ig, 3.05 mmol) and sodium triacetoxyborodeuteride (0.2 g, 4.76 mmol) in dichloroethane (15 mL), acetic acid (1.65 g, 27.5 mmol) was added and reaction stirred at 5-10° C. for 2 h. Then acetaldehyde-d4 (0.264 g, 6.00 mmol) was added at 0° C. and reaction stirred at room temperature for overnight. On completion, reaction was quenched with aqueous sodium bicarbonate, organic phase was separated and aqueous phase was extracted with dichloromethane. Combined organic layers were dried over sodium sulphate and concentrated under reduced pressure to give crude material was purified by column chromatography to afford desired product (1 g, 91%).

Steps 2 and 3: Synthesis of 5-bromo-N-((4,6-dimethyl-2-oxo-1,2-dihydropyridin-3-yl) methyl)-3-(ethyl-d$_5$(tetrahydro-2H-pyran-4-yl) amino)-2-methylbenzamide Aqueous NaOH (0.166 g, 4.15 mmol) was added to a solution of compound methyl 5-bromo-3-(ethyl-d$_5$(tetrahydro-2H-pyran-4-yl)amino)-2-methylbenzoate (1 g, 2.77 mmol) in ethanol (10 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. Combined organic layers were dried concentrated giving respective acid (0.7 g, 2.01 mmol, 73%), which was then dissolved in DMSO (7 mL) and 3-(amino methyl)-4,6-dimethylpyridin-2(1H)-one (0.611 g, 4.01 mmol) was added to it. The reaction mixture was stirred at room temperature for 15 min before PYBOP (1.56 g, 3.01 mmol) was added to it and stirring was continued for overnight. After completion of conversion, the reaction mass was poured into ice, extracted with 10% MeOH/DCM. Combined organic layers were dried, concentrated to obtain crude; which then purified by solvent washings to afford desired product (0.6 g, 62%).

Step 4: Synthesis of N-((4,6-dimethyl-2-oxo-1,2-dihydropyridin-3-yl) methyl)-5-(ethyl-d$_5$(tetrahydro-2H-pyran-4-yl) amino)-4'-formyl-4-methyl-[1,1'-biphenyl]-3-carboxamide To a stirred solution of compound 5-bromo-N-((4,6-dimethyl-2-oxo-1,2-dihydropyridin-3-yl) methyl)-3-(ethyl-d$_5$ (tetrahydro-2H-pyran-4-yl) amino)-2-methylbenzamide (0.3 g, 0.62 mmol) and (4-(morpholinomethyl) phenyl) boronic acid (0.283 g, 0.93 mmol) in dioxane/water mixture, Na$_2$CO$_3$ (0.24 g, 2.26 mmol) was added and solution purged with argon for 15 min. Then Pd (PPh$_3$)$_4$ (0.072 g, 0.062 mmol) was added and the mixture was purged again for 10 min. Reaction mass was heated at 100° C. for 4 h. On completion, reaction mixture was diluted with water and extracted with 10% MeOH/DCM. Combined organic layers were dried over Na$_2$SO$_4$ and solvent removed under reduced pressure to afford crude material which was purified by column chromatography over silica gel to afford desired title compound (0.22 g, 61%). Analytical Data of N-((4,6-dimethyl-2-oxo-1,2-dihydropyridin-3-yl) methyl)-5-(ethyl-d$_5$ (tetrahydro-2H-pyran-4-yl) amino)-4'-formyl-4-methyl-[1,1'-biphenyl]-3-carboxamide: LCMS: 578.35 (M+1)$^+$; HPLC: 98.50% (@ 254 nm) (R$_t$; 4.176; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (bs, 1H), 8.19 (t, 1H), 7.57 (d, 2H, J=7.6), 7.36-7.39 (m, 3H), 7.21 (s, 1H), 5.86 (s, 1H), 4.29 (d, 2H, J=3.2 Hz), 3.81-3.84 (m, 2H), 3.48-3.57 (m, 6H), 3.22-3.25 (m, 2H), 3.02 (m, 1H), 2.36 (m, 4H), 2.24 (s, 3H), 2.20 (s, 3H), 2.10 (s, 3H), 1.51-1.67 (m, 4H).

Example 144: Synthesis of 5-((2,2-difluoroethyl) (tetrahydro-2H-pyran-4-yl)amino)-N-((4,6-dimethyl-2-oxo-1,2-dihydropyridin-3-yl)methyl)-4-methyl-4'-(morpholinomethyl)-[1,1'-biphenyl]-3-carboxamide Compound 144

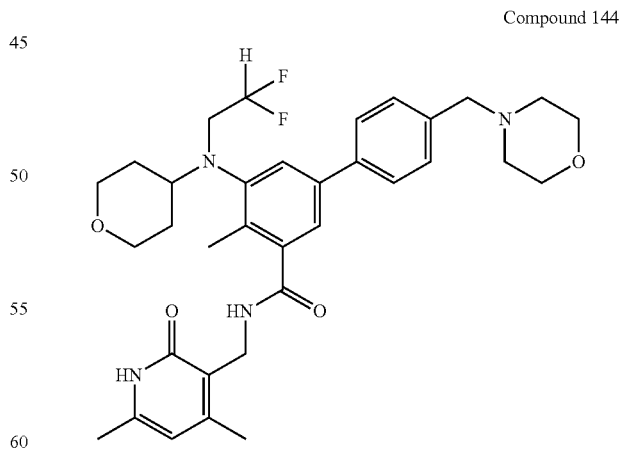

Step 1: Synthesis of methyl 5-bromo-3-[(2,2-difluoroethyl)(oxan-4-yl)amino]-2-methylbenzoate In a 2-necked, 100 ml RBF, a stirred solution of methyl 5-bromo-2-methyl-3-[(oxan-4-yl)amino]benzoate (500 mg, 1.5 mmol) in difluoroacetic acid (15 ml), was treated with sodium tetrahydroborate (1000 mg, 26 mmol) portionwise over 12 minutes (CARE!). The reaction mixture was warmed to 50° C. and stirred for 4 hours. The reaction mixture was allowed to reach room temperature and then poured over ice (130 ml) and left for 5 minutes. The mixture was basified by the addition of 6M NaOH (aq) (35 ml) and the pH adjusted to 7 using 1M HCl (aq) (20 ml). The resulting suspension was allowed to stand until the solution was clear and the resulting solid collected by filtration and dried in-vacuo at 40° C. to give the title compound (572 mg, 96%) as a white solid. LC-MS 100%, 2.32 min (3.5 minute LC-MS method), m/z=391.9, 392.9, 393.9, 394.9; 1H NMR (500 MHz, Chloroform-d) δ ppm 7.79 (d, J=1.89 Hz, 1H) 7.44 (d, J=1.89 Hz, 1H) 5.44-5.71 (m, 1H) 4.00 (dd, J=11.51, 4.10 Hz, 2H) 3.91 (s, 3H) 3.41 (td, J=13.99, 4.18 Hz, 2H) 3.32 (t, J=11.27 Hz, 2H) 2.97 (tt, J=11.37, 3.84 Hz, 1H) 2.47 (s, 3H) 1.72-1.81 (m, 2H) 1.59-1.67 (m, 2H).

Step 2: Synthesis of 5-bromo-3-[(2,2-difluoroethyl)(oxan-4-yl)amino]-2-methylbenzoic acid To a stirred solution of methyl 5-bromo-3-[(2,2-difluoroethyl)(oxan-4-yl)amino]-2-methylbenzoate (571 mg, 1.5 mmol) in a mixture of THF (14.6 ml) and MeOH (2.2 ml), was added 4M NaOH (14.6 ml). The reaction mixture was stirred at 50° C. for 7 hours. The heat was switched off and the reaction mixture was stirred at room temperature for 16.5 hours. THF was removed in-vacuo and the aqueous residue was acidified to pH 4 by the addition of 6M HCl (aq) (10 ml) with ice cooling. The resulting solid was collected by filtration and washed with water (20 ml), dried in-vacuo at 30-40° C. for 3 hours to give the title compound (526 mg, 96%) as a light beige solid. LC-MS 100%, 1.98 min (3.5 minute LC-MS method), m/z=377.9, 378.9, 379.9, 380.9; $^1$H NMR (500 MHz, Chloroform-d) δ ppm 7.91 (d, J=1.58 Hz, 1H) 7.49 (d, J=1.58 Hz, 1H) 5.43-5.75 (m, 1H) 4.01 (dd, J=11.43, 3.55 Hz, 2H) 3.42 (td, J=13.95, 3.78 Hz, 2H) 3.32 (t, J=11.35 Hz, 2H) 2.98 (tt, J=11.37, 3.53 Hz, 1H) 2.52 (s, 3H) 1.77 (d, J=10.88 Hz, 2H) 1.56-1.69 (m, 2H). OH not visible.

Step 3: Synthesis of 5-bromo-3-[(2,2-difluoroethyl)(oxan-4-yl)amino]-N-[(4,6-dimethyl-2-oxo-1,2-dihydropyridin-3-yl)methyl]-2-methylbenzamide A stirred solution of 5-bromo-3-[(2,2-difluoroethyl)(oxan-4-yl)amino]-2-methylbenzoic acid (250 mg, 0.66 mmol) in dry DMF (3.0 ml) at 0° C. under a balloon of nitrogen, was treated with HATU (327 mg, 0.86 mmol) and DIPEA (230 μl, 1.3 mmol) dropwise. The resulting solution was stirred for 5 minutes and then treated with 3-(aminomethyl)-4,6-dimethyl-1,2-dihydropyridin-2-one (89%, 136 mg, 0.79 mmol). The resulting suspension was stirred at 0° C. for 20 minutes and then stirred at room temperature overnight. After 18 hours, 3-(aminomethyl)-4,6-dimethyl-1,2-dihydropyridin-2-one (25 mg) was added and stirring continued for a further 25 hours. The reaction mixture was diluted with water (30 ml) and CH$_2$Cl$_2$ (30 ml). The layers were separated and the aqueous phase was extracted with CH$_2$Cl$_2$ (3×15 ml). The combined organic phases were washed with a saturated solution of NaHCO$_3$ (aq) (45 ml), water (2×50 ml), brine (2×50 ml), dried (MgSO$_4$), filtered and concentrated in-vacuo. The residue was purified by column chromatography (10 g SNAP cartridge, Isolera, 0-3% MeOH:CH$_2$Cl$_2$) and then triturated with ether. The resulting solid was collected by filtration and dried in-vacuo at 40° C. to give the title compound (259 mg, 77%) as an off white solid. LC-MS 100%, 4.04 min (7 minute LC-MS method), m/z=512.0, 513.0, 514.0, 515.0; $^1$H NMR (500 MHz, Acetone) δ 10.71 (s, 1H), 7.57-7.49 (m, 2H), 7.25 (d, J=1.9 Hz, 1H), 5.91 (s, 1H), 5.76 (tt, J=56.2, 4.3 Hz, 1H), 4.40 (d, J=5.5 Hz, 2H), 3.88 (dd, J=11.3, 4.2 Hz, 2H), 3.52 (td, J=14.6, 4.2 Hz, 2H), 3.33-3.23 (m, 2H), 3.02 (tt, J=11.6, 3.9 Hz, 1H), 2.32 (s, 3H), 2.28 (s, 3H), 2.24 (s, 3H), 1.73 (dd, J=12.4, 1.9 Hz, 2H), 1.59 (qd, J=12.2, 4.5 Hz, 2H).

Step 4: Synthesis of 5-((2,2-difluoroethyl)(tetrahydro-2H-pyran-4-yl)amino)-N-((4,6-dimethyl-2-oxo-1,2-dihydropyridin-3-yl)methyl)-4-methyl-4'-(morpholinomethyl)-[1,1'-biphenyl]-3-carboxamide In a 2 necked RBF, 5-bromo-3-[(2,2-difluoroethyl)(oxan-4-yl)amino]-N-[(4,6-dimethyl-2-oxo-1,2-dihydropyridin-3-yl)methyl]-2-methylbenzamide (200 mg, 0.39 mmol) and 4-[4-(4,4,5,5-tetramethyl-1,3,2-dioxaborolan-2-yl)benzyl]morpholine (130 mg, 0.43 mmol) in dioxane (3.0 ml) were treated with a solution of Na$_2$CO$_3$ (145 mg, 1.4 mmol) in water (1.0 ml). The mixture was briefly sonicated and nitrogen was bubbled through the resulting suspension with a long needle for 5 minutes. The suspension was then treated with palladium-triphenylphosphane (1:4) (45 mg, 0.04 mmol) and nitrogen was bubbled through the resulting suspension for a further 5 minutes. The reaction mixture was then heated to 100° C. for 8 hours and stirred at room temperature for 16 hours. The reaction mixture was treated with water (20 ml) and 10% MeOH/CH$_2$Cl$_2$ (15 ml). The layers were separated and the aqueous layer was extracted with 10% MeOH/CH$_2$Cl$_2$ (3×15 ml). The combined organics were washed with brine (55 ml), dried (MgSO$_4$), filtered and concentrated in-vacuo. The crude residue was purified by column chromatography (10 g SNAP cartridge, Isolera, 0-5% MeOH/CH$_2$Cl$_2$) and treated with ether (10 ml), briefly sonicated, warmed in a water bath and cooled on ice. The resulting white solid was collected by filtration and washed with ether (5 ml). The solid was dried in-vacuo at 40° C. for 35 hours to give the title compound (159 mg, 67%) as an off-white solid. LC-MS 100%, 3.09 min (7 minute LC-MS method), m/z=609.15; $^1$H NMR (500 MHz, Acetone) δ 10.72 (s, 1H), 7.63 (d, J=1.5 Hz, 1H), 7.60 (d, J=8.1 Hz, 2H), 7.54 (t, J=5.2 Hz, 1H), 7.41 (d, J=1.6 Hz, 1H), 7.39 (d, J=8.1 Hz, 2H), 5.91 (s, 1H), 5.76 (ttt, J=56.4, 30.4, 4.4 Hz, 1H), 4.44 (d, J=5.5 Hz, 2H), 3.89 (dd, J=11.4, 3.9 Hz, 2H), 3.65-3.55 (m, 6H), 3.50 (s, 2H), 3.29 (t, J=11.3 Hz, 2H), 3.07 (tt, J=11.5, 3.6 Hz, 1H), 2.40 (s, 4H), 2.37 (s, 3H), 2.34 (s, 3H), 2.22 (s, 3H), 1.82-1.75 (m, 2H), 1.61 (qd, J=11.9, 4.1 Hz, 2H).

Example 145: N-((4,6-dimethyl-2-oxo-1,2-dihydro-pyridin-3-yl)methyl)-3-(((1s,4s)-4-(dimethylamino)cyclohexyl)(ethyl)amino)-2-methyl-5-(1-methyl-1H-pyrazol-4-yl) benzamide

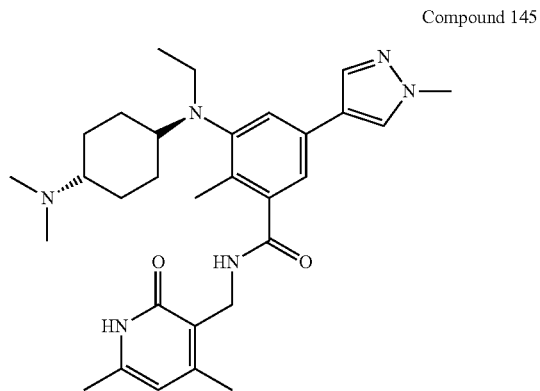

Compound 145

Step 1: Synthesis of 3-(((1s,4s)-4-aminocyclohexyl)(ethyl)amino)-5-bromo-N-((4,6-dimethyl-2-oxo-1,2-dihydropyridin-3-yl)methyl)-2-methylbenzamide To a cooled solution of compound tert-butyl ((1s,4s)-4-((5-bromo-3-(((4,6-dimethyl-2-oxo-1,2-dihydropyridin-3-yl)methyl)carbamoyl)-2-methylphenyl)(ethyl)amino)cyclohexyl) carbamate (1.0 g, 1.60 mmol) in 10 ml of DCM, 2 ml of TFA was added drop wise and reaction mixture was stirred at rt for 2 h. Reaction mass was concentrated to dryness under reduced pressure, obtained crude was dissolved in 10% MeOH in DCM and washed with sat NaHCO$_3$, water and brine. Organic phase was dried over Na$_2$SO$_4$, concentrated under reduced pressure to obtain crude desired compound (650 mg, 81%).

Step 2: Synthesis of 5-bromo-N-((4,6-dimethyl-2-oxo-1,2-dihydropyridin-3-yl)methyl)-3-(((1s,4s)-4-(dimethylamino)cyclohexyl)(ethyl)amino)-2-methyl-benzamide To a stirred solution of crude compound 3-(((1s,4s)-4-aminocyclohexyl)(ethyl)amino)-5-bromo-N-((4,6-dimethyl-2-oxo-1,2-dihydropyridin-3-yl)methyl)-2-methylbenzamide (650 mg, 1.32 mmol) and formaldehyde (0.5 ml of 38% solution, 13.26 mmol) in 10 ml of methanol, sodium cyanoborohydride (82 mg, 1.32 mmol) was added at 0° C. and stirred at room temperature for overnight. Reaction mixture was partitioned between water and 10% MeOH in DCM, organic layer was dried over Na$_2$SO$_4$, concentrated under reduced pressure. Crude was purified by basic alumina column purification to give desired product compound (450 mg, 65%).

Step 3: Synthesis of N-((4,6-dimethyl-2-oxo-1,2-dihydropyridin-3-yl)methyl)-3-(((1s,4s)-4-(dimethylamino)cyclohexyl)(ethyl)amino)-2-methyl-5-(1-methyl-1H-pyrazol-4-yl) benzamide A solution of compound 5-bromo-N-((4,6-dimethyl-2-oxo-1,2-dihydropyridin-3-yl)methyl)-3-(((1s,4s)-4-(dimethylamino)cyclohexyl)(ethyl)amino)-2-methylbenzamide (150 mg, 0.29 mmol), (1-methyl-1H-pyrazol-4-yl)boronic acid (72 mg, 0.34 mmol), sodium carbonate (110 mg, 1.06 mmol) in 10 ml of dioxane was degassed with argon for 20 min, Pd(PPh$_3$) (33 mg, 0.03 mmol) was added to the mixture and heated to 100° C. for overnight. Reaction was cooled to room temperature and diluted with water, compound was extracted in 10% MeOH in DCM, dried over Na$_2$SO$_4$, concentrated and crude was purified by silica gel (100-200) chromatography to obtain title compound (40 mg, 26%).

Analytical Data: LCMS: 519.40 (M+1)$^+$; HPLC: 95.98% (@ 254 nm) (R$_t$; 3.987; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (bs, 1H), 8.12-8.09 (m, 2H), 7.80 (s, 1H), 7.29 (s, 1H), 7.10 (s, 1H), 5.86 (s, 1H), 4.27 (d, 2H, J=4.8 Hz), 3.84 (s, 3H), 3.07-305 (m, 2H), 2.67-2.63 (m, 2H), 2.21 (s, 3H), 2.15 (s, 3H), 2.12-2.11 (s, 3H+3H+3H), 1.79-1.75 (m, 4H), 1.36-1.11 (m, 4H), 0.80 (t, 3H, J=6.0 Hz).

Example 146: N-((4,6-dimethyl-2-oxo-1,2-dihydropyridin-3-yl)methyl)-5-(((1s,4s)-4-(dimethylamino)cyclohexyl)(ethyl)amino)-4-methyl-4'-((4-methyl-1,4-diazepan-1-yl)methyl)-[1,1'-biphenyl]-3-carboxamide

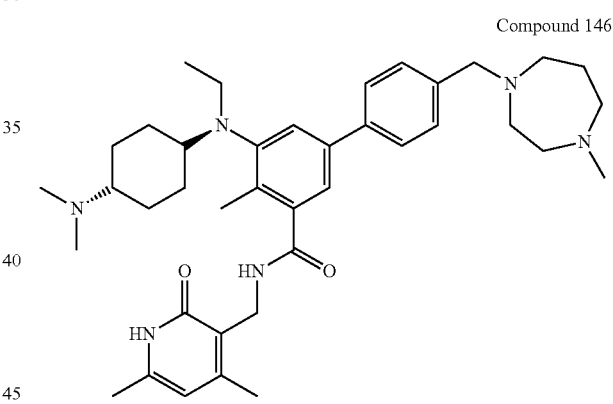

Compound 146

Step 1: Synthesis of N-((4,6-dimethyl-2-oxo-1,2-dihydropyridin-3-yl)methyl)-5-(((1s,4s)-4-(dimethylamino)cyclohexyl)(ethyl)amino)-4'-formyl-4-methyl-[1,1'-biphenyl]-3-carboxamide A solution of compound 5-bromo-N-((4,6-dimethyl-2-oxo-1,2-dihydropyridin-3-yl)methyl)-3-(((1s,4s)-4-(dimethylamino)cyclohexyl)(ethyl)amino)-2-methylbenzamide (380 mg, 0.73 mmol), (4-formylphenyl)boronic acid (165 mg, 1.10 mmol), sodium carbonate (280 mg, 2.6 mmol) in 5 ml of dioxane was degassed with argon for 20 min, Pd(PPh$_3$) (84 mg, 0.07 mmol) was added to the mixture and heated to 100° C. for 5 h. Reaction was cooled to room temperature and diluted with water, compound was extracted in 10% MeOH in DCM, dried over Na$_2$SO$_4$, concentrated and crude was purified by silica gel (100-200) chromatography to obtain the desired compound (250 mg, 63%).

Step 2: Synthesis of N-((4,6-dimethyl-2-oxo-1,2-dihydropyridin-3-yl)methyl)-5-(((1s,4s)-4-(dimethylamino)cyclohexyl)(ethyl)amino)-4-methyl-4'-((4-methyl-1,4-diazepan-1-yl)methyl)-[1,1'-biphenyl]-3-carboxamide To a stirred solution of compound N-((4,6-dimethyl-2-oxo-1,2-dihydropyridin-3-yl)methyl)-5-(((1s,4s)-4-(dimethylamino)cyclohexyl)(ethyl)amino)-4'-formyl-4-methyl-[1,1'-biphenyl]-3-carboxamide (90 mg, 0.16 mmol) and 1-methyl-1,4-diazepane (0.56 g, 0.49 mmol) in 2 ml of methanol, acetic acid (0.03 mL, 0.49 mmol) was added and stirred at room temperature for 20 minutes. Reaction mixture was cooled to 0° C. and sodium cyanoborohydride (25 mg, 0.41 mmol) was added and stirred at room temperature for 4 h. Reaction mixture was neutralized with sat. NaHCO$_3$ and compound was extracted in DCM, dried over Na$_2$SO$_4$, concentrated under reduced pressure, purified by prep. HPLC to give the title compound (26 mg, 25%).

Analytical data of TFA salt: LCMS: 641.50 (M+1)$^+$; HPLC: 97.72% (@ 254 nm) (R$_t$: 3.783; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-D6, 400 MHz) δ 11.45 (bs, 1H), 9.54 (s, 1H), 8.20 (s, 1H), 7.74 (d, J=7.6 Hz, 2H), 7.57 (d, J=7.6 Hz, 2H), 7.42 (s, 1H), 7.26 (s, 1H), 5.87 (s, 1H), 4.29 (d, J=4.0 Hz, 2H), 3.83 (m, 4H), 3.25 (m, 3H), 3.17-3.12 (m, 4H), 2.84 (s, 3H), 2.69, 2.68 (2s, 6H), 2.24 (s, 3H), 2.21 (s, 3H), 2.11 (s, 3H), 2.10-1.89 (m, 6H), 1.46-1.44 (m, 4H), 0.84 (t, J=7.2 Hz, 3H).

Example 147: N-((4,6-dimethyl-2-oxo-1,2-dihydropyridin-3-yl)methyl)-5-(((1r,4r)-4-(dimethylamino)cyclohexyl)(ethyl)amino)-4-methyl-[1,1'-biphenyl]-3-carboxamide Compound 147

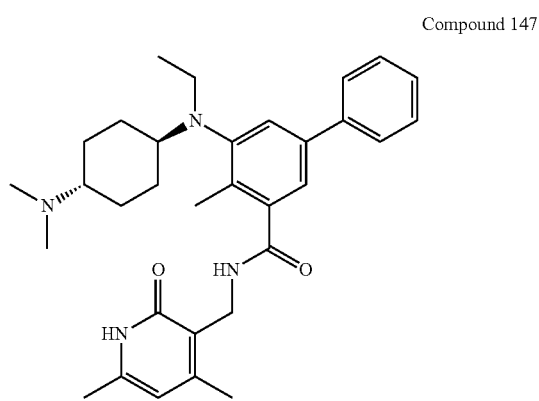 [SMILES: CCN(c1cc(-c2ccccc2)cc(C(=O)NCc2c(C)cc(C)[nH]c2=O)c1C)[C@H]1CC[C@H](N(C)C)CC1]

Step 1: methyl 5-bromo-3-(((1r,4r)-4-((tert-butoxycarbonyl)amino)cyclohexyl)-(ethyl)amino)-2-methylbenzoate To a stirred solution of methyl 5-bromo-3-(((1r,4r)-4-((tert-butoxycarbonyl)amino)-cyclohexyl)amino)-2-methylbenzoate (10 g, 22.72 mmol) and acetaldehyde (2.99 g, 67.95 mmol) in dichloroethane (100 mL), acetic acid (8.18 g, 136.33 mmol) was added. The reaction mixture was stirred at room temperature for 20 minutes. Then sodium triacetoxyborohydride (14.45 g, 68.16 mmol) was added at 0° C. and reaction mixture stirred overnight at room temperature. The solvent was removed under reduced pressure, the residue taken up in water and extracted using 5% MeOH/DCM. The combined extracts were dried and concentrated to give methyl 5-bromo-3-(((1r,4r)-4-((tert-butoxycarbonyl)amino)cyclohexyl)-(ethyl)amino)-2-methylbenzoate which was used as is in further reactions (9 g, 84.66%).

Step 2: tert-butyl ((1r,4r)-4-((5-bromo-3-(((4,6-dimethyl-2-oxo-1,2-dihydropyridin-3-yl)methyl)carbamoyl)-2-methylphenyl)amino)cyclohexyl)carbamate Aqueous NaOH (1.15 g, 28.84 mmol) was added to a solution of methyl 5-bromo-3-(((1r,4r)-4-((tert-butoxycarbonyl)amino)cyclohexyl)-(ethyl)amino)-2-methylbenzoate (9 g, 19.23 mmol) in ethanol (10 mL) and stirred at 60° C. for 1 h. The ethanol was removed under reduced pressure and acidified to pH 6 using dilute HCl and then to pH 4 using citric acid. The mixture was extracted with acetate. The combined organic layers were dried and concentrated to give the respective acid (8.6 g, 98.50%).

The above acid (8.6 g, 18.90 mmol) was dissolved in DMSO (7 mL) and 3-(amino methyl)-4,6-dimethylpyridin-2(1H)-one (5.74 g, 37.80 mmol) was added. The reaction mixture was stirred at room temperature for 15 min before PyBOP (14.70 g, 28.35 mmol) was added. The reaction mixture was stirred overnight. The reaction mixture was poured into ice water and extracted with 10% MeOH/DCM. The combined extracts were dried and concentrated to obtain the crude product which purified by solvent washings to afford tert-butyl ((1r,4r)-4-((5-bromo-3-(((4,6-dimethyl-2-oxo-1,2-dihydropyridin-3-yl)methyl)carbamoyl)-2-methylphenyl)amino)cyclohexyl)carbamate (10.2 g, 91.89%).

Step 3: 3-(((1r,4r)-4-aminocyclohexyl)(ethyl)amino)-5-bromo-N-((4,6-dimethyl-2-oxo-1,2-dihydropyridin-3-yl)methyl)-2-methylbenzamide tert-butyl ((1r,4r)-4-((5-bromo-3-(((4,6-dimethyl-2-oxo-1,2-dihydropyridin-3-yl)methyl)carbamoyl)-2-methylphenyl)amino)cyclohexyl)carbamate (3 g, 5.10 mmol) was taken up in DCM (20 mL) to which TFA (5 mL) was then added. The reaction mixture was stirred at room temperature for 1 h. The solvent was removed under reduced pressure and saturated NaHCO$_3$ solution was added. The mixture was extracted with 10% MeOH/DCM and the combined extracts washed with water and brine, dried over anhydrous Na$_2$SO$_4$, filtered and concentrated under reduced pressure to give 3-(((1r,4r)-4-aminocyclohexyl)(ethyl)amino)-5-bromo-N-((4,6-dimethyl-2-oxo-1,2-dihydropyridin-3-yl)methyl)-2-methylbenzamide (2.2 g, 87.50%).

Step 4: 5-bromo-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide 3-(((1r,4r)-4-aminocyclohexyl)(ethyl)amino)-5-bromo-N-((4,6-dimethyl-2-oxo-1,2-dihydropyridin-3-yl)methyl)-2-methylbenzamide (2.2 g, 4.50 mmol) was dissolved in DCM (25 mL) and cooled to 0° C.; formalin (0.49 g, 16.26 mmol) was then added. The reaction mixture was stirred at same temperature for 20 minutes. Sodium triacetoxyborohydride (2.39 g, 11.22 mmol) was then added and the reaction mixture stirred for 1 h. The solvent were removed under reduced pressure and water was added to the residue. The mixture was extracted using 10% MeOH/DCM. The combined extracts were dried and concentrated under reduced pressure giving 5-bromo-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide (2.3 g, 98.71%) which was used as is in further reactions.

Step 5: N-((4,6-dimethyl-2-oxo-1,2-dihydropyridin-3-yl)methyl)-5-(((1r,4r)-4-(dimethylamino)cyclohexyl)(ethyl)amino)-4-methyl-[1,1'-biphenyl]-3-carboxamide To a stirred solution of 5-bromo-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide (1 eq) and phenylboronic acid (1.5 eq) in dioxane/water mixture, $Na_2CO_3$ (3.6 eq) was added and the solution purged with argon for 15 min. Pd $(PPh_3)_4$ (0.1 eq) was then added and the reaction mixture again purged with argon for 10 min. The reaction mixture was heated at 100° C. for 2 h. The reaction mixture was diluted with water and extracted with 10% MeOH/DCM. The combined extracts were dried over $Na_2SO_4$ and the solvent removed under reduced pressure to afford the crude product which was purified by chromatography over silica gel to afford the title compound as a TFA salt (0.07 g, 23.92%). LCMS: 515.45 $(M+1)^+$; HPLC: 92.45% (@254 nm) ($R_t$: 4.672; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-d6, 400 MHz) δ 11.48 (bs, 1H), 9.41 (bs, 1H), 8.23 (bs, 1H), 7.63 (d, 2H, J=4.8 Hz), 7.50-7.20 (m, 5H), 5.86 (s, 1H), 4.29 (d, 2H), 3.12 (m, 3H), 2.68 (s, 6H), 2.25 (s, 3H), 2.20 (s, 3H), 2.10 (s, 3H), 1.95 (m, 4H), 1.44 (m, 4H), 0.84 (t, 3H).

Example 148: N-((4,6-dimethyl-2-oxo-1,2-dihydropyridin-3-yl)methyl)-5-(((1r,4r)-4-(dimethylamino)cyclohexyl)(ethyl)amino)-4,4'-dimethyl-[1,1'-biphenyl]-3-carboxamide

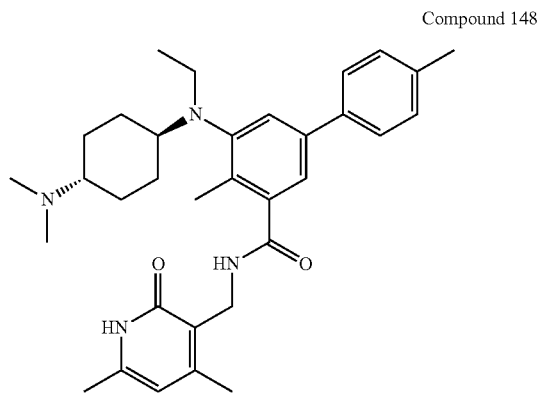

Compound 148

Step 1: N-((4,6-dimethyl-2-oxo-1,2-dihydropyridin-3-yl)methyl)-5-(((1r,4r)-4-(dimethylamino)cyclohexyl)(ethyl)amino)-4,4'-dimethyl-[1,1'-biphenyl]-3-carboxamide To a stirred solution of 5-bromo-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide (1 eq) and p-tolylboronic acid (1.5 eq) in dioxane/water mixture, $Na_2CO_3$ (3.6 eq) was added and the solution purged with argon for 15 min. Pd $(PPh_3)_4$ (0.1 eq) was then added and the reaction mixture again purged with argon for 10 min. The reaction mixture was heated at 100° C. for 2 h. The reaction mixture was diluted with water and extracted with 10% MeOH/DCM. The combined extracts were dried over $Na_2SO_4$ and the solvent removed under reduced pressure to afford the crude product which was purified by chromatography over silica gel to afford the title compound as a TFA salt (0.15 g, 51.30%). LCMS: 529.40 $(M+1)^+$; HPLC: 93.61% (@254 nm) ($R_t$: 4.761; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-d6, 400 MHz) δ 11.47 (bs, 1H), 9.40 (bs, 1H), 8.21 (bs, 1H), 7.53 (d, 2H, J=6.8 Hz), 7.38 (bs, 1H), 7.26 (d, 2H, J=7.6 Hz), 5.86 (s, 1H), 4.29 (d, 2H, J=4 Hz), 3.15 (m, 2H), 2.69 (s, 3H), 2.68 (s, 3H), 2.33 (s, 3H), 2.24 (s, 3H), 2.20 (s, 3H), 2.10 (s, 3H), 1.95 (m, 4H), 1.44 (m, 4H), 0.84 (t, 3H).

Example 149: N-((4,6-dimethyl-2-oxo-1,2-dihydropyridin-3-yl)methyl)-5-(((1r,4r)-4-(dimethylamino)cyclohexyl)(ethyl)amino)-4-methyl-4'-(trifluoromethyl)-[1,1'-biphenyl]-3-carboxamide

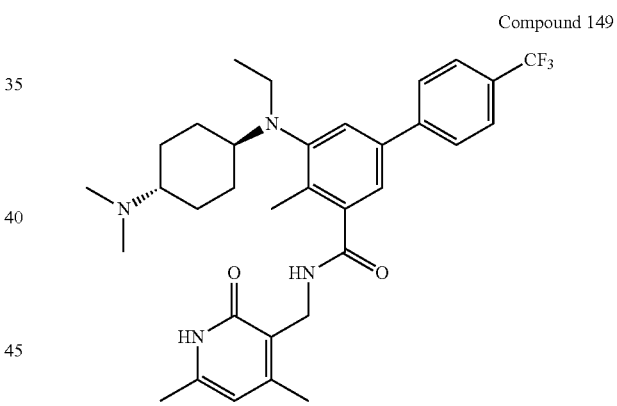

Compound 149

Step 1: N-((4,6-dimethyl-2-oxo-1,2-dihydropyridin-3-yl)methyl)-5-(((1r,4r)-4-(dimethylamino)cyclohexyl)(ethyl)amino)-4-methyl-4'-(trifluoromethyl)-[1,1'-biphenyl]-3-carboxamide To a stirred solution of 5-bromo-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide (1 eq) and (4-(trifluoromethyl)phenyl)boronic acid (1.5 eq) in dioxane/water mixture, $Na_2CO_3$ (3.6 eq) was added and the solution purged with argon for 15 min. Pd $(PPh_3)_4$ (0.1 eq) was then added and the reaction mixture again purged with argon for 10 min. The reaction mixture was heated at 100° C. for 2 h. The reaction mixture was diluted with water and extracted with 10% MeOH/DCM. The combined extracts were dried over $Na_2SO_4$ and the solvent removed under reduced pressure to afford the crude product which was purified by chromatography over silica gel to afford the title compound as a TFA salt (0.08 g, 23.52%). LCMS: 583.45 (M+1)⁺; HPLC: 94.04% (@ 254 nm) (R$_t$; 5.168; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d6, 400 MHz) δ 11.48 (s, 1H), 9.41 (bs, 1H), 8.27 (bs, 1H), 7.88 (d, 2H, J=8 Hz), 7.81 (d, 2H, J=8 Hz), 7.51 (s, 1H), 7.34 (s, 1H), 5.87 (s, 1H), 4.30 (d, 2H, J=4.4 Hz), 3.16 (m, 3H), 2.85 (m, 1H), 2.69 (s, 3H), 2.68 (s, 3H), 2.26 (s, 3H), 2.21 (s, 3H), 2.11 (s, 3H), 1.94 (m, 4H), 1.45 (m, 4H), 0.85 (t, 3H, J=6.8 Hz).

Example 150: N-((4,6-dimethyl-2-oxo-1,2-dihydropyridin-3-yl)methyl)-5-(((1r,4r)-4-(dimethylamino) cyclohexyl)(ethyl)amino)-4-methyl-4'-(methylsulfonyl)-[1,1'-biphenyl]-3-carboxamide Compound 150

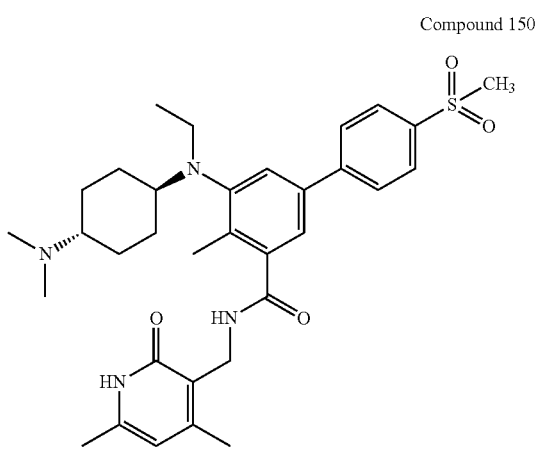

Step 1: N-((4,6-dimethyl-2-oxo-1,2-dihydropyridin-3-yl)methyl)-5-(((1r,4r)-4-(dimethylamino)cyclohexyl)(ethyl)amino)-4-methyl-4'-(methyl sulfonyl)-[1,1'-biphenyl]-3-carboxamide To a stirred solution of 5-bromo-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide (1 eq) and (4-(methylsulfonyl)phenyl)boronic acid (1.5 eq) in dioxane/water mixture, Na₂CO₃ (3.6 eq) was added and the solution purged with argon for 15 min. Pd (PPh₃)₄ (0.1 eq) was then added and the reaction mixture again purged with argon for 10 min. The reaction mixture was heated at 100° C. for 2 h. The reaction mixture was diluted with water and extracted with 10% MeOH/DCM. The combined extracts were dried over Na₂SO₄ and the solvent removed under reduced pressure to afford the crude product which was purified by chromatography over silica gel to afford the title compound as a TFA salt (0.12 g, 34.68%). LCMS: 593.45 (M+1)⁺; HPLC: 98.74% (@ 254 nm) (R$_t$; 4.194; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d6, 400 MHz) δ 11.48 (bs, 1H), 9.43 (s, 1H), 8.26 (s, 1H), 7.99 (d, 2H, J=8.4 Hz), 7.93 (d, 2H, J=8.4 Hz), 7.51 (s, 1H), 7.34 (s, 1H), 5.87 (s, 1H), 4.30 (d, 2H, J=4.4 Hz), 3.24 (s, 3H), 3.30 (m, 3H), 2.80 (m, 1H), 2.69 (s, 3H), 2.68 (s, 3H), 2.26 (s, 3H), 2.21 (s, 3H), 2.11 (s, 3H), 1.93 (m, 4H), 1.45 (m, 4H), 0.84 (t, 3H, J=6.8 Hz).

Example 151: N-((4,6-dimethyl-2-oxo-1,2-dihydropyridin-3-yl)methyl)-3-(((1r,4r)-4-(dimethylamino) cyclohexyl)(ethyl)amino)-2-methyl-5-(pyrimidin-5-yl)benzamide Compound 151

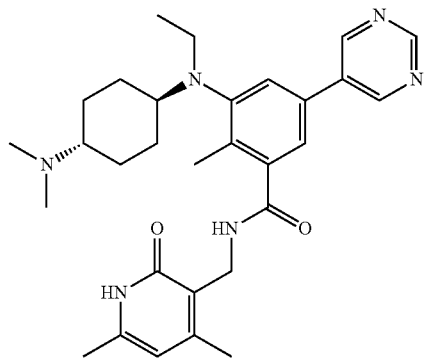

Step 1: N-((4,6-dimethyl-2-oxo-1,2-dihydropyridin-3-yl)methyl)-3-(((1r,4r)-4-(dimethylamino)cyclohexyl)(ethyl)amino)-2-methyl-5-(pyrimidin-5-yl) benzamide To a stirred solution of 5-bromo-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide (1 eq) and pyrimidin-5-ylboronic acid (1.5 eq) in dioxane/water mixture, Na₂CO₃ (3.6 eq) was added and the solution purged with argon for 15 min. Pd (PPh₃)₄ (0.1 eq) was then added and the reaction mixture again purged with argon for 10 min. The reaction mixture was heated at 100° C. for 2 h. The reaction mixture was diluted with water and extracted with 10% MeOH/DCM. The combined extracts were dried over Na₂SO₄ and the solvent removed under reduced pressure to afford the crude product which was purified by chromatography over silica gel to afford N-((4,6-dimethyl-2-oxo-1,2-dihydropyridin-3-yl)methyl)-3-(((1r,4r)-4-(dimethylamino) cyclohexyl)(ethyl)amino)-2-methyl-5-(pyrimidin-5-yl) benzamide TFA salt (0.12 g, 39.33%). LCMS: 517.60 (M+1)⁺; HPLC: 99.55% (@ 210 nm-370 nm) (R$_t$; 3.996; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d₆, 400 MHz) δ 11.47 (bs, 1H), 9.43 (bs, 1H), 9.18 (s, 1H), 9.14 (s, 2H), 8.22 (s, 1H), 7.59 (s, 1H), 7.41 (s, 1H), 5.87 (s, 1H), 4.30 (d, 2H), 3.14 (m, 3H), 2.69 (s, 3H+3H), 2.27 (s, 3H), 2.22 (s, 3H), 2.11-2.07 (m, 4H), 1.95 (m, 4H), 1.44 (m, 4H), 0.84 (t, 3H).

Example 152: Synthesis of N-((4,6-dimethyl-2-oxo-1,2-dihydropyridin-3-yl)methyl-3-(((1r,4r)-4-(dimethylamino)cyclohexyl)(ethyl)amino)-5-(furan-2-yl)-2-methylbenzamide TFA salt

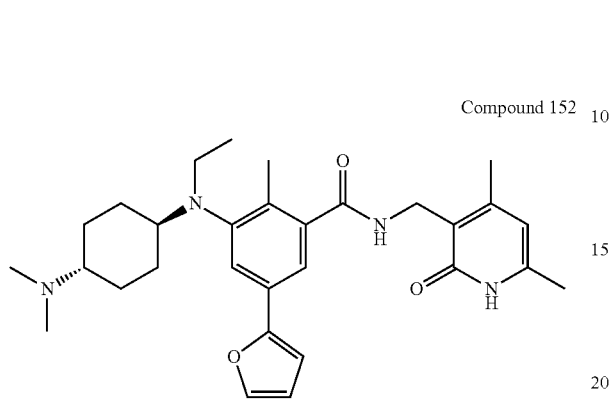

Compound 152

Step 1: Synthesis of methyl 5-bromo-3-(((1r,4r)-4-((tert-butoxycarbonyl)-amino)-cyclohexyl)amino)-2-methylbenzoate

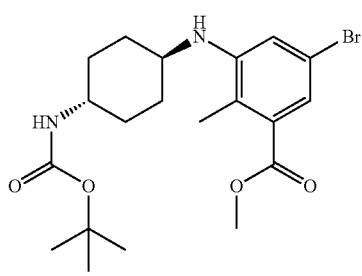 [SMILES: COC(=O)c1cc(Br)cc(N[C@H]2CC[C@H](NC(=O)OC(C)(C)C)CC2)c1C]

To a stirred solution of methyl 3-amino-5-bromo-2-methylbenzoate (5.0 g, 2.0 mmol) and 4-N-Boc-aminocyclohexanone (5.69 g, 2.67 mmol) in dichloroethane (50 mL) was added acetic acid (7.4 g, 12 mmol). Sodium triacetoxyborohydride (13.1 g, 6.17 mmol) was added at 0° C. and the mixture was stirred at room temperature for 16 hours. The reaction mixture was quenched with aqueous sodium bicarbonate, the organic phase separated and the aqueous phase extracted with dichloromethane. The combined organic layers were dried over anhydrous sodium sulphate and concentrated in-vacuo. The crude compound was purified by column chromatography over silica gel (100-200 mesh size) eluting with 10% ethyl acetate in hexane to afford 3.5 g of the more polar trans-isomer 5-bromo-3-(((1r,4r)-4-((tert-butoxycarbonyl)-amino)-cyclohexyl)amino)-2-methylbenzoate (38%) of isomer as an off-white solid. $^1$H NMR (CDCl$_3$, 400 MHz) δ 7.21 (s, 1H), 6.89 (s, 1H), 4.41 (bs, 1H), 3.85 (s, 3H), 3.41-3.64 (m, 2H), 2.11-2.21 (m, 6H), 1.42 (s, 9H), 1.22-1.36 (m, 5H),

Step 2: Synthesis of synthesis of methyl 5-bromo-3-(((1r,4r)-4-((tert-butoxycarbonyl)-amino)-cyclohexyl)(ethyl)-amino)-2-methylbenzoate

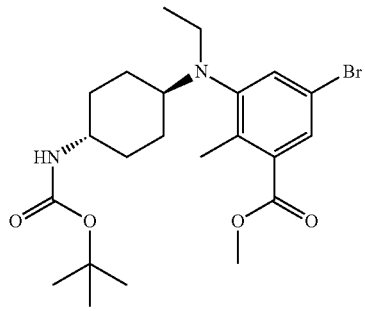 [SMILES: CCN(c1cc(Br)cc(C(=O)OC)c1C)[C@H]1CC[C@H](NC(=O)OC(C)(C)C)CC1]

To a stirred solution of 5-bromo-3-(((1r,4r)-4-((tert-butoxycarbonyl)-amino)-cyclohexyl)amino)-2-methylbenzoate (55 g, 0.12 mol) and acetaldehyde (11 g, 0.25 mol) in dichloroethane (550 mL) was added acetic acid (44.6 g, 0.74 mol). Sodium triacetoxyborohydride (79 g, 0.37 mol) was added at 0° C. and the mixture was stirred at room temperature for 16 hours. Aqueous sodium bicarbonate was added, the organic phase was separated and the aqueous phase extracted with dichloromethane. The combined organic layers were dried over anhydrous sodium sulphate and concentrated in-vacuo. The crude compound was purified by column chromatography over silica get to afford the title compound (35 g, 59%) as an off-white solid.

Step 3: Synthesis of tert-butyl ((1r,4r)-4-((5-bromo-3-(((4,6-dimethyl-2-oxo-1,2-dihydropyridin-3-yl)-methyl)carbamoyl)-2-methylphenyl(ethyl)amino)cyclohexyl)carbamate

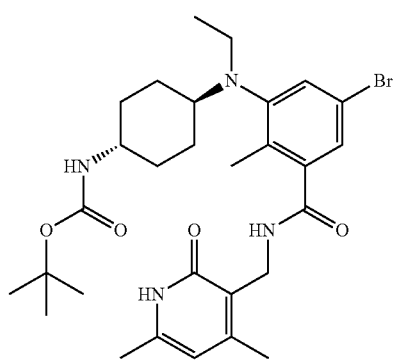 [SMILES: CCN(c1cc(Br)cc(C(=O)NCc2c(C)cc(C)[nH]c2=O)c1C)[C@H]1CC[C@H](NC(=O)OC(C)(C)C)CC1]

To a stirred solution of methyl 5-bromo-3-(((1r,4r)-4-((tert-butoxycarbonyl)-amino)-cyclohexyl)(ethyl)-amino)-2-methylbenzoate (25 g, 0.053 mol) in EtOH (100 mL) was added aqueous NaOH (3.5 g, 0.08 mol in 10 mL H$_2$O). After stirring at 60° C. for 1 h, the mixture was acidified to pH 4 and extracted with 10% methanol in DCM. The combined organic layers were dried and concentrated to give 24.2 g of the corresponding acid. To a stirred solution of the acid (24 g, 0.053 mol) and 3-(amino methyl)-4,6-dimethylpyridin-2 (1H)-one (16 g, 0.11 mol) and triethyl amine (5.3 g, 0.053 mmol) in DMSO (50 mL) was added PyBop (41 g, 0.079 mol). After stirring overnight at room temperature, the mixture was poured into ice water and extracted with 10% MeOH/DCM. The combined organic layers were dried over sodium sulphate and concentrated under reduced pressure. The crude material was washed water (1 L×2) followed by acetonitrile (150 mL×3) to afford the title compound (24 g, 77%).

Step 4: Synthesis of 3-(((1r,4r)-4-aminocyclohexyl)(ethyl)amino)-5-bromo-N-((4,6-dimethyl-2-oxo-1,2-dihydropyridin-3-yl)methyl)-2-methylbenzamide

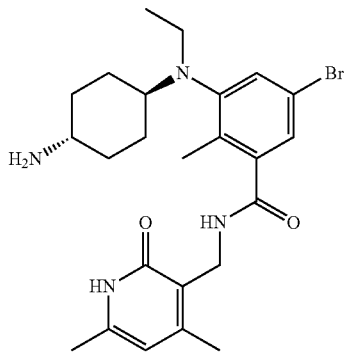 [SMILES: CCN(c1cc(Br)cc(C(=O)NCc2c(C)cc(C)[nH]c2=O)c1C)[C@H]1CC[C@H](N)CC1]

To a stirred solution of tert-butyl ((1r,4r)-4-((5-bromo-3-(((4,6-dimethyl-2-oxo-1,2-dihydropyridin-3-yl)-methyl)carbamoyl)-2-methylphenyl(ethyl)amino)cyclohexyl)carbamate (6.0 g, 10 mol) in DCM (30 mL), was added TFA (10 mL) at 0° C. The reaction mixture was stirred for 2 h at room temperature and concentrated to dryness. The residue was neutralized by addition of saturated bicarbonate solution (40 mL) followed by extraction with 20% methanol in DCM (100 mL×4). The combined organic phases were dried over Na$_2$SO$_4$ and the solvent was removed under reduced pressure to afford 5.0 g of the title compound which was used without further purification.

Step 4: Synthesis of 5-bromo-N-((4,6-dimethyl-2-oxo-1,2-dihydropyridin-3-yl)methyl)-3-(((1r, 4r)-4-(dimethylamino)cyclohexyl)(ethyl)amino)-2-methylbenzamide

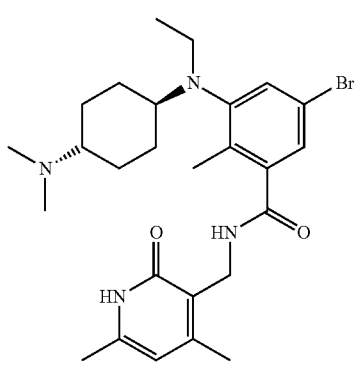

To a stirred solution of 3-(((1r,4r)-4-aminocyclohexyl)(ethyl)amino)-5-bromo-N-((4,6-dimethyl-2-oxo-1,2-dihydropyridin-3-yl)methyl)-2-methylbenzamide (5.0 g, 10 mmol) in dichloromethane (50 mL) was added aq. 35% formaldehyde solution (2.9 g, 36 mmol) at 0° C. Na(OAc)$_3$BH (5.43 g, 25.6 mmol) was added and the mixture was stirred for 2 h at 0° C. Water (100 mL) was added followed by extraction with 20% methanol in DCM (200 mL×3). The combined organic layers were dried over Na$_2$SO$_4$ and the solvent was removed under reduced pressure. The residue was purified by column chromatography over basic alumina eluting with 6-7% MeOH in DCM to afford the title compound (4.5 g, 94%).

General Suzuki reaction procedure for the synthesis of Compounds 152-156, 158-162, 165, and 167

To a stirred solution of 5-bromo-N-((4,6-dimethyl-2-oxo-1,2-dihydropyridin-3-yl)methyl)-3-(((1r, 4r)-4-(dimethylamino)cyclohexyl)(ethyl)amino)-2-methylbenzamide (1 eq.) and given boronic acids/pinacol esters (1.2 eq.) in dioxane/water mixture (4:1), was added Na$_2$CO$_3$ (3.6 eq.). The solution was purged with argon for 15 min. Pd(PPh$_3$)$_4$ (0.1 eq.) was added. The stirred reaction mixture was heated at 100° C. for 2-4 h under argon. After cooling to room temperature, the mixture was diluted with 10% MeOH/DCM and filtered. The filtrate was concentrated, diluted with water and extracted with 10% MeOH in DCM. The combined organic layers were dried over Na$_2$SO$_4$ and the solvent removed under reduced pressure. The crude products were purified either by column chromatography over silica gel (100-200 mesh) or by preparative HPLC to give products as free base or TFA salt respectively.

Analytical Data of N-((4,6-dimethyl-2-oxo-1,2-dihydropyridin-3-yl)methyl)-3-(((1r,4r)-4-(dimethylamino)cyclohexyl)(ethyl)amino)-5-(furan-2-yl)-2-methylbenzamide TFA salt (0.08 g, 27%); LCMS: 505.55 (M+1)$^+$; HPLC: 97.76% (@ 210 nm-370 nm) (R$_t$: 4.192; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (bs, 1H), 8.21 (s, 1H), 8.17 (s, 1H), 7.71 (s, 1H), 7.42 (s, 1H), 7.25 (s, 1H), 6.93 (s, 1H), 6.57 (s, 1H), 5.86 (s, 1H), 4.29 (d, 2H), 3.08-3.06 (m, 3H), 2.67 (m, 1H), 2.21 (s, 3H+3H+3H), 2.18-2.11 (s, 3H+3H), 1.80 (m, 4H), 1.37-1.19 (m, 4H), 0.81 (t, 3H).

Example 153: N-((4,6-dimethyl-2-oxo-1,2-dihydropyridin-3-yl)methyl)-3-(((1r,4r)-4-(dimethylamino)cyclohexyl)(ethyl)amino)-2-methyl-5-(quinolin-8-yl)-benzamide TFA salt (0.09 g, 27%)

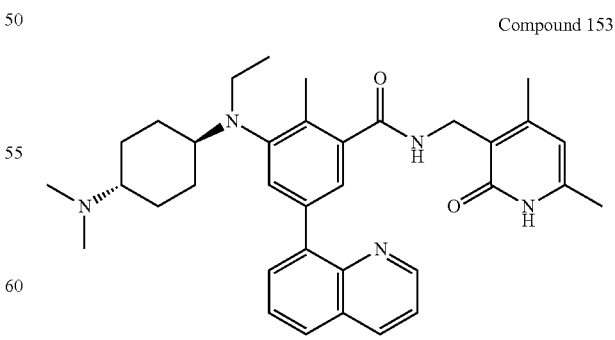

Compound 153

Analytical Data of TFA salt: LCMS: 566.70 (M+1)$^+$; HPLC: 93.94% (@ 210 nm-370 nm) (R$_t$: 4.352; Method: Column: YMC ODS-A 150 mm×4.6 mm×5µ; Mobile Phase: A; 0.05% TFA in water/B; 0.05% TFA in acetonitrile; Inj.

Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d₆, 400 MHz) δ 11.43 (bs, 1H), 9.34 (bs, 1H), 8.88 (s, 1H), 8.45 (d, 1H, J=7.6 Hz), 8.16 (t, 1H), 8.00 (d, 1H, J=7.2 Hz), 7.80-7.79 (m, 1H), 7.70-7.69 (m, 1H), 7.59-7.57 (m, 1H), 7.49 (m, 1H), 7.29 (s, 1H), 5.85 (s, 1H), 4.28 (d, 2H, J=3.6 Hz), 3.16-3.11 (m, 3H), 2.70-2.69 (m, 1H+3H+3H), 2.30 (s, 3H), 2.19 (s, 3H), 2.09 (s, 3H), 1.99 (m, 4H), 1.45 (m, 4H), 0.93 (t, 3H).

Example 154: 5-(2-aminopyrimidin-5-yl)-N-((4,6-dimethyl-2-oxo-1,2-dihydropyridin-3-yl)methyl-3-(((1r,4r)-4-(dimethylamino)cyclohexyl)(ethyl)amino-2-methylbenzamide TFA salt (0.14 g, 45%)

Compound 154

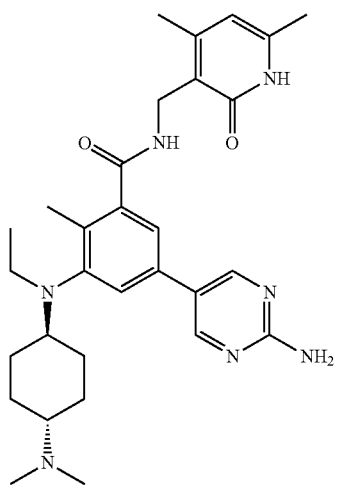

Analytical Data of TFA salt: LCMS: 532.65 (M+1)⁺; HPLC: 98.49% (@ 210 nm-370 nm) (R$_t$: 3.692; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d₆, 400 MHz) δ 11.48 (bs, 1H), 9.45 (bs, 1H), 8.17 (s, 1H), 7.42 (s, 1H), 7.24 (s, 1H), 5.87 (s, 1H), 4.28 (d, 2H, J=4.4 Hz), 3.12 (m, 3H), 2.69 (s, 3H+3H), 2.23 (s, 3H), 2.21 (s, 3H), 2.11 (s, 3H), 1.96 (m, 4H), 1.43 (m, 4H), 0.83 (t, 3H).

Example 155: N-((4,6-dimethyl-2-oxo-1,2-dihydropyridin-3-yl)methyl-3-(((1r,4r)-4-(dimethylamino)cyclohexyl)(ethyl)amino-2-methyl-5-(pyridin-4-yl)-benzamide TFA salt (0.17 g, 56%)

Compound 155

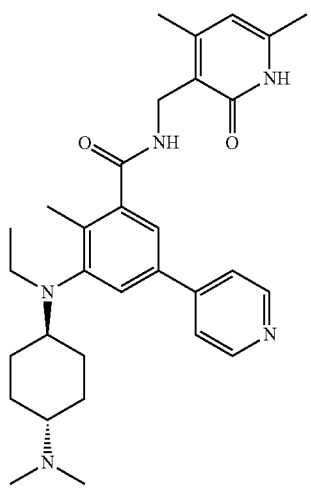

Analytical Data of TFA salt: LCMS: 516.60 (M+1)⁺; HPLC: 92.58% (@ 210 nm-370 nm) (R$_t$: 3.775; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d₆, 400 MHz) δ 11.45 (bs, 1H), 9.74 (bs, 1H), 8.85 (d, 2H, J=5.2 Hz), 8.30 (t, 1H), 8.24 (d, 2H, J=4.8 Hz), 7.71 (s, 1H), 7.55 (s, 1H), 5.88 (s, 1H), 4.31 (d, 2H, J=4.4 Hz), 3.16 (m, 3H), 2.79 (m, 1H), 2.69 (s, 3H+3H), 2.28 (s, 3H), 2.22 (s, 3H), 2.11 (s, 3H), 1.98-1.90 (m, 4H), 1.47-1.45 (m, 4H), 0.84 (t, 3H).

Example 156: N-((4,6-dimethyl-2-oxo-1,2-dihydropyridin-3-yl)methyl-3-(((1r,4r)-4-(dimethylamino)cyclohexyl)(ethyl)amino)-2-methyl-5-(thiophen-3-yl)-benzamide TFA salt (0.07 g, 56%)

Compound 156

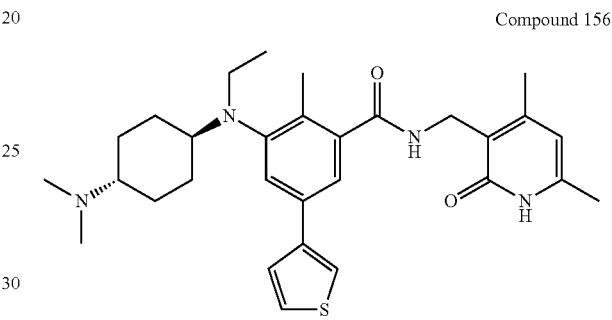

Analytical Data of TFA salt: LCMS: 521.55 (M+1)⁺; HPLC: 98.64% (@ 210 nm-370 nm) (R$_t$: 4.366; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d₆, 400 MHz) δ 11.47 (bs, 1H), 9.45 (bs, 1H), 8.18 (s, 1H), 7.87 (s, 1H), 7.63 (s, 1H), 7.54 (m, 2H), 7.32 (s, 1H), 5.87 (s, 1H), 4.29 (d, 2H), 3.13 (m, 3H), 2.69 (m, 6H+1H), 2.22 (s, 3H+3H), 2.11 (s, 3H), 1.96 (m, 4H) 1.44 (m, 4H), 0.84 (t, 3H).

Example 158: N-((4,6-dimethyl-2-oxo-1,2-dihydropyridin-3-yl)methyl)-3-(((1r,4r)-4-(dimethylamino)cyclohexyl)(ethyl)amino)-2-methyl-5-(6-methylpyridin-3-yl)benzamide Compound 158

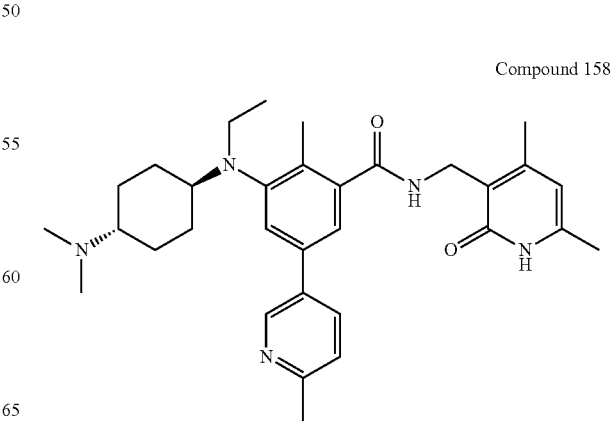

Analytical Data: LCMS: 530.55 (M+1)+; HPLC: 96.45% (@ 210 nm-370 nm) (R$_t$; 4.192; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (bs, 1H), 8.70 (s, 1H), 8.19 (s, 1H), 7.95-7.90 (d, 1H, J=8.0 Hz), 7.39 (s, 1H), 7.35-7.30 (d, 1H, J=7.6 Hz), 7.22 (s, 1H), 5.86 (s, 1H), 4.29 (d, 2H), 3.05-3.15 (m, 2H), 2.60-2.70 (m, 1H), Three protons merged in solvent peak, 2.25-2.35 (m, 6H+1H), 2.0-2.25 (3H+3H+3H), 1.70-1.90 (m, 4H), 1.30-1.20 (m, 2H), 1.0-1.20 (m, 2H), 0.75-0.85 (t, 3H)

Example 159: N-((4,6-dimethyl-2-oxo-1,2-dihydropyridin-3-yl)methyl-3-(((1r,4r)-4-(dimethylamino) cyclohexyl)(ethyl)amino)-5-(3,5-dimethylisoxazol-4-yl)-2-methylbenzamide TFA salt (0.13 g, 50%)

Compound 159

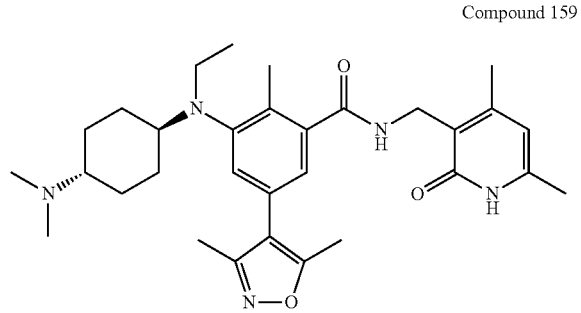

Analytical Data of TFA salt: LCMS: 534.60 (M+1)+; HPLC: 96.65% (@ 210 nm-370 nm) (R$_t$; 4.352; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (bs, 1H), 9.42 (s, 1H), 8.17 (s, 1H), 7.13 (s, 1H), 6.92 (s, 1H), 5.85 (s, 1H), 4.25-4.30 (d, 2H), 3.0-3.20 (m, 3H), 2.65-2.75 (m, 3H+3H), Three protons merged in solvent peak, 2.39 (s, 3H), 2.05-2.25 (m, 3H+3H+3H+1H), 1.90-2.0 (m, 2H), 1.80-1.90 (m, 2H), 1.35-1.50 (m, 4H), 0.80-0.90 (t, 3H).

Example 160: 5-(1,5-dimethyl-1H-pyrazol-4-yl)-N-((4,6-dimethyl-2-oxo-1,2-dihydropyridin-3-yl) methyl)-3-(((1r,4r)-4-(dimethylamino)cyclohexyl) (ethyl)amino)-2-methylbenzamide TFA salt (0.06 g, 58%)

Compound 160

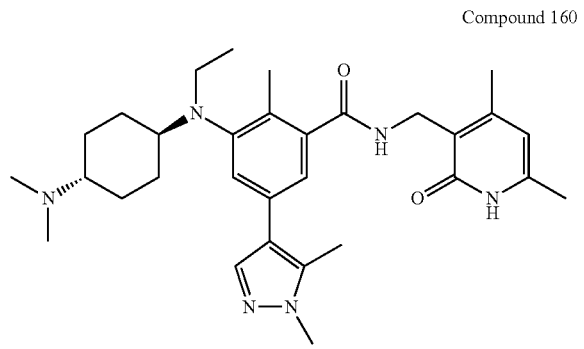

Analytical Data of TFA salt: LCMS: 533.80 (M+1)+; HPLC: 90.76% (@ 254 nm) (R$_t$; 5.583; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6,400 MHz) δ 11.45 (bs, 1H), 9.27 (s, 1H), 8.11 (s, 1H), 7.52 (s, 1H), 7.11 (s, 1H), 6.95 (s, 1H), 5.85 (s, 1H), 4.20-4.30 (d, 2H), 3.76 (s, 2H), 3.0-3.20 (m, 2H), 2.60-2.75 (m, 3H+3H), 2.33 (s, 3H), 2.19 (s, 3H), 2.10 (s, 3H), 1.80-2.0 (m, 4H), 1.35-1.50 (m, 4H), 0.80-0.90 (t, 3H).

Example 161: N-((4,6-dimethyl-2-oxo-1,2-dihydropyridin-3-yl)methyl-3-(((1r,4r)-4-(dimethylamino) cyclohexyl)(ethyl)amino)-5-(1-methylpyrazol-3-yl)-2-methylbenzamide TFA salt (0.1 g, 33%)

Compound 161

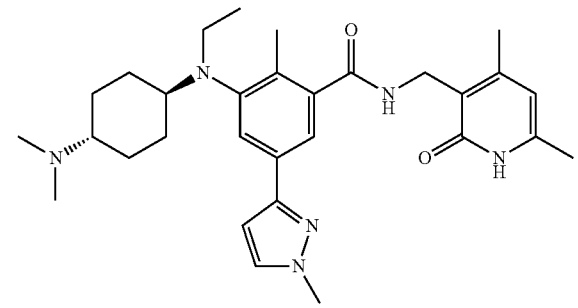

Analytical Data of TFA salt: LCMS: 519.45 (M+1)+; HPLC: 96.61% (@ 254 nm) (R$_t$; 6.026; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.47 (bs, 1H), 9.46 (s, 1H), 8.20 (s, 1H), 7.45 (s, 1H), 7.28 (s, 1H), 7.06 (s, 1H), 6.38 (s, 1H), 5.86 (s, 1H), 4.20-4.25 (d, 2H), 3.83 (s, 3H), 3.0-3.15 (m, 3H), 2.60-2.80 (m, 1H+3H+3H), 2.24 (s, 3H), 2.19 (s, 3H), 2.10 (s, 3H), 1.80-2.0 (m, 2H+2H), 1.40-1.50 (m, 4H), 0.80-0.90 (t, 3H).

Example 162: N-((4,6-dimethyl-2-oxo-1,2-dihydropyridin-3-yl)methyl-3-(((1r,4r)-4-(dimethylamino) cyclohexyl)(ethyl)amino)-5-(pyridin-3-yl)-2-methylbenzamide TFA salt (0.1 g, 33%)

Compound 162

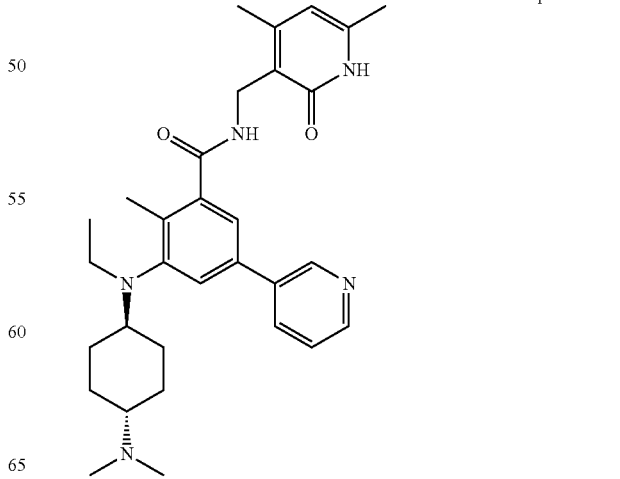

Analytical Data of TFA salt: LCMS: 516.50 (M+1)+; HPLC: 89.96% (@ 254 nm) (R$_t$: 6.026; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (bs, 1H), 9.35 (s, 1H), 8.96 (s, 1H), 8.63 (s, 1H), 8.22 (m, 2H), 7.61 (s, 1H), 7.51 (s, 1H), 7.33 (s, 1H), 5.86 (s, 1H), 4.25-4.35 (d, 2H), 3.05-3.15 (m, 3H), 2.6-2.80 (m, 1H+3H+3H), 2.25 (s, 3H), 2.21 (s, 3H), 2.10 (s, 3H), 1.90-2.0 (m, 2H+2H), 1.40-1.50 (m, 4H), 0.80-0.90 (t, 3H).

Example 163: N N-((4,6-dimethyl-2-oxo-1,2-dihydropyridin-3-yl)methyl)-5-(((1r,4r)-4-(dimethylamino)cyclohexyl)(ethyl)amino)-4-methyl-4'-(2H-tetrazol-5-yl)-[1,1'-biphenyl]-3-carboxamide

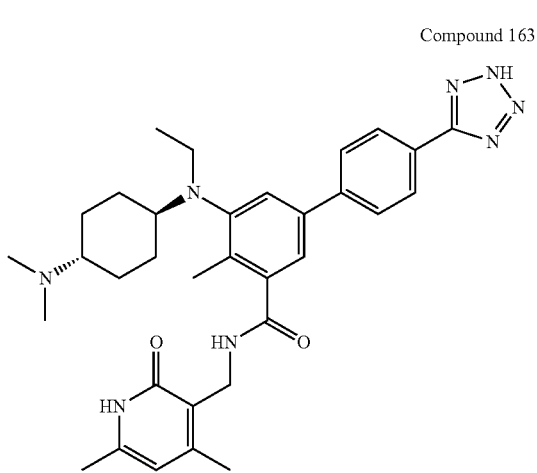 [SMILES: CCN(c1cc(-c2ccc(-c3nn[nH]n3)cc2)cc(C(=O)NCc2c(C)cc(C)[nH]c2=O)c1C)[C@H]1CC[C@H](N(C)C)CC1]

Compound 163

To a stirred solution of 5-bromo-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide (1 eq) and 5-(4-(4,4,5,5-tetramethyl-1,3,2-dioxaborolan-2-yl)phenyl)-2H-tetrazole (1.5 eq) in dioxane/water mixture, Na$_2$CO$_3$ (3.6 eq) was added and the solution purged with argon for 15 min. Pd (PPh$_3$)$_4$ (0.1 eq) was then added and the reaction mixture again purged with argon for 10 min. The reaction mixture was heated at 100° C. for 2 h. The reaction mixture was diluted with water and extracted with 10% MeOH/DCM. The combined extracts were dried over Na$_2$SO$_4$ and the solvent removed under reduced pressure to afford the crude product which was purified by chromatography over silica gel then prep. HPLC to afford the title compound as a TFA salt (0.125 g, 35.50%). LCMS: 583.40 (M+1)+; HPLC: 90.26% (@ 210-370 nm) (R$_t$: 4.130; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (bs, 1H), 9.32 (bs, 1H), 8.23-8.11 (m, 3H), 7.90 (d, 2H, J=7.2 Hz), 7.50 (s, 1H), 7.34 (s, 1H), 5.87 (s, 1H), 4.30 (d, 2H, J=4.4 Hz), 3.59 (s, 1H), 3.13 (m, 3H), 2.69-2.68 (m, 6H), 2.26-2.10 (m, 9H), 1.94 (m, 4H), 1.44 (m, 4H) 0.85 (m, 3H).

Example 164: N-((4,6-dimethyl-2-oxo-1,2-dihydropyridin-3-yl)methyl)-3-(((1r,4r)-4-(dimethylamino)cyclohexyl)(ethyl)amino)-2-methyl-5-(2-methylpyrimidin-5-yl)benzamide

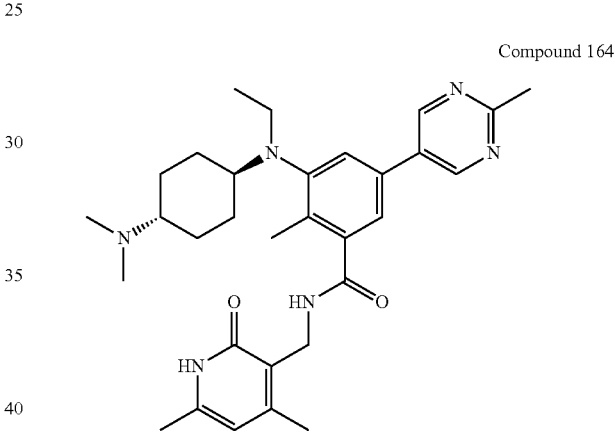

Compound 164

To a stirred solution of 5-bromo-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide (1 eq) and 2-methyl-5-(4,4,5,5-tetramethyl-1,3,2-dioxaborolan-2-yl)pyrimidine (1.5 eq) in dioxane/water mixture, Na$_2$CO$_3$ (3.6 eq) was added and the solution purged with argon for 15 min. Pd (PPh$_3$)$_4$ (0.1 eq) was then added and the reaction mixture again purged with argon for 10 min. The reaction mixture was heated at 100° C. for 2 h. The reaction mixture was diluted with water and extracted with 10% MeOH/DCM. The combined extracts were dried over Na$_2$SO$_4$ and the solvent removed under reduced pressure to afford the crude product which was purified by chromatography over silica gel then prep HPLC to afford the title compound as a TFA salt (0.08 g, 25.97%). LCMS: 531.65 (M+1)+; HPLC: 99.61% (@ 210-370 nm) (R$_t$: 3.981; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.47 (bs, 1H),9.46 (bs, 1H), 9.00 (m, 2H), 8.20 (s, 1H), 7.53 (s, 1H), 7.35 (s, 1H), 5.86 (s, 1H), 4.29 (m, 2H), 3.125-3.127 (m, 3H), 2.69-2.50 (m, 10H), 2.25-2.10 (m, 9H), 1.94 (m, 4H), 1.43 (m, 4H), 0.83 (m, 3H).

Example 165: 5-(1,3-dimethyl-1H-pyrazol-4-yl)-N-((4,6-dimethyl-2-oxo-1,2-dihydropyridin-3-yl)methyl-3-(((1r,4r)-4-(dimethylamino)cyclohexyl)(ethyl)amino-2-methylbenzamide TFA salt (0.18 g, 69%)

Compound 165

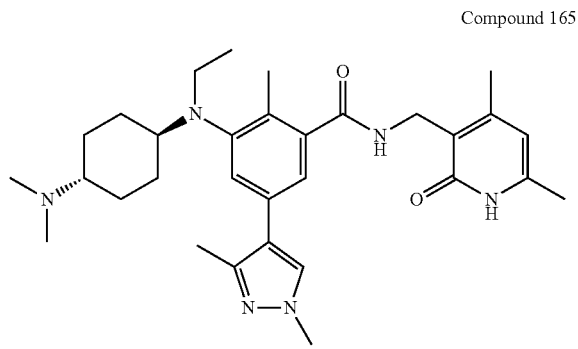

Analytical Data of TFA salt: LCMS: 533.80 (M+1)$^+$; HPLC: 87.18% (@ 210-370 nm) (R$_t$; 3.946; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (D$_2$O-d$_6$, 400 MHz) δ 7.93 (s, 1H), 7.62-7.57 (m, 2H), 6.31 (s, 1H), 4.492-4.494 (m, 2H), 3.92-3.80 (m, 6H), 3.33 (m, 1H), 2.82 (m, 6H), 2.39-2.28 (m, 16H), 1.66 (m, 4H), 1.04 (m, 3H).

Example 166: N-((4,6-dimethyl-2-oxo-1,2-dihydro-pyridin-3-yl)methyl)-3-(((1r,4r)-4-(dimethylamino)cyclohexyl)(ethyl)amino)-2-methyl-5-(thiazol-4-yl)benzamide Compound 166

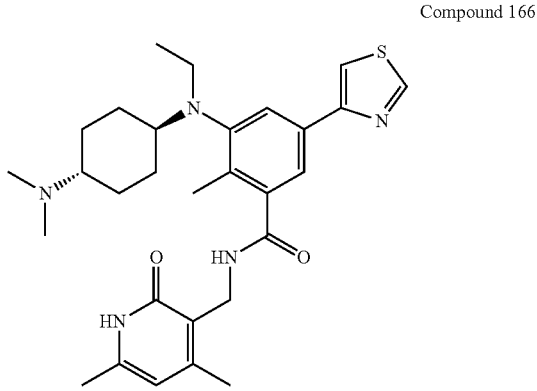 [SMILES: CCN(c1cc(-c2cscn2)cc(C(=O)NCc2c(C)cc(C)[nH]c2=O)c1C)[C@H]1CC[C@H](N(C)C)CC1]

To a stirred solution of 5-bromo-N-((4,6-dimethyl-2-oxo-1,2-dihydropyridin-3-yl)methyl)-3-(((1r,4r)-4-(dimethylamino)cyclohexyl)(ethyl)amino)-2-methylbenzamide (1 eq) and 4-(4,4,5,5-tetramethyl-1,3,2-dioxaborolan-2-yl)thiazole (1.5 eq) in dioxane/water mixture, Na$_2$CO$_3$ (3.6 eq) was added and the solution purged with argon for 15 min. Pd (PPh$_3$)$_4$ (0.1 eq) was then added and the reaction mixture again purged with argon for 10 min. The reaction mixture was heated at 100° C. for 2 h. The reaction mixture was diluted with water and extracted with 10% MeOH/DCM. The combined extracts were dried over Na$_2$SO$_4$ and the solvent removed under reduced pressure to afford the crude product which was purified by chromatography over silica gel then prep HPLC to afford the title compound as a TFA salt (0.07 g, 28.40%). LCMS: 522.50 (M+1)$^+$; HPLC: 99.22% (@ 210-370 nm) (R$_t$; 4.114; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.48 (bs, 1H), 9.36 (bs, 1H), 9.18 (s, 1H), 8.19 (bs, 2H), 7.79 (s, 1H), 7.58 (s, 1H), 5.87 (s, 1H), 4.30 (d, 2H, J=4.4 Hz), 3.11 (m, 3H), 2.73-2.68 (m, 7H), 2.22 (s, 6H), 2.11 (s, 3H), 1.95 (m, 4H), 1.44 (m, 4H), 0.83 (t, 3H).

Example 167: N-((4,6-dimethyl-2-oxo-1,2-dihydro-pyridin-3-yl)methyl-3-(((1r,4r)-4-(dimethylamino)cyclohexyl)(ethyl)amino)-2-methyl-5-(thiophen-2-yl)-benzamide TFA salt (0.05 g, 50%)

Compound 167

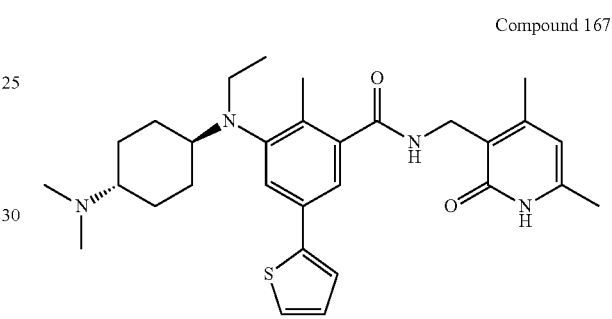

Analytical Data: LCMS: 521.55 (M+1)$^+$; HPLC: 88.13% (@ 210-370 nm) (R$_t$; 4.412; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.47 (bs, 1H), 9.32 (bs, 1H), 8.22 (t, 1H), 7.53-7.38 (m, 3H), 7.20-7.13 (m, 2H), 5.87 (s, 1H), 4.28 (d, 2H, J=3.6 Hz), 3.10 (m, 3H), 2.69-2.68 (m, 7H), 2.21 (s, 6H), 2.11 (s, 3H), 1.95-1.90 (m, 4H), 1.44 (m, 4H), 0.83 (t, 3H).

Example 168: Synthesis of N-((4,6-dimethyl-2-oxo-1,2-dihydropyridin-3-yl)methyl-3-(((1r,4r)-4-(dimethylamino)cyclohexyl)(ethyl)amino)-2-methyl-5-(thiazol-2-yl)-benzamide TFA salt Compound 168

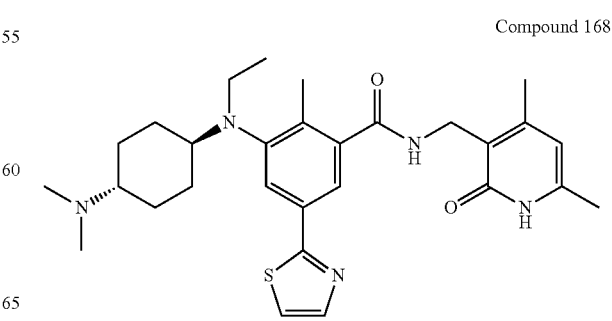

Step 1: Synthesis of methyl 3-(((1r,4r)-4-((tert-butoxycarbonyl)-amino)-cyclohexyl)-(ethyl)-amino)-2-methyl-5-(thiazol-2-yl)benzoate To a stirred solution of methyl 3-(((1r,4r)-4-((tert-butoxycarbonyl)-amino)-cyclohexyl)-(ethyl)-amino)-2-methyl-5-(4,4,5,5-tetramethyl-1,3,2-dioxaborolan-2-yl)benzoate (0.5 g, 1.2 mmol) and 2-bromothiazole (0.22 g, 1.38 mmol) in dioxane/water mixture, was added $Cs_2CO_3$ (0.94 g, 2.88 mmol) at room temperature. The solution was purged with argon for 15 min. and $PdCl_2(PPh_3)_2$ (0.08 g, 0.11 mmol) was added. The mixture was heated at 100° C. for 3 h under argon, diluted with water and extracted with 10% MeOH/DCM. The combined organic layers were dried over $Na_2SO_4$ and the solvent was removed under reduced pressure. The crude material was purified by column chromatography over silica gel to afford the title compound (0.36 g, 71%).

Step 2: Synthesis of tert-butyl ((1r,4r)-4-((3-(((4,6-dimethyl-2-oxo-1,2-dihydropyridin-3-yl)methyl)carbamoyl)-2-methyl-5-(thiazol-2-yl)-phenyl)-(ethyl)-amino)-cyclohexyl)-carbamate To a stirred solution of methyl 3-(((1r,4r)-4-((tert-butoxycarbonyl)-amino)-cyclohexyl)-(ethyl)-amino)-2-methyl-5-(thiazol-2-yl)benzoate (0.36 g, 0.76 mmol) in ethanol (5 mL) was added aqueous NaOH (0.064 g, 1.60 mmol) at room temperature. The mixture was heated at 60° C. for 1 h. and concentrated under reduced pressure. The concentrate was acidified to pH 4 and extracted with ethyl acetate. The combined organic layers were dried and concentrated to give 0.26 g of crude acid. To a stirred solution of the crude acid (0.26 g, ca. 0.56 mmol) and 3-(amino methyl)-4,6-dimethylpyridin-2(1H)-one (0.17 g, 1.13 mmol) in DMSO (3 mL) was added PYBOP (0.44 g, 0.85 mmol) at room temperature. After stirring overnight, the mixture was poured onto ice and extracted with 10% MeOH/DCM. The combined organic layers were washed with water, dried, and concentrated under reduced pressure to give the title compound (0.15 g) which was used directly in the next step.

Step 3: Synthesis of 3-(((1r,4r)-4-aminocyclohexyl)(ethyl)amino)-N-((4,6-dimethyl-2-oxo-1,2-dihydropyridin-3-yl)methyl)-2-methyl-5-(thiazol-2-yl)benzamide To a stirred solution of tert-butyl ((1r,4r)-4-((3-(((4,6-dimethyl-2-oxo-1,2-dihydropyridin-3-yl)methyl)carbamoyl)-2-methyl-5-(thiazol-2-yl)-phenyl)-(ethyl)-amino)-cyclohexyl)-carbamate (0.15 g, 0.25 mmol) in dichloromethane (3 mL) was added TFA (1 mL). The mixture was stirred at room temperature for 1 h., concentrated under reduced pressure and $NaHCO_3$ solution was added to the concentrate. After extracting with 10% MeOH/DCM, the combined organic layers were washed with water and brine, dried over anhydrous $Na_2SO_4$ and concentrated under reduced pressure to give 0.11 g of the title compound which was used directly for the next step.

Step 4: Synthesis of N-((4,6-dimethyl-2-oxo-1,2-dihydropyridin-3-yl)methyl)-3-(((1r,4r)-4-(dimethylamino)cyclohexyl)(ethyl)amino)-2-methyl-5-(thiazol-2-yl)-benzamide TFA salt To a stirred solution of 3-(((1r,4r)-4-aminocyclohexyl)(ethyl)amino)-N-((4,6-dimethyl-2-oxo-1,2-dihydropyridin-3-yl)methyl)-2-methyl-5-(thiazol-2-yl)benzamide (0.1 g, 0.20 mmol) in methanol (3 mL) was added formalin (0.06 g, 2.0 mmol) at 0° C. Sodium cyanoborohydride (0.025 g, 0.59 mmol) was added, and the mixture was stirred at room temperature for 1 h. The reaction mixture was quenched with water and extracted with 10% MeOH/DCM. The combined organic layers were dried and concentrated under reduced pressure to a solid which was purified by preparative HPLC to afford the title compound as a TFA salt (0.06 g, 56%). Analytical Data of TFA Salt: LCMS: 522.60 $(M+1)^+$; HPLC: 92.00% (@ 210-370 nm) ($R_t$: 4.255; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.46 (bs, 1H), 9.39 (bs, 1H), 8.30 (t, 1H), 7.90 (d, 1H, J=3.2 Hz), 7.78 (d, 1H, J=2.4 Hz), 7.71 (s, 1H), 7.47 (s, 1H), 5.88 (s, 1H), 4.30 (d, 2H, J=4 Hz), 3.11 (m, 3H), 2.77-2.68 (m, 7H), 2.24 (s, 3H), 2.21 (s, 3H), 2.11 (s, 3H), 1.96-1.89 (m, 4H), 1.45 (m, 4H), 0.84 (t, 3H, J=6.4 Hz).

Example 169: Synthesis of N-((4,6-dimethyl-2-oxo-1,2-dihydropyridin-3-yl)methyl-3-(((1r,4r)-4-(dimethylamino)cyclohexyl)(ethyl)amino)-2-methyl-5-(1-methyl-1H-imidazol-2-yl)-benzamide

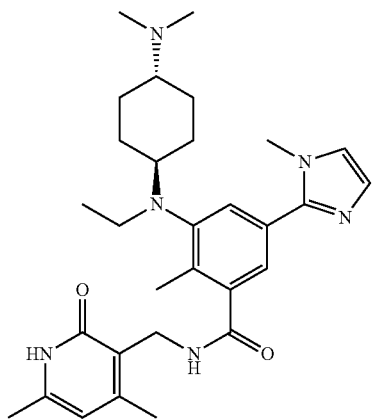

Compound 169

Step 1: Synthesis of methyl 3-(((1r,4r)-4-((tert-butoxycarbonyl)-amino)-cyclohexyl)-(ethyl)amino)-2-methyl-5-(1-methyl-1H-imidazol-2-yl)benzoate To a stirred solution of methyl 3-(((1r,4r)-4-((tert-butoxycarbonyl)-amino)-cyclohexyl)-(ethyl)-amino)-2-methyl-5-(4,4,5,5-tetramethyl-1,3,2-dioxaborolan-2-yl)benzoate (0.5 g, 1.15 mmol) and 2-bromo-1-methyl-1H-imidazole (0.22 g, 1.38 mmol) in dioxane/water mixture was added $Cs_2CO_3$ (0.94 g, 2.88 mmol) under argon. $PdCl_2(PPh_3)_2$ (0.08 g, 0.11 mmol) was added and the mixture was heated at 100° C. for 4 h under argon. Water was added and the mixture was extracted with 10% MeOH/DCM. The combined organic layers were dried over $Na_2SO_4$ and the solvent was removed under reduced pressure to afford crude material which was purified by column chromatography over silica gel to afford methyl 3-(((1r,4r)-4-((tert-butoxycarbonyl)-amino)-cyclohexyl)-(ethyl)amino)-2-methyl-5-(1-methyl-1H-imidazol-2-yl)benzoate (0.22 g, 40%).

Step 2: Synthesis of tert-butyl ((1r,4r)-4-((3-(((4,6-dimethyl-2-oxo-1,2-dihydropyridin-3-yl)methyl)carbamoyl)-2-methyl-5-(1-methyl-1H-imidazol-2-yl)-phenyl)-(ethyl)-amino)cyclohexyl)carbamate To a stirred solution of methyl 3-(((1r,4r)-4-((tert-butoxycarbonyl)-amino)-cyclohexyl)-(ethyl)amino)-2-methyl-5-(1-methyl-1H-imidazol-2-yl)benzoate (0.22 g, 0.47 mmol) in ethanol (3 mL) was added aqueous NaOH (0.028 g, 0.70 mmol). After stirring at 60° C. for 1 h., the mixture was concentrated under reduced pressure, acidified to pH 4 and extracted with ethyl acetate. The combined organic layers were dried and concentrated to give 0.16 g of crude acid. To a stirred solution of the crude acid (0.16 g, 0.35 mmol) and 3-(amino methyl)-4,6-dimethylpyridin-2(1H)-one (0.11 g, 0.70 mmol) in DMSO (3 mL) was added PYBOP (0.27 g, 0.53 mmol). After stirring overnight the mixture was poured into ice water and extracted with 10% MeOH/DCM. The combined organic layers were washed with water, dried and concentrated under reduced pressure to afford 0.12 g of tert-butyl ((1r,4r)-4-((3-(((4,6-dimethyl-2-oxo-1,2-dihydropyridin-3-yl)methyl)carbamoyl)-2-methyl-5-(1-methyl-1H-imidazol-2-yl)-phenyl)-(ethyl)-amino)cyclohexyl)carbamate which was used directly without further purification.

Synthesis of 3-(((1r,4r)-4-aminocyclohexyl)(ethyl)amino)-N-((4,6-dimethyl-2-oxo-1,2-dihydropyridin-3-yl)methyl)-2-methyl-5-(1-methyl-1H-imidazol-2-yl)benzamide To a stirred solution of tert-butyl ((1r,4r)-4-((3-(((4,6-dimethyl-2-oxo-1,2-dihydropyridin-3-yl)methyl)carbamoyl)-2-methyl-5-(1-methyl-1H-imidazol-2-yl)-phenyl)-(ethyl)-amino)cyclohexyl)carbamate (0.12 g, 0.20 mmol) in DCM (3 mL) was added TFA (1 mL). After stirring for 1 h. at room temperature, the mixture was concentrated under reduced pressure. Saturated NaHCO$_3$ solution was added to the residue followed by extraction with 10% MeOH/DCM. The combined organic layers were washed with water and brine; dried and concentrated under reduced pressure to give 0.1 g of 3-(((1r,4r)-4-aminocyclohexyl)(ethyl)amino)-N-((4,6-dimethyl-2-oxo-1,2-dihydropyridin-3-yl)methyl)-2-methyl-5-(1-methyl-1H-imidazol-2-yl)benzamide which was used directly without further purification.

Synthesis of N-((4,6-dimethyl-2-oxo-1,2-dihydropyridin-3-yl)methyl)-3-(((1r,4r)-4-(dimethylamino)cyclohexyl)(ethyl)amino)-2-methyl-5-(1-methyl-1H-imidazol-2-yl)benzamide TFA salt To a stirred solution of 3-(((1r,4r)-4-aminocyclohexyl)(ethyl)amino)-N-((4,6-dimethyl-2-oxo-1,2-dihydropyridin-3-yl)methyl)-2-methyl-5-(1-methyl-1H-imidazol-2-yl)benzamide (0.1 g, 0.20 mmol) in methanol (3 mL) was added formalin (0.06 g, 2.0 mmol) at 0° C. Sodium cyanoborohydride (0.025 g, 0.59 mmol) was added, and the mixture was stirred at room temperature for 1 h. Water was added followed by extraction with 10% MeOH/DCM. The combined organic layers were dried and concentrated under reduced pressure to a solid which was purified by preparative HPLC to afford the title compound as a TFA salt (0.03 g, 28%). Analytical Data of TFA Salt: LCMS: 519.65 (M+1)$^+$; HPLC: 96.10% (@ 254 nm) (R$_t$: 3.976; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.47 (bs, 1H), 9.60 (bs, 1H), 8.24 (bs, 1H), 7.82 (s, 1H), 7.78 (s, 1H), 7.52 (s, 1H), 7.35 (s, 1H), 5.87 (s, 1H), 4.30 (bs, 2H), 3.86 (s, 3H), 3.10 (m, 3H), 2.69 (bs, 7H), 2.28 (s, 3H), 2.22 (s, 3H), 2.11 (s, 3H), 1.96-1.88 (m, 4H), 1.46 (m, 4H), 0.84 (bs, 3H).

Example 170: N-((4,6-dimethyl-2-oxo-1,2-dihydropyridin-3-yl)methyl)-3-(((1r,4r)-4-(dimethylamino)cyclohexyl)(ethyl)amino)-2-methyl-5-(6-(4-methylpiperazin-1-yl)pyridin-3-yl)benzamide

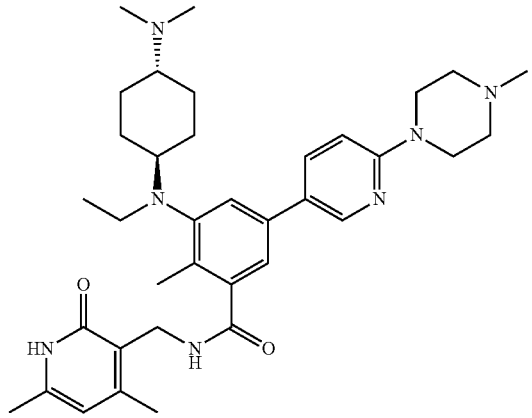

Compound 170

Compound 170 was prepared with the method similar to that described in Example 183 below.

Analytical Data: LCMS: 614.75 (M+1)$^+$; HPLC: 98.17% (@ 210-370 nm) (R$_t$: 3.598; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (bs, 1H), 10.10 (bs, 1H), 9.68 (bs, 1H), 8.21 (m, 2H), 7.47 (s, 1H), 7.38 (s, 1H), 7.16 (s, 1H), 7.05 (d, 1H, J=4.8 Hz), 5.87 (s, 1H), 4.54-4.51 (m, 2H), 4.30 (d, 2H, J=4 Hz), 3.53 (m, 2H), 3.13 (m, 7H), 2.86 (s, 3H), 2.76-2.68 (m, 7H), 2.24 (s, 3H), 2.22 (s, 3H), 2.11 (s, 3H), 1.97-1.90 (m, 4H), 1.43 (m, 4H), 0.83 (t, 3H, J=6.4 Hz).

Example 171: N-((4,6-dimethyl-2-oxo-1,2-dihydro-pyridin-3-yl)methyl)-3-(ethyl(tetrahydro-2H-pyran-4-yl)amino)-2-methyl-5-(6-(4-methylpiperazin-1-yl)pyridin-3-yl)benzamide Compound 171

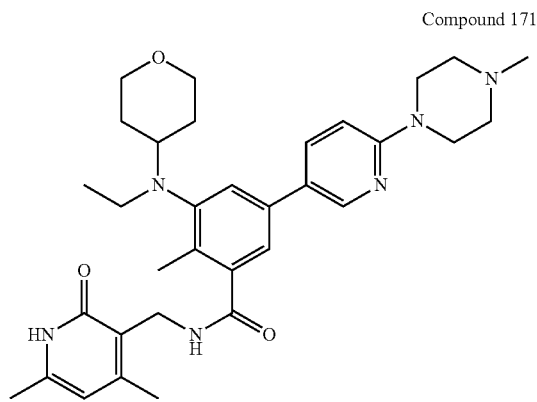

Compound 171 was prepared with the method similar to that described in Example 183 below.

Analytical Data: LCMS: 573.75 (M+1)$^+$; HPLC: 95.92% (@ 210-370 nm) (R$_t$: 3.891; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (bs, 1H), 8.19 (t, 1H), 8.14 (d, 1H, J=4.8 Hz), 7.44 (s, 1H), 7.32 (s, 1H), 6.97 (s, 1H), 6.88 (d, 1H, J=4.8 Hz), 5.86 (s, 1H), 4.29 (d, 2H, J=4.4 Hz), 3.84-3.81 (m, 2H), 3.54 (m, 4H), 3.28-3.22 (m, 2H), 3.10-3.02 (m, 3H), 2.42 (m, 4H), 2.24 (s, 3H), 2.23 (s, 3H), 2.10 (s, 3H), 2.10 (s, 3H), 1.66-1.50 (m, 4H), 0.82 (t, 3H, J=6.4 Hz).

Example 172: N-((4,6-dimethyl-2-oxo-1,2-dihydro-pyridin-3-yl)methyl)-3-(((1r,4r)-4-(dimethylamino)cyclohexyl)(ethyl)amino)-2-methyl-5-(6-(piperazin-1-yl)pyridin-3-yl)benzamide Compound 172

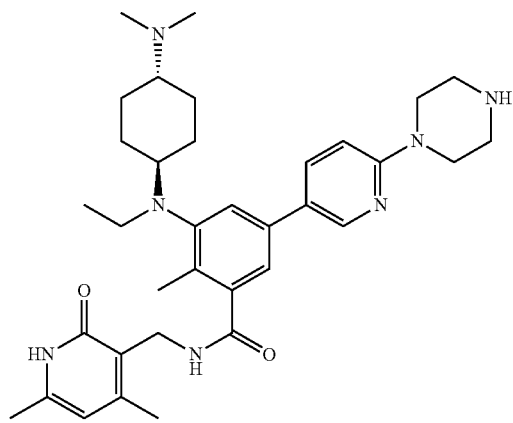

Compound 172 was prepared with the method similar to that described in Example 183 below.

Analytical Data: LCMS: 600.75 (M+1)$^+$; HPLC: 99.58% (@ 210-370 nm) (R$_t$: 3.460; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (bs, 1H), 9.59 (bs, 1H), 8.92 (bs, 2H), 8.47 (s, 1H), 8.16 (s, 1H), 7.92 (d, 1H, J=7.6 Hz), 7.39 (bs, 1H), 7.21 (bs, 1H), 7.01 (d, 1H, J=8.8 Hz), 5.87 (s, 1H), 4.29 (d, 2H, J=5.2 Hz), 3.75 (q, 4H, J=5.2 Hz), 3.22 (m, 4H), 3.12 (m, 3H), 2.75 (m, 1H), 2.69 (s, 3H), 2.68 (s, 3H), 2.23 (s, 3H), 2.21 (s, 3H), 2.11 (s, 3H), 1.97 (m, 4H), 1.44 (m, 4H), 0.83 (t, 3H, J=6.8 Hz).

Example 173: N-((4,6-dimethyl-2-oxo-1,2-dihydro-pyridin-3-yl)methyl)-3-(ethyl(tetrahydro-2H-pyran-4-yl)amino)-2-methyl-5-(6-(piperazin-1-yl)pyridin-3-yl)benzamide Compound 173

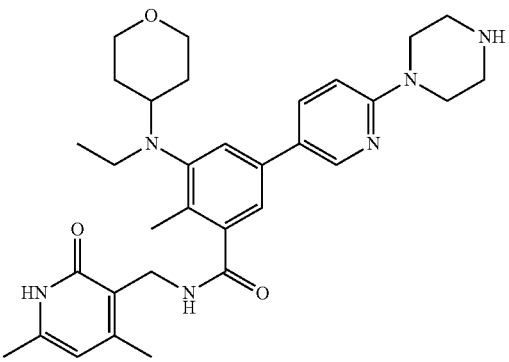

Compound 173 was prepared with the method similar to that described in Example 183 below.

Analytical Data: LCMS: 559.55 (M+1)$^+$; HPLC: 98.43% (@ 210-370 nm) (R$_t$: 3.731; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (bs, 1H), 8.86 (s, 2H), 8.48 (bs, 1H), 8.21 (bs, 1H), 7.94 (bs, 1H), 7.45 (bs, 1H), 7.25 (bs, 1H), 7.02 (d, 1H, J=8.4 Hz), 5.87 (s, 1H), 4.29 (d, 2H, J=3.6 Hz), 3.83 (m, 3H), 3.76 (bs, 4H), 3.30-3.15 (m, 7H), 3.10 (m, 1H), 2.25 (s, 3H), 2.21 (s, 3H), 2.11 (s, 3H), 1.75-1.50 (m, 4H), 0.84 (t, 3H).

Example 174: Synthesis of N-((4,6-dimethyl-2-oxo-1,2-dihydropyridin-3-yl)methyl)-3-(((1r,4r)-4-(dimethylamino)cyclohexyl)(ethyl)amino)-2-methyl-5-(pyrazin-2-yl)-benzamide Compound 174

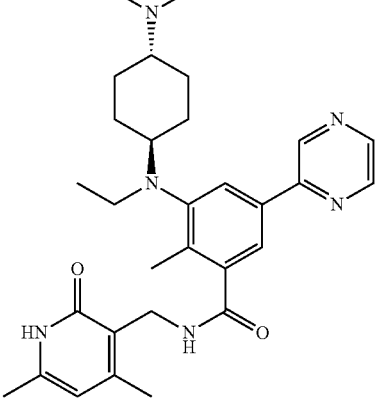

Step 1: Synthesis of methyl 5-bromo-3-(((1r,4r)-4-((tert-butoxycarbonyl)-amino)-cyclohexyl)(ethyl)-amino)-2-methylbenzoate To a stirred solution of 5-bromo-3-(((1r,4r)-4-((tert-butoxycarbonyl)-amino)-cyclohexyl)amino)-2-methylbenzoate (10 g, 23 mmol) and acetaldehyde (2.99 g, 68 mmol) in dichloroethane (100 mL), was added acetic acid (8.18 g, 136 mmol) and reaction stirred at room temperature for 20 minutes. Sodium triacetoxyborohydride (14.45 g, 68 mmol) was added at 0° C. and the mixture was stirred overnight at room temperature. The solvent was removed under reduced pressure and water was added followed by extraction with 5% MeOH/DCM. The combined organic layers were dried and concentrated to give 9 g of the title compound which was used without further purification.

Step 2: Synthesis of methyl 3-(((1r,4r)-4-((tert-butoxycarbonyl)-amino)-cyclohexyl)-(ethyl)-amino)-2-methyl-5-(4,4,5,5-tetramethyl-1,3,2-dioxaborolan-2-yl)benzoate To a stirred solution of methyl 5-bromo-3-(((1r,4r)-4-((tert-butoxycarbonyl)-amino)-cyclohexyl)(ethyl)-amino)-2-methylbenzoate (2.0 g, 4.3 mmol) and bis pinacolatodiboron (5.42 g, 21 mmol) in dioxane was added potassium acetate (1.25 g, 12.82 mmol) under argon. PdCl$_2$(dppf)DCM (0.35 g, 0.42 mmol) was added and the mixture was heated at 80° C. for 3 h under argon. Water was added followed by extraction with ethyl acetate. The combined organic layers were dried over Na$_2$SO$_4$, and the solvent was removed under reduced pressure. The crude product was purified by column chromatography over silica gel to afford the title compound (1.3 g, 70%).

Step 3: Synthesis of methyl 3-(((1r,4r)-4-((tert-butoxycarbonyl)-amino)-cyclohexyl)-(ethyl)-amino)-2-methyl-5-(pyrazin-2-yl)benzoate To a stirred solution of methyl 3-(((1r,4r)-4-((tert-butoxycarbonyl)-amino)-cyclohexyl)-(ethyl)-amino)-2-methyl-5-(4,4,5,5-tetramethyl-1,3,2-dioxaborolan-2-yl)benzoate (0.50 g, 1.15 mmol) and 2-bromopyrazine (0.24 g, 1.49 mmol) in dioxane/water mixture) was added CS$_2$CO$_3$ (0.94 g, 2.89 mmol under argon. PdCl$_2$ (PPh$_3$)$_2$ (0.08 g, 0.11 mmol) was added and the mixture was heated at 100° C. for 3 h. under argon. Water was added followed by extraction with 10% MeOH/DCM. The combined organic layers were dried over Na$_2$SO$_4$ and the solvent removed under reduced pressure. The crude product was purified by column chromatography over silica gel to afford the title compound (0.29 g, 53%).

Step 4: Synthesis of tert-butyl ((1r,4r)-4-((3-(((4,6-dimethyl-2-oxo-1,2-dihydropyridin-3-yl)-methyl)carbamoyl)-2-methyl-5-(pyrazin-2-yl)-phenyl)-(ethyl)-amino)-cyclohexyl)-carbamate To a stirred solution of methyl 3-(((1r,4r)-4-((tert-butoxycarbonyl)-amino)-cyclohexyl)-(ethyl)-amino)-2-methyl-5-(pyrazin-2-yl)benzoate (0.29 g, 0.62 mmol) in ethanol (3 mL) was added aqueous NaOH (0.037 g, 0.93 mmol) at room temperature, After stirring at 60° C. for 1 h., the mixture was concentrated under reduced pressure, acidified to pH 4 and extracted with ethyl acetate. The combined organic layers were dried and concentrated to give 0.24 g of crude acid. To a stirred solution of the crude acid (0.24 g, 0.52 mmol) and 3-(amino methyl)-4,6-dimethylpyridin-2 (1H)-one (0.16 g, 1.05 mmol) in DMSO (3 mL) was added PYBOP (0.41 g, 0.79 mmol). After stirring overnight the mixture was poured into ice water and extracted with 10% MeOH/DCM. The combined organic layers were washed with water, dried and concentrated under reduced pressure to give 0.3 g of the title compound which was used directly without further purification.

Step 5: Synthesis of 3-(((1r,4r)-4-aminocyclohexyl)(ethyl)amino)-N-((4,6-dimethyl-2-oxo-1,2-dihydropyridin-3-yl)methyl)-2-methyl-5-(pyrazin-2-yl)benzamide To a stirred solution of tert-butyl ((1r,4r)-4-((3-(((4,6-dimethyl-2-oxo-1,2-dihydropyridin-3-yl)-methyl)carbamoyl)-2-methyl-5-(pyrazin-2-yl)-phenyl)-(ethyl)-amino)-cyclohexyl)-carbamate (0.3 g, 0.51 mmol) in DCM (3 mL) was added TFA (1 mL). After stirring at room temperature for 1 h., the mixture was concentrated under reduced pressure. Saturated NaHCO$_3$ solution was added followed by extraction with 10% MeOH/DCM. The combined organic layers were washed with water and brine, dried and concentrated under reduced pressure to give 0.24 g of the title compound which used directly without further purification.

Step 6: Synthesis of N-((4,6-dimethyl-2-oxo-1,2-dihydropyridin-3-yl)methyl)-3-(((1r,4r)-4-(dimethylamino)cyclohexyl)(ethyl)amino)-2-methyl-5-(pyrazin-2-yl)benzamide TFA salt To a stirred solution of 3-(((1r,4r)-4-aminocyclohexyl)(ethyl)amino)-N-((4,6-dimethyl-2-oxo-1,2-dihydropyridin-3-yl)methyl)-2-methyl-5-(pyrazin-2-yl)benzamide (0.24 g, 0.51 mmol) in methanol (3 mL) was added formalin (0.15 g, 5.1 mmol) at 0° C. Sodium cyanoborohydride (0.06 g, 1.0 mmol) was added, and the mixture was stirred at room temperature for 1 h. Water was added followed by extraction with 10% MeOH/DCM. The combined organic layers were dried and concentrated under reduced pressure. The solid obtained was purified by preparative HPLC to afford the title compound as a TFA salt (0.12 g, 47%). Analytical Data of TFA Salt: LCMS: 517.50 (M+1)$^+$; HPLC: 99.49% (@ 210-370 nm) (R$_t$; 4.072; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.47 (bs, 1H), 9.45 (bs, 1H), 9.26 (s, 1H), 8.71 (s, 1H), 8.61 (s, 1H), 8.23 (t, 1H), 7.92 (s, 1H), 7.74 (s, 1H), 5.88 (s, 1H), 4.31 (d, 2H, J=4 Hz), 3.13 (m, 3H), 2.78 (m, 1H), 2.69 (d, 6H, J=4.8 Hz), 2.28 (s, 3H), 2.22 (s, 3H), 2.12 (s, 3H), 1.96-1.92 (m, 4H), 1.45 (m, 3H), 0.84 (t, 3H, J=6.4 Hz).

Example 175: Synthesis of N-((4,6-dimethyl-2-oxo-1,2-dihydropyridin-3-yl)methyl-3-(((1r,4r)-4-(dimethylamino)cyclohexyl)(ethyl)amino)-2-methyl-5-(5-methylpyrazin-2-yl)-benzamide

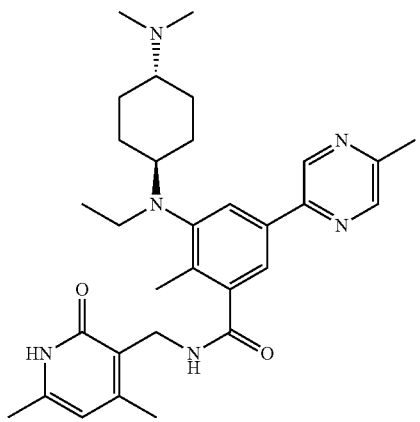

Compound 175

Step 1: Synthesis of methyl 3-(((1r,4r)-4-((tert-butoxycarbonyl)-amino)-cyclohexyl)-(ethyl)-amino)-2-methyl-5-(5-methylpyrazin-2-yl)benzoate To a stirred solution of methyl 3-(((1r,4r)-4-((tert-butoxycarbonyl)-amino)-cyclohexyl)-(ethyl)-amino)-2-methyl-5-(4,4,5,5-tetramethyl-1,3,2-dioxaborolan-2-yl)benzoate (0.40 g, 0.92 mmol) and 2-bromo-5-methylpyrazine (0.21 g, 1.19 mmol) in dioxane/water mixture was added $Cs_2CO_3$ (0.75 g, 2.30 mmol) under argon. $PdCl_2(PPh_3)_2$ (0.064 g, 0.092 mmol) was added and the mixture was heated at 100° C. for 3 h. under argon. Water was added followed by extraction with 10% MeOH/DCM. The combined organic layers were dried over $Na_2SO_4$ and the solvent was removed under reduced pressure to afford crude material which was purified by column chromatography over silica gel to afford the title compound (0.3 g, 56%).

Step 2: Synthesis of tert-butyl ((1r,4r)-4-((3-(((4,6-dimethyl-2-oxo-1,2-dihydropyridin-3-yl)methyl)carbamoyl)-2-methyl-5-(5-methylpyrazin-2-yl)-phenyl)-(ethyl)-amino)-cyclohexyl)carbamate To a solution of methyl 3-(((1r,4r)-4-((tert-butoxycarbonyl)-amino)-cyclohexyl)-(ethyl)-amino)-2-methyl-5-(5-methylpyrazin-2-yl)benzoate (0.29 g, 0.49 mmol) in ethanol (3 mL)) was added aqueous NaOH (0.029 g, 0.75 mmol) at room temperature. After stirring at 60° C. for 1 h., the mixture was concentrated under reduced pressure, acidified to pH 4 and extracted with ethyl acetate. The combined organic layers were dried and concentrated to give 0.25 g of crude acid. To a stirred solution of the crude acid (0.25 g, 0.44 mmol) and 3-(amino methyl)-4,6-dimethylpyridin-2 (1H)-one (0.13 g, 0.88 mmol) in DMSO (3 mL) was added PYBOP (0.34 g, 0.66 mmol) at room temperature. After stirring was continued for overnight, the mixture was poured into ice water and extracted with 10% MeOH/DCM. The combined organic layers were washed with water, dried and concentrated under reduced pressure to give 0.2 g of the title compound which was used directly without further purification.

Step 3: Synthesis of 3-(((1r,4r)-4-aminocyclohexyl)(ethyl)amino)-N-((4,6-dimethyl-2-oxo-1,2-dihydropyridin-3-yl)methyl)-2-methyl-5-(5-methylpyrazin-2-yl)benzamide To a stirred solution of tert-butyl ((1r,4r)-4-((3-(((4,6-dimethyl-2-oxo-1,2-dihydropyridin-3-yl)methyl)carbamoyl)-2-methyl-5-(5-methylpyrazin-2-yl)-phenyl)-(ethyl)-amino)-cyclohexyl)carbamate (0.2 g, 0.33 mmol) in DCM (3 mL) was added TFA (1 mL). After stirring at room temperature for 1 h., the mixture was concentrated under reduced pressure. Saturated $NaHCO_3$ solution was added followed by extraction with 10% MeOH/DCM. The combined organic layers were washed with water and brine, dried and concentrated under reduced pressure to give 0.15 g of the title compound which was used directly without further purification.

Step 4: Synthesis of N-((4,6-dimethyl-2-oxo-1,2-dihydropyridin-3-yl)methyl)-3-(((1r,4r)-4-(dimethylamino)cyclohexyl)(ethyl)amino)-2-methyl-5-(5-methylpyrazin-2-yl)-benzamide TFA salt To a stirred solution of 3-(((1r,4r)-4-aminocyclohexyl)(ethyl)amino)-N-((4,6-dimethyl-2-oxo-1,2-dihydropyridin-3-yl)methyl)-2-methyl-5-(5-methylpyrazin-2-yl)benzamide (0.15 g, 0.29 mmol) in methanol (3 mL) was added formalin (0.089 g, 2.98 mmol) at 0° C. Sodium cyanoborohydride (0.037 g, 0.59 mmol) was added and the mixture was stirred at room temperature for 1 h. Water was added followed by extraction with 10% MeOH/DCM. The combined organic layers were dried and concentrated under reduced pressure. The solid obtained was further purified by preparative HPLC to the title compound as a TFA salt (0.12 g, 75%). Analytical Data of TFA Salt: LCMS: 531.50 $(M+1)^+$; HPLC: 88.93% (@ 210-370 nm) ($R_t$; 4.130; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1H$ NMR (DMSO-$d_6$, 400 MHz) δ 11.49 (bs, 1H), 9.54 (bs, 1H), 9.10 (s, 1H), 8.59 (s, 1H), 8.23 (t, 1H), 7.88 (s, 1H), 7.69 (s, 1H), 5.87 (s, 1H), 4.30 (bs, 2H), 3.12 (m, 3H), 2.77-2.69 (m, 7H), 2.53 (s, 3H), 2.26 (s, 3H), 2.22 (s, 3H), 2.11 (s, 3H), 1.95-1.91 (m, 4H), 1.44 (m, 4H), 0.83 (t, 3H).

Example 176: Synthesis of 5-(ethyl(tetrahydro-2H-pyran-4-yl)amino)-4-methyl-N-((6-methyl-2-oxo-4-propyl-1,2-dihydropyridin-3-yl)methyl)-4'-(morpholinomethyl)-[1,1'-biphenyl]-3-carboxamide

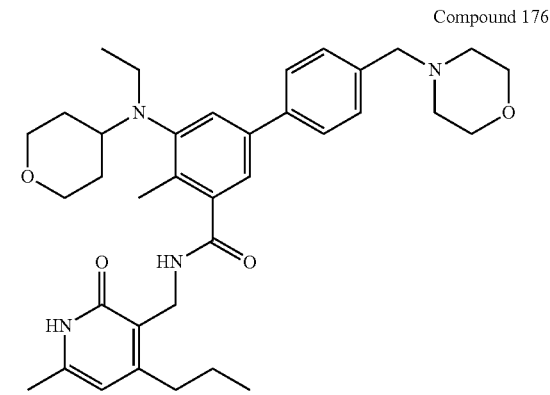 [SMILES: CCCc1cc(C)[nH]c(=O)c1CNC(=O)c1cc(-c2ccc(CN3CCOCC3)cc2)cc(N(CC)C2CCOCC2)c1C]

Compound 176

Step 1: Synthesis of 6-methyl-2-oxo-4-propyl-1,2-dihydropyridine-3-carbonitrile To a stirred solution of t-BuOK (Ig, 8.9 mmol) in DMSO (15 mL) at rt, was added compound cyanoacetamide (0.824 g, 9.8 mmol) and (E)-hept-3-en-2-one (Ig, 8.91 mmol). Reaction mixture was stirred for 30 min at rt. Additional t-BuOK (3 g, 26.7 mmol) was added and reaction was stirred at rt in presence of air. On completion, it was diluted with H₂O and slowly by 4N HCl. Precipitated solid was filtered, washed with water and dried. Crude product was triturated with ether to afford the title compound (0.5 g, 33%).

Step 2: Synthesis of 3-(aminomethyl)-6-methyl-4-propylpyridin-2(1H)-one

To a solution of 6-methyl-2-oxo-4-propyl-1,2-dihydropyridine-3-carbonitrile (1.3 g, 7.38 mmol) in methanol and aq. ammonia solution (50 mL, 9:1), catalytic amount of Raney Nickel was added. Reaction mass was stirred at room temperature under hydrogen pressure (balloon pressure) for 5 h. On completion of reaction, it was filtered through celite bed and filtrate was concentrated under reduce pressure to afford the title compound (1.2 g, 92%).

Step 3: Synthesis of 5-bromo-N-((4,6-dimethyl-2-oxo-1,2-dihydropyridin-3-yl) methyl)-3-(ethyl (tetrahydro-2H-pyran-4-yl) amino)-2-methylbenzamide Aqueous NaOH (2.36 g, 59.15 mmol) was added to a solution of methyl 5-bromo-3-(ethyl (tetrahydro-2H-pyran-4-yl) amino)-2-methylbenzoate (14 g, 39.43 mmol) in ethanol (100 mL) and stirred at 60° C. for 1 h. After completion of the reaction, ethanol was removed under reduced pressure and acidified using dilute HCl up to pH 6 and pH 4 was adjusted using citric acid. Extraction was carried out using ethyl acetate. Combined organic layers were dried concentrated giving respective acid (13.9 g, 99%).

The above acid (0.6 g, 1.75 mmol) was then dissolved in DMSO (5 mL) and 3-(aminomethyl)-6-methyl-4-propylpyridin-2(1H)-one (0.64 g, 3 mmol) and triethyl amine (0.49 g, 5.26 mmol) was added to it. The reaction mixture was stirred at room temperature for 15 min before PyBOP (1.36 g, 2.63 mmol) was added to it and stirring was continued for overnight. After completion of the reaction, the reaction mixture was poured into ice, extracted with 10% MeOH/DCM. Combined organic layers were dried, concentrated to obtain crude; which then purified by solvent washings to afford 5 the title compound (0.75 g, 84.7%).

Step 4: Synthesis of 5-(ethyl(tetrahydro-2H-pyran-4-yl)amino)-4-methyl-N-((6-methyl-2-oxo-4-propyl-1,2-dihydropyridin-3-yl)methyl)-4'-(morpholinomethyl)-[1,1'-biphenyl]-3-carboxamide To a stirred solution of 5-bromo-N-((4,6-dimethyl-2-oxo-1,2-dihydropyridin-3-yl) methyl)-3-(ethyl (tetrahydro-2H-pyran-4-yl) amino)-2-methylbenzamide (0.3 g, 0.59 mmol) and 4-((morpholino)methyl) phenylboronicacid pinacol ester (0.22 g, 0.71 mmol) in dioxane/water mixture (5 mL+1 mL), Na₂CO₃ (0.23 g, 2.14 mmol) was added and solution was purged with argon for 15 min. Then Pd(PPh₃)₄ (0.068 g, 0.059 mmol) was added and argon was purged again for 10 min. Reaction mass was heated at 100° C. for 4 h. On completion, reaction mixture was diluted with water and extracted with 10% MeOH/DCM. Combined organic layers were dried over Na₂SO₄ and solvent removed under reduced pressure to afford crude material which was purified by column chromatography over silica gel to afford the title compound (0.25 g, 70%). LCMS: 601.55 (M+1)⁺; HPLC: 97.21% (@ 210-370 nm) (R$_t$; 4.380; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d₆, 400 MHz) δ 11.46 (bs, 1H), 8.16 (bs, 1H), 7.57 (d, 2H, J=7.6 Hz), 7.38 (t, 3H, J=6.8 Hz), 7.21 (s, 1H), 5.89 (s, 1H), 4.30 (m, 2H), 3.84-3.82 (m, 2H), 3.57 (bs, 3H), 3.48 (s, 3H), 3.28-3.22 (m, 2H), 3.09-3.02 (m, 3H), 2.36 (bs, 4H), 2.25 (s, 3H), 2.11 (s, 3H), 1.67-1.54 (m, 6H), 0.93 (t, 3H, J=7 Hz), 0.84 (t, 3H). 2H merged in solvent peak.

Example 177: Synthesis of N-((5-bromo-4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide

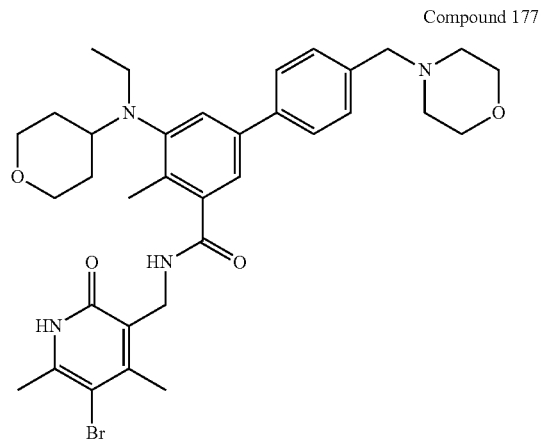 [SMILES: CCN(c1cc(-c2ccc(CN3CCOCC3)cc2)cc(C(=O)NCc2c(C)c(Br)c(C)[nH]c2=O)c1C)C1CCOCC1]

Compound 177

Step 1: Synthesis of methyl 5-(ethyl(tetrahydro-2H-pyran-4-yl)amino)-4-methyl-4'-(morpholinomethyl)-[1,1'-biphenyl]-3-carboxylate To a stirred solution of methyl 5-bromo-3-(ethyl-(tetrahydro-2H-pyran-4-yl) amino)-2-methylbenzoate (1 g, 2.82 mmol) and 4-((morpholino)methyl) phenylboronic acid pinacol ester (1.03 g, 3.38 mmol) in dioxane/water mixture (10 mL+2 mL), Na₂CO₃ (1.08 g, 10.14 mmol) was added and solution purged with argon for 15 min. Then Pd (PPh₃)₄ (0.325 g, 0.28 mmol) was added and argon was purged again for 10 min. Reaction mass was heated at 100° C. for 2 h. On completion, reaction mixture was diluted with water and extracted with 10% MeOH/DCM. Combined organic layers were dried over Na₂SO₄ and solvent removed under reduced pressure to afford crude material which was purified by column chromatography over silica gel to afford the title compound (0.75 g, 59%).

Step 2: Synthesis of 5-bromo-4,6-dimethyl-2-oxo-1,2-dihydropyridine-3-carbonitrile To a stirred suspension of 4,6-dimethyl-2-oxo-1,2-dihydropyridine-3-carbonitrile (5 g, 33.78 mmol) in AcOH (25 mL) was dropwise added bromine (2.5 mL) at rt. Resulting solution was stirred for 1 h. Solvent was removed under reduced pressure. Obtained solid was recrystallised in hot EtOH and H₂O to give the title compound as a white solid (5.5 g, 72%).

Step 3: Synthesis of 3-(aminomethyl)-5-bromo-4,6-dimethylpyridin-2(1H)-one

To a stirred solution of 5-bromo-4,6-dimethyl-2-oxo-1,2-dihydropyridine-3-carbonitrile (1 g, 4.44 mmol) and NiCl₂.6H₂O (0.21 g, 0.89 mmol) in methanol at 0° C., NaBH₄ (0.68 g, 17.78 mmol) was added portion wise. Reaction mixture was then stirred at rt for overnight period. On completion, it was acidified using 3N HCl and stirred at rt for 3 h. Solvent was removed under reduced pressure. Residue was washed with diethyl ether and basified with aq. NH₄OH. Compound was extracted in 10% MeOH in DCM and dried over anhydrous Na₂SO₄ to give the title compound (0.96 g, 94%) which was used as such for coupling reaction.

Step 4: Synthesis of N-((5-bromo-4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide Aqueous NaOH (0.06 g, 1.66 mmol) was added to a solution of compound 7 (0.5 g, 1.11 mmol) in EtOH:H₂O (4:1) (10 mL) and stirred at 60° C. for 1 h. After completion of the reaction, ethanol was removed under reduced pressure and reaction mass was acidified using dilute HCl up to pH 6 and pH 4 was adjusted using citric acid. Extraction was carried out using 10% MeOH in DCM. Combined organic layers were dried and concentrated giving respective acid (0.35 g, 72%).

The above acid (0.266 g, 0.61 mmol) was then dissolved in DMSO (2.5 mL) and 3-(aminomethyl)-5-bromo-4,6-dimethylpyridin-2(1H)-one (0.42 g, 1.83 mmol) and triethyl amine (0.095 g, 0.91 mmol) were added to it. The reaction mixture was stirred at room temperature for 15 min before PYBOP (0.63 g, 1.22 mmol) was added to it and stirring was continued for overnight. After completion of the reaction, reaction mass was poured into ice, extracted with 10% MeOH/DCM. Combined organic layers were dried, concentrated to obtain crude; which then purified by solvent washings to afford the title compound (0.035 g, 7.6%).

LCMS: 653.65 (M+1)⁺, HPLC: 89.23% (@ 210-370 nm) (R$_t$; 4.421; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d6, 400 MHz) δ 9.88 (bs, 1H), 8.30 (bs, 1H), 7.76 (m, 2H), 7.57 (d, 2H, J=7.6 Hz), 7.44 (bs, 1H), 7.27 (bs, 1H), 4.39 (m, 4H), 3.99-3.96 (m, 5H), 3.84 (d, 2H, J=8.4 Hz), 3.65-3.62 (m, 2H), 3.28-3.23 (m, 4H), 3.12 (m, 4H), 2.35 (s, 3H), 2.31 (s, 3H), 2.26 (s, 3H), 1.65-1.55 (m, 4H), 0.84 (t, 3H).

Example 178: 4-chloro-N-((4,6-dimethyl-2-oxo-1,2-dihydropyridin-3-yl)methyl)-5-(ethyl(tetrahydro-2H-pyran-4-yl)amino)-4'-(morpholinomethyl)-[1,1'-biphenyl]-3-carboxamide

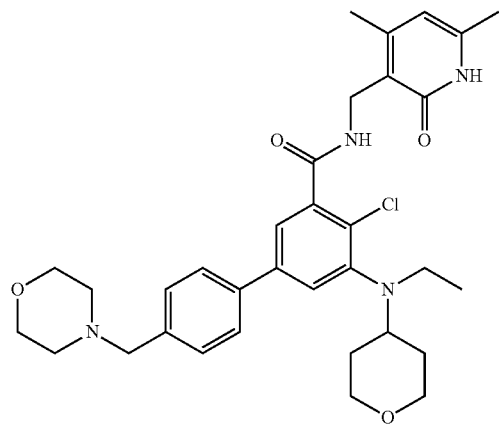

Compound 178

Compound 178 was prepared with the method similar to that described in Example 177.

Analytical Data: LCMS: 593.60 (M+1)⁺; HPLC: 95.50% (@ 210-370 nm) (R$_t$; 4.566; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d₆, 400 MHz) δ 11.46 (s, 1H), 8.34 (m, 1H), 7.61-7.24 (m, 6H), 5.86 (s, 1H), 4.29 (m, 2H), 3.86-3.84 (m, 2H), 3.57-3.49 (m, 6H), 3.25-3.16 (m, 5H), 2.36 (m, 4H), 2.21 (s, 3H), 2.10 (s, 3H), 1.68-1.58 (m, 4H), 0.86 (t, 3H).

Example 179: Synthesis of 5-(ethyl(tetrahydro-2H-pyran-4-yl)amino)-N-((5-fluoro-4,6-dimethyl-2-oxo-1,2-dihydropyridin-3-yl)methyl)-4-methyl-4'-(morpholinomethyl)-[1,1'-biphenyl]-3-carboxamide

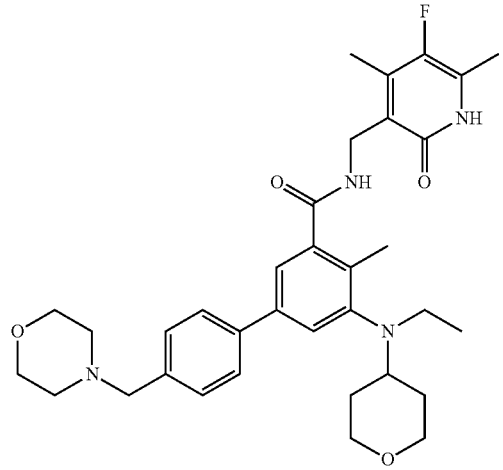

Compound 179

Step 1: Synthesis of 5-fluoro-4,6-dimethyl-2-oxo-1,2-dihydropyridine-3-carbonitrile To a stirred solution of 2-cyanoacetamide (689 mg, 8.2 mmol) in anhydrous EtOH (7.0 ml) at 75° C., was added 3-fluoropentane-2,4-dione (880 mg, 7.5 mmol), followed by piperidine (96 µl, 0.97 mmol). The reaction mixture was stirred at this temperature for 3 hours and the reaction mixture left to reach room temperature before being stored in the refrigerator for 4 days. The beige solid was collected by filtration and rinsed with cold EtOH (4×0.4 ml) until the filtrate ran clear. The resulting beige solid was dried in-vacuo at 40° C. for 5 hours to give the title compound (733 mg, 58%) as a beige solid. LC-MS 97%, 1.18 min (3.5 minute LC-MS method); m/z=166.9, $^1$H NMR (500 MHz, Chloroform-d) δ ppm 13.67 (br. s., 1H) 2.46 (d, J=2.05 Hz, 3H) 2.45 (d, J=2.84 Hz, 3H).

Step 2: Synthesis of 3-(aminomethyl)-5-fluoro-4,6-dimethyl-1,2-dihydropyridin-2-one A solution of 0.05M 5-fluoro-4,6-dimethyl-2-oxo-1,2-dihydropyridine-3-carbonitrile (731 mg, 4.4 mmol) in 1.75M NH$_3$/MeOH (87 ml) was passed through the H-Cube at 80° C. and 50 bar at a flow rate of 1 ml/min. The resulting solution was concentrated in-vacuo. The resulting solid was split into 2 batches and 350 mg of the crude product was purified by column chromatography (25 g SNAP cartridge, Isolera, 0-25% MeOH (containing 10% NH$_4$OH):CH$_2$Cl$_2$) to give the title compound (307 mg, 20%) as an off white solid and a 1:1 mixture of product:starting material. LC-MS (ELS) 100%, 0.23 min (3.5 minute LC-MS method), m/z=170.9, $^1$H NMR (500 MHz, Chloroform-d) δ ppm 3.79 (s, 2H) 2.31 (d, J=2.84 Hz, 3H) 2.25 (d, J=2.05 Hz, 3H).

Step 3: Synthesis of 5-(ethyl(tetrahydro-2H-pyran-4-yl)amino)-N-((5-fluoro-4,6-dimethyl-2-oxo-1,2-dihydropyridin-3-yl)methyl)-4-methyl-4'-(morpholinomethyl)-[1,1'-biphenyl]-3-carboxamide A stirred solution of 3-[ethyl(oxan-4-yl)amino]-2-methyl-5-[4-(morpholin-4-ylmethyl)phenyl]benzoic acid (100 mg, 0.22 mmol) in anhydrous DMF (4.0 ml) at 0° C. under a balloon of nitrogen, was treated with HATU (99 mg, 0.26 mmol) and DIPEA (75 µl, 0.43 mmol) dropwise. The resulting solution was stirred for 10 minutes and then treated with 3-(aminomethyl)-5-fluoro-4,6-dimethyl-1,2-dihydropyridin-2-one (50%, 81 mg, 0.24 mmol). The resulting suspension was stirred at 0° C. for 30 minutes and then stirred at room temperature for 18 hours. The reaction mixture was partitioned between water (20 ml) and CH$_2$Cl$_2$ (15 ml). The layers were separated and the aqueous phase was extracted with CH$_2$Cl$_2$ (3×15 ml). The combined organics were washed with a saturated solution of NaHCO$_3$ (aq) (40 ml), water (2×25 ml), brine (20 ml), dried (MgSO$_4$), filtered and concentrated in-vacuo. The crude residue was purified by flash column chromatography (10 g SNAP cartridge, Isolera, 0-6% MeOH/CH$_2$Cl$_2$) and then dissolved in a mixture of EtOAc (40 ml) and CH$_2$Cl$_2$ (10 ml), and washed with water (6×30 ml), brine (2×30 ml), dried (MgSO$_4$), filtered and concentrated in-vacuo. The solid was thoroughly dried in-vacuo at 40° C. for 40 hours to give 5-(ethyl(tetrahydro-2H-pyran-4-yl)amino)-N-((5-fluoro-4,6-dimethyl-2-oxo-1,2-dihydropyridin-3-yl)methyl)-4-methyl-4'-(morpholinomethyl)-[1,1'-biphenyl]-3-carboxamide (93 mg, 73%) as a powdery white solid. LC-MS 100%, 2.76 min (7 minute LC-MS method), m/z=591.2; $^1$H NMR (500 MHz, Chloroform-d) δ 11.79 (s, 1H), 7.44 (d, J=8.1 Hz, 2H), 7.34 (d, J=8.4 Hz, 3H), 7.08 (t, J=6.0 Hz, 1H), 4.56 (d, J=6.0 Hz, 2H), 3.95 (d, J=11.2 Hz, 2H), 3.76-3.66 (m, 4H), 3.51 (s, 2H), 3.31 (td, J=11.3, 2.7 Hz, 2H), 3.10 (q, J=7.0 Hz, 2H), 3.00 (tt, J=9.6, 4.6 Hz, 1H), 2.45 (s, 4H), 2.43 (d, J=1.8 Hz, 3H), 2.34 (s, 3H), 2.13 (d, J=2.7 Hz, 3H), 1.74-1.62 (m, 4H), 0.89 (t, J=7.0 Hz, 3H). One proton assumed to be coincident with a solvent peak.

Example 180: N-((4,6-dimethyl-2-oxo-1,2-dihydropyridin-3-yl)methyl)-3-(((1r,4r)-4-(dimethylamino)cyclohexyl)(ethyl)amino)-2-methyl-5-(1-methyl-1H-imidazol-4-yl)benzamide

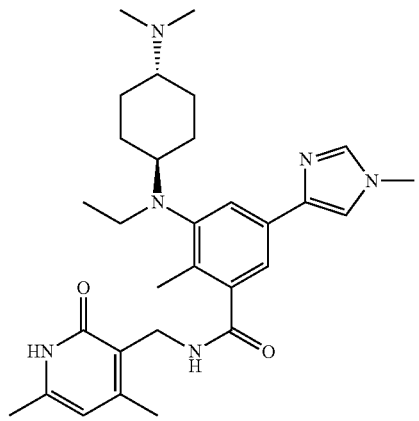

Compound 180

Compound 180 was prepared with the method similar to that described in Example 169.

Analytical Data: LCMS: 519.55 (M+1)$^+$; HPLC: 89.93% (@ 210-370 nm) (R$_t$: 3.676; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.50 (bs, 1H), 9.77 (bs, 1H), 9.11 (s, 1H), 8.20-8.17 (m, 2H), 7.60 (s, 1H), 7.38 (s, 1H), 5.87 (s, 1H), 4.30 (d, 2H, J=5.2 Hz), 3.87 (s, 3H), 3.11 (m, 3H), 2.68-2.67 (m, 6H), 2.72-2.64 (m, 1H), 2.22 (s, 6H), 2.11 (s, 3H), 1.99-1.87 (m, 4H), 1.48-1.40 (m, 4H), 0.81 (t, 3H, J=6.8 Hz).

Example 181: 4'-(azetidine-1-carbonyl)-N-((4,6-dimethyl-2-oxo-1,2-dihydropyridin-3-yl)methyl)-5-(((1r,4r)-4-(dimethylamino)cyclohexyl)(ethyl)amino)-4-methyl-[1,1'-biphenyl]-3-carboxamide Compound 181

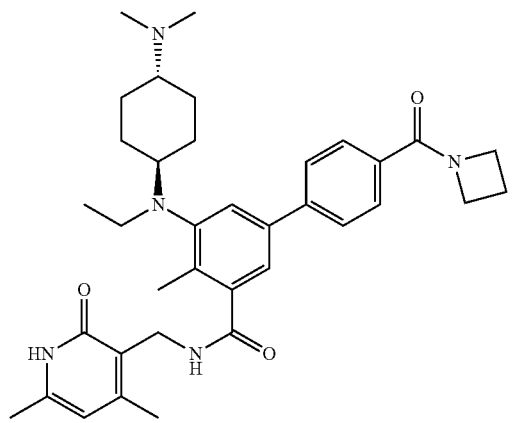

Analytical Data: LCMS: 598.60 (M+1)⁺; HPLC: 94.88% (@ 210-370 nm) (R_t; 3.823; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d₆, 400 MHz) δ 11.44 (bs, 1H), 9.56 (bs, 1H), 8.21 (m, 1H), 8.05-7.96 (m, 4H), 7.54 (bs, 1H), 7.38 (bs, 1H), 5.87 (s, 1H), 4.82-4.81 (m, 2H), 4.31 (d, 2H, J=4.8 Hz), 3.69 (t, 2H, J=5.6 Hz), 3.17-3.14 (m, 3H), 2.77 (bs, 1H), 2.69-2.68 (m, 6H), 2.26 (s, 3H), 2.22 (s, 3H), 2.11 (s, 3H), 1.97-1.91 (m, 4H), 1.46-1.44 (m, 4H), 0.85 (t, 3H, J=6.8 Hz). 2H merged in solvent peak.

Example 182: N3-((4,6-dimethyl-2-oxo-1,2-dihydropyridin-3-yl)methyl)-5-(((1r,4r)-4-(dimethylamino)cyclohexyl)(ethyl)amino)-N4'-(3-hydroxypropyl)-4-methyl-[1,1'-biphenyl]-3,4'-dicarboxamide Compound 182

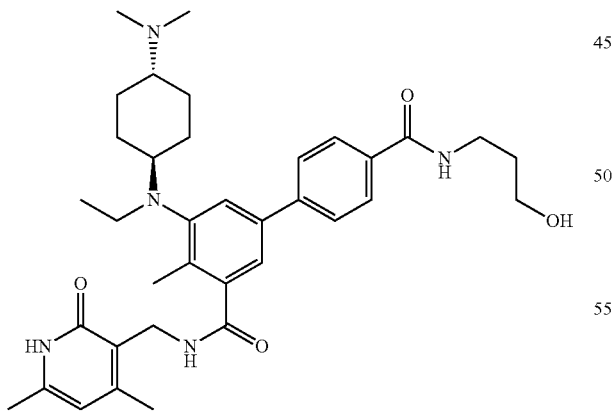

Analytical Data: LCMS: 617.70 (M+1)⁺; HPLC: 93.27% (@ 210-370 nm) (R_t; 4.009; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d₆, 400 MHz) δ 11.46 (bs, 1H), 9.47 (bs, 1H), 8.48 (m, 1H), 8.23 (bs, 1H), 7.93-7.73 (m, 4H), 7.47 (bs, 1H), 7.31 (bs, 1H), 5.87 (s, 1H), 4.31-4.30 (m, 2H), 3.47 (t, 2H, J=6 Hz), 3.34-3.33 (m, 2H), 3.13 (bs, 3H), 2.69-2.68 (m, 6H), 2.26 (s, 3H), 2.21 (s, 3H), 2.11 (s, 3H), 1.96 (m, 4H), 1.69 (t, 2H, J=6.6 Hz), 1.45 (m, 4H), 0.85 (t, 3H). 1H merged in solvent peak.

Example 183: 3-(ethyl(tetrahydro-2H-pyran-4-yl)amino)-2-methyl-N-((6-methyl-2-oxo-4-propyl-1,2-dihydropyridin-3-yl)methyl)-5-(6-(4-methylpiperazin-1-yl)pyridin-3-yl)benzamide Compound 183

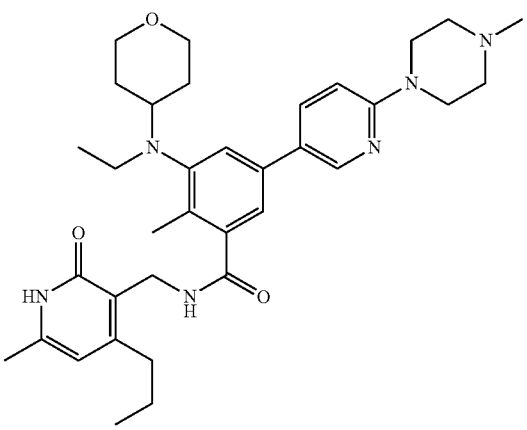

Analytical Data: LCMS: 601.65 (M+1)⁺; HPLC: [99.85% (@ 210 nm-370 nm) (R_t; 4.256; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); ¹H NMR (DMSO-d₆, 400 MHz) δ 11.48 (bs, 1H), 9.84 (bs, 1H), 8.47 (bs, 1H), 8.17 (bs, 1H), 7.94 (s, 1H), 7.41 (m, 2H), 7.04 (d, 1H, J=8 Hz), 5.89 (s, 1H), 4.44 (d, 2H, J=12 Hz), 4.30 (s, 2H), 3.84 (bs, 2H), 3.52 (d, 2H, J=9 Hz), 3.12-3.24 (m, 8 Hz), 2.85 (s, 3H), 2.25 (s, 3H), 2.11 (s, 3H), 1.54-1.65 (m, 6H), 0.84-0.94 (m, 6H). 3 Protons merged in solvent peak.

Example 184: Synthesis of 3-(ethyl(tetrahydro-2H-pyran-4-yl)amino)-2-methyl-N-((6-methyl-2-oxo-4-propyl-1,2-dihydropyridin-3-yl)methyl)-5-(6-(piperazin-1-yl)pyridin-3-yl)benzamide Compound 184

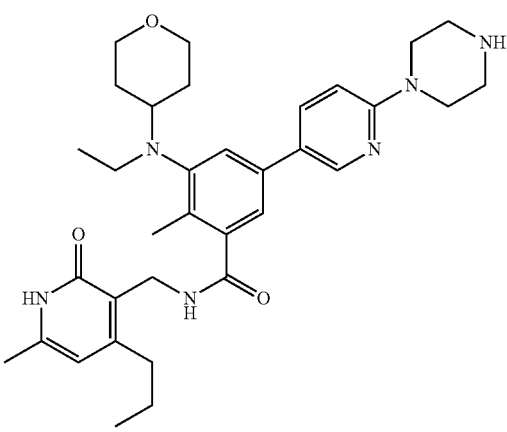

A solution of 5-bromo-3-(ethyl(tetrahydro-2H-pyran-4-yl)amino)-2-methyl-N-((6-methyl-2-oxo-4-propyl-1,2-dihydropyridin-3-yl)methyl)benzamide (0.7 g, 1.38 mmol), respective boronate ester (0.601 g, 2.08 mmol), and tetrakis (0.160 g, 0.138 mmol) in dioxane (10 mL) was purged with argon for 10 min. To this, aq. Na$_2$CO$_3$ (0.529 g, 4.99 mmol, 2 mL) was added and again degassed for 10 min. Reaction mixture was heated at 100° C. for 16 h. On completion, it was concentrated to obtain crude material which was column purified to afford the title compound (0.50 g, 61.5%). Analytical Data: LCMS: 587.55 (M+1)$^+$; HPLC: 97.87% (@ 210-370 nm) (R$_t$: 4.217; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (bs, 1H), 8.38 (d, 1H, J=2.4 Hz), 8.14 (t, 1H, J=4.4 Hz), 7.78 (dd, 1H, J=2.4, 9.2 Hz), 7.35 (d, 1H, J=1.2 Hz), 7.15 (d, 1H, J=1.2 Hz), 6.85 (d, 1H, J=8.4 Hz), 5.88 (s, 1H), 4.29 (d, 2H, J=4.8 Hz), 3.82 (d, 2H, J=10 Hz), 3.43 (t, 4H, J=5.2 Hz), 3.24 (t, 2H, J=11.2 Hz), 3.10-2.98 (m, 3H), 2.78 (t, 4H, J=4.8 Hz), 2.22 (s, 3H), 2.11 (s, 3H), 1.67-1.47 (m, 6H), 0.93 (t, 3H, J=7.2 Hz), 0.81 (t, 3H, J=6.8 Hz).

Example 185: Synthesis of 3-(ethyl(tetrahydro-2H-pyran-4-yl)amino)-N-((4-isopropyl-6-methyl-2-oxo-1,2-dihydropyridin-3-yl)methyl)-2-methyl-5-(6-(piperazin-1-yl)pyridin-3-yl) benzamide

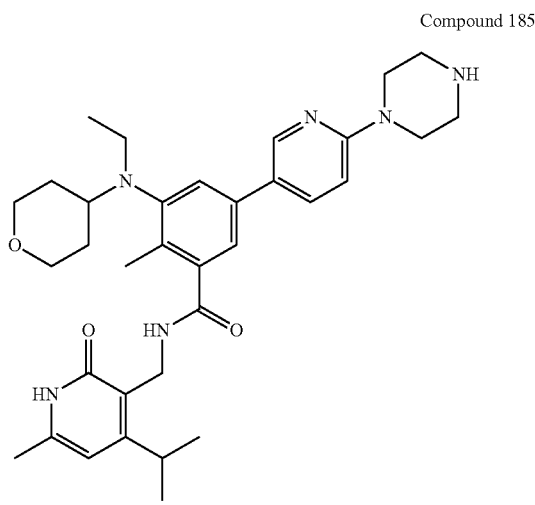 [SMILES: CCN(c1cc(-c2ccc(N3CCNCC3)nc2)cc(C(=O)NCc2c(C(C)C)cc(C)[nH]c2=O)c1C)C1CCOCC1]

Compound 185

A solution of 5-bromo-3-(ethyl(tetrahydro-2H-pyran-4-yl)amino)-N-((4-isopropyl-6-methyl-2-oxo-1,2-dihydropyridin-3-yl)methyl)-2-methylbenzamide (0.5 g, 0.99 mmol), 1-(5-(4,4,5,5-tetramethyl-1,3,2-dioxaborolan-2-yl)pyridin-2-yl)piperazine (0.43 g, 1.48 mmol), and tetrakis (0.114 g, 0.09 mmol) in dioxane (7 mL) was purged with argon for 10 min. To this, aq. Na$_2$CO$_3$ (0.377 g, 3.5 mmol, 2 mL) was added and again degassed for 10 min. Reaction mixture was heated at 100° C. for 16 h. On completion, it was concentrated to obtain crude material which was column purified to afford the title compound (0.35 g, 60.13%).

Analytical Data: LCMS: 586.36 (M+1)$^+$; HPLC: 97.03% (@ 210-370 nm) (R$_t$: 4.10; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.45 (bs, 1H), 8.37 (bs, 1H), 8.17 (bs, 1H), 7.78 (d, 1H, J=7.6 Hz), 7.35 (s, 1H), 7.15 (s, 1H), 6.85 (d, 1H, J=8.8 Hz), 5.99 (s, 1H), 4.34 (d, 2H, J=4 Hz), 3.83-3.81 (m, 2H), 3.42 (bs, 4H), 3.27-3.21 (m, 3H), 3.02-3.01 (m, 3H), 2.77 (bs, 4H), 2.22 (s, 3H), 2.13 (s, 3H), 1.67-1.49 (m, 4H), 1.13 (s, 3H), 1.12 (s, 3H), 0.81 (t, 3H, J=6.4 Hz).

Example 186: Synthesis of 3-(ethyl(tetrahydro-2H-pyran-4-yl)amino)-N-((4-isopropyl-6-methyl-2-oxo-1,2-dihydropyridin-3-yl)methyl)-2-methyl-5-(6-(4-methylpiperazin-1-yl)pyridin-3-yl)benzamide

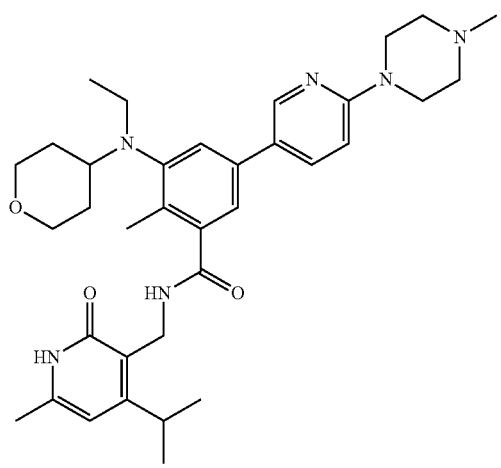

Compound 186

Step 1: Synthesis of 4-isopropyl-6-methyl-2-oxo-1,2-dihydropyridine-3-carbonitrile To a stirred solution of 2-cyanoacetamide (4.1 g, 49 mmol) and t-BuOK (4.9 g, 44.6 mmol) in DMSO at 0° C., 5-methylhex-3-en-2-one (5 g, 44.6 mmol) was added and stirred for 30 min. Additional t-BuOK (15 g, 133.9 mmol) was added to reaction mixture and stirred at room temperature under for further 1 h. On completion, the reaction mixture was diluted with water (50 mL) and slowly acidified with 4N HCl. The precipitate was filtered and washed with water and dried to get the compound B (2.2 g, 28.2%).

Step 2: Synthesis of 3-(aminomethyl)-4-isopropyl-6-methylpyridin-2(1H)-one

To a solution of cyano compound B (2.2 g, 12.5 mmol) in methanol and aq. ammonia solution (10 mL, 4:1), catalytic amount of Raney Nickel was added. Reaction mass was stirred at room temperature under hydrogen pressure (balloon pressure) for 4 h. On completion of reaction, it was filtered through celite bed and filtrate was concentrated under reduce pressure to afford the title compound (2 g, 91%).

Step 3: Synthesis of 5-bromo-3-(ethyl(tetrahydro-2H-pyran-4-yl)amino)-N-((4-isopropyl-6-methyl-2-oxo-1,2-dihydropyridin-3-yl)methyl)-2-methylbenzamide 5-bromo-3-(ethyl(tetrahydro-2H-pyran-4-yl)amino)-2-methylbenzoic acid (2.0 g, 0.0058 mol) was dissolved in DMSO (20 mL) and 3-(aminomethyl)-4-isopropyl-6-methylpyridin-2(1H)-one (2.1 g, 11.7 mmol) and triethyl amine (0.585 g, 5.8 mmol) was added to it. The reaction mixture was stirred at room temperature for 15 min before PyBOP (4.5 g, 8.7 mmol) was added to it and stirring was continued for overnight. After completion of the reaction, the reaction mixture was poured into ice, extracted with 10% MeOH/DCM. Combined organic layers were dried, concentrated to obtain crude; which then purified by solvent washings to afford the title compound (2.0 g, 68.9%).

Step 4: Synthesis of 3-(ethyl(tetrahydro-2H-pyran-4-yl)amino)-N-((4-isopropyl-6-methyl-2-oxo-1,2-dihydropyridin-3-yl)methyl)-2-methyl-5-(6-(4-methylpiperazin-1-yl)pyridin-3-yl)benzamide A solution of 5-bromo-3-(ethyl(tetrahydro-2H-pyran-4-yl)amino)-N-((4-isopropyl-6-methyl-2-oxo-1,2-dihydropyridin-3-yl)methyl)-2-methylbenzamide (0.3 g, 0.99 mmol), respective boronic acid pinacol ester (0.216 g, 0.715 mmol), and tetrakis (0.068 g, 0.0596 mmol) in dioxane (10 mL) was purged with argon for 10 min. To this, aq. $Na_2CO_3$ (0.227 g, 2.14 mmol, 2 mL) was added and again degassed for 10 min. Reaction mixture was heated at 100° C. for 16 h. On completion, it was concentrated to obtain crude material which was purified using prep. HPLC to afford the title compound as a TFA salt (0.12 g, 33.6%).

Analytical Data of TFA Salt: MS: 601.55 (M+1)+. HPLC: 96.78% (@ 210-370 nm) ($R_t$: 4.197; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.49 (bs, 1H), 9.94 (bs, 1H), 8.493 (d, 1H, 6 Hz), 7.957 (bs, 1H), 7.65-7.258 (m, 3H), 7.056 (d, 1H, 8.4 Hz), 6.014 (s, 1H), 4.46 (d, 2H, 12.8 Hz), 4.349 (d, 2H, 4.8 Hz), 3.849 (d, 2H, 7.2 Hz), 3.530 (d, 2H, 10.8 Hz), 3.28-3.075 (m, 10H), 2.85 (s, 3H), 2.26 (bs, 3H), 2.14 (s, 3H), 1.64 (bs, 2H), 1.56 (bs, 2H),1.14 (s, 3H), 1.12 (s, 3H), 0.845 (t, 3H, 7.6 Hz).

Example 187: Synthesis of N-((4,6-dimethyl-2-oxo-1,2-dihydropyridin-3-yl)methyl)-3-(ethyl(tetrahydro-2H-pyran-4-yl)amino)-2-methyl-5-(6-(4-(1-methylpiperidin-4-yl)piperazin-1-yl)pyridin-3-yl)benzamide Compound 187

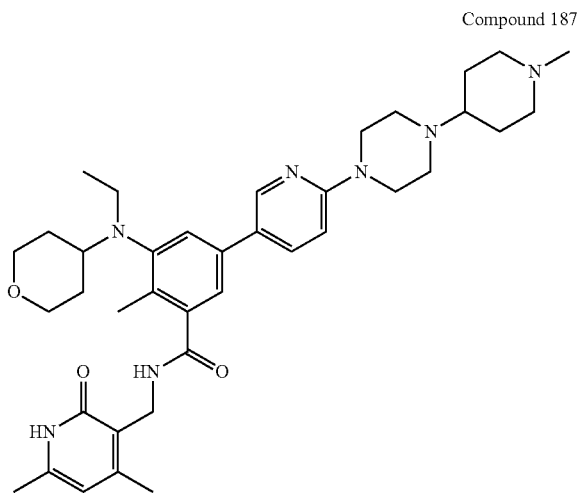

To a stirred solution of N-((4,6-dimethyl-2-oxo-1,2-dihydropyridin-3-yl)methyl)-3-(ethyl(tetrahydro-2H-pyran-4-yl)amino)-2-methyl-5-(6-(piperazin-1-yl)pyridin-3-yl)benzamide (0.1 g, 0.179 mmol) and 1-methylpiperidin-4-one (0.04 g, 0.358 mmol) in dichloroethane (2 mL), acetic acid (0.07 mL, 1.07 mmol) was added and reaction stirred at room temperature for 15 min. Then sodium triacetoxyborohydride (0.113 g, 0.53 mmol) was added at 0° C. and reaction stirred overnight at room temperature. On completion, reaction was quenched with aqueous sodium bicarbonate, organic phase was separated and aqueous phase was extracted with dichloromethane. Combined organic layers were dried over sodium sulphate and concentrated under reduced pressure to give crude material was purified by prep. HPLC to afford the title compound as a TFA salt (0.08 g, 22.72%).

Analytical Data of TFA salt: ESMS: 656.41 (M+1)+; HPLC: [97.76% (@ 210 nm-370 nm) ($R_t$: 3.667; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.49 (bs, 1H), 10.33 (bs, 1H), 9.86 (bs, 1H), 8.49 (bs, 1H), 8.20 (bs, 1H), 7.96 (bs, 1H), 7.24-7.39 (m, 2H), 7.07 (d, 1H, J=9 Hz), 5.87 (s, 1H), 4.47 (bs, 2H), 4.28 (d, 2H, J=4 Hz), 3.84 (s, 2H), 3.60 (d, 5H, J=11 Hz), 3.16-3.28 (m, 7H), 2.99 (bs, 2H), 2.79 (s, 3H), 2.11-2.25 (m, 11H), 1.87-1.90 (m, 2H), 1.56-1.64 (m, 3H), 0.85 (s, 3H).

Example 188: Synthesis of 3-(ethyl(tetrahydro-2H-pyran-4-yl)amino)-N-((4-isopropyl-6-methyl-2-oxo-1,2-dihydropyridin-3-yl)methyl)-2-methyl-5-(6-(4-(1-methylpiperidin-4-yl)piperazin-1-yl)pyridin-3-yl)benzamide Compound 188

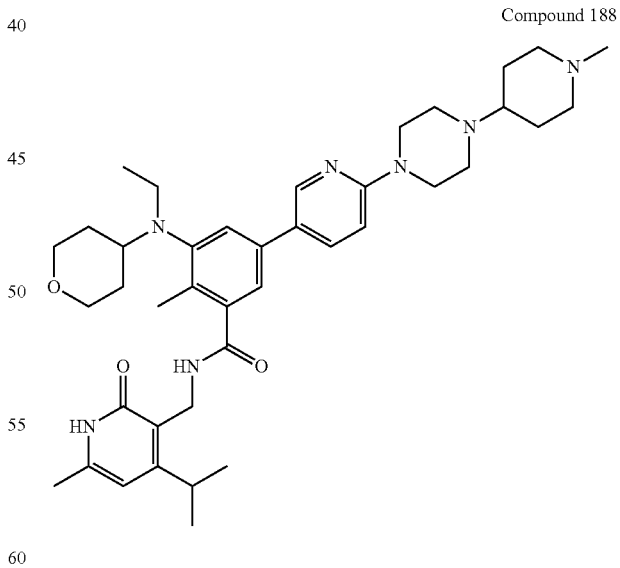

To a stirred solution of 3-(ethyl(tetrahydro-2H-pyran-4-yl)amino)-N-((4-isopropyl-6-methyl-2-oxo-1,2-dihydropyridin-3-yl)methyl)-2-methyl-5-(6-(piperazin-1-yl)pyridin-3-yl) benzamide (0.3 g, 0.51 mmol) and 1-methylpiperidin-4-one (0.086 g, 0.76 mmol) in dichloroethane (5 mL), acetic acid (0.18 g, 3.06 mmol) was added and reaction stirred at room temperature for 20 minutes.

Then sodium triacetoxyborohydride (0.33 g, 1.55 mmol) was added at 0° C. and reaction stirred at room temperature for 2 h. On completion, reaction was quenched with aqueous sodium bicarbonate, organic phase was separated and aqueous phase was extracted with dichloromethane. Combined organic layers were dried over sodium sulphate and concentrated under reduced pressure to give crude material was purified by prep. HPLC to afford the title compound (0.12 g, 34.38%).

Analytical Data: LCMS: 683.45 (M+1)$^+$; HPLC: 98.65% (@ 210-370 nm) (R$_t$: 4.04; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.47 (bs, 1H), 10.24 (bs, 1H), 9.79 (bs, 1H), 8.46 (bs, 1H), 8.19 (bs, 1H), 7.92 (bs, 1H), 7.38 (bs, 1H), 7.19 (bs, 1H), 7.06 (d, 1H, J=9.2 Hz), 6.0 (s, 1H), 4.47 (bs, 2H), 4.34 (d, 2H, J=7.6 Hz), 3.83 (d, 2H J=8.8 Hz), 3.6 (d, 4H, J=12 Hz), 3.43 (m, 1H), 3.27-3.16 (m, 8H), 2.99-2.97 (m, 3H), 2.79 (s, 3H), 2.37-2.33 (m, 3H), 2.24 (bs, 3H), 2.13 (s, 3H), 1.90-1.82 (m, 2H), 1.64-1.53 (m, 4H), 1.13 (s, 3H), 1.12 (s, 3H), 0.83 (t, 3H, J=6.8 Hz)

Example 189: Synthesis of 3-(ethyl(tetrahydro-2H-pyran-4-yl)amino)-2-methyl-N-((6-methyl-2-oxo-4-propyl-1,2-dihydropyridin-3-yl)methyl)-5-(6-(4-(1-methylpiperidin-4-yl)piperazin-1-yl)pyridin-3-yl)benzamide

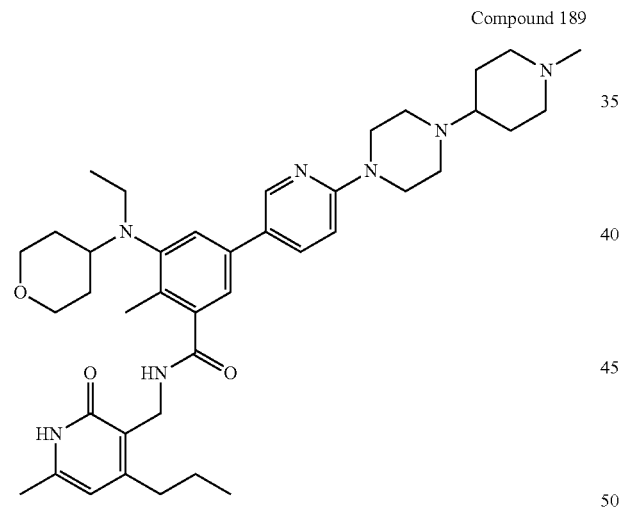

Compound 189

To a stirred solution of 3-(ethyl(tetrahydro-2H-pyran-4-yl)amino)-2-methyl-N-((6-methyl-2-oxo-4-propyl-1,2-dihydropyridin-3-yl)methyl)-5-(6-(piperazin-1-yl)pyridin-3-yl) benzamide (0.45 g, 0.76 mmol) and 1-methylpiperidin-4-one (0.173 g, 1.53 mmol) in dichloroethane (10 mL), acetic acid (0.276 g, 4.6 mmol) was added and reaction stirred at room temperature for 20 minutes. Then sodium triacetoxyborohydride (0.488 g, 2.3 mmol) was added at 0° C. and reaction stirred at room temperature for 2 h. On completion, reaction was quenched with aqueous sodium bicarbonate, organic phase was separated and aqueous phase was extracted with dichloromethane. Combined organic layers were dried over sodium sulphate and concentrated under reduced pressure to give crude material was purified by column chromatography to afford the title compound (0.215 g, 41%).

Analytical Data: LCMS: 684.45 (M+1)$^+$; HPLC: 93.41% (@ 210 nm-370 nm) (R$_t$: 4.140; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.46 (bs, 1H), 8.38 (s, 1H), 8.13 (bs, 1H), 7.78 (d, 1H, J=9 Hz), 7.35 (s, 1H), 7.15 (s, 1H), 6.8 (d, 1H, J=9), 5.88 (s, 1H), 4.28 (d, 2H, J=4 Hz), 3.82 (d, 2H, 10 Hz), 3.49 (s, 4H), 3.24 (t, 2H, J=11 Hz), 3.0-3.08 (m, 3H), 2.78 (d, 2H, J=10 Hz), 2.56 (s, 4H), 2.22 (s, 3H), 2.13 (s, 1H), 2.11 (s, 1H), 1.57-1.86 (m, 6H), 1.46-1.55 (m, 6H), 0.91 (t, 3H, J=8 Hz), 0.81 (t, 3H, J=6 Hz).

Example 190: Synthesis of 3-(ethyl(tetrahydro-2H-pyran-4-yl)amino)-N-((4-isopropyl-6-methyl-2-oxo-1,2-dihydropyridin-3-yl)methyl)-2-methyl-5-(6-(morpholinomethyl)pyridin-3-yl)benzamide

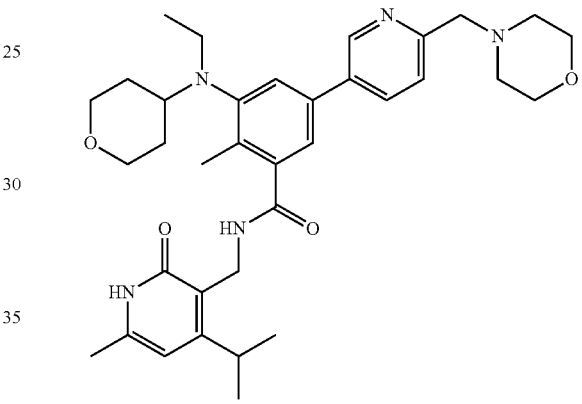

Compound 190

Step 1: Synthesis of 3-(ethyl(tetrahydro-2H-pyran-4-yl)amino)-5-(6-formylpyridin-3-yl)-N-((4-isopropyl-6-methyl-2-oxo-1,2-dihydropyridin-3-yl)methyl)-2-methylbenzamide A solution of 5-bromo-3-(ethyl(tetrahydro-2H-pyran-4-yl)amino)-N-((4-isopropyl-6-methyl-2-oxo-1,2-dihydropyridin-3-yl)methyl)-2-methylbenzamide (0.4 g, 0.793 mmol), 5-(4,4,5,5-tetramethyl-1,3,2-dioxaborolan-2-yl)picolinaldehyde (0.28 g, 1.19 mmol) and tetrakis (0.091 g, 0.079 mmol) in dioxane (5 mL) was purged with argon for 10 min. To this, aq. Na$_2$CO$_3$ (0.301 g, 2.83 mmol) was added and again degassed for 10 min. Reaction mixture was heated at 100° C. for 16 h. On completion, it was concentrated to obtain crude material which was column purified to afford the title compound (0.28 g, 66.50%).

Step 2: Synthesis of 3-(ethyl(tetrahydro-2H-pyran-4-yl)amino)-N-((4-isopropyl-6-methyl-2-oxo-1,2-dihydropyridin-3-yl)methyl)-2-methyl-5-(6-(morpholinomethyl)pyridin-3-yl)benzamide To a stirred solution of 3-(ethyl(tetrahydro-2H-pyran-4-yl)amino)-5-(6-formylpyridin-3-yl)-N-((4-isopropyl-6-methyl-2-oxo-1,2-dihydropyridin-3-yl)methyl)-2-methylbenzamide (0.28 g, 0.528 mmol) and morpholine (0.07 g, 0.79 mmol) in dichloroethane (3 mL), acetic acid (0.19 g, 3.16 mmol) was added and reaction stirred at room temperature for 20 minutes. Then sodium triacetoxyborohydride (0.33 g, 1.55 mmol) was added at 0° C. and reaction stirred at room temperature for 2 h. On completion, reaction was quenched with aqueous sodium bicarbonate, organic phase was separated and aqueous phase was extracted with dichloromethane. Combined organic layers were dried over sodium sulphate and concentrated under reduced pressure to give crude material was purified by prep. HPLC to afford the title compound (0.12 g, 38.70%).

Analytical Data of TFA salt: LCMS: 601.36 (M+1)$^+$; HPLC: 95.48% (@ 210-370 nm) ($R_t$; 4.28; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$, 400 MHz) δ 11.45 (bs, 1H), 10.45 (bs, 1H), 8.95 (s, 1H), 8.23-8.21 (m, 2H), 7.62-7.52 (m, 2H), 7.34 (bs, 1H), 6.01 (s, 1H), 4.55 (s, 2H), 4.35 (d, 2H, J=5.2 Hz), 3.84 (bs, 6H), 3.29-3.13 (m, 8H), 2.27 (s, 3H), 2.13 (s, 3H), 1.66-1.56 (m, 4H), 1.13 (s, 3H), 1.12 (s, 3H), 0.83 (t, 3H, J=6.8). 2H protons merged in solvent peaks.

Example 191: Synthesis of 3-(ethyl(tetrahydro-2H-pyran-4-yl)amino)-2-methyl-N-((6-methyl-2-oxo-4-propyl-1,2-dihydropyridin-3-yl)methyl)-5-(6-(morpholinomethyl)pyridin-3-yl) benzamide

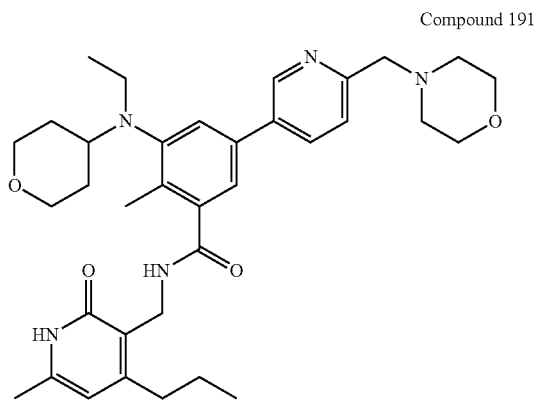 [SMILES: CCCc1cc(C)[nH]c(=O)c1CNC(=O)c1cc(-c2ccc(CN3CCOCC3)nc2)cc(N(CC)C2CCOCC2)c1C]

Compound 191

Step 1: Synthesis of 3-(ethyl(tetrahydro-2H-pyran-4-yl)amino)-5-(6-formylpyridin-3-yl)-2-methyl-N-((6-methyl-2-oxo-4-propyl-1,2-dihydropyridin-3-yl)methyl)benzamide A solution of 5-bromo-3-(ethyl(tetrahydro-2H-pyran-4-yl)amino)-2-methyl-N-((6-methyl-2-oxo-4-propyl-1,2-dihydropyridin-3-yl)methyl)benzamide (0.5 g, 0.99 mmol), 5-(4,4,5,5-tetramethyl-1,3,2-dioxaborolan-2-yl)picolinaldehyde (0.346 g, 1.48 mmol), and tetrakis (0.114 g, 0.99 mmol) in dioxane (10 mL) was purged with argon for 10 min. To this, aq. $Na_2CO_3$ (0.378 g, 3.56 mmol, 1.8 mL) was added and again degassed for 10 min. Reaction mixture was heated at 100° C. for 16 h. On completion, it was concentrated to obtain crude material which was column purified to afford the title compound (0.40 g, 76.0%).

Step 2: Synthesis of 3-(ethyl(tetrahydro-2H-pyran-4-yl)amino)-2-methyl-N-((6-methyl-2-oxo-4-propyl-1,2-dihydropyridin-3-yl)methyl)-5-(6-(morpholinomethyl)pyridin-3-yl) benzamide To a stirred solution of 3-(ethyl(tetrahydro-2H-pyran-4-yl)amino)-5-(6-formylpyridin-3-yl)-2-methyl-N-((6-methyl-2-oxo-4-propyl-1,2-dihydropyridin-3-yl)methyl) benzamide (0.315 g, 0.59 mmol) in EDC (8 mL) at 0° C., was added morpholine (0.1 g, 1.18 mmol) and stirred at rt for 10 min. NaBH(OAc)$_3$ (0.377 g, 1.78 mmol) was then added and stirred for 16 h. On completion, reaction was quenched with water. MeOH (8 mL) was added and layers were separated and extracted with 10% MeOH in DCM, and purified on column chromatography to afford the title compound (0.2 g, 56%).

Analytical Data: LCMS: 602.60 (M+1)$^+$; HPLC: 98.12% (@ 210 nm-370 nm) ($R_t$; 4.374; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.48 (s, 1H), 8.75 (s, 1H), 8.19 (t, 1H, J=4 Hz), 7.99-8.02 (m, 1H), 7.49 (t, 2H, J=8 Hz), 7.26 (s, 1H), 5.88 (s, 1H), 4.29 (d, 2H, J=4 Hz), 3.82 (d, 2H, J=10 Hz), 3.59-3.61 (m, 6H), 3.24 (t, 2H, J=12 Hz), 2.99-3.10 (m, 3H), 2.42 (s, 4H), 2.25 (s, 3H), 2.11 (s, 3H), 1.48-1.67 (m, 6H), 0.926 (t, 3H, J=8 Hz), 0.824 (t, 3H, J=7 Hz).

Example 192: N-((4,6-dimethyl-2-oxo-1,2-dihydropyridin-3-yl)methyl)-5-(6-(4-(dimethylamino)piperidin-1-yl)pyridin-3-yl)-3-(ethyl(tetrahydro-2H-pyran-4-yl)amino)-2-methylbenzamide

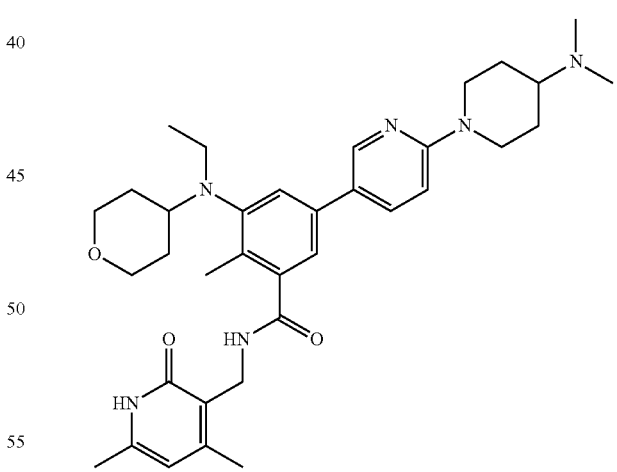

Compound 192

Step 1: Synthesis of tert-butyl (1-(5-(3-(((4,6-dimethyl-2-oxo-1,2-dihydropyridin-3-yl)methyl) carbamoyl)-5-(ethyl(tetrahydro-2H-pyran-4-yl)amino)-4-methylphenyl)pyridin-2-yl) piperidin-4-yl) carbamate (9)

To a stirred solution of 5-bromo-N-((4,6-dimethyl-2-oxo-1,2-dihydropyridin-3-yl)methyl)-3-(ethyl(tetrahydro-2H-pyran-4-yl)amino)-2-methylbenzamide (0.35 g, 0.736 mmol) and respective boronic acid pinacol ester (0.35 g, 0.88 mmol) in dioxane (5 mL), Na$_2$CO$_3$ (0.28 g, 2.65 mmol) was added and solution was purged with argon for 15 min. Then tetrakis (0.085 g, 0.073 mmol) was added and argon was purged again for 10 min. Reaction mass was heated at 100° C. for 4 h. On completion, reaction mixture was diluted with water and extracted with 10% MeOH/DCM. Combined organic layers were dried over Na$_2$SO$_4$ and solvent removed under reduced pressure and purified on column chromatography to afford the title compound (0.39 g, 79%)

Step 2: Synthesis of 5-(6-(4-aminopiperidin-1-yl)pyridin-3-yl)-N-((4,6-dimethyl-2-oxo-1,2-dihydropyridin-3-yl)methyl)-3-(ethyl(tetrahydro-2H-pyran-4-yl)amino)-2-methylbenzamide (10)

To a stirred solution of tert-butyl (1-(5-(3-(((4,6-dimethyl-2-oxo-1,2-dihydropyridin-3-yl)methyl) carbamoyl)-5-(ethyl (tetrahydro-2H-pyran-4-yl)amino)-4-methylphenyl)pyridin-2-yl) piperidin-4-yl)carbamate (0.39 g, 0.058 mmol) in DCM (4 mL) at 0° C., TFA (2 mL) was added and reaction was stirred for 1 h at room temperature. After completion, reaction was concentrated to dryness. The residue was then basified with aqueous sat. bicarbonate solution (30 mL) till pH 8 and aqueous layer extracted with 20% methanol in DCM (50 mL×4). Combined organic phase was dried over Na$_2$SO$_4$ and solvent removed under reduced pressure to afford the title compound (0.3 g, 90.63%) which was used as such for next reaction.

Step 3: Synthesis of N-((4,6-dimethyl-2-oxo-1,2-dihydropyridin-3-yl)methyl)-5-(6-(4-(dimethylamino)piperidin-1-yl)pyridin-3-yl)-3-(ethyl(tetrahydro-2H-pyran-4-yl)amino)-2-methylbenzamide To a stirred solution of 5-(6-(4-aminopiperidin-1-yl)pyridin-3-yl)-N-((4,6-dimethyl-2-oxo-1,2-dihydropyridin-3-yl)methyl)-3-(ethyl(tetrahydro-2H-pyran-4-yl)amino)-2-methylbenzamide (0.3 g, 0.524 mmol) in DCM (3 mL) at 0° C., was added 37-41% aq. formalin solution (0.277 g, 1.31 mmol) and stirred rt for 10 min. NaBH(OAc)$_3$ (0.277 g, 1.31 mmol) was then added and stirred for 2 h. On completion, reaction was quenched with water. MeOH (10 mL) was added and layers were separated and extracted with 10% MeOH in DCM, and column purified to afford the title compound (0.12 g, 38%).

Analytical Data: LCMS: 602.00 (M+1)$^+$; HPLC: 97.22% (@ 210-370 nm) (R$_t$: 3.757; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (bs, 1H), 8.38 (s, 1H), 8.15 (t, 1H), 7.78 (d, 1H, J=8.4 Hz), 7.35 (s, 1H), 7.16 (s, 1H), 6.90 (d, 1H, J=8.8 Hz), 5.85 (s, 1H), 4.35 (d, 2H, J=13.2 Hz), 4.28 (d, 2H, J=4 Hz), 3.82 (d, 2H, J=10 Hz), 3.30-3.20 (m, 2H), 3.10-3.00 (m, 3H), 2.90-2.80 (m, 2H), 2.28 (s, 6H), 2.22 (s, 3H), 2.20 (s, 3H), 2.10 (s, 3H), 1.90-1.80 (m, 3H), 1.70-1.60 (m, 2H), 1.60-1.50 (m, 2H), 1.40-1.30 (m, 2H), 0.82 (t, 3H, J=6.4 Hz).

Example 193: Synthesis of 5-(6-(4-(dimethylamino) piperidin-1-yl)pyridin-3-yl)-3-(ethyl(tetrahydro-2H-pyran-4-yl)amino)-N-((4-isopropyl-6-methyl-2-oxo-1,2-dihydropyridin-3-yl)methyl)-2-methylbenzamide

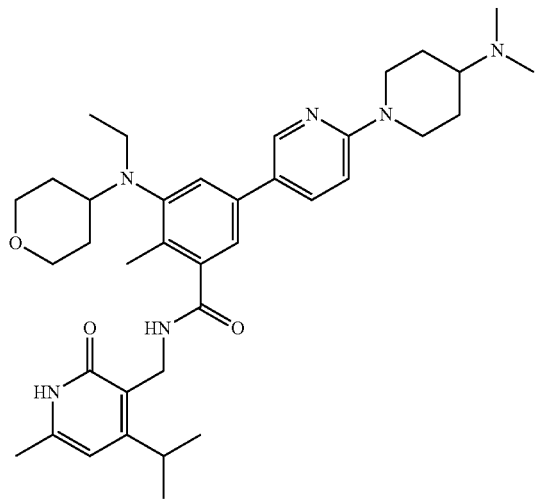

Compound 193

Synthesis of tert-butyl (1-(5-(3-(ethyl(tetrahydro-2H-pyran-4-yl)amino)-5-(((4-isopropyl-6-methyl-2-oxo-1,2-dihydropyridin-3-yl)methyl)carbamoyl)-4-methylphenyl)pyridin-2-yl)piperidin-4-yl)carbamate A solution of 5-bromo-3-(ethyl(tetrahydro-2H-pyran-4-yl)amino)-N-((4-isopropyl-6-methyl-2-oxo-1,2-dihydropyridin-3-yl)methyl)-2-methylbenzamide (0.35 g, 0.69 mmol), tert-butyl (1-(5-(4,4,5,5-tetramethyl-1,3,2-dioxaborolan-2-yl)pyridin-2-yl)piperidin-4-yl)carbamate (0.33 g, 0.83 mmol), and tetrakis (0.079 g, 0.069 mmol) in dioxane (5 mL) was purged with argon for 10 min. To this, aq. Na$_2$CO$_3$ (0.263 g, 2.48 mmol, 2 mL) was added and again degassed for 10 min. Reaction mixture was heated at 100° C. for 16 h. On completion, it was concentrated to obtain crude material which was column purified to afford the title compound (0.31 g, 63%).

Synthesis of 5-(6-(4-aminopiperidin-1-yl)pyridin-3-yl)-3-(ethyl(tetrahydro-2H-pyran-4-yl)amino)-N-((4-isopropyl-6-methyl-2-oxo-1,2-dihydropyridin-3-yl) methyl)-2-methylbenzamide tert-butyl (1-(5-(3-(ethyl(tetrahydro-2H-pyran-4-yl) amino)-5-(((4-isopropyl-6-methyl-2-oxo-1,2-dihydropyridin-3-yl)methyl)carbamoyl)-4-methylphenyl)pyridin-2-yl) piperidin-4-yl)carbamate (0.31 g, 0.44 mmol) was taken in DCM (5 mL) and TFA (1 mL) was added to it and stirred at rt for 2 h. After completion of reaction, solvent was removed under reduced pressure and saturated NaHCO$_3$ solution was added to it. Extraction was carried out using 10% MeOH/DCM; the combined organic layers were washed with water and brine; dried over anhydrous Na$_2$SO$_4$; filtered and concentrated under reduced pressure to give the title compound (0.26 g, 98.11%)

Synthesis of 5-(6-(4-(dimethylamino)piperidin-1-yl)pyridin-3-yl)-3-(ethyl-(tetrahydro-2H-pyran-4-yl)-amino)-N-((4-isopropyl-6-methyl-2-oxo-1,2-dihydropyridin-3-yl)-methyl)-2-methylbenzamide To a stirred solution of 5-(6-(4-aminopiperidin-1-yl)pyridin-3-yl)-3-(ethyl(tetrahydro-2H-pyran-4-yl)amino)-N-((4-isopropyl-6-methyl-2-oxo-1,2-dihydropyridin-3-yl)methyl)-2-methylbenzamide (0.26 g, 0.43 mmol) in DCM (4 mL), formalin (0.045 g, 1.51 mmol) was added and reaction stirred at 0° C. of for 10 minutes. Then sodium triacetoxyborohydride (0.23 g, 1.08 mmol) was added at 0° C. and reaction stirred for 1 h. On completion, water was added to the reaction mass and extraction was carried out using DCM. Combined organic layers were washed with bicarbonate solution, dried over sodium sulphate and concentrated under reduced pressure to give crude material which then purified by solvent washings to give the title compound (0.17 g, 62%).

Analytical Data: LCMS: 629.70 (M+1)$^+$; HPLC: 97.74% (@ 210-370 nm) (R$_t$; 4.176; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (s, 1H), 10.33 (bs, 1H), 8.39 (d, 1H), 8.16 (t, 1H), 7.81 (d, 1H, J=6.8 Hz), 7.35 (s, 1H), 7.16 (s, 1H), 6.97 (d, 1H, J=9.2 Hz), 5.99 (s, 1H), 4.50 (d, 2H, J=12.8 Hz), 4.34 (d, 2H, J=4.4 Hz), 3.82 (d, 2H, J=9.6 Hz), 3.39 (m, 1H), 3.24 (m, 3H), 3.10-3.00 (m, 3H), 2.90-2.80 (m, 2H), 2.69 (s, 6H), 2.22 (s, 3H), 2.13 (s, 3H), 2.10-2.05 (m, 2H), 1.70-1.60 (m, 2H), 1.60-1.45 (m, 4H), 1.13 (d, 6H, J=6.4 Hz), 0.82 (t, 3H, J=6.8 Hz).

Example 194: Synthesis of 5-(6-(4-(dimethylamino)piperidin-1-yl)pyridin-3-yl)-3-(ethyl(tetrahydro-2H-pyran-4-yl)amino)-2-methyl-N-((6-methyl-2-oxo-4-propyl-1,2-dihydropyridin-3-yl)methyl)benzamide Compound 194

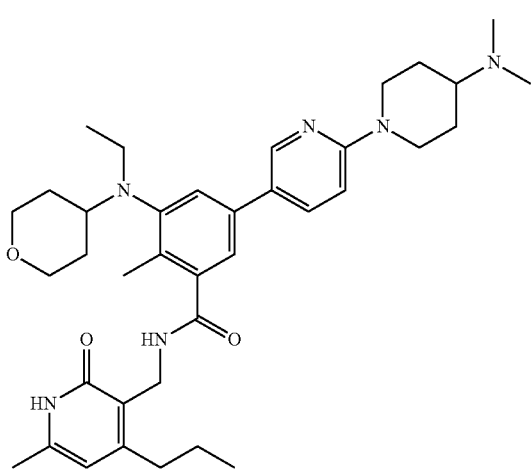

Synthesis of tert-butyl (1-(5-(3-(ethyl(tetrahydro-2H-pyran-4-yl)amino)-4-methyl-5-(((6-methyl-2-oxo-4-propyl-1,2-dihydropyridin-3-yl)methyl)carbamoyl)phenyl) pyridine-2-yl)piperidin-4-yl)carbamate A solution of 5-bromo-3-(ethyl(tetrahydro-2H-pyran-4-yl)amino)-2-methyl-N-((6-methyl-2-oxo-4-propyl-1,2-dihydropyridin-3-yl)methyl)benzamide (0.5 g, 0.99 mmol), respective boronic acid pinacol ester (0.6 g, 1.48 mmol), and tetrakis (0.114 g, 0.99 mmol) in dioxane (7 mL) was purged with argon for 10 min. To this, aq. Na$_2$CO$_3$ (0.377 g, 3.5 mmol, 2 mL) was added and again degassed for 10 min. Reaction mixture was heated at 100° C. for 16 h. On completion, it was concentrated to obtain crude material which was column purified to afford the title compound (0.40 g, 57.47%).

Synthesis of 5-(6-(4-aminopiperidin-1-yl)pyridin-3-yl)-3-(ethyl(tetrahydro-2H-pyran-4-yl)amino)-2-methyl-N-((6-methyl-2-oxo-4-propyl-1,2-dihydropyridin-3-yl)methyl)benzamide To a stirred solution of tert-butyl (1-(5-(3-(ethyl(tetrahydro-2H-pyran-4-yl)amino)-4-methyl-5-(((6-methyl-2-oxo-4-propyl-1,2-dihydropyridin-3-yl)methyl)carbamoyl)phenyl) pyridine-2-yl)piperidin-4-yl)carbamate (0.4 g, 0.00051 mol) in DCM (10 mL) at 0° C., TFA (10 mL) was added and reaction was stirred for 2 h at room temperature. After completion, reaction was concentrated to dryness. The residue was then basified with aqueous sat. bicarbonate solution (80 mL) till pH 8 and aqueous layer extracted with 20% methanol in DCM (60 mL×4). Combined organic phase was dried over Na$_2$SO$_4$ and solvent removed under reduced pressure to afford the title compound (0.315 g, 92.1%) which was used as such for next reaction.

Synthesis of 5-(6-(4-(dimethylamino)piperidin-1-yl)pyridin-3-yl)-3-(ethyl(tetrahydro-2H-pyran-4-yl)amino)-2-methyl-N-((6-methyl-2-oxo-4-propyl-1,2-dihydropyridin-3-yl)methyl)benzamide To a stirred solution of 5-(6-(4-aminopiperidin-1-yl)pyridin-3-yl)-3-(ethyl(tetrahydro-2H-pyran-4-yl)amino)-2-methyl-N-((6-methyl-2-oxo-4-propyl-1,2-dihydropyridin-3-yl)methyl)benzamide (0.315 g, 0.52 mmol) in DCM (8 mL) at 0° C., was added 37-41% aq. formalin solution (0.078 g, 2.6 mmol) and stirred rt for 10 min. NaBH(OAc)$_3$ (0.275 g, 1.3 mmol) was then added and stirred for 2 h. On completion, reaction was quenched with water. MeOH (8 mL) was added and layers were separated and extracted with 10% MeOH in DCM, and recrystallized from ether, acetonitrile and pentane to afford the title compound (0.27 g, 82%).

Analytical Data: LCMS: 630.00 (M+1)$^+$; HPLC: 98.21% (@ 210-370 nm) (R$_t$; 4.155; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d$_6$, 400 MHz) δ 11.46 (s, 1H), 8.37 (d, 1H, J=1.6 Hz), 8.13 (t, 1H, J=4.4 Hz), 7.76 (dd, 1H, J=2.4&9.2 Hz), 7.35 (s, 1H), 7.15 (s, 1H), 6.89 (d, 1H, J=8.8 Hz), 5.88 (s, 1H), 4.25-4.35 (m, 4H), 3.82 (d, 2H, J=10 Hz), 3.24 (m, 2H), 3.10-3.00 (m, 3H), 2.90-2.80 (m, 2H), 2.35 (m, 1H), 2.22 (s, 3H), 2.18 (s, 6H), 2.11 (s, 3H), 1.80 (m, 2H), 1.70-1.60 (m, 2H), 1.60-1.45 (m, 4H), 1.40-1.30 (m, 2H), 0.93 (t, 3H, J=7.2 Hz), 0.81 (t, 3H, J=6.8 Hz).

Example 195: Synthesis of 3-(ethyl(tetrahydro-2H-pyran-4-yl)amino)-N-((5-fluoro-4-isopropyl-6-methyl-2-oxo-1,2-dihydropyridin-3-yl)methyl)-2-methyl-5-(6-(piperazin-1-yl)pyridin-3-yl)benzamide Compound 195

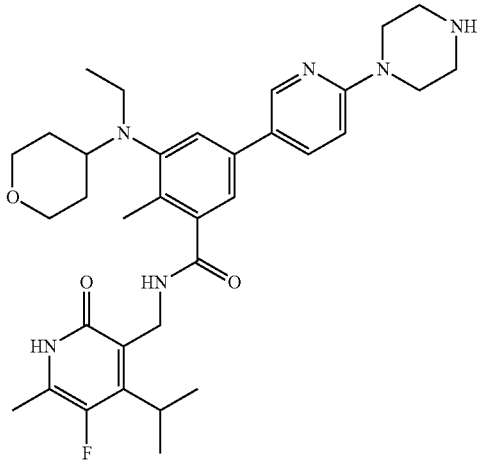

Step 1: Synthesis of 5-Fluoro-4-isopropyl-6-methyl-2-oxo-1,2-dihydropyridine-3-carbonitrile To a stirred solution of 6-methyl-2-oxo-4-(propan-2-yl)-1,2-dihydropyridine-3-carbonitrile (225 mg, 1.277 mmol) in MeCN (6 mL) was added Selectfluor (620 mg, 1.75 mmol). The reaction mixture was stirred at 50° C. for 3 h. After cooling to 23° C., the reaction mixture was concentrated in vacuo. The residue was purified by column chromatography (50% to 100% EtOAc-heptane to obtain the titled compound (90 mg, 36%). $^1$H NMR (400 MHz, CDCl$_3$) δ ppm 3.39 (m, 1H), 2.44 (d, J=3.1 Hz, 3H), 1.41 (dd, J=7.0, 3.1 Hz, 6H); LCMS E-S (M+H)=195.2.

Step 2: Synthesis of 3-(Aminomethyl)-5-fluoro-4-isopropyl-6-methylpyridin-2(1H)-one 5-Fluoro-4-isopropyl-6-methyl-2-oxo-1,2-dihydropyridine-3-carbonitrile (100 mg, 0.515 mmol) in 100 mL flask was dissolved in a mixture of MeOH (6 mL) and 2 mL NH$_{3aq}$ (2 mL, 25%). Reduction was conducted using H-Cube with Raney-Ni as a catalyst at room temperature for 3-4 h. On completion of reaction (monitored by TLC), reaction was concentrated under reduced pressure to afford titled compound as a grey solid (90 mg, 90%). $^1$H NMR (400 MHz, CD$_3$OD) δ ppm 4.04 (s, 2H), 3.22 (m, 1H), 2.24 (d, J=3.4 Hz, 3H), 1.32 (dd, J=7.0, 1.8 Hz, 6H); LCMS E-S (M+H)=199.2.

Step 3: tert-Butyl 4-(5-(3-(ethyl(tetrahydro-2H-pyran-4-yl)amino)-5-(methoxycarbonyl)-4-methylphenyl)pyridin-2-yl)piperazine-1-carboxylate Prepared following the general procedure of Suzuki coupling reaction $^1$H-NMR (400 MHz, CDCl$_3$) δ ppm 8.42 (dd, J=2.4 Hz, 1H), 7.70-7.74 (m, 2H), 7.41 (d, J=2.1 Hz, 1H), 6.72 (d, J=8.8 Hz, 1H), 3.97 (m, 2H), 3.93 (s, 3H), 3.58 (s, 8H), 3.34 (m, 2H), 3.11 (q, J=7.0 Hz, 2H), 3.02 (m, 1H), 2.53 (s, 3H), 1.64-1.76 (m, 4H), 1.50 (s, 9H), 0.91 (t, J=7.0 Hz, 3H). MS (ES) (M+H)=539.5.

Step 4: Synthesis of tert-Butyl 4-(5-(3-(ethyl(tetrahydro-2H-pyran-4-yl)amino)-5-(((5-fluoro-4-isopropyl-6-methyl-2-oxo-1,2-dihydropyridin-3-yl)methyl)carbamoyl)-4-methylphenyl)pyridin-2-yl)piperazine-1-carboxylate Hydrolysis of tert-Butyl 4-(5-(3-(ethyl(tetrahydro-2H-pyran-4-yl)amino)-5-(methoxycarbonyl)-4-methylphenyl)pyridin-2-yl)piperazine-1-carboxylate following the similar methods for examples described earlier resulted in a crude corresponding carboxylic acid 5-(6-(4-(tert-butoxycarbonyl)piperazin-1-yl)pyridin-3-yl)-3-(ethyl(tetrahydro-2H-pyran-4-yl)amino)-2-methylbenzoic acid. This acid was then coupled with 3-(aminomethyl)-5-fluoro-4-isopropyl-6-methylpyridin-2(1H)-one following similar methods described earlier. After purification by reverse phase HPLC (ACN-H$_2$O containing 0.1% formic acid), the titled compound was obtained. $^1$H-NMR (400 MHz, CD$_3$OD) δ ppm 8.33 (d, J=2.6 Hz, 1H), 7.81 (dd, J=2.6, 8.8 Hz, 1H), 7.41 (d, J=2.0 Hz, 1H), 7.26 (d, J=2.0 Hz, 1H), 6.91 (d, J=8.8 Hz, 1H), 4.54 (s, 2H), 3.92 (m, 2H), 3.46-3.56 (m, 9H), 3.34 (m, 2H), 3.07-3.18 (m, 3H), 2.33 (s, 3H), 2.24 (d, J=3.2 Hz, 3H), 1.74-1.77 (m, 2H), 1.62-1.69 (m, 2H), 1.49 (s, 9H), 1.37 (dd, J=1.6, 6.8 Hz, 6H), 0.90 (t, J=6.8 Hz, 3H); MS (ES) (M+H) 705.7.

Step 5: Synthesis of 3-(Ethyl(tetrahydro-2H-pyran-4-yl)amino)-N-((5-fluoro-4-isopropyl-6-methyl-2-oxo-1,2-dihydropyridin-3-yl)methyl)-2-methyl-5-(6-(piperazin-1-yl)pyridin-3-yl)benzamide formate To a solution of tert-butyl 4-(5-(3-(ethyl(tetrahydro-2H-pyran-4-yl)amino)-5-(((5-fluoro-4-isopropyl-6-methyl-2-oxo-1,2-dihydropyridin-3-yl)methyl)carbamoyl)-4-methylphenyl)pyridin-2-yl)piperazine-1-carboxylate (450 mg, 0.639 mmol) in ethanol (4.3 mL) at room temperature was added 4 M HCl in dioxane (2 mL, 8.00 mmol). LC/MS after 2 h showed both product and remaining starting material. Additional 4 M HCl in 1,4-dioxane (1.5 ml, 6.00 mmol) was added, and LC/MS after total 4 h showed that reaction was completed. The reaction mixture was concentrated to dryness, azeotroped with toluene-methanol to give crude hydrochloride salt (454 mg, 111%). A 125 mg sample of crude hydrochloride salt was purified by reverse phase HPLC/MS (ACN-H$_2$O, 0.1% formic acid) to give 3-(ethyl(tetrahydro-2H-pyran-4-yl)amino)-N-((5-fluoro-4-isopropyl-6-methyl-2-oxo-1,2-dihydropyridin-3-yl)methyl)-2-methyl-5-(6-(piperazin-1-yl)pyridin-3-yl)benzamide formate (65 mg) as a colorless glassy film. $^1$H-NMR (400 MHz, CD$_3$OD) δ ppm 8.35-8.40 (m, 2H), 7.86 (dd, J=2.4, 8.8 Hz, 1H), 7.42 (d, J=1.6 Hz, 1H), 7.27 (d, J=1.6 Hz, 1H), 6.99 (d, J=8.8 Hz, 1H), 4.54 (s, 2H), 3.92 (m, 2H), 3.84 (m, 4H), 3.54 (m, 1H), 3.30-3.38 (m, 6H), 3.07-3.18 (m, 3H), 2.33 (s, 3H), 2.24 (d, J=2.8 Hz, 3H), 1.73-1.76 (m, 2H), 1.62-1.68 (m, 2H), 1.37 (d, J=6.8 Hz, 6H), 0.89 (t, J=6.8 Hz, 3H); MS (ES) (M+H) 605.6.

Example 196: Synthesis of 3-(ethyl(tetrahydro-2H-pyran-4-yl)amino)-N-((5-fluoro-4-isopropyl-6-methyl-2-oxo-1,2-dihydropyridin-3-yl)methyl)-2-methyl-5-(6-(4-methylpiperazin-1-yl)pyridin-3-yl)benzamide

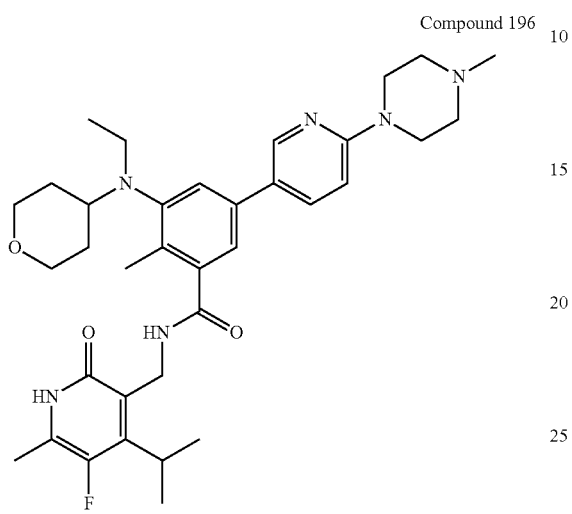

Compound 196

To a solution of 3-(ethyl(tetrahydro-2H-pyran-4-yl)amino)-N-((5-fluoro-4-isopropyl-6-methyl-2-oxo-1,2-dihydropyridin-3-yl)methyl)-2-methyl-5-(6-(piperazin-1-yl)pyridin-3-yl)benzamide hydrochloride (160 mg, 0.25 mmol) in methanol (2 mL) at 0° C. was added 35% solution of formaldehyde in water (0.196 mL, 2.495 mmol). After stirring for 20 min, sodium cyanoborohydride (31.4 mg, 0.499 mmol) was added. After 1.5 h at 0° C., the reaction was quenched with water (3 mL), cooling bath was removed, mixture was stirred for 10 min. Then DCM (10 mL) and saturated aq NaHCO₃ (1 mL) were added. The organic layer was separated and the aqueous layer was extracted with DCM (2×15 mL) and the combined organic extracts were dried over sodium sulfate, filtered and concentrated. The product was purified by reverse phase HPLC/MS (ACN-H₂O, 0.5% formic acid) to afford 3-(Ethyl (tetrahydro-2H-pyran-4-yl)amino)-N-((5-fluoro-4-isopropyl-6-methyl-2-oxo-1,2-dihydropyridin-3-yl)methyl)-2-methyl-5-(6-(4-methylpiperazin-1-yl)pyridin-3-yl)benzamide formate (31 mg, 0.047 mmol, 19% yield) as a colorless glassy film.

$^1$H-NMR (400 MHz, CD$_3$OD) δ ppm 8.42 (br. s, 1H), 8.38 (d, J=2.4 Hz, 1H), 7.85 (dd, J=2.8, 8.8 Hz, 1H), 7.42 (d, J=1.6 Hz, 1H), 7.27 (d, J=1.6 Hz, 1H), 6.98 (d, J=8.8 Hz, 1H), 4.54 (s, 2H), 3.91 (m, 2H), 3.82 (br. s, 4H), 3.54 (m, 1H), 3.31-3.38 (m, 2H), 3.05-3.21 (m, 7H), 2.81 (s, 3H), 2.33 (s, 3H), 2.24 (d, J=2.8 Hz, 3H), 1.73-1.76 (m, 2H), 1.58-1.68 (m, 2H), 1.37 (dd, J=1.6, 6.8 Hz, 6H), 0.89 (t, J=6.8 Hz, 3H); MS (ES) (M+H) 619.7.

Example 197: Synthesis of 3-(ethyl(tetrahydro-2H-pyran-4-yl)amino)-N-((5-fluoro-4-isopropyl-6-methyl-2-oxo-1,2-dihydropyridin-3-yl)methyl)-2-methyl-5-(6-(morpholinomethyl)pyridin-3-yl)benzamide

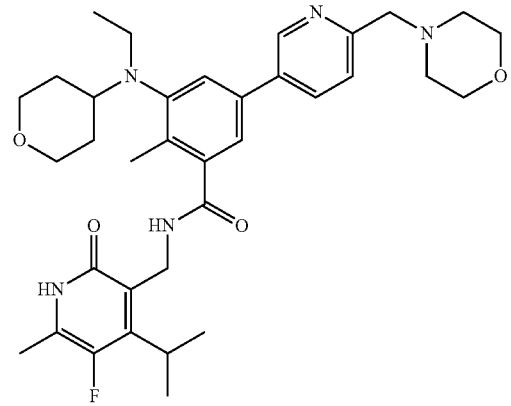

Compound 197

Step 1: Methyl 3-(ethyl(tetrahydro-2H-pyran-4-yl)amino)-2-methyl-5-(6-(morpholinomethyl)pyridin-3-yl)benzoate Compound 197 was prepared following the general procedure of Suzuki coupling reaction. $^1$H-NMR (400 MHz, CDCl$_3$) δ ppm 8.77 (dd, J=0.9, 2.4 Hz, 1H), 7.84 (dd, J=2.4, 7.9 Hz, 1H), 7.78 (d, J=1.8 Hz, 1H), 7.49 (d, J=7.9 Hz, 1H), 7.45 (d, J=2.1 Hz, 1H), 3.98 (m, 2H), 3.94 (s, 3H), 3.75-3.78 (m, 4H), 3.72 (s, 2H), 3.34 (m, 2H), 3.13 (q, J=7.1 Hz, 2H), 3.03 (m, 1H), 2.56 (m, 7H), 1.64-1.76 (m, 4H), 0.92 (t, J=7.1 Hz, 3H). MS (ES) (M+H)=454.5.

Step 2: 3-(Ethyl(tetrahydro-2H-pyran-4-yl)amino)-N-((5-fluoro-4-isopropyl-6-methyl-2-oxo-1,2-dihydropyridin-3-yl)methyl)-2-methyl-5-(6-(morpholinomethyl)pyridin-3-yl)benzamide formate Hydrolysis of methyl 3-(ethyl(tetrahydro-2H-pyran-4-yl)amino)-2-methyl-5-(6-(morpholinomethyl)pyridin-3-yl)benzoate following similar methods described earlier resulted in the corresponding carboxylic acid 3-(ethyl(tetrahydro-2H-pyran-4-yl) amino)-5-(6-(morpholinomethyl) pyridin-3-yl)benzoic acid. This acid was then coupled with 3-(aminomethyl)-5-fluoro-4-isopropyl-6-methylpyridin-2 (1H)-one following a similar method described earlier. After purification by reverse phase HPLC (ACN-H₂O containing 0.1% formic acid), the title compound was obtained. $^1$H-NMR (400 MHz, CD$_3$OD) δ ppm 8.77 (d, J=1.8 Hz, 1H), 8.25 (br. s, 1H), 8.07 (dd, J=2.3, 8.2 Hz, 1H), 7.61 (d, J=8.2 Hz, 1H), 7.52 (d, J=1.8 Hz, 1H), 7.37 (d, J=1.8 Hz, 1H), 4.54, (s, 2H), 3.97 (s, 2H), 3.91 (m, 2H), 3.78 (m, 4H), 3.55 (m, 1H), 3.35 (m, 2H), 3.08-3.20 (m, 3H), 2.81 (m, 4H), 2.36 (s, 3H), 2.24 (d, J=2.9 Hz, 3H), 1.60-1.77 (m, 4H), 1.37 (dd, J=1.5, 7.0 Hz, 6H), 0.90 (t, J=6.9 Hz, 3H). MS (ES) (M+H) 620.6.

Example 198: Bioassay Protocol and General Methods

Protocol for Wild-Type and Mutant PRC2 Enzyme Assays
General Materials.
S-adenosylmethionine (SAM), S-adenosylhomocyteine (SAH), bicine, KCl, Tween20, dimethylsulfoxide (DMSO)

and bovine skin gelatin (BSG) were purchased from Sigma-Aldrich at the highest level of purity possible. Dithiothreitol (DTT) was purchased from EMD. $^3$H-SAM was purchased from American Radiolabeled Chemicals with a specific activity of 80 Ci/mmol. 384-well streptavidin Flashplates were purchased from PerkinElmer.

Substrates.

Peptides representative of human histone H3 residues 21-44 containing either an unmodified lysine 27 (H3K27me0) or dimethylated lysine 27 (H3K27me2) were synthesized with a C-terminal G(K-biotin) linker-affinity tag motif and a C-terminal amide cap by 21$^{st}$ Century Biochemicals. The peptides were high-performance liquid chromatography (HPLC) purified to greater than 95% purity and confirmed by liquid chromatography mass spectrometry (LC-MS). The sequences are listed below.

```
H3K27me0:
                                    (SEQ ID NO: 1)
ATKAARKSAPATGGVKKPHRYRPGGK(biotin)-amide H3K27me2:
                                    (SEQ ID NO: 2)
ATKAARK(me2)SAPATGGVKKPHRYRPGGK(biotin)-amide
```

Chicken erythrocyte oligonucleosomes were purified from chicken blood according to established procedures.

Recombinant PRC2 Complexes.

Human PRC2 complexes were purified as 4-component enzyme complexes co-expressed in *Spodoptera fugiperda* (sf9) cells using a baculovirus expression system. The subunits expressed were wild-type EZH2 (NM_004456) or EZH2 Y641F, N, H, S or C mutants generated from the wild-type EZH2 construct, EED (NM_003797), Suz12 (NM_015355) and RbAp48 (NM_005610). The EED subunit contained an N-terminal FLAG tag that was used to purify the entire 4-component complex from sf9 cell lysates. The purity of the complexes met or exceeded 95% as determined by SDS-PAGE and Agilent Bioanalyzer analysis. Concentrations of enzyme stock concentrations (generally 0.3-1.0 mg/mL) was determined using a Bradford assay against a bovine serum albumin (BSA) standard.

General Procedure for PRC2 Enzyme Assays on Peptide Substrates.

The assays were all performed in a buffer consisting of 20 mM bicine (pH=7.6), 0.5 mM DTT, 0.005% BSG and 0.002% Tween20, prepared on the day of use. Compounds in 100% DMSO (1 μL) were spotted into polypropylene 384-well V-bottom plates (Greiner) using a Platemate 2×3 outfitted with a 384-channel pipet head (Thermo). DMSO (1 μL) was added to columns 11, 12, 23, 24, rows A-H for the maximum signal control, and SAH, a known product and inhibitor of PRC2 (1 μL) was added to columns 11, 12, 23, 24, rows I-P for the minimum signal control. A cocktail (40 μL) containing the wild-type PRC2 enzyme and H3K27me0 peptide or any of the Y641 mutant enzymes and H3K27me2 peptide was added by Multidrop Combi (Thermo). The compounds were allowed to incubate with PRC2 for 30 min at 25° C., then a cocktail (10 μL) containing a mixture of non-radioactive and $^3$H-SAM was added to initiate the reaction (final volume=51 L). In all cases, the final concentrations were as follows: wild-type or mutant PRC2 enzyme was 4 nM, SAH in the minimum signal control wells was 1 mM and the DMSO concentration was 1%. The final concentrations of the rest of the components are indicated in Table 2, below. The assays were stopped by the addition of non-radioactive SAM (10 μL) to a final concentration of 600 μM, which dilutes the $^3$H-SAM to a level where its incorporation into the peptide substrate is no longer detectable. 50 μL of the reaction in the 384-well polypropylene plate was then transferred to a 384-well Flashplate and the biotinylated peptides were allowed to bind to the streptavidin surface for at least 1 h before being washed three times with 0.1% Tween20 in a Biotek ELx405 plate washer. The plates were then read in a PerkinElmer TopCount platereader to measure the quantity of $^3$H-labeled peptide bound to the Flashplate surface, measured as disintegrations per minute (dpm) or alternatively, referred to as counts per minute (cpm).

TABLE 2

Final concentrations of components for each assay variation based upon EZH2 identity (wild-type or Y641 mutant EZH2)

| PRC2 Enzyme (denoted by EZH2 identity) | Peptide (nM) | Non-radioactive SAM (nM) | $^3$H-SAM (nM) |
| --- | --- | --- | --- |
| Wild-type | 185 | 1800 | 150 |
| Y641F | 200 | 850 | 150 |
| Y641N | 200 | 850 | 150 |
| Y641H | 200 | 1750 | 250 |
| Y641S | 200 | 1300 | 200 |
| Y641C | 200 | 3750 | 250 |

General Procedure for Wild-Type PRC2 Enzyme Assay on Oligonucleosome Substrate.

The assays was performed in a buffer consisting of 20 mM bicine (pH=7.6), 0.5 mM DTT, 0.005% BSG, 100 mM KCl and 0.002% Tween20, prepared on the day of use. Compounds in 100% DMSO (1 μL) were spotted into polypropylene 384-well V-bottom plates (Greiner) using a Platemate 2×3 outfitted with a 384-channel pipet head (Thermo). DMSO (1 μL) was added to columns 11, 12, 23, 24, rows A-H for the maximum signal control, and SAH, a known product and inhibitor of PRC2 (1 μL) was added to columns 11, 12, 23, 24, rows I-P for the minimum signal control. A cocktail (40 μL) containing the wild-type PRC2 enzyme and chicken erythrocyte oligonucleosome was added by Multidrop Combi (Thermo). The compounds were allowed to incubate with PRC2 for 30 min at 25° C., then a cocktail (10 μL) containing a mixture of non-radioactive and $^3$H-SAM was added to initiate the reaction (final volume=51 μL). The final concentrations were as follows: wild-type PRC2 enzyme was 4 nM, non-radioactive SAM was 430 nM, $^3$H-SAM was 120 nM, chicken erythrocyte oligonucleosome was 120 nM, SAH in the minimum signal control wells was 1 mM and the DMSO concentration was 1%. The assay was stopped by the addition of non-radioactive SAM (10 μL) to a final concentration of 600 μM, which dilutes the $^3$H-SAM to a level where its incorporation into the chicken erythrocyte oligonucleosome substrate is no longer detectable. 50 μL of the reaction in the 384-well polypropylene plate was then transferred to a 384-well Flashplate and the chicken erythrocyte nucleosomes were immobilized to the surface of the plate, which was then washed three times with 0.1% Tween20 in a Biotek ELx405 plate washer. The plates were then read in a PerkinElmer TopCount platereader to measure the quantity of $^3$H-labeled chicken erythrocyte oligonucleosome bound to the Flashplate surface, measured as disintegrations per minute (dpm) or alternatively, referred to as counts per minute (cpm).

% Inhibition Calculation

Where dpm=disintegrations per minute, cmpd=signal in assay well, and min and max are the respective minimum and maximum signal controls.

Four-parameter $IC_{50}$ fit $$Y = \text{Bottom} + \frac{(\text{Top} - \text{Bottom})}{1 + \left(\frac{X}{IC_{50}}\right)^{\text{Hill Coefficient}}}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

$IC_{50}$ values for the PRC2 enzyme assays on peptide substrates (e.g., EZH2 wild type and Y641F) are presented in Table 3 below.

WSU-DLCL2 Methylation Assay

WSU-DLCL2 suspension cells were purchased from DSMZ (German Collection of Microorganisms and Cell Cultures, Braunschweig, Germany). RPMI/Glutamax Medium, Penicillin-Streptomycin, Heat Inactivated Fetal Bovine Serum, and D-PBS were purchased from Life Technologies, Grand Island, N.Y., USA. Extraction Buffer and Neutralization Buffer (5×) were purchased from Active Motif, Carlsbad, Calif., USA. Rabbit anti-Histone H3 antibody was purchased from Abcam, Cambridge, Mass., USA. Rabbit anti-H3K27me3 and HRP-conjugated anti-rabbit-IgG were purchased from Cell Signaling Technology, Danvers, Mass., USA. TMB "Super Sensitive" substrate was sourced from BioFX Laboratories, Owings Mills, Md., USA. IgG-free Bovine Serum Albumin was purchased from Jackson ImmunoResearch, West Grove, Pa., USA. PBS with Tween (10×PBST) was purchased from KPL, Gaithersburg, Md., USA. Sulfuric Acid was purchased from Ricca Chemical, Arlington, Tex., USA. Immulon ELISA plates were purchased from Thermo, Rochester, N.Y., USA. V-bottom cell culture plates were purchased from Corning Inc., Corning, N.Y., USA. V-bottom polypropylene plates were purchased from Greiner Bio-One, Monroe, N.C., USA.

WSU-DLCL2 suspension cells were maintained in growth medium (RPMI 1640 supplemented with 10% v/v heat inactivated fetal bovine serum and 100 units/mL penicillin-streptomycin) and cultured at 37° C. under 5% $CO_2$. Under assay conditions, cells were incubated in Assay Medium (RPMI 1640 supplemented with 20% v/v heat inactivated fetal bovine serum and 100 units/mL penicillin-streptomycin) at 37° C. under 5% $CO_2$ on a plate shaker.

WSU-DLCL2 cells were seeded in assay medium at a concentration of 50,000 cells per mL to a 96-well V-bottom cell culture plate with 200 L per well. Compound (1 µL) from 96 well source plates was added directly to V-bottom cell plate. Plates were incubated on a titer-plate shaker at 37° C., 5% CO2 for 96 hours. After four days of incubation, plates were spun at 241×g for five minutes and medium was aspirated gently from each well of cell plate without disturbing cell pellet. Pellet was resuspended in 200 L DPBS and plates were spun again at 241×g for five minutes. The supernatant was aspirated and cold (4° C.) Extraction buffer (100 µL) was added per well. Plates were incubated at 4° C. on orbital shaker for two hours. Plates were spun at 3427× g×10 minutes. Supernatant (80 µL per well) was transferred to its respective well in 96 well V-bottom polypropylene plate. Neutralization Buffer 5× (20 µL per well) was added to V-bottom polypropylene plate containing supernatant. V-bottom polypropylene plates containing crude histone preparation (CHP) were incubated on orbital shaker×five minutes. Crude Histone Preparations were added (2 µL per well) to each respective well into duplicate 96 well ELISA plates containing 100 µL Coating Buffer (1×PBS+BSA 0.05% w/v). Plates were sealed and incubated overnight at 4° C. The following day, plates were washed three times with 300 µL per well 1×BST. Wells were blocked for two hours with 300 L per well ELISA Diluent ((PBS (1×) BSA (2% w/v) and Tween20 (0.05% v/v)). Plates were washed three times with 1×PBST. For the Histone H3 detection plate, 100 µL per well were added of anti-Histone-H3 antibody (Abcam, ab1791) diluted 1:10,000 in ELISA Diluent. For H3K27 trimethylation detection plate, 100 µL per well were added of anti-H3K27me3 diluted 1:2000 in ELISA diluent. Plates were incubated for 90 minutes at room temperature. Plates were washed three times with 300 L 1×PBST per well. For Histone H3 detection, 100 µL of HRP-conjugated anti-rabbit IgG antibody diluted to 1:6000 in ELISA diluent was added per well. For H3K27me3 detection, 100 L of HRP conjugated anti-rabbit IgG antibody diluted to 1:4000 in ELISA diluent was added per well. Plates were incubated at room temperature for 90 minutes. Plates were washed four times with 1×PBST 300 µL per well. TMB substrate 100 µL was added per well. Histone H3 plates were incubated for five minutes at room temperature. H3K27me3 plates were incubated for 10 minutes at room temperature. The reaction was stopped with sulfuric acid 1N (100 µL per well). Absorbance for each plate was read at 450 nm.

First, the ratio for each well was determined by:

$$\left(\frac{H3\ K27me3\ OD450\ \text{value}}{Histons\ H3\ OD450\ \text{value}}\right)$$

Each plate included eight control wells of DMSO only treatment (Minimum Inhibition) as well as eight control wells for maximum inhibition (Background wells).

The average of the ratio values for each control type was calculated and used to determine the percent inhibition for each test well in the plate. Test compound was serially diluted three-fold in DMSO for a total of ten test concentrations, beginning at 25 µM. Percent inhibition was determined and $IC_{50}$ curves were generated using duplicate wells per concentration of compound. $IC_{50}$ values for this assay are presented in Table 3 below.

Percent Inhibition = 100 −

$$\left(\left(\frac{\text{Individual Test Sample Ratio}) - (\text{Background } Avg\ \text{Ratio})}{(\text{Minimum Inhibition Ratio}) - (\text{Background Average Ratio})}\right) * 100\right)$$

Cell Proliferation Analysis

WSU-DLCL2 suspension cells were purchased from DSMZ (German Collection of Microorganisms and Cell Cultures, Braunschweig, Germany). RPMI/Glutamax Medium, Penicillin-Streptomycin, Heat Inactivated Fetal Bovine Serum were purchased from Life Technologies, Grand Island, N.Y., USA. V-bottom polypropylene 384-well plates were purchased from Greiner Bio-One, Monroe, N.C., USA. Cell culture 384-well white opaque plates were purchased from Perkin Elmer, Waltham, Mass., USA. Cell-Titer Glo® was purchased from Promega Corporation, Madison, Wis., USA. SpectraMax M5 plate reader was purchased from Molecular Devices LLC, Sunnyvale, Calif., USA.

WSU-DLCL2 suspension cells were maintained in growth medium (RPMI 1640 supplemented with 10% v/v heat inactivated fetal bovine serum and cultured at 37° C. under 5% $CO_2$. Under assay conditions, cells were incubated in Assay Medium (RPMI 1640 supplemented with 20% v/v heat inactivated fetal bovine serum and 100 units/mL penicillin-streptomycin) at 37° C. under 5% $CO_2$.

For the assessment of the effect of compounds on the proliferation of the WSU-DLCL2 cell line, exponentially growing cells were plated in 384-well white opaque plates at a density of 1250 cell/ml in a final volume of 50 μl of assay medium. A compound source plate was prepared by performing triplicate nine-point 3-fold serial dilutions in DMSO, beginning at 10 mM (final top concentration of compound in the assay was 20 μM and the DMSO was 0.2%). A 100 nL aliquot from the compound stock plate was added to its respective well in the cell plate. The 100% inhibition control consisted of cells treated with 200 nM final concentration of staurosporine and the 0% inhibition control consisted of DMSO treated cells. After addition of compounds, assay plates were incubated for 6 days at 37° C., 5% $CO_2$, relative humidity >90% for 6 days. Cell viability was measured by quantization of ATP present in the cell cultures, adding 35 μl of Cell Titer Glo® reagent to the cell plates. Luminescence was read in the SpectraMax M5. The concentration inhibiting cell viability by 50% was determined using a 4-parametric fit of the normalized dose response curves. $IC_{50}$ values for this assay are also presented in Table 3 below.

TABLE 3

| Compound No. | EZH2 IC50 peptide v2 (μM) | Y641F $IC_{50}$ (μM) | WSU prolif $IC_{50}$ (μM) | WSU ELISA $IC_{50}$ (μM) |
|---|---|---|---|---|
| 1 | 0.01745 | | 0.56475 | |
| 2 | 0.0549 | | | |
| 3 | 0.24203 | | | |
| 4 | 0.28847 | | | |
| 5 | 11.21319 | | | |
| 6 | 0.12452 | | | |
| 7 | 28.43469 | | | |
| 8 | 0.13466 | | | |
| 9 | 0.169 | | | |
| 10 | 0.10131 | | | |
| 11 | 0.01409 | | 1.46188 | |
| 12 | 0.07053 | | | |
| 13 | 0.03835 | | | |
| 14 | 0.05688 | | | |
| 15 | 0.1125 | | | |
| 16 | 0.05995 | | | |
| 17 | 0.02059 | | | |
| 18 | 0.11596 | | | |
| 19 | 0.05865 | | | |
| 20 | 0.03908 | | | |
| 21 | 0.04017 | | | |
| 22 | 0.09501 | | | |
| 23 | 0.04153 | | | |
| 24 | 0.03473 | 0.0101 | | |
| 25 | 0.05556 | | | |
| 26 | 0.0396 | 0.0273 | | |
| 27 | 0.02365 | 0.00721 | 2.88863 | |
| 28 | 0.03924 | | | |
| 29 | 0.0919 | | | |
| 30 | 0.11932 | | | |
| 31 | 0.045 | | | |
| 32 | 0.06179 | | | |
| 35 | 0.04574 | 0.01625 | | |
| 36 | 0.0149 | 0.00845 | 1.54311 | |
| 37 | 0.02701 | 0.05492 | | |
| 38 | 0.0821 | 0.06699 | | |
| 39 | 0.01275 | 0.01432 | 0.44838 | |
| 40 | 0.03107 | 0.01129 | | |
| 41 | 0.03176 | 0.01044 | | |
| 42 | 0.04322 | 0.02206 | | |
| 43 | 0.02548 | 0.03009 | 0.8697 | |
| 44 | 0.01299 | 0.01107 | 0.369 | 0.29 |
| 45 | 0.07098 | 0.06219 | | |
| 46 | 0.0999 | 0.07546 | | |
| 47 | 0.03985 | 0.02028 | | |
| 48 | 0.09673 | 0.07426 | | |
| 49 | 0.0675 | 0.04624 | | |
| 50 | 0.05468 | 0.0484 | | |
| 51 | 0.1252 | 0.1399 | | |
| 52 | 0.05805 | 0.03053 | | |
| 53 | 0.05837 | 0.05602 | | |
| 54 | 0.01367 | 0.01527 | 2.40618 | |
| 55 | 0.06006 | 0.02521 | | |
| 56 | 0.03609 | 0.01737 | | |
| 57 | 0.03226 | 0.02333 | | |
| 59 | 0.01098 | 0.01513 | 0.52906 | |
| 60 | 0.23283 | 0.21286 | | |
| 61 | 0.04662 | 0.0414 | | |
| 62 | 0.17274 | 0.26915 | | |
| 63 | 0.0857 | 0.06826 | | |
| 64 | 0.01055 | 0.01235 | | |
| 65 | 0.01132 | 0.0089 | 0.15349 | |
| 66 | 0.07159 | 0.04481 | 0.16735 | |
| 67 | 0.00653 | 0.00586 | 0.11483 | |
| 68 | 0.01343 | 0.02623 | 0.19913 | |
| 69 | 0.00349 | 0.0026 | 0.10184 | |
| 70 | 0.03787 | 0.02958 | 0.20278 | |
| 71 | 0.00415 | 0.00219 | 0.18483 | |
| 72 | 0.01052 | 0.00841 | 0.27494 | |
| 73 | 0.00884 | 0.00698 | 0.17821 | |
| 74 | 0.00842 | 0.00632 | 0.24789 | |
| 75 | 0.00507 | 0.00348 | 0.07676 | |
| 76 | 0.00374 | 0.00572 | 0.09675 | |
| 77 | 0.00989 | 0.00512 | 0.15768 | |
| 78 | 0.00324 | 0.00476 | 2.64294 | |
| 79 | 0.00608 | 0.00778 | 0.15765 | |
| 80 | 0.00311 | 0.00388 | 0.14286 | |
| 81 | 0.01054 | 0.01073 | 0.40873 | |
| 82 | 0.00352 | 0.00281 | 0.11923 | |
| 83 | 0.00544 | 0.00418 | 0.18335 | |
| 84 | 0.01128 | 0.00612 | 0.27874 | |
| 86 | 0.00499 | 0.00112 | 0.42897 | |
| 87 | 0.00568 | 0.00429 | 0.15758 | 0.3332 |
| 88 | 0.00856 | 0.00591 | 0.15727 | |
| 89 | 0.00546 | | 0.46186 | |
| 90 | 0.00199 | 0.00361 | 0.15639 | |
| 91 | 0.00315 | 0.00052 | 0.13796 | |
| 92 | 0.01169 | 0.01936 | | |
| 93 | 0.00258 | 0.00087 | 0.10715 | |
| 94 | 0.00246 | 0.00207 | 0.08649 | |
| 95 | 0.00277 | 0.00155 | 0.49957 | |
| 96 | 0.01193 | 0.00899 | 1.52182 | |
| 97 | 0.0034 | 0.00296 | 0.08061 | |
| 98 | 0.00582 | 0.00708 | 0.35879 | |
| 99 | 0.00237 | 0.00256 | 0.37993 | |
| 100 | 0.02155 | 0.0297 | 0.43561 | |
| 101 | 0.00446 | 0.01163 | 0.79789 | |
| 102 | 0.02536 | 0.01484 | 0.58584 | |
| 103 | 0.00502 | 0.0082 | 0.35135 | |
| 104 | 0.00963 | 0.01291 | 0.33294 | |
| 105 | 0.00451 | 0.01065 | 0.16055 | |
| 108 | 0.02337 | | 2.54651 | |
| 109 | 0.01921 | 0.01627 | 0.68878 | |

TABLE 3-continued

| Compound No. | EZH2 IC50 peptide v2 (μM) | Y641F IC$_{50}$ (μM) | WSU prolif IC$_{50}$ (μM) | WSU ELISA IC$_{50}$ (μM) |
|---|---|---|---|---|
| 110 | 0.00591 | 0.01239 | 0.11551 | |
| 111 | 0.00766 | 0.00718 | | |
| 112 | 0.01831 | 0.01171 | 1.17698 | |
| 113 | 0.01883 | 0.01083 | 0.35799 | |
| 114 | 0.01503 | 0.01044 | 0.50615 | |
| 115 | 0.00783 | 0.00446 | 0.21772 | |
| 116 | 1.79155 | 1.2309 | | |
| 117 | 3.81396 | 2.30794 | >20.0 uM | |
| 118 | 0.53042 | 0.388 | 4.87739 | |
| 119 | 1.5035 | 0.65543 | >20.0 uM | |
| 120 | 0.03304 | 0.01566 | 0.31157 | |
| 121 | 0.03614 | 0.03716 | 0.29603 | |
| 122 | 0.10684 | 0.07602 | 0.70354 | |
| 123 | 0.01159 | 0.01009 | 0.29189 | |
| 124 | 0.0129 | 0.00879 | 0.29994 | |
| 125 | 0.02473 | 0.02022 | 0.44695 | |
| 126 | 0.01495 | 0.01178 | 0.4696 | |
| 127 | 0.01177 | 0.02567 | 0.3175 | |
| 128 | 0.00594 | 0.00695 | 0.26136 | |
| 129 | 0.01782 | 0.02561 | 0.29282 | |
| 130 | 0.01581 | 0.03293 | 0.63755 | |
| 131 | 0.01136 | 0.02444 | 0.38733 | |
| 132 | 0.00466 | 0.01225 | 0.71249 | |
| 133 | 0.01687 | 0.02975 | 0.49827 | |
| 134 | 0.01118 | 0.0189 | 0.49018 | |
| 135 | 0.02757 | 0.0484 | 11.06003 | |
| 136 | 0.04262 | 0.08657 | 12.29135 | |
| 137 | 0.03317 | 0.02548 | 1.56152 | |
| 138 | 0.01173 | | 1.40104 | |
| 139 | 0.00707 | 0.00503 | 0.30711 | |
| 140 | 0.00369 | 0.00454 | 0.37804 | |
| 141 | 0.00151 | 0.00195 | 0.07815 | 0.05978 |
| 142 | 1.20523 | 0.88814 | 13.37514 | |
| 143 | 0.00319 | 0.01274 | 0.174 | |
| 144 | 0.00806 | 0.00791 | 0.9863 | |
| 145 | 0.00139 | 0.00553 | 0.44891 | |
| 146 | 0.01633 | 0.01575 | 1.45675 | |
| 147 | 0.00344 | 0.00794 | 0.19934 | |
| 148 | 0.01171 | 0.02295 | 0.18403 | |
| 149 | 0.04316 | 0.07359 | 0.63041 | |
| 150 | 0.01596 | 0.0559 | 1.46316 | |
| 151 | 0.03901 | 0.03888 | | |
| 152 | 0.01101 | 0.02114 | 0.4062 | |
| 153 | 0.00437 | 0.00603 | 0.29683 | |
| 154 | 0.02378 | 0.02848 | | |
| 155 | 0.01732 | 0.01753 | 1.23055 | |
| 156 | 0.00357 | 0.00814 | 0.1114 | |
| 158 | 0.0043 | 0.00509 | 0.27572 | |
| 159 | 0.01524 | 0.01214 | 1.74831 | |
| 160 | 0.01211 | 0.01466 | | |
| 161 | 0.00438 | 0.00471 | | |
| 162 | 0.00574 | 0.00679 | | |
| 163 | 0.00981 | 0.00995 | 4.04577 | |
| 164 | 0.01324 | 0.00514 | 0.5309 | |
| 165 | 0.01133 | 0.00498 | 0.54719 | |
| 166 | 0.04563 | 0.01346 | 0.80396 | |
| 167 | 0.02564 | 0.00796 | 0.24542 | |
| 168 | 0.00995 | | 0.59705 | |
| 169 | 0.01238 | 0.00274 | 3.26552 | |
| 170 | 0.00579 | 0.00163 | 0.41075 | |
| 171 | 0.00397 | 0.00076 | 0.3574 | 0.35597 |
| 172 | 0.00926 | 0.00421 | | |
| 173 | 0.01293 | 0.00928 | 0.62489 | |
| 174 | 0.0067 | 0.00289 | 0.38381 | |
| 175 | 0.01195 | 0.00955 | 0.28812 | |
| 176 | 0.01339 | 0.01035 | 0.37475 | |
| 177 | >10.0 uM | 3.28759 | 8.1459 | |
| 178 | 0.01447 | 0.00507 | | |
| 179 | 0.24404 | 0.18351 | | >25.0 uM |
| 180 | 0.00994 | 0.00807 | | |
| 181 | 0.00512 | 0.00223 | | |
| 182 | 0.00666 | 0.00569 | | |
| 183 | 0.00466 | 0.00387 | | 1.52598 |
| 184 | 0.00092 | | | 0.57596 |
| 185 | 0.00338 | 0.00374 | | 0.41458 |
| 186 | 0.00984 | | | 0.52611 |
| 188 | 0.01121 | | | 0.52668 |
| 189 | 0.00164 | 0.00182 | | 0.1809 |
| 190 | 0.01559 | | | 0.53272 |
| 191 | 0.00384 | 0.00282 | | 0.37332 |
| 192 | 0.00322 | | | 0.34642 |
| 193 | 0.00675 | 0.0082 | | 0.34313 |
| 194 | 0.00462 | 0.00536 | | 0.64562 |

Example 199: Derivation of the Lowest Cytotoxic Concentration (LCC)

It is well established that cellular proliferation proceeds through cell division that results in a doubling of the number of cells after division, relative to the number of cells prior to division. Under a fixed set of environmental conditions (e.g., pH, ionic strength, temperature, cell density, medium content of proteins and growth factors, and the like) cells will proliferate by consecutive doubling (i.e., division) according to the following equation, provided that sufficient nutrients and other required factors are available.

$$N_t = N_0 \times 2^{\frac{t}{t_D}} \tag{A.1}$$

where $N_t$ is the cell number at a time point (t) after initiation of the observation period, No is the cell number at the initiation of the observation period, t is the time after initiation of the observation period and $t_D$ is the time interval required for cell doubling, also referred to as the doubling time. Equation A.1 can be converted into the more convenient form of an exponential equation in base e, taking advantage of the equality, $0.693 = \ln(2)$.

$$N_t = N_0 e^{\frac{0.693 t}{t_D}} \tag{A.2}$$

The rate constant for cell proliferation ($k_p$) is inversely related to the doubling time as follows.

$$k_p = \frac{0.693}{t_D} \tag{A.3}$$

Combining equation A.2 and A.3 yields, $$N_t = N_0 e^{k_p t} \tag{A.4}$$

Thus, according to equation A.4 cell number is expected to increase exponentially with time (FIG. 1 A) during the early period of cell growth referred to as log-phase growth. Exponential equations like equation A.4 can be linearized by taking the natural logarithm of each side.

$$\ln(N_t) \ln(N_0) + k_p t \tag{A.5}$$

Figure 1:
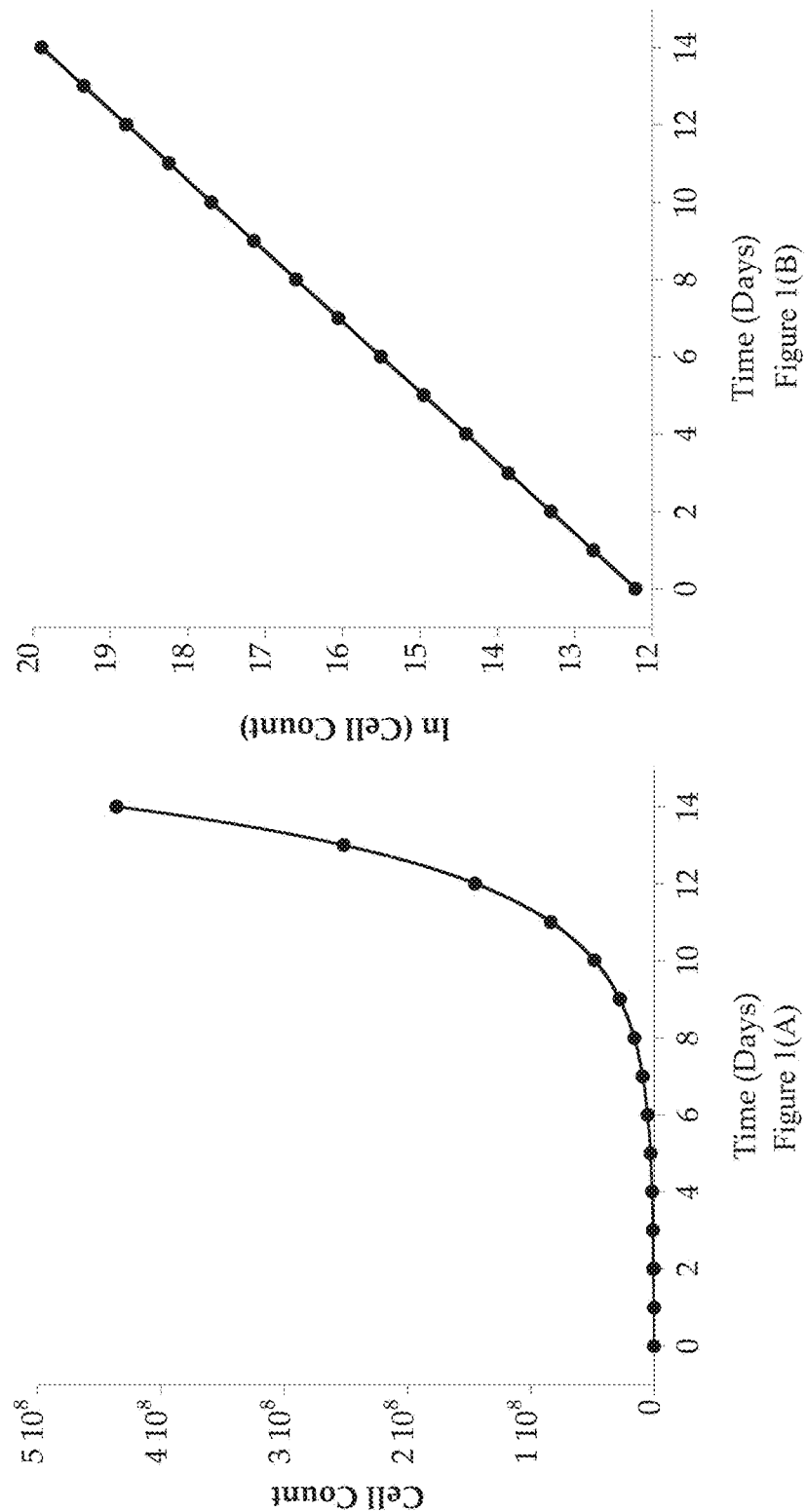
FIG. 1 (A) is an idealized plot of cell count (i.e., cell number) as a function of time showing exponential proliferation during log-phase cell growth.

Thus a plot of $\ln(N_t)$ as a function of time is expected to yield an ascending straight line with slope equal to $k_p$ and y-intercept equal to $\ln(N_0)$, as illustrated in FIG. 1 B.

Changes in environmental conditions can result in a change in the rate of cellular proliferation that is quantifiable as changes in the proliferation rate constant $k_p$. Among conditions that may result in a change in proliferation rate is the introduction to the system of an antiproliferative compound at the initiation of the observation period (i.e., at t=0). When an antiproliferative compound has an immediate impact on cell proliferation, one expects that plots of $\ln(N_t)$ as a function of time will continue to be linear at all compound concentrations, with diminishing values of $k_p$ at increasing concentrations of compound.

Depending on the mechanistic basis of antiproliferative action, some compounds may not immediately effect a change in proliferation rate. Instead, there may be a period of latency before the impact of the compound is realized. In such cases a plot of $\ln(N_t)$ as a function of time will appear biphasic, and a time point at which the impact of the compound begins can be identified as the breakpoint between phases (FIG. 2). Regardless of whether a compound's impact on proliferation is immediate or begins after a latency period, the rate constant for proliferation at each compound concentration is best defined by the slope of the $\ln(N_t)$ vs. time curve from the time point at which compound impact begins to the end of the observation period of the experiment.

A compound applied to growing cells may affect the observed proliferation in one of two general ways: by inhibiting further cell division (cytostasis) or by cell killing (cytotoxicity). If a compound is cytostatic, increasing concentration of compound will reduce the value of $k_p$ until there is no further cell division. At this point, the rate of cell growth, and therefore the value of $k_p$, will be zero. If, on the other hand, the compound is cytotoxic, then the value of $k_p$ will be composed of two rate constants: a rate constant for continued cell growth in the presence of the compound ($k_g$) and a rate constant for cell killing by the compound ($k_d$). The overall rate constant for proliferation at a fixed concentration of compound will thus be the difference between the absolute values of these opposing rate constants.

$$k_p = |k_g| - |k_d| \quad (A.6)$$

At compound concentrations for which the rate of cell growth exceeds that of cell killing, the value of $k_p$ will have a positive value (i.e., $k_p$>0). At compound concentrations for which the rate of cell growth is less than that for cell killing, the value of $k_p$ will have a negative value (i.e., $k_p$<0) and the cell number will decrease with time, indicative of robust cytotoxicity. When $k_g$ exactly matches $k_d$ then the overall proliferation rate constant, $k_p$, will have a value of zero. We can thus define the lowest cytotoxic concentration (LCC) as that concentration of compound that results in a value of $k_p$ equal to zero, because any concentration greater than this will result in clearly observable cytotoxicity. Nota bene: at concentrations below the LCC there is likely to be cell killing occurring, but at a rate that is less than that of residual cell proliferation. The treatment here is not intended to define the biological details of compound action. Rather, the goal here is to merely define a practical parameter with which to objectively quantify the concentration of compound at which the rate of cell killing exceeds new cell growth. Indeed, the LCC represents a breakpoint or critical concentration above which frank cytotoxicity is observed, rather than a cytotoxic concentration per se. In this regard, the LCC can be viewed similar to other physical breakpoint metrics, such as the critical micelle concentration (CMC) used to define the concentration of lipid, detergent or other surfactant species above which all molecules incorporate into micellar structures.

Traditionally, the impact of antiproliferative compounds on cell growth has been most commonly quantified by the $IC_{50}$ value, which is defined as that concentration of compound that reduces the rate of cell proliferation to one half that observed in the absence of compound (i.e., for the vehicle or solvent control sample; FIG. 2). The $IC_{50}$, however, does not allow the investigator to differentiate between cytostatic and cytotoxic compounds. The LCC, in contrast, readily allows one to make such a differentiation and to further quantify the concentration at which the transition to robust cytotoxic behavior occurs.

If one limits the observation time window to between the start of impact (as defined above and in FIG. 2) and the end of the experiment, then the data will generally fit well to a linear equation when plotted as $\ln(N_t)$ as a function of time (vide supra). From fits of this type, the value of $k_p$ can be determined at each concentration of compound tested. A replot of the value of $k_p$ as a function of compound concentration ([I]) will have the form of a descending isotherm, with a maximum value at [I]=0 of $k_{max}$ (defined by the vehicle or solvent control sample) and a minimum value at infinite compound concentration of $k_{min}$ (FIG. 3).

$$k_p = \frac{(k_{max} - k_{min})}{1 + \frac{[I]}{I_{mid}}} + k_{min} \quad (A.7)$$

where $I_{mid}$ is the concentration of compound yielding a value of $k_p$ that is midway between the values of $k_{max}$ and $k_{min}$ (note that the value of $I_{mid}$ is not the same as the $IC_{50}$, except in the case of a complete and purely cytostatic compound). Thus, fitting the replot data to equation A.7 provides estimates of $k_{max}$, $k_{min}$ and $I_{mid}$. If a compound is cytostatic (as defined here), the value of $k_{min}$ cannot be less than zero. For cytotoxic compounds, $k_{min}$ will be less than zero and the absolute value of $k_{min}$ will relate directly to the effectiveness of the compound in killing cells.

The fitted values derived from equation A.7 can also be used to determine the value of the LCC. By definition, when [I]=LCC, $k_p$=0. Thus, under these conditions equation A.7 becomes.

$$0 = \frac{(k_{max} - k_{min})}{1 + \frac{LCC}{I_{mid}}} + k_{min} \quad (A.8)$$

Algebraic rearrangement of equation A.8 yields an equation for the LCC.

$$LCC = I_{mid}\left[\left(\frac{k_{max} - k_{min}}{-k_{min}}\right) - 1\right] \quad (A.9)$$

This analysis is simple to implement with nonlinear curve fitting software and may be applied during cellular assays of compound activity throughout the drug discovery and development process. In this manner, the LCC may provide a valuable metric for the assessment of compound SAR (structure-activity relationship).

Table 4 below provides LCC and $IC_{50}$ data for certain compounds of the invention on WSU-DLCL2 cells.

TABLE 4

| Compound No. | 11-day LCC (uM) WSU-DLCL2 | IC50 (uM) WSU-DLCL2 |
|---|---|---|
| 1 | 0.68 | 0.087 |
| 2 | 1.79 | 0.082 |
| 13 | 0.707 | 0.018 |
| 17 | 3.32 | 0.0072 |
| 36 | 0.368 | 0.011 |
| 44 | 0.182 | 0.0093 |
| 59 | 3.15 | 0.026 |
| 65 | 0.122 | 0.0018 |
| 69 | 0.0811 | 0.0062 |
| 75 | 0.0559 | 0.00097 |
| 87 | 0.0597 | 0.0057 |
| 67 | 0.084 | 0.0028 |
| 76 | 0.165 | 0.0062 |
| 141 | 0.0153 | 0.0023 |

Example 200: In Vivo Assays

Mice

Female Fox Chase SCID® Mice (CB 17/Icr-Prkdc$_{scid}$/IcrIcoCrl, Charles River Laboratories) or athymic nude mice (Crl:NU(Ncr)-Foxn1$_{nu}$, Charles River Laboratories) were 8 weeks old and had a body-weight (BW) range of 16.0-21.1 g on D1 of the study. The animals were fed ad libitum water (reverse osmosis 1 ppm Cl) and NIH 31 Modified and Irradiated Lab Diet® consisting of 18.0% crude protein, 5.0% crude fat, and 5.0% crude fiber. The mice were housed on irradiated Enrich-o'cobs™ bedding in static microisolators on a 12-hour light cycle at 20-22° C. (68-72° F.) and 40-60% humidity. All procedures comply with the recommendations of the *Guide for Care and Use of Laboratory Animals* with respect to restraint, husbandry, surgical procedures, feed and fluid regulation, and veterinary care.

Tumor Cell Culture

Human lymphoma cell lines line were obtained from different sources (ATCC, DSMZ), e.g., WSU-DLCL2 obtained from DSMZ. The cell lines were maintained at Piedmont as suspension cultures in RPMI-1640 medium containing 100 units/mL penicillin G sodium salt, 100 g/mL streptomycin, and 25 g/mL gentamicin. The medium was supplemented with 10% fetal bovine serum and 2 mM glutamine. The cells were cultured in tissue culture flasks in a humidified incubator at 37° C., in an atmosphere of 5% $CO_2$ and 95% air.

In Vivo Tumor Implantation

Human lymphoma cell lines, e.g., WSU-DLCL2 cells, were harvested during mid-log phase growth, and re-suspended in PBS with 50% Matrigel™ (BD Biosciences). Each mouse received $1 \times 10^7$ cells (0.2 mL cell suspension) subcutaneously in the right flank. Tumors were calipered in two dimensions to monitor growth as the mean volume approached the desired 80-120 mm³ range. Tumor size, in mm³, was calculated from:

$$\text{Tumor volume} = \frac{w^2 \times l}{2}$$

where w=width and l=length, in mm, of the tumor. Tumor weight can be estimated with the assumption that 1 mg is equivalent to 1 mm$_3$ of tumor volume. After 10-30 days mice with 108-126 mm³ tumors were sorted into treatment groups with mean tumor volumes of 117-119 mm³.

Test Articles

Test compounds were stored at room temperature and protected from light. On each treatment day, fresh compound formulations (e.g., formulation of Compound 44 tri-HCl salt or Compound 87 tri-HCl salt), were prepared by suspending the powders in 0.5% sodium carboxymethylcellulose (NaCMC) and 0.1% Tween® 80 in deionized water. Compound 141 (free base) was dissolved in sterile saline and the pH was adjusted to 4.5 with HCl fresh every day. The vehicles, 0.5% NaCMC and 0.1% Tween® 80 in deionized water or sterile saline pH 4.5, were used to treat the control groups at the same schedules. Formulations were stored away from light at 4° C. prior to administration. Unless otherwise specified, compounds referred to and tested in this experiment were in their specific salt forms mentioned in this paragraph.

Treatment Plan

Mice were treated at compound doses ranging from 12.5-600 mg/kg and at TID (three time a day every 8 h), BID (2 times a day every 12 h) or QD (once a day) schedules for various amounts of days by oral gavage (Compound 44 or 87) or injections via the intraperitoneal route (Compound 141). Each dose was delivered in a volume of 0.2 mL/20 g mouse (10 mL/kg), and adjusted for the last recorded weight of individual animals. The maximal treatment length was 28 days.

Median Tumor Volume (MTV) and Tumor Growth Inhibition (TGI) Analysis

Treatment efficacy was determined on the last treatment day. MTV(n), the median tumor volume for the number of animals, n, evaluable on the last day, was determined for each group. Percent tumor growth inhibition (% TGI) can be defined several ways. First, the difference between the MTV(n) of the designated control group and the MTV(n) of the drug-treated group is expressed as a percentage of the MTV(n) of the control group:

$$\% \ TGI = \left( \frac{MTV(n)_{control} - MTV(n)_{treated}}{MTV(n)_{control}} \right) \times 100$$

Another way of calculating % TGI is taking the change of the tumor size from day 1 to day n into account with n being the last treatment day.

$$\% \ TGI = \left( \frac{\Delta MTV_{control} - \Delta MTV_{treated}}{\Delta MTV_{control}} \right) \times 100$$

$$\Delta MTV_{control} = MTV(n)_{control} - MTV(1)_{control}$$

$$\Delta MTV_{treated} = MTV(n)_{treated} - MTV(1)_{treated}$$

Toxicity

Animals were weighed daily on Days 1-5, and then twice weekly until the completion of the study. The mice were examined frequently for overt signs of any adverse, treatment related side effects, which were documented. Acceptable toxicity for the maximum tolerated dose (MTD) was defined as a group mean BW loss of less than 20% during the test, and not more than 10% mortality due to TR deaths. A death was to be classified as TR if it was attributable to treatment side effects as evidenced by clinical signs and/or necropsy, or due to unknown causes during the dosing period. A death was to be classified as NTR if there was evidence that the death was unrelated to treatment side effects. NTR deaths during the dosing interval would typically be categorized as NTRa (due to an accident or human error) or NTRm (due to necropsy-confirmed tumor dissemination by invasion and/or metastasis). Orally treated animals that die from unknown causes during the dosing period may be classified as NTRu when group performance does not support a TR classification and necropsy, to rule out a dosing error, is not feasible.

Sampling

On days 7 or 28 during the studies mice were sampled in a pre-specified fashion to assess target inhibition in tumors. Tumors were harvested from specified mice under RNAse free conditions and bisected. Frozen tumor tissue from each animal was snap frozen in liquid N2 and pulverized with a mortar and pestle.

Statistical and Graphical Analyses

All statistical and graphical analyses were performed with Prism 3.03 (GraphPad) for Windows. To test statistical significance between the control and treated groups over the whole treatment time course a repeated measures ANOVA test followed by Dunnets multiple comparison post test or a 2 way ANOVA test were employed. Prism reports results as non-significant (ns) at P>0.05, significant (symbolized by "*") at $0.01<P<0.05$, very significant ("") at $0.001<P<0.01$ and extremely significant ("*") at $P<0.001$.

Histone Extraction

For isolation of histones, 60-90 mg tumor tissue was homogenized in 1.5 ml nuclear extraction buffer (10 mM Tris-HCl, 10 mM MgCl2, 25 mM KCl, 1% Triton X-100, 8.6% Sucrose, plus a Roche protease inhibitor tablet 1836145) and incubated on ice for 5 minutes. Nuclei were collected by centrifugation at 600 g for 5 minutes at 4° C. and washed once in PBS. Supernatant was removed and histones extracted for one hour, with vortexing every 15 minutes, with 0.4 N cold sulfuric acid. Extracts were clarified by centrifugation at 10000 g for 10 minutes at 4° C. and transferred to a fresh microcentrifuge tube containing 10× volume of ice cold acetone. Histones were precipitated at −20° C. for 2 hours-overnight, pelleted by centrifugation at 10000 g for 10 minutes, and resuspended in water.

ELISA

Histones were prepared in equivalent concentrations in coating buffer (PBS+0.05% BSA) yielding 0.5 ng/ul of sample, and 100 ul of sample or standard was added in duplicate to 2 96-well ELISA plates (Thermo Labsystems, Immulon 4HBX #3885). The plates were sealed and incubated overnight at 4° C. The following day, plates were washed 3× with 300 ul/well PBST (PBS+0.05% Tween 20; 10×PBST, KPL #51-14-02) on a Bio Tek plate washer. Plates were blocked with 300 ul/well of diluent (PBS+2% BSA+0.05% Tween 20), incubated at RT for 2 hours, and washed 3× with PBST. All antibodies were diluted in diluent. 100 ul/well of anti-H3K27me3 (CST #9733, 50% glycerol stock 1:1,000) or anti-total H3 (Abcam ab1791, 50% glycerol 1:10,000) was added to each plate. Plates were incubated for 90 min at RT and washed 3× with PBST. 100 ul/well of anti-Rb-IgG-HRP (Cell Signaling Technology, 7074) was added 1:2,000 to the H3K27Me3 plate and 1:6,000 to the H3 plate and incubated for 90 min at RT. Plates were washed 4× with PBST. For detection, 100 ul/well of TMB substrate (BioFx Laboratories, #TMBS) was added and plates incubated in the dark at RT for 5 min. Reaction was stopped with 100 ul/well 1N $H_2SO_4$. Absorbance at 450 nm was read on SpectaMax M5 Microplate reader.

Results:

7 Day PD Study with Compound 87

In order to test whether Compound 87 can modulate the H3K27me3 histone mark in tumors in vivo, WSU-DLCL2 xenograft tumor bearing mice were treated with Compound 87 at either 200 mg/kg BID or 400 mg/kg QD or vehicle (BID schedule) for 7 days. There were 4 animals per group. Animals were euthanized 3 h after the last dose and tumor was preserved in a frozen state as described above. Following histone extraction the samples were applied to ELISA assays using antibodies directed against the trimethylated state of histone H3K27 (H3K27me3) or total histone H3. Based on these data the ratio of globally methylated to total H3K27 was calculated. FIG. 4 shows the mean global methylation ratios for all groups as measures by ELISA and indicates target inhibition ranging from app. 62.5% (400 mg/kg QD×7) and 37.5% (200 mg/kg BID×7) compared to vehicle.

28 Day Efficacy Study with Compound 141 in WSU-DLCL2 Xenograft Model

In order to test whether Compound 141 could induce a tumor growth inhibition in vivo WSU-DLCL2 xenograft tumor bearing mice were treated with Compound 141 at 12.5, 25 or 50 mg/kg QD for 28 days via intraperitoneal injection. Tumor volume and body weights were determined twice a week. Compound 141 was well tolerated at all doses with minimal body weight loss. A parallel cohort of mice (n=4 per group) was treated at the same doses for 7 days, and mice were euthanized on day 7, 3 h after the last dose for tumor sampling and assessment of target inhibition. FIG. 5 shows the result of the ELISA measuring global methylation of H3K27me3 normalized to total H3. Dose dependent target inhibition ranging from 39% to 67% compared to vehicle can be observed.

FIG. 6 shows the tumor growth over the treatment course of 28 days for the groups treated with vehicle or Compound 141.

An effect of administration of the vehicle given via the intraperitoneal route could be observed as tumor growth was slower in the vehicle group vs. the untreated group. Only the highest dose group of Compound 141 (50 mg/kg QD×28) showed tumor growth inhibition compared to the vehicle group (33% calculated from day 1, 43% calculated from day 7). The tumor growth was not statistically significant compared to vehicle when using a repeated measures ANOVA followed by Dunnets post test, but the terminal tumor size was significantly smaller in the 50 mg/kg DQ group compared to vehicle (2 way ANOVA, Bonferroni post test, p<0.0001).

Efficacy Study with Increasing Doses of Compound 44 in WSU-DLCL2 Xenograft Model In order to test whether compound 44 could induce an anti-tumor effect in vivo WSU-DLCL2 xenograft tumor bearing mice were treated with compound 44 at 37.5, 75 or 150 mg/kg TID for 28 days. There were 12 mice per group for the efficacy arm of the experiment. A parallel cohort was dosed for 7 days at the same doses and schedules for assessment of target inhibition after 7 days (n=6 per group). FIG. 7 shows the tumor growth over the treatment course of 28 days for vehicle and compound 44 treated groups. A clear dose dependent tumor growth inhibition could be observed. Only the highest dose group was statistically significant from vehicle by repeated measures ANOVA and Dunnett's post test. The tumor growth inhibition for the highest dose group was 58% (from day 1) or 73% (from day 7) compared to vehicle.

Histones were extracted from tumors collected after 7 days of dosing (parallel PD cohort) and at the end of the study on day 28 for the efficacy cohort (3 h after the last dose for both cohorts). FIG. 8 shows that the H3K27me3 methyl mark is modulated with treatment in a dose dependent matter and that there is statistically significant better target inhibition on day 28 compared to day 7 for the highest dose group (150 mg/kg TID).

Efficacy Study with Compound 44 at Different Dose Schedules

To assess whether Compound 44 would lead to tumor growth inhibition at other dosing schedules but TID a WSU-DLCL2 xenograft efficacy study was performed where TID, BID and QD schedules were compared side by side. There were 12 animals per group, and mice were treated for 28 days. FIG. 9 shows the tumor growth over the treatment course of 28 days for vehicle and Compound 44 treated groups. Tumor growth inhibition could be achieved at all doses and schedules (Table 5 below: summary of tumor growth inhibitions induced by different dosing schedules of Compound 44 in WSU-DLXC2 xenografts). While only the 150 mg/kg TID and 225 mg/kg BID were statistically significant from vehicle by repeated measures ANOVA and Dunnett's post test all terminal tumor sizes in Compound 44 treated groups were statistically different from vehicle by 2 way ANOVA and Bonferroni post test (p<0.0001).

TABLE 5

| Group | % TGI from day 1 | % TGI from day 7 |
| --- | --- | --- |
| 150 mg/kg TID | 73 | 86 |
| 225 mg/kg BID | 71 | 80 |
| 300 mg/kg BID | 57 | 67 |
| 600 mg/kg QD | 58 | 70 |

On day 28 mice were euthanized and tumors were collected 3 h after the last dose for assessment of target inhibition. FIG. 10 shows that treatment with Compound 44 induced similar degrees of target inhibition for all doses and schedules.

Example 201: Anti-Cancer Effect of Compound 44 on the KARPAS-422 Human Diffused Large B-Cell Lymphoma Mouse Xenograft Model Compound 44 (tri-HCl salt form) was tested for its anti-cancer activity in KARPAS-422 mouse xenograft model, which is a human diffused large B-Cell lymphoma xenograft model. Unless otherwise specified, Compound 44 referred to and tested in this experiment was its tri-HCl salt form. 45 female of CAnN.Cg-Foxn1nu/CrlCrlj mice (Charles River Laboratories Japan) with KARPAS-422 tumors whose mean tumor volume (TV) reached approximately 150 mm$^3$ were selected based on their TVs, and were randomly divided into five groups. The oral administration of Compound 44 (80.5, 161, 322, and 644 mg/kg) or vehicle was started on day 1. Compound 44 was given once daily on day 1 and day 29 and twice daily everyday from day 2 to day 28. The administration volume (0.1 mL/10 g body weight) was calculated from the body weight before administration. The TV and body weight were measured twice a week. The design for this experiment is shown in Table 6.

TABLE 6

| | | Dosing Scheme | |
| --- | --- | --- | --- |
| Group | No. of Animals | Treatment (twice a day) | Route and Schedule |
| 1 | 9 | Vehicle (0.5% Methyl Cellulose, 0.1% Tween-80) | PO; BID × 28 days |
| 2 | 9 | 80.5 mg/kg Compound 44 (tri-HCl salt) | PO; BID × 28 days |
| 3 | 9 | 161 mg/kg Compound 44 (tri-HCl salt) | PO; BID × 28 days |
| 4 | 9 | 322 mg/kg Compound 44 (tri-HCl salt) | PO; BID × 28 days |
| 5 | 9 | 644 mg/kg Compound 44 (tri-HCl salt) | PO; bid × 28 days |

TV is calculated from caliper measurements by the formula for the volume of a prolate ellipsoid $(L \times W^2)/2$ where L and W are the respective orthogonal length and width measurements (mm).

Data are expressed as the mean+standard deviation (SD). The differences in TV between the vehicle-treated and Compound 44-treated groups were analyzed by a repeated measures analysis of variance (ANOVA) followed by the Dunnett-type multiple comparison test. A value of P<0.05 (two sided) was considered statistically significant. Statistical analyses were performed using the Prism 5 software package version 5.04 (GraphPad Software, Inc., CA, USA).

During the treatment period, the dosage of 644 mg/kg resulted in the death of two out of nine mice. The maximum tolerated dose was determined as 322 mg/kg, at which dosage no mortality or no body weight loss was recorded, in the study (FIG. 11 and Table 7).

Compound 44 showed significant antitumor effects against a human diffuse large B cell lymphoma KARPAS-422 xenograft at all of the doses on day 29 in a dose dependent manner (FIG. 12). Tumor growth-inhibition effect was observed at 80.5 mg/kg. Tumor regressions were observed at 161 and 322 mg/kg.

TABLE 7

Effect of Compound 44 on Mouse Mortality

| Treatment twice a day | Number dead/total |
| --- | --- |
| Vehicle | 0/9 |
| Cpd 44 (tri-HCl salt) 80.5 mg/kg | 0/9 |
| Cpd 44 (tri-HCl salt) 161 mg/kg | 0/9 |
| Cpd 44(tri-HCl salt) 322 mg/kg | 0/9 |
| Cpd 44 (tri-HCl salt) 644 mg/kg | 2/9 |

INCORPORATION BY REFERENCE

The entire disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of treating soft tissue sarcoma, comprising administering to a subject in need thereof a therapeutically effective amount of a compound of Formula (I) or a pharmaceutically acceptable salt thereof:

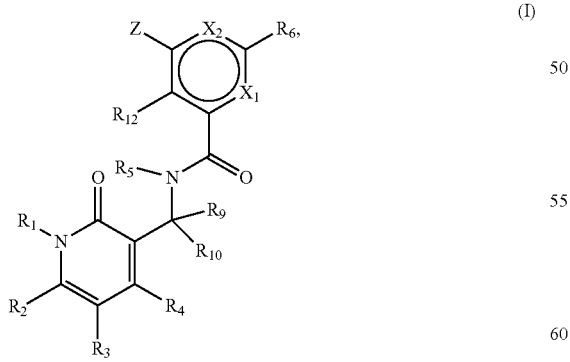

(I)

wherein $X_1$ is N or $CR_{11}$;

$X_2$ is N or $CR_{13}$;

Z is $NR_7R_8$, $OR_7$, $S(O)_nR_7$, or $CR_7R_8R_{14}$, in which n is 0, 1, or 2;

each of $R_1$, $R_5$, $R_9$, and $R_{10}$, independently, is H or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

each of $R_2$, $R_3$, and $R_4$, independently, is -$Q_1$-$T_1$, in which $Q_1$ is a bond or $C_1$-$C_3$ alkyl linker optionally substituted with halo, cyano, hydroxyl or $C_1$-$C_6$ alkoxy, and $T_1$ is H, halo, hydroxyl, COOH, cyano, or $R_{S1}$, in which $R_{S1}$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, amino, mono-$C_1$-$C_6$ alkylamino, di-$C_1$-$C_6$ alkylamino, 4 to 12-membered heterocycloalkyl, or 5- or 6-membered heteroaryl, and $R_{S1}$ is optionally substituted with one or more substituents selected from the group consisting of halo, hydroxyl, oxo, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_6$ is $C_6$-$C_{10}$ aryl or 5- or 6-membered heteroaryl, each of which is optionally substituted with one or more -Q$_2$-T$_2$, wherein Q$_2$ is a bond or C$_1$-C$_3$ alkyl linker optionally substituted with halo, cyano, hydroxyl or C$_1$-C$_6$ alkoxy, and T$_2$ is H, halo, cyano, —OR$_a$, —NR$_a$R$_b$, —(NR$_a$R$_b$R$_c$)$^+$A$^-$, —C(O)R$_a$, —C(O)OR$_a$, —S(O)$_2$R$_a$, —S(O)$_2$NR$_a$R$_b$, —NR$_b$C(O)R$_a$, —NR$_b$C(O)OR$_a$, —S(O)$_2$R$_a$, —S(O)$_2$NR$_a$R$_b$, or R$_{S2}$, in which each of R$_a$, R$_b$, and R$_c$, independently is H or R$_{S3}$, A$^-$ is a pharmaceutically acceptable anion, each of R$_{S2}$ and R$_{S3}$, independently, is C$_1$-C$_6$ alkyl, C$_3$-C$_8$ cycloalkyl, C$_6$-C$_{10}$ aryl, 4 to 12-membered heterocycloalkyl, or 5- or 6-membered heteroaryl, or R$_a$ and R$_b$, together with the N atom to which they are attached, form a 4 to 12-membered heterocycloalkyl ring having 0 or 1 additional heteroatom, and each of R$_{S2}$, R$_{S3}$, and the 4 to 12-membered heterocycloalkyl ring formed by R$_a$ and R$_b$, is optionally substituted with one or more -Q$_3$-T$_3$, wherein Q$_3$ is a bond or C$_1$-C$_3$ alkyl linker each optionally substituted with halo, cyano, hydroxyl or C$_1$-C$_6$ alkoxy, and T$_3$ is selected from the group consisting of halo, cyano, C$_1$-C$_6$ alkyl, C$_3$-C$_8$ cycloalkyl, C$_6$-C$_{10}$ aryl, 4 to 12-membered heterocycloalkyl, 5- or 6-membered heteroaryl, OR$_c$, COOR$_d$, —S(O)$_2$R$_d$, —NR$_d$R$_e$, and —C(O)NR$_d$R$_e$, each of R$_d$ and R$_e$ independently being H or C$_1$-C$_6$ alkyl, or -Q$_3$-T$_3$ is oxo; or any two neighboring -Q$_2$-T$_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—C$_1$-C$_6$ alkyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 12-membered heterocycloalkyl, and 5- or 6-membered heteroaryl;

R$_7$ is -Q$_4$-T$_4$, in which Q$_4$ is a bond, C$_1$-C$_4$ alkyl linker, or C$_2$-C$_4$ alkenyl linker, each linker optionally substituted with halo, cyano, hydroxyl or C$_1$-C$_6$ alkoxy, and T$_4$ is H, halo, cyano, NR$_f$R$_g$, —OR$_f$, —C(O)R$_f$, —C(O)OR$_f$, —C(O)NR$_f$R$_g$, —C(O)NR$_f$OR$_g$, —NR$_f$C(O)R$_g$, —S(O)$_2$R$_f$ or R$_{S4}$, in which each of R$_f$ and R$_g$, independently is H or R$_{S5}$, each of R$_{S4}$ and R$_{S5}$, independently is C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 12-membered heterocycloalkyl, or 5- or 6-membered heteroaryl, and each of R$_{S4}$ and R$_{S5}$ is optionally substituted with one or more -Q$_5$-T$_5$, wherein Q$_5$ is a bond, C(O), C(O)NR$_k$, NR$_k$C(O), S(O)$_2$, or C$_1$-C$_3$ alkyl linker, R$_k$ being H or C$_1$-C$_6$ alkyl, and T$_5$ is H, halo, C$_1$-C$_6$ alkyl, hydroxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 12-membered heterocycloalkyl, 5- or 6-membered heteroaryl, or S(O)$_q$R$_q$ in which q is 0, 1, or 2 and R$_q$ is C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 12-membered heterocycloalkyl, or 5- or 6-membered heteroaryl, and T$_5$ is optionally substituted with one or more substituents selected from the group consisting of halo, C$_1$-C$_6$ alkyl, hydroxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 12-membered heterocycloalkyl, and 5- or 6-membered heteroaryl except when T$_5$ is H, halo, hydroxyl, or cyano; or -Q$_5$-T$_5$ is oxo;

each of R$_8$, R$_{11}$, R$_{12}$, and R$_{13}$, independently, is H, halo, hydroxyl, COOH, cyano, R$_{S6}$, OR$_{S6}$, or COOR$_{S6}$, in which R$_{S6}$ is C$_1$-C$_6$ alkyl, C$_2$-C$_6$ alkenyl, C$_2$-C$_6$ alkynyl, C$_3$-C$_8$ cycloalkyl, 4 to 12-membered heterocycloalkyl, amino, mono-C$_1$-C$_6$ alkylamino, or di-C$_1$-C$_6$ alkylamino, and R$_{S6}$ is optionally substituted with one or more substituents selected from the group consisting of halo, hydroxyl, COOH, C(O)O—C$_1$-C$_6$ alkyl, cyano, C$_1$-C$_6$ alkoxyl, amino, mono-C$_1$-C$_6$ alkylamino, and di-C$_1$-C$_6$ alkylamino; or R$_7$ and R$_8$, together with the N atom to which they are attached, form a 4 to 11-membered heterocycloalkyl ring having 0 to 2 additional heteroatoms, or R$_7$ and R$_8$, together with the C atom to which they are attached, form C$_3$-C$_8$ cycloalkyl or a 4 to 11-membered heterocycloalkyl ring having 1 to 3 heteroatoms, and each of the 4 to 11-membered heterocycloalkyl rings or C$_3$-C$_8$ cycloalkyl formed by R$_7$ and R$_8$ is optionally substituted with one or more -Q$_6$-T$_6$, wherein Q$_6$ is a bond, C(O), C(O)NR$_m$, NR$_m$C(O), S(O)$_2$, or C$_1$-C$_3$ alkyl linker, R$_m$ being H or C$_1$-C$_6$ alkyl, and T$_6$ is H, halo, C$_1$-C$_6$ alkyl, hydroxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 12-membered heterocycloalkyl, 5- or 6-membered heteroaryl, or S(O)$_p$R$_p$ in which p is 0, 1, or 2 and R$_p$ is C$_1$-C$_6$ alkyl, C$_2$-C$_6$ alkenyl, C$_2$-C$_6$ alkynyl, C$_3$-C$_8$ cycloalkyl, C$_6$-C$_{10}$ aryl, 4 to 12-membered heterocycloalkyl, or 5- or 6-membered heteroaryl, and T$_6$ is optionally substituted with one or more substituents selected from the group consisting of halo, C$_1$-C$_6$ alkyl, hydroxyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 12-membered heterocycloalkyl, and 5- or 6-membered heteroaryl except when T$_6$ is H, halo, hydroxyl, or cyano; or -Q$_6$-T$_6$ is oxo; and R$_{14}$ is absent, H, or C$_1$-C$_6$ alkyl optionally substituted with one or more substituents selected from the group consisting of halo, hydroxyl, COOH, C(O)O—C$_1$-C$_6$ alkyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 12-membered heterocycloalkyl, and 5- or 6-membered heteroaryl.

2. The method of claim 1, wherein:

X$_1$ is N or CR$_{11}$;

X$_2$ is N or CR$_{13}$;

Z is NR$_7$R$_8$, OR$_7$, SR$_7$, or CR$_7$R$_8$R$_{14}$;

each of R$_1$, R$_5$, R$_9$, and R$_{10}$, independently, is H or C$_1$-C$_6$ alkyl optionally substituted with one or more substituents selected from the group consisting of halo, hydroxyl, COOH, C(O)O—C$_1$-C$_6$ alkyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, C$_6$-C$_{10}$ aryl, 4 to 7-membered heterocycloalkyl, and 5- or 6-membered heteroaryl;

each of R$_2$, R$_3$, and R$_4$, independently, is -Q$_1$-T$_1$, in which Q$_1$ is a bond or C$_1$-C$_3$ alkyl linker optionally substituted with halo, cyano, hydroxyl or C$_1$-C$_6$ alkoxy, and T$_1$ is H, halo, hydroxyl, COOH, cyano, or R$_{S1}$, in which R$_{S1}$ is C$_1$-C$_3$ alkyl, C$_2$-C$_6$ alkenyl, C$_2$-C$_6$ alkynyl, C$_1$-C$_6$ alkoxyl, C(O)O—C$_1$-C$_6$ alkyl, C$_3$-C$_8$ cycloalkyl, C$_6$-C$_{10}$ aryl, amino, mono-C$_1$-C$_6$ alkylamino, di-C$_1$-C$_6$ alkylamino, 4 to 7-membered heterocycloalkyl, or 5- or 6-membered heteroaryl, and R$_{S1}$ is optionally substituted with one or more substituents selected from the group consisting of halo, hydroxyl, oxo, COOH, C(O)O—C$_1$-C$_6$ alkyl, cyano, C$_1$-C$_6$ alkoxyl, amino, mono-C$_1$-C$_6$ alkylamino, di-C$_1$-C$_6$ alkylamino, C$_3$-C$_8$ cycloalkyl, $C_6$-$C_{10}$ aryl, 4 to 7-membered heterocycloalkyl, and 5- or 6-membered heteroaryl;

$R_6$ is $C_6$-$C_{10}$ aryl or 5- or 6-membered heteroaryl, each of which is optionally substituted with one or more -$Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is H, halo, cyano, —$OR_a$, —$NR_aR_b$, —$(NR_aR_bR_c)^+A^-$, —$C(O)R_a$, —$C(O)OR_a$, —$C(O)NR_aR_b$, —$NR_bC(O)R_a$, —$NR_bC(O)OR_a$, —$S(O)_2R_a$, —$S(O)_2NR_aR_b$, or $R_{S2}$, in which each of $R_a$, $R_b$, and $R_c$, independently is H or $R_{S3}$, $A^-$ is a pharmaceutically acceptable anion, each of $R_{S2}$ and $R_{S3}$, independently, is $C_1$-$C_6$ alkyl, $C_3$-$C_8$ cycloalkyl, $C_6$-$C_{10}$ aryl, 4 to 7-membered heterocycloalkyl, or 5- or 6-membered heteroaryl, or $R_a$ and $R_b$, together with the N atom to which they are attached, form a 4 to 7-membered heterocycloalkyl ring having 0 or 1 additional heteroatom, and each of $R_{S2}$, $R_{S3}$, and the 4 to 7-membered heterocycloalkyl ring formed by $R_a$ and $R_b$, is optionally substituted with one or more one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 7-membered heterocycloalkyl, 5- or 6-membered heteroaryl, $OR_d$, $COOR_d$, —$S(O)_2R_d$, —$NR_dR_e$, and —$C(O)NR_dR_e$, each of $R_d$ and $R_e$ independently being H or $C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5- or 6-membered heteroaryl; provided that -$Q_2$-$T_2$ is not H;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, —$OR_f$, —$C(O)R_f$, —$C(O)OR_f$, —$C(O)NR_fR_g$, —$C(O)NR_fOR_g$, —$NR_fC(O)R_g$, —$S(O)_2R_f$, or $R_{S4}$, in which each of $R_f$ and $R_g$, independently is H or $R_{S5}$, each of $R_{S4}$ and $R_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and each of $R_{S4}$ and $R_{S5}$ is optionally substituted with one or more -$Q_5$-$T_5$, wherein $Q_5$ is a bond, C(O), C(O)$NR_k$, $NR_kC(O)$, $S(O)_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5- or 6-membered heteroaryl except when Ts is H, halo, hydroxyl, or cyano; or -$Q_5$-$T_5$ is oxo; provided that $R_7$ is not H;

each of $R_8$, $R_{11}$, $R_{12}$, and $R_{13}$, independently, is H, halo, hydroxyl, COOH, cyano, $R_{S6}$, $OR_{S6}$, or $COOR_{S6}$, in which $R_{S6}$ is $C_1$-$C_6$ alkyl, $C_2$-$C_6$ alkenyl, $C_2$-$C_6$ alkynyl, amino, mono-$C_1$-$C_6$ alkylamino, or di-$C_1$-$C_6$ alkylamino, and $R_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 11-membered heterocycloalkyl ring having 0 to 2 additional heteroatoms, or $R_7$ and $R_8$, together with the C atom to which they are attached, form $C_3$-$C_8$ cycloalkyl or a 4 to 11-membered heterocycloalkyl ring having 1 to 3 heteroatoms, and each of the 4 to 11-membered heterocycloalkyl rings or $C_3$-$C_8$ cycloalkyl formed by $R_7$ and $R_8$ is optionally substituted with one or more -$Q_6$-$T_6$, wherein $Q_6$ is a bond, C(O), C(O)$NR_m$, $NR_mC(O)$, $S(O)_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5- or 6-membered heteroaryl except when $T_6$ is H, halo, hydroxyl, or cyano; or -$Q_6$-$T_6$ is oxo; and $R_{14}$ is absent, H, or $C_1$-$C_6$ alkyl optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5- or 6-membered heteroaryl.

3. The method of claim 2, wherein the compound is of Formula (II):

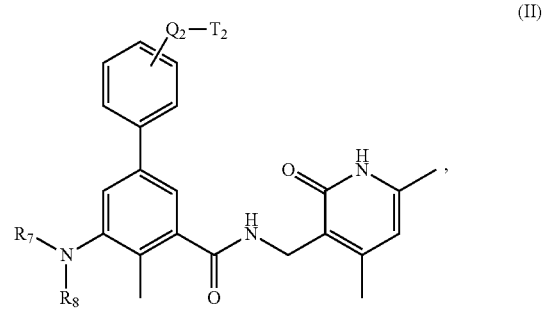

wherein $Q_2$ is a bond or methyl linker, $T_2$ is H, halo, —$OR_a$, —$NR_aR_b$, —$(NR_aR_bR_c)^+A^-$, or —$S(O)_2NR_aR_b$, $R_7$ is piperidinyl, tetrahydropyran, cyclopentyl, or cyclohexyl, each optionally substituted with one -$Q_5$-$T_5$ and $R_8$ is ethyl.

4. The method of claim 1, wherein the compound is of Formula (Ia):

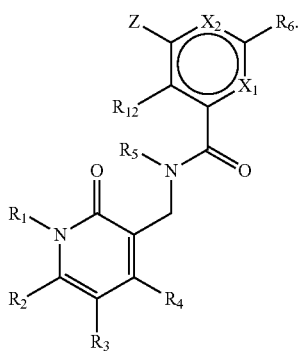

(Ia)

5. The method of claim 1, wherein $R_6$ is phenyl substituted with one or more $-Q_2-T_2$.

6. The method of claim 1, wherein $R_6$ is 5- or 6-membered heteroaryl containing 1-3 additional heteroatoms selected from N, O, and S and optionally substituted with one or more $-Q_2-T_2$.

7. The method of claim 6, wherein $R_6$ is pyridinyl, pyrazolyl, pyrimidinyl, quinolinyl, tetrazolyl, oxazolyl, isoxazolyl, thiazolyl, isothiazolyl, furyl, or thienyl, each of which is optionally substituted with one or more $-Q_2-T_2$.

8. The method of claim 1, wherein $T_2$ is $-NR_aR_b$ or $-C(O)NR_aR_b$, in which each of $R_a$ and $R_b$, independently is H or $C_1-C_6$ alkyl, or $R_a$ and $R_b$, together with the N atom to which they are attached, form a 4 to 12-membered heterocycloalkyl ring having 0 or 1 additional heteroatom, the $C_1-C_6$ alkyl and the 4 to 12-membered heterocycloalkyl ring being optionally substituted with one or more $-Q_3-T_3$.

9. The method of claim 1, wherein $Q_2$ is $C_1-C_3$ alkyl linker optionally substituted with halo or hydroxyl.

10. The method of claim 1, wherein $R_7$ is $C_1-C_6$ alkyl, $C_3-C_8$ cycloalkyl or 4 to 12-membered heterocycloalkyl, each optionally substituted with one or more $-Q_5-T_5$.

11. The method of claim 10, wherein $R_7$ is piperidinyl, tetrahydropyran, tetrahydro-2H-thiopyranyl, cyclopentyl, or cyclohexyl, each optionally substituted with one or more $-Q_5-T_5$.

12. The method of claim 1, wherein one or more $-Q_5-T_5$ are oxo; or when $Q_5$ is a bond, $T_5$ is amino, mono-$C_1-C_6$ alkylamino, di-$C_1-C_6$ alkylamino, $C_1-C_6$ alkyl, $C_3-C_8$ cycloalkyl, or 4 to 12-membered heterocycloalkyl; or when $Q_5$ is CO, $S(O)_2$, or NHC(O), $T_5$ is $C_1-C_6$ alkyl, $C_1-C_6$ alkoxyl, $C_3-C_8$ cycloalkyl, or 4 to 12-membered heterocycloalkyl; or when $Q_5$ is $C_1-C_3$ alkyl linker, $T_5$ is H, $C_6-C_{10}$ aryl, $C_3-C_8$ cycloalkyl, 4 to 12-membered heterocycloalkyl, or $S(O)_qR_q$.

13. The method of claim 1, wherein $R_{11}$ is H.

14. The method of claim 1, wherein each of $R_2$ and $R_4$, independently is H or $C_1-C_6$ alkyl optionally substituted with amino, mono-$C_1-C_6$ alkylamino, di-$C_1-C_6$ alkylamino, or $C_6-C_{10}$ aryl.

15. The method of claim 1, wherein $R_1$ is H.

16. The method of claim 1, wherein $R_{12}$ is H, methyl, ethyl, ethenyl, or halo.

17. The method of claim 1, wherein $R_8$ is H, methyl, or ethyl.

18. The method of claim 1, wherein Z is $NR_7R_8$ or $CR_7R_8R_{14}$ wherein $R_7$ and $R_8$, together with the atom to which they are attached, form a ring selected from the group consisting of piperidinyl, morpholinyl, piperazinyl, and cyclohexenyl, each optionally substituted with one $-Q_6-T_6$.

19. The method of claim 1, wherein $R_{13}$ is H or methyl.

20. The method of claim 1, wherein the compound is of Formula (Ie):

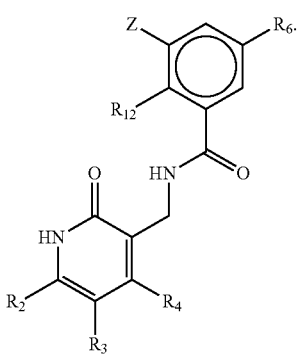

(Ie)

21. The method of claim 1, wherein the compound is of Formula (Ig):

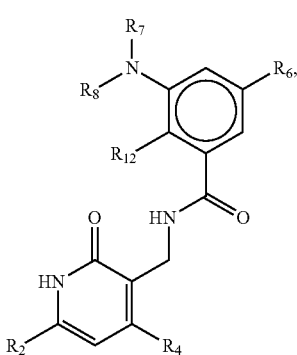

(Ig)

wherein $R_2$, $R_4$ and $R_{12}$ are each, independently $C_{1-6}$ alkyl.

22. The method of claim 21, wherein $R_6$ is $C_6-C_{10}$ aryl or 5- or 6-membered heteroaryl, each of which is optionally, independently substituted with one or more $-Q_2-T_2$, wherein $Q_2$ is a bond or $C_1-C_3$ alkyl linker, and $T_2$ is H, halo, cyano, $-OR_a$, $-NR_aR_b$, $-(NR_aR_bR_c)^+A^-$, $-C(O)NR_aR_b$, $-NR_bC(O)R_a$, $-S(O)_2R_a$, or $R_{S2}$, in which each of $R_a$ and $R_b$, independently is H or $R_{S3}$, each of $R_{S2}$ and $R_{S3}$, independently, is $C_1-C_6$ alkyl, or $R_a$ and $R_b$, together with the N atom to which they are attached, form a 4 to 7-membered heterocycloalkyl ring having 0 or 1 additional heteroatom, and each of $R_{S2}$, $R_{S3}$, and the 4 to 7-membered heterocycloalkyl ring formed by $R_a$ and $R_b$, is optionally, independently substituted with one or more $-Q_3-T_3$, wherein $Q_3$ is a bond or $C_1-C_3$ alkyl linker and $T_3$ is selected from the group consisting of halo, $C_1-C_6$ alkyl, 4 to 7-membered heterocycloalkyl, $OR_d$, $-S(O)_2R_d$, and $-NR_dR_e$, each of $R_d$ and $R_e$ independently being H or $C_1-C_6$ alkyl, or $-Q_3-T_3$ is oxo; or any two neighboring $-Q_2-T_2$, together with the atoms to which they are attached form a 5- or 6-membered ring optionally containing 1-4 heteroatoms selected from N, O and S.

23. The method of claim 21, wherein the compound is of Formula (IIa):

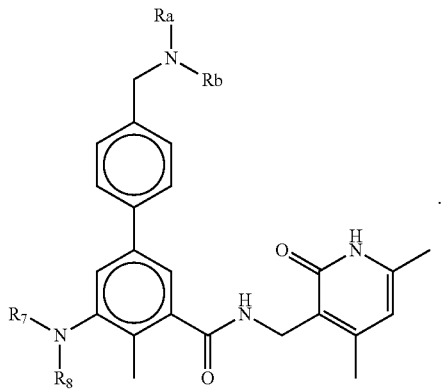

(IIa)

24. The method of claim 23, wherein $R_a$ and $R_b$, together with the N atom to which they are attached, form a 4 to 7-membered heterocycloalkyl ring having 0 or 1 additional heteroatoms to the N atom and the ring is optionally substituted with one or more -$Q_3$-$T_3$, wherein the heterocycloalkyl is azetidinyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, or morpholinyl.

25. The method of claim 24, wherein $R_7$ is $C_3$-$C_8$ cycloalkyl or 4 to 7-membered heterocycloalkyl, each optionally substituted with one or more -$Q_5$-$T_5$.

26. The method of claim 25, wherein $R_7$ is piperidinyl, tetrahydropyran, tetrahydro-2H-thiopyranyl, cyclopentyl, cyclohexyl, pyrrolidinyl, or cycloheptyl, each optionally substituted with one or more -$Q_5$-$T_5$.

27. The method of claim 26, $R_8$ is H or $C_1$-$C_6$ alkyl which is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino.

28. The method of claim 1, wherein the compound is selected from Compounds 13, 1, 2, 11, 12, 17, 20, 21, 36, 42, 43, 44, 59, 65, 67, 68, 69, 73, 75, 76, 78, 80, 82, 83, 87, 88, 89, 90, 91, 94, 97, 103, 105, 138 and 141, and their pharmaceutically acceptable salts thereof.

29. A method of treating soft tissue sarcoma, comprising administering to a subject in need thereof a therapeutically effective amount of

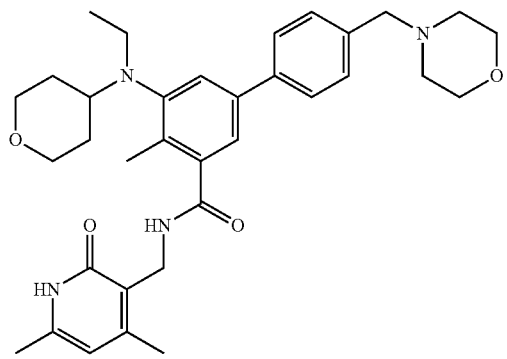 [SMILES: CCN(c1cc(-c2ccc(CN3CCOCC3)cc2)cc(C(=O)NCc2c(C)cc(C)[nH]c2=O)c1C)C1CCOCC1]

or a pharmaceutically acceptable salt thereof.

* * * * *

UNITED STATES PATENT AND TRADEMARK OFFICE
CERTIFICATE OF CORRECTION

PATENT NO. : 10,155,002 B2
APPLICATION NO. : 15/346677
DATED : December 18, 2018
INVENTOR(S) : Kevin Wayne Kuntz et al.

It is certified that error appears in the above-identified patent and that said Letters Patent is hereby corrected as shown below:

At Column 421, Line number 23, in Claim 1:
"heteroaryl, $OR_c$, $COOR_d$, $-S(O)_2R_d$, $-NR_dR_e$, and"
Should read:
-- heteroaryl, $OR_d$, $COOR_d$, $-S(O)_2R_d$, $-NR_dR_e$, and --

At Column 423, Line number 65, in Claim 2:
"or 6-membered heteroaryl except when $T_s$ is H, halo,"
Should read:
-- or 6-membered heteroaryl except when $T_5$ is H, halo, --

Signed and Sealed this
Nineteenth Day of February, 2019

Andrei Iancu
*Director of the United States Patent and Trademark Office*